US012565680B2

(12) United States Patent
Wang et al.

(10) Patent No.: US 12,565,680 B2
(45) Date of Patent: Mar. 3, 2026

(54) CANCER NEOANTIGENS AND THEIR UTILITIES IN CANCER VACCINES AND TCR-BASED CANCER IMMUNOTHERAPY

(71) Applicant: THE METHODIST HOSPITAL SYSTEM, Houston, TX (US)

(72) Inventors: Rongfu Wang, Houston, TX (US); Yicheng Wang, Houston, TX (US); Lili Zhang, Shanghai (CN); Chen Qian, Houston, TX (US)

(73) Assignee: THE METHODIST HOSPITAL SYSTEM, Houston, TX (US)

(*) Notice: Subject to any disclaimer, the term of this patent is extended or adjusted under 35 U.S.C. 154(b) by 1105 days.

(21) Appl. No.: 17/050,586

(22) PCT Filed: Apr. 25, 2019

(86) PCT No.: PCT/US2019/029107

§ 371 (c)(1),
(2) Date: Oct. 26, 2020

(87) PCT Pub. No.: WO2020/036646

PCT Pub. Date: Feb. 20, 2020

(65) Prior Publication Data

US 2022/0307087 A1 Sep. 29, 2022

Related U.S. Application Data

(60) Provisional application No. 62/662,495, filed on Apr. 25, 2018.

(51) Int. Cl.

| | |
|---|---|
| ***A61K 40/42*** | (2025.01) |
| ***A61K 39/00*** | (2006.01) |
| ***A61K 40/11*** | (2025.01) |
| ***A61K 40/32*** | (2025.01) |
| ***C12N 5/0783*** | (2010.01) |
| ***C12Q 1/6872*** | (2018.01) |
| ***C12Q 1/6886*** | (2018.01) |

(52) U.S. Cl.

CPC ........ *C12Q 1/6886* (2013.01); *A61K 39/0011* (2013.01); *A61K 39/001112* (2018.08); *A61K 39/001188* (2018.08); *A61K 39/00119* (2018.08); *A61K 40/11* (2025.01); *A61K 40/32* (2025.01); *A61K 40/42* (2025.01); *A61K 40/4201* (2025.01); *A61K 40/4211* (2025.01); *A61K 40/4242* (2025.01); *A61K 40/4269* (2025.01); *C12N 5/0638* (2013.01); *C12Q 1/6872* (2013.01); *A61K 2239/31* (2023.05); *A61K 2239/38* (2023.05); *A61K 2239/48* (2023.05); *A61K 2239/57* (2023.05); *A61K 2239/58* (2023.05); *C12Q 2600/156* (2013.01)

(58) Field of Classification Search

CPC .............. C12Q 1/6886; A61K 39/0011; A61K 39/001112; A61K 39/00119; A61K 39/4611; A61K 39/4632; A61K 39/4644; A61K 39/464401; A61K 39/464412; C12N 5/0638; C12N 2501/999; C07K 14/7051

See application file for complete search history.

(56) References Cited

U.S. PATENT DOCUMENTS

| | | | | |
|---|---|---|---|---|
| 4,452,901 | A | 6/1984 | Gordon et al. | |
| 2006/0040262 | A1 | 2/2006 | Morris et al. | |
| 2008/0274954 | A1 | 11/2008 | Ohara et al. | |
| 2017/0202939 | A1* | 7/2017 | Carreno | A61K 35/17 |
| 2019/0000880 | A1* | 1/2019 | Motz | C12N 5/0636 |

FOREIGN PATENT DOCUMENTS

| | | | | |
|---|---|---|---|---|
| CN | 107541498 | A | 1/2018 | |
| EP | 0045665 | A1 | 2/1982 | |
| WO | WO-2017114497 | A1 * | 7/2017 | A61K 31/00 |
| WO | 2018012895 | A1 | 1/2018 | |
| WO | 2018059549 | A1 | 4/2018 | |

OTHER PUBLICATIONS

Otto et al. An Immunogenic Personal Neoantigen Vaccine for Melanoma Patients. Nature Jul. 13, 2017; 547(7662): 217-221. (Year: 2017).*

Tran, et al., "T-Cell Transfer Therapy Targeting Mutant KRAS in Cancer", N Engl J Med. Dec. 2016, 375(23): 2255-2262.

Tran, et al., "T-Cell Transfer Therapy Targeting Mutant KRAS in Cancer—Supplementary Appendix", N Engl J Med. Dec. 2016, 375(23): 2255-2262.

Extended European Search Report for European patent application No. 19850632.1 issued Jul. 4, 2022.

Office Action in Chinese Counterpart Application No. 201980039937.0 dated Jul. 30, 2024 in 11 pages; English. translation provided.

Cherkassky, et al., "Human CAR T cells with cell-intrinsic PD-1 checkpoint blockade resist tumor-mediated inhibition", J Clin Invest., Aug. 2016, 126(8):3130-3144.

Serroukh, et al., "The transcription factors Runx3 and ThPOK cross-regulate acquisition of cytotoxic function by human Th1 lymphocytes", Elife, Feb. 2018, 7:e30496.

Partial European Search Report for European patent application No. 19850632.1 issued Feb. 7, 2022.

Almquist, et al., "Synthesis and biological activity of a ketomethylene analogue of a tripeptide inhibitor of angiotensin converting enzyme" J Med Chem., Dec. 1980, 23(12):1392-1398.

Bagshawe, "The First Bagshawe lecture. Towards generating cytotoxic agents at cancer sites," Br J Cancer., Sep. 1989, 60(3): 275-281.

Balachandran, et al. "Identification of unique neoantigen qualities in long-term survivors of pancreatic cancer," Nature, Nov. 2017, 551: 512-516.

Battelli, et al., "T lymphocyte killing by a xanthine-oxidase-containing immunotoxin," Cancer Immunol. Immunother., 1992, 35(6):421-425.

(Continued)

*Primary Examiner* — Shafiqul Haq

(74) *Attorney, Agent, or Firm* — DUANE MORRIS LLP

(57) ABSTRACT

Disclosed are compositions and methods for identifying neoantigens and using neoantigens in the use of treating cancer, as well as autoimmune diseases, where antigens causing tissue destruction.

Figure 1:
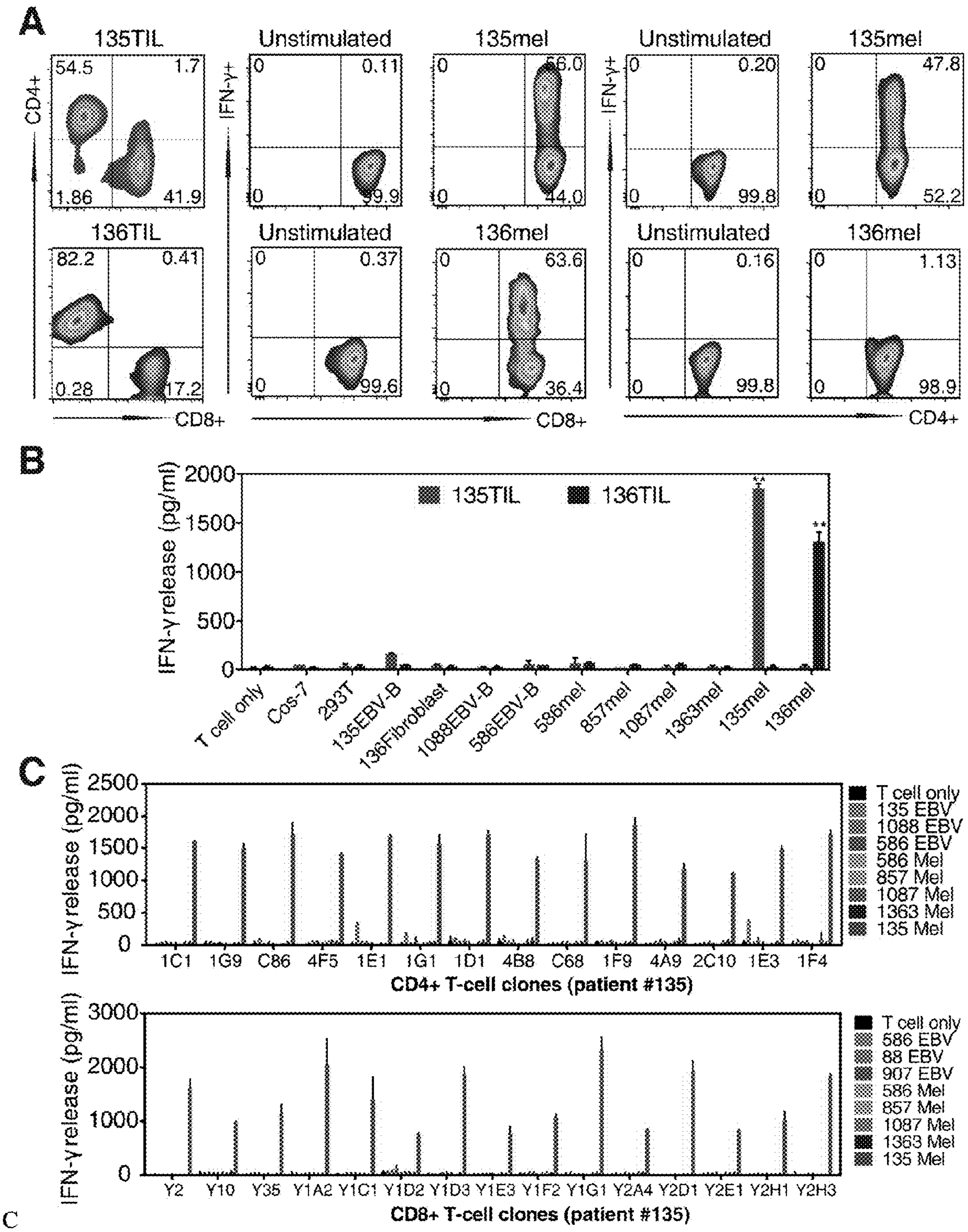

4 Claims, 21 Drawing Sheets
(19 of 21 Drawing Sheet(s) Filed in Color)

Specification includes a Sequence Listing.

(56) References Cited

OTHER PUBLICATIONS

Birnbaum, et al., "Deconstructing the peptide-MHC specificity of T cell recognition," Cell, May 2014, 157(5): 1073-1087.
Bolotin, et al., "Antigen receptor repertoire profiling from RNA-seq data," Nature Biotechnology, Oct. 2017, 35(10): 908-911.
Braumüller, et al., "T-helper-1-cell cytokines drive cancer into senescence," Nature, Feb. 2013, 494: 361-365.
Brown, et al., "Molecular and cellular mechanisms of receptor-mediated endocytosis," DNA and Cell Biology, Jul.-Aug. 1991, 10:(6): 399-409 (abstract only).
Carpenter, et al., "Control of Regulatory T Cell Differentiation by the Transcription Factors Thpok and LRF," Journal of Immunology, Sep. 2017, 199(5): 1716-1728.
Carreno, et al., "Cancer immunotherapy. A dendritic cell vaccine increases the breadth and diversity of melanoma heoantigen-specific T cells," Science, May 2015, 348: 803-808.
Chen, et al., "Anti-PD-1/PD-L1 therapy of human cancer: past, present, and future," The Journal of clinical Investigation, Sep. 2015, 125 (9): 3384-3391.
Chen, et al., "A testicular antigen aberrantly expressed in human cancers detected by autologous antibody screening," Proc Natl Acad Sci U S A, Mar. 1997, 94(5): 1914-1918.
Chowell, et al. "Patient HLA class I genotype influences cancer response to checkpoint blockade immunotherapy," Science, Feb. 2018, 359: 582-587.
Cibulskis, et al., "Sensitive detection of somatic point mutations in impure and heterogeneous cancer samples," Nature Biotechnology, Mar. 2013, 31(3): 213-219.
Cole, et al., "Hotspot autoimmune T cell receptor binding underlies pathogen and insulin peptide cross-reactivity," J. Clin. Invest., Jun. 2016, 126(6): 2191-2204.
Cole, et al. "Hotspot autoimmune T cell receptor binding underlies pathogen and insulin peptide cross-reactivity," J. Clin. Invest., Jun. 2016, 126(6): 3626.
Bollag, et al. "Protein Methods," 2nd edition, Wiley, Jul. 1996.
De la Herran-Arita, et al. "CD4+ T cell autoimmunity to hypocretin/orexin and cross-reactivity to a 2009 H1N1 influenza A epitope in narcolepsy," Sci Transl Med., Dec. 2013, 5: 216ra176.
Gubin, et al. "Checkpoint blockade cancer immunotherapy targets tumour-specific mutant antigens," Nature, Nov. 2014, 515: 577-581.
Guo, et al., "Neoantigen Vaccine Delivery for Personalized Anti-cancer Immunotherapy", Front Immunol., Jul. 2018, 9:1499.
Han, et al., "Linking T-cell receptor sequence to functional phenotype at the single-cell level," Nature biotechnology, Jul. 2014, 32(7): 684-692.
Hann, et al. "On the double bond isostere of the peptide bond: preparation of an enkephalin analogue," J. Chem. Soc Perkin Trans. I, 1982: 307-314.
He, et al., "The role of ThPOK in control of CD4/CD8 lineage commitment," Annual review of immunology, 2010, 28: 295-320.
Hellmann, et al., "Tumor Mutational Burden and Efficacy of Nivolumab Monotherapy and in Combination with pilimumab in Small-Cell Lung Cancer," Cancer cell, May 2018, 33(5): 853-861.
Holladay, et al., "Synthesis of hydroxyethylene and ketomethylene dipeptide isosteres," Tetrahedron. Lett., 1983, 24(41): 4401-4404.
Hudson, et al., "Methionine Enkephalin and Isosteric Analogues I. Synthesis on a Phenolic Resin Support," Int J Pept Prot Res., 1979, 14:177-185.
Hughes et al., "Monoclonal antibody targeting of liposomes to mouse lung in vivo," Cancer Research, Nov. 1989, 49(22): 6214-6220.
Hruby, "Conformational Restrictions of Biologically Active Peptides via Amino Acid Side Chain Groups" Life Sciences, 1982, 31(3):189-199.
Hung, et al., "The central role of CD4(+) T cells in the antitumor immune response" J Exp Med., Dec. 1998, 188(12): 2357-2368.
Jaeger, et al., "Predicting optimal and suboptimal secondary structure for RNA," Methods Enzymol. 1990, 183:281-306.
Jaeger, et al., "Improved predictions of secondary structures for RNA", Proc Natl Acad Sci U S A. Oct. 1989, 86(20):7706-7710.
Jennings-White, et al., "Synthesis of ketomethylene analogs of dipeptides", Tetrahedron Letters 1982, 23(25): 2533-2534.
Kang, et al., "Senescence surveillance of pre-malignant hepatocytes limits liver cancer development", Nature Nov. 2011, 479: 547-551 (abstract only).
Kastenmuller, et al., "Cross-competition of CD8+ T cells shapes the immunodominance hierarchy during boost vaccination", The Journal of experimental medicine Sep. 2007, 204(9): 2187-2198.
Kreiter, et al., "Mutant MHC class II epitopes drive therapeutic immune responses to cancer", Nature Apr. 2015, 520: 692-696.
La Gruta, et al., "Understanding the drivers of MHC restriction of T cell receptors," Nat Rev Immunol., Jul. 2018, (7):467-478.
Laemmli, "Cleavage of structural proteins during the assembly of the head of bacteriophage T4" Nature, Aug. 1970, 227:680-685.
Laumont, et al., "Noncoding regions are the main source of targetable tumor-specific antigens", Sci Transl Med. Dec. 2018, 10(470) (abstract only).
Le, et al., "Mismatch repair deficiency predicts response of solid tumors to PD-1 blockade", Science, Jul. 2017, 357:409-413.
Letsinger, et al., "Cholesteryl-conjugated oligonucleotides: synthesis, properties, and activity as inhibitors of replication of human immunodeficiency virus in cell culture" Proc Natl Acad Sci U S A, Sep. 1989, 86(17):6553-6556.
Li, et al., "Fast and accurate short read alignment with Burrows-Wheeler transform", Bioinformatics, Jul. 2009, 25(14):1754-1760.
Linnemann, et al., "High-throughput epitope discovery reveals frequent recognition of neo-antigens by CD4+ T cells in human melanoma", Nat Med., Jan. 2015, 21(1):81-85.
Litzinger, et al., "Biodistribution and immunotargetability of ganglioside-stabilized dioleoylphosphatidylethanolamine liposomes", Biochim Biophys Acta., Feb. 1992, 1104(1):179-187.
Lu, et al., "Efficient identification of mutated cancer antigens recognized by T cells associated with durable tumor regressions", Clin Cancer Res., Jul. 2014, 20(13):3401-3410.
Luckey, et al., "The transcription factor ThPOK suppresses Runx3 and imposes CD4(+) lineage fate by inducing the SOCS suppressors of cytokine signaling", Nat Immunol. Jul. 2014, 15(7):638-645.
Łuksza, et al., "A neoantigen fitness model predicts tumour response to checkpoint blockade immunotherapy", Nature, Nov. 2017, 551:517-520.
Malandro, et al., "Clonal Abundance of Tumor-Specific CD4(+) T Cells Potentiates Efficacy and Alters Susceptibility to Exhaustion" Immunity, Jan. 2016, 44(1):179-193.
Manguso, et al., "In vivo CRISPR screening identifies Ptpn2 as a cancer immunotherapy target", Nature, Jul. 2017, 547(7664):413-418.
Pyke,et al., "Evolutionary Pressure against MHC Class II Binding Cancer Mutations" Cell, Oct. 2018, 175(2):416-428.
Marty, et al., "MHC-I Genotype Restricts the Oncogenic Mutational Landscape", Cell, Nov. 2017, 171(6):1272-1283.
Jikuya, et al., FLJ00298 protein, partial [*Homo sapiens*]. Genbank entry (online). National Institute of Biotechnology Information. Jul. 26, 2016 [Retrieved on Mar. 10, 2020]. Retrieved from the Internet: <URL: https://www.ncbi.nlm.nih.gov/protein/BAD18714.1 >; pp. 1-2.
Sonntag, et al., "Immune monitoring and TCR sequencing of CD4 T cells in a long term responsive patient with metastasized pancreatic ductal carcinoma treated with individualized, neoepitope-derived multipeptide vaccines: a case report", J Transl Med., Feb. 2018, 16(1):23.
Rech, et al., "T-Cell Transfer Therapy Targeting Mutant KRAS", N Engl J Med., Feb. 2017, 376(7):e11.
Kabawat, et al., "Monoclonal Antibodies in Diagnostic Pathology", Handbook of Monoclonal Antibodies, Noyes Publications, Park Ridge, N.J., 1985, pp. 293-328.
Schultz, et al., "Monoclonal Antibodies in Diagnostic Pathology", Handbook of Monoclonal Antibodies, Noyes Publications, Park Ridge, N.J., 1985, pp. 329-346.
Johnson, et al., "Monoclonal Antibodies and Melanomas", Handbook of Monoclonal Antibodies, Noyes Publications, Park Ridge, N.J., 1985, pp. 347-359.

(56) References Cited

OTHER PUBLICATIONS

Bach, et al., "Monoclonal Antibodies as Therapeutic Tools in Medicine", Antibodies in Human Diagnosis and Therapy, Raven Press, New York, 1977, pp. 419-435.
Smith, et al., "Cardiac Glycoside-Specific Antibodies in the Treatment of Digitalis Intoxication", Antibodies in Human Diagnosis and Therapy, Raven Press, New York, 1977, pp. 365-389.
Spatola, "Peptide Backbone Modifications: A Structure-Activity Analysis of Peptides Containing Amide Bond Surrogates, Conformational Constraints, and Relationships" Chemistry and Biochemistry of Amino Acids, Peptides and Proteins, vol. 7, Marcel Dekker, Inc., New York, 1983, pp. 267-357.
Creighton, "Proteins: Structures and Molecular Principles", W.H. Freeman and Company, New York, 1984, pp. 79-86.
Matsudaira, et al., "SDS microslab linear gradient polyacrylamide gel electrophoresis", Anal Biochem., Jul. 1978 87(2):386-96.
McGranahan, et al., "Allele-Specific HLA Loss and Immune Escape in Lung Cancer Evolution", Cell, Nov. 2017, 171(6):1259-1271.
McKenna, et al., "The Genome Analysis Toolkit: a MapReduce framework for analyzing next-generation DNA sequencing data", Genome Res., Sep. 2010, 20(9):1297-303.
Morley, "Modulation of the action of regulatory peptides by structural modification", Trends Pharm Sci., 1980: 463-468.
Mucida, et al., "Transcriptional reprogramming of mature $CD4^+$ helper T cells generates distinct MHC class II-restricted cytotoxic T lymphocytes", Nat Immunol., Mar. 2013, 14(3):281-289.
Needleman, et al., "A general method applicable to the search for similarities in the amino acid sequence of two proteins" J Mol Biol., Mar. 1970, 48(3):443-453.
Nelson, et al., "T cell receptor cross-reactivity between similar foreign and self peptides influences naive cell population size and autoimmunity", Immunity, Jan. 2015, 42(1):95-107.
Neuhoff, et al., "Clear backaground and highly sensitive protein staining with Coomassie Blue dyes in polyacrylamide gels: A systemic analysis", Electrophoresis, 1985, 6: 427-448.
Neuhoff, et al., "Improved staining of proteins in polyacrylamide gels including isoelectric focusing gels with clear background at nanogram sensitivity using Coomassie Brilliant Blue G-250 and R-250", Electrophoresis, 1988, 6: 427-448.
Ornstein, "Disc Electrophoresis. I. Background and Theory", Ann N Y Acad Sci. Dec. 1964, 121:321-349.
Pan, et al., "A major chromatin regulator determines resistance of tumor cells to T cell-mediated killing", Science, Feb. 2018, 359(6377):770-775.
Patel, et al., "Identification of essential genes for cancer immunotherapy", Nature, Aug. 2017, 548(7669):537-542.
Pearson, et al. "Improved tools for biological sequence comparison", Proc Natl Acad Sci U S A, Apr. 1988, 85(8):2444-8.
Pietersz, et al., "Antibody conjugates for the treatment of cancer", Immunol Rev., Oct. 1992, 129:57-80.
Porter, et al., "Chimeric antigen receptor-modified T cells in chronic lymphoid leukemia", N Engl J Med Aug. 2011, 365(8):725-733.
Zhang, et al., "Breast Cancer Neoantigens Can Induce CDS+ T-Cell Responses and Antitumor Immunity", Cancer Immunol Res., Jul. 2017, 5(7):516-523.
Rizvi, et al., "Cancer immunology. Mutational landscape determines sensitivity to PD-1 blockade in non-small cell lung cancer", Science, Apr. 2015, 348(6230):124-128.
Robbins, et al., "Mining exomic sequencing data to identify mutated antigens recognized by adoptively transferred tumor-reactive T cells", Nat Med. Jun. 2013, 19(6):747-752.
Robins, et al., "Comprehensive assessment of T-cell receptor beta-chain diversity in alphabeta T cells" Blood, Nov. 2009, 114(19):4099-4107.
Roffler, et al. "Anti-neoplastic glucuronide prodrug treatment of human tumor cells targeted with a monoclonal antibody-enzyme conjugate", Biochem Pharmacol., Oct. 1991, 42(10):2062-2065 (abstract only).
Rosenberg, et al., "Adoptive cell transfer as personalized immunotherapy for human cancer", Science. Apr. 2015, 348(6230):62-68.
Schumacher, et al., "Neoantigens in cancer immunotherapy" Science, Apr. 2015, 348(6230):69-74.
Schumacher, et al., "Cancer Neoantigens" Annu Rev Immunol., Apr. 2019, 37:173-200.
Senter, et al., "Generation of 5-fluorouracil from 5-fluorocytosine by monoclonal antibody-cytosine deaminase conjugates", Bioconjug Chem., Nov.-Dec. 1991, 2(6):447-451.
Senter, et al., "Generation of cytotoxic agents by targeted enzymes", Bioconjug Chem., Jan.-Feb. 1993, 4(1):3-9.
Sercarz, et al., "Dominance and crypticity of T cell antigenic determinants", Annu Rev Immunol., 1993, 11:729-66.
Sharma, et al., "Immune checkpoint targeting in cancer therapy: toward combination strategies with curative potential" Cell, Apr. 2015, 161(2):205-214.
Shastri, et al., "Producing nature's gene-chips: the generation of peptides for display by MHC class I molecules", Annu Rev Immunol., 2002, 20:463-493.
Shedlock, et al., "Requirement for CD4 T cell help in generating functional CD8 T cell memory", Science, Apr. 2003, 300(5617):337-339.
Smith, et al., "Comparison of biosequences", Advances in Applied Mathematics, Dec. 1981, 2(4): 482-489 (abstract only).
Spatola, et al., "Structure-activity relationships of enkephalins containing serially replaced thiomethylene amide bond surrogates", Life Sci., Apr. 1986, 38(14):1243-1249.
Starck, et al., "Translation from the 5' untranslated region shapes the integrated stress response" Science, Jan. 2016, 351(6272):aad3867.
Stronen, et al., "Targeting of cancer neoantigens with donor-derived T cell receptor repertoires" Science, Jun. 2016, 352(6291):1337-1341.
Sun, et al., "Defective CD8 T cell memory following acute infection without CD4 T cell help", Science, Apr. 2003, 300(5617):339-342.
Topalian, et al., "Immune checkpoint blockade: a common denominator approach to cancer therapy", Cancer Cell, Apr. 2015, 27(4):450-461.
Tran, et al., "Immunogenicity of somatic mutations in human gastrointestinal cancers", Science, Dec. 2015, 350(6266):1387-1390.
Tran, et al., "Cancer immunotherapy based on mutation-specific CD4+ T cells in a patient with epithelial cancer", Science, May 2014, 344(6184):641-645.
Vacchio, et al., "ThPOK-LRF transcriptional node maintains the integrity and effector potential of post-thymic CD4+ T cells", Nat Immunol., Oct. 2014, 15(10):947-956.
Wang, et al., "Tumor-specific human CD4+ regulatory T cells and their ligands: implications for immunotherapy", Immunity, Jan. 2004, 20(1):107-118.
Wang, et al., "Recognition of a new ARTC1 peptide ligand uniquely expressed in tumor cells by antigen-specific CD4+ regulatory T cells", J Immunol., Mar. 2005, 174(5):2661-2670.
Wang, et al., "Identification of a mutated fibronectin as a tumor antigen recognized by CD4+ T cells: its role in extracellular matrix formation and tumor metastasis", J Exp Med., Jun. 2002, 195(11):1397-1406.
Wang, "The role of MHC class II-restricted tumor antigens and CD4+ T cells in antitumor immunity", Trends Immunol., May 2001, 22(5):269-276.
Wang, et al., "Immune targets and neoantigens for cancer immunotherapy and precision medicine", Cell Res., Jan. 2017, 27(1):11-37.
Wang, et al, "A breast and melanoma-shared tumor antigen: T cell responses to antigenic peptides translated from different open reading frames", J Immunol., Oct. 1998, 161(7):3598-3606.
Wang, et al., "Utilization of an alternative open reading frame of a normal gene in generating a novel human cancer antigen", J Exp Med., Mar. 1996, 183(3):1131-1140.
Wang, et al., "Identification of a novel major histocompatibility complex class II-restricted tumor antigen resulting from a chromosomal rearrangement recognized by CD4(+) T cells", J Exp Med., May 1999, 189(10):1659-1668.
Wang, et al., "Cloning genes encoding MHC class II-restricted antigens: mutated CDC27 as a tumor antigen" Science., May 1999, 284(5418):1351-1354.

(56) References Cited

OTHER PUBLICATIONS

Zacharakis, et al., "Immune recognition of somatic mutations leading to complete durable regression in metastatic breast cancer", Nat Med., Jun. 2018, 24(6):724-730.
Zuker, "On finding all suboptimal foldings of an RNA molecule", Science., Apr. 1989, 244(4900):48-52.
International Search Report and Written Opinion for PCT International Application No. PCT/US2019/029107 issued Apr. 16, 2020.
Office Action in Australian Counterpart Application No. 2019322795, dated Mar. 7, 2025, in 7 pages.
Stromnes, Ingunn M., et al. "Re-adapting T cells for cancer therapy: from mouse models to clinical trials." Immunological Reviews 257.1 (2014): 145-164.
Fesnak, Andrew D., Carl H. June, and Bruce L. Levine. "Engineered T cells: the promise and challenges of cancer immunotherapy." Nature Reviews Cancer 16.9 (2016): 566-581.
Baulu, Estelle, et al. "TCR-engineered T cell therapy in solid tumors: State of the art and perspectives." Science Advances 9.7 (2023): eadf3700, 16 pages.
Shafer, Paul, Lauren M. Kelly, and Valentina Hoyos. "Cancer therapy with TCR-engineered T cells: current strategies, challenges, and prospects." Frontiers in Immunology 13 (2022): 835762, 24 pages.

* cited by examiner

C

FIG. 1A, FIG. 1B, and FIG. 1C

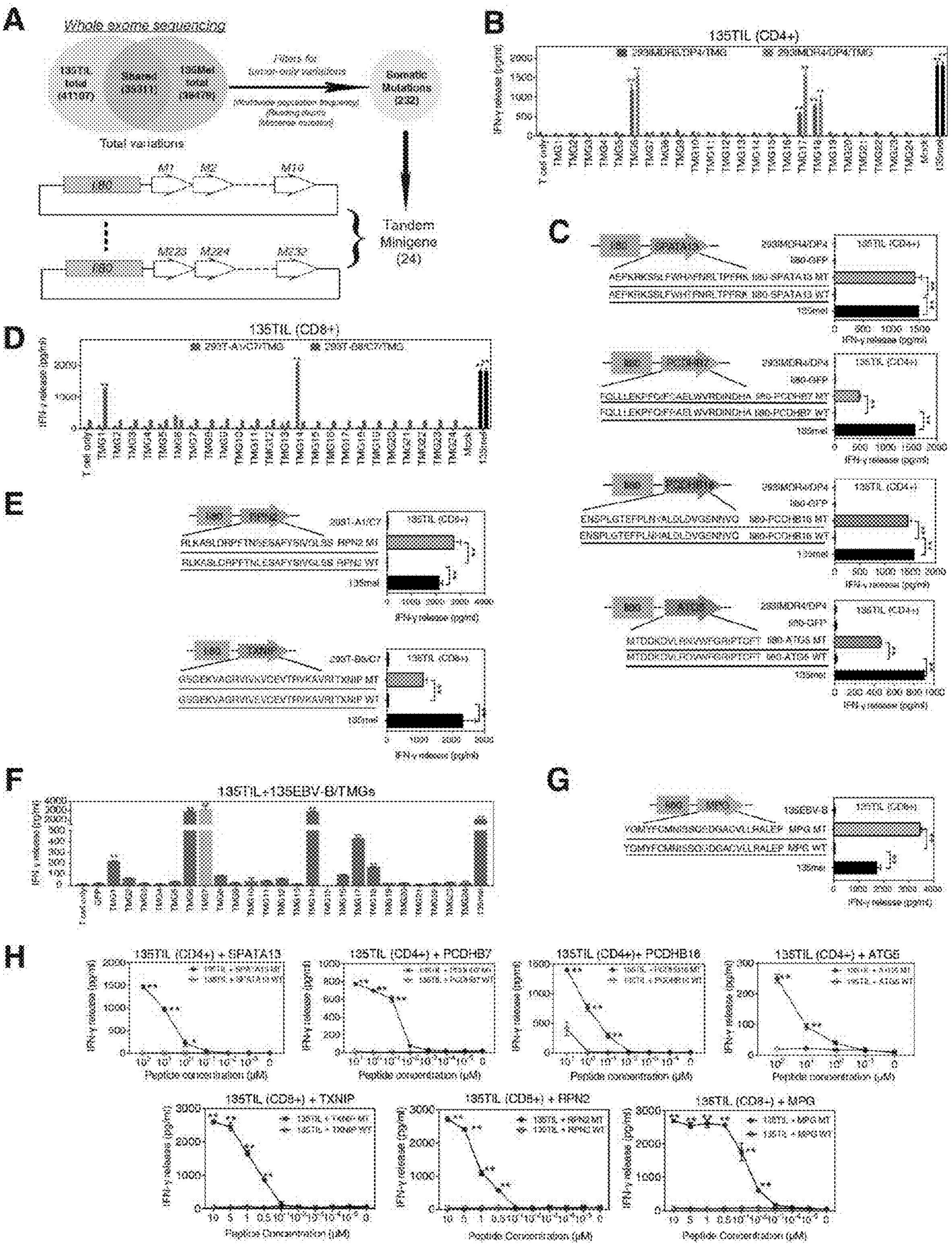
FIG. 3A, FIG. 3B, FIG. 3C, FIG. 3D, FIG. 3E, FIG. 3F, FIG. 3G, and FIG. 3H

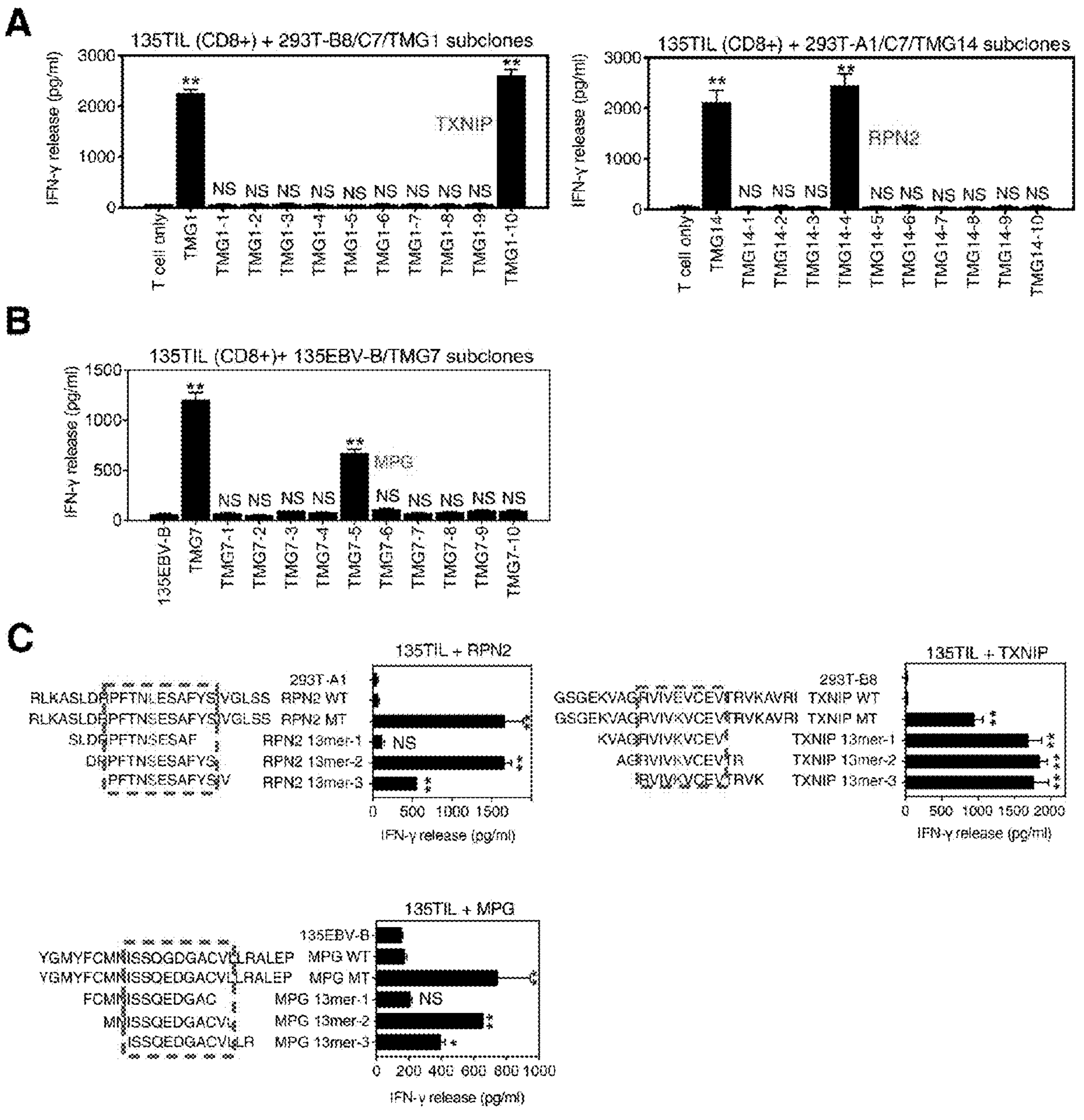
FIG. 5A, FIG. 5B, and FIG. 5C

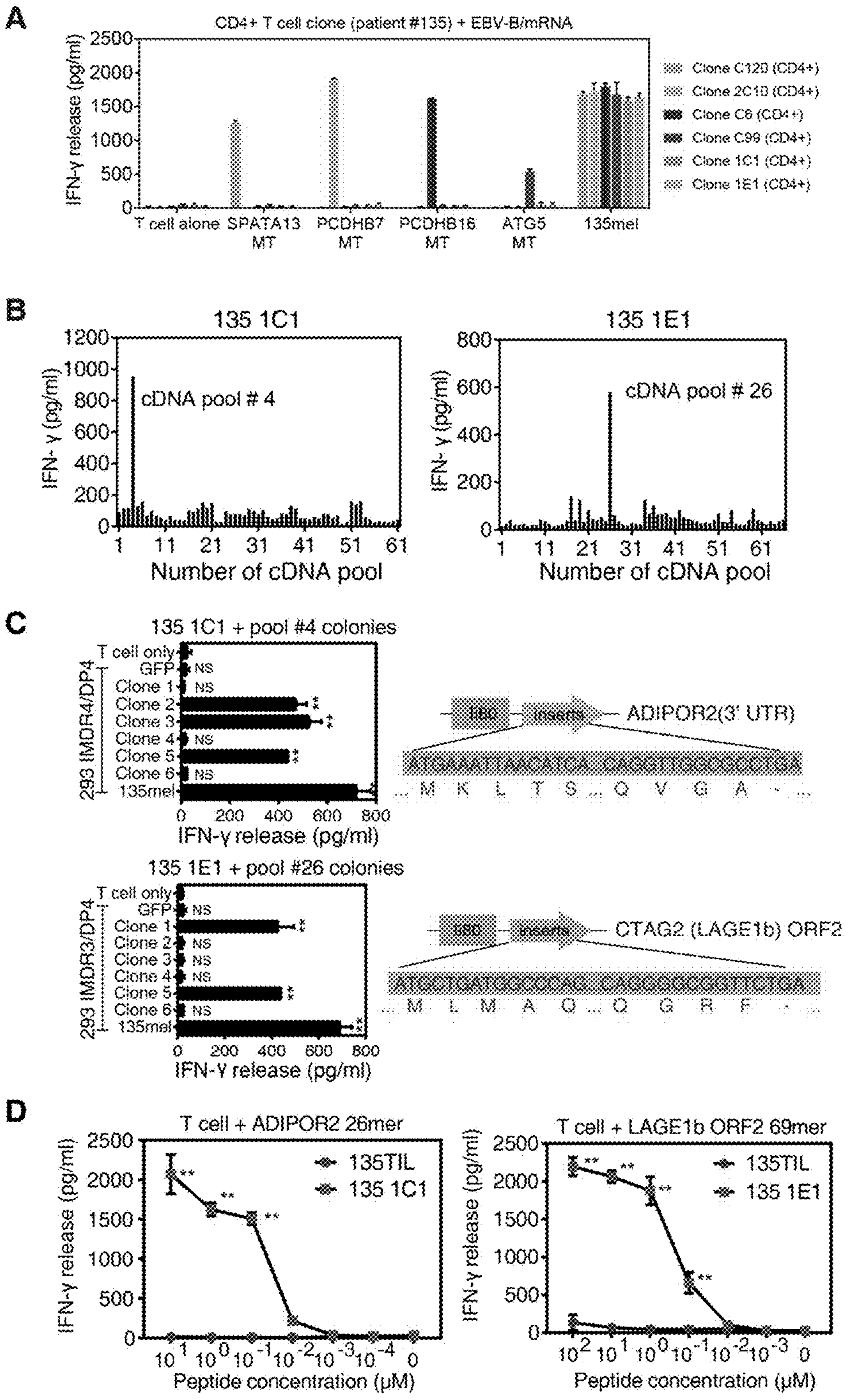
FIG. 6A, FIG. 6B, FIG. 6C, and FIG. 6D

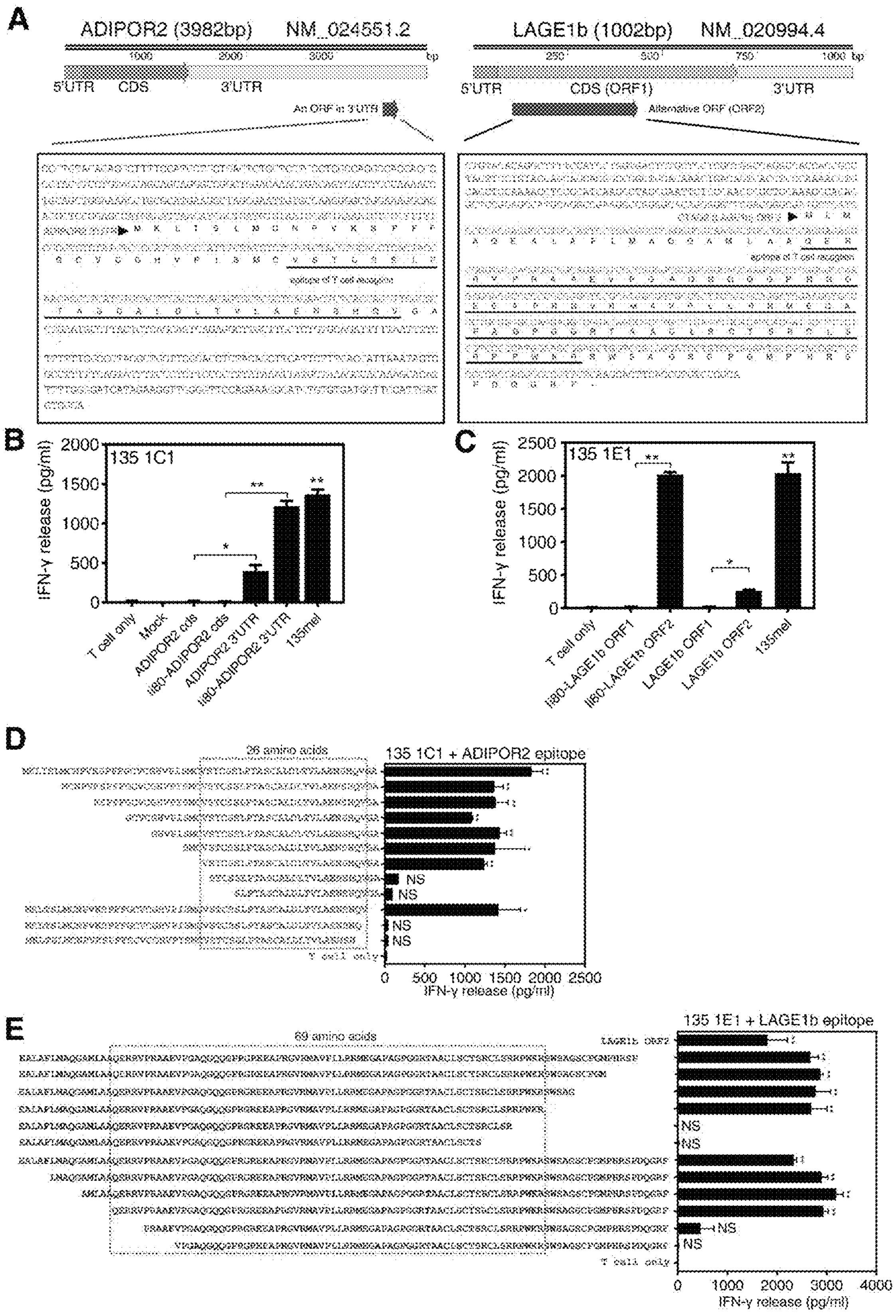
FIG. 7A, FIG. 7B, FIG. 7C, FIG. 7D, and FIG. 7E

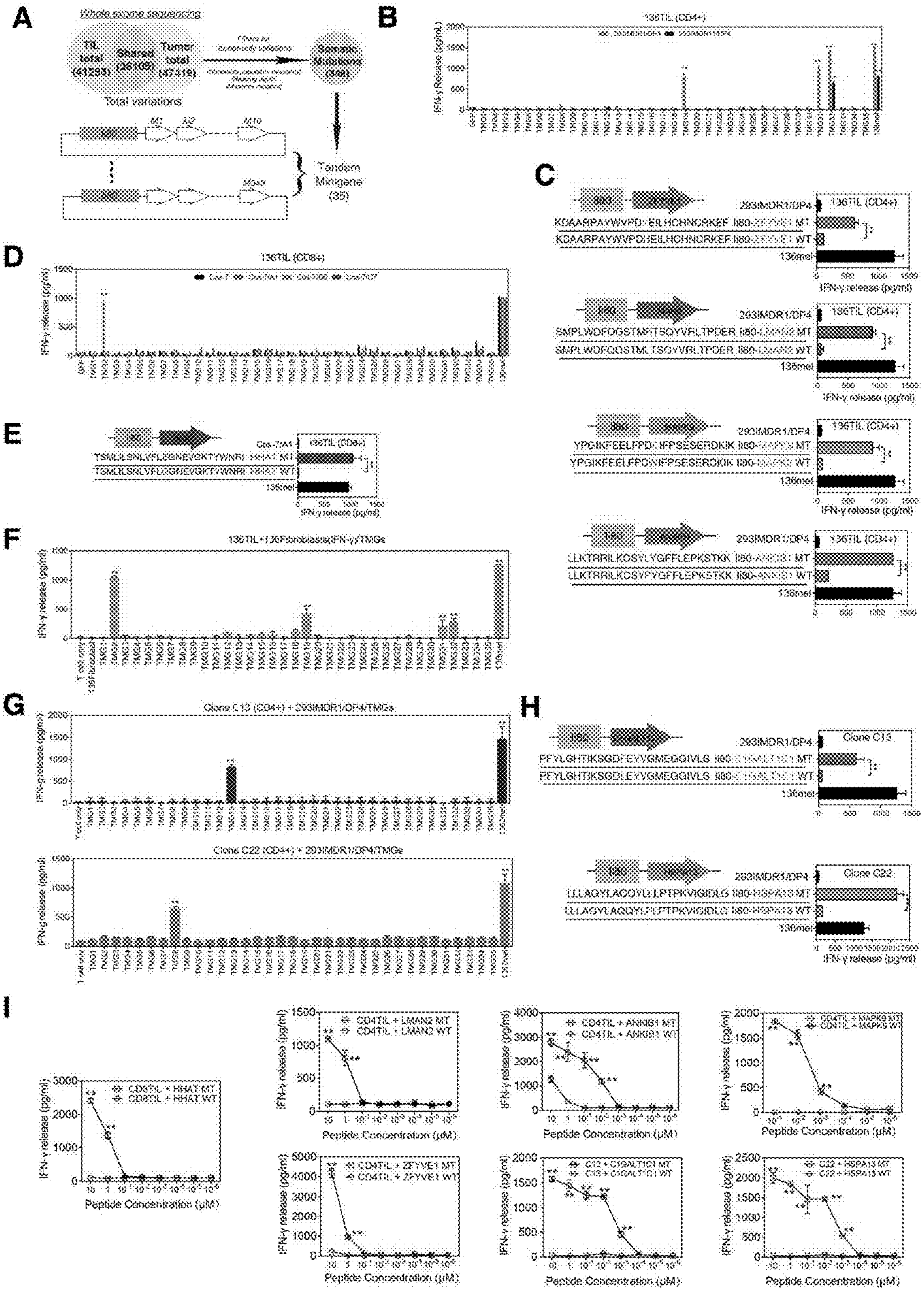
FIG. 8A, FIG. 8B, FIG. 8C, FIG. 8D, FIG. 8E, FIG. 8F, FIG. 8G, FIG. 8H, and FIG. 8I

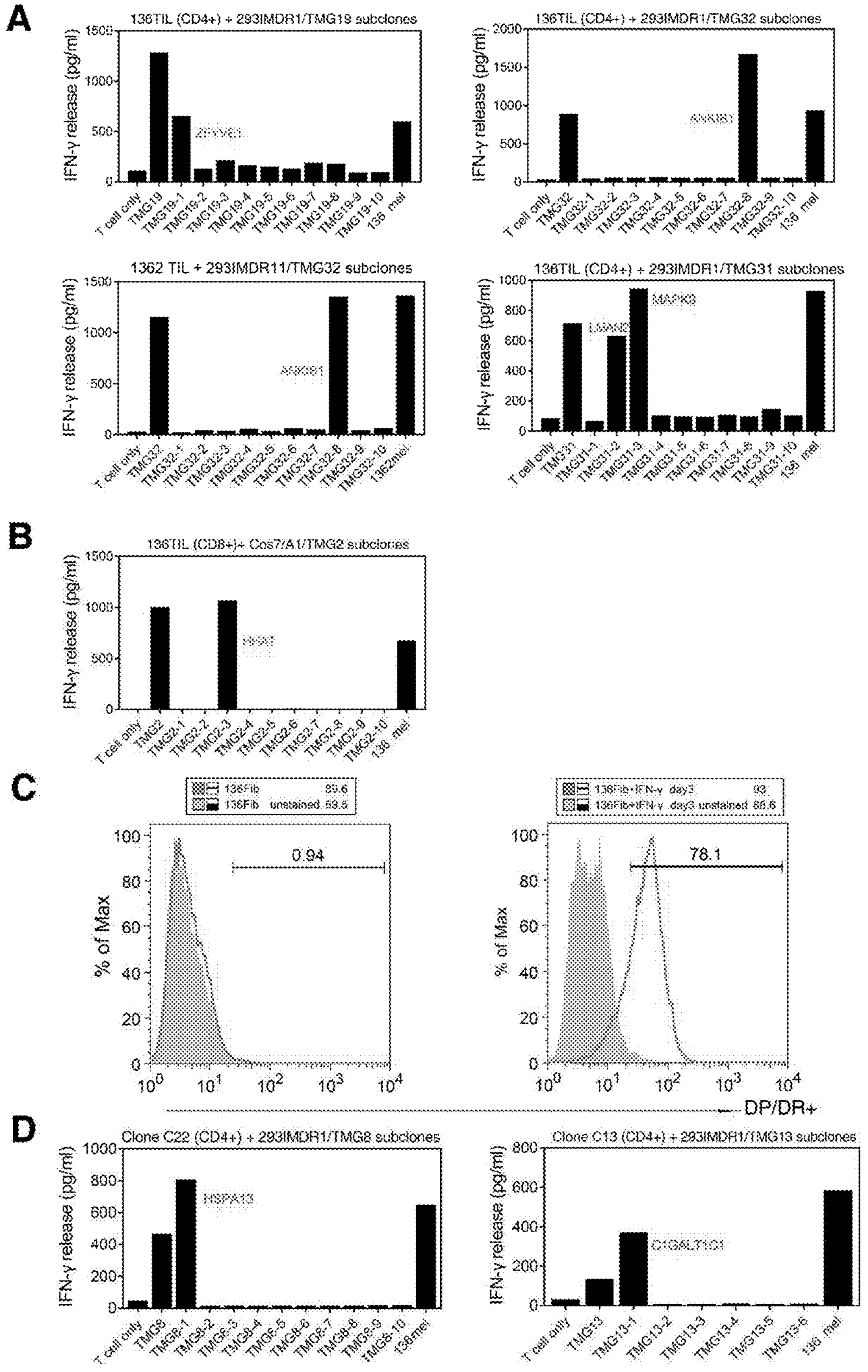
FIG. 9A, FIG. 9B, FIG. 9C, and FIG. 9D

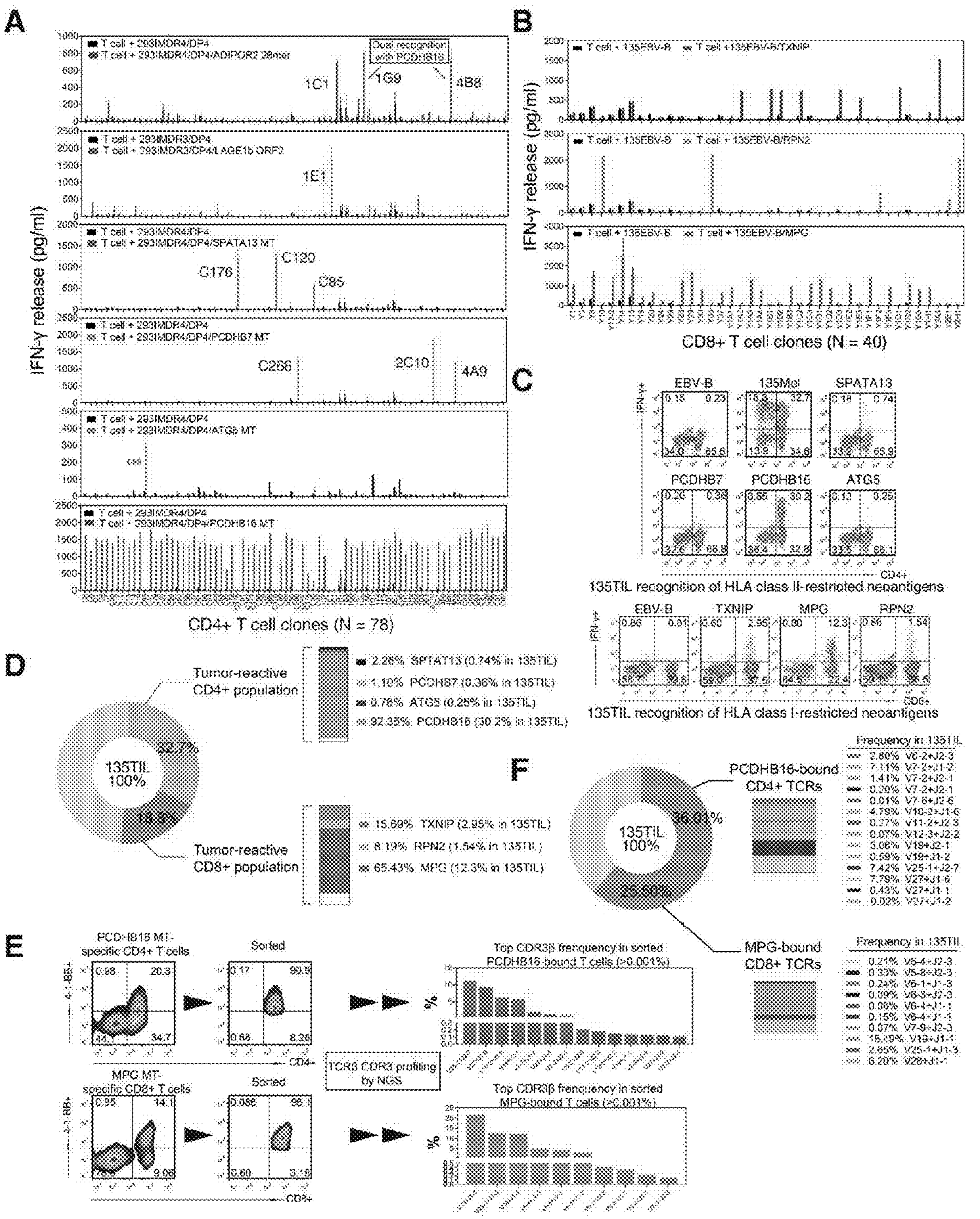
FIG. 10A, FIG. 10B, FIG. 10C, FIG. 10D, FIG. 10E, and FIG. 10F

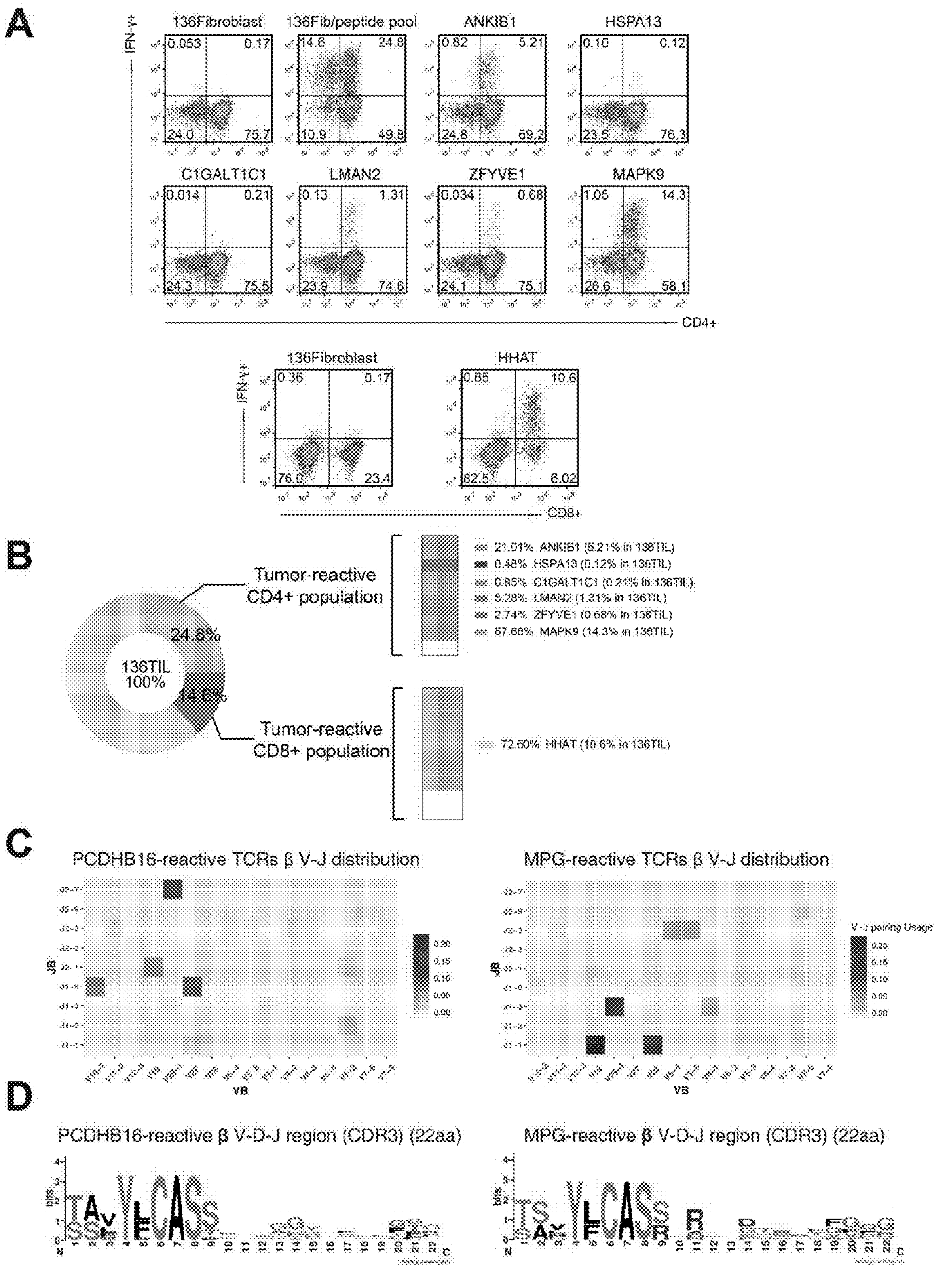
FIG. 11A, FIG. 11B, FIG. 11C, and FIG. 11D

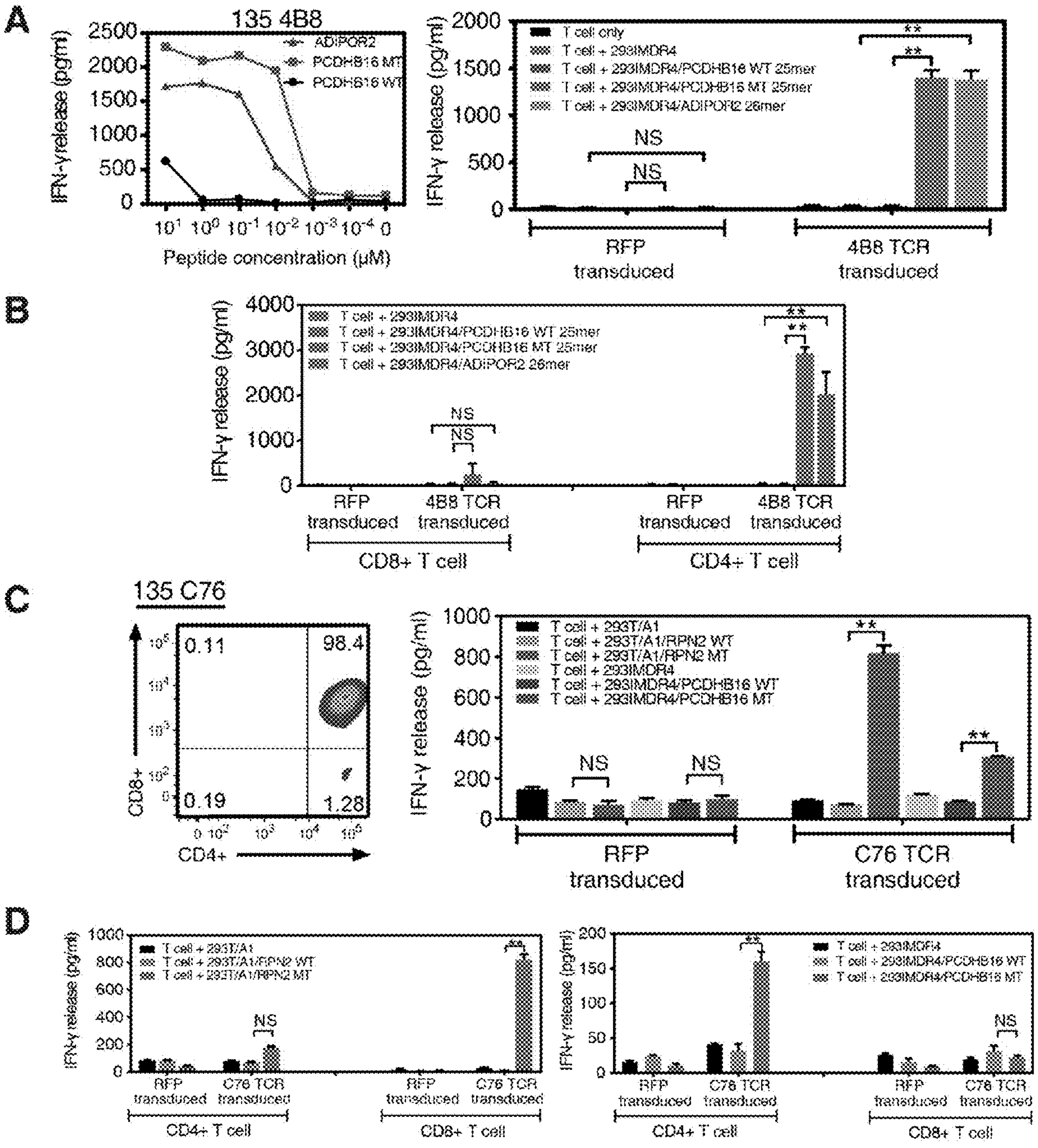
FIG. 13A, FIG. 13B, FIG. 13C, and FIG. 13D

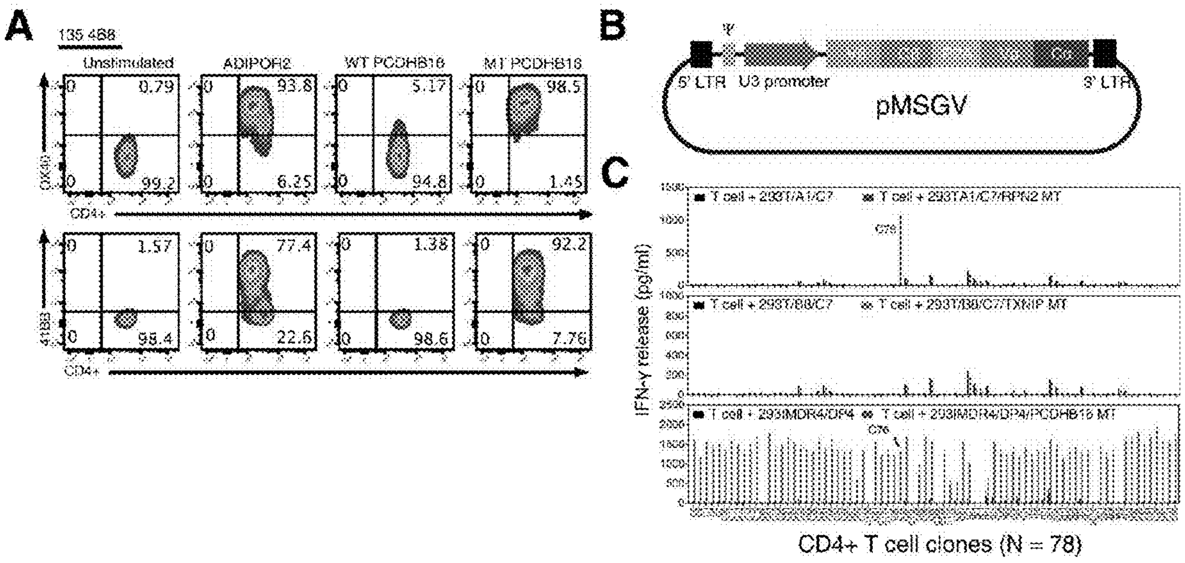
FIG. 14A, FIG. 14B, and FIG. 14C

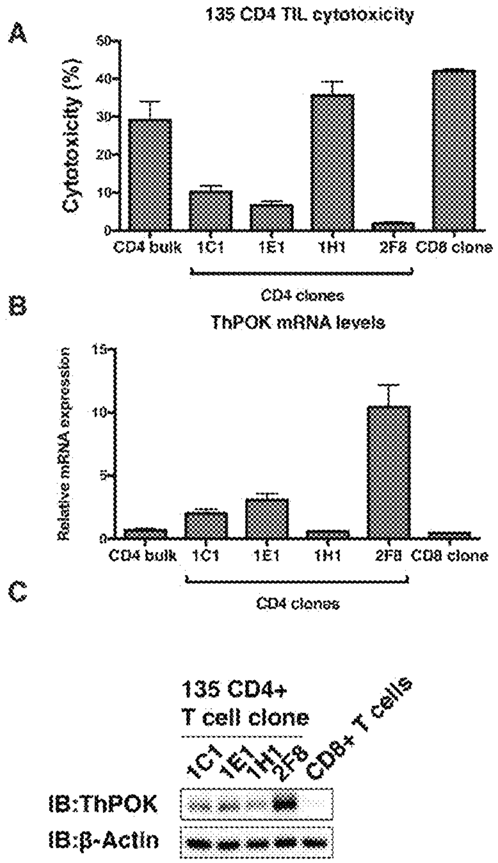
FIG. 15A, FIG. 15B, and FIG. 15C

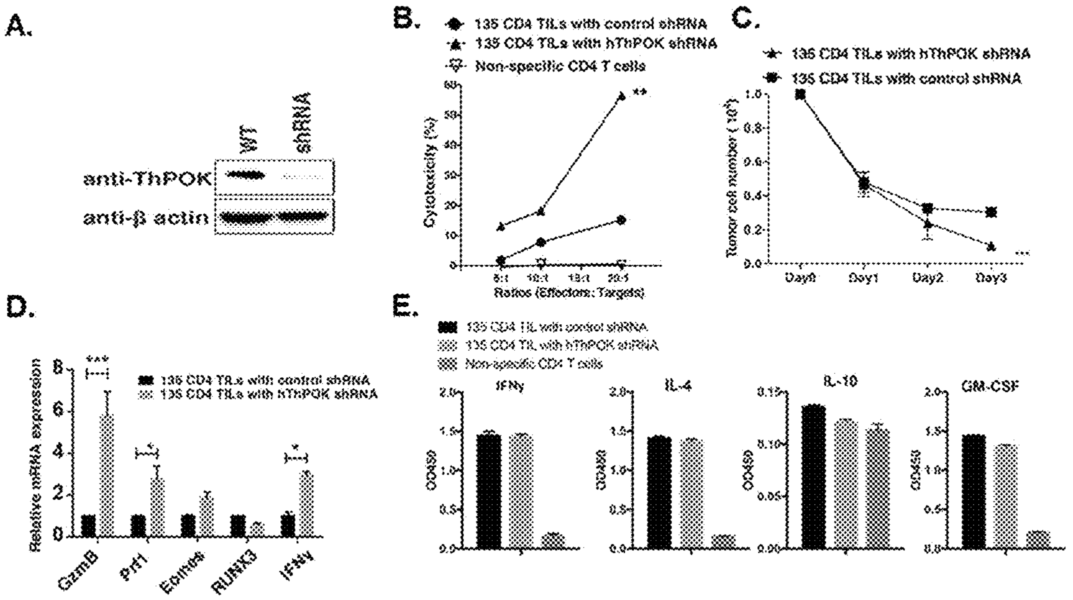
FIG. 16A, FIG. 16B, FIG. 16C, FIG. 16D, and FIG. 16E

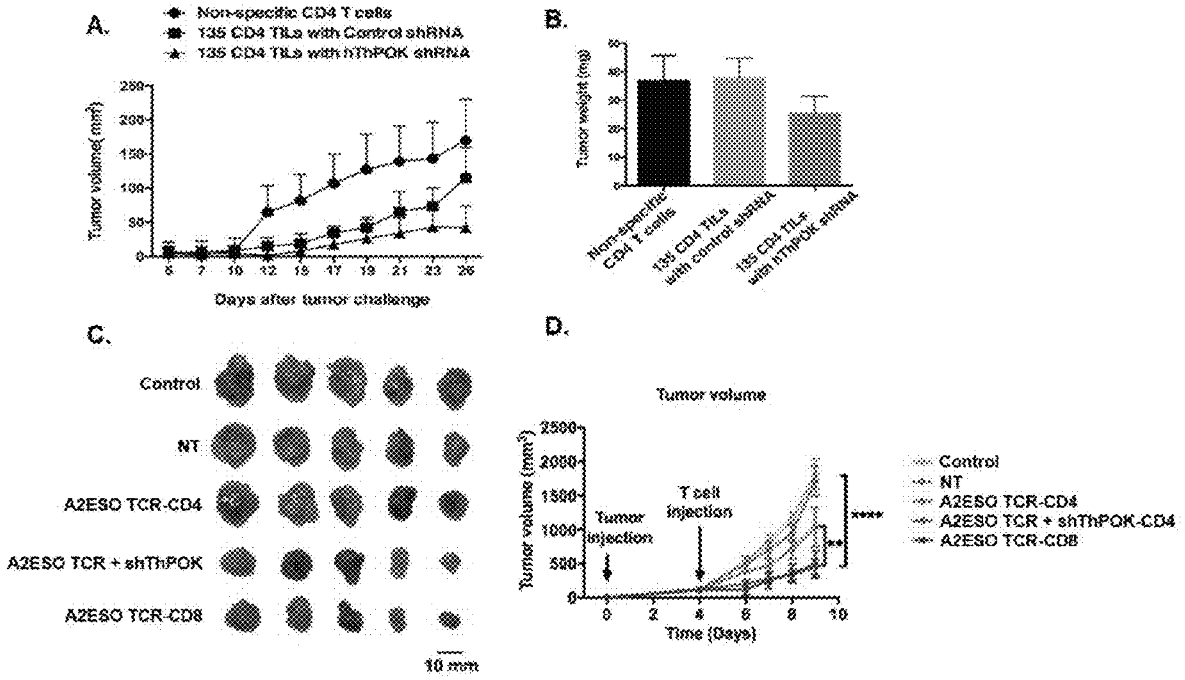
FIG. 17A, FIG. 17B, FIG. 17C, and FIG. 17D

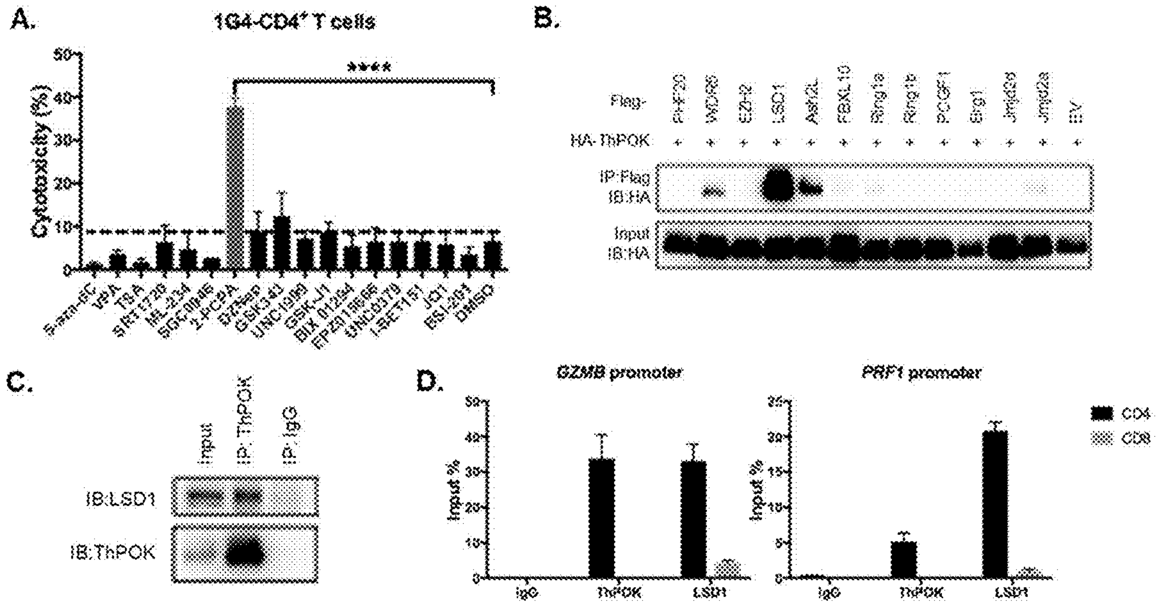
FIG. 18A, FIG. 18B, FIG. 18C, and FIG. 18D

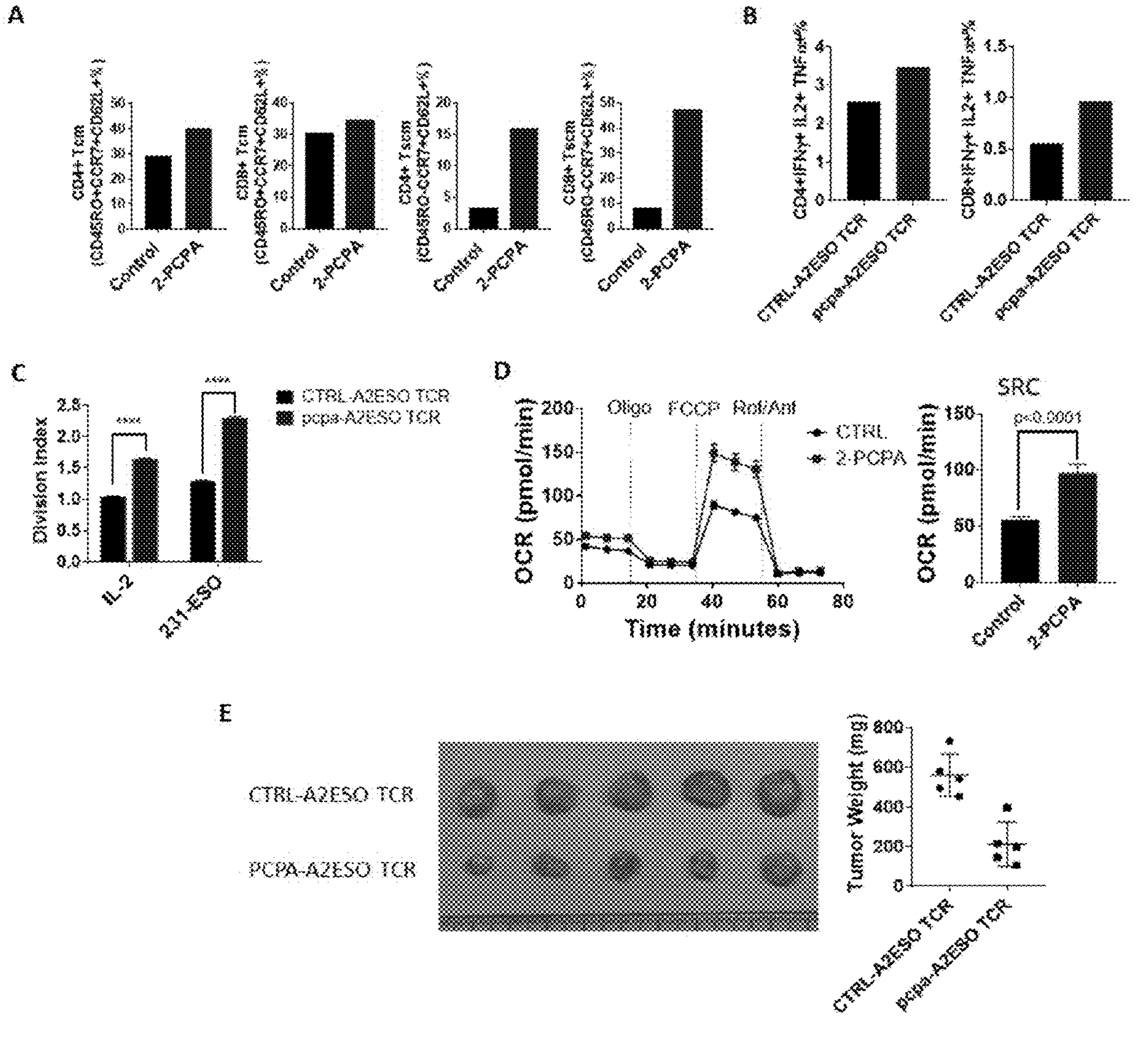
FIG. 20A, FIG. 20B, FIG. 20C, FIG. 20D, and FIG. 20E

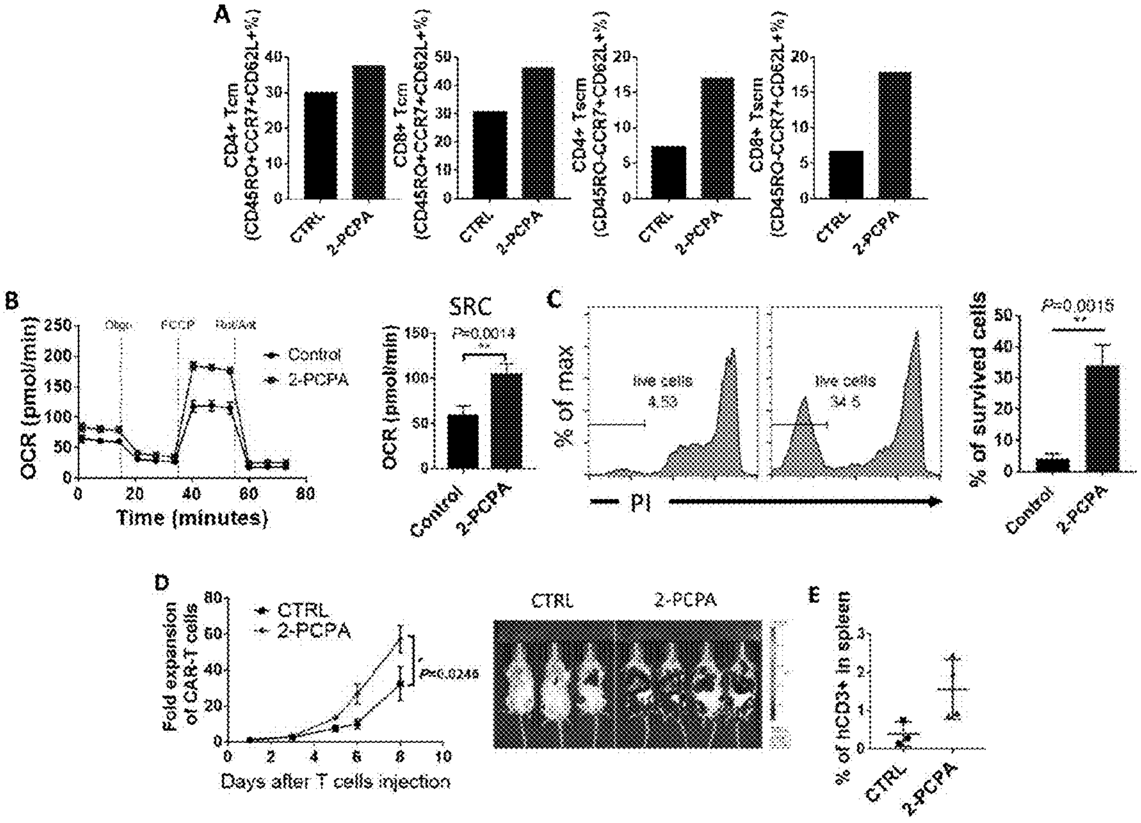
FIG. 21A, FIG. 21B, FIG. 21C, FIG. 21D, and FIG. 21E

CANCER NEOANTIGENS AND THEIR UTILITIES IN CANCER VACCINES AND TCR-BASED CANCER IMMUNOTHERAPY

This application claims the benefit of U.S. Provisional Application No. 62/662,495, filed on Apr. 25, 2018, and PCT/US2019/029107, filed on Apr. 25, 2019, both of which are incorporated herein by reference in their entirety.

I. BACKGROUND

Cancer immunotherapy through checkpoint blockade and T cell-based approaches has produced impressive and durable clinical benefits for cancer patients. Increasing evidence indicates that tumor regression induced by checkpoint blockade therapy relies on the recognition of mutation-derived neoantigens expressed by cancer cells. Mutational landscape of cancer patients is the strong prediction biomarker for checkpoint blockade therapy. Despite the larger numbers (several hundreds) of somatic mutations can be identified from each cancer tissue to serve as neoantigens, only a few (1-3 immunogenic epitopes per cancer patient) have been identified for T cell recognition. What are needed are new methods for identifying neoantigens and methods and compositions for using neoantigens identified by said methods.

II. SUMMARY

Disclosed are methods and compositions related to identifying novel neoantigens, and methods of using said neoantigens in the treatment of cancer.

In one aspect, disclosed herein are methods of identifying neoantigens from a cancer in a human subject comprising a) performing whole exome sequencing on a nucleic acid sample from a cancer cell; b) mapping the sequence to a reference genome sequence (such as, for example a human genome); c) filtering sequence variations to remove common variations in tumors and normal cells; d) creating one or more single mutation peptide constructs comprising at least one uncommon amino acid variation and one or more flanking amino acids; e) synthesizing one or more minigenes encoding one or more single mutation peptide constructs of step d; f) transfecting one or more minigenes into one or more cells or cell lines expressing MHC class I or MHC class II molecules; g) co-culturing one or more T cells or T cells lines with the transfected cells of step f); h) measuring T cell activity of the co-cultured T cells or T cell lines; i) and assaying single mutation peptides from each minigene in transfected cell lines that induced T cell activity for the ability to induce T cell activity alone.

In one aspect, also disclosed herein are methods of identifying neoantigens of any preceding aspect, further comprising mapping the mutation to a specific peptide epitope and/or further comprising assaying the HLA restriction of the peptide epitope.

Also disclosed herein are methods of identifying neoantigens of any preceding aspect, wherein the single mutation constructs comprise at least 1, 2, 3, 4, 5, 6, 7, 8, 9, 10, 11, 12, 13, 14, 15, 16, 17, 18, 19, 20, 21, 22, 23, 24, or 25 amino acids on either side of the mutation.

Also disclosed herein are methods of identifying neoantigens of any preceding aspect, wherein the minigene comprises at least 1, 2, 3, 4, 5, 6, 7, 8, 9, 10, 11, 12, 13, 14, 15, 16, 17, 18, 19, 20, 21, 22, 23, 24, or 25 single mutation constructs.

In one aspect, also disclosed herein are methods of identifying neoantigens of any preceding aspect, wherein the one or more cell or cell lines (such as, for example HEK293 cells, HEK293T cells, Cos-7, MA104 cells, CHO cells, Fibroblasts, B cells, VERO cells, Madin-Darby Canine Kidney (MDCK) cells, HEp-2 cells, HeLa cells, MRC-5 cells, WI-38 cells, EB66, or PER C6 cells) expressing MHC class I or class II molecules, are engineered to express an MHC molecule.

Also disclosed herein are methods of identifying neoantigens of any preceding aspect, wherein the T cell activity (such as, for example, release of cytokines including, but not limited to IFN-γ, TGF-β, lymphotoxin-α, IL-2, IL-4, IL-10, IL-17, or IL-25) is measured by ELISA, ELISpot, Intracellular cytokine staining, or Chromium Release.

In one aspect, also disclosed herein are methods of identifying neoantigens of any preceding aspect, wherein the cancer is selected from the group consisting of B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, lung cancers, small cell lung cancer, non-small cell lung cancer, neuroblastoma, glioblastoma, ovarian cancer, pancreatic cancer, prostate cancer, skin cancers, melanoma, basal cell carcinoma, squamous cell carcinoma, liver cancer, squamous cell carcinomas of the mouth, throat, larynx, and lung, cervical cancer, cervical carcinoma, breast cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, AIDS-related lymphomas, or AIDS-related sarcomas.

In one aspect, also disclosed herein are neoantigens (including, but not limited to peptides, polypeptides, and proteins of the neoantigens) identified by the methods of identifying neoantigens of any preceding aspect. For example, disclosed herein are a peptides, polypeptides, or proteins comprising the amino acid sequence AEPKRKSSLFWHAFNRLTPFRK (SEQ ID NO: 2) or a fragment thereof comprising at least 9 amino acids, wherein any fragment of the peptide, polypeptide, or proteinat least comprises the sequence LFWHAFNRL (SEQ ID NO: 7) (for example, SSLFWHAFNRLTP (SEQ ID NO: 4), RKSSLFWHAFNRL (SEQ ID NO: 3), RKSSLFWHAFNRLTPFR (SEQ ID NO: 6), and LFWHAFNRLTPFR (SEQ ID NO: 5); a polypeptide comprising the amino acid sequence FQLLLEKPFQIFCAELWVRDINDHA (SEQ ID NO: 9) or a fragment thereof comprising at least 13 amino acids, wherein any fragment of the polypeptide at least comprises the sequence LEKPFQIFCAELW (SEQ ID NO: 12); a polypeptide comprising the amino acid sequence ENSPLGTEFPLNYALDLDVGSNNVQ (SEQ ID NO: 14) or a fragment thereof comprising at least 13 amino acids, wherein any fragment of the polypeptide at least comprises the sequence LGTEFPLNYALDL (SEQ ID NO: 17); a polypeptide comprising the amino acid sequence MTDDKDVLRNVWFGRIPTCFT (SEQ ID NO: 19) or a fragment thereof comprising at least 11 amino acids, wherein any fragment of the polypeptide at least comprises the sequence KDVLRNVWFGR (SEQ ID NO: 23) (for example, DDKDVLRNVWFGR (SEQ ID NO: 22), KDVLRNVWFGRIP (SEQ ID NO: 21), and DDKDVLRNVWFGRIP (SEQ ID NO: 24)); a polypeptide comprising the amino acid sequence RLKASLDRPFTNSESAFYSIVGLSS (SEQ ID NO: 26) or a fragment thereof comprising at least 11 amino acids, wherein any fragment of the polypeptide at least comprises the sequence RPFTNSESAFY (SEQ ID NO: 30) (for example, DRPFTNSESAFYS (SEQ ID NO: 28)); a polypeptide comprising the amino acid sequence GSGEKVAGRVIVKVCEVTRVKAVRI (SEQ ID NO: 32) or a fragment thereof comprising at least 9 amino acids, wherein any fragment of the polypeptide at least comprises the sequence RVIVKVCEV (SEQ ID NO: 36) (for example, KVAGRVIVKVCEV (SEQ ID NO: 33), AGRVIVKVCEVTR (SEQ ID NO: 34), KVAGRVIVKVCEVTRVK (SEQ ID NO: 32), and RVIVKVCEVTRVK (SEQ ID NO: 35)); a polypeptide comprising the amino acid sequence YGMYFCMNISSQEDGACVLLRALEP (SEQ ID NO: 39) or a fragment thereof comprising at least 10 amino acids, wherein any fragment of the polypeptide at least comprises the sequence ISSQEDGACV (SEQ ID NO: 43)(for example, MNISSQEDGACVL (SEQ ID NO: 41), ISSQEDGACVLLR (SEQ ID NO: 42), MNISSQEDGACVLLR (SEQ ID NO: 44), ISSQEDGACVL (SEQ ID NO: 132), ISSQEDGACVLL (SEQ ID NO: 133), NISSQEDGACV (SEQ ID NO: 134), NISSQEDGACVL (SEQ ID NO: 135), NISSQEDGACVLL, (SEQ ID NO: 136), NISSQEDGACVLLR (SEQ ID NO: 137), and MNISSQEDGACVLL (SEQ ID NO: 138)); a polypeptide comprising the amino acid sequence MKLTSLMCNPVKSPFFGCVCGHVPISMCVSTCSSLPTASCALDLTVLAENSHQVGA (SEQ ID NO: 46) or a fragment thereof comprising at least 26 amino acids, wherein any fragment of the polypeptide at least comprises the sequence VSTCSSLPTASCALDLTVLAENSHQV (SEQ ID NO: 60) (for example, MCNPVKSPFFGCVCGHVPISMCVSTCSSLPTASCALDLTVLAENSHQVGA (SEQ ID NO: 49), KSPFFGCVCGHVPISMCVSTCSSLPTASCALDLTVLAENSHQVGA (SEQ ID NO: 50), GCVCGHVPISMCVSTCSSLPTASCALDLTVLAENSHQVGA (SEQ ID NO: 51), GHVPISMCVSTCSSLPTASCALDLTVLAENSHQVGA (SEQ ID NO: 52), SMCVSTCSSLPTASCALDLTVLAENSHQVGA (SEQ ID NO: 53), VSTCSSLPTASCALDLTVLAENSHQVGA (SEQ ID NO: 54), MCNPVKSPFFGCVCGHVPISMCVSTCSSLPTASCALDLTVLAENSHQV (SEQ ID NO: 57), VSTCSSLPTASCALDLTVLAENSHQVG (SEQ ID NO: 139), CVSTCSSLPTASCALDLTVLAENSHQV (SEQ ID NO: 140), MCVSTCSSLPTASCALDLTVLAENSHQV (SEQ ID NO: 141), MCVSTCSSLPTASCALDLTVLAENSHQVG (SEQ ID NO: 142), SMCVSTCSSLPTASCALDLTVLAENSHQV (SEQ ID NO: 143), and SMCVSTCSSLPTASCALDLTVLAENSHQVG (SEQ ID NO: 144)); and/or a polypeptide comprising the amino acid sequence MLMAQEALAFLMAQGAMLAAQERRVPRAAEVPGAQGQQGPRGREEAPRGVRMAVPLLRR MEGAPAGPGGRTAACLSCTSRCLSRRPWKRSWSAGSCPGMPHRSPDQGRF (SEQ ID NO: 67) or a fragment thereof comprising at least 61 amino acids, wherein any fragment of the polypeptide at least comprises the sequence VPRAAEVPGAQGQQGPRGREEAPRGVRMAVPLLRRMEGAPAGPGGRTAACLSCTSRCLSRR (SEQ ID NO: 73) (for example, QERRVPRAAEVPGAQGQQGPRGREEAPRGVRMAVPLLRRMEGAPAGPGGRTAACLSCTSRC LSRRPWKR (SEQ ID NO: 74), RVPRAAEVPGAQGQQGPRGREEAPRGVRMAVPLLRRMEGAPAGPGGRTAACLSCTSRCLSR R (SEQ ID NO: 145), RRVPRAAEVPGAQGQQGPRGREEAPRGVRMAVPLLRRMEGAPAGPGGRTAACLSCTSRCLS RR (SEQ ID NO: 146), ERRVPRAAEVPGAQGQQGPRGREEAPRGVRMAVPLLRRMEGAPAGPGGRTAACLSCTSRCL SRR (SEQ ID NO: 147), QERRVPRAAEVPGAQGQQGPRGREEAPRGVRMAVPLLRRMEGAPAGP GGRTAACLSCTSRC LSRR (SEQ ID NO: 148), RVPRAAEVPGAQGQQGPRGREEAPRGVRMAVPLLRRMEGAPAGPGGRTAACLSCTSRCLSR RP (SEQ ID NO: 149), RRVPRAAEVPGAQGQQGPRGREEAPRGVRMAVPLLRRMEGAPAGPGGRTAACLSCTSRCLS RRP (SEQ ID NO: 150), ERRVPRAAEVPGAQGQQGPRGREEAPRGVRMAVPLLRRMEGAPAGP GGRTAACLSCTSRCL SRRP (SEQ ID NO: 151), QERRVPRAAEVPGAQGQQGPRGREEAPRGVRMAVPLLRRMEGAPAGPGGRTAACLSCTSRC LSRRP (SEQ ID NO: 152), RVPRAAEVPGAQGQQGPRGREEAPRGVRMAVPLLRRMEGAPAGPGGRTAACLSCTSRCLSR RPW (SEQ ID NO: 153), RRVPRAAEVPGAQGQQGPRGREEAPRGVRMAVPLLRRMEGAPAGPGGRTAACLSCTSRCLS RRPW (SEQ ID NO: 154), ERRVPRAAEVPGAQGQQGPRGREEAPRGVRMAVPLLRRMEGAPAGPGGRTAACLSCTSRCL SRRPW (SEQ ID NO: 155), QERRVPRAAEVPGAQGQQGPRGREEAPRGVRMAVPLLRRMEGAPAGPGGRTAACLSCTSRC LSRRPW (SEQ ID NO: 156), RVPRAAEVPGAQGQQGPRGREEAPRGVRMAVPLLRRMEGAPAGPGGRTAACLSCTSRCLSR RPWK (SEQ ID NO: 157), RRVPRAAEVPGAQGQQGPRGREEAPRGVRMAVPLLRRMEGAPAGPGGRTAACLSCTSRCLS RRPWK (SEQ ID NO: 158), ERRVPRAAEVPGAQGQQGPRGREEAPRGVRMAVPLLRRMEGAPAGPGGRTAACLSCTSRCL SRRPWK (SEQ ID NO: 159), QERRVPRAAEVPGAQGQQGPRGREEAPRGVRMAVPLLRRMEGAPAGPGGRTAACLSCTSRC LSRRPWK (SEQ ID NO: 160), RVPRAAEVPGAQGQQGPRGREEAPRGVRMAVPLLRRMEGAPAGPGGRTAACLSCTSRCLSR RPWKR (SEQ ID NO: 161), RRVPRAAEVPGAQGQQGPRGREEAPRGVRMAVPLLRRMEGAPAGPGGRTAACLSCTSRCLS RRPWKR (SEQ ID NO: 162), ERRVPRAAEVPGAQGQQGPRGREEAPRGVRMAVPLLRRMEGAPAGPGGRTAACLSCTSRCL SRRPWKR (SEQ ID NO: 163), EALAFLMAQGAMLAAQERRVPRAAEVPGAQGQQGPRGREEAPRGVRMAVPLLRRMEGAPA GPGGRTAACLSCTSRCLSRRPWKRSWSAGSCPGMPHRSP (SEQ ID NO: 61), EALAFLMAQGAMLAAQERRVPRAAEVPGAQGQQGPRGREEAPRGVRMAVPLLRRMEGAPA GPGGRTAACLSCTSRCLSRRPWKRSWSAGSCPGM (SEQ ID NO: 62), EALAFLMAQGAMLAAQERRVPRAAEVPGAQGQQGPRGREEAPRGVRMAVPLLRRMEGAPA GPGGRTAACLSCTSRCLSRRPWKRSWSAG (SEQ ID NO: 63), EALAFLMAQGAMLAAQERRVPRAAEVPGAQGQQGPRGREEAPRGVRMAVPLLRRMEGAPA GPGGRTAACLSCTSRCLSRRPWKR (SEQ ID NO: 64), LMAQGAMLAAQERRVPRAAEVPGAQGQQGPRGREEAPRGVRMAVPLLRRMEGAPAGPGG RTAACLSCTSRCLSRRPWKRSWSAGSCPGMPHRSPDQGRF (SEQ ID NO: 68), AMLAAQERRVPRAAEVPGAQGQQGPRGREEAPRGVRMAVPLLRRMEGAPAGPGGRTAACL SCTSRCLSRRPWKRSWSAGSCPGMPHRSPDQGRF (SEQ ID NO: 69), and QERRVPRAAEVPGAQGQQGPRGREEAPRGVRMAVPLLRRMEGAPAGPGGRTAACLSCTSRC LSRRPWKRSWSAGSCPGMPHRSPDQGRF (SEQ ID NO: 70)). Also disclosed herein are variants of any polypeptide or polypeptide fragment disclosed herein wherein the variant comprises a conservative amino acid substitution.

In one aspect, also disclosed herein are nucleic acids encoding a polypeptide neoantigen of any preceding aspect.

Also disclosed herein are compositions comprising a therapeutically effective amount of one or more of the neoantigens of any preceding aspect (including, but not limited to peptides, polypeptides, and proteins of the neoantigens) or one or more minigene mRNAs encoding one or more neoantigens of any preceding aspect.

Also disclosed herein are compositions comprising a therapeutically effective amount of one or more chimeric antigen receptor (CAR) T cells, T cell receptor (TCR) T-cells, and/or tumor infiltrating lymphocytes (TILs); wherein the CAR T cell, TCR T cell, and/or TIL has been engineered to express a receptor (such as, for example, a T cell receptor or chimeric antigen receptor) that recognizes one or more of the neoantigens of any preceding aspect (including, but not limited to peptides, polypeptides, and proteins of the neoantigens). In one aspect, the TCR T cell, CAR T cell, or TIL specific for one or more of the neoantigens of any preceding aspect is further engineered to knockout or knockdown Zinc finger and BTB domain-containing protein 7B (ThPOK), Lysine-specific histone demethylase 1 (LSD1), programmed cell death protein (PD1), Proteine phosphatase 2 (PP2A) to enhance their function such as cytotoxic activity and persistence or survival in vivo after adoptive transfer to a cancer patient. In one aspect, the TCR T cell, CAR T cell, or TIL specific for one or more of the neoantigens of any preceding aspect is treated with a small molecular inhibitor such 2-PAPC to enhance T cell cytotoxic activity or the ability to proliferate and survive in vivo.

In one aspect, also disclosed herein are methods of stimulating an immunological response against a cancer or treating, inhibiting, and/or preventing a cancer comprising administering to a subject a composition comprising a therapeutically effective amount of a neoantigen of any preceding aspect (including, but not limited to peptides, polypeptides, and proteins of the neoantigens) and/or identified by the method of identifying a neoantigen of any preceding aspect.

III. BRIEF DESCRIPTION OF THE DRAWINGS

The patent or application file contains at least one drawing executed in color. Copies of this patent or patent application publication with color drawing(s) will be provided by the Office upon request and payment of the necessary fee. The accompanying drawings, which are incorporated in and constitute a part of this specification, illustrate several embodiments and together with the description illustrate the disclosed compositions and methods.

FIGS. 1A, 1B, and 1C show specificity of tumor-reactive TILs and T-cell clones. FIG. 1A shows tumor-infiltrating lymphocytes (TILs) expanded from cancer tissues of patient #135 and #136 and their composition analyzed by flow cytometry analysis with CD4 or CD8 antibody. Both $CD4^+$ and $CD8^+$ T-cell populations were isolated from the 135TIL or 136TIL lines, and activation of these T-cell populations by 135 mel or 136 mel was determined based on the expression of interferon-γ (upper, patient #135; lower, patient #136). FIG. 1B shows the specificity of 135TIL and 136TIL was determined after incubation with multiple cell lines. FIG. 1C shows the specificity and activation of 14 of 78 $CD4^+$ and 14 of 40 $CD8^+$ T-cell clones of patient #135 were determined by the release of IFN-γ after incubation with 135 mel or EBV-B and other melanoma cell lines. (upper, $CD4^+$; lower, $CD8^+$). Data are presented as representatives of three independent experiments.

Figure 2:
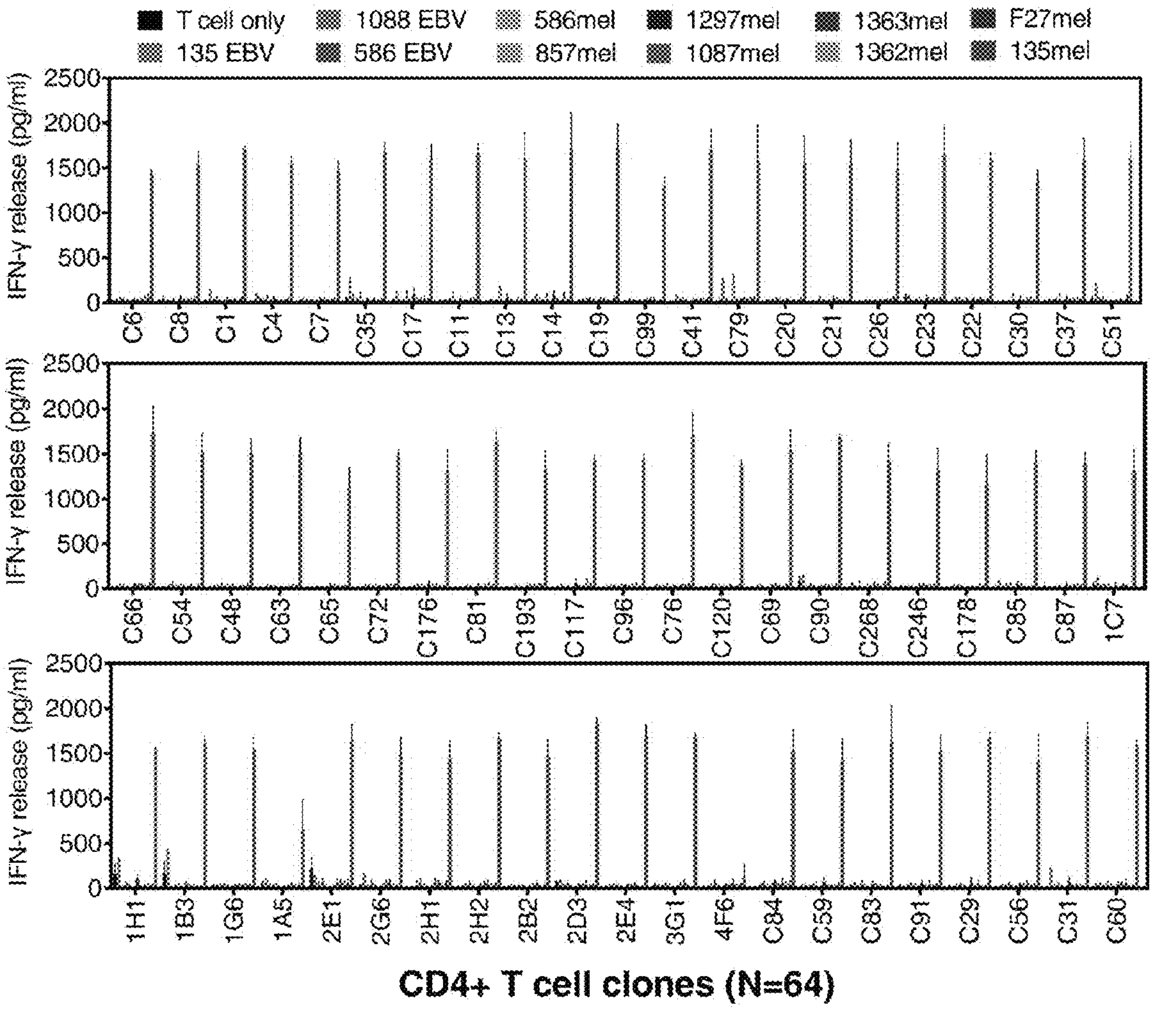

FIG. 2 shows the specificity of other $CD4^+$ tumor-reactive T-cell clones. The activation of 64 (out of 78) $CD4^+$ T-cell clones was determined by the release of IFN-γ after incubation with 135 mel as well as EBV-B and melanoma cell lines of other patients. Data are presented as representatives of three independent experiments.

FIGS. 3A, 3B, 3C, 3D, 3E, 3F, 3G, and 3H show the identification of multiple neoantigens of patient #135 using whole-exome sequencing and tandem minigene screening with T cells. FIG. 3A shows somatic mutations of 135 mel cells were identified by whole-exome sequencing and analyzed by a series of filtering criteria, resulting in 232 somatic mutations and 24 TMG constructs. FIG. 3B shows screening of TMGs presented by MHC-II molecules in artificial APCs with use of 135TILs ($CD4^+$ population). IFN-γ ELISA showed that TMG6, TMG17, TMG18 were strongly recognized by $CD4^+$ TILs respectively. FIG. 3C shows the identification of MHC-II neoantigens in positive TMGs, based on IFN-γ ELISA of four HLA class II neoantigens: SPATA13 (T>A) [TMG6-1] (SEQ ID NO: 1 (WT) and SEQ ID NO: 2 (MT)), PCDHB7 (R>C) [TMG17-6] (SEQ ID NO: 8 (WT) and SEQ ID NO: 9 (MT)), PCDHB16 (H>Y) [TMG17-7] (SEQ ID NO: 13 (WT) and SEQ ID NO: 14 (MT)), and ATG5 (D>N) [TMG18-10] (SEQ ID NO: 18 (WT) and SEQ ID NO: 19 (MT)). The wild type of each neoantigen was not recognized. FIG. 3D shows the screening of TMGs presented by MHC-I molecules in artificial APCs with use of 135TILs ($CD8^+$ population). IFN-γ ELISA showed that TMG1 and TMG14 were strongly recognized by $CD8^+$ TILs respectively. FIG. 3E shows the identification of MHC-I neoantigens in positive TMGs, based on IFN-γ ELISA of two MHC-I neoantigens: RPN2 (L>S) [TMG14-4] (SEQ ID NO: 25 (WT) and SEQ ID NO: 26 (MT)) and TXNIP (E>K) [TMG1-10] (SEQ ID NO: 31 (WT) and SEQ ID NO: 32 (MT)). The wild type of each neoantigen was not recognized. FIG. 3F shows the screening of TMGs presented by 135EBV-B cells with use of 135TILs. Besides positive TMGs identified in (D), TMG7 was also recognized by 135TILs. FIG. 3G shows the identification of one MHC-I neoantigens based on IFN-γ ELISA after 135TILs cocultured with 24 TMGs presented by autologous EBV-B cells: MPG (G>E) [TMG7-5] (SEQ ID NO: 38 (WT) and SEQ ID NO: 39 (MT)). The wild type was not recognized. FIG. 3H shows IFN-γ ELISA of serially diluted peptides of HLA class II and class I neoantigens (mutant and wild type) incubated with 135TIL. Data in B-H are plotted as means±SD of three independent experiments. *$P<0.05$, **$P<0.01$ by comparison with mock controls or WT peptide controls using Student's t-test.

Figures 4A, 4B:
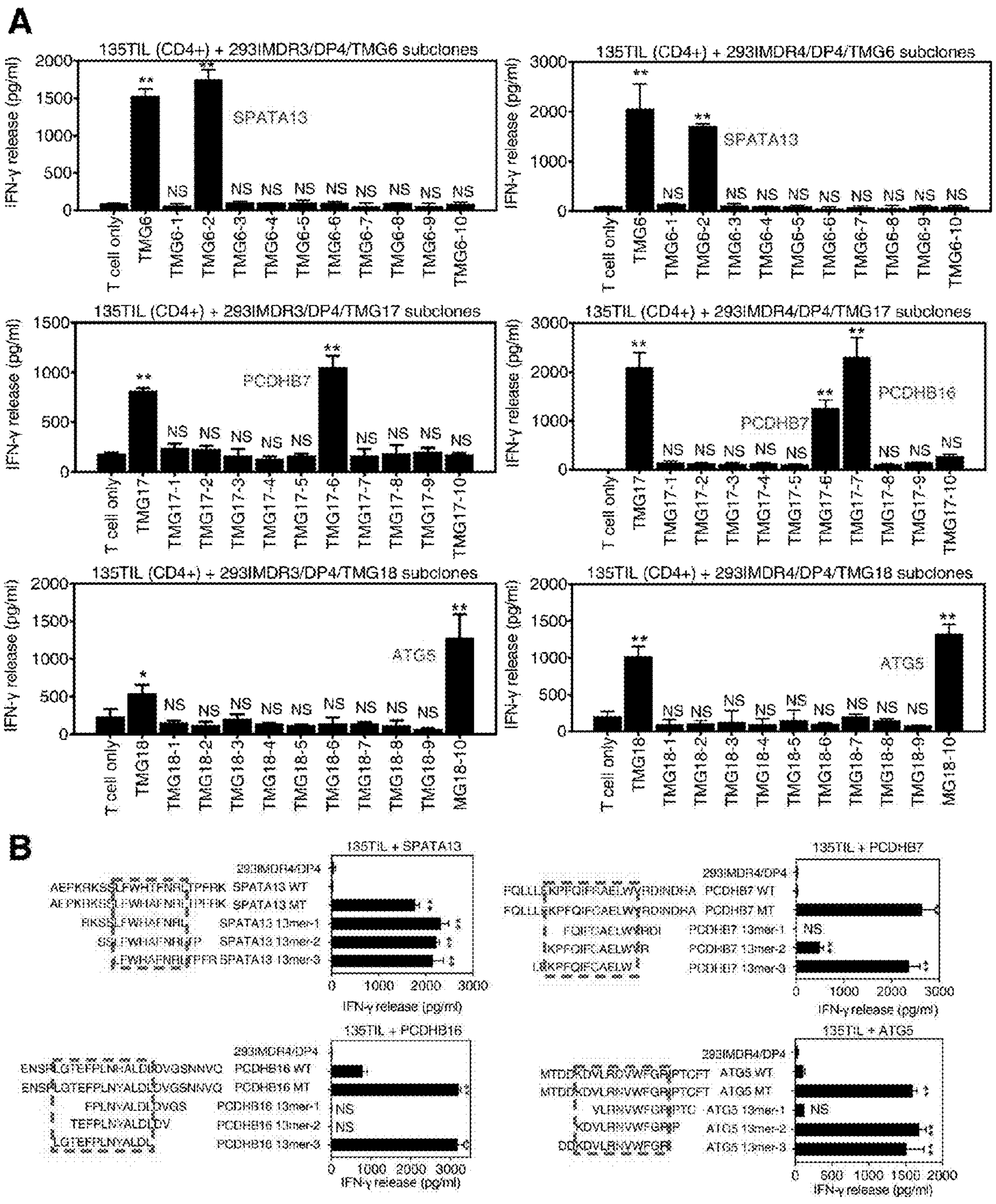

FIGS. 4A and 4B show the identification of subcloned MHC-II neoantigens of 135 mel from TMGs and their epitopes. FIG. 4A shows that each positive MHC-II TMG recognized by $CD4^+$ 135TILs was subcloned into 10 separated constructs encoding one mutated gene each, and then assayed with $CD4^+$ 135TILs. IFN-γ ELISA showed one or two subcloned genes in each TMG, which were recognized by $CD4^+$ 135TILs when presented by 293IMDR3/DP4 and 293IMDR4/DP4 respectively. Each positive subclone was sequenced and identified as a patient-derived neoantigen. FIG. 4B shows that SPATA13 (SPATA13 WT (SEQ ID NO: 1), SPATA13 MT (SEQ ID NO: 2), SPATA13 13 mer-1 (SEQ ID NO: 3), SPATA13 13 mer-2 (SEQ ID NO: 4), SPATA13 13 mer-3 (SEQ ID NO: 5)), PCDHB16 (PCDHB16 WT (SEQ ID NO: 13), PCDHB16 MT (SEQ ID NO: 14), PCDHB16 13 mer-1 (SEQ ID NO: 15), PCDHB16 13 mer-2 (SEQ ID NO: 16), PCDHB16 13 mer-3 (SEQ ID NO: 17)), PCDHB7 (PCDHB7 WT (SEQ ID NO: 8), PCDHB7 MT (SEQ ID NO: 9), PCDHB7 13 mer-1 (SEQ ID NO: 10), PCDHB7 13 mer-2 (SEQ ID NO: 11), PCDHB7 13 mer-3 (SEQ ID NO: 12)), and ATG5 (ATG5 WT (SEQ ID NO: 18), ATG5 MT (SEQ ID NO: 19), ATG5 13 mer-1 (SEQ ID NO: 20), ATG5 13 mer-2 (SEQ ID NO: 21), ATG5 13 mer-3 (SEQ ID NO: 22)) neoantigens were truncated to three constructs each encoding 13 aa of the mutation. The truncated peptides were assayed with 135TIL, and recognition was determined by the release of IFN-γ. The epitope of each neoantigen was refined to 9-13 aa. Data are plotted as means±SD of three independent experiments. *P<0.05, **P<0.01 by comparison with mock controls using Student's t-test. NS, not significant.

FIGS. 5A, 5B, and 5C show the identification of subcloned HLA class I neoantigens of 135 mel from TMG and their epitopes. FIG. 5A shows positive MHC-I TMGs were subcloned and assayed with $CD8^+$ 135TIL. Each positive subclone presented by artificial APCs was sequenced and identified as a neoantigen. FIG. 5B shows that TMG7 were subcloned and assayed with $CD8^+$ 135TIL presented by 135EBV-B cells. The positive subclone was sequenced and identified as a neoantigen. FIG. 5C shows that RPN2 (RPN2 WT (SEQ ID NO: 25), RPN2 MT (SEQ ID NO: 26), RPN2 13 mer-1 (SEQ ID NO: 27), RPN2 13 mer-2 (SEQ ID NO: 28), RPN2 13 mer-3 (SEQ ID NO: 29)), TXNIP (TXNIP WT (SEQ ID NO: 31), TXNIP MT (SEQ ID NO: 32), TXNIP 13 mer-1 (SEQ ID NO: 33), TXNIP 13 mer-2 (SEQ ID NO: 34), TXNIP 13 mer-3 (SEQ ID NO: 35)), and MPG (MPG WT (SEQ ID NO: 38), MPG MT (SEQ ID NO: 39), MPG 13 mer-1 (SEQ ID NO: 40), MPG 13 mer-2 (SEQ ID NO: 41), MPG 13 mer-3 (SEQ ID NO: 42)) neoantigens were truncated to three constructs encoding 13 aa containing the mutation and assayed with 135TIL as well. The epitope of RPN2 was truncated to 13 aa, the epitope of MPG was truncated to 11 aa and the epitope of TXNIP was truncated to 9 aa. Data are plotted as means±SD of three independent experiments. **P<0.01 by comparison with mock controls using Student's t-test. NS, not significant.

FIGS. 6A, 6B, 6C, and 6D show the identification of two non-mutated antigens of patient #135 by cDNA library screening with T-cell clones. FIG. 6A shows representative data after all CD4+ T-cell clones assayed with identified MHC-II neoantigens in 135 mel presented by EBV-B cells. Two $CD4^+$ tumor-reactive T-cell clones (1C1 and 1E1) did not recognize any MHC-II neoantigens. FIG. 6B shows two cDNA pools (pools #4 and #26) were recognized by $CD4^+$ T-cell clones 1C1 and 1E1, respectively. cDNA pools were transfected into 293IMDR3/DP4 or 293IMDR4/DP4 cells and then cocultured with different T-cell clones. FIG. 6C shows IFN-γ ELISA of cloned antigens in pool #4 for 1C1 and pool #26 for 1E1, showing that both were recognized by 1C1 and 1E1, respectively, when presented by 293IMDR4 or 293IMDR3 cells. Identification of positive antigens by sequencing analysis (shown are 3' and 5' ends of SEQ ID NOs 45 and 46 of ADIPOR2 3' UTR (ellipsis representing nucleotides or amino acids not shown in figure) and 3' and 5' ends of SEQ ID NOs: 47 and 48 for LAGE1b ORF2 (ellipsis representing nucleotides or amino acids not shown in figure)). FIG. 6D shows IFN-γ ELISA of serially diluted peptides of ADIPOR2 and LAGE1b in alternative ORFs incubated with 135TILs and antigen-specific T-cell clones, respectively. Data in C and D are plotted as means±SD of three independent experiments. **P<0.01 compared with controls using Student's t-test.

FIGS. 7A, 7B, 7C, 7D, and 7E show the identification of two non-mutated antigens of 135 mel. FIG. 7A shows the sequence of non-mutated antigens identified by $CD4^+$ T-cell clones. The antigen recognized by 1C1 was a 56 aa reading frame located in the 3'UTR sequence of gene ADIPOR2 (SEQ ID NO: 45 shows the nucleic acid sequence of ADIPOR2 and SEQ ID NO: 46 shows the amino acid sequence of the 3'UTR and epitope of T cell recognition). The antigen recognized by 1E1 was a 109 aa peptide located in the coding sequence of gene CTAG2 (LAGE1b) (SEQ ID NO: 47 shows the nucleic acid sequence of LAGE1b and SEQ ID NO: 48 shows the amino acid sequence of the ORF2 and epitope of T cell recognition), but in a frame-shifted reading frame. FIG. 7B shows IFN-γ ELISA of ADIPOR2 coding sequence and the antigen in 3'UTR assayed with 1C1. 1C1 only recognized the identified antigen in the 3'UTR, but not ADIPOR2 coding sequence. FIG. 7C shows IFN-γ ELISA of LAGE1b in normal reading frame (ORF1) and alternative reading frame (ORF2) assayed with 1E1. 1E1 only recognized ORF2 but not ORF1. Data are presented as means±SD of three independent experiments. *P<0.05, P<0.01 by comparison with mock or specified controls using Student's t-test. FIGS. 7D and 7**E show that serial truncations were carried out on ADIPOR2 and LAGE1b antigens. Each truncate was assayed with the corresponding T-cell clone and tested by IFN-γ ELISA. The minimum linear truncate of ADIPOR2 recognized by 1C1 was 26 aa, while the minimum linear truncate of LAGE1b recognized by 1E1 was 69 aa. Data are plotted means±SD of three independent experiments. *P<0.05, **P<0.01 by comparison with T cell alone using Student's t-test. NS, not significant.

FIGS. 8A, 8B, 8C, 8D, 8E, 8F, 8G, 8H, and 8I show the identification of multiple neoantigens of patient #136. FIG. 8A shows the identification of somatic mutations of 136 mel cells, resulting in 348 somatic mutations and 35 TMG constructs. FIG. 8B shows the screening of TMGs presented by MHC-II molecules in artificial APCs with use of 136TILs ($CD4^+$ population). IFN-γ ELISA showed that TMG19, TMG31, TMG32 were strongly recognized by $CD4^+$ TILs respectively. FIG. 8C shows the identification of MHC-II neoantigens in positive TMGs, based on IFN-γ ELISA of four HLA class II neoantigens: ZFYVE1 (H>Y) [TMG19-1] (SEQ ID NO: 75 (WT) and SEQ ID NO: 76 (MT)), LMAN2 (L>R) [TMG31-2] (SEQ ID NO: 77 (WT) and SEQ ID NO: 78 (MT)), MAPK9 (W>C) [TMG31-3] (SEQ ID NO: 79 (WT) and SEQ ID NO: 80 (MT)), and ANKIB1 (P>L) [TMG32-8] (SEQ ID NO: 81 (WT) and SEQ ID NO: 82 (MT)). The wild type of each neoantigen was not recognized. FIG. 8D shows the screening of TMGs presented by MHC-I molecules in artificial APCs with use of 136TILs ($CD8^+$ population). IFN-γ ELISA showed that only TMG2 was strongly recognized by $CD8^+$ TILs respectively. FIG. 8E shows the identification of MHC-I neoantigens in positive TMGs, based on IFN-γ ELISA of the only one MHC-I neoantigen: HHAT (G>E) [TMG2-3] (SEQ ID NO: 165 (WT) and SEQ ID NO: 166 (MT)). The wild type of this neoantigen was not recognized. FIG. 8F shows the screening of TMGs presented by fibroblasts of patient #136 pretreated by IFN-γ for expression of HLA molecules. No additional positive TMGs were identified. FIG. 8G shows the screening of TMGs presented by MHC-II molecules in artificial APCs with use of $CD4^+$ T-cell clones of 136TIL (C13 and C22). IFN-γ ELISA showed that TMG13 and TMG8 were strongly recognized by clone C13 and C22 respectively. FIG. 8H shows the identification of MHC-II neoantigens only recognized by T-cell clones, based on IFN-γ ELISA of two MHC-II neoantigens: C1GALT1C1 (L>F) [TMG13-1] (SEQ ID NO: 83 (WT) and SEQ ID NO: 84 (MT)) and HSPA13 (P>L) [TMG8-1] (SEQ ID NO: 85 (WT) and SEQ ID NO: 86 (MT)). The wild type of each neoantigen was not recognized. FIG. 8I shows IFN-γ ELISA of serially diluted peptides MHC-II and MHC-I neoantigens (mutant and wild type) incubated with 136TIL or T-cell clones. Data in B-I are plotted as means±SD of three independent experiments. *P<0.05, **P<0.01 by comparison with mock controls or WT peptide controls using Student's t-test.

FIGS. 9A, 9B, 9C, and 9D show the identification of subcloned HLA class I and class II neoantigens of 136 mel from TMGs. FIG. 9A shows positive MHC-II TMGs were subcloned and assayed with $CD4^+$ 136TIL. Each positive subclone presented by 293IMDR1/DP4 or 293IMDR11/DP4 cells was sequenced and identified as a neoantigen. FIG. 9B shows the only positive MHC-I TMG2 recognized by $CD8^+$ 136TILs was subcloned into 10 separated constructs encoding one mutated gene each, and then assayed with $CD8^+$ 136TILs. IFN-γ ELISA showed one subcloned gene in each TMG, which were recognized by $CD8^+$ 136TILs when presented by Cos7-A1 cells and then sequenced and identified as a patient-derived neoantigen. FIG. 9C shows that 136 Fibroblasts were treated with IFN-γ for three days and the expression of MHC-II molecules before and after treatment were compared. FIG. 9D shows two positive MHC-II TMGs only recognized by $CD4^+$ T-cell clones of 136TILs were subcloned and assayed with $CD4^+$ T-cell clones respectively. Each positive subclone presented by 293IMDR1/DP4 cells was sequenced and identified as a neoantigen.

FIGS. 10A, 10B, 10C, 10D, 10E, and 10F show the recognition of given neoantigens of patient #135 and #136 by dominant population of tumor-reactive T cells. FIG. 10A shows IFN-γ ELISA of all 78 $CD4^+$ tumor-reactive T-cell clones of 135TIL assayed with MHC-II neoantigens: SPATA13, PCDHB7, PCDHB16, ATG5, ADIPOR2 26 mer and LAGE1b ORF2 respectively. FIG. 10B shows IFN-γ ELISA of all 40 $CD8^+$ tumor-reactive T-cell clones of 135TIL assayed with MHC-I neoantigens: RPN2, MPG and TXNIP respectively. FIG. 10C shows the tumor and neoantigen peptides-reactive populations of $CD4^+$ (upper) and $CD8^+$ (lower) 135TILs stained intracellularly by IFN-γ antibody and sorted by FACS. FIG. 10D shows the statistic result of the ratio of each identified neoantigen in 135 mel in the summary of all peptide-reactive $CD4^+$ or $CD8^+$ T cell populations respectively. FIG. 10E shows PCDHB16 and MPG peptides-bound T cells in 135TIL were sorted. TCRβ CDR3 profiling were performed with sorted T cells and 135TIL. Top sequence frequencies of neoantigen-specific TCRs in sorted T cell groups are shown. FIG. 10F shows the percentage in 135TIL of PCDHB16 or MPG-bound TCRs after TCRβ CDR3 profiling. FIGS. 11A, 11B, 11C, and 11D show TCRβ CDR3 repertoire analysis of dominant neoantigen-reactive T cells in 135TIL and 136TIL. FIG. 11A shows the tumor and neoantigen peptides-reactive populations of $CD4^+$ (upper) and $CD8^+$ (lower) 136TILs stained intracellularly by IFN-γ antibody and sorted by FACS. FIG. 11B shows the statistic result of the ratio of each identified neoantigen in 136 mel in the summary of all peptide-reactive $CD4^+$ or $CD8^+$ T cell populations respectively. FIG. 11C shows the usage of combined V-J sequences in TCR β CDR3 of PCDHB16-reactive T cells (left) and MPG-reactive T cells (right) in 135TILs. FIG. 11D shows the amino acid usage of V-J joint in TCR β CDR3 of PCDHB16-reactive T cells (left, SEQ ID NO: 87) and MPG-specific T cells (right, SEQ ID NO: 164) in 135TILs.

Figures 12A, 12B, 12C, 12D, 12E, 12F:
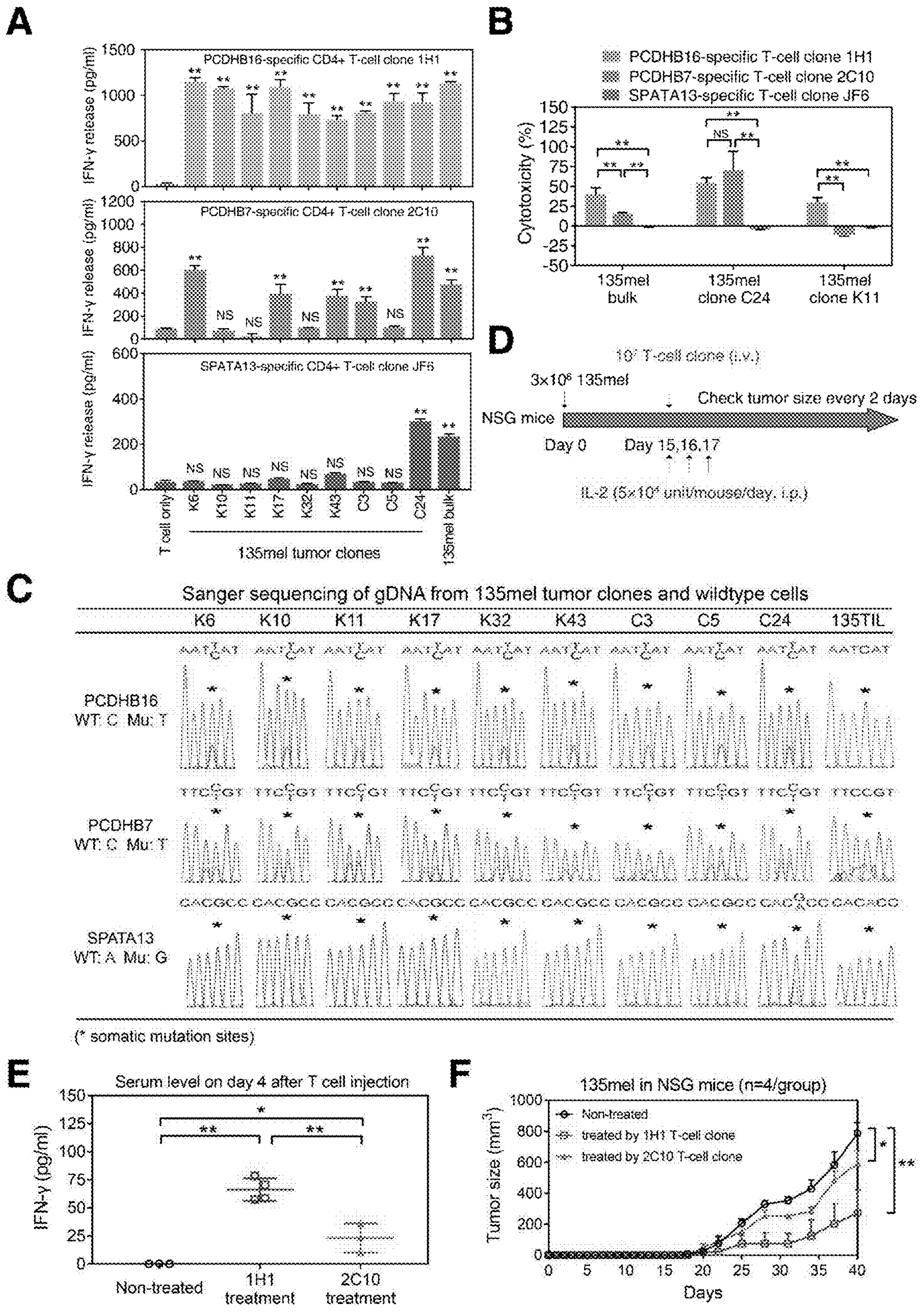

FIGS. 12A, 12B, 12C, 12D, 12E, and 12F show the anti-tumor effect in vitro and in vivo when targeting dominant neoantigen of 135 mel. FIG. 12A shows single cell tumor clones were generated from 135 mel tumor cell lines by limiting dilution or single cell cloning method. Dominant PCDHB16 neoantigen-specific T-cell clone 1H1, as well as subdominant/cryptic neoantigen 2C10 (PCDHB7-specific) and JF6 (SPATA13-specific) were used to test their ability to recognize single tumor clones and bulk 135 mel tumor cell line. Data are plotted as means±SD of three independent experiments. FIG. 12B shows the dominant neoantigen PCDHB16-specific T-cell clones 1H1 showed higher percentage of tumor cell killing than subdominant/cryptic neoantigen-specific T-cell clones on 135 mel against bulk and selected single tumor cell clones. FIG. 12C shows sanger sequencing of 135 mel tumor clones and 135TIL at the mutation sites of PCDHB16, PCDHB7 and SPATA13, revealing that the somatic mutation of each neoantigen existed in the genome of each clone. FIG. 12D shows the scheme of NSG mice injected with 135 mel and treated by 135 T-cell clones. FIG. 12E shows murine serum level of IFN-γ in vivo on day 4 after T-cell injection. FIG. 12F shows the change of 135 mel tumor size in vivo after injection of T-cell clones targeting different neoantigens. Data are plotted as means±SD of three independent experiments. **P<0.01 compared with control using Student's t-test. NS, not significant.

FIGS. 13A, 13B, 13C, and 13D show the recognition of multiple neoantigens by a single TCR. FIG. 13A shows that T-cell clone 4B8 simultaneously recognized the product translated from the ADIPOR2 3'UTR mRNA and PCDHB16 neoantigen by IFN-γ ELISA of serially diluted peptides. The same assay of naïve T cells transduced with 4B8 TCR confirmed this dual recognition. FIG. 13B shows IFN-γ ELISA of separated $CD4^+$ and $CD8^+$ T cells transduced with 4B8 TCR. Only $CD4^+$ T cells recognized both antigens after the transduction. FIG. 13C shows flow cytometric analysis of T-cell clone C76, showing its $CD4^+/CD8^+$ double positivity. Naïve T cells transduced by C76 TCR recognized HLA class I-restricted RPN2 neoantigen and HLA class II-restricted PCDHB16 neoantigen by IFN-γ release assay. FIG. 13D shows that $CD8^+$ T cells transduced with C76 TCR recognized HLA-A1-presented RPN2 neoantigen, while transduced $CD4^+$ T cells recognized only HLA-DR4-restricted PCDHB16 neoantigen. Data are presented as means±SD of three independent experiments. **P<0.01 compared with controls using Student's t-test. NS, not significant.

FIGS. 14A, 14B, and 14C show that one T-cell receptor can recognize dual neoantigens. FIG. 14A shows FACS analysis of $CD4^+$ T-cell clone 4B8 of 135TILs reacted with two neoantigens, PCDHB16 and ADIPOR2 26 mer. FIG. 14B shows a map of TCRα and β chains cloned into the retroviral vector pMSGV. FIG. 14C shows IFN-γ ELISA of all 78 $CD4^+$ T-cell clones assayed with HLA class I neoantigens. One PCDHB16-recognizing $CD4^+$ T-cell clone C76 was discovered to recognize RPN2 presented by HLA-A1 spontaneously, leading to the further identification of C76 TCR dual recognition. Data are presented as representatives of three independent experiments.

FIGS. 15A, 15B, 15C show that ThPOK expression correlates with 135 TIL $CD4^+$ clones cytotoxicity. FIG. 15A shows the cytotoxicity of 135 TIL CD4+ clones was conducted by LDH assay. Effectors: Targets=20:1. FIG. 15B shows quantitative real-time PCR of mRNA level. FIG. 15C shows western blot analysis of ThPOK expression in 135 $CD4^+$ TIL clones.

FIGS. 16A, 16B, 16C, 16D, and 16E show the knockdown of ThPOK in human 135 $CD4^+$ 135TILs increases their cytotoxicity. FIG. 16A shows western blot analysis of ThPOK Knockdown efficiency. FIG. 16B shows that an LDH assay was conducted after ThPOK shRNA first transduction 72 hours at different E:T ratio. FIG. 16C shows that 135 mel tumor cells co-cultured with or without ThPOK shRNA knockdown in $CD4^+$ 135TIL clone 1D1 for three days. FIG. 16D shows quantitative real-time PCR analysis of typical CD8+ CTL cytolytic molecules after ThPOK knockdown 72 hours. FIG. 16E shows ThPOK knockdown in $CD4^+$ 135TIL clone 1D1 maintains the CD4 property in vitro, ELISA test of cytokine secretion of IFN-γ, GM-CSF, IL-4, IL-10.

FIGS. 17A, 17B, 17C, and 17D show knockdown of hThPOK enhances the anti-tumor efficacy of tumor specific T cells in vivo. FIG. 17A shows that $2\times10^6$ 135 mel tumor cells were inoculated into the flank of SCID (beige) mice (n=5). $5\times10^6$ $CD4^+$ 135TILs modified with hThPOK shRNA were adoptively transferred on Day 5. Tumor growth was monitored every 2-3 days with an electronic caliper. FIG. 17B shows mice were sacrificed when control group length reach 10 mm. Tumor was excised and weighed on Day 26 after inoculation. FIG. 17C shows human $CD4^+$ or $CD8^+$ T cells transduced with A2ESO TCR or A2ESO TCR-ThPOK shRNA were injected into mouse at day 4 after tumor cell injection. Tumor volume was measured every day. FIG. 17D shows mice were sacrificed at day 9 and tumor morphology were measured.

FIGS. 18A, 18B, 18C, and 18D show that ThPOK inhibits $CD4^+$ tumor specific T cell cytotoxicity by interacting with LSD1. FIG. 18A shows epigenetic inhibitor screening identified LSD1 inhibition increases cytotoxicity of antigen specific $CD4^+$ T cells. FIG. 18B shows ThPOK interacting epigenetic gene screening identified LSD1 could directly interact with ThPOK. FIG. 18C shows endogenous immunoprecipitation in $CD4^+$ T cells validated ThPOK could interact with LSD1 in $CD4^+$ T cells. FIG. 18D shows the relative occupancy of ThPOK and LSD1 in GZMB and PRF1 gene promoters. Q-PCR analysis of recovered DNA from the anti-ThPOK and LSD1 Chromatin immunoprecipitation assay.

Figures 19A, 19B:
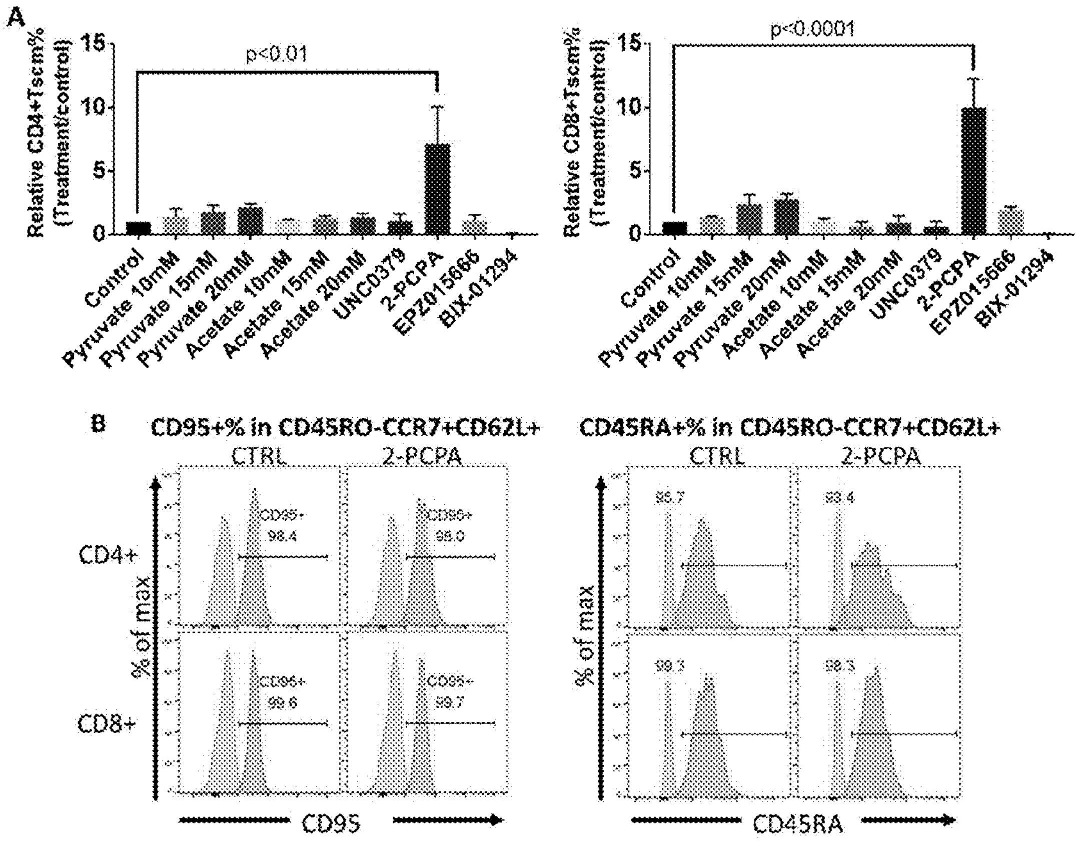

FIGS. 19A and 19B shows the identification of 2-PCPA as a positive regulator of the generation of stem cell-like memory T cells through in vitro screening. FIG. 19A shows that T cells were activated by plate-bound OKT3 for 2 days and cultured for additional 12 days before flow cytometry analysis of stem cell-like memory T cells (Tscm) percentage. Metabolites or inhibitors were added at the time of activation. Results were shown as the fold change of Tscm percentage between treated and untreated T cells. Tscm subset was identified as CCR7CD62L+ CD45RO−. FIG. 19B shows the determining other Tscm markers CD95 and CD45RA expression on control of 2-PCPA treated T cells. Isotype controls were shown as blue peaks.

FIGS. 20A, 20B, 20C, 20D, and 20E show 2-PCPA treatment promoted the in vitro and in vitro function of A2ESO TCR-T cells. FIG. 20A shows that T cells from healthy donors were activated by plate-bound OKT3 for 2 days and transduced with PG13-A2ESO TCR virus. Transduced T cells were cultured for additional 8 days. 2-PCPA or DMSO (control) treatment were added before activation. CD4 and CD8 memory phenotype was detected by flow cytometry at day 10. FIG. 20B shows DMSO or 2-PCPA treated A2ESO TCR-T cells were stimulated by PMA and ionomycin for 5 hours, fixed, permeabilized and IFN-γ, IL-2 and TNFα expression in CD4+ and CD8+ T cells were checked. FIG. 20C shows DMSO or 2-PCPA treated A2ESO TCR-T cells were labeled with CFSE and cultured under IL-2 or stimulated by 231-ESO cells for 3 days. Division Index was calculated by FlowJo software. FIG. 20D shows 2-PCPA treatment render A2ESO TCR-T cells with increased OXPHOS and spare respiratory capacity (SRC). OCR was detected by Seahorse XFe96 Analyzer. FIG. 20E shows NSG mice were injected with 231-ESO breast cancer cell line at fat pad. 3 days later, DMSO or 2-PCPA treated A2ESO TCR-T cells were injected intravenously. Tumors were isolated and weight after 2 weeks.

FIGS. 21A, 21B, 21C, 21D, and 21E show that 2-PCPA treatment promoted the in vitro and in vitro function of CAR-T cells. FIG. 21A shows that T cells from healthy donors were activated by plate-bound OKT3 for 2 days and transduced with PG13-CD19 CAR virus. Transduced T cells were cultured for additional 10 days. 2-PCPA or DMSO (control) treatment were added before activation. $CD4^+$ and $CD8^+$ memory phenotype was detected by flow cytometry at day 12. FIG. 21B shows 2-PCPA treatment render CAR-T cells with increased OXPHOS and spare respiratory capacity (SRC). OCR was detected by Seahorse XFe96 Analyzer. FIG. 21C shows DMSO or 2-PCPA treated CAR-T cells were washed extensively and cultured in IL-2-free medium for 4 days and survived cells were detected by PI staining. FIG. 21D shows that NSG mice were intravenously injected with Raji lymphoma cells. 10 days later, DMSO or 2-PCPA treated CD19 CAR and luciferase-transduced T cells were injected intravenously. Proliferation of CAR-T cells were tracked through in vivo imaging. FIG. 21E shows Human $CD3^+$ cells percentage within spleen at day 8 detected by flow cytometry.

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

As used in the specification and the appended claims, the singular forms “a,” “an” and “the” include plural referents unless the context clearly dictates otherwise. Thus, for example, reference to “a pharmaceutical carrier” includes mixtures of two or more such carriers, and the like.

Ranges can be expressed herein as from “about” one particular value, and/or to “about” another particular value. When such a range is expressed, another embodiment includes from the one particular value and/or to the other particular value. Similarly, when values are expressed as approximations, by use of the antecedent “about,” it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as “about” that particular value in addition to the value itself. For example, if the value “10” is disclosed, then “about 10” is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

The term "subject" refers to any individual who is the target of administration or treatment. The subject can be a vertebrate, for example, a mammal. In one aspect, the subject can be human, non-human primate, bovine, equine, porcine, canine, or feline. The subject can also be a guinea pig, rat, hamster, rabbit, mouse, or mole. Thus, the subject can be a human or veterinary patient. The term "patient" refers to a subject under the treatment of a clinician, e.g., physician.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. METHODS OF IDENTIFYING NEOANTIGENS

Although in vitro stimulation of T cells from normal healthy donors with neoantigen peptides could increase the number of neoantigens capable of activating T cells, prior to the present disclosure it remained unknown about the number and recognition pattern of neoantigens by T cells in cancer patients. Furthermore, it was largely unknown whether a single T cell receptor (TCR) can recognize two or multiple neoantigens in cancer patients. Despite recent identification of many HLA class I-restricted neoantigens using exome sequencing and computer-assisted prediction programs, increasing evidence demonstrates that neoantigen-specific CD4+ T cells are more dominant than neoantigen-specific CD8+ T cells, and play a critical role in tumor regression. However, the current prediction programs in use in the art for MHC II-restricted neoantigens are not accurate and much poorer than the prediction programs of MHC I-restricted neoantigens due to the open pockets of MHC II molecules, thus limiting the ability to identify neoantigens and develop neoantigen-based immunotherapy.

Tumor regression induced by checkpoint blockade therapy and T cell-based immunotherapy relies on T-cell recognition of tumor antigens, particularly mutation-derived neoantigens, expressed by cancer cells. However, despite the larger numbers of somatic mutations identified in cancer tissues that could generate neoantigens, only a few immunogenic peptide epitopes (per cancer patient) for T-cell recognition have been reported. The underlying mechanisms of these observations remain poorly understood. Herein identification of four MHC class II-restricted neoantigens and two MHC class I-restricted neoantigens is reported. Further analysis of neoantigens for recognition by CD4+ T-cell clones revealed the dominance of one neoantigen, which was recognized by 87% of the T-cell clones, while several low-frequency T-cell clones recognized 3 additional neoantigens. Overall, 98% of the CD4+ T cells recognized neoantigens, compared with only 34% of the CD8+ T cell clones. Additionally, 2 T-cell clones did not recognize mutation-derived neoantigen, but instead recognized neoepitopes derived from gene products translated from the 3' untranslated region of the ADIPOR2 gene or from an alternative open reading frame of LAGE1b. Finally, it was demonstrated herein that a single TCR can recognize two neoantigens, but not other antigens in normal cells. Also demonstrated was the utility and power of neoantigen-specific T cells in inhibiting tumor growth. The findings have identified immune regulatory mechanisms that restrain T-cell response to a limited number of neoantigens with one as dominant, and should have important implications in personalized immunotherapy that targets dominant neoantigens and TCRs with multiple neoantigen specificity.

In one aspect, disclosed herein are methods of identifying neoantigens from a cancer in a human subject comprising a) exome sequencing on a nucleic acid sample from a cancer cell (in some instances the method can further comprise isolating DNA from cancer cells, capturing DNA fragments, and constructing an exome library); b) mapping the sequencing result to a reference genome sequence data (for example human genome GRCh38/hg38); c) filtering sequence variations to remove common variations in tumors and normal cells; d) creating one or more single mutation peptide constructs comprising at least one uncommon amino acid variation and one or more flanking amino acids; e) synthesizing one or more minigenes encoding one or more single mutation peptide constructs of step d; f) transfecting one or more minigenes into one or more cells or cell lines expressing MHC class I or MHC class II molecules; g) co-culturing one or more T cells or T cells lines with the transfected cells of step f); h) measuring T cell activity of the co-cultured T cells or T cell lines; i) and assaying single mutation peptides from each minigene in transfected cell lines that induced T cell activity for the ability to induce T cell activity alone.

In one aspect, also disclosed herein are methods of identifying any neoantigendisclosed herein, further comprising mapping the mutation to a specific peptide epitope by serial truncation and/or further comprising assaying the HLA restriction of the peptide epitope by HLA antibody blocking.

As noted herein, the single mutation constructs created in the disclosed methods can have one or more amino acids on either or both sides of the mutations. Thus, for example, disclosed herein are methods of identifying any neoantigen disclosed herein, wherein the single mutation constructs comprise at least 1, 2, 3, 4, 5, 6, 7, 8, 9, 10, 11, 12, 13, 14, 15, 16, 17, 18, 19, 20, 21, 22, 23, 24, or 25 amino acids on either side of the mutation.

It is understood and herein contemplated that the minigenes created in the disclosed methods can comprise 1, 2, 3, 4, 5, 6, 7, 8, 9, 10, 11, 12, 13, 14, 15, 16, 17, 18, 19, 20, 21, 22, 23, 24, 25 or more single mutation constructs. Thus, in one aspect, disclosed herein are methods of identifying any neoantigen disclosed herein, wherein the minigene comprises at least 1, 2, 3, 4, 5, 6, 7, 8, 9, 10, 11, 12, 13, 14, 15, 16, 17, 18, 19, 20, 21, 22, 23, 24, or 25 single mutation constructs.

In one aspect, it is understood and herein contemplated that the disclosed also disclosed herein are methods of identifying any neoantigen disclosed herein, wherein the one or more cell or cell lines (such as, for example HEK293 cells, HEK293T cells, Cos-7, MA104 cells, CHO cells, Fibroblasts, B cells, VERO cells, Madin-Darby Canine Kidney (MDCK) cells, HEp-2 cells, HeLa cells, MRC-5 cells, WI-38 cells, EB66, or PER C6 cells) expressing MHC class I or class II molecules, are engineered to express an MHC molecule.

It is understood and herein contemplated that there are numerous methods known in the art for measuring T cell activity that could be used in the disclosed methods of identifying neoantigens, including, but not limited to chromium release assays, ELISA, ELISpot, intracellular cytokine staining, flow cytometry, MHC class I tetramer staining, MHC class II tetramer staining, radioimmunoassay, or other immunoassay. The immunoassays can measure the release of any number of effector cytokines (such as, for example, release of cytokines including, but not limited to IFN-γ, TGF-β, lymphotoxin-α, IL-2, IL-4, IL-10, IL-17, or IL-25) or expression of cell surface markers associated with T cell activation (CD69, CD62L, CD44, CD45 RA, CD45RO, and/or CCR7).

1. Immunoassays and Fluorochromes

52. The steps of various useful immunodetection methods have been described in the scientific literature, such as, e.g., Maggio et al., Enzyme-Immunoassay, (1987) and Nakamura, et al., Enzyme Immunoassays: Heterogeneous and Homogeneous Systems, Handbook of Experimental Immunology, Vol. 1: Immunochemistry, 27.1-27.20 (1986), each of which is incorporated herein by reference in its entirety and specifically for its teaching regarding immunodetection methods. Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

In general, immunoassays involve contacting a sample suspected of containing a molecule of interest (such as the disclosed biomarkers) with an antibody to the molecule of interest or contacting an antibody to a molecule of interest (such as antibodies to the disclosed biomarkers) with a molecule that can be bound by the antibody, as the case may be, under conditions effective to allow the formation of immunocomplexes. Contacting a sample with the antibody to the molecule of interest or with the molecule that can be bound by an antibody to the molecule of interest under conditions effective and for a period of time sufficient to allow the formation of immune complexes (primary immune complexes) is generally a matter of simply bringing into contact the molecule or antibody and the sample and incubating the mixture for a period of time long enough for the antibodies to form immune complexes with, i.e., to bind to, any molecules (e.g., antigens) present to which the antibodies can bind. In many forms of immunoassay, the sample-antibody composition, such as a tissue section, ELISA plate, dot blot or Western blot, can then be washed to remove any non-specifically bound antibody species, allowing only those antibodies specifically bound within the primary immune complexes to be detected.

Immunoassays can include methods for detecting or quantifying the amount of a molecule of interest (such as the disclosed biomarkers or their antibodies) in a sample, which methods generally involve the detection or quantitation of any immune complexes formed during the binding process. In general, the detection of immunocomplex formation is well known in the art and can be achieved through the application of numerous approaches. These methods are generally based upon the detection of a label or marker, such as any radioactive, fluorescent, biological or enzymatic tags or any other known label.

As used herein, a label can include a fluorescent dye, a member of a binding pair, such as biotin/streptavidin, a metal (e.g., gold), or an epitope tag that can specifically interact with a molecule that can be detected, such as by producing a colored substrate or fluorescence. Substances suitable for detectably labeling proteins include fluorescent dyes (also known herein as fluorochromes and fluorophores) and enzymes that react with colorometric substrates (e.g., horseradish peroxidase). The use of fluorescent dyes is generally preferred in the practice of the invention as they can be detected at very low amounts. Furthermore, in the case where multiple antigens are reacted with a single array, each antigen can be labeled with a distinct fluorescent compound for simultaneous detection. Labeled spots on the array are detected using a fluorimeter, the presence of a signal indicating an antigen bound to a specific antibody.

Fluorophores are compounds or molecules that luminesce. Typically fluorophores absorb electromagnetic energy at one wavelength and emit electromagnetic energy at a second wavelength. Representative fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-Hydroxy Tryptamine (5-HAT); 5-ROX (carboxy-X-rhodamine); 6-Carboxyrhodamine 6G; 6-CR 6G; 6-JOE; 7-Amino-4-methylcoumarin; 7-Aminoactinomycin D (7-AAD); 7-Hydroxy-4-I methylcoumarin; 9-Amino-6-chloro-2-methoxyacridine (ACMA); ABQ; Acid Fuchsin; Acridine Orange; Acridine Red; Acridine Yellow; Acriflavin; Acriflavin Feulgen SITSA; Aequorin (Photoprotein); AFPs—AutoFluorescent Protein—(Quantum Biotechnologies) see sgGFP, sgBFP; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; Aminomethylcoumarin (AMCA); AMCA-X; Aminoactinomycin D; Aminocoumarin; Anilin Blue; Anthrocyl stearate; APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); Blue Fluorescent Protein; BFP/GFP FRET; Bimane; Bisbenzemide; Bisbenzimide (Hoechst); bis-BTC; Blancophor FFG; Blancophor SV; BOBO™-1; BOBO™-3; Bodipy 492/515; Bodipy 493/503; Bodipy 500/510; Bodipy; 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue; Calcium Crimson—; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue™; Cascade Yellow; Catecholamine; CCF2 (GeneBlazer); CFDA; CFP (Cyan Fluorescent Protein); CFP/YFP FRET; Chlorophyll; Chromomycin A; Chromomycin A; CL-NERF; CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM I Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3'DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di 16-ASP); Dichlorodihydrofluorescein Diacetate (DCFH); DiD-Lipophilic Tracer; DiD (Di1C18(5)); DIDS; Dihydorhodamine 123 (DHR); Dil (Di1C18(3)); I Dinitrophenol; DiO (DiOC18(3)); DiR; DiR (Di1C18(7)); DM-NERF (high pH); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (111) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow SGF; GeneBlazer; (CCF2); GFP (S65T); GFP red shifted (rsGFP); GFP wild type' non-UV excitation (wtGFP); GFP wild type, UV excitation (wtGFP); GFPuv; Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1 low calcium; Indodicarbocyanine (DiD); Indotricarbocyanine (DiR); Intrawhite Cf; JC-1; JO JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; *Lucifer* Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-lndo-1; Magnesium Green; Magnesium Orange; Malachite Green; Marina Blue; I Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxedidole; Noradrenaline; Nuclear Fast Red; i Nuclear Yellow; Nylosan Brilliant lavin EBG; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-I PRO-3; Primuline; Procion Yellow; Propidium lodid (P1); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine: Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron I Brilliant Red B; Sevron Orange; Sevron Yellow L; sgBFP™ (super glow BFP); sgGFP™ (super glow GFP); SITS (Primuline; Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3 sulfopropyl) quinolinium); Stilbene; Sulphorhodamine B and C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TON; Thiolyte; Thiozole Orange; Tinopol CBS (Calcofluor White); TIER; TO-PRO-1; TO-PRO-3; TO-PRO-5; TOTO-1; TOTO-3; TriColor (PE-Cy5); TRITC TetramethylRodaminelsoThioCyanate; True Blue; Tru Red; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO 3; YOYO-1; YOYO-3; Sybr Green; Thiazole orange (interchelating dyes); semiconductor nanoparticles such as quantum dots; or caged fluorophore (which can be activated with light or other electromagnetic energy source), or a combination thereof.

A modifier unit such as a radionuclide can be incorporated into or attached directly to any of the compounds described herein by halogenation. Examples of radionuclides useful in this embodiment include, but are not limited to, tritium, iodine-125, iodine-131, iodine-123, iodine-124, astatine-210, carbon-11, carbon-14, nitrogen-13, fluorine-18. In another aspect, the radionuclide can be attached to a linking group or bound by a chelating group, which is then attached to the compound directly or by means of a linker. Examples of radionuclides useful in the apset include, but are not limited to, Tc-99m, Re-186, Ga-68, Re-188, Y-90, Sm-153, Bi-212, Cu-67, Cu-64, and Cu-62. Radiolabeling techniques such as these are routinely used in the radiopharmaceutical industry.

The radiolabeled compounds are useful as imaging agents to diagnose neurological disease (e.g., a neurodegenerative disease) or a mental condition or to follow the progression or treatment of such a disease or condition in a mammal (e.g., a human). The radiolabeled compounds described herein can be conveniently used in conjunction with imaging techniques such as positron emission tomography (PET) or single photon emission computerized tomography (SPECT).

Labeling can be either direct or indirect. In direct labeling, the detecting antibody (the antibody for the molecule of interest) or detecting molecule (the molecule that can be bound by an antibody to the molecule of interest) include a label. Detection of the label indicates the presence of the detecting antibody or detecting molecule, which in turn indicates the presence of the molecule of interest or of an antibody to the molecule of interest, respectively. In indirect labeling, an additional molecule or moiety is brought into contact with, or generated at the site of, the immunocomplex. For example, a signal-generating molecule or moiety such as an enzyme can be attached to or associated with the detecting antibody or detecting molecule. The signal-generating molecule can then generate a detectable signal at the site of the immunocomplex. For example, an enzyme, when supplied with suitable substrate, can produce a visible or detectable product at the site of the immunocomplex. ELISAs use this type of indirect labeling.

As another example of indirect labeling, an additional molecule (which can be referred to as a binding agent) that can bind to either the molecule of interest or to the antibody (primary antibody) to the molecule of interest, such as a second antibody to the primary antibody, can be contacted with the immunocomplex. The additional molecule can have a label or signal-generating molecule or moiety. The additional molecule can be an antibody, which can thus be termed a secondary antibody. Binding of a secondary antibody to the primary antibody can form a so-called sandwich with the first (or primary) antibody and the molecule of interest. The immune complexes can be contacted with the labeled, secondary antibody under conditions effective and for a period of time sufficient to allow the formation of secondary immune complexes. The secondary immune complexes can then be generally washed to remove any non-specifically bound labeled secondary antibodies, and the remaining label in the secondary immune complexes can then be detected. The additional molecule can also be or include one of a pair of molecules or moieties that can bind to each other, such as the biotin/avidin pair. In this mode, the detecting antibody or detecting molecule should include the other member of the pair.

Other modes of indirect labeling include the detection of primary immune complexes by a two-step approach. For example, a molecule (which can be referred to as a first binding agent), such as an antibody, that has binding affinity for the molecule of interest or corresponding antibody can be used to form secondary immune complexes, as described above. After washing, the secondary immune complexes can be contacted with another molecule (which can be referred to as a second binding agent) that has binding affinity for the first binding agent, again under conditions effective and for a period of time sufficient to allow the formation of immune complexes (thus forming tertiary immune complexes). The second binding agent can be linked to a detectable label or signal-genarating molecule or moiety, allowing detection of the tertiary immune complexes thus formed. This system can provide for signal amplification.

Immunoassays that involve the detection of as substance, such as a protein or an antibody to a specific protein, include label-free assays, protein separation methods (i.e., electrophoresis), solid support capture assays, or in vivo detection. Label-free assays are generally diagnostic means of determining the presence or absence of a specific protein, or an antibody to a specific protein, in a sample. Protein separation methods are additionally useful for evaluating physical properties of the protein, such as size or net charge. Capture assays are generally more useful for quantitatively evaluating the concentration of a specific protein, or antibody to a specific protein, in a sample. Finally, in vivo detection is useful for evaluating the spatial expression patterns of the substance, i.e., where the substance can be found in a subject, tissue or cell.

Provided that the concentrations are sufficient, the molecular complexes ([Ab-Ag]n) generated by antibody-antigen interaction are visible to the naked eye, but smaller amounts may also be detected and measured due to their ability to scatter a beam of light. The formation of complexes indicates that both reactants are present, and in immunoprecipitation assays a constant concentration of a reagent antibody is used to measure specific antigen ([Ab-Ag]n), and reagent antigens are used to detect specific antibody ([Ab-Ag]n). If the reagent species is previously coated onto cells (as in hemagglutination assay) or very small particles (as in latex agglutination assay), “clumping” of the coated particles is visible at much lower concentrations. A variety of assays based on these elementary principles are in common use, including Ouchterlony immunodiffusion assay, rocket immunoelectrophoresis, and immunoturbidometric and nephelometric assays. The main limitations of such assays are restricted sensitivity (lower detection limits) in comparison to assays employing labels and, in some cases, the fact that very high concentrations of analyte can actually inhibit complex formation, necessitating safeguards that make the procedures more complex. Some of these Group 1 assays date right back to the discovery of antibodies and none of them have an actual “label” (e.g. Ag-enz). Other kinds of immunoassays that are label free depend on immunosensors, and a variety of instruments that can directly detect antibody-antigen interactions are now commercially available. Most depend on generating an evanescent wave on a sensor surface with immobilized ligand, which allows continuous monitoring of binding to the ligand. Immunosensors allow the easy investigation of kinetic interactions and, with the advent of lower-cost specialized instruments, may in the future find wide application in immunoanalysis.

The use of immunoassays to detect a specific protein can involve the separation of the proteins by electrophoresis. Electrophoresis is the migration of charged molecules in solution in response to an electric field. Their rate of migration depends on the strength of the field; on the net charge, size and shape of the molecules and also on the ionic strength, viscosity and temperature of the medium in which the molecules are moving. As an analytical tool, electrophoresis is simple, rapid and highly sensitive. It is used analytically to study the properties of a single charged species, and as a separation technique.

Generally the sample is run in a support matrix such as paper, cellulose acetate, starch gel, agarose or polyacrylamide gel. The matrix inhibits convective mixing caused by heating and provides a record of the electrophoretic run: at the end of the run, the matrix can be stained and used for scanning, autoradiography or storage. In addition, the most commonly used support matrices—agarose and polyacrylamide—provide a means of separating molecules by size, in that they are porous gels. A porous gel may act as a sieve by retarding, or in some cases completely obstructing, the movement of large macromolecules while allowing smaller molecules to migrate freely. Because dilute agarose gels are generally more rigid and easy to handle than polyacrylamide of the same concentration, agarose is used to separate larger macromolecules such as nucleic acids, large proteins and protein complexes. Polyacrylamide, which is easy to handle and to make at higher concentrations, is used to separate most proteins and small oligonucleotides that require a small gel pore size for retardation.

Proteins are amphoteric compounds; their net charge therefore is determined by the pH of the medium in which they are suspended. In a solution with a pH above its isoelectric point, a protein has a net negative charge and migrates towards the anode in an electrical field. Below its isoelectric point, the protein is positively charged and migrates towards the cathode. The net charge carried by a protein is in addition independent of its size—i.e., the charge carried per unit mass (or length, given proteins and nucleic acids are linear macromolecules) of molecule differs from protein to protein. At a given pH therefore, and under non-denaturing conditions, the electrophoretic separation of proteins is determined by both size and charge of the molecules.

Sodium dodecyl sulphate (SDS) is an anionic detergent which denatures proteins by "wrapping around" the polypeptide backbone—and SDS binds to proteins fairly specifically in a mass ratio of 1.4:1. In so doing, SDS confers a negative charge to the polypeptide in proportion to its length. Further, it is usually necessary to reduce disulfide bridges in proteins (denature) before they adopt the random-coil configuration necessary for separation by size; this is done with 2-mercaptoethanol or dithiothreitol (DTT). In denaturing SDS-PAGE separations therefore, migration is determined not by intrinsic electrical charge of the polypeptide, but by molecular weight.

Determination of molecular weight is done by SDS-PAGE of proteins of known molecular weight along with the protein to be characterized. A linear relationship exists between the logarithm of the molecular weight of an SDS-denatured polypeptide, or native nucleic acid, and its Rf. The Rf is calculated as the ratio of the distance migrated by the molecule to that migrated by a marker dye-front. A simple way of determining relative molecular weight by electrophoresis (Mr) is to plot a standard curve of distance migrated vs. log 10 MW for known samples, and read off the log Mr of the sample after measuring distance migrated on the same gel.

In two-dimensional electrophoresis, proteins are fractionated first on the basis of one physical property, and, in a second step, on the basis of another. For example, isoelectric focusing can be used for the first dimension, conveniently carried out in a tube gel, and SDS electrophoresis in a slab gel can be used for the second dimension. One example of a procedure is that of O'Farrell, P. H., High Resolution Two-dimensional Electrophoresis of Proteins, J. Biol. Chem. 250:4007-4021 (1975), herein incorporated by reference in its entirety for its teaching regarding two-dimensional electrophoresis methods. Other examples include but are not limited to, those found in Anderson, L and Anderson, NG, High resolution two-dimensional electrophoresis of human plasma proteins, Proc. Natl. Acad. Sci. 74:5421-5425 (1977), Ornstein, L., Disc electrophoresis, L. Ann. N.Y. Acad. Sci. 121:321349 (1964), each of which is herein incorporated by reference in its entirety for teachings regarding electrophoresis methods. Laemmli, U.K., Cleavage of structural proteins during the assembly of the head of bacteriophage T4, Nature 227:680 (1970), which is herein incorporated by reference in its entirety for teachings regarding electrophoresis methods, discloses a discontinuous system for resolving proteins denatured with SDS. The leading ion in the Laemmli buffer system is chloride, and the trailing ion is glycine. Accordingly, the resolving gel and the stacking gel are made up in Tris-HCl buffers (of different concentration and pH), while the tank buffer is Tris-glycine. All buffers contain 0.1% SDS.

One example of an immunoassay that uses electrophoresis that is contemplated in the current methods is Western blot analysis. Western blotting or immunoblotting allows the determination of the molecular mass of a protein and the measurement of relative amounts of the protein present in different samples. Detection methods include chemiluminescence and chromogenic detection. Standard methods for Western blot analysis can be found in, for example, D. M. Bollag et al., *Protein Methods* (2d edition 1996) and E. Harlow & D. Lane, *Antibodies, a Laboratory Manual* (1988), U.S. Pat. No. 4,452,901, each of which is herein incorporated by reference in their entirety for teachings regarding Western blot methods. Generally, proteins are separated by gel electrophoresis, usually SDS-PAGE. The proteins are transferred to a sheet of special blotting paper, e.g., nitrocellulose, though other types of paper, or membranes, can be used. The proteins retain the same pattern of separation they had on the gel. The blot is incubated with a generic protein (such as milk proteins) to bind to any remaining sticky places on the nitrocellulose. An antibody is then added to the solution which is able to bind to its specific protein.

The attachment of specific antibodies to specific immobilized antigens can be readily visualized by indirect enzyme immunoassay techniques, usually using a chromogenic substrate (e.g. alkaline phosphatase or horseradish peroxidase) or chemiluminescent substrates. Other possibilities for probing include the use of fluorescent or radioisotope labels (e.g., fluorescein, $^{125}I$). Probes for the detection of antibody binding can be conjugated anti-immunoglobulins, conjugated staphylococcal Protein A (binds IgG), or probes to biotinylated primary antibodies (e.g., conjugated avidin/streptavidin).

The power of the technique lies in the simultaneous detection of a specific protein by means of its antigenicity, and its molecular mass. Proteins are first separated by mass in the SDS-PAGE, then specifically detected in the immunoassay step. Thus, protein standards (ladders) can be run simultaneously in order to approximate molecular mass of the protein of interest in a heterogeneous sample.

The gel shift assay or electrophoretic mobility shift assay (EMSA) can be used to detect the interactions between DNA binding proteins and their cognate DNA recognition sequences, in both a qualitative and quantitative manner. Exemplary techniques are described in Ornstein L., Disc electrophoresis—I: Background and theory, Ann. NY Acad. Sci. 121:321-349 (1964), and Matsudiara, PT and DR Burgess, SDS microslab linear gradient polyacrylamide gel electrophoresis, Anal. Biochem. 87:386-396 (1987), each of which is herein incorporated by reference in its entirety for teachings regarding gel-shift assays.

In a general gel-shift assay, purified proteins or crude cell extracts can be incubated with a labeled (e.g., $^{32}P$-radiolabeled) DNA or RNA probe, followed by separation of the complexes from the free probe through a nondenaturing polyacrylamide gel. The complexes migrate more slowly through the gel than unbound probe. Depending on the activity of the binding protein, a labeled probe can be either double-stranded or single-stranded. For the detection of DNA binding proteins such as transcription factors, either purified or partially purified proteins, or nuclear cell extracts can be used. For detection of RNA binding proteins, either purified or partially purified proteins, or nuclear or cytoplasmic cell extracts can be used. The specificity of the DNA or RNA binding protein for the putative binding site is established by competition experiments using DNA or RNA fragments or oligonucleotides containing a binding site for the protein of interest, or other unrelated sequence. The differences in the nature and intensity of the complex formed in the presence of specific and nonspecific competitor allows identification of specific interactions.

Gel shift methods can include using, for example, colloidal forms of COOMASSIE (Imperial Chemicals Industries, Ltd) blue stain to detect proteins in gels such as polyacrylamide electrophoresis gels. Such methods are described, for example, in Neuhoff et al., Electrophoresis 6:427-448 (1985), and Neuhoff et al., Electrophoresis 9:255-262 (1988), each of which is herein incorporated by reference in its entirety for teachings regarding gel shift methods. In addition to the conventional protein assay methods referenced above, a combination cleaning and protein staining composition is described in U.S. Pat. No. 5,424,000, herein incorporated by reference in its entirety for its teaching regarding gel shift methods. The solutions can include phosphoric, sulfuric, and nitric acids, and Acid Violet dye.

Radioimmune Precipitation Assay (RIPA) is a sensitive assay using radiolabeled antigens to detect specific antibodies in serum. The antigens are allowed to react with the serum and then precipitated using a special reagent such as, for example, protein A sepharose beads. The bound radiolabeled immunoprecipitate is then commonly analyzed by gel electrophoresis. Radioimmunoprecipitation assay (RIPA) is often used as a confirmatory test for diagnosing the presence of HIV antibodies. RIPA is also referred to in the art as Farr Assay, Precipitin Assay, Radioimmune Precipitin Assay; Radioimmunoprecipitation Analysis; Radioimmunoprecipitation Analysis, and Radioimmunoprecipitation Analysis.

While the above immunoassays that utilize electrophoresis to separate and detect the specific proteins of interest allow for evaluation of protein size, they are not very sensitive for evaluating protein concentration. However, also contemplated are immunoassays wherein the protein or antibody specific for the protein is bound to a solid support (e.g., tube, well, bead, or cell) to capture the antibody or protein of interest, respectively, from a sample, combined with a method of detecting the protein or antibody specific for the protein on the support. Examples of such immunoassays include Radioimmunoassay (RIA), Enzyme-Linked Immunosorbent Assay (ELISA), Flow cytometry, protein array, multiplexed bead assay, and magnetic capture.

Radioimmunoassay (RIA) is a classic quantitative assay for detection of antigen-antibody reactions using a radioactively labeled substance (radioligand), either directly or indirectly, to measure the binding of the unlabeled substance to a specific antibody or other receptor system. Radioimmunoassay is used, for example, to test hormone levels in the blood without the need to use a bioassay. Non-immunogenic substances (e.g., haptens) can also be measured if coupled to larger carrier proteins (e.g., bovine gamma-globulin or human serum albumin) capable of inducing antibody formation. RIA involves mixing a radioactive antigen (because of the ease with which iodine atoms can be introduced into tyrosine residues in a protein, the radioactive isotopes $^{125}I$ or $^{131}I$ are often used) with antibody to that antigen. The antibody is generally linked to a solid support, such as a tube or beads. Unlabeled or "cold" antigen is then adding in known quantities and measuring the amount of labeled antigen displaced. Initially, the radioactive antigen is bound to the antibodies. When cold antigen is added, the two compete for antibody binding sites—and at higher concentrations of cold antigen, more binds to the antibody, displacing the radioactive variant. The bound antigens are separated from the unbound ones in solution and the radioactivity of each used to plot a binding curve. The technique is both extremely sensitive, and specific.

Enzyme-Linked Immunosorbent Assay (ELISA), or more generically termed EIA (Enzyme ImmunoAssay), is an immunoassay that can detect an antibody specific for a protein. In such an assay, a detectable label bound to either an antibody-binding or antigen-binding reagent is an enzyme. When exposed to its substrate, this enzyme reacts in such a manner as to produce a chemical moiety which can be detected, for example, by spectrophotometric, fluorometric or visual means. Enzymes which can be used to detectably label reagents useful for detection include, but are not limited to, horseradish peroxidase, alkaline phosphatase, glucose oxidase, β-galactosidase, ribonuclease, urease, catalase, malate dehydrogenase, staphylococcal nuclease, asparaginase, yeast alcohol dehydrogenase, alpha.-glycerophosphate dehydrogenase, triose phosphate isomerase, glucose-6-phosphate dehydrogenase, glucoamylase and acetylcholinesterase.

Variations of ELISA techniques are known to those of skill in the art. In one variation, antibodies that can bind to proteins can be immobilized onto a selected surface exhibiting protein affinity, such as a well in a polystyrene microtiter plate. Then, a test composition suspected of containing a marker antigen can be added to the wells. After binding and washing to remove non-specifically bound immunocomplexes, the bound antigen can be detected. Detection can be achieved by the addition of a second antibody specific for the target protein, which is linked to a detectable label. This type of ELISA is a simple "sandwich ELISA." Detection also can be achieved by the addition of a second antibody, followed by the addition of a third antibody that has binding affinity for the second antibody, with the third antibody being linked to a detectable label.

Another variation is a competition ELISA. In competition ELISA's, test samples compete for binding with known amounts of labeled antigens or antibodies. The amount of reactive species in the sample can be determined by mixing the sample with the known labeled species before or during incubation with coated wells. The presence of reactive species in the sample acts to reduce the amount of labeled species available for binding to the well and thus reduces the ultimate signal.

Regardless of the format employed, ELISAs have certain features in common, such as coating, incubating or binding, washing to remove non-specifically bound species, and detecting the bound immunecomplexes. Antigen or antibodies can be linked to a solid support, such as in the form of plate, beads, dipstick, membrane or column matrix, and the sample to be analyzed applied to the immobilized antigen or antibody. In coating a plate with either antigen or antibody, one will generally incubate the wells of the plate with a solution of the antigen or antibody, either overnight or for a specified period of hours. The wells of the plate can then be washed to remove incompletely adsorbed material. Any remaining available surfaces of the wells can then be "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, a secondary or tertiary detection means rather than a direct procedure can also be used. Thus, after binding of a protein or antibody to the well, coating with a non-reactive material to reduce background, and washing to remove unbound material, the immobilizing surface is contacted with the control clinical or biological sample to be tested under conditions effective to allow immunecomplex (antigen/antibody) formation. Detection of the immunecomplex then requires a labeled secondary binding agent or a secondary binding agent in conjunction with a labeled third binding agent.

Enzyme-Linked Immunospot Assay (ELISpot) is an immunoassay that can detect an antibody specific for a protein or antigen. In such an assay, a detectable label bound to either an antibody-binding or antigen-binding reagent is an enzyme. When exposed to its substrate, this enzyme reacts in such a manner as to produce a chemical moiety which can be detected, for example, by spectrophotometric, fluorometric or visual means. Enzymes which can be used to detectably label reagents useful for detection include, but are not limited to, horseradish peroxidase, alkaline phosphatase, glucose oxidase, β-galactosidase, ribonuclease, urease, catalase, malate dehydrogenase, staphylococcal nuclease, asparaginase, yeast alcohol dehydrogenase, alpha.-glycerophosphate dehydrogenase, triose phosphate isomerase, glucose-6-phosphate dehydrogenase, glucoamylase and acetylcholinesterase. In this assay a nitrocellulose microtiter plate is coated with antigen. The test sample is exposed to the antigen and then reacted similarly to an ELISA assay. Detection differs from a traditional ELISA in that detection is determined by the enumeration of spots on the nitrocellulose plate. The presence of a spot indicates that the sample reacted to the antigen. The spots can be counted and the number of cells in the sample specific for the antigen determined.

"Under conditions effective to allow immunecomplex (antigen/antibody) formation" means that the conditions include diluting the antigens and antibodies with solutions such as BSA, bovine gamma globulin (BGG) and phosphate buffered saline (PBS)/Tween so as to reduce non-specific binding and to promote a reasonable signal to noise ratio.

The suitable conditions also mean that the incubation is at a temperature and for a period of time sufficient to allow effective binding. Incubation steps can typically be from about 1 minute to twelve hours, at temperatures of about 20° to 30° C., or can be incubated overnight at about 0° C. to about 10° C.

Following all incubation steps in an ELISA, the contacted surface can be washed so as to remove non-complexed material. A washing procedure can include washing with a solution such as PBS/Tween or borate buffer. Following the formation of specific immunecomplexes between the test sample and the originally bound material, and subsequent washing, the occurrence of even minute amounts of immunecomplexes can be determined.

To provide a detecting means, the second or third antibody can have an associated label to allow detection, as described above. This can be an enzyme that can generate color development upon incubating with an appropriate chromogenic substrate. Thus, for example, one can contact and incubate the first or second immunecomplex with a labeled antibody for a period of time and under conditions that favor the development of further immunecomplex formation (e.g., incubation for 2 hours at room temperature in a PBS-containing solution such as PBS-Tween).

After incubation with the labeled antibody, and subsequent to washing to remove unbound material, the amount of label can be quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation can then be achieved by measuring the degree of color generation, e.g., using a visible spectra spectrophotometer.

Protein arrays are solid-phase ligand binding assay systems using immobilized proteins on surfaces which include glass, membranes, microtiter wells, mass spectrometer plates, and beads or other particles. The assays are highly parallel (multiplexed) and often miniaturized (microarrays, protein chips). Their advantages include being rapid and automatable, capable of high sensitivity, economical on reagents, and giving an abundance of data for a single experiment. Bioinformatics support is important; the data handling demands sophisticated software and data comparison analysis. However, the software can be adapted from that used for DNA arrays, as can much of the hardware and detection systems.

One of the chief formats is the capture array, in which ligand-binding reagents, which are usually antibodies but can also be alternative protein scaffolds, peptides or nucleic acid aptamers, are used to detect target molecules in mixtures such as plasma or tissue extracts. In diagnostics, capture arrays can be used to carry out multiple immunoassays in parallel, both testing for several analytes in individual sera for example and testing many serum samples simultaneously. In proteomics, capture arrays are used to quantitate and compare the levels of proteins in different samples in health and disease, i.e. protein expression profiling. Proteins other than specific ligand binders are used in the array format for in vitro functional interaction screens such as protein-protein, protein-DNA, protein-drug, receptor-ligand, enzyme-substrate, etc. The capture reagents themselves are selected and screened against many proteins, which can also be done in a multiplex array format against multiple protein targets.

For construction of arrays, sources of proteins include cell-based expression systems for recombinant proteins, purification from natural sources, production in vitro by cell-free translation systems, and synthetic methods for peptides. Many of these methods can be automated for high throughput production. For capture arrays and protein function analysis, it is important that proteins should be correctly folded and functional; this is not always the case, e.g. where recombinant proteins are extracted from bacteria under denaturing conditions. Nevertheless, arrays of denatured proteins are useful in screening antibodies for cross-reactivity, identifying autoantibodies and selecting ligand binding proteins.

Protein arrays have been designed as a miniaturization of familiar immunoassay methods such as ELISA and dot blotting, often utilizing fluorescent readout, and facilitated by robotics and high throughput detection systems to enable multiple assays to be carried out in parallel. Commonly used physical supports include glass slides, silicon, microwells, nitrocellulose or PVDF membranes, and magnetic and other microbeads. While microdrops of protein delivered onto planar surfaces are the most familiar format, alternative architectures include CD centrifugation devices based on developments in microfluidics (Gyros, Monmouth Junction, NJ) and specialised chip designs, such as engineered microchannels in a plate (e.g., The Living Chip™, Biotrove, Woburn, MA) and tiny 3D posts on a silicon surface (Zyomyx, Hayward CA). Particles in suspension can also be used as the basis of arrays, providing they are coded for identification; systems include colour coding for microbeads (Luminex, Austin, TX; Bio-Rad Laboratories) and semiconductor nanocrystals (e.g., QDots™, Quantum Dot, Hayward, CA), and barcoding for beads (UltraPlex™, SmartBead Technologies Ltd, Babraham, Cambridge, UK) and multimetal microrods (e.g., Nanobarcodes™ particles, Nanoplex Technologies, Mountain View, CA). Beads can also be assembled into planar arrays on semiconductor chips (LEAPS technology, BioArray Solutions, Warren, NJ).

Immobilization of proteins involves both the coupling reagent and the nature of the surface being coupled to. A good protein array support surface is chemically stable before and after the coupling procedures, allows good spot morphology, displays minimal nonspecific binding, does not contribute a background in detection systems, and is compatible with different detection systems. The immobilization method used are reproducible, applicable to proteins of different properties (size, hydrophilic, hydrophobic), amenable to high throughput and automation, and compatible with retention of fully functional protein activity. Orientation of the surface-bound protein is recognized as an important factor in presenting it to ligand or substrate in an active state; for capture arrays the most efficient binding results are obtained with orientated capture reagents, which generally require site-specific labeling of the protein.

Both covalent and noncovalent methods of protein immobilization are used and have various pros and cons. Passive adsorption to surfaces is methodologically simple, but allows little quantitative or orientational control; it may or may not alter the functional properties of the protein, and reproducibility and efficiency are variable. Covalent coupling methods provide a stable linkage, can be applied to a range of proteins and have good reproducibility; however, orientation may be variable, chemical derivatization may alter the function of the protein and requires a stable interactive surface. Biological capture methods utilizing a tag on the protein provide a stable linkage and bind the protein specifically and in reproducible orientation, but the biological reagent must first be immobilized adequately and the array may require special handling and have variable stability.

Several immobilization chemistries and tags have been described for fabrication of protein arrays. Substrates for covalent attachment include glass slides coated with amino- or aldehyde-containing silane reagents. In the Versalinx™ system (Prolinx, Bothell, WA) reversible covalent coupling is achieved by interaction between the protein derivatised with phenyldiboronic acid, and salicylhydroxamic acid immobilized on the support surface. This also has low background binding and low intrinsic fluorescence and allows the immobilized proteins to retain function. Noncovalent binding of unmodified protein occurs within porous structures such as HydroGel™ (PerkinElmer, Wellesley, MA), based on a 3-dimensional polyacrylamide gel; this substrate is reported to give a particularly low background on glass microarrays, with a high capacity and retention of protein function. Widely used biological coupling methods are through biotin/streptavidin or hexahistidine/Ni interactions, having modified the protein appropriately. Biotin may be conjugated to a poly-lysine backbone immobilized on a surface such as titanium dioxide (Zyomyx) or tantalum pentoxide (Zeptosens, Witterswil, Switzerland).

Array fabrication methods include robotic contact printing, ink-jetting, piezoelectric spotting and photolithography. A number of commercial arrayers are available [e.g. Packard Biosciences] as well as manual equipment [V & P Scientific] . Bacterial colonies can be robotically gridded onto PVDF membranes for induction of protein expression in situ.

At the limit of spot size and density are nanoarrays, with spots on the nanometer spatial scale, enabling thousands of reactions to be performed on a single chip less than 1 mm square. BioForce Laboratories have developed nanoarrays with 1521 protein spots in 85 sq microns, equivalent to 25 million spots per sq cm, at the limit for optical detection; their readout methods are fluorescence and atomic force microscopy (AFM).

Fluorescence labeling and detection methods are widely used. The same instrumentation as used for reading DNA microarrays is applicable to protein arrays. For differential display, capture (e.g., antibody) arrays can be probed with fluorescently labeled proteins from two different cell states, in which cell lysates are directly conjugated with different fluorophores (e.g. Cy-3, Cy-5) and mixed, such that the color acts as a readout for changes in target abundance. Fluorescent readout sensitivity can be amplified 10-100 fold by tyramide signal amplification (TSA) (PerkinElmer Lifesciences). Planar waveguide technology (Zeptosens) enables ultrasensitive fluorescence detection, with the additional advantage of no intervening washing procedures. High sensitivity can also be achieved with suspension beads and particles, using phycoerythrin as label (Luminex) or the properties of semiconductor nanocrystals (Quantum Dot). A number of novel alternative readouts have been developed, especially in the commercial biotech arena. These include adaptations of surface plasmon resonance (HTS Biosystems, Intrinsic Bioprobes, Tempe, AZ), rolling circle DNA amplification (Molecular Staging, New Haven CT), mass spectrometry (Intrinsic Bioprobes; Ciphergen, Fremont, CA), resonance light scattering (Genicon Sciences, San Diego, CA) and atomic force microscopy [BioForce Laboratories].

Capture arrays form the basis of diagnostic chips and arrays for expression profiling. They employ high affinity capture reagents, such as conventional antibodies, single domains, engineered scaffolds, peptides or nucleic acid aptamers, to bind and detect specific target ligands in high throughput manner.

Antibody arrays have the required properties of specificity and acceptable background, and some are available commercially (BD Biosciences, San Jose, CA; Clontech, Mountain View, CA; BioRad; Sigma, St. Louis, MO). Antibodies for capture arrays are made either by conventional immunization (polyclonal sera and hybridomas), or as recombinant fragments, usually expressed in *E. coli*, after selection from phage or ribosome display libraries (Cambridge Antibody Technology, Cambridge, UK; Biolnvent, Lund, Sweden; Affitech, Walnut Creek, CA; Biosite, San Diego, CA). In addition to the conventional antibodies, Fab and scFv fragments, single V-domains from camelids or engineered human equivalents (Domantis, Waltham, MA) may also be useful in arrays.

The term "scaffold" refers to ligand-binding domains of proteins, which are engineered into multiple variants capable of binding diverse target molecules with antibody-like properties of specificity and affinity. The variants can be produced in a genetic library format and selected against individual targets by phage, bacterial or ribosome display. Such ligand-binding scaffolds or frameworks include 'Affibodies' based on Staph. *aureus* protein A (Affibody, Bromma, Sweden), 'Trinectins' based on fibronectins (Phylos, Lexington, MA) and 'Anticalins' based on the lipocalin structure (Pieris Proteolab, Freising-Weihenstephan, Germany). These can be used on capture arrays in a similar fashion to antibodies and may have advantages of robustness and ease of production.

Nonprotein capture molecules, notably the single-stranded nucleic acid aptamers which bind protein ligands with high specificity and affinity, are also used in arrays (SomaLogic, Boulder, CO). Aptamers are selected from libraries of oligonucleotides by the Selex™ procedure and their interaction with protein can be enhanced by covalent attachment, through incorporation of brominated deoxyuridine and UV-activated crosslinking (photoaptamers). Photocrosslinking to ligand reduces the crossreactivity of aptamers due to the specific steric requirements. Aptamers have the advantages of ease of production by automated oligonucleotide synthesis and the stability and robustness of DNA; on photoaptamer arrays, universal fluorescent protein stains can be used to detect binding.

Protein analytes binding to antibody arrays may be detected directly or via a secondary antibody in a sandwich assay. Direct labelling is used for comparison of different samples with different colors. Where pairs of antibodies directed at the same protein ligand are available, sandwich immunoassays provide high specificity and sensitivity and are therefore the method of choice for low abundance proteins such as cytokines; they also give the possibility of detection of protein modifications. Label-free detection methods, including mass spectrometry, surface plasmon resonance and atomic force microscopy, avoid alteration of ligand. What is required from any method is optimal sensitivity and specificity, with low background to give high signal to noise. Since analyte concentrations cover a wide range, sensitivity has to be tailored appropriately; serial dilution of the sample or use of antibodies of different affinities are solutions to this problem. Proteins of interest are frequently those in low concentration in body fluids and extracts, requiring detection in the pg range or lower, such as cytokines or the low expression products in cells.

An alternative to an array of capture molecules is one made through 'molecular imprinting' technology, in which peptides (e.g., from the C-terminal regions of proteins) are used as templates to generate structurally complementary, sequence-specific cavities in a polymerizable matrix; the cavities can then specifically capture (denatured) proteins that have the appropriate primary amino acid sequence (ProteinPrint™, Aspira Biosystems, Burlingame, CA).

Another methodology which can be used diagnostically and in expression profiling is the ProteinChip® array (Ciphergen, Fremont, CA), in which solid phase chromatographic surfaces bind proteins with similar characteristics of charge or hydrophobicity from mixtures such as plasma or tumour extracts, and SELDI-TOF mass spectrometry is used to detection the retained proteins.

Large-scale functional chips have been constructed by immobilizing large numbers of purified proteins and used to assay a wide range of biochemical functions, such as protein interactions with other proteins, drug-target interactions, enzyme-substrates, etc. Generally they require an expression library, cloned into *E. coli*, yeast or similar from which the expressed proteins are then purified, e.g. via a His tag, and immobilized. Cell free protein transcription/translation is a viable alternative for synthesis of proteins which do not express well in bacterial or other in vivo systems.

For detecting protein-protein interactions, protein arrays can be in vitro alternatives to the cell-based yeast two-hybrid system and may be useful where the latter is deficient, such as interactions involving secreted proteins or proteins with disulphide bridges. High-throughput analysis of biochemical activities on arrays has been described for yeast protein kinases and for various functions (protein-protein and protein-lipid interactions) of the yeast proteome, where a large proportion of all yeast open-reading frames was expressed and immobilised on a microarray. Large-scale 'proteome chips' promise to be very useful in identification of functional interactions, drug screening, etc. (Proteometrix, Branford, CT).

As a two-dimensional display of individual elements, a protein array can be used to screen phage or ribosome display libraries, in order to select specific binding partners, including antibodies, synthetic scaffolds, peptides and aptamers. In this way, 'library against library' screening can be carried out. Screening of drug candidates in combinatorial chemical libraries against an array of protein targets identified from genome projects is another application of the approach.

A multiplexed bead assay, such as, for example, the BD™ Cytometric Bead Array, is a series of spectrally discrete particles that can be used to capture and quantitate soluble analytes. The analyte is then measured by detection of a fluorescence-based emission and flow cytometric analysis. Multiplexed bead assay generates data that is comparable to ELISA based assays, but in a "multiplexed" or simultaneous fashion. Concentration of unknowns is calculated for the cytometric bead array as with any sandwich format assay, i.e. through the use of known standards and plotting unknowns against a standard curve. Further, multiplexed bead assay allows quantification of soluble analytes in samples never previously considered due to sample volume limitations. In addition to the quantitative data, powerful visual images can be generated revealing unique profiles or signatures that provide the user with additional information at a glance.

Accordingly, in one aspect, disclosed herein are methods of identifying neoantigens any neoantigen disclosed herein, wherein the T cell activity (such as, for example, release of cytokines including, but not limited to IFN-γ, TGF-β, lymphotoxin-α, IL-2, IL-4, IL-10, IL-17, or IL-25) is measured by ELISA, ELISpot, Intracellular cytokine staining, or Chromium Release.

It is understood and herein contemplated that the disclosed methods of identifying neoantigens can be used to identify neoantigens in any cancer, including, but not limited to B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, lung cancers, small cell lung cancer, non-small cell lung cancer, neuroblastoma, glioblastoma, ovarian cancer, pancreatic cancer, prostate cancer, skin cancers, melanoma, basal cell carcinoma, squamous cell carcinoma, liver cancer, squamous cell carcinomas of the mouth, throat, larynx, and lung, cervical cancer, cervical carcinoma, breast cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, AIDS-related lymphomas, or AIDS-related sarcomas. Therefore, in one aspect, also disclosed herein are methods of identifying any neoantigen disclosed herein, wherein the cancer is selected from the group consisting of B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, lung cancers, small cell lung cancer, non-small cell lung cancer, neuroblastoma, glioblastoma, ovarian cancer, pancreatic cancer, prostate cancer, skin cancers, melanoma, basal cell carcinoma, squamous cell carcinoma, liver cancer, squamous cell carcinomas of the mouth, throat, larynx, and lung, cervical cancer, cervical carcinoma, breast cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, AIDS-related lymphomas, or AIDS-related sarcomas.

C. COMPOSITIONS

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular neoantigen is disclosed and discussed and a number of modifications that can be made to a number of molecules including the neoantigen are discussed, specifically contemplated is each and every combination and permutation of neoantigen and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

The methods disclosed herein identify neoantigens that can be used in compositions for the treatment of cancer (either as a therapeutic treatment or prophylactic treatment) as well as for the creating of CAR T cells, TCR T cells, and/or TILs that can be used to treat cancer. Thus, in one aspect, also disclosed herein are neoantigens identified by the methods of identifying any neoantigen disclosed herein. For example, disclosed herein are polypeptides comprising the amino acid sequence AEPKRKSSLFWHAFNRLTPFRK (SEQ ID NO: 2) or a fragment thereof comprising at least 9 amino acids, wherein any fragment of the sequence at least comprises LFWHAFNRL (SEQ ID NO: 7), for example, SSLFWHAFNRLTP (SEQ ID NO: 4), RKSSLFWHAFNRL (SEQ ID NO: 3), RKSSLFWHAFNRLTPFR (SEQ ID NO: 6), LFWHAFNRLTPFR (SEQ ID NO: 5), SLFWHAFNRL (SEQ ID NO: 88), SSLFWHAFNRL (SEQ ID NO: 89), SSLFWHAFNRLT (SEQ ID NO: 90), LFWHAFNRLT (SEQ ID NO: 91), LFWHAFNRLTP (SEQ ID NO: 92), SLFWHAFNRLT (SEQ ID NO: 93), LFWHAFNRLTPF (SEQ ID NO: 94); a polypeptide comprising the amino acid sequence FQLLLEKPFQIFCAELWVRDINDHA (SEQ ID NO: 9) or a fragment thereof comprising at least 13 amino acids, wherein any fragment of the sequence at least comprises LEKPFQIFCAELW (SEQ ID NO: 12), for example, LEKPFQIFCAELWV (SEQ ID NO: 95) and LEKPFQIFCAELWVR (SEQ ID NO: 96); a polypeptide comprising the amino acid sequence ENSPLGTEFPLNYALDLDVGSNNVQ (SEQ ID NO: 14) or a fragment thereof comprising at least 13 amino acids, wherein any fragment of the sequence at least comprises LGTEFPLNYALDL (SEQ ID NO: 17), for example LGTEFPLNYALDLD (SEQ ID NO: 97), LGTEFPLNYALDLDV (SEQ ID NO: 98), LGTEFPLNYALDLDVG (SEQ ID NO: 99), LGTEFPLNYALDLDVGS (SEQ ID NO: 100), LGTEFPLNYALDLDVGSN (SEQ ID NO: 101), LGTEFPLNYALDLDVGSNN (SEQ ID NO: 102), LGTEFPLNYALDLDVGSNNV (SEQ ID NO: 103), LGTEFPLNYALDLDVGSNNVQ (SEQ ID NO: 104), ENSPLGTEFPLNYALDL (SEQ ID NO: 105), NSPLGTEFPLNYALDL (SEQ ID NO: 106), SPLGTEFPLNYALDL (SEQ ID NO: 107), PLGTEFPLNYALDL (SEQ ID NO: 108), PLGTEFPLNYALDLD (SEQ ID NO: 109), PLGTEFPLNYALDLDV (SEQ ID NO: 110), SPLGTEFPLNYALDLD (SEQ ID NO: 111), SPLGTEFPLNYALDLDV (SEQ ID NO: 112), NSPLGTEFPLNYALDLDV (SEQ ID NO: 113), and ENSPLGTEFPLNYALDLDV (SEQ ID NO: 114); a polypeptide comprising the amino acid sequence MTDDKDVLRNVWFGRIPTCFT (SEQ ID NO: 19) or a fragment thereof comprising at least 11 amino acids, wherein any fragment of the sequence at least comprises KDVLRNVWFGR (SEQ ID NO: 23), for example, DDKDVLRNVWFGR (SEQ ID NO: 22), KDVLRNVWFGRIP (SEQ ID NO: 21), DDKDVLRNVWFGRIP (SEQ ID NO: 24), DKDVLRNVWFGR (SEQ ID NO: 115), KDVLRNVWFGRI (SEQ ID NO: 116), DKDVLRNVWFGRI (SEQ ID NO: 117), DKDVLRNVWFGRIP (SEQ ID NO: 118), DDKDVLRNVWFGRI (SEQ ID NO: 119), DDKDVLRNVWFGRIPT (SEQ ID NO: 120), DDKDVLRNVWFGRIPTC (SEQ ID NO: 121), and TDDKDVLRNVWFGRIPT (SEQ ID NO: 122); a polypeptide comprising the amino acid sequence RLKASLDRPFTNSESAFYSIVGLSS (SEQ ID NO: 26) or a fragment thereof comprising at least 10 amino acids, wherein any fragment of the sequence at least comprises PFTNSESAFY (SEQ ID NO: 30), for example, DRPFTNSESAFYS (SEQ ID NO: 28), PFTNSESAFYS (SEQ ID NO: 123), PFTNSESAFYSI (SEQ ID NO: 124), PFTNSESAFYSIV (SEQ ID NO: 29), RPFTNSESAFY (SEQ ID NO: 125), RPFTNSESAFYS (SEQ ID NO: 126), RPFTNSESAFYSI (SEQ ID NO: 127), RPFTNSESAFYSIV (SEQ ID NO: 128), DRPFTNSESAFY (SEQ ID NO: 129), DRPFTNSESAFYSI (SEQ ID NO: 130), and DRPFTNSESAFYSIV (SEQ ID NO: 131); a polypeptide comprising the amino acid sequence GSGEKVAGRVIVKVCEVTRVKAVRI (SEQ ID NO: 32) or a fragment thereof comprising at least 9 amino acids, wherein any fragment of the sequence at least comprises RVIVKVCEV (SEQ ID NO: 36), for example, KVAGRVIVKVCEV (SEQ ID NO: 33), AGRVIVKVCEVTR (SEQ ID NO: 34), KVAGRVIVKVCEVTRVK (SEQ ID NO: 32), RVIVKVCEVTRVK (SEQ ID NO: 35), and KVAGRVIVKVCEVTRVK (SEQ ID NO: 37); a polypeptide comprising the amino acid sequence YGMYFCMNISSQEDGACVLLRALEP (SEQ ID NO: 39) or a fragment thereof comprising at least 10 amino acids, wherein any fragment of the sequence at least comprises ISSQEDGACV (SEQ ID NO: 43), for example, MNISSQEDGACVL (SEQ ID NO: 41), ISSQEDGACVLLR (SEQ ID NO: 42), MNISSQEDGACVLLR (SEQ ID NO: 44), ISSQEDGACVL (SEQ ID NO: 132), ISSQEDGACVLL (SEQ ID NO: 133), NISSQEDGACV (SEQ ID NO: 134), NISSQEDGACVL (SEQ ID NO: 135), NISSQEDGACVLL, (SEQ ID NO: 136), NISSQEDGACVLLR (SEQ ID NO: 137), and MNISSQEDGACVLL (SEQ ID NO: 138); a polypeptide comprising the amino acid sequence MKLTSLMCNPVKSPFFGCVCGHVPISMCVSTCSSLPTASCALDLTVLAENSHQVGA (SEQ ID NO: 46) or a fragment thereof comprising at least 26 amino acids, wherein any fragment of the sequence at least comprises VSTCSSLPTASCALDLTVLAENSHQV (SEQ ID NO: 60), for example, MCNPVKSPFFGCVCGHVPISMCVSTCSSLPTASCALDLTVLAENSHQVGA (SEQ ID NO: 49), KSPFFGCV CGHVPISMCVSTCSSLPTASCALDLTVLAENSHQVGA (SEQ ID NO: 50), GCVCGHVPISMCVSTCSSLPTASCALDLTVLAENSHQVGA (SEQ ID NO: 51), GHV PISMCVSTCSSLPTASCALDLTVLAENSHQVGA (SEQ ID NO: 52), SMCVSTCSSLPTASCALDLTVLAENSHQ VGA (SEQ ID NO: 53), VSTCSSLPTASCALDLTVLAENSHQVGA (SEQ ID NO: 54), MCNPVKSPF FGCVCGHVPISMCVSTCSSLPTASCALDLTVLAENSHQV (SEQ ID NO: 57), VSTCSSLPTASCALDLTVLAENSHQVG (SEQ ID NO: 139), CVSTCSSLPTASCALDLTVLAENSHQV (SEQ ID NO: 140), MCV STCSSLPTASCALDLTVLAENSHQV (SEQ ID NO: 141), MCVSTCSSLPTASCALDLTVLAENSHQVG (SEQ ID NO: 142), SMCVSTCSSLPTASCALDLTVLAENSHQV (SEQ ID NO: 143), SMCVSTCSSLPTASCALDLTVLAENSHQVG (SEQ ID NO: 144); a polypeptide comprising the amino acid sequence MLMAQEALAFLMAQGAMLAAQERRVPRAAEVPGAQGQQGPRGREEAPRGVRMAVPLLRR MEGAPAGPGGRTAACLSCTSRCLSRRPWKRSWSAGSCPGMPHRSPDQGRF (SEQ ID NO: 67) or a fragment thereof comprising at least 61 amino acids, wherein any fragment of the sequence at least comprises VPRAAEVPGAQGQQGPRGREEAPRGVRMAVPLLRRMEGAPAGPGGRTAACLSCTSRCLSRR (SEQ ID NO: 73), for example, QERRVPRAAEVPGAQGQQGPRGREEAPRGVRMAVPLLRRMEGAPAGPGGRTAACLSCTSRC LSRRPWKR (SEQ ID NO: 74), RVPRAAEVPGAQGQQGPRGREEAPRGVRMAVPLLRRMEGAPAGPGGRTAACLSCTSRCLSR R (SEQ ID NO: 145), RRVPRAAEVPGAQGQQGPRGREEAPRGVRMAVPLLRRMEGAPAGPGGRTAACLSCTSRCLS RR (SEQ ID NO: 146), ERRVPRAAEVPGAQGQQGPRGREEAPRGVRMAVPLLRRMEGAPAGPGGRTAACLSCTSRCL SRR (SEQ ID NO: 147), QERRVPRAAEVPGAQGQQGPRGREEAPRGVRMA VPLLRRMEGAPAGPGGRTAACLSCTSRC LSRR (SEQ ID NO: 148), RVPRAAEVPGAQGQQGPRGREEAP RGVRMAVPLLRRMEGAPAGPGGRTAACLSCTSRCLSR RP (SEQ ID NO: 149), RRVPRAAEVPGA QGQQGPRGREEAPRGVRMAVPLLRRMEGAPAGPGGRTAACLSCTSRCLS RRP (SEQ ID NO: 150), ERRVPRAAEVPGAQGQQGPRGREEAPRGVRMAV PLLRRMEGAPAGPGGRTAACLSCTSRCL SRRP (SEQ ID NO: 151), QERRVPRAAEVPGAQGQQGPRGREEAPRGVRMAVPLLRRMEGAPAGPGGRTAACLSCTSRC LSRRP (SEQ ID NO: 152), RVPRAAEVPGAQGQQGPRGREEAPRGVRMAVPLLRRMEGAPAGPGGRTAACLSCTSRCLSR RPW (SEQ ID NO: 153), RRV PRAAEVPGAQGQQGPRGREEAPRGVRMAVPLLRRMEGAPAGPGGRTAACLSCTSRCLS RRPW (SEQ ID NO: 154), ERRVPRAAEVPGAQGQQGPRGREEAPRG VRMAVPLLRRMEGAPAGPGGRTAACLSCTSRCL SR RPW (SEQ ID NO: 155), QERRVPRAAEVPGAQGQ QGPRGREEAPRGVRMAVPLLRRMEGAPAGPGGRTAACLSCTSRC LSRRPW (SEQ ID NO: 156), RVPRAAEVPGAQGQQGPRGREEAPRGVRMAVPLL RRMEGAPAGPGGRTAACLSCTSRCLSR RPWK (SEQ ID NO: 157), RRVPRAAEVPGAQGQQGPRGREEAPRGVRMAVPLLRRMEGAPAGPGGRTAACLSCTSRCLS RRPWK (SEQ ID NO: 158), ERRVPRAAEVPGAQGQQGPRGREEAPRGVRMAVPLLRRMEGAPAGPGGRTAACLSCTSRCL SRRPWK (SEQ ID NO: 159), QERRVPRAAEVPGAQGQQGPRGREEAPRGVRMAV PLLRRMEGAPAGPGGRTAACLSCTSRC LSRRPWK (SEQ ID NO: 160), RVPRAAEVPGAQGQQGPRGREEAPRGVRMAVPLLRRMEGAPAGPGGRTAACLSCTSRCLSR RPWKR (SEQ ID NO: 161), RRVPRAAEVPGAQGQQGPRGREEAPRGVRMAVPLLRRMEGAPAGPGGRTAACLSCTSRCLS RRPWKR (SEQ ID NO: 162), ERRVPRAAEVPGAQGQQGPRGREEAPRGVRMAV PLLRRMEGAPAGPGGRTAACLSCTSRCL SRRPWKR (SEQ ID NO: 163), EALAFLMAQGAMLAAQER RVPRAAEVPGAQGQQGPRGREEAPRGVRMAVP LLRRMEGAPA GPGGRTAACLSCTSRCLSRRPWKRSWSAGSCPGMPHRSP (SEQ ID NO: 61), EALAFLMAQGAMLAAQERRVPRAAEVPGAQGQQGPRGREEAPRGVRMAVPLLRRMEGAPA GPGGRTAACLSCT SRCLSRRPWKRSWSAGSCPGM (SEQ ID NO: 62), EALAFLMAQGAMLAAQERRVPRAAEVPGAQG QQ GPRGREEAPRGVRMAVPLLRRMEGAPA GPGGRTAACLSCTSRCLSRRPWKRSWSAG (SEQ ID NO: 63), EALAFLMAQGAMLAAQERRVPRAAEVPGAQGQQ GPRGREEAPRGVRMAVPLLRRMEGAPA GPGGRTAACLSCTSRCLSRRPWKR (SEQ ID NO: 64), LMAQGAMLAAQERRVPRAAEVPGAQGQQGPRGREEAPRGVRMAVPLLRRMEGAPAGPGG RTAACLSCTSRCLSR RPWKRSWSAGSCPGMPHRSPDQGRF (SEQ ID NO: 68), AMLAAQERRVPRAAEVPGAQGQQGPRGREEAPRGVRMAVPLLRRMEGAPAGPGGRTAACL SCTSRCLSRRPWKRSWSAGSCPGMPHRSPDQGRF (SEQ ID NO: 69), and QERRVPRAAEVPGAQGQQGPRGREEAPRGVRMAVPLLRRMEGAPAGPGGRTAACLSCTSRC LSRRPWKRSWSAGSCPGMPHRSPDQGRF (SEQ ID NO: 70); a polypeptide comprising the amino acid sequence as set forth in SEQ ID NO: 76 (KDAARPAYWVPDYEILHCHNCRKEF); a polypeptide comprising the amino acid sequence as set forth in SEQ ID NO: 78 (SMPLWDFQGSTMRTSQYVRLTPDER); a polypeptide comprising the amino acid sequence as set forth in SEQ ID NO: 80 (YPGIKFEELFPDCIFPSESERDKIK); a polypeptide comprising the amino acid sequence as set forth in SEQ ID NO: 82 (LLKTRRILKCSYLYGFFLEPKSTKK); a polypeptide comprising the amino acid sequence as set forth in SEQ ID NO: 84 (PFYLGHTIKSGDFEYVGMEGGIVLS); a polypeptide comprising the amino acid sequence as set forth in SEQ ID NO: 86 (LLLAGYLAQQYLLLPTPKVIGIDLG); a polypeptide comprising the amino acid sequence as set forth in SEQ ID NO: 166 (TSMLILSNLVFLEGNEVGKTYWNRI); and/or variant of any of the preceding polypeptides or polypeptide fragments comprising a conservative amino acid substitution. Also disclosed are CAR T cells engineered to express a receptor (such as, for example, a T cell receptor) that can recognize one or more of the neoantigens disclosed herein. In one aspect, the TCR T cell, CAR T cell, or TIL specific for one or more of the neoantigens disclosed herein can be further engineered to knockout or knockdown Zinc finger and BTB domain-containing protein 7B (ThPOK), Lysine-specific histone demethylase 1 (LSD1), programmed cell death protein (PD1), and/or protein phosphatase (PP2A) to enhance their function such as cytotoxic activity and persistence or survival in vivo after adoptive transfer to a cancer patient. In one aspect, the TCR T cell, CAR T cell, or TIL specific for one or more of the neoantigens disclosed herein is treated with a small molecular inhibitors such 2-PAPC to enhance T cell cytotoxic activity or the ability to proliferate and survive in vivo.

It is understood and herein contemplated that the disclosed that once the sequence of the neoantigens is identified, the skilled artisan would have full knowledge of the nucleic acids that would encode said amino acid neoantigens and it would be well within the skill set of the skilled artisan to make said nucleic acid constructs. Thus, in one aspect, also disclosed herein are nucleic acids encoding a polypeptide for any neoantigen disclosed herein.

1. Homology

It is understood that one way to define any known variants and derivatives or those that might arise, of the disclosed genes and proteins herein is through defining the variants and derivatives in terms of homology and/or identify to specific known sequences. For example SEQ ID NO: 1 sets forth a particular sequence of an MHC Class II epitope peptide. Specifically disclosed are variants of these and other genes and proteins herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent homology to the stated sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman *Adv. Appl. Math.* 2: 482 (1981), by the homology alignment algorithm of Needleman and Wunsch, *J. MoL Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, WI), or by inspection.

The same types of homology can be obtained for nucleic acids by for example the algorithms disclosed in Zuker, M. *Science* 244:48-52, 1989, Jaeger et al. Proc. Natl. Acad. Sci. USA 86:7706-7710, 1989, Jaeger et al. *Methods Enzymol.* 183:281-306, 1989 which are herein incorporated by reference for at least material related to nucleic acid alignment.

2. Nucleic Acids

There are a variety of molecules disclosed herein that are nucleic acid based, including for example the nucleic acids that encode, for example SEQ ID NO: 1, or any of the nucleic acids disclosed herein or fragments thereof, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

a) Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate). There are many varieties of these types of molecules available in the art and available herein.

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties. There are many varieties of these types of molecules available in the art and available herein.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid. There are many varieties of these types of molecules available in the art and available herein.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., *Proc. Natl. Acad. Sci. USA,* 1989, 86, 6553-6556). There are many varieties of these types of molecules available in the art and available herein.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

b) Primers and Probes

Disclosed are compositions including primers and probes, which are capable of interacting with the disclosed nucleic acids, such as the neoantigens disclosed herein. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the disclosed nucleic acids or region of the nucleic acids or they hybridize with the complement of the nucleic acids or complement of a region of the nucleic acids.

The size of the primers or probes for interaction with the nucleic acids in certain embodiments can be any size that supports the desired enzymatic manipulation of the primer, such as DNA amplification or the simple hybridization of the probe or primer. A typical primer or probe would be at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments a primer or probe can be less than or equal to 6, 7, 8, 9, 10, 11, 12 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In certain embodiments this product is at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments the product is less than or equal to 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

3. Peptides a) Protein Variants

As discussed herein there are numerous variants of the neoantigens that are known and herein contemplated. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

Amino Acid Abbreviations

| Amino Acid | Abbreviations | |
|---|---|---|
| Alanine | Ala | A |
| allosoleucine | AIle | |
| Arginine | Arg | R |
| asparagine | Asn | N |
| aspartic acid | Asp | D |
| Cysteine | Cys | C |
| glutamic acid | Glu | E |
| Glutamine | Gln | Q |
| Glycine | Gly | G |
| Histidine | His | H |
| Isolelucine | Ile | I |
| Leucine | Leu | L |
| Lysine | Lys | K |
| phenylalanine | Phe | F |
| proline | Pro | P |
| pyroglutamic acid | pGlu | |
| Serine | Ser | S |
| Threonine | Thr | T |
| Tyrosine | Tyr | Y |

TABLE 1-continued

| Amino Acid Abbreviations | | |
|---|---|---|
| Amino Acid | Abbreviations | |
| Tryptophan | Trp | W |
| Valine | Val | V |

TABLE 2

| Amino Acid Substitutions Original Residue Exemplary Conservative Substitutions, others are known in the art. | |
|---|---|
| Ala | Ser |
| Arg | Lys; Gln |
| Asn | Gln; His |
| Asp | Glu |
| Cys | Ser |
| Gln | Asn, Lys |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman *Adv. Appl. Math.* 2: 482 (1981), by the homology alignment algorithm of Needleman and Wunsch, *J. MoL Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, WI), or by inspection.

The same types of homology can be obtained for nucleic acids by for example the algorithms disclosed in Zuker, M. *Science* 244:48-52, 1989, Jaeger et al. Proc. Natl. Acad. Sci. USA 86:7706-7710, 1989, Jaeger et al. *Methods Enzymol.* 183:281-306, 1989.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

It is understood that there are numerous amino acid and peptide analogs which can be incorporated into the disclosed compositions. For example, there are numerous D amino acids or amino acids which have a different functional substituent then the amino acids shown in Table 1 and Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way.

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—, —CH═CH— (cis and trans), —$COCH_2$—, —CH(OH)$CH_2$—, and —$CHH_2SO$— (These and others can be found in Spatola, A. F. in *Chemistry and Biochemistry of Amino Acids, Peptides, and Proteins*, B. Weinstein, eds., Marcel Dekker, New York, p. 267 (1983); Spatola, A. F., *Vega Data* (March 1983), Vol. 1, Issue 3, Peptide Backbone Modifications (general review); Morley, *Trends Pharm Sci* (1980) pp. 463-468; Hudson, D. et al., Int J Pept Prot Res 14:177-185 (1979) (—$CH_2NH$—, $CH_2CH_2$—); Spatola et al. *Life Sci* 38:1243-1249 (1986) (—CH $H_2$—S); Hann *J. Chem. Soc Perkin Trans*. I 307-314 (1982) (—CH—CH—, cis and trans); Almquist et al. *J. Med. Chem.* 23:1392-1398 (1980) (—$COCH_2$—); Jennings-White et al. Tetrahedron Lett 23:2533 (1982) (—$COCH_2$—); Szelke et al. European Appln, EP 45665 CA (1982): 97:39405 (1982) (—CH(OH)$CH_2$—); Holladay et al. *Tetrahedron*. Lett 24:4401-4404 (1983) (—C(OH)$CH_2$—); and Hruby *Life Sci* 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations.

4. Pharmaceutical Carriers/Delivery of Pharmaceutical Products

In one aspect, it is understood and herein contemplated that the disclosed neoantigens can be administered as compositions to a subject with a cancer or likely to develop a cancer. Accordingly, disclosed herein are compositions comprising a therapeutically effective amount of one or more of the neoantigens disclosed herein (including, but not limited to peptides, polypeptides, and proteins of the neoantigens). Additionally, disclosed herein are compositions comprising a therapeutically effective amount of one or more CAR T cells, TCR T-cells and/or TILs; wherein the CAR T cell, TCR T cell, and/or TIL has been engineered to express a receptor for one or more of the neoantigens disclosed herein. In one aspect, the TCR T cell, CAR T cell, or TIL specific for one or more of the neoantigens disclosed herein can be further engineered to knockout or knockdown Zinc finger and BTB domain-containing protein 7B (ThPOK), Lysine-specific histone demethylase 1 (LSD1), programmed cell death protein (PD1), and/or Protein phosphatase 2 (PP2A) to enhance their function such as cytotoxic activity and persistence or survival in vivo after adoptive transfer to a cancer patient. In one aspect, the TCR T cell, CAR T cell, or TIL specific for one or more of the neoantigens disclosed herein is treated with a small molecular inhibitors such 2-PAPC to enhance T cell cytotoxic activity or the ability to proliferate and survive in vivo.

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.,* 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.,* 4:3-9, (1993); Battelli, et al., *Cancer Immunol. Immunother.,* 35:421-425, (1992); Pietersz and McKenzie, *Immunolog. Reviews,* 129:57-80, (1992); and Roffler, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, PA 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of the antibody used alone might range from about 1 μg/kg to up to 100 mg/kg of body weight or more per day, depending on the factors mentioned above.

D. METHODS OF USING THE COMPOSITIONS

1. Method of Treating Cancer

The disclosed compositions can be used to treat any disease where uncontrolled cellular proliferation occurs such as cancers. Accordingly, in one aspect, disclosed herein are methods of stimulating an immunological response against a cancer or treating, inhibiting, and/or preventing a cancer comprising administering to a subject a composition comprising a therapeutically effective amount of any of the neoantigens disclosed herein (for example SEQ ID NO: 2, SEQ ID NO: 3, SEQ ID NO: 4, SEQ ID NO: 5, SEQ ID NO: 6, SEQ ID NO: 7, SEQ ID NO: 9, SEQ ID NO: 12, SEQ ID NO: 14, SEQ ID NO: 17, SEQ ID NO: 19, SEQ ID NO: 21, SEQ ID NO: 22, SEQ ID NO: 23, SEQ ID NO: 24, SEQ ID NO: 26, SEQ ID NO: 28, SEQ ID NO: 29, SEQ ID NO: 30, SEQ ID NO: 32, SEQ ID NO: 33, SEQ ID NO: 34, SEQ ID NO: 35, SEQ ID NO: 36, SEQ ID NO: 37, SEQ ID NO: 39, SEQ ID NO: 41, SEQ ID NO: 42, SEQ ID NO: 43, SEQ ID NO: 44, SEQ ID NO: 46, SEQ ID NO: 49, SEQ ID NO: 50, SEQ ID NO: 51, SEQ ID NO: 52, SEQ ID NO: 53, SEQ ID NO: 54, SEQ ID NO: 57, SEQ ID NO: 60, SEQ ID NO: 61, SEQ ID NO: 62, SEQ ID NO: 63, SEQ ID NO: 64, SEQ ID NO: 67, SEQ ID NO: 68, SEQ ID NO: 69, SEQ ID NO: 70, SEQ ID NO: 73, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, and/or SEQ ID NO: 163) and/or any neoantigens identified by the method of identifying a neoantigen disclosed herein. In one aspect, it is understood and herein contemplated that the disclosed neoantigens include peptide, polypeptides, and/or proteins of any disclosed neoantigen.

The term "therapeutically effective" refers to the amount of the composition used is of sufficient quantity to ameliorate one or more causes or symptoms of a disease or disorder. Such amelioration only requires a reduction or alteration, not necessarily elimination.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

A non-limiting list of different types of cancers that can be treated by the disclosed methods is as follows: lymphomas (Hodgkins and non-Hodgkins), leukemias, carcinomas, carcinomas of solid tissues, squamous cell carcinomas, adenocarcinomas, sarcomas, gliomas, high grade gliomas, blastomas, neuroblastomas, plasmacytomas, histiocytomas, melanomas, adenomas, hypoxic tumors, myelomas, AIDS-related lymphomas or sarcomas, metastatic cancers, or cancers in general.

A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon cancer, and/or rectal cancers.

2. Methods of Treating Autoimmune Diseases

In one aspect, it is understood and herein contemplated that the disclosed neoantigens can be used in the treatment of autoimmune diseases. As used herein, "autoimmune disease" refers to a set of diseases, disorders, or conditions resulting from an adaptive immune response (T cell and/or B cell response) against the host organism. In such conditions, either by way of mutation or other underlying cause, the host T cells and/or B cells and/or antibodies are no longer able to distinguish host cells from non-self-antigens and attack host cells baring an antigen for which they are specific. Examples of autoimmune diseases that can cause an inflammatory skin disorder include, but are not limited to Achalasia, Acute disseminated encephalomyelitis, Acute motor axonal neuropathy, Addison's disease, Adiposis dolorosa, Adult Still's disease, Agammaglobulinemia, Alopecia areata, Alzheimer's disease, Amyloidosis, Ankylosing spondylitis, Anti-GBM/Anti-TBM nephritis, Antiphospholipid syndrome, Aplastic anemia, Autoimmune angioedema, Autoimmune dysautonomia, Autoimmune encephalomyelitis, Autoimmune enteropathy, Autoimmune hemolytic anemia, Autoimmune hepatitis, Autoimmune inner ear disease (AIED), Autoimmune myocarditis, Autoimmune oophoritis, Autoimmune orchitis, Autoimmune pancreatitis, Autoimmune polyendocrine syndrome, Autoimmune retinopathy, Autoimmune urticaria, Axonal & neuronal neuropathy (AMAN), Baló disease, Behcet's disease, Benign mucosal emphigoid, Bickerstaffs encephalitis, Bullous pemphigoid, Castleman disease (CD), Celiac disease, Chagas disease, Chronic fatigue syndrome, Chronic inflammatory demyelinating polyneuropathy (CIDP), Chronic recurrent multifocal osteomyelitis (CRMO), Churg-Strauss Syndrome (CSS), Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Diabetes mellitus type 1, Discoid lupus, Dressler's syndrome, Endometriosis, Enthesitis, Eosinophilic esophagitis (EoE), Eosinophilic fasciitis, Erythema nodosum, Essential mixed cryoglobulinemia, Evans syndrome, Felty syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's encephalopathy, Hashimoto's thyroiditis, Hemolytic anemia, Henoch-Schonlein purpura (HSP), Herpes gestationis or pemphigoid gestationis (PG), Hidradenitis Suppurativa (HS) (Acne Inversa), Hypogammalglobulinemia, IgA Nephropathy, IgG4-related sclerosing disease, Immune thrombocytopenic purpura (ITP), Inclusion body myositis (IBM), Interstitial cystitis (IC), Inflamatory Bowel Disease (IBD), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus nephritis, Lupus vasculitis, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Ord's thyroiditis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome, Polyarteritis *nodosa*, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Rheumatoid vasculitis, Sarcoidosis, Schmidt syndrome, Schnitzler syndrome, Scleritis, Scleroderma, Sjögren's syndrome, Sperm & testicular autoimmunity, Stiff person syndrome (SPS), Subacute bacterial endocarditis (SBE), Susac's syndrome, Sydenham chorea, Sympathetic ophthalmia (SO), Systemic Lupus Erythematosus, Systemic scleroderma, Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Urticaria, Urticarial vasculitis, Uveitis, Vasculitis, Vitiligo, Vogt-Koyanagi-Harada Disease, and Wegener's granulomatosis (or Granulomatosis with Polyangiitis (GPA)). Accordingly, in one aspect, disclosed herein are methods of stimulating an immunological response against an autoimmune disease or treating, inhibiting, and/or preventing an autoimmune disease comprising administering to a subject a composition comprising a therapeutically effective amount of any of the neoantigens disclosed herein (for example SEQ ID NO: 2, SEQ ID NO: 3, SEQ ID NO: 4, SEQ ID NO: 5, SEQ ID NO: 6, SEQ ID NO: 7, SEQ ID NO: 9, SEQ ID NO: 12, SEQ ID NO: 14, SEQ ID NO: 17, SEQ ID NO: 19, SEQ ID NO: 21, SEQ ID NO: 22, SEQ ID NO: 23, SEQ ID NO: 24, SEQ ID NO: 26, SEQ ID NO: 28, SEQ ID NO: 29, SEQ ID NO: 30, SEQ ID NO: 32, SEQ ID NO: 33, SEQ ID NO: 34, SEQ ID NO: 35, SEQ ID NO: 36, SEQ ID NO: 37, SEQ ID NO: 39, SEQ ID NO: 41, SEQ ID NO: 42, SEQ ID NO: 43, SEQ ID NO: 44, SEQ ID NO: 46, SEQ ID NO: 49, SEQ ID NO: 50, SEQ ID NO: 51, SEQ ID NO: 52, SEQ ID NO: 53, SEQ ID NO: 54, SEQ ID NO: 57, SEQ ID NO: 60, SEQ ID NO: 61, SEQ ID NO: 62, SEQ ID NO: 63, SEQ ID NO: 64, SEQ ID NO: 67, SEQ ID NO: 68, SEQ ID NO: 69, SEQ ID NO: 70, SEQ ID NO: 73, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, and/or SEQ ID NO: 163) and/or any neoantigens identified by the method of identifying a neoantigen disclosed herein. In one aspect, it is understood and herein contemplated that the disclosed neoantigens include peptide, polypeptides, and/or proteins of any disclosed neoantigen.

E. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations have been accounted for. Unless indicated otherwise, parts are parts by weight, temperature is in ° C. or is at ambient temperature, and pressure is at or near atmospheric.

Example 1: Dominant Neoantigen-Specific T Cell Response and Multiple-Antigen Specificity of Single T Cell Receptors Tumor regression induced by checkpoint blockade therapy and T-cell-based immunotherapy depends on T-cell recognition of tumor antigens, particularly mutation-derived neoantigens. Increasing evidence indicates that tumor mutation loads are positively correlated with clinical response to checkpoint blockade therapy. However, despite the relatively larger numbers of somatic mutations in cancer tissues, the number of neoantigens identified from human cancer patients using tumor-reactive T cells has been unexpectedly low. The molecular mechanisms underlying the low number of neoantigens for T cell recognition remain poorly understood.

The mutated proteins must be naturally processed to short peptides [generally 9 amino acids for MHC class I molecules and variable length (13-15 amino acids) for MHC-II molecules] with specific MHC-I or -II binding motifs, and then presented on the cell surface for T cell stimulation. Furthermore, the binding affinity of neoantigens to MHC-I or -II molecules is a critical determinant of its immunogenicity and dependent on MHC-I (HLA-A, -B and -C) or MHC-II (HLA-DR, -DQ and DP) molecules. More importantly, there is accumulating evidence supporting that the mutated amino acid of neoantigenic peptides either increases the binding affinity of peptide-MHC complexes or triggers T cell receptor (TCR) to elicit T cell response through MHC/peptide-TCR contact. Therefore, antigen processing, HLA genotypes and TCRs can influence the number and quality of neoantigens that elicit T cell response against cancer cells. Recent studies show that tumor cells may develop multiple strategies to invade immune destruction by regulating antigen processing and specific loss of HLA alleles, thus rendering them susceptible or resistant to immunotherapy. Despite recent identification of many HLA class I-restricted neoantigens and their importance in cancer immunotherapy, growing evidence indicates that neoantigen-specific $CD4^+$ T cells and their cognate neoantigens play a critical role in tumor regression. However, the current prediction programs for neoantigens are not accurate, particularly for MHC II-restricted neoantigens owing to the open pockets of MHC II molecules, thus limiting our ability to identify the full-spectrum of immunogenic neoantigens.

Because of the importance of mutation-derived neoantigens in tumor regression induced by checkpoint blockade therapy, a systemic approach may be required for identifying mutation-derived neoantigens for better understanding of T-cell recognition repertoire and potential mechanisms that control the number and quality of neoantigens for T cell recognition. Furthermore, whether a single T-cell receptor (TCR) can recognize two or more neoantigens in cancer patients remains largely unknown. In this study, is described a systemic approach to identify all possible mutation-derived neoantigens recognized by $CD4^+$ and $CD8^+$ T cells, and discover the immunodominance of neoantigen recognition by T cell lines and clones derived from cancer patients. The immunodominant neoantigen recognition by T cells is further supported by T cell clone analysis, intracellular staining and TCR profiling of primary T cells. Interestingly, one single TCR has the ability to recognize two neoantigen epitopes in an MHC II restricted fashion, while another TCR recognizes a MHC-I restricted neoantigen epitope when it is expressed in $CD8^+$ T cells, but recognizes a MHC II-restricted neoantigen epitope when it is expressed in $CD4^+$ T cells.

a) Results (1) Systemic Identification of Somatic Mutation-Derived Neoantigens in 135 Mel To systemically identify the maximal number of neoantigens recognized by T cells, primary tumor-infiltrating lymphocyte (TIL) lines were generated from fresh cancer tissues that had been surgically removed from two melanoma patients (#135 and #136). The resultant two TIL cell lines consisted of 54.5% $CD4^+$, 41.9% $CD8^+$ T cells (#135) and 82.2% $CD4^+$, 17.2% $CD8^+$ T cells (#136) and elicited tumor-specific responses against 135 mel and 136 mel tumor cells, respectively (FIG. 1A). Meanwhile two melanoma cell lines derived from primary patients' tumor tissues were passaged (135 mel and 136 mel). The ability of 135TIL and 136TIL to recognize autologous tumor cell lines (135 mel and 136 mel, respectively) was tested along with other control cells, including allogeneic tumor cell lines, Epstein-Barr virus-transformed B (EBV-B) cells and 293 cells (FIG. 1B), demonstrating that both 135TIL and 136TIL were autologous tumor-specific. After purification of $CD4^+$ and $CD8^+$ T cell populations from early TILs, tumor-reactive T-cell clones were established by limited dilution (0.3 cells/well) to eliminate the competition and loss of tumor-reactive T cells due to their differential growth property in bulk T cells. The distribution of T-cell clones on 96-well plates was completely unbiased, from which each tumor-reactive clone was picked and expanded. Tumor-reactivity of $CD4^+$ and $CD8^+$ T-cell clones was tested against autologous EBV-B cells, autologous tumor cells, and other allogeneic tumor cell lines, and found that these T cell clones were specific for autologous tumor cells, but did not respond to autologous EBV-B cells and other targets. Some representative T-cell clones are shown in FIG. 1C and FIG. 2, indicating that like their parental T cell lines, these T cell clones maintain specific recognition of autologous tumor cells.

Whole-exome sequencing was performed on libraries generated from genomic DNAs of 135 mel and 135TIL cells. Based on the next-generation sequencing results, around 40,000 single nucleotide variations (SNVs) were distinguished in 135 mel and 135TIL respectively after alignment with the Human Genome Version 19 (hg19). Then a multiple-step filtering pipeline was applied to determine the lower bound of SNV frequency, remove common variations in tumor and normal T cells and limit the SNV type. Finally, 232 somatic missense mutations unique to 135 mel tumor cells (FIG. 3A) were identified. Because of poor prediction of neoantigens by currently available computer-assistant algorithm, a library of 24 tandem minigenes (TMGs) containing all 232 mutations was designed and constructed. Each mutation was included in a 25 amino acid (aa) peptide sequence with 12 aa flanking each side of the mutated amino acid. The synthesized TMGs with 10 mutations per TMG were cloned into the Ii80-fusion targeting expression vector pTSX for efficient processing and presentation of T-cell epitopes to T cells for recognition.

To identify true neoantigens among the TMGs recognized by tumor-reactive T cells, HEK293 cells engineered to express MHC-I (HLA-A1, HLA-B8 or HLA-C7) and/or MHC-II molecules (HLA-DR1, HLA-DR3, HLA-DR4, HLA-DR11 and/or HLA-DP4) were used as artificial antigen-presenting cells (APCs). Based on HLA typing of patient #135, 293T-A1 and 293T-B8 (which naturally express HLA-C7) were generated for MHC-I antigen presentation, and 293IMDR3/DP4 and 293IMDR4/DP4 (expressing various HLA-DR molecules and HLA-DP4) for MHC-II antigen presentation. Neoantigens were screened for T cell recognition by transfection of 24 TMG constructs into 2931IMDR3/DP4 and 293IMDR4/DP4 cells, respectively, followed by adding $CD4^+$135TILs for co-culture overnight. Significant IFN-γ release was found from T cells that were co-cultured with 293IMDR3/DP4 or 293IMDR4/DP4 cells transfected with TMG6, TMG17 or TMG18 (FIG. 3B). To identify individual neoantigens, all single mutations (25 aa) from TMG6, 17 and 18 were subcloned to the same vector. Each single mutation-containing construct was tested with $CD4^+$ tumor-reactive T cells in the same MHC-II APCs. These experiments led to identification of four mutation-derived neoantigens [SPATA13 (T>A) in TMG6, PCDHB7 (R>C) and PCDHB16 (H>Y) in TMG17, and ATG5 (D>N) in TMG18] that were strongly recognized by $CD4^+$135TILs (FIG. 4A). Next, the wild-type (WT) counterparts of each mutation-derived neoantigen were generated and tested them together with the mutated constructs, and found that 135TIL strongly recognized four neoantigens, but not WT counterparts (FIG. 3C). To further define the T-cell epitopes of these neoantigens, peptides encoding different 13-mers locating around the mutation sites were synthesized and tested for 135TIL cell recognition. Based on their ability to activate T cell response, these neoepitopes were narrowed down to 9-13 mer long through a series of deletions and truncation of T cell epitopes (FIG. 4B).

To identify MHC-I restricted neoantigens, 293T-A1 or 293T-B8 cells were co-transfected with 24 TMGs, followed by co-culture with $CD8^+$135TIL cells, and found that $CD8^+$ 135TIL cells recognized TMG1 presented by 293T-B8 cells, as well as TMG14 presented by 293T-A1 cells (FIG. 3D). Further experiments through subcloning each mutation from the positive TMG (containing 10 mutations), the two neoantigens [TXNIP (E>K) in TMG1 and RPN2 (L>S) in TMG14] were identified (FIG. 3E and FIG. 5A). However, These $CD8^+$135TIL cells did not respond to WT counterparts (FIG. 3E).

Because the 293-engineered APCs do not express all HLA types, immortalized autologous APCs (135EBV-B) were used to serve as APCs for identification of all possible neoantigens presented different MHC-I and II molecules. Due to low transfection efficiency of EBV-B cells, in vitro transcribed (IVT) RNA of 24 TMGs were generated and then electroporated them into 135EBV-B cells, followed by adding 135TIL cells for antigen recognition based on cytokine release assay. All neoantigen-containing TMGs identified above positively responded for T cell recognition, but one new construct (TMG7) presented by EBV-B cells was identified that was strongly recognized by 135TIL, indicating more neoantigens presented by HLA molecules that the artificial APCs did not cover (FIG. 3F). Further investigation by TMG subcloning and re-testing revealed that MPG (G>E) in TMG7 was another MHC-I presented neoantigen (FIG. 3G and FIG. 5B), while other positive TMGs were the same as those identified above. Using the same approach to MHC-II neoantigens, all three MHC-I neoantigens were further defined to 9-11 mer peptides for T cell recognition (FIG. 5C). Titration experiments of all MHC-I and MHC-II neoantigens were performed and showed that tumor-reactive T cells strongly recognized these neoantigen peptides in a dose-dependent manner, but with little or no recognition of WT peptide sequences (FIG. 3H).

(2) Identification of Two Non-Mutated Antigens Derived from Alternative Open Reading Frames and 3' UTR Region in 135Mel Tumor Cells It is shown herein that tumor-reactive T cells are capable of recognizing T cell epitopes derived alternative open reading frames (ORF) and long-noncoding genes. Thus, immunogenic antigens can be generated from various sources or mechanisms [such as alternative ORFs, noncoding regions (3' and 5' UTRs, introns, noncoding RNA)]. To explore the possibility that some tumor-reactive T cells can recognize the cryptic T cell epitope, rather than just in the coding region based on exome sequence, the established $CD4^+$ T-cell clones were tested for their ability recognize four newly identified MHC-II neoantigens, and CD8+ T-cell clones for their ability to recognize three MHC-1 neoantigens in 135 mel. Among all T cell clones, two T cell clones were identified that recognized 135 mel tumor cells, but did not respond to any neoantigen identified. A representative data are shown in FIG. 6A. All other tumor-reactive $CD4^+$ T-cell clones and $CD8^+$ T-cell clones recognized the mutation-derived neoantigens. These two T-cell clones did not respond to EBV-B cells transfected with 24 TMGs RNAs, indicating that these T cell clones recognize antigenic peptides presented by 135 mel cells through other sources, but not from somatic mutations in the coding regions. To identify these two antigens recognized by these two $CD4^+$ T-cell clones, an Ii-fusion cDNA library derived from 135 mel tumor cells was constructed using experimental procedures. The Ii-fusion cDNA library pools (approximately 100 cDNA clones per pool) were transfected into 293IMDR3/DP4 or 293IMDR4/DP4 cells, followed by co-culturing with $CD4^+$ T-cell clones (135-1C1 or 135-1E1). After $2\times10^5$ cDNA clones, positive cDNA library pools that stimulate two T-cell clones, respectively, were identified based on IFN-γ release by ELISA (FIG. 6B). The positive pools were then transformed into Stbl3™ *Escherichia coli*, and single bacteria colonies were picked for plasmid DNA isolation. The screening assays were repeated in the same APCs transfected with the single cDNA-containing plasmids, and identified three clones that were able to stimulate 135-1C1 T cells, and two clones that reacted with 135-1E1 T cells (FIG. 6C). Sequencing of each positive cDNA clone and a database search revealed that 135-1C1 T cells recognized the same antigen, which had a 56 aa open reading frame (ORF) translated from the 3'UTR of the ADIPOR2 gene (FIG. 6C and FIG. 7A). The 135-1E1 T cell-reactive cDNA clones encoded the product translated from an alternative reading frame of CTAG2 (LAGE1b) (FIG. 6C and FIG. 7A). To further demonstrate the reactivity and specificity of these two T-cell responses, ADIPOR2 and LAGE1b were constructed with their normal reading frames in the Ii-fusion vector, and found that 135-1C1 T-cell clones only responded to peptides translated from the 3' UTR region of ADIPOR2 gene (FIG. 7B). By contrast, 135-1E1 T cells recognized the gene products translated from the alternative ORF2 of the CTAG2 gene, but did not respond to the gene products of their normal ORFs (FIG. 7C). LAGE1 is a cancer-testis antigen, with over 80% amino acid sequence identical to NY-ESO-1 protein, which is the most immunogenic tumor antigen identified to date. To define the T cell epitopes, wee generated a series of deletions and truncations of 3' UTR region of ADIPOR2 gene, and narrowed down T cell epitope to a 26 aa peptide-coding sequence that stimulate 135-1C1 T cell response (FIG. 7D). Using similar approach, T cell epitopes were narrowed down to a 69 aa peptide-coding sequence of the LAGE1b alternative ORF2 for 135-1E1 T-cell recognition (FIG. 7E). Peptide titration experiments showed that 135-1C1 and 135-1E1 T-cell clones strongly recognized antigen peptides in a dose-dependent manner, but the bulk 135TIL cell lines showed little or no activity (FIG. 6D), indicating that 135-1C1 and 135-1E1 T-cell clones are relatively rare in the original T cell population. Taken together, these results indicate that these two tumor-reactive $CD4^+$ T cell clones recognize nonmutated but aberrant neoantigen peptides translated from either the 3' UTR sequence of ADIPOR2 gene or alternative ORF of CTAG2 gene.

(3) Systemic Identification of Neoantigens from the Second Patient Tumor by Tumor-Reactive T Cells Using several different approaches (293-engineered APCs and B cells, as well as different libraries) and tumor-reactive T cells (TIL lines and clones), 6 MHC-II antigens (4 mutation-derived neoantigens and 2 derived from alternative ORF and 3' UTR region) were identified and 3 MHC-I neoantigens in 135 mel tumor cells. It appears that the number of neoantigens recognized by T cells is rather limited, even though there are 232 somatic mutations (Table 3). To extend the findings, exome sequencing of genomic DNAs isolated from the second patient tumor (136 mel) and 136TIL cells (as a control) was performed and identified 348 somatic mutations that were unique to 136 tumor cells (FIG. 8A) (Table 4). A library was designed and constructed containing 35 TMGs (10 mutations in each TMG) in pTSX targeting expression vector based on somatic mutations. To identify MHC-II neoantigens presented by HLA-DR1, DR11 and DP4 molecules based on the HLA typing of patient #136, 293IMDR1/DP4 and 293IMDR11/DP4 cells were transfected with 35 TMGs, respectively, followed by adding tumor-reactive CD4$^+$ T cells isolated from 136TIL cells by antibody-coated magnetic beads. As shown in FIG. 8B, three TMGs (TMG19, TMG31 and TMG 32) were identified that were positive for T cell recognition in 293IMDR1/DP4 cells, and found one TMG (TMG32) that was able stimulate CD4$^+$ T cells to release IFN-γ in 293IMDR11/DP4 cells. After subcloning of 10 minigenes of each positive TMG into pTSX expression vector, they were tested for their ability to stimulate T cell activation in 293IMDR1/DP4 cells, and found that four neoantigens, including ZFYVE1 (H>Y) in TMG19, LMAN2 (L>R) and MAPK9 (W>C) in TMG31, and ANKIB1 (P>L) in TMG32, were capable of stimulating CD4$^+$ T cells for IFN-γ release after overnight co-culture with T cells (FIG. 8C and FIG. 9A). By contrast, no appreciable T cell activity was observed against the corresponding WT counterparts (FIG. 8C). Because ANKIB1 can be presented by both 293IMDR1/DP4 and 293IMDR11/DP4 cells (FIG. 8B), it is likely that ANKIB1 is presented by HLA-DP4 molecules for T cell recognition. These results indicate that four MHC-II restricted neoantigens are processed and presented for T cell recognition.

TABLE 3

Amino acid sequences of somatic mutations (patient #135) for screening in each TMG

| TMG No. | Gene name and locus | Mutant AA sequence |
|---|---|---|
| TMG1 | AGRN location:chr1:987171 the 33 -th exon(s) of ENST00000379370 | VDTLAFDGRTFVGYLNAVTESEKAL (SEQ ID NO: 167) |
| | MORN1 location:chr1:2267954 the 12 -th exon(s) of ENST00000378531 | KKAGGRSRGGLHSRGTPPTAQEPPG (SEQ ID NO: 168) |
| | CLCN6 location:chr1:11894611 the 16 -th exon(s) of ENST00000312413 | GIYDIHVGLRGVLLLEWETEVEMDK (SEQ ID NO: 169) |
| | ATP13A2 location:chr1:17320224 the 16 -th exon(s) of ENST00000452699 | PLVPEPRRLPVGLLLRALATCHALS (SEQ ID NO: 170) |
| | KIF17 location:chr1:20998671 the 12 -th exon(s) of EN5T00000247986 | EKMQRKLRAAEVKIKDLQSEFQLEK (SEQ ID NO: 171) |
| | CELA3B location:chr1:22310198 the 5 -th exon(s) of ENST00000337107 | WNRSCVACGNDIVLIKLSRSAQLGD (SEQ ID NO: 172) |
| | EPHA10 location:chr1:38197088 the 7 -th exon(s) of ENST00000373048 | QSFNPSIEVQTLEEAASGSRDQSPA (SEQ ID NO: 173) |
| | TIE1 location:chr1:43773506 the 7 -th exon(s) of EN5T00000372476 | CAPGHFGADCRLRCQCQNGGTCDRF (SEQ ID NO: 174) |
| | AGBL4 location:chr1:48999906 the 14 -th exon(s) of ENST00000371839 | KHPLLRGPASNYLNSKGDKKSSVNH (SEQ ID NO: 175) |
| | TXNIP location:chr1:145438902 the 1 -th exon(s) of ENST00000582401 | GSGEKVAGRVIVKVCEVTRVKAVRI (SEQ ID NO: 176) |
| TMG2 | POGZ location:chr1:151380993 the 14 -th exon(s) of ENST00000271715 | PRTVPVSSNDTPLSALQEAAPLTSS (SEQ ID NO: 177) |
| | RORC location:chr1:151789697 the 2 -th exon(s) of ENST00000356728 | KICGDKSSGIHYRVITCEGCKGFFR (SEQ ID NO: 178) |
| | FLG2 location:chr1:152326075 the 3 -th exon(s) of ENST00000388718 | VHERHETTYGQTEEATGHGHSGHGQ (SEQ ID NO: 179) |
| | IVL location:chr1:152883669 the 2 -th exon(s) of ENST00000368764 | EQQVGQPKNLEQKEKQLELPEQQEG (SEQ ID NO: 180) |
| | FCRL1 location:chr1:157767607 the 8 -th exon(s) of ENST00000358292 | TPGQLQPIYENELREQSVAVHGRQQ (SEQ ID NO: 181) |
| | LY9 location:chr1:160783603 the 3 -th exon(s) of ENST00000263285 | SESNGGSILTVSQTPCDPDLPYICT (SEQ ID NO: 182) |
| | TBX19 location:chr1:168278072 the 7 -th exon(s) of ENST00000367821 | WTSLSSTPHASIMSVPHTNGPINPG (SEQ ID NO: 183) |

TABLE 3-continued

Amino acid sequences of somatic mutations (patient #135) for screening in each TMG

| TMG No. | Gene name and locus | Mutant AA sequence |
|---|---|---|
| | RGS16 location:chr1:182572416 the 2 -th exon(s) of ENST00000367558 | LGIFLHKSELGCNTGSTGKFEWGSK (SEQ ID NO: 184) |
| | FAM129A location:chr1:184792424 the 8 -th exon(s) of ENST00000367511 | LEEAYTLVQHQVPEGLSALKEECRA (SEQ ID NO: 185) |
| | BRINP3 location:chr1:190129856 the 7 -th exon(s) of ENST00000367462 | QLFLKAQKIVHKFFSLSKRCHKQPL (SEQ ID NO: 186) |
| TMG3 | CRB1 location:chr1:197403848 the 7 -th exon(s) of ENST00000367399 | QPVLQGFECIANVVFNGQSGQILFR (SEQ ID NO: 187) |
| | NENF location:chr1:212619328 the 4 -th exon(s) of ENST00000366988 | NLDFKPEDQPHFYIKDEF (SEQ ID NO: 188) |
| | USH2A location:chr1:216074197 the 39 -th exon(s) of ENST00000307340 | LPPRLSSATPTSIQVVWSTPARNNA (SEQ ID NO: 189) |
| | CCDC185 location:chr1:223568085 the 1 -th exon(s) of ENST00000366875 | HAVEGQKKVQDTSLSSLINYQARKV (SEQ ID NO: 190) |
| | ABCB10 location:chrl :229654072 the 13 -th exon(s) of ENST00000344517 | LMDGRTVLVIAHCLSTIKNANMVAV (SEQ ID NO: 191) |
| | RYR2 location:chr1:237777461 the 37 -th exon(s) of ENST00000366574 | ALGNHRVAHALCNHVDEPQLLYAIE (SEQ ID NO: 192) |
| | OR2L3 location:chr1:248224771 the 1 -th exon(s) of ENST00000359959 | YAPFVYTYLRPRFLRSPTEDKVLAV (SEQ ID NO: 193) |
| | CUBN location:chr10:16893368 the 60 -th exon(s) of ENST00000377833 | NNTFASPDSDSNRMYDKNLNCVWII (SEQ ID NO: 194) |
| | SH2D4B location:chr10:82363415 the 5 -th exon(s) of ENST00000339284 | QRARDEYRHHSLCAIQKGTVAGLSS (SEQ ID NO: 195) |
| | ATRNL1 location:chr10:117154225 the 20-th exon(s) of ENST00000355044 | ANICHLHTGKCFRTTKGIKGDQCQL (SEQ ID NO: 196) |
| TMG4 | MUC6 location:chr11:1031883 the 3 -th exon(s) of ENST00000421673 | VQLRRGPDGSISWIIVELGASVVTV (SEQ ID NO: 197) |
| | OR51A4 location:chr11:4967678 the 1 -th exon(s) of ENST00000380373 | LCLMVDFILIAVFYTLILKTVLGIA (SEQ ID NO: 198) |
| | HBD location:chr11:5255429 the 2 -th exon(s) of ENST00000380299 | VGGEALGRLLVVFPWTQRFFESFGD (SEQ ID NO: 199) |
| | OR52E4 location:chr11:5906376 the 1 -th exon(s) of ENST00000316987 | IHILLANLYVVVLPALNPVIYGVRT (SEQ ID NO: 200) |
| | NCR3LG1 location:chr11:17390500 the 4 -th exon(s) of ENST00000338965 | IGVGLVLLIVLISWKKICNKSSSAY (SEQ ID NO: 201) |
| | E2F8 location:chr11:19247118 the 12 -th exon(s) of ENST00000250024 | PVTSSELTAVNFSSFHVTPLKLMVS 202 |
| | OR5D16 location:chr11:55607024 the 1 -th exon(s) of ENST00000378396 | HGTILFLYCVPNFKNSRHTVKVASV 203 |
| | TRIM49 location:chr11:89537525 the 3 -th exon(s) of ENST00000329758 | VTIDCGHSFCRPSFYLNWQDIPFLV 204 |
| | TMPRSS5 location:chr11:113565338 the 8 -th exon(s) of ENST00000299882 | LRCSECGARPLAFRIVGGQSVAPGR 205 |
| | CEP164 location:chr11:117258122 the 15 -th exon(s) of ENST00000278935 | EEILRLHQQKEQFLSSLRERLQKAI 206 |

TABLE 3-continued

Amino acid sequences of somatic mutations (patient #135) for screening in each TMG

| TMG No. | Gene name and locus | Mutant AA sequence |
|---|---|---|
| TMG5 | PLEKHG6 location:chr12:6426830 the 9 -th exon(s) of ENST00000396988 | PLLLHAVLKRSPKARAQEALNAMIE 207 |
| | C1S location:chr12:7169847 the 3 -th exon(s) of ENST00000328916 | VYAEPTMYGEILFPNYPQAYPSEVE 208 |
| | GDF3 location:chr12:7843214 the 2 -th exon(s) of ENST00000329913 | KLLYFNLSAIKEGEQLTLAQLGLDL 209 |
| | KRT83 location:chr12:52709846 the 7 -th exon(s) of ENST00000293670 | AAVAQSEQQGEATLSDARCKLAELE 210 |
| | LRP1 location:chr12:57589739 the 54 -th exon(s) of ENST00000243077 | SRQWECDGENDCLDQSDEAPKNPHC 211 |
| | KIF5A location:chr12:57965854 the 14 -th exon(s) of ENST00000286452 | RLQEVSGHQRKRIAEVLNGLMKDLS 212 |
| | NR2C1 location:chr12:95442978 the 9 -th exon(s) of ENST00000333003 | SRAFDTLAKALNAGESTACQSSVAG 213 |
| | CUX2 location:chr12:111757993 the 17 -th exon(s) of ENST00000261726 | EVAPRGRSVPPSLPERPSLATASQN 214 |
| | PTPN11 location:chr12:112892407 the 5 -th exon(s) of ENST00000392597 | LKYDVGGGERFDALTDLVEHYKKNP 215 |
| | TBX3 location:chr12:115117732 the 3 -th exon(s) of ENST00000257566 | FPSDHATWQGNYGFGTQTILNSMHK 216 |
| TMG6 | NCOR2 location:chr12:124810031 the 48 -th exon(s) of ENST00000429285 | PPPPGLPAGSGPFAGPHHAWDEEPK 217 |
| | SPATA13 location:chr13:24876879 the 13 -th exon(s) of ENST00000382108 | AEPKRKSSLFWHAFNRLTPFRK 218 |
| | CCDC168 location:chr13:103388489 the 4 -th exon(s) of ENST00000322527 | PSQPKLPISSGAEKSRLANSNEGIS 219 |
| | COL4A1 location:chr13:110826298 the 40 -th exon(s) of ENST00000375820 | TPGPTGPAGQKGKPGSDGIPGSAGE 220 |
| | ARHGAP5 location:chr14:32561340 the 2 -th exon(s) of ENST00000345122 | RHQREIVEKAKEKFQEMLFEHSELF 221 |
| | MIPOL1 location:chr14:37838743 the 11 -th exon(s) of ENST00000327441 | AALSKCKRLEQEFHHVKEQNQTSAN 222 |
| | SPTB location:chr14:65263382 the 10 -th exon(s) of ENST00000389722 | EEAEYRRELALRHELIRQEKLEQLA 223 |
| | NPAP1 location:chr15:24924213 the 1 -th exon(s) of ENST00000329468 | GQAAWDPTGHSMTAAPQGASNIPVF 224 |
| | RYR3 location:chr15:34065794 the 64 -th exon(s) of ENST00000389232 | YHILCSLYSLGTRKNIYVERQRPAL 225 |
| | RASGRP1 location:chr15:38808442 the 6 -th exon(s) of ENST00000310803 | LLFDHLEPEELSKHLTYLEFKSFRR 226 |
| TMG7 | RASGRP1 location:chr15:38856810 the 1 -th exon(s) of ENST00000310803 | MGTLGKEREAPRKPSHGCR 227 |
| | TRIM69 location:chr15:45047438 the 2 -th exon(s) of ENST00000329464 | KKLPLLKGHPQCQEHGENLKLFSKP 228 |
| | CYP11A1 location:chr15:74636279 the 4 -th exon(s) of ENST00000268053 | FGERQGMLEEVVSPEAQRFIDAIYQ 229 |
| | CHSY1 location:chr15:101775370 the 2 -th exon(s) of ENST00000254190 | RRMVPHIGKCLRKMYTTHEDVEVGR 230 |

TABLE 3-continued

Amino acid sequences of somatic mutations (patient #135) for screening in each TMG

| TMG No. | Gene name and locus | Mutant AA sequence | |
|---|---|---|---|
| | MPG location:chr16:135400 the 4 -th exon(s) of ENST00000397817 | YGMYFCMNISSQEDGACVLLRALEP | 231 |
| | CLEC16A location:chr16:11272324 the 23 -th exon(s) of EN5T00000409790 | VARSAAVETASLFPSLVPARQPTIS | 232 |
| | TXNDC11 location:chr16:11830039 the 2 -th exon(s) of ENST00000283033 | VIIPAKPPVSFFFLRSPVLDLFQGQ | 233 |
| | ABCC1 location:chr16:16139715 the 9 -th exon(s) of ENST00000399410 | PQILKLLIKFVNNTKAPDWQGYFYT | 234 |
| | Cl6orf58 location:chr16:31504800 the 9 -th exon(s) of EN5T00000327237 | PAPSLSLGVPLHLLVSSVFELQQLV | 235 |
| | ADCY7 location:chr16:50324484 the 2 -th exon(s) of ENST00000254235 | YVECLLRRWLRAFALLTWACLVALG | 236 |
| TMG8 | ADCY7 location:chr16:50324485 the 2 -th exon(s) of ENST00000254235 | VECLLRRWLRALTLLTWACLVALGY | 237 |
| | DYNC1LI2 location:chr16:66783144 the 3 -th exon(s) of ENST00000258198 | KLQGAEHGKKGRDLEYLYLSVHDED | 238 |
| | FBXL8 location:chr16:67196929 the 3 -th exon(s) of ENST00000258200 | RAPGLRGLRLECCGEKPLFDAGRDV | 239 |
| | SLC12A4 location:chr16:67995561 the 3 -th exon(s) of ENST00000316341 | IRPKVSSLLGKLISYTNLTQGAKEH | 240 |
| | PMFBP1 location:chr16:72174425 the 6 -th exon(s) of ENST00000237353 | DHSKVRIYTSPCIIQEHQETQKRLS | 241 |
| | MYH4 location:chr17:10356983 the 23 -th exon(s) of ENST00000255381 | DDLELTLAKVEKKKHATENKVKNLT | 242 |
| | DNAH9 location:chr17:11833330 the 9 -th exon(s) of ENST00000608377 | SPEGHIIPQGILQNSIKITNEPPTG | 243 |
| | FLCN location:chr17:17117084 the 14 -th exon(s) of ENST00000285071 | EDTQKLLSILGAFEEDNVKLLKFWM | 244 |
| | FLII location:chr17:18160249 the 2 -th exon(s) of ENST00000545457 | LKLNRTGLCYLPKELAALQKLEHLS | 245 |
| | SHMT1 location:chr17:18232625 the 10 -th exon(s) of ENST00000352886 | TPALTSRGLLEKNFQKVAHFIHRGI | 246 |
| TMG9 | FBXW10 location:chr17:18682399 the 13 -th exon(s) of ENST00000301938 | RIYTALDPFRVNAEFVLLTVKEEKE | 247 |
| | SLFN14 location:chr17:33884597 the 1 -th exon(s) of ENST00000415846 | LREKGFRAQRGRLRVKKLHPQQVLN | 248 |
| | KRT24 location:chr17:38859509 the 1 -th exon(s) of ENST00000264651 | GLFSGGEKQTMQSLNDRLANYLDKV | 249 |
| | KRT31 location:chr17:39551303 the 6 -th exon(s) of ENST00000251645 | LQAQHNLRDSLEKTLTESEARYSSQ | 250 |
| | CDC27 location:chr17:45234359 the 7 -th exon(s) of ENST00000066544 | PDTVPLGTGTSIFSKQVQNKPKTGR | 251 |
| | CDC27 location:chr17:45234397 the 7 -th exon(s) of ENST00000066544 | SSVSYIDSAVISSDTVPLGTGTSIL | 252 |
| | BZRAP1 location:chr17:56395792 the 13 -th exon(s) of ENST00000268893 | GSGPKDLDLPPGFPGRCTPKSSEPA | 253 |
| | ABCA8 location:chr17:66871534 the 36 -th exon(s) of ENST00000430352 | VAIMVSGRLRCICSIQHLKSKFGKD | 254 |

TABLE 3-continued

| Amino acid sequences of somatic mutations (patient #135) for screening in each TMG | | |
|---|---|---|
| TMG No. | Gene name and locus | Mutant AA sequence |
| | C17orf62 location:chr17:80402458 the 5 -th exon(s) of ENST00000434650 | TLFRAGHDQVVVQLHDVRDVSVEEE 255 |
| | FOXK2 location:chr17:80543800 the 7 -th exon(s) of ENST00000335255 | AQSAPGSPLSSQSVLITVQRQLPQA 256 |
| TMG10 | L3MBTL4 location:chr18:6244527 the 6 -th exon(s) of ENST00000400105 | NGFQIGMRLEGIHPRHPSVFCVLSV 257 |
| | DSC1 location:chr18:28720131 the 10 -th exon(s) of ENST00000257197 | MCTTTVTVKIIDNDEGPECHPPVKV 258 |
| | CCDC178 location:chr18:30825250 the 14 -th exon(s) of ENST00000403303 | GTLFHLTKHKTDKMEDKIAEVRRKF 259 |
| | TCEB3B location:chr18:44560939 the 1 -th exon(s) of ENST00000332567 | VSHSKGHKSSRQKKRPLCAQGDWHS 260 |
| | CPLX4 location:chr18:56964118 the 3 -th exon(s) of ENST00000299721 | EMDENQIQMAGDNVDLPEDLRKMVD 261 |
| | MUC16 location:chr19:9046760 the 5 -th exon(s) of ENST00000397910 | VDTRSGVPTTTILPSIPGVVTSQVT 262 |
| | ZNF560 location:chr19:9577898 the 10 -th exon(s) of ENST00000301480 | LRTHAGEKPYECIKCGKAFTERSYL 263 |
| | ATG4D location:chr19:10662790 the 8 -th exon(s) of ENST00000309469 | CQPTVDVSQADFLLESFHCTSPRKM 264 |
| | ZNF91 location:chr19:23544724 the 4 -th exon(s) of ENST00000300619 | KRIHTGEKPYKCEECGKAFSNSSTL 265 |
| | KIRREL2 location:chr19:36349639 the 4 -th exon(s) of ENST00000360202 | LVPPEAPQVLGGLSVSLVAGVPANL 266 |
| TMG11 | ZNF607 location:chr19:38189938 the 5 -th exon(s) of ENST00000355202 | TAPHTFESVEKPFKCEECGKAFSVH 267 |
| | CYP2A13 location:chr19:41595958 the 3 -th exon(s) of ENST00000330436 | ATFDWLFKGYGVVFSNGERAKQLRR 268 |
| | PRKD2 location:chr19:47177874 the 19 -th exon(s) of ENST00000595515 | RYITHESDDARWEQFAAEHPLPGSG 269 |
| | PRKD2 location:chr19:47177874 the 17 -th exon(s) of ENST00000600194 | RWEQFAAEHPLPESGLPTDRDLGGA 270 |
| | LRRC4B location:chr19:51021783 the 3 -th exon(s) of ENST00000389201 | KCRTGTSMTSVNLLTPNGTLMTHGS 271 |
| | SIGLEC10 location:chr19:51914457 the 10 -th exon(s) of ENST00000353836 | STQAPESQESQEKLHYATLNFPGVR 272 |
| | KIR2DL1 location:chr19:55286836 the 4 -th exon(s) of ENST00000336077 | FPLGPATHGGTYKCFGSFHDSPYEW 273 |
| | NLRP2 location:chr19:55494015 the 5 -th exon(s) of ENST00000537859 | CGDWEKKKPVPVILGSLLNRVMLPK 274 |
| | NLRP4 location:chr19:56379171 the 6 -th exon(s) of ENST00000301295 | NNKKLTYLNVSCKQLDTGVPLLCEA 275 |
| | OTOF location:chr2:26684954 the 25 -th exon(s) of ENST00000338581 | FFTGEKSSDIFVKGWLKGQQEDKQD 276 |
| TMG12 | SOS1 location:chr2:39213258 the 23 -th exon(s) of ENST00000402219 | VFSSSPLHLQPPSLGKKSDHGNAFF 277 |

TABLE 3-continued

Amino acid sequences of somatic mutations (patient #135) for screening in each TMG

| TMG No. | Gene name and locus | Mutant AA sequence |
|---|---|---|
| | EGR4 location:chr2:73519196 the 2 -th exon(s) of ENST00000545030 | APGDLGEGAEGLSGLLTPPSGEGGS 278 |
| | DNAH6 location:chr2:84949894 the 60 -th exon(s) of ENST00000389394 | MYFVIASLSEIDLMYQYSLKYFKQL 279 |
| | TBC1D8 location:chr2:101654034 the 8 -th exon(s) of ENST00000376840 | KSPLMHPDALVTVFQQSGSQSPDSR 280 |
| | RNF149 location:chr2:101898473 the 6 -th exon(s) of ENST00000295317 | GDVQEMPAPESPLGRDPAANLSLAL 281 |
| | ZC3H6 location:chr2:113089764 the 12 -th exon(s) of ENST00000409871 | GGLKSSDKTEPSLGEAILPQKPSPN 282 |
| | PTPN4 location:chr2:120734607 the 27 -th exon(s) of ENST00000263708 | RFVCEAILKVYEDGFVKPLTTSTNK 283 |
| | PTPN4 location:chr2:120734627 the 27 -th exon(s) of ENST00000263708 | LKVYEEGFVKPLKTSTNK 284 |
| | BIN1 location:chr2:127821176 the 9 -th exon(s) of ENST00000351659 | FYVNTFQSIAGLQENFHKEMSKLNQ 285 |
| | NEB location:chr2:152380916 the 153 -th exon(s) of ENST00000427231 | QAAKQASEVEYRVKHRKEGSHGLSM 286 |
| TMG13 | NEB location:chr2:152380916 the 125 -th exon(s) of ENST00000409198 | TVADRPDIKKATLAAKQASEVEYRA 287 |
| | NEB location:chr2:152527587 the 38 -th exon(s) of ENST00000427231 | QHPDTVKFTSVPNSMGMVLAQHNTK 288 |
| | PMS1 location:chr2:190656594 the 2 -th exon(s) of ENST00000441310 | TVRLLSSSQIITLVVSVVKELIENS 289 |
| | ABCA12 location:chr2:215917230 the 5 -th exon(s) of ENST00000272895 | GTYTFNGSQVLAQILGLEKLLKQNS 290 |
| | ZNF142 location:chr2:219521044 the 4 -th exon(s) of ENST00000449707 | LLIPPPLSNRGIMGPVQSPCPSRDP 291 |
| | SLC23A3 location:chr2:220026722 the 11 -th exon(s) of ENST00000295738 | PLPEDPGDEEGGFSEPEEMADLLPG 292 |
| | TRPM8 location:chr2:234888922 the 18 -th exon(s) of ENST00000324695 | LGLFYFIAGIVFWLHSSNKSSLYSG 293 |
| | COL6A3 location:chr2:238274484 the 11 -th exon(s) of ENST00000353578 | VSVVANTPSGPVKAFDFDEYQPEML 294 |
| | UBE2F location:chr2:238925240 the 5 -th exon(s) of ENST00000272930 | PDEGYYQGGKFQLETEVPDAYNMVP 295 |
| | EBF4 location:chr20:2690234 the 7 -th exon(s) of ENST00000380648 | LTHEIMCSRCCDQKSCGNRNETPSD 296 |
| TMG14 | PLCB1 location:chr20:8862399 the 32 -th exon(s) of ENST00000338037 | ISEDSNHGSAPLFLSSDPGKVNHKT 297 |
| | PAK7 location:chr20:9561130 the 4 -th exon(s) of ENST00000353224 | LSKPSEYSDLKWKYQRASSSSPLDY 298 |
| | FLRT3 location:chr20:14306307 the 3 -th exon(s) of ENST00000341420 | ISKEEFVIHTIFSPNGMNLYKNNHS 299 |
| | RPN2 location:chr20:35812712 the 2 -th exon(s) of ENST00000373622 | RLKASLDRPFTNSESAFYSIVGLSS 300 |
| | ZNFX1 location:chr20:47887948 the 3 -th exon(s) of ENST00000396105 | DNFQQWRTPHQKLTEQPQQAKKLGY 301 |

TABLE 3-continued

Amino acid sequences of somatic mutations (patient #135) for screening in each TMG

| TMG No. | Gene name and locus | Mutant AA sequence |
|---|---|---|
| | RNF114 location:chr20:48561937 the 3 -th exon(s) of ENST00000244061 | HGCRKNFFLSKIWSHVATCSKYQNY 302 |
| | ATP9A location:chr20:50290746 the 11 -th exon(s) of ENST00000338821 | LVMVALQHFAGRSYLQIIRFLLLFS 303 |
| | CTCFL location:chr20:56093816 the 4 -th exon(s) of ENST00000608158 | PFKCSMCKYASVKVKPFLDLKLHGI 304 |
| | CTCFL location:chr20:56093816 the 4 -th exon(s) of ENST00000432255 | PFKCSMCKYASVKERHMTAHIRTHT 305 |
| | CLIC6 location:chr21:36079611 the 2 -th exon(s) of ENST00000349499 | KAGYDGESIGNCSFSQRLFMILWLK 306 |
| TMG15 | CECR1 location:chr22:17662383 the 10 -th exon(s) of ENST00000399837 | WKKRWDKFIADVDTK 307 |
| | MYO18B location:chr22:26348292 the 38 -th exon(s) of EN5T00000335473 | QVAQMRIEYLEQFTVDRAIVSRQEA 308 |
| | MYO18B location:chr22:26388383 the 40 -th exon(s) of ENST00000335473 | LAAVRQTLQTDLKTSIRRIADLQAA 309 |
| | SEZ6L location:chr22:26709798 the 9 -th exon(s) of ENST00000360929 | GVVLSPNWPEPYLEGEDCIWKIHVG 310 |
| | ELFN2 location:chr22:37770923 the 3 -th exon(s) of ENST00000402918 | VTKNYDRLQCESSREFAGYPLLVPR 311 |
| | GTPBP1 location:chr22:39122341 the 8 -th exon(s) of ENST00000216044 | IKLNDTLLLGPDSLGNFLSIAVKSI 312 |
| | EFCAB6 location:chr22:44064813 the 16 -th exon(s) of ENST00000262726 | GPPTVSPVLVPKNQLLSEHLQKDEQ 313 |
| | PNPLA3 location:chr22:44323024 the 2 -th exon(s) of ENST00000216180 | VSDGENVLVSDFWSKDEVVDALVCS 314 |
| | GRAMD4 location:chr22:47033834 the 2 -th exon(s) of ENST00000361034 | DRLNEIKGHLEIGLLEKHFLQEELR 315 |
| | NUP210 location:chr3:13383354 the 23 -th exon(s) of ENST00000254508 | TLVALDEALDNYIITFLIRGVAIGQ 316 |
| TMG16 | SEMA3G location:chr3:52469912 the 16 -th exon(s) of ENST00000231721 | IVASQLDNLFPPKPKPEEPPARGGL 317 |
| | FOXP1 location:chr3:71026116 the 17 -th exon(s) of ENST00000615603 | EIYNWFTRMFAYLRRNAATWKGAIR 318 |
| | ABI3BP location:chr3:100513845 the 22 -th exon(s) of ENST00000284322 | KPYPEVSQSEPASLETRGIPFIPMI 319 |
| | RBPJ location:chr4:26426018 the 7 -th exon(s) of ENST00000355476 | TKVALFNRLRSQRVSTRYLHVEGGN 320 |
| | MMRN1 location:chr4:90856108 the 6 -th exon(s) of ENST00000264790 | SSLSEDLESTRQKIQKVNESVVSIA 321 |
| | BANK1 location:chr4:102965052 the 11 -th exon(s) of ENST00000444316 | RRQSDDDKFCGLSKKQDRARIESPA 322 |
| | NPY1R location:chr4:164247357 the 2 -th exon(s) of ENST00000296533 | HWVFGEAMCKLNLFVQCVSITVSIF 323 |
| | TLL1 location:chr4:166915559 the 4 -th exon(s) of ENST00000061240 | IGFGLEQNNTVKRKVPLQFSGQNEK 324 |
| | TLL1 location:chr4:166924631 the 6 -th exon(s) of ENST00000061240 | GKNCDKFGIVVHKLGHVIGFWHEHT 325 |

TABLE 3-continued

Amino acid sequences of somatic mutations (patient #135) for screening in each TMG

| TMG No. | Gene name and locus | Mutant AA sequence |
|---|---|---|
| | FRG1 location:chr4:190878626 the 6 -th exon(s) of ENST00000226798 | IRCNEAGDIEAKNKTAGEEEMIKIR 326 |
| TMG17 | DNAH5 location:chr5:13901576 the 14 -th exon(s) of ENST00000265104 | DMISKLYTKQKYNPPLARNQPPIAG 327 |
| | IL7R location:chr5:35873708 the 5 -th exon(s) of ENST00000303115 | DHYFKGFWSEWSSSYYFRTPEINNS 328 |
| | C7 location:chr5:40979942 the 17 -th exon(s) of ENST00000313164 | HCQGRNYTLTGRNSCTLPASAEKAC 329 |
| | FBN2 location:chr5:127640712 the 45 -th exon(s) of ENST00000262464 | NVCSHGLCVDLQRSYQCICHNGFKA 330 |
| | PCDHA9 location:chr5:140230541 the 1 -th exon(s) of ENST00000378122 | IIFFLERYYRLLSGAVQIVLFIFLE 331 |
| | PCDHB7 location:chr5:140552768 the 1 -th exon(s) of ENST00000231137 | FQLLLEKPFQIFCAELWVRDINDHA 332 |
| | PCDHB16 location:chr5:140562600 the 1 -th exon(s) of ENST00000609684 | ENSPLGTEFPLNYALDLDVGSNNVQ 333 |
| | GRIA1 location:chr5:153085554 the 11 -th exon(s) of ENST00000518783 | EGRDQTTSDQSNKFGIFNSLWFSLG 334 |
| | PWWP2A location:chr5:159519583 the 2 -th exon(s) of ENST00000307063 | RKDNGLLVRQEACISWFGSPTTSFL 335 |
| | GABRP location:chr5:170235679 the 8 -th exon(s) of ENST00000265294 | RNVLYFILETYVLSTFLVVLSWVSF 336 |
| TMG18 | F13A1 location:chr6:6318782 the 2 -th exon(s) of ENST00000264870 | LPTVELQGVVPRDVNLQEFLNVTSV 337 |
| | ZSCAN31 location:chr6:28294281 the 3 -th exon(s) of ENST00000446474 | NEHRRSHTGEKPHQCKECGKAFSAS 338 |
| | GLTSCR1L location:chr6:42796807 the 5 -th exon(s) of ENST00000394168 | SQIILKGSGQQASSNVSGGLLVHRQ 339 |
| | ADGRF5 location:chr6:46834827 the 13 -th exon(s) of ENST00000265417 | CIFRYKNSYSIAAKDVIVHPLPLKL 340 |
| | PKHD1 location:chr6:51893144 the 30 -th exon(s) of ENST00000340994 | TLSRNISNIAGGKTLVIGVARLMNY 341 |
| | GFRAL location:chr6:55264062 the 7 -th exon(s) of ENST00000340465 | KHANKITLTGFHFPFNGEVIYAAMC 342 |
| | EYS location:chr6:66044988 the 11 -th exon(s) of ENST00000503581 | CSCLSEEDSQEYWYLCFLRWAGNMY 343 |
| | TBX18 location:chr6:85447046 the 8 -th exon(s) of ENST00000369663 | VPATHPHLLSGSFCSSPAFHLGPNT 344 |
| | MAP3K7 location:chr6:91296538 the 1 -th exon(s) of ENST00000369325 | SSSSSAGEMIEALSQVLNFEEIDYK 345 |
| | ATG5 location:chr6:106764056 the 2 -th exon(s) of ENST00000343245 | MTDDKDVLRNVWFGRIPTCFT 346 |
| TMG19 | REV3L location:chr6:111678229 the 19 -th exon(s) of ENST00000358835 | AADEKALFHEIASIIKRYDPDILLG 347 |
| | NHSL1 location:chr6:138753933 the 6 -th exon(s) of ENST00000343505 | APANRENGSQAMSYNCRNNLAFPAH 348 |
| | DGKB location:chr7:14733729 the 8 -th exon(s) of ENST00000399322 | LEEWIQGGMTTISLLVLLGLENNVK 349 |

TABLE 3-continued

Amino acid sequences of somatic mutations (patient #135) for
screening in each TMG

| TMG No. | Gene name and locus | Mutant AA sequence | |
|---------|---------------------|--------------------|---|
| | SP4 location:chr7:21468406 the 2 -th exon(s) of ENST00000222584 | PENNNKKPKTSGFQDSQPSPLALLA | 350 |
| | GHRHR location:chr7:31015410 the 10 -th exon(s) of ENST00000326139 | IVLSVGVNFGLFFNIIRILVRKLEP | 351 |
| | SEPT14 location:chr7:55910709 the 5 -th exon(s) of ENST00000388975 | LFEYHDSRVHVCFYFISPTGHSLKS | 352 |
| | PCLO location:chr7:82785328 the 2 -th exon(s) of ENST00000333891 | KEQGKPEGIIKPLLQQQPPKPIPKQ | 353 |
| | LRRD1 location:chr7:91793994 the 1 -th exon(s) of ENST00000430130 | IKYVKYLYLDKNKIKTFQGADSGDL | 354 |
| | TSPAN12 location:chr7:120428705 the 8 -th exon(s) of EN5T00000222747 | SVELLKPSLSRILEHTSMANSFNTH | 355 |
| | ZNF783 location:chr7:148963799 the 2 -th exon(s) of ENST00000434415 | RNRNFWILRLPPDSKGEAPKVPVTF | 356 |
| TMG20 | TMEM176A location:chr7:150500521 the 4 -th exon(s) of ENST00000004103 | VAVLAGAAAFIYKKRGGTYWALLRT | 357 |
| | MSRA location:chr8:10102709 the 3 -th exon(s) of ENST00000317173 | TQVGFAGGYTSNSTYKEVCSEKTGH | 358 |
| | TEX15 location:chr8:30701132 the 1 -th exon(s) of ENST00000256246 | QVNECEAIMEHCFDCFDFSLSVPFT | 359 |
| | FGFR1 location:chr8:38287286 the 3 -th exon(s) of ENST00000397091 | TRITGEEVEVQDFVPADSGLYACVT | 360 |
| | PCMTD1 location:chr8:52732961 the 4 -th exon(s) of ENST00000544451 | PQNLLREKIMKLSLPESLKAYLTYF | 361 |
| | TOX location:chr8:59728090 the 7 -th exon(s) of EN5T00000361421 | MHPSLPRNIAPKLNNQMPVTVSIAN | 362 |
| | COPS5 location:chr8:67958099 the 7 -th exon(s) of ENST00000357849 | AQLGRGSFMLGLQTHDRKSEDKLAK | 363 |
| | TG location:chr8:133925498 the 20 -th exon(s) of ENST00000220616 | FYQVLTSEASQDRLGCVKCPEGSYS | 364 |
| | GSDMD location:chr8:144642058 the 3 -th exon(s) of ENST00000262580 | APGQAKIAGGAAESDSSSTSMNVYS | 365 |
| | VPS13A location:chr9:79986036 the 67 -th exon(s) of ENST00000357409 | GAVARPTGGIIDIASSTFQGIKRAT | 366 |
| TMG21 | DIRAS2 location:chr9:93375725 the 2 -th exon(s) of ENST00000375765 | MLVGNKCDESPSCEVQSSEAEALAR | 367 |
| | CDK5RAP2 location:chr9:123290182 the 10 -th exon(s) of ENST00000360190 | EERIQALEEDLRKKEREIATEKKNS | 368 |
| | FBXW2 location:chr9:123550377 the 3 -th exon(s) of ENST00000608872 | RHLSNNLETLLKWDFLKLLPLELSF | 369 |
| | ST6GALNAC6 location:chr9:130648830 the 7 -th exon(s) of ENST00000373142 | LWDLRRVRGEAAFAQPLGQGPSSGQ | 370 |
| | TLR7 location:chrX:12904948 the 3 -th exon(s) of ENST00000380659 | SVNKISPSGDSSKVGFCSNARTSVE | 371 |
| | MAGEB1 location:chrX:30269305 the 4 -th exon(s) of ENST00000378981 | IWKFMNVLGAYDEEEHLIYGEPRKF | 372 |
| | FAM47C location:chrX:37027628 the 1 -th exon(s) of ENST00000358047 | PPEAGVSHLCPELPKTRVPPLRPET | 373 |

TABLE 3-continued

Amino acid sequences of somatic mutations (patient #135) for screening in each TMG

| TMG No. | Gene name and locus | Mutant AA sequence |
|---|---|---|
| | GPR34 location:chrX:41555747 the 3 -th exon(s) of ENST00000378142 | FTICFVPYHAFRLIYISSQLNVSSC 374 |
| | ZNF81 location:chrX:47775337 the 5 -th exon(s) of ENST00000338637 | CGKAFTQKSTLRTHQRIHTGERSYI 375 |
| | HDAC6 location:chrX:48673271 the 13 -th exon(s) of ENST00000334136 | LEFQPQLVLVAARFDALQGDPKGEM 376 |
| TMG22 | XAGE3 location:chrX:52896139 the 2 -th exon(s) of ENST00000346279 | MIWRGRSTCRPRPRRSV 377 |
| | PHF8 location:chrX:54040917 the 7 -th exon(s) of ENST00000322659 | SWVENLWPEECVVERPNVQKYCLMS 378 |
| | TEX11 location:chrX:69828949 the 23 -th exon(s) of ENST00000395889 | SLESRANEAQWFQKTAWNLAVQCDK 379 |
| | ACRC location:chrX:70823968 the 8 -th exon(s) of ENST00000373696 | SDDSEAPDDSSDNSEASDDSSDDSE 380 |
| | PCDH19 location:chrX:99551483 the 5 -th exon(s) of ENST00000420881 | PLHLKSSLPTKPFVSYTIALAPPAR 381 |
| | NRK location:chrX:105167164 the 18 -th exon(s) of ENST00000243300 | VGKISPPVYLTNKWVGYNALSEIFR 382 |
| | COL4A6 location:chrX:107464534 the 4 -th exon(s) of ENST00000334504 | TGPQGFTGSTGLLGLKGERGFPGLL 383 |
| | OR13H1 location:chrX:130678638 the 1 -th exon(s) of ENST00000338616 | KLTCSDTSLNEFIILITSIFTLLLP 384 |
| | MAGEC1 location:chrX:140995378 the 4 -th exon(s) of ENST00000285879 | EDSLSPLHFPQFSPQGEDFQSSLQS 385 |
| | MAMLD1 location:chrX:149613849 the 1 -th exon(s) of ENST00000426613 | KSMLPHFAMVGNCQEPRKLQESGTV 386 |
| TMG23 | PDZD4 location:chrX:153073863 the 2 -th exon(s) of ENST00000164640 | GTQTDITFEHIMVLGKLRPPTPPMV 387 |
| | FLNA location:chrX:153593209 the 12 -th exon(s) of ENST00000369850 | VGKSADFVVEAIEDDVGTLGFSVEG 388 |
| | F8 location:chrX:154157374 the 14 -th exon(s) of ENST00000360256 | IKWNEANRPGKVLFLRVATESSAKT 389 |
| | ATP13A2 location:chr1:17320225 the 16 -th exon(s) of ENST00000452699 | PLVPEPRRLPVGSLLRALATCHALS 390 |
| | UBE2F location:chr2:238925240 the 3 -th exon(s) of ENST00000414443 | KDEGYYQGGKFQLETEVPDAYNMVP 391 |
| | ZNFX1 location:chr20:47887949 the 3 -th exon(s) of ENST00000396105 | DNFQQWRTPHQKSTEQPQQAKKLGY 392 |
| TMG24 | CTCFL location:chr20:56093816 the 5 -th exon(s) of ENST00000371196 | PFKCSMCKYASVKASKLKRHVRSHT 393 |
| | FOXP1 location:chr3:71026116 the 11 -th exon(s) of ENST00000614176 | EIYNWFTRMFAYLRRNAATWKNAVR 394 |
| | F13A1 location:chr6:6318783 the 2 -th exon(s) of ENST00000264870 | LPTVELQGVVPRSVNLQEFLNVTSV 395 |
| | TG location:chr8:133925499 the 20 -th exon(s) of ENST00000220616 | FYQVLTSEASQDELGCVKCPEGSYS 396 |

TABLE 3-continued

Amino acid sequences of somatic mutations (patient #135) for screening in each TMG

| TMG No. | Gene name and locus | Mutant AA sequence |
|---|---|---|
| | HDAC6 location:chrX:48673272 the 13 -th exon(s) of ENST00000334136 | LEFQPQLVLVAAEFDALQGDPKGEM 397 |
| | MAMLD1 location:chrX:149613849 the 1 -th exon(s) of ENST00000262858 | KSMLPHFAMVGNCQEPRKLQESGKK 398 |

TABLE 4

Amino acid sequences of somatic mutations (patient #136) for screening in each TMG

| TMG No. | Gene name and locus | Mutant AA sequence |
|---|---|---|
| TMG1 | PRDM16:NM_022114:exon14: c.C3139T:p.H1047Y, | APVSQHPGVLTNYLGTSASSPTSES 399 |
| | C1QC:NM_172369:exon3:c.G446A: p.G149E, | LIRFNAVLTNPQEDYDTSTGKFTCK 400 |
| | PIGV:NM_017837:exon3:c.G1111A: p.D371N, | QRSKNNKTLEKPNLGFLSPQVFVYV 401 |
| | HPDL:NM_032756:exon1:c.G377C: p.G126A, | GAATYAVVSSPAAILSLTLLERAGY 402 |
| | MROH7:NM 001039464:exon12: c.C2099G:p.A700G, | FLGPQQIKDLLLGALEGLKGSSEAP 403 |
| | LRRIQ3:NM_001105659:exon7: c.C1135T:p.P379S, | NAVLREKKQHFFSAYPQPIYTTHPK 404 |
| | FAM19A3:NM_182759:exon4: c.G326A:p.C109Y, | WCQMEPCLPGEEYKVLPDLSGWSCS 405 |
| | FCRL5:NM_001195388:exon12: c.G2573C:p.S858T, | GPFATGVAGGLLTIAGLAAGALLLY 406 |
| | FCRL1:NM_001159398:exon2: c.C35T:p.P12L, | MLPRLLLLICALLCEPAELFLIAS 407 |
| | OR6K2:NM_001005279:exon1: c.C394T:p.P132S, | DHYLAICSPLHYSSIMTPKLCTQLT 408 |
| TMG2 | VSIG8:NM_001013661:exon3: c.C365T:p.A122V, | SINLMNLQVSDTVTYECRVKKTTMA 409 |
| | RASAL2:NM_170692:exon14: c.C3197T:p.S1066F, | QNGSRSRQQSSSFRESPVPKVRAIQ 410 |
| | HHAT:NM_001170588:exon10: c.G1148A:p.G383E, | TSMLILSNLVFLEGNEVGKTYWNRI 411 |
| | KCNK1:NM_002245:exon2:c.G727A: p.E243K, | YVPGEGYNQKFRKLYKIGITCYLLL 412 |
| | OR2G3:NM_001001914:exon1: c.C364T:p.R122W, | TECILLADMALDWYIAVCKPLHYVV 413 |
| | OSBPL5:NM_145638:exon12: c.C1226T:p.S409F, | TDSRTFYIAEQVFHHPPVSAFHVSN 414 |
| | MRGPRX1:NM_147199:exon1: c.C314T:p.S105F, | TISKILYPVMMFFYFAGLSFLSAVS 415 |
| | AGBL2:NM_024783:exon10:c.C955T: p.R319C, | FRVQNTRKDATYCFTIVNLLKPKSL 416 |
| | OR4A16:NM_001005274:exon1: c.G240T:p.M80I, | DAIYSTAMSPKLIIDLLCDKIAISL 417 |
| | OR4C15:NM_001001920:exon1: c.C152T:p.S51F, | RLYMIPVGAFIFFLGNMQNQSFVTE 418 |
| TMG3 | OR4C15:NM_001001920:exon1: c.T379G:p.S127A, | FLGFLSFLDACFASVITPKMIVDSL 419 |
| | OR5F1:NM_003697:exon1:c.G886A: p.E296K, | MLNPLIYSLRSKKVKKALANVISRK 420 |
| | OR8K3:NM_001005202:exon1: c.G135A:p.M45I, | MIYVISVMGNLGIIVLTKLDSRLQT 421 |
| | SLC22A10:NM_001039752:exon5: c.G841A:p.E281K, | FFVFFLLSRWLVKSARWLIITNKLD 422 |
| | PPME1:NM_016147:exon6:c.G476C: p.G159A, | PPPIMLIGHSMGAAIAVHTASSNLV 423 |
| | MMP10:NM_002425:exon8:c.G1135A: p.G379S, | VQAGYPRGIHTLSFPPTIRKIDAAV 424 |
| | BUD13:NM_032725:exon3:c.G271T: p.V91L, | VVAEFVDERPEELKQMEAFRSSAKW 425 |

TABLE 4-continued

Amino acid sequences of somatic mutations (patient #136) for screening in each TMG

| TMG No. | Gene name and locus | Mutant AA sequence |
|---|---|---|
| | ADAMTS15:NM_139055:exon8: c.C2375T:p.P792L, | TVEVLSVGKMTPLRVRYSFYLPKEP 426 |
| | SLC6A12:NM_001122848:exon11: c.C1079T:p.P360L, | QGVPISEVAESGLGLAFIAFPKAVT 427 |
| | CD163L1:NM_001297650:exon7: c.C1456A:p.L486I, | AGVICSDKADLDIRLVGAHSPCYGR 428 |
| TMG4 | OR6C75:NM_001005497:exon1: c.G355A:p.D119N, | VTEFYLLAAMSYNRCMAICKPLHYT 429 |
| | SLC5A8:NM_145913:exon10: c.G1178A:p.G393E, | LSWISQGMSVVYEALCIGMAALASL 430 |
| | BTBD11:NM_001018072:exon2: c.C1247T:p.S416F, | MFSQSELRTIEQFLLATRVGSIAEL 431 |
| | RASAL1:NM_001193520:exon17: c.C1808T:p.S603F, | KKRYVWLSGETLFFSKSPEWQMCHS 432 |
| | OR4K5:NM_001005483:exon1: c.C443T:p.S148F, | MSRRTCTVLVMIFWAVSLVHTLSQL 433 |
| | STON2:NM_033104:exon6:c.C2686T: p.L896F, | PFVHPTTLPLLFFLAMLTMFAW 434 |
| | CHD2:NM_001271:exon17:c.G2096A: p.R699Q, | QSLHKVLEPFLLQRVKKDVEKSLPA 435 |
| | CHD2:NM_001271:exon20:c.C2519T: p.S840F, | TIKHYPFQRLDGFIKGEIRKQALDH 436 |
| | TSC2:NM_000548:exon31:c.C3680T: p.P1227L, | PLSPFSSDINNMLLQELSNALMAAE 437 |
| | CACNG3:NM_006539:exon3:c.G436A: p.G146R, | VILSAGIFFVSARLSNIIGIIVYIS 438 |
| TMG5 | LPCAT2:NM_017839:exon1:c.C127T: p.P43S, | RQASFFPPPVPNSFVQQTQIGSARR 439 |
| | LPCAT2:NM_017839:exon1:c.C128T: p.P43L, | RQASFFPPPVPNLFVQQTQIGSARR 440 |
| | OR1G1:NM_003555:exon1:c.A125G: p.N42S, | SFLFMYLVTVAGSLLIILVIITDTQ 441 |
| | DNAH9:NM_001372:exon45: c.G8586A:p.M2862I, | TLRKGYQIQDFKIDLASLCLKAGVK 442 |
| | WSB1:NM_134265:exon5:c.C463T: p.P155S, | DILMEFGHLFPPSTPIFAGGANDRW 443 |
| | GPATCH8:NM_001304943:exon5: c.C4010T:p.P1337L, | AQVHHIPQPHLTLISLSHLTHSIIP 444 |
| | ANKRD29:NM_173505:exon5:c.C415T: p.H139Y, | VVETLLKHGANIYDQLYDGATALFL 445 |
| | LRG1:NM_052972:exon2:c.A808T: p.N270Y, | GLRQLDMLDLSNYSLASVPEGLWAS 446 |
| | ZNF559-ZNF177:NM_001172650: exon12:c.T404C:p.F135S, | PYECSDCGKAFISQSSLKKHMRSHT 447 |
| | ANKLE1:NM_001278445:exon8: c.G1637T:p.R546L, | CFQHVVAVEAYTLEACIVEALGIQT 448 |
| TMG6 | ZNF585B:NM_152279:exon5:c.C764T: p.S255F, | ECTDCGKAFTQKFTLKIHQKIHTGE 449 |
| | RYR1:NM_001042723:exon33: c.C4921T:p.P1641S, | CQEPLTMMALHISEENRCMDILELS 450 |
| | RYR1:NM_001042723:exon33: c.C4922T:p.P1641L, | CQEPLTMMALHILEENRCMDILELS 451 |
| | FCGBP:NM_003890:exon28: c.C12971A:p.A4324D, | CMGGGDRDILCKDLASYVAACQAAG 452 |
| | C19orf47:NM_001256440:exon5: c.C397T:p.R133C, | VPCSPSPLAGEICRGTSAASRMITN 453 |
| | FOXA3:NM_004497:exon2:c.C575T: p.A192V, | RSPDKPGKGSYWVLHPSSGNMFENG 454 |
| | TULP2:NM_003323:exon8:c.C908T: p.P303L, | TRDKHGVDKGLFLLYYLYLETSDSL 455 |
| | FPR2:NM_001005738:exon2:c.C866T: p.S289F, | YKIIDILVNPTSFLAFFNSCLNPML 456 |
| | USP29:NM_020903:exon4:c.A875G: p.N292S, | SQQLQQGFPNLGSTCYMNAVLQSLF 457 |
| | ZNF418:NM_001317029:exon5: c.C1964T:p.S655L, | GERPYECSECGKLFHRSSSLLRHQR 458 |
| TMG7 | APOB:NM_000384:exon9:c.G1081A: p.E361K, | NKLVTELRGLSDKAVTSLLPQLIEV 459 |
| | MAP4K3:NM_003618:exon9:c.A651T: p.L217F, | IELAELQPPMFDFHPMRALFLMTKS 460 |

TABLE 4-continued

Amino acid sequences of somatic mutations (patient #136) for screening in each TMG

| TMG No. | Gene name and locus | Mutant AA sequence |
|---|---|---|
| | ANTXR1:NM_053034:exon3:c.A271G: p.T91A, | RMSFIVFSTRGTALMKLTEDREQIR 461 |
| | STEAP3:NM_182915:exon5:c.G1121A: p.G374E, | EEVWRMEIYLSLEVLALGTLSLLAV 462 |
| | GALNT13:NM_052917:exon5:c.C370T: p.H124Y, | DELPNTSVVIVFYNEAWSTLLRTVY 463 |
| | UBR3:NM_172070:exon8:c.T1238C: p.V413A, | FLLNMLPDQEYKAAFTKTFVQHYAF 464 |
| | TTN:NM_001267550:exon326: c.G75232A:p.E25078K, | FEVTGLVEDHRYKFRVIARNAAGVF 465 |
| | DNAH7:NM_018897:exon49:c.C9271T: p.L3091F, | FYITTKLRNPHYFPETSVKVTLLNF 466 |
| | HECW2:NM_020760:exon4:c.C464T: p.P155L, | YHGISGALRATTLCITVKNPAVMMG 467 |
| | NPBWR2:NM_005286:exon1:c.C423A: p.D141E, | FSSIYFLAVMSVERYLVVLATVRSR 468 |
| TMG8 | HSPA13:NM_006948:exon2:c.C80T: p.P27L, | LLLAGYLAQQYLLLPTPKVIGIDLG 469 |
| | SLC5A3:NM_006933:exon2:c.T953G: p.M318R, | KLLPMFIIVVPGRISRILFTDDIAC 470 |
| | DSCAM:NM_001271534:exon15: c.C2816T:p.S939F, | DSWDSAQRTKDVFPQLNSATIIDIH 471 |
| | APOL3:NM_145642:exon4:c.C322T: p.P108S, | RAIRQARARARLSVTTWRISAGSGG 472 |
| | SLC4A7:NM_001258379:exon16: c.C2162T:p.S721L, | CVILFFTTFFLSLFLKQFKTKRYFP 473 |
| | GADL1:NM_207359:exon14:c.A1381G: p.K461E, | LREMEEGPEFWAELNLVAPAIKERM 474 |
| | SCN5A:NM_001099405:exon23: c.G4223A:p.G1408E, | TKVKVNFDNVGAEYLALLQVYEEQP 475 |
| | COL7A1:NM_000094:exon5:c.G638A: p.R213Q, | FSILRTLLPLVSQRVCTTAGGVPVT 476 |
| | MON1A:NM_032355:exon4:c.C1388T: p.P463L, | SSSSFREGEAWTLVCLPKFNAAGFF 477 |
| | SLC38A3:NM_006841:exon8:c.T553C: p.W185R, | QTFLNLEEKTSDRYMNGNYLVILVS 478 |
| TMG9 | POLQ:NM_199420:exon29:c.C7615T: p.H2539Y, | CPIRGGFFILQLYDELLYEVAEEDV 479 |
| | SAMD7:NM_182610:exon6:c.G484A: p.G162R, | LHFHRSTLRNLQRNPMLAATAPHFE 480 |
| | SPATA16:NM_031955:exon2:c.C425T: p.S142F, | IDEMGVRYEFVEFFMSTGSQPTCQA 481 |
| | ATP13A5:NM_198505:exon26: c.G3007A:p.E1003K, | AFLYVKQQPWYCKVYQYSECFLANQ 482 |
| | MUC4:NM_138297:exon13:c.C1751T: p.T584I, | GSPEEMLFHFGMIWQINGTGLLGKR 483 |
| | MUC4:NM_018406:exon2:c.G8482A: p.G2828S, | SLPVTDASSVFTSHATSLPVTIPSS 484 |
| | GABRA4:NM_001204266:exon7: c.T761C:p.L254P, | IQTYIPCIMTVIPSQVSFWINKESV 485 |
| | PDGFC:NM_016205:exon6:c.C968T: p.S323L, | LRPKTGVRGLHKLLTDVALEHHEEC 486 |
| | SLC6A18:NM_182632:exon9: c.G1324A:p.E442K, | LDVGVLPRWVPKKALTGLVCLVCFL 487 |
| | NIPBL:NM_133433:exon23:c.C4753T: p.L1585F, | VNKPEWPAAELLFSLLGRLLVHQFS 488 |
| TMG10 | C6:NM_000065:exon7:c.G769A: p.D257N, | TAEDDLKTDFYKNLTSLGHNENQQG 489 |
| | FAM170A:NM_182761:exon3:c.G805A: p.G269S, | CHVFHLTMAQLTSNMESESTQDEQE 490 |
| | PCDHB8:NM_019120:exon1:c.C1709T: p.S570F, | NSPFVLYPLQNGFAPCTELVPRAAE 491 |
| | NDST1:NM_001543:exon7:c.C1444T: p.P482S, | RRGFIHNGIMVLSRQTCGLFTHTIF 492 |
| | SLIT3:NM_001271946:exon1:c.G44C: p.R15P, | PGWAGVGAAVRAPLALALALASVLS 493 |
| | BMP5:NM_021073:exon1:c.G160A: p.E54K, | RLRNHERREIQRKILSILGLPHRPR 494 |
| | SOGA3:NM_001012279:exon6: c.T2392C:p.F798L, | VRNIRCLTPTRSLYPAPGPWPKSFS 495 |
| | SLC22A2:NM_003058:exon7: c.G1073A:p.S358N, | KHTMILMYNWFTNSVLYQGLIMHMG 496 |

TABLE 4-continued

| Amino acid sequences of somatic mutations (patient #136) for screening in each TMG | | |
|---|---|---|
| TMG No. | Gene name and locus | Mutant AA sequence |
| | MAD1L1:NM_003550:exon19: c.C2018T:p.S673F, | DCLIFKATSPSGFKMQLLETEFSHT 497 |
| | AMZ1:NM_001284355:exon2:c.C259T: p.R87W, | EDFQTFHASLQHWKPRLARKHIYLQ 498 |
| TMG11 | COL1A2:NM_000089:exon44: c.C2867T:p.P956L, | HKGERGYPGNIGLVGAAGAPGPHGP 499 |
| | PLXNA4:NM_020911:exon2:c.G721A: p.D241N, | IPSDTFTIIPDFNIYYVYGFSSGNF 500 |
| | PTPRN2:NM_001308268:exon6: c.C901T:p.P301S, | QYLLRAPSRMPRSLLAPAAPQKWPS 501 |
| | CLVS1:NM_173519:exon2:c.C83T: p.A28V, | WNGDLAKMTHLQVGLSPETIEKARL 502 |
| | DNAJC5B:NM_033105:exon4:c.G250A: p.G84R, | TDISKRSIYDKYRSLGLYVAEQFGD 503 |
| | ANGPT1:NM_001146:exon2:c.G336A: p.M112I, | LENYIVENMKSEIAQIQQNAVQNHT 504 |
| | CYHR1:NM_001129888:exon2:c.G19A: p.A7T, | MAPKPGTEWSTALSHLVLG 505 |
| | CNTNAP3:NM_033655:exon13: c.C1973T:p.A658V, | APSGHPRSAVSFVYAAGAGQLRSAV 506 |
| | NTRK2:NM_001018065:exon14: c.G1558A:p.G520R, | SSSEGGPDAVIIRMTKIPVIENPQY 507 |
| | OR13C3:NM_001001961:exon1: c.C668T:p.S223F, | ILAVLKLACADIFLNIITMVISNMA 508 |
| TMG12 | OR13C8:NM_001004483:exon1: c.G98T:p.W33L, | PKLQTVFFVLILLMYLMILLGNGVL 509 |
| | OR13C8:NM_001004483:exon1: c.G122A:p.G41E, | VLILWMYLMILLENGVLISVIIFDS 510 |
| | SLC2A6:NM_001145099:exon6: c.C788T:p.S263L, | IQDNVRRQSSRVLWAEARAPHVCRP 511 |
| | TLR8:NM_138636:exon2:c.A1422C: p.L474F, | DPHSNFYHFTRPFIKPQCAAYGKAL 512 |
| | SMS:NM_004595:exon5:c.G476A: p.G159E, | YQNIKILHSKQFENILILSGDVNLA 513 |
| | CASK:NM_001126054:exon18: c.G1672A:p.E558K, | NQTVEQLQKMLRKMRGSITFKIVPS 514 |
| | CCNB3:NM_033031:exon5:c.G2092A: p.E698K, | SGSLFQEALVLQKKTDAEEDSLKNL 515 |
| | FAM120C:NM_001300788:exon3: c.C1012T:p.P338S, | AAFHWSLLGPEHSLASLKVRAHQLV 516 |
| | SRPX2:NM_014467:exon5:c.C401T: p.T134I, | CHALPFITSGTYICTNGVLLDSRCD 517 |
| | XKRX:NM_212559:exon2:c.C593T: p.P198L, | YQLYVSLISAEVLLGRVVLMVFSLV 518 |
| TMG13 | C1GALT1C1:NM_001011551:exon2: c.C532T:p.L178F, | PFYLGHTIKSGDFEYVGMEGGIVLS 519 |
| | USP26:NM_031907:exon1:c.C208T: p.H70Y, | NVVLKSYRGNQNYLHLTLQNNNGLF 520 |
| | MAGEC1:NM_005462:exon4:c.C3196T: p.R1066C, | LEYREVPNSSPPCYEFLWGPRAHSE 521 |
| | JAKM1P2:NM_014790:exon21: c.G2429A:p.G810E, | IKDLEEKSNRKHE 522 |
| | IRF6:NM_006147:exon9:c.C1397T: p.P466L,IRF6:NM_001206696: exon7:c.C1112T:p.P371L, | PTPSMQLPPALPLQ 523 |
| | AFF2:NM_001169123:exon1:c.G4A: p.D2N, | MNLFDFFRDWDLEQ 524 |
| TMG14 | IFNLR1:NM_173064:exon7:c.C1039T: p.P347S, | GVDSGRPRAPLVSSEGSSAWDSSDR 525 |
| | HMGB4:NM_145205:exon2:c.G220A: p.E74K, | ALAKLDKARYQEKMMNYVGKRKKRR 526 |
| | RIMS3:NM_014747:exon3:c.G101A: p.G34E, | SISGEICGSQQAEGGAGTTTAKKRR 527 |
| | KANK4:NM_181712:exon3:c.C59T: p.P20L, | DQSSQGDEEKDPLKSHPYSVETPYG 528 |
| | SLC44A5:NM_152697:exon4:c.G70A: p.D24N, | SEEEDFGDPRTYNPDFKGPVANRSC 529 |
| | FCGR1A:NM_000566:exon6:c.G899A: p.G300E, | PVWFHVLFYLAVEIMFLVNTVLWVT 530 |
| | SV2A:NM_014849:exon2:c.C305T: p.P102L, | DDEIYEGEYQGILRAESGGKGERMA 531 |

TABLE 4-continued

| Amino acid sequences of somatic mutations (patient #136) for screening in each TMG | | |
|---|---|---|
| TMG No. | Gene name and locus | Mutant AA sequence |
| | TCHHL1:NM_001008536:exon3: c.C788T:p.S263L, | FGEQEGNLATQSLPPKEATQRPCED 532 |
| | HRNR:NM_001009931:exon3: c.G5792A:p.R1931H, | SSSSYGQHGSGSHQSLGHGQHGSGS 533 |
| | FLG:NM_002016:exon3:c.G10285A: p.E3429K, | QARDSSRHSASQKGQDTIRGHPGSS 534 |
| TMG15 | UBAP2L:NM_001287816:exon7: c.G617A:p.G206E, | GSGRRGGRFSAQEMGTFNPADYAEP 535 |
| | CD1E:NM_030893:exon3:c.C520T: p.R174C, | GIRAQNICKVLNCYLDIKEILQSLL 536 |
| | OR10J5:NM_001004469:exon1: c.C166T:p.H56Y, | IIVTIICIDHHLYTPMYFFLSMLAS 537 |
| | KCNT2:NM_001287819:exon9: c.G665A:p.R222Q, | IFTCICGIQHLEQIGKKLNLFDSLY 538 |
| | CFHR2:NM_001312672:exon3: c.T366G:p.H122Q, | GDIVEFVCKSGYQPTKSHSFRAMCQ 539 |
| | NFASC:NM_015090:exon6:c.C487T: p.P163S, | PLTLQCNPPPGLSSPVIFWMSSSME 540 |
| | TUBB8:NM_177987:exon4:c.A1241G: p.N414S, | GMDEMEFTEAESSMNDLVSEYQQYQ 541 |
| | FAM208B:NM_017782:exon12: c.C1241T:p.T414I, | GAEVLTAQFVQKIKLDRKNQEAPIS 542 |
| | ARID5B:NM_001244638:exon7: c.G1721A:p.R574K, | EIQEGKDKLLEKKALPHSHMPSFLA 543 |
| | SFTPA2:NM_001098668:exon3: c.G172A:p.G58S, | GRDGVKGDPGPPSPMGPPGETPCPP 544 |
| TMG16 | SFTPA1:NM_001164644:exon3: c.G172A:p.G58S, | GRDGLKGDPGPPSPMGPPGEMPCPP 545 |
| | DNMBP:NM_015221:exon5:c.C2401T: p.R801W, | IEELLQTERDYIWDLEMCIERIMVP 546 |
| | TECTB:NM_058222:exon7:c.G682A: p.D228N, | LQWQLINKGCPTNETVLVHENGRDH 547 |
| | MUC5B:NM_002458:exon31:c.G1229 2A:p.A4098T, | TPGHTTATSRTTTTATPSKTRTSTL 548 |
| | TRPM5:NM_014555:exon12:c.C1754T: p.S585F, | EAKYERLALDLFFECYSNSEARAFA 549 |
| | OR51G1:NM_001005237:exon1: c.C94T:p.P32S, | QGLEGLHGWISISFCFIYLTVILGN 550 |
| | TPP1:NM_000391:exon11:c.C1424T: p.S475L, | SNRVPIPWVSGTLASTPVFGGILSL 551 |
| | OR10A4:NM_207186:exon1:c.T452G: p.F151C, | HISCAQLAAASWCSGFSVATVQTTW 552 |
| | AMPD3:NM_001172431:exon10: c.C1136T:p.S379F, | VDDESKHSDHMFFDKSPNPDVWTSE 553 |
| | LUZP2:NM_001009909:exon11: c.G889A:p.E297K, | QDEGRPCSMKHKKSPPSNATAETEP 554 |
| TMG17 | BBOX1:NM_003986:exon6:c.G589T: p.G197W, | DKIDANNVAYTTWKLSFHTDYPALH 555 |
| | KCNA4:NM_002233:exon2:c.C1148T: p.S383F, | FFIVETVCIVWFFFEFVVRCFACPS 556 |
| | PAMR1:NM_001282675:exon8: c.C700T:p.L234F, | CLAGYTGQRCENFLEERNCSDPGGP 557 |
| | NARS2:NM_024678:exon2:c.C164T: p.S55F, | RIKIQGWIRSVRFQKEVLFLHVNDG 558 |
| | CRACR2A:NM_001144958:exon16: c.C1802T:p.T601M, | VDNSQVALQLWDMAGQERYRCITQQ 559 |
| | CCND2:NM_001759:exon5:c.G803A: p.G268E, | NSLQQYRQDQRDESKSEDELDQAST 560 |
| | TAS2R46:NM_176887:exon1:c.G198C: p.W66C, | SRVGLLWVLVLNCYATELNPAFNSI 561 |
| | SLC38A4:NM_018018:exon17: c.G1618A:p.D540N, | GSMALIIIDWIYNPPNSKHH 562 |
| | KMT2D:NM_003482:exon10:c.C2584T: p.P862S, | HLSPELEKPPLSSRPEKPPEEPGQC 563 |
| | LUM:NM_002345:exon2:c.G743A: p.G248E, | LSHNELADSGIPENSFNVSSLVELD 564 |
| TMG18 | CFAP54:NM_001306084:exon60: c.G8177A:p.G2726E, | VSEAVLAINLLIEKKNTRMHKVNQV 565 |
| | HECTD4:NM_001109662:exon63: c.C10705T:p.L3569F, | TPAKPIRVSDIYFSKEQINSQTPGN 566 |

TABLE 4-continued

Amino acid sequences of somatic mutations (patient #136) for screening in each TMG

| TMG No. | Gene name and locus | Mutant AA sequence |
|---|---|---|
| | PARP4:NM_006437:exon13: c.C1470A:p.H490Q, | FSDSLSTSIKYSQPGETDGTRLLLI 567 |
| | FREM2:NM_207361:exon1:c.C3661T: p.P1221S, | DTPILNAADADVSLDDLTFTITQFP 568 |
| | PROSER1:NM_025138:exon11: c.C1846T:p.P616S, | PVMIKTEPTSPTSSAFKGPSHSGNP 569 |
| | SLITRK6:NM_032229:exon2: c.G1796A:p.R599Q, | PATTTNTADTILQSLTDAVPLSVLI 570 |
| | METTL21C:NM_001010977:exon2: c.G224A:p.G75E, | YASYTQEHYRFAEKEIVIQESIESY 571 |
| | CCDC168:NM_001146197:exon4: c.T18244A:p.L6082I, | PLSPKRKDQKGRITIRDLKRELSTK 572 |
| | TRIM9:NM_015163:exon8:c.G1871A: p.R624Q, | DDKAWAMYVDNNQSWFMHNNSHTNR 573 |
| | SMOC1:NM_001034852:exon8: c.C745T:p.P249S, | EAQQNPREGIVISECAPGGLYKPVQ 574 |
| TMG19 | ZFYVE1:NM_021260:exon12: c.C2146T:p.H716Y, | KDAARPAYWVPDYEILHCHNCRKEF 575 |
| | SLC12A1:NM_001184832:exon11: c.G1321A:p.A441T, | VAICVGACVVRDTTGNMNDTIISGM 576 |
| | UNC13C:NM_001080534:exon1: c.A247G:p.S83G, | STHNLSTEEDEAGKEFSLSPTFSYR 577 |
| | CGNLI:NM_001252335:exon3: c.C893T:p.S298L, | PVLDGARSRRSSLSSTTPTSANSLY 578 |
| | ITGA11:NM_001004439:exon14: c.G1690A:p.A564T, | LNQDSYNDVVVGTPLEDNHAGAIYI 579 |
| | GOLGA6C:NM_001164404:exon17: c.C1915T:p.P639S, | AQNPADEPTPGASAPQELGAAGEQD 580 |
| | NTRK3:NM_001007156:exon10: c.G964A:p.E322K, | LEEPELRLEHCIKFVVRGNPPPTLH 581 |
| | RGS11:NM_003834:exon16: c.G1226A:p.R409H, | LAEAGIPLEMKRHVFPFTWRPRHSS 582 |
| | SMIM122:NM_001253793:exon4: c.G224A:p.G75E, | PRRESPRKERPKEVDNLALEP 583 |
| | DCUN1D3:NM_173475:exon3: c.C805T:p.L269F, | LSNYSEDEAWPSFFDTFVEWEMERR 584 |
| TMG20 | MVP:NM_005115:exon3:c.C244T: p.R82W, | QGLVLFDVTGQVWLRHADLEIRLAQ 585 |
| | GPT2:NM_001142466:exon10: c.G986A:p.G329E, | AKLTEDLFNQVPEIHCNPLQGAMYA 586 |
| | AMFR:NM_001144:exon11:c.C1507T: p.P503S, | DNILEGRIQVPFSTQRSDSIRPALN 587 |
| | NFATC3:NM_004555:exon9:c.C2797T: p.P933S, | GSATTASPAASHSLASSPLSGPPSP 588 |
| | ZNF469:NM_001127464:exon2: c.G6397T:p.G2133C, | QLPASPSCRDPPCPQQLLACSPAWA 589 |
| | CDH15:NM_004933:exon5:c.G553A: p.D185N, | RAEATDADDPETNNAALRFSILQQG 590 |
| | RPH3AL:NM_001190413:exon7: c.G757A:p.G253R, | GETGTGSADPPGRPRPGLTRRAPVK 591 |
| | ZNF594:NM_032530:exon2:c.G451A: p.G151R, | SSNLIIHQRIHTRNKPYVCNECGKD 592 |
| | NEURL4:NM_001005408:exon1: c.C74T:p.P25L, | GGPGPGPGGGGGLSGSGSGPGSNGG 593 |
| | NEURL4:NM_001005408:exon1: c.C73T:p.P25S, | GGPGPGPGGGGGSSGSGSGPGSNGG 594 |
| TMG21 | MYH2:NM_017534:exon12:c.G1039A: p.E347K, | TDSAIDILGFTNKEKVSIYKLTGAV 595 |
| | MYOCD:NM_153604:exon10:c.G1661A: p.R554K, | VEELRMQLQKQKKNNCSEKKPLPFL 596 |
| | PLD6:NM_178836:exon2:c.G548A: p.R183K, | SLNWTTQAIQNNKENVLITEDDEYV 597 |
| | MRC2:NM_006039:exon6:c.C1114T: p.P372S, | KKKPNATAEPTPSDRWANVKVECEP 598 |
| | ACE:NM_000789:exon16:c.G2383A: p.G795R, | LLWAWEGWRDKARRAILQFYPKYVE 599 |
| | CD300LF:NM_001289083:exon3: c.A398C:p.E133A, | VQVTIDPAPVTQAETSSSPTLTGHH 600 |
| | RNF213:NM_001256071:exon29: c.C8618T:p.P2873L, | HPLLEDGCIEDDLAPHKKVGFVGIS 601 |
| | DSG4:NM_001134453:exon4:c.G322A: p.E108K, | PYGVFTINPRTGKINITSVVDREIT 602 |

TABLE 4-continued

Amino acid sequences of somatic mutations (patient #136) for screening in each TMG

| TMG No. | Gene name and locus | Mutant AA sequence |
|---|---|---|
| | DSG4:NM_001134453:exon8:c.G901A: p.D301N, | RLQAIDLDEEGTNNWLAQYLILSGN 603 |
| | RNF165:NM_152470:exon2:c.C286T: p.P96S, | PLPTLQFQDVTGSSFLPQALHQQYL 604 |
| TMG22 | PLIN4:NM_001080400:exon3: c.G325A:p.G109R, | ASVVDVAKGVVQRGLDTTRSALTGT 605 |
| | RFX2:NM_000635:exon8:c.C811T: p.R271C, | TRGNSKYHYYGICLKPDSPLNRLQE 606 |
| | DENND1C:NM_001290331:exon20: c.C1603T:p.P535S, | LSMGAKSAGSLRSSQSLDCCHRGDL 607 |
| | MUC16:NM_024690:exon5:c.T33443A: p.V11148E, | EASSAVLTVSPEEPGMVTSLVTSSR 608 |
| | C19orf43:NM_024038:exon3: c.C514T:p.R172W, | YKAHQCGDDDKTWPLVK 609 |
| | KMT2B:NM_014727:exon3:c.C1919T: p.S640F, | PPAPSPPPAPATFSRRPLLLRAPQF 610 |
| | ZNF585A:NM_199126:exon6:c.C625T: p.H209Y, | TQKSTLKMHQKIYTGERSYICIECG 611 |
| | SIPA1L3:NM_015073:exon3: c.C1343T:p.5448F, | GECERNVSFSRAFVGSPSSGEGHLA 612 |
| | HNRNPL:NM_001533:exon8:c.C1004T: p.P335L, | GYHSHYHDEGYGLPPPHYEGRRMGP 613 |
| | ZNF574:NM_022752:exon2:c.A74G: p.Y25C, | EHRYVCSECNQLCGSLEEVLMHQNS 614 |
| TMG23 | LILRA4:NM_012276:exon6:c.G1172A: p.G391E, | EFPMSPVTSAHAETYRCYGSRSSNP 615 |
| | NLRP11:NM_145007:exon8:c.C2336T: p.5779L, | CDALLHPNCTLILLVLVFCCLTENC 616 |
| | NLRP5:NM_153447:exon7:c.G866A: p.G289E, | FRPRTVVLHGKSEIGKSALARRIVL 617 |
| | ZNF256:NM_005773:exon3:c.G1383T: p.R461S, | DLIVHERVHTGESPYECSECGKSFT 618 |
| | GCKR:NM_001486:exon12:c.C1055T: p.T352I, | IIAIMDGVECIHIFGADFRDVRGFL 619 |
| | BIRC6:NM_016252:exon68: c.A13508T:p.K4503I, | ATTSLRQANQEKILGEYSKKAAMKP 620 |
| | DYSF:NM_001130979:exon28: c.G2956A:p.E986K, | DAGHLSFVEEVFKNQTRLPGGQWIY 621 |
| | DNAH6:NM_001370:exon51:c.C8413T: p.P2805S, | ADISEIRVFTKPSDLVMTVMEAISI 622 |
| | MARCO:NM_006770:exon5:c.G533A: p.G178E, | GAPGPPGPPAEKEAKGAMGRDGATG 623 |
| | BAZ2B:NM_001289975:exon28: c.C4933T:p.P1645S, | LTSNVASSKSESSVPQNEKATSAQP 624 |
| TMG24 | SCN2A:NM_001040142:exon17: c.G3368A:p.S1123N, | ESDFENLNTEEFNSESDMEESKEKL 625 |
| | SCN1A:NM_001165963:exon24: c.G4574A:p.R1525Q, | KLGSKKPQKPIPQPGNKFQGMVFDF 626 |
| | TTN:NM_001267550:exon28: c.G6085A:p.E2029K, | ELKSRKKDESYEKLLRKTKDELLHW 627 |
| | CERKL:NM_001030311:exon8: c.C1073T:p.A358V, | FSAMFGFGGRTLVLAEKYRWMSPNQ 628 |
| | DNAH7:NM_018897:exon5:c.A277G: p.K93E, | QSHAEYMERFGKEGKLPHQVDDSYV 629 |
| | SPAG16:NM_024532:exon7:c.C734T: p.S245F, | KHHTLLKEKMLTFLERDKVVGQISG 630 |
| | PRKAG3:NM_017431:exon4:c.C329T: p.P110L, | PLAQADPAGVGTLPTGWDCLPSDCT 631 |
| | DES:NM_001927:exon6:c.G1232A: p.G411E, | DVEIATYRKLLEEEESRINLPIQTY 632 |
| | COL4A3:NM_000091:exon28: c.C2059T:p.L687F, | IPGSLGKCGDPGFPGPDGEPGIPGI 633 |
| | SPHKAP:NM_030623:exon7:c.C2486T: p.S829F, | SHRVPDSSTATTFSKEIYLKGIAGE 634 |
| TMG25 | FAM209B:NM_001013646:exon2: c.G352A:p.E118K, | SLYKDCVFNTLNKLEVELLKFVSEV 635 |
| | KCNJ15:NM_001276437:exon4: c.A667C:p.K223Q, | QLSGKLLQTHVTQEGERILLNQATV 636 |
| | UMODL1:NM_001199527:exon11: c.C1771T:p.L591F, | VNPSQGSPSQGSFRQESTSQASPSQ 637 |

TABLE 4-continued

Amino acid sequences of somatic mutations (patient #136) for screening in each TMG

| TMG No. | Gene name and locus | Mutant AA sequence |
|---|---|---|
| | SEZ6L:NM_001184773:exon4: c.T1144G:p.F382V, | YFRTFQDDGLGTVQLHYQAFMLSCN 638 |
| | MKL1:NM_001282662:exon15: c.C2368A:p.P790T, | GEAIPEDSLWVPTGSTAITFC 639 |
| | DLEC1:NM_007337:exon3:c.C658T: p.H220Y, | SPEDYYTDTVPFYSAPKGISLPGCS 640 |
| | SEMA3F:NM_004186:exon8:c.G646A: p.E216K, | DPKLDTASALINKELYAGVYIDFMG 641 |
| | STAB1:NM_015136:exon47:c.G4819A: p.E1607K, | ASFFSLRLLEYKKLKGDGPFTIFVP 642 |
| | LRTM1:NM020678:exon3:c.G1016A: p.R339Q, | QTNDPGKVEEKEQFDSSPA 643 |
| | LRTM1:NM_020678:exon3:c.G1006A: p.E336K, | PLAQTNDPGKVEKKERFDSSPA 644 |
| TMG26 | LRTM1:NM_020678:exon2:c.G158A: p.R53Q, | LAEIPSHLPPQTQTLHLQDNQIHHL 645 |
| | ERC2:NM_015576:exon2:c.G89A: p.R30Q, | SPRLPRSPRLGHQRTSSGGGGGTGK 646 |
| | COL8A1:NM_020351:exon4:c.G440A: p.G147E, | PGLPGHGIPGIKEKPGPQGYPGVGK 647 |
| | USF3:NM_001009899:exon7: c.C3625T:p.P1209S, | NSQGSIEATMERSLEKPSCSLGIKT 648 |
| | TIMMDC1:NM_016589:exon2:c.A338T: p.Y113F, | KQQYIEQSQAEIFHNRFDAVQSAHR 649 |
| | CCDC14:NM_001308317:exon12: c.G2168A:p.R723H, | DWSISSFSTFTSHDEQDFRNGLAAL 650 |
| | ACAD9:NM_014049:exon11:c.C1117T: p.P373S, | YLTAGMLDQPGFSDCSIEAAMVKVF 651 |
| | FNDC3B:NM_001135095:exon5: c.C289T:p.R97C, | YISQVIEDSTGVCRVVVTPQSPECY 652 |
| | BCL6:NM_001706:exon5:c.A496C: p.N166H, | IMAYRGREVVENHLPLRSAPGCESR 653 |
| | UBE2K:NM_001312646:exon3: c.C208T:p.P70S, | LEIKIPETYPFNSPKYKQNPEMFKQ 654 |
| TMG27 | BEND4:NM_001159547:exon3: c.G943A:p.E315K, | GHPSSSTLPEEEKEEDEEGYCPRCQ 655 |
| | GABRB1:NM_000812:exon9:c.G1129A: p.E377K, | GNILLSTLEIRNKTSGSEVLTSVSD 656 |
| | NOA1:NM_032313:exon6:c.C1807T: p.L603F, | MGGKERMAGFPPFVAEDIMLKEGLG 657 |
| | ADGRL3:NM_015236:exon7:c.C1369T: p.P457S, | RTTTLSPGRSTTSSVSGRRNRSTST 658 |
| | ANKRD17:NM_198889:exon27: c.T4466G:p.V1489G, | KKVSVPSTVISRGIGRGGCNINAIR 659 |
| | FRAS1:NM_025074:exon63:c.C9566T: p.S3189F, | HVEEVTKEGVKKFPSPGYPLVCVTP 660 |
| | ADH1A:NM_000667:exon7:c.C890T: p.P297L, | EACGTSVIVGVPLDSQNLSMNPMLL 661 |
| | BANK1:NM_001127507:exon8: c.G977A:p.G326E, | ADGAEANEMEGEEKQNGSGMETKHS 662 |
| | ENPEP:NM_001977:exon16:c.C2237T: p.S746F, | NDAGDHVTKLLRFSVLGFACKMGDR 663 |
| | KIAA1109:NM_015312:exon71: c.G12395C:p.S4132T, | SGLGSPLGRSRHTSSQSDLTSSSSS 664 |
| TMG28 | INTU:NM_015693:exon12:c.A2110G: p.T704A, | CRRTLFGDYSLKARKPSPSCSSGGS 665 |
| | LARP1B:NM_018078:exon10: c.A1103G:p.D368G, | MSRGLSTSLPDLGSEPWIEVKKRHQ 666 |
| | NPY5R:NM_006174:exon4:c.T998A: p.V333D, | SQLSSSSKFIPGDPTCFEIKPEENS 667 |
| | GLRA3:NM_001042543:exon6: c.G686A:p.R229Q, | LPQFLLKEEKDLQYCTKHYNTGKFT 668 |
| | TENM3:NM_001080477:exon27: c.G7223A:p.S2408N, | IHDVKDYITDVNNWLVTFGFHLHNA 669 |
| | STOX2:NM_020225:exon3:c.G1091A: p.R364Q, | HHSGRSKKSRTHQKSHGKSRSHSKT 670 |
| | PLEKHG4B:NM_052909:exon3: c.C631G:p.R211G, | QSGVVTLPGTRDGHGRAVVQVRTRS 671 |
| | DNAH5:NM_001369:exon73: c.A12638G:p.N4213S, | FGALGWNIPYEFSQADFNATVQFIQ 672 |
| | DNAH5:NM_001369:exon14:c.G1837A: p.D613N, | DMISKLYTKQKYNPPLARNQPPIAG 673 |

TABLE 4-continued

Amino acid sequences of somatic mutations (patient #136) for screening in each TMG

| TMG No. | Gene name and locus | Mutant AA sequence |
|---|---|---|
| | DNAH5:NM_001369:exon4:c.G364T: p.A122S, | KPKVFVTEGNDVSLTGVCVFFIRTD 674 |
| TMG29 | PRLR:NM_000949:exon10:c.A1297T: p.I433F, | PSQHNPRSSYHNFTDVCELAVGPAG 675 |
| | RICTOR:NM_001285439:exon1: c.G41A:p.R14Q, | AAIGRGRSLKNLQVRGRNDSGEENV 676 |
| | MROH2B:NM_173489:exon30: c.G3031A:p.E1011K, | FIPNEEILMFLEKMLDGLESLNPTC 677 |
| | CMYA5:NM_153610:exon2:c.C9670T: p.P3224S, | SEGDSVNSEASFSSRNSDTDDGTGI 678 |
| | VCAN:NM_001164098:exon7: c.T1966C:p.F656L, | PFPSQHRTEIELLPYSGDKILVEGI 679 |
| | VCAN:NM_001164098:exon7: c.C3955T:p.H1319Y, | LSTPQPPASTKFYPDINVYIIEVRE 680 |
| | VCAN:NM_001164097:exon7: c.C2687T:p.T896I, | SPHVETTFSTEPIGLVLSTVMDRVV 681 |
| | ADGRV1:NM_032119:exon20: c.C4024T:p.P1342S, | FTGLEGAFGTVNSKYHPSRNNTIAN 682 |
| | NR2F1:NM_005654:exon2:c.G476A: p.G159E, | LKVGMRREAVQRERMPPTQPNPGQY 683 |
| | LIX1:NM_153234:exon4:c.C412T: Pp.138S, | ASTSGTLDDADDSSTSVGAYHYMLE 684 |
| TMG30 | EPB41L4A:NM_022140:exon6: c.G436A:p.E146K, | TAAQLGAYAIQSKLGDYDPYKHTAG 685 |
| | KDM3B:NM_016604:exon14: c.C3590G:p.S1197W, | DIRSEEPLKTDSWASNSNSELKAIR 686 |
| | GRXCR2:NM_001080516:exon1: c.C47T:p.P16L, | PEKKLNQKSDGKLRKVRFKISSSYS 687 |
| | LARS:NM_020117:exon29:c.A3033C: p.Q1011H, | NLEKMGPRILDLHLEFDEKAVLMEN 688 |
| | GRIA1:NM_000827:exon11:c.G1496T: p.R499L, | DVAVAPLTITLVLEEVIDFSKPFMS 689 |
| | FAXDC2:NM_032385:exon9:c.C985T: p.P329S, | GFTPLSESIPDSSKRME 690 |
| | THVID4:NM_001146726:exon2: c.G164A:p.G55E, | SSWSHNSNSMCWEKDQCPYSGCKEA 691 |
| | NIPAL4:NM_001099287:exon1: c.G148A:p.A50T, | SRPPAPELGSPGTVRPRVGSCAPGP 692 |
| | GABRG2:NM_198904:exon6:c.C701T: p.S234F, | WKRSSVEVGDTRFWRLYQFSFVGLR 693 |
| | STC2:NM_003714:exon4:c.G871A: p.E291K, | LGAQGPSGSSEWKDEQSEYSDIRR 694 |
| TMG31 | FGFR4:NM_213647:exon13: c.C1720T.p.P574S, | LRARRPPGPDLSSDGPRSSEGPLSF 695 |
| | LMAN2:NM_006816:exon2:c.T248G: p.L83R, | SMPLWDFQGSTMRTSQYVRLTPDER 696 |
| | MAPK9:NM_002752:exon8:c.G834C: p.W278C, | YPGIKFEELFPDCIFPSESERDKIK 697 |
| | DEK:NM_001134709:exon2:c.G123C: p.E41D, | REESEEEEDEDDDEEEEEEKGKGQK 698 |
| | LRRC16A:NM_017640:exon33: c.C3254A:p.T1085K, | LIKSRSKSERPPKILMTEEPSSPKG 699 |
| | RNF8:NM_183078:exon3:c.C664T: p.P222S, | LEPSKTTGAPIYSGFPKVTEVHHEQ 700 |
| | RNF8:NM_183078:exon3:c.C665T: p.P222L, | LEPSKTTGAPIYLGFPKVTEVHHEQ 701 |
| | KCNK16:NM_001135106:exon5: c.C871T:p.P291S, | SDPSGLPRPQKISISA 702 |
| | KLHDC3:NM_057161:exon2:c.C37T: p.R13C, | MLRWTVHLEGGPCRVNHAAVAVGHR 703 |
| | HSP90AB1:NM_001271969:exon10: c.T1724C:p.V575A, | LCKLMKEILDKKAEKVTISNRLVSS 704 |
| TMG32 | OOEP:NM_001080507:exon1:c.C50T: p.P17L, | AGAAESQRGKQTLAHSLEQLRRLPL 705 |
| | IMPG1:NM_001282368:exon2: c.A192T:p.K64N, | CQQETFCLFDIGNNFSNSQEHLDLL 706 |
| | MANEA:NM_024641:exon5:c.G1253A: p.R418K, | HEGTQIEKAVPKKTSNTVYLDYRPH 707 |
| | AK9:NM_001145128:exon23: c.C2467T:p.P823S, | TVVLPEFPEDSYSDVPEMEPFKEKI 708 |

TABLE 4-continued

| Amino acid sequences of somatic mutations (patient #136) for screening in each TMG | | |
|---|---|---|
| TMG No. | Gene name and locus | Mutant AA sequence |
| | BCLAF1:NM_014739:exon5:c.G1111A: p.A371T, | EASKEKGSEKGRTEGEWEDQEALDY 709 |
| | ADCYAP1R1:NM_001118:exon7: c.G334A:p.G112R, | FGDSNSLDLSDMRVVSRNCTEDGWS 710 |
| | PDE1C:NM_001191058:exon16: c.G1825A:p.E609K, | EKARLAAEEQQKKMEAKSQAEEGAS 711 |
| | ANK1B1:NM_019004:exon15: c.C1994T:p.P665L, | LLKTRRILKCSYLYGFFLEPKSTKK 712 |
| | BRAF:NM_004333:exon15:c.T1799A: p.V600E, | LTVKIGDFGLATEKSRWSGSHQFEQ 713 |
| | ZNF398:NM_170686:exon6:c.C1277T: p.P426L, | TYHLRVHNSTERLFPCPDCPKRFAD 714 |
| TMG33 | ABCB8:NM_001282293:exon15: c.G1816A:p.A606T, | KGGLYAELIRRQTLDAPRTAAPPPK 715 |
| | CSMD1:NM_033225:exon66: c.C10042T:p.P3348S, | REVNETVTKTPVSSDVFFVNSLWKG 716 |
| | FGF20:NM_019851:exon3:c.C601T: p.P201S, | HFLPRPVDPERVSELYKDLLMYT 717 |
| | C8orf34:NM_052958:exon9: c.G1250A:p.G417E, | TLNICSRCARLQEDNLEERTEESLP 718 |
| | ZFHX4:NM_024721:exon10:c.A7093G: p.T2365A, | MDATDQVVYKHCAVSGQTDAAKNAA 719 |
| | ZC2HC1A:NM_016010:exon8:c.T741G: p.S247R, | GANVKPRNSTPPRLARNPAPGVLTN 720 |
| | ATP6V0D2:NM_152565:exon2: c.G211T:p.D71Y, | ANHTNPLTVSKIYTEMRKRLCGEFE 721 |
| | MMP16:NM_005941:exon10:c.C1564T: p.P522S, | FNNQILKVEPGYSRSILKDFMGCDG 722 |
| | PKHD1L1:NM_177531:exon16: c.A1564G:p.N522D, | VQVITLENWETTDAINEVQKIKVTS 723 |
| | GML:NM_002066:exon3:c.C181T: p.R61C, | PYHIRRCMTISICINSRELLVYKNC 724 |
| TMG34 | CEP78:NM_032171:exon11:c.T1307C: p.V436A, | VTVTVESPSSSEAEEVDDSSESVHE 725 |
| | NAA35:NM_024635:exon17:c.C1409T: p.A470V, | ATLQDEAEKVDAVLHTMLLKQEPQR 726 |
| | GRIN3A:NM_133445:exon1:c.C329T: p.S110F, | LGSTLHGRGPPGFRKPGEGARAEAL 727 |
| | FKTN:NM_006731:exon10:c.G1339A: p.G447R, | DWKRSPPNVQPNRIWPISEWDEVIQ 728 |
| | OR1J4:NM_001004452:exon1: c.T349A:p.S117T, | IFFTDLDNFLLTTMAYDRYVAICHP 729 |
| | IER5L:NM_203434:exon1:c.G949A: p.D317N, | YPGQEEEEDDEENAGGLGAEPPGGA 730 |
| | VCX3B:NM_001001888:exon3: c.G679A:p.E227K, | SQESQVEEPLSQKSEMEEPLSQESE 731 |
| | ARHGAP6:NM_006125:exon4:c.C995T: p.S332L, | NKRQNKELSSSNLSLSSTSETPNES 732 |
| | FRMPD4:NM_014728:exon2:c.C68T: p.P23L, | KLSSHRTKSSGWLPPSGTWGLSQVP 733 |
| | BMX:NM_001721:exon15:c.G1567A: p.G523S, | SQLLEMCYDVCESMAFLESHQFIHR 734 |
| TMG35 | PHEX:NM_000444:exon4:c.C386T: p.T129I, | ELLEKSISRRRDIEAIQKAKILYSS 735 |
| | DMD:NM_004009:exon10:c.G1000A: p.E334K, | EDKSFGSSLMESKVNLDRYQTALEE 736 |
| | FAM47C:NM_001013736:exon1: c.C1099T:p.R367C, | CPEPPETRVSPLCQLPPEAGVSHLC 737 |
| | SHROOM4:NM_020717:exon4: c.G1714A:p.G572R, | PKECSRMGGRRSRGTRGRSIQNRRK 738 |
| | IQSEC2:NM_001111125:exon7: c.G2534A:p.R845Q, | LDDALRKFQSHIQVQGEAQKVERLI 739 |
| | PCDH11X:NM_032968:exon1:c.C277T: p.R93C, | TGEIFTTGARIDCEKLCAGIPRDEH 740 |
| | PCDH19:NM_001105243:exon4: c.C2704T:p.H902Y, | TSVTSMGSQMPDYDQNEGFHCREEC 741 |
| | TENM1:NM_014253:exon10:c.C1774T: p.P592S, | CRHGWKGPECDVSEEQCIDPTCFGH 742 |
| | ZNF75D:NM_001185063:exon4: c.C673T:p.P225S, | MKIAQKTMGRENSGDTHSVQKWHRA 743 |
| | MAGEC1:NM_005462:exon4:c.G367A: p.D123N, | PLEISQSPPEGENVQSPLQNPASSF 744 |

TABLE 4-continued

Amino acid sequences of somatic mutations (patient #136) for screening in each TMG

| TMG No. | Gene name and locus | Mutant AA sequence |
|---|---|---|
| | IDS:NM_006123:exon6:c.G820A: p.E274K, | VAYNPWMD1RQRKDVQALNISVPYG 745 |
| | ABCD1:NM_000033:exon1:c.C22G: p.R8G, | MPVLSRPGPWRGNTLKRTAV 746 |

To identify MHC-I neoantigens, MHC-I expressing Cos7 cells were transfected (Cos7-A1, Cos7-B8 and Cos7-C7) cells with 35 TMGs, respectively, followed by adding $CD8^+$ T cells isolated from 136 TILs. ELISA analysis revealed that one TMG (i.e. TMG2) was positive for activating T cell response in Cos7-A1, but not in Cos7-B8 or Cos7-C7 cells (FIG. 8D). Further experiments using individual minigene-expressing vectors identified HHAT (G>E) in TMG2 as HLA-A1 restricted neoantigen in 136 mel (FIG. 8E and FIG. 9B). To exclude the possibility that other MHC-I and II molecules could also present neoantigens for T cell recognition, fibroblasts were generated from patient #136 tumor samples and used as APCs to express all MHC I and II molecules after IFN-γ pretreatment (FIG. 9C). The IFN-γ—pretreated fibroblasts were electroporated with in IVT mRNA of 136 mel TMGs, and then co-cultured with 136TILs. TMG2, TMG19, TMG31 and TMG32 were identified as positive again for T cell recognition in the IFN-γ-pretreated fibroblasts, but did not identify new TMG using 136TIL (FIG. 8F).

As shown in 135 mel, ADIPOR2 and LAGE1b were identified as tumor antigens recognized by T cell clones that were in relatively low abundance in the bulk TIL population. Thus, T cell clones generated from 136TILs were tested for their ability to recognize the newly identified as well as unknown neoantigens. 293IMDR1/DP4 and 293IMDR11/DP4 cells were transfected with 35 TMGs, respectively, followed by co-culturing with T cells clones for overnight. It was found that $CD4^+$136-C13 and 136-C22 T cell clones were capable of recognizing TMG13 and TMG8 presented by 293IMDR1/DP4 cells (FIG. 8G). Further experiments using individual minigenes identified C1GALT1C1 (L>F) in TMG13 and HSPA13 (P>L) in TMG8 as two MHC-II neoantigens (FIG. 8H and FIG. 9D). Titration experiments using synthesized neoantigens and their corresponding WT peptides demonstrated that $CD4^+$136TIL and $CD8^+$136TIL cells can recognize 4 MHC II neoantigens and one HLA-A1-restricted neoantigen, respectively, while T cell clones (136-C13 and 136-C22) recognized two MHC-II restricted neoantigens (FIG. 8I). By contrast, these T cell lines or clones showed no or little reactivity against their corresponding WT peptides (FIG. 8I), indicating that these are true neoantigens recognized by tumor-reactive T cells.

(4) Discovery of Immunodominance for Neoantigen Recognition Patterns by Tumor-Reactive T Cells Using systemic and multiple approaches, 8 cancer neoantigens were identified in 135 mel and 7 neoantigens in 136 mel. To understand the potential mechanisms that restrain the number of neoantigens that could induce T cell response, it was asked whether these neoantigens were equally recognized by T cells. To test this possibility, 78 $CD4^+$ tumor-reactive T-cell clones established from 135TILs were tested for their ability to recognize neoantigens, and unexpectedly found that 69 of 78 T cell clones (88%) were capable of recognizing the PCDHB16 neoantigen in 293IMDR4/DP4 cells, while 3 (3.8%) recognized SPATA13, 3 (3.8%) recognized PCDHB7, and 1 (1.3%) recognized ATG5 (FIG. 10A), indicating that PCDHB16 neoantigen is an immunodominant neoantigen that stimulates $CD4^+$ T cell response. Similarly, 40 $CD8^+$ tumor-reactive T-cell clones were tested for their ability to recognize MHC-I restricted neoantigens (RPN2, MPG and TXNIP), and found that 27 of 40 $CD8^+$ T-cell clones (67.5%) recognized MPG, while 5 of 40 (12.5%) recognized RPN2 and 8 of 40 (20%) recognized TXNIP, respectively (FIG. 10B), indicating that MPG is an immunodominant neoantigen responsible for $CD8^+$ T-cell recognition.

To exclude the possibility that T cell growth selection during T cell cloning may contribute to the observed immunodominance, primary neoantigen-specific T cell population (without long-time culture and expansion) were freshly generated and performed intracellular cytokine staining after specific neoantigen peptide stimulation, and found that tumor-reactive $CD4^+$ T cell populations accounted for 32.7% in the total T cell population when stimulated with 135 mel tumor cells. Importantly, PCDHB16 neoantigen-specific $CD4^+$ T cell population accounted for 30.2% in the total T cell population (FIG. 10C), which indicated that 92% of tumor-reactive $CD4^+$ T cells are PCDHB16 neoantigen-specific T cells (FIG. 10D). By contrast, other neoantigens (SPATA13, PCDHB7 and ATG5) specific T cells accounted for very small percentage of tumor-reactive T cells (FIGS. 10C and 10D). Using a similar approach, it was shown that 18.8% of tumor-reactive $CD8^+$ T cells were presented in the total T cell population when stimulated with 135 mel tumor cells, but 12.3% of them accounted for recognition of MPG neoantigen, while 2.95 and 1.54% accounted for recognition of TXNIP and RPN2, respectively (FIG. 10C), indicating that MPG neoantigen functions as an immunodominant antigen for $CD8^+$ T cell response, which accounts for 65% of tumor-reactive $CD8^+$ T cells (FIG. 10D). These results indicate that PCDHB16 and MPG neoantigens are immunodominant neoantigens recognized by a large majority of $CD4^+$ or $CD8^+$ tumor-reactive T cells, respectively.

Interestingly a similar recognition pattern was observed in the second patient-derived T cells (136TIL) for their neoantigen recognition. Intracellular staining of the freshly generated 136TIL population after stimulation with fibroblasts loaded with neoantigen peptide pools or individual one showed that tumor-reactive of $CD4^+$ or $CD8^+$ T cells accounted for 24.8% and 14.6% in the total T cell population, respectively (FIG. 11A). Among them, MAPK9 and ANKIB1 neoantigen-specific $CD4^+$ T cells accounted for 14.3% and 5.2% in the total T cell population, which accounted for 58% and 21% in the total tumor-reactive $CD4^+$ T cell population, respectively (FIG. 11B). By contrast, other neoantigen-specific $CD4^+$ T cells accounted for only a small percentage of T cells in the total T cell population (FIG. 11A). Since HHAT is only one MHC-I neoantigen, it was shown that HHAT neoantigen-specific $CD8^+$ T cells accounted for 10.6% in the total T cell population when stimulation with HHAT peptide (FIG. 11A), which accounted for 73% in the total tumor-reactive $CD8^+$ T cell population (FIG. 11B). Taken together, these results indicate that the mutated MAPK9 and ANKIB1 antigens are MHC-II restricted immunodominant neoantigens, while HHAT is the only MHC-I restricted neoantigen.

Although T cell clones and intracellular staining analysis demonstrate immunodominant neoantigen recognition patterns by T cells, it is not clear whether immunodominant neoantigens are recognized by T cells with the same or different TCR α and β chains. To address this issue, PCDHB16 neoantigen-specific $CD4^+$ T cells were isolated by FACS sorting of PCDHB16-neoantigen T cells from freshly generated bulk T cells after stimulated PCDHB16 neoepitope peptide-pulsed 135EBV-B cells. Using the similar approach, MPG-specific CD8+ T cells were also purified from freshly generated bulk T cells after stimulated MPG neoepitope peptide-pulsed 135EBV-B cells. Genomic DNAs were isolated from the two purified neoantigen-specific T cell populations, as well as the parental bulk T cells, and used as templates for TCR β-chain CDR3 repertoire amplification. Since there is only one copy of genomic DNA in a single T cell, specific TCR β-chain sequence abundance can represent the frequency of neoantigen-specific T cells in the total T cell population. TCRβ CDR3 were then amplified with a set of primers targeting mature V-D-J rearranged T cells. After the amplicons (from PCDHB16-, MPG-specific T cells and bulk 135TIL) were subjected to deep-sequenced via next-generation sequencing (reads>100,000 per sample), followed by bioinformatic analysis and TCR repertoire alignment. Dysfunctional TCR sequences and redundant sequences in all three groups were removed. PCDHB16 and MPG neoantigen-specific TCR sequences (CDR3β VDJ) with top frequencies (>0.001%) were identified in the sequencing result and used to determine the relative frequencies of neoantigen-specific TCRs in the total T cell population (FIG. 10E). The relative TCR sequence frequencies that were identical to those in PCDHB16-specific T cells and MPG-specific T cells were determined in total 135TIL cell population (FIG. 10F). PCDHB16-specific TCRs accounted for 36% in the total 135TIL TCRs, which was close to 32% identified by intracellular staining and FACS analysis (FIG. 10B and FIG. 10F). MPG-specific TCRs accounted for 25.5% in the total TCR sequences in 135TIL, which is higher than 12.3% identified by intracellular staining (FIG. 10B and FIG. 10F). It should be noted that intracellular staining approach identifies the functional T cells, while TCR sequence analysis might contain both functional and non-functional TCRs. These results indicate that PCDHB16- and MPG-specific TCRs are dominant in the total TCR sequences, even though some TCRs with similar sequence may not function in T cell recognition assay. Importantly, it was shown that the same neoantigen-specific TCRs exhibited the strong diversity in the TCR VP CDR3 region (V-J segment) (FIG. 10F, FIGS. 11C and 11D). These results indicate that PCDHB16- and MPG-bound T cells maintain their TCR diversities, with the same neoantigen specificity. Taken together, different approaches (T cell clone analysis, intracellular staining as well as TCR profiling analysis) indicate immunodominant neoantigens in T cell response and recognition in cancer patients.

(5) Differential Recognition of Tumor Cells In Vitro and In Vivo by Neoantigen-Specific T Cells To further understand the cause and impact of immunodominant neoantigens on immunotherapy, it was hypothesized that immunodominant neoantigens may be highly expressed and presented by all tumor cells, while cryptic (subdominant) neoantigens are expressed and presented by some, but not all tumor cells. To test this possibility, single tumor-cell clones of 135 mel were generated by limited dilution (0.3 cells/well) in 96-well plates. Each clone was expanded from one single 135 mel cell and then tested for their recognition by different neoantigen-specific T-cell clones. As expected, the PCDHB16-specific T-cell clone $1H_1$ recognized every single tumor cell clone that was generated, but other subdominant neoantigen-specific T-cell clones (such as 2C10 specific for PCDHB7 and JF6 specific for SPATA13) recognized only a few of single tumor cell clones (FIG. 12A). Similarly, PCDHB16-specific T-cell clone showed significant $CD4^+$ T cell killing activity against 135 mel bulk and clones (FIG. 12B). By contrast, subdominant PCDHB7-specific T-cell clone showed its killing activity against the tumor clone that it recognized, but much weaker activity against bulk tumor cells or no activity against tumor cell clones it failed to recognize (FIG. 12B). Surprisingly, after genomic DNA were isolated from each tumor clone and sent to Sanger sequencing, all tumor clones showed genomic mutations in all three neoantigens same as the result of whole-exome sequencing [PCDHB16 (C>T), PCDHB7 (C>T), SPATA13 (A>G)], while the same sites in 135TIL showed wildtype sequences (FIG. 12C). This result indicated that the loss of T-cell recognition in different tumor clones was not derived from the existence of wildtype genes, but the dysfunctional antigen processing and presentation of mutated antigens.

To further demonstrate in vivo recognition of single tumor cell clones by different neoantigen-specific T cells, 135 mel cells were injected in NSG mice at day 0 and followed by treatment with adoptive transfer of different neoantigen-specific T cell clones ($1H_1$ specific for PCDHB16 and 2C10 specific for PCDHB7) on day 15. Exogenous interleukin-2 was given on day 15 for three consecutive days to maintain T cell proliferation and survival in vivo (FIG. 12D). On day 19 (4 days after T-cell injection), the serum level of IFN-γ was examined and it was found that the tumor-bearing mice treated with dominant neoantigen PCDHB16-specific T-cells produced higher amounts of IFN-γ compared to those treated with PCDHB7-specific T cells (FIG. 12E), indicating strong in vivo recognition of 135 mel tumor cells by PCDHB16-specific T-cells, but weak recognition by PCDHB7-specific T cells. Consistent with these observations, it was found that PCDHB16-specific T cells markedly inhibited 135 mel tumor growth, but PCDHB7-specific T cells showed weak antitumor activity (FIG. 12F). These results indicate that the dominant neoantigen-specific T cells exhibit much stronger in vitro and in vivo tumor recognition and antitumor immunity than those subdominant neoantigen-specific T cells, thus providing a rational design for neoantigen-specific immunotherapy.

(6) Dual Recognition of Two Neoantigens by a Single TCR

Because of large TCR sequence diversity for the same neoantigen, it was noticed that a few tumor-reactive T-cell clones for the dominant neoantigen PCGHB16 had cross-reactivity against other neoantigens (ADIPOR2) (FIG. 10A). Further experiments showed that 135-4B8 T-cell clone recognized both PCDHB16 and ADIPOR2 neoantigen peptides in a dose-dependent manner (FIG. 13A and FIG. 14A). To exclude the possibility that the 135-4B8 T-cell clone contained more than one T-cell receptor (TCR) or mixed with two antigen-specific T cells, a TCR (α and β) gene was cloned from 135-4B8 T cells. Sequencing analysis revealed that these T cells expressed TRAV8-6 and TRBV5-1, indicating that 135-4B8 is a pure T-cell clone expressing a single TCR. Its full-length α and β chain of this TCR was then cloned into the retroviral vector pMSGV (FIG. 14B) and transduced bulk T cells isolated from a healthy donor. After co-culturing of TCR-engineered T cells with PCDHB16 and ADIPOR2 neoantigen peptides, it was shown that 4B8-TCR-transduced T cells were capable of recognizing both PCDHB16 and ADIPOR2 neoantigens (FIG. 13B). To determine whether 4B8-TCR mediates antigen recognition through $CD4^+$ or $CD8^+$ T cells, $CD4^+$ and $CD8^+$ naïve T cells were transduced with 4B8-TCR, and then tested their ability to recognize the target neoantigens. It was found that 4B8 TCR-transduced $CD4^+$ T cells recognized both the PCDHB16 and ADIPOR2 antigens, whereas the 4B8-TCR transduced $CD8^+$ T cells failed to do so (FIG. 13C).

The $CD4^+$ T-cell clone 135-C76 was analyzed for dual recognition of the PCDHB16 neoantigen presented by HLA-DP4 molecules and RPN2 neoantigens presented by HLA-A1 molecules (FIG. 14C). Flow cytometric analysis revealed that 135-C76 T cells were CD4 and CD8 double positive (FIG. 13D). After cloning 135-C76 TCR (TRAV29, TRBV15), it was inserted into pMSGV retroviral vector to test its activity. It was found that 135-C76 TCR-transduced T cells containing $CD8^+$ and $CD4^+$ T-cell populations were capable of recognizing both mutated PCDHB16 and RPN2 neoantigens (FIG. 13D). However, further experiments revealed that 135-C76 TCR-transduced $CD8^+$ T cells recognized the HLA-A1-restricted RPN2 neoantigen, but not the PCDHB16 neoantigen (FIG. 13E). By contrast, 135-C76 TCR-transduced $CD4^+$ T cells recognized PCDHB16 neoantigen, but not the RPN2 neoantigen (FIG. 13E). These results indicate that 135-C76 TCR can recognize an MHC-I-restricted antigen by $CD8^+$ T cells, and MHC-II-restricted neoantigen by $CD4^+$ T cells.

(7) Knockdown of ThPOK in CD4+ 135TIL and Other CD4+ T Cells Increases their Cytolytic Activity In Vitro and In Vivo $CD8^+$ and $CD4^+$ T cells are the major components of T cell-based antitumor immunity. $CD8^+$ T cells, also known as cytotoxic T lymphocytes (CTL), are capable of specific antigen recognition presented by MHC-I molecules and have high cytotoxicity to kill target cells. $CD4^+$ T cells also show specific antigen recognition presented by MHC-II molecules but much lower killing ability than $CD8^+$ T cells. Although the data of T-cell clones of 135TIL show rather high cytolytic activity when targeting PCDHB16 neoantigen, in most cases $CD4^+$ antigen-specific T cells have rare killing ability when they recognize target cells. Thus it will be a new challenge to reprogram $CD4^+$ T cells and improve their cytolytic activity. The transcription factor T-helper-inducing POZ/Krueppel-like factor (ThPOK) and is a master regulator of $CD4^+$ T cell development and negatively regulates the cytolytic ability of $CD4^+$ T cells. After immigration from the thymus, naïve $CD4^+$ T cells maintain the expression of ThPOK, indicating that ThPOK can still play important roles for the maintenance of $CD4^+$ T cells phenotype and function.

To address this problem, single T cell clones were generated from 135 mel cancer cell-reactive $CD4^+$ TIL via limited dilution. Cytotoxicity analysis of those T-cell clones were performed with expanded T-cell clones, showing different cytotoxic ability in each T cell clone (FIG. 15A). Next, the expression of ThPOK was checked in both mRNA and protein level in those $CD4^+$ T-cell clones by quantitative PCR and western blotting (FIG. 15B and FIG. 15C). The result showed a negative association of ThPOK expression level of both mRNA and protein with $CD4^+$ T cell's killing ability. ThPOK is highly expressed in weak cytotoxic $CD4^+$ T cell clones (2F8) and vice versa ($1H_1$), indicating $CD4^+$ T cell's cytolytic activity was negatively regulated by ThPOK.

To abolish the expression of ThPOK in antigen-specific $CD4^+$ human T cells, lentiviral shRNA plasmid from the human shRNA library was applied to degrade ThPOK mRNA generation. Western blotting analysis confirmed ThPOK was effectively knockdown 72 h after lentiviral transduction in $CD4^+$135TILs (FIG. 16A). Then $CD4^+$ 135TIL with or without ThPOK knockdown were compared in the LDH assay with E/T ratio from 5:1 to 20:1. The ThPOK-knockdown $CD4^+$ TIL significantly had higher cytotoxicity against 135 mel at every E/T point (up to 55% which exceeds most normal $CD4^+$ T cells, FIG. 16B). In another experiment, the number of live 135 mel cells incubating with ThPOK-knockdown $CD4^+$ TIL decreased about 20% more than normal $CD4^+$ 135TIL after three-day culture (FIG. 16C). The two results demonstrated a dramatic improvement of cytolytic activity in ThPOK-knockdown $CD4^+$135TIL in vitro. The mRNA level of gene GZMB, PRF1, EOMES, RUNX3 and IFN-γ in ThPOK-knockdown $CD4^+$135TIL was also examined, which are positive regulators for T cell cytotoxicity. The significant up-regulation of GzmB, Prf1 stands for a remarkable enhancement of T cell cytotoxicity (FIG. 16D). Although the mRNA level of IFN-γ was also up-regulated (FIG. 16D), a significant change in protein level was not found via ELISA (FIG. 16E). Furthermore, ThPOK knockdown did not affect other $CD4^+$ T cell cytokines, such as IL-4, IL-10 and GM-CSF (FIG. 16E). Those results indicated that knockdown of ThPOK can increase $CD4^+$ T-cell cytotoxicity but maintains their CD4+ property in vitro.

Based on the results in vitro, the 135 mel mouse model was applied to test knockdown of ThPOK in vivo. 135 mel tumor cells were inoculated into the NSG mice. $CD4^+$ 135TIL modified by ThPOK shRNA lentiviruses were adoptively transferred on the $5^{th}$ day after the tumor inoculation, together with unmodified CD4+ 135TIL and non-specific $CD4^+$ T cells. From day 5 to day25, 135 mel growth in each group was observed. Tumor growth treated by ThPOK-knockdown $CD4^+$135TIL was inhibited significantly, leaving the smallest tumor size, compared to unmodified $CD4^+$ 135TIL and non-specific CD4+ T cells (FIG. 17A and FIG. 17B). To further validate in vivo function of ThPOK-knockdown $CD4^+$ T cells, a $CD4^+$ TCR-T model besides 135TIL was applied. A TCR targeting MHC-A2-presented NY-ESO-1 epitope was retrovirally transduced in normal human $CD4^+$ and $CD8^+$ T cells respectively. A human prostate cancer cell line PC3 expressing NY-ESO-1 and MHC-A2 (A2ESO) was subcutaneously inoculated in NSG mice and followed by injection of TCR-transduced or untransduced $CD4^+$ and $CD8^+$ T cells with or without ThPOK knockdown in a similar time manner as above. Interestingly it was found that the tumor suppression effect of ThPOK-knockdown TCR-transduced $CD4^+$ T cells was very similar as that of TCR-transduced $CD8^+$ T cells, which inhibited the tumor growth profoundly, while none-specific CD4+ T cells and ThPOK-expressing $CD4^+$ TCR-T cells showed minor tumor suppression effect (FIG. 17C and FIG. 17D). All in vivo experiment confirmed knockdown of ThPOK in tumor-reactive $CD4^+$ T cells improved T-cell antitumor activity and decelerated the tumor growth in NSG mice. Taken together, ThPOK is selectively expressed in $CD4^+$ T cells while low level of ThPOK corresponds to an improved cytolytic activity of $CD4^+$ T cells, which has been demonstrated by in vitro and in vivo experiments.

(8) ThPOK Inhibits CD4+ Tumor Specific T Cell Cytolytic Activity by Interacting with LSD1

It was hypothesized that the improvement killing ability of $CD4^+$ T cells due to ThPOK knockdown is procedure of T-cell reprogramming via epigenetic regulation. To distinguish how ThPOK reprogrammed $CD4^+$ T cells to cytolytic $CD4^+$ T cells, a screening of A2ESO TCR-transduced $CD4^+$ T cells treated by various epigenetic inhibitors was performed. After measuring the change of cytotoxicity of $CD4^+$ TCR-T cells against tumor, it was found that 2-PCPA, the inhibitor of Lysine-specific histone demethylase 1A (LSD1) was the only one inhibitor which dramatically enhanced the cytolytic activity of $CD4^+$ TCR-T cells, that was similar as depletion of ThPOK (FIG. 18A). To further investigate the correlation between ThPOK and LSD1, immunoprecipitation screening was performed by overexpression tagged proteins in HEK293T host cells with various epigenetic regulators and ThPOK. Suprisingly, LSD1 showed the strongest binding with ThPOK among all epigenetic regulators (FIG. 18B). The direct interaction between LSD1 and ThPOK was further confirmed by endogenous immunoprecipitation in primary human $CD4^+$ T cells (FIG. 18C). Since LSD1 functions in regulating target gene expression by modifying their promoter histone methylation status, CHIP-PCR was performed by pulling down bound DNAs with ThPOK and LSD1 antibodies respectively in $CD4^+$ and $CD8^+$ T cells. Detection of high level of promoter regions of genes GZMB and PRF1 in $CD4^+$ T cells revealed that ThPOK and LSD1 both had strong binding with the promoters of these two genes only in $CD4^+$ T cells (FIG. 18D). The co-occupancy of ThPOK and LSD1 at the promoters of GZMB and PRF1 can block the transcription of these two the key cytotoxic genes and deprived the cytolytic activity of $CD4^+$ cells.

(9) Inhibition of LSD1 by 2-PCPA Positively Regulates of the Generation of Stem Cell-Like Memory T Cells To identify key regulators of the generation and maintenance of stem cell-like memory T cells (Tscm), an in vitro small molecules screening platform was established that works directly on ex vivo primary human T cells. Briefly, T cells were activated with plate-bound OKT3 and treated them with small molecules including different metabolites and inhibitors. Half volume of culture medium was changed, and metabolites or inhibitors were added every 2 or 3 days. The memory phenotypes of both $CD4^+$ and $CD8^+$ T cell populations were detected at day 12 through staining with key memory markers CD45RO, CCR7 and CD62L. Tscm subset in this platform was identified as $CD45RO^-$, $CCR7^+$ and $CD62L^+$ population by flow cytometry. In activated T cells that don't contain naïve T cells, these three markers were able to identify three memory T cells subsets, Tscm, Tcm and Tem (Lugli et al., 2013). Small molecules that were extremely toxic and dramatically suppressed T cells growth were excluded from this platform. With this method of T cells culture, T cells differentiated significantly and very limited percentage of Tscm cells in both $CD4^+$ and $CD8^+$ T cells can be obtained. 2-PCPA, an inhibitor of LSD1, was identified as the only one positive regulator of Tscm generation that increased the population of Tscm in both $CD4^+$ and $CD8^+$ T cells (FIG. 19A). To further confirm that the $CD45RO^-$ $CCR7^+$ $CD62L^+$ population were truly Tscm cells, the other 2 Tscm markers, CD45RA and CD95 were analyzed within CD45RO− CCR7+ $CD62L^+$ population and found that the cells were almost 100% positive in these 2 markers (FIG. 19B), validating the purity of Tscm population. In conclusion, it was shown that 2-PCPA was effective in promoting Tscm generation in both $CD4^+$ and $CD8^+$ T cells.

(10) Inhibition of LSD1 by 2-PCPA in TCR-T and CAR-T Cells Increases T-Cell Antitumor Activity In Vitro and In Vivo To test how the inhibition of LSD1 by 2-PCPA treatment affects TCR-T cells, 2-PCPA (8 uM) was directly administered at the beginning of TCR-T cell generation. Activated human T cells were transduced on day 2 and day 3 with A2ESO TCR viruses that were packaged by PG13-A2ESO TCR clone. Results showed that 2-PCPA treatment increased both Tscm and Tcm percentages in A2ESO TCR-T cells, indicating a less-differentiated phenotype (FIG. 20A). To investigate the functional change of A2ESO TCR-T cells after 2-PCPA treatment, intracellular staining (ICS) was performed to check the expression of effector cytokines, targeting IL-2, IFN-γ and TNF-α. Interestingly, although 2-PCPA treatment maintained A2ESO TCR-T cells in a less-differentiated phenotype, it didn't reduce but slightly increased the frequency of A2ESO TCR-T cells with polyfunctional cytokine secretion (FIG. 20B). As high proliferation potential is a key characteristic of Tscm cells, the in vitro proliferation assay by using CFSE staining and by stimulating A2ESO TCR-T cells with IL-2 or 231-ESO cells confirmed this feature of 2-PCPA treated A2ESO TCR-T cells (FIG. 20C). Another key feature of less-differentiated T cell is increased oxidative metabolism and mitochondrial respiratory capacity. It was also reported that LSD1-inhibition upregulated oxidative metabolism genes in myogenic cells (Anan et al., 2018). The results also showed that 2-PCPA treatment rendered A2ESO TCR-T cells with increased oxidative metabolism and elevated spare respiratory capacity (SRC) (FIG. 20D).

The results of 2-PCPA-treated A2ESO TCR-T cells in vitro showed less-differentiated memory phenotype and increased function and proliferation, an attempt was made to test to in vivo effect of 2-PCPA-treated A2ESO TCR-T cells. A breast cancer model was established using MDA-MB-231 cells expressing HLA-A2 and NY-ESO-1 antigen in 8 weeks old NOD-scid IL2Rγnull (NSG) mice. The in vivo antitumor function of A2ESO TCR-T cells was significantly enhanced by 2-PCPA treatment (FIG. 20E). Through determining the memory phenotype of T cells after adoptive transfer, it was found that Tscm population was barely detectable in control A2ESO TCR-T cells, while 2-PCPA treated A2ESO TCR-T cells maintained higher frequency of both Tscm and Tcm cells (FIG. 14F). These results indicated that 2-PCPA treatment promotes Tscm generation in A2ESO TCR-T cells with higher proliferation potential and self-renewal ability.

To determine whether 2-PCPA treatment was also effective on CAR-T cells as well as TCR-T cells, 2-PCPA treatment was applied when generating CAR-T cells. Activated T cells were transduced with CD19-specific chimeric antigen receptor (CAR) possessing CD28 co-stimulatory domain virus packaged by PG13 clone. Memory phenotype analysis showed that 2-PCPA treatment similarly increased the frequencies of less-differentiated memory T cells subsets (FIG. 21A). The metabolic reprogramming effect is consistent with its effect on A2ESO TCR-T cells (FIG. 21B). In vitro survival assay showed that 2-PCPA treated CAR-T cells survived better under IL-2 free condition than control CAR-T cells (FIG. 21C). However, this effect was not seen on 2-PCPA-treated A2ESO TCR-T cells. Next, in vivo proliferation of CAR-T cells was observed with or without 2-PCPA treatment. Both CAR and luciferase were transduced into activated T cells and transfer into NSG mice that have been injected with Raji lymphoma cells. In vivo imaging showed that 2-PCPA-treated CAR-T cells grew faster than control CAR-T cells (FIG. 21D). To further confirmed the results from in vivo imaging, the mice were sacrificed and checked the existence of human T cells within the spleen (FIG. 21E). These results demonstrated that 2-PCPA treatment promoted both in vitro and in vivo antitumor function of CAR-T cells.

b) Discussion

The findings presented here identify a distinct pattern of T-cell reactivity against mutation-derived neoantigen; that is, a dominant neoantigen was recognized by the majority of tumor-reactive $CD4^+$ or $CD8^+$ T cells, while several other neoantigens were infrequently recognized by T cells. Interestingly, in the case of patient #135 it was shown that large majority of the tumor-reactive $CD4^+$ or $CD8^+$ TIL population/T-cell clones recognized neoantigens derived from somatic missense mutations respectively which was demonstrated via FACS and TCR sequencing analysis. Importantly, dominant neoantigen-specific T cells show better recognition and killing ability of single tumor cell clones, compared with subdominant/cryptic neoantigen-specific T-cell clones, implying that dominant neoantigen-specific T cells can play a critical role in tumor regression in checkpoint immunotherapy. Although two tumor-reactive $CD4^+$ T-cell clones did not recognize mutation-derived neoantigens, they did respond to neoepitopes derived from the gene product of the 3'UTR region of ADIPOR2 mRNA or translated from an alternative ORF of the LAGE1b gene. Thus, gene products derived from aberrant translation of an mRNA can serve as neoantigens in cancer cells. By contrast, it was found that all tumor-reactive $CD8^+$ T-cell clones recognized neoantigens derived from somatic missense mutations. Further investigation of neoantigens in another melanoma patient (patient #136) revealed the similar pattern of neoantigen recognition as seen with melanoma patient #135, indicating that although neoantigens capable of eliciting a specific T-cell response can be different among cancer patients, the regulation and control of neoantigen-specific response and recognition pattern appear consistent among patients within the same type of cancer.

Immunodominant and cryptic antigens have been reported in autoimmunity and infectious diseases, the study indicates that similar mechanisms can operate in response to cancer neoantigens. In this study, tumor clones growing from single cells were generated and checked the specific neoantigen presentation on tumor clones by recognition of T-cell clones. The data confirms that the presentation level of neoantigens varies in one tumor tissue and there are normally a few neoantigens presented by most of tumor cells, inducing the expansion of their specific T cells to the largest population in primary tumor-reactive T cells. These dominant neoantigens are ideal targets for T-cell based immunotherapy and contribute more in tumor suppression and elimination rather than those subdominant neoantigens, which has been demonstrated by the in vitro and in vivo study.

A single TCR has been reported to recognize multiple antigens in infectious and autoimmune diseases, but it has not demonstrated that a single TCR can recognize dual cancer neoantigens. By taking advantage of tumor-reactive single T-cell clones, provided herein is clear evidence that a single TCR can recognize two neoantigens presented by the same MHC II molecules, without amino acid sequence similarity. Surprisingly, a single TCR from 135-C76 T cells recognized the PCDHB16 neoantigen presented by HLA-DR4 molecules when transduced into $CD4^+$ T cells, while the same TCR responded only to the RPN2 neoantigens presented by HLA-A1 molecules when expressed on $CD8^+$ T cells. Hence, the use of TCRs with dual neoantigen specificity can enhance the potency of T cells used in TCR-based cancer immunotherapy.

c) Methods (1) Human Samples

Fresh tumor tissues were obtained from melanoma patients (#135 and #136) under an approved Institutional Review Board (IRB) protocol of Houston Methodist. Both patients were HLA typed (#135: HLA-A1, B8, C7, DR3, DR4, DP4; #136: HLA-A1, B8, C7, DR1, DR11, DP4).

(2) Primary and Cell Lines

All cells are grown at 37° C. with 5% $CO_2$ unless otherwise stated. Patients' melanoma cell lines (135 mel and 136 mel) were generated and expanded in RPMI 1640 medium (Fisher scientific) with 10% (v/v) fetal bovine serum (Valley Biomedical Inc.) supplemented with 1% (v/v) penicillin-streptomycin (Thermo Fisher Scientific).

All types of human T-cell containing cells, including peripheral blood mononuclear cell (PBMCs), tumor-infiltrated lymphocytes (135TIL and 136TIL), T-cell clones etc. were established and maintained in T-cell culture medium (TCM) containing RPMI 1640 medium with 10% (v/v) human AB serum (Corning) supplemented with 1% (v/v) HEPES (Thermo Fisher Scientific), 1% (v/v) GlutaMAX (Thermo Fisher Scientific) and 0.1% (v/v) 2-mercaptoethanol (Thermo Fisher Scientific)) supplemented with recombinant human interleukin-2 (IL-2, 300 IU/ml) (Peprotech).

Epstein-Barr virus-transformed B (EBV-B) cells derived from patient #135 were cultured in RPMI 1640 medium with 10% (v/v) fetal bovine serum supplemented with 1% (v/v) penicillin-streptomycin.

Fibroblasts derived from patient #136 were cultured in Dulbecco's Modified Eagle Medium (DMEM) (Fisher Scientific) with 10% (v/v) fetal bovine serum (FBS) containing 1% penicillin-streptomycin.

HEK293-based antigen presenting cells (APCs), including 293IMDR3/DP4, 293IMDR4/DP4, 293IMDR1/DP4, 293IMDR11/DP4 were generated, and maintained in Dulbecco's DMEM with 10% (v/v) FBS containing 1% (v/v) penicillin-streptomycin. HEK293T cells, 239T-HLA-A1 and 293T-HLA-B8 cells were maintained in DMEM with 10% (v/v) fetal bovine serum containing 1% (v/v) penicillin-streptomycin.

Cos-7 cells were cultured in DMEM with 10% (v/v) fetal bovine serum containing 1% (v/v) penicillin-streptomycin.

Phoenix-AMPHO cells were cultured in DMEM with 10% (v/v) fetal bovine serum containing 1% (v/v) penicillin-streptomycin.

(3) T-Cell Cloning and T-Cell Expansion

T-cell cloning and expansion were performed. Briefly, T-cell clones from 135TILs were generated by a limited dilution (0.3 cell/well) in 96-well plates. Allogeneic PBMCs from normal donors were irradiated (60 Gy) and then seeded as feeder cells ($7\times10^4$/well) in TCM containing 35 ng/ml OKT3 (anti-hCD3 antibody) (R&D Systems) and 35 ng/ml anti-hCD28 antibody (R&D Systems). On day 1, recombinant IL-2 was added to the final concentration of 300 IU/ml. On day 5, half of the culture medium was replaced with fresh TCM containing recombinant IL-2, and then the medium was changed every other day or when the medium color turned yellow. On day 14, T-cell clones were harvested, counted, tested for tumor reactivity. Tumor reactive T-cell clones were further expanded.

For T-cell expansion, $2.5\times10^5$ T cells were transferred into 25 ml flasks with 20 ml of TCM. $2\times10^7$ irradiated PBMCs (60 Gy) and $5\times10^6$ irradiated EBV-B cells (210 Gy) were added as feeder cells. OKT3 and anti-hCD28 antibody were added to the final concentration of 35 ng/ml. On day 1, recombinant interleukin-2 was added to the final concentration of 300 IU/ml. Culture medium was changed, as described above, starting on day 5. On day 14, expanded T cells were harvested, counted, and restored in liquid nitrogen until use.

(4) T-Cell Reactivity Assay 96-well tissue culture plates were coated with phosphate-buffered saline (PBS, GenDEPOT) containing 50 μg/ml poly-L-lysine (Millipore Sigma) at 37° C. 10 min later, the plates were rinsed twice with PBS. Tumor cells or 293-APCs were seeded at $5\times10^4$/well in the 96-well plate and cultured at 37° C., 5% $CO_2$ for at least 4 h. For plasmid transfection, 250 ng of plasmid DNA were transfected into 293-APCs per well with 0.5 μl of Lipofectamine 2000 (Thermo Fisher Scientific) according to the manufacturer's instructions and incubated at 37° C., in 5% $CO_2$ overnight. For peptide presentation, synthesized peptides (GeneScript) were added to each well at different final concentrations from $10^2$ to $10^{-4}$ μM and incubated at 37° C., 5% $CO_2$. The cells transfected with plasmids or pulsed with peptides were washed with TCM twice, and then cocultured with T cells ($1\times10^5$/well). After overnight culture, 50 μl of supernatant was collected for measuring cytokine release with an ELISA assay.

96-well microplate (Greiner Bio-one) was coated with 50 μl of PBS containing anti-human IFN-γ (Thermo Fisher Scientific, primary antibody, 1 μg/ml) per well and incubated at 4° C. overnight. After three washes with PBS, each well was blocked by 200 μl of 1% (w/v) bovine serum albumin (BSA) in PBS and incubated at room temperature for at least 1 h. After three washes with PBS, 50 μl of culture supernatant or human IFN-γ standard (Peprotech) was added to each well at different concentrations in PBS and incubated at room temperature for 1 h. After three washes, 50 μl of biotin-labeled anti-human IFN-γ antibody (Thermo Fisher Scientific, secondary antibody, 1:1000 dilution) in 2% (v/v) FBS-containing PBS buffer was added to each well, and then incubated at room temperature for 1 h. The 96-well plate was washed six times with PBS containing 1% (v/v) Tween-20. 50 μl of 1:5000 diluted poly-HRP Streptavidin (Thermo Fisher Scientific) in PBS containing 1% (w/v) BSA was then added per well, and incubated in the dark at room temperature for 30 min. After six washes with PBS containing 1% (v/v) Tween-20, 100 μl of 3,3',5,5'-tetramethylbenzidine substrate solution (TMB, Millipore Sigma) was added per well and incubated at room temperature for 10 min. The color reaction was terminated by adding 50 μl of 2.5 M $H_2SO_4$. The plate was read at OD450 nm. The concentration of IFN-γ was calculated by standard reading.

(5) Whole-Exome Sequencing of Tumor and Control Cells

Whole-exome sequencing was performed by a standard protocol. Briefly, genomic DNA from 135 mel and 135TILs were extracted with the Quick-DNA™ Miniprep Kit (Zymo Research). DNA library construction, exome capture, and sequencing were performed by the standard procedure of Illumina HiSeq 3000. The average reads were around 150× of the coverage on each base. Over 8 billion bases of sequence data were obtained from each sequenced sample. Output from Illumina was processed to yield BAM files, which contained aligned reads to the NCBI Human Reference Genome Build hg19 with well-calibrated quality scores. Somatic mutations were detected referred to previous reports and determined after filtering with the following parameters: filtering out variants in TIL sequencing; read depth >10; 1000 human genome frequency <0.01; missense mutation. Finally, somatic mutations were identified for the tandem minigene construction.

(6) Construction of Tandem Minigenes (TMGs) and Screening with T Cells

The tandem minigene construct was designed to encode 10 mutations-containing peptides with 12 amino acids flanked on both sides. The codons for double-strained nucleotide synthesis were optimized to avoid EcoRI and XhoI sites for cloning. The synthesized tandem minigenes (Integrated DNA Technologies) were then cloned into pTSX expression vector with in-frame fusion with the Ii80 open reading frame.

The screening of antigen-specific T cells against TMGs were performed as described in T-cell reactivity assay above. Briefly, TMGs were transfected with Lipofectamine 2000 in the artificial APCs according to the patient's HLA typing respectively. The transfected cells were cocultured with tumor-reactive T cells overnight and the IFN-γ release in the supernatant in each well was determined by ELISA on the second day.

(7) In Vitro Transcription of TMGs

In vitro transcription (IVT) of TMGs was performed with a standard protocol of HiScribe™ T7 ARCA mRNA Kit (New England Biolabs). Briefly, each TMG construct was linearized by cutting of XhoI (New England Biolabs) and gel-purified with DNA Recovery Kit (Zymo Research). The linearized DNA (1 μg) were used as template for RNA synthesis respectively and mixed with T7 RNA polymerase and reaction buffer in a 20 μl mixture as the kit instruction. The reaction was incubated at 37° C. for at least 30 min. Then the DNA templates were removed by adding 2 μl of DNase I and incubating at 37° C. for 15 min. Next the poly (A) tailing reaction (50 μl) was completed by mixing the IVT reaction with Poly(A) polymerase and reaction buffer as the kit instruction and incubating at 37° C. for 30 min.

Each 5'-capped and 3'-tailed IVT-RNAs were purified by adding ½ volume of LiCl to the reaction as the kit instruction. After the incubation at −20° C. for 30 min, the RNAs were spun down by at 4° C. for 15 min at top speed and then the pellets were washed with 500 μl of cold 70% ethanol and air-dried. The pellets were finally resuspended and dissolved in suitable RNA storage solution.

(8) Electroporation of EBV-B Cells and Screening with T Cells

The electroporation was performed as with a modified protocol of Amaxa® Cell Line Nucleofector® Kit V (Lonza). Briefly $1\times10^5$ EBV-B cells were spun down and resuspended in 50 μl of electroporation solution (Nucleofector® Solution:Supplement=9:2) and transferred into a kit-attached 100 μl cuvette immediately. 500 ng of IVT-RNA of TMGs were added to the cuvette respectively. The electroporation was completed by placing the cuvette in the Nucleofector™ 2b device and running a pre-set program (T-020).

The electroporated EBV-B cells were cultured in grow medium at 37° C. overnight and then cocultured with tumor-reactive T cells as described above. The IFN-γ release in the supernatant in each well was determined by ELISA on the second day.

(9) Ii80-cDNA Library Construction and Screening with T Cells

For cDNA library construction and screening, total RNAs of 135 mel tumor cells were extracted with TRIzol reagent (Thermo Fisher Scientific) according to the manufacturer's instructions. mRNA was further purified from total RNAs, and converted into cDNA using a cDNA construction kit (Thermo Fisher Scientific) with an oligo-dT primer. After ligation with adaptors, cDNAs were cloned into a pTSX vector containing an Ii80 fragment upstream of the cloning sites, and then transformed into Stbl3™ *Escherichia coli* bacteria (Thermo Fisher Scientific). The cDNA bacterial library was divided into pools with each consisted of approximately 100 cDNA clones. Each plasmid pool was isolated from bacteria and transfected into 293-based APCs per well with 0.5 μl of Lipofectamine 2000 and incubated at 37° C., 5% $CO_2$ overnight. After gentle washes, transfected cells were cocultured with T-cell clone ($1\times10^5$/well) overnight. The positive pools were identified based on cytokine release from T cells by ELISA. Bacterial colonies transformed with the positive pool plasmid DNA were picked and prepared for DNA isolation. Several hundreds of individual colonies were repeated for screening with T cells. The positive clones were sequenced to identify target antigens recognized by T cells.

(10) Intracellular Staining of IFN-γ

T cells were stimulated by various in vitro methods, such as tumor cells, peptides or DNA encoding neoantigens, etc. and induced to release cytokines. Stimulated T cells were resuspended in 100 μl of Cytofix/Cytoperm solution (BD Biosciences) per well for microwell plates (or 250 μl for tubes) and incubated for 20 min at 4° C. for cell fixation. Fixed cells were permeabilized by washing twice in 1× Perm/Wash buffer (BD Biosciences). Then the fixed/permeabilized cells were thoroughly resuspended in 50 μl of 1× Perm/Wash buffer containing 1 μl of phycoerythrin (PE)-conjugated IFN-γ antibody (Thermo Fisher Scientific) and incubate at 4° C. for 30 min in the dark. After that the cells were washed twice with 1× Perm/Wash buffer and ready for flow cytometric analysis.

(11) Live-Cell IFN-γ Staining

Cytokine Secretion Assay-Detection Kit (MACS Miltenyi Biotec) was used in cell-surface IFN-γ staining based on a commercial protocol. Briefly $1\times10^6$ T cells were washed with growth medium and spun down at 300×g for 10 min and then resuspended in 100 μl of grow medium containing 5% human serum. Washed cells were transferred in one well of a 96-well plate and added with antigenic peptides to the concentration of 1-10m/ml and incubated for 3-6 h at 37° C. in 5% $CO_2$. After in vitro stimulation of T cells, they were transferred to 15 ml closable tube and washed with 1 ml of cold buffer (cold PBS containing 2% FBS (v/v) and 5 mM EDTA) and spun down. The cell pellets were resuspended in 90 μl of cold growth medium and added with 10 μl of IFN-γ Catch Reagent and incubated for 5 min on ice. After that, 1 ml of warm growth medium (37° C.) was added in the tube and the cells were incubated in closed tube for 45 min at 37° C. under slow continuous rotation. The tube was transferred on ice after incubation and the cells were washed with cold buffer and spun down. The cell pellets were resuspended in 90 μl of cold buffer and then added with 10 μl of IFN-γ Detection Antibody and incubated for 10 min on ice. Finally cells were washed with cold buffer and ready for flow cytometric analysis.

(12) Tumor Cell Cloning 135 mel tumor cells were suspended in 1× Keratinocyte-SFM and supplements (Thermo Fisher Scientific) with additional 10% (v/v) fetal bovine serum and 1% (v/v) penicillin-streptomycin at the density of 1.5 cell/ml after trypsinization, then 200 μl of mixture was added per well to 96-well plates and incubated at 37° C., 5% $CO_2$. On day 5, wells containing a single colony were marked after observation under the microscope. On day 10, the medium was changed with fresh culture medium. The plates were incubated until day 20. The tumor clones in marked wells were trypsinized, and then expanded in larger flasks separately.

(13) Cytotoxicity Assay

CytoTox 96® Non-Radioactive Cytotoxicity Assay Kit (Promega) was applied to measure T cell-tumor cytotoxicity. Briefly, T cells (effectors) and tumor cells (targets) were mixed in TCM at the E/T ratio from 2:1 to 20:1, then cocultured at 100 μl/well in a 96-well plate at 37° C., 5% $CO_2$ for at least 4 h. After the incubation, lactate dehydrogenase (LDH) concentration in the supernatant of each well was measured with the Kit following the manufacturer's instructions and the cytotoxicity percentage was calculated.

(14) In Vivo Adoptive T Cell-Based Antitumor Assay

NSG mice (female) were 6-8 weeks of age, which were obtained from Jackson Laboratories. All NSG mice-related experiments were performed in animal housing facilities under specific pathogen-free conditions at Houston Methodist. All animal studies were performed as instructed by the NIH guidelines and approved by the Animal Care and Use Committee of Houston Methodist.

Subcutaneous injection of 135 mel tumor lines in NSG mice was performed to construct an animal model for adoptive T cell-based therapy (4 mice in each group). Briefly, $3\times10^6$ 135 mel cells were injected on day 0 per mouse. On day 15, different neoantigen-specific T cell clones were intravenously injected at $10^7$ T cells per mouse, followed by the intraperitoneal injection of $5\times10^4$ unit of interleukin-2 per mouse on day 15, 16 and 17. The serum level of IFN-γ in each tumor-bearing mouse was collected on day 19 and measured via ELISA. The growth of 135 mel in each mouse was tracked until day 40.

(15) TCR β CDR3 Repertoire Analysis

The TCR β CDR3 analysis were referred to a previous description (Robins et al., 2009). Neoantigen-specific T cells were isolated after the flow cytometric sorting of peptide-stimulated TIL bulk by live-cell IFN-γ staining. Genomic DNAs were isolated from sorted T cells with Quick-DNA™ Miniprep Kit (Zymo Research) according to a commercial protocol. The isolated genomic DNAs were used as templates for PCR amplification of rearranged TCR β CDR3 in mature T cells. A 50 μl PCR mixture was set up with 16 ng/μl genomic DNA templates, 1 μM of forward BV primer sets and 1 μM of reverse BJ primer sets (Table 5), 10× reaction buffer and 0.2 μl of AccuPrime Taq DNA Polymerase HF (Thermo Fisher Scientific). The PCR was performed for 35 cycles (95° C. for 30 s, 59° C. for 30 s and 68° C. for 1 min). The PCR amplicons were gel-purified by DNA Recovery Kit (Zymo Research) and sent for amplicon next-generation sequencing (Genewiz). The sequencing result was analyzed via a laboratory pipeline for data filtering and TCR repertoire alignment.

TABLE 5

| Primers for TCR β CDR3 amplification | | |
|---|---|---|
| PRIMER SETS | PRIMER NAME | SEQUENCE (5'→3') |
| BV-F | TRBV2 | TCAAATTTCACTCTGAAGATCCGGTCCACAA (SEQ ID NO: 747) |
| | TRBV3-1 | GCTCACTTAAATCTTCACATCAATTCCCTGG 748 |
| | TRBV4-1 | CTTAAACCTTCACCTACACGCCCTGC 749 |
| | TRBV4-2, 4-3 | CTTATTCCTTCACCTACACACCCTGC 750 |
| | TRBV5-1 | GCTCTGAGATGAATGTGAGCACCTTG 751 |
| | TRBV5-3 | GCTCTGAGATGAATGTGAGTGCCTTG 752 |
| | TRBV5-4, 5-5, 5-6, 5-7, 5-8 | GCTCTGAGCTGAATGTGAACGCCTTG 753 |
| | TRBV6-1 | TCGCTCAGGCTGGAGTCGGCTG 754 |
| | TRBV6-2, 6-3 | GCTGGGGTTGGAGTCGGCTG 755 |
| | TRBV6-4 | CCCTCACGTTGGCGTCTGCTG 756 |
| | TRBV6-5 | GCTCAGGCTGCTGTCGGCTG 757 |
| | TRBV6-6 | CGCTCAGGCTGGAGTTGGCTG 758 |
| | TRBV6-7 | CCCCTCAAGCTGGAGTCAGCTG 759 |
| | TRBV6-8 | CACTCAGGCTGGTGTCGGCTG 760 |
| | TRBV6-9 | CGCTCAGGCTGGAGTCAGCTG 761 |
| | TRBV7-1 | CCACTCTGAAGTTCCAGCGCACAC 762 |
| | TRBV7-2 | CACTCTGACGATCCAGCGCACAC 763 |
| | TRBV7-3 | CTCTACTCTGAAGATCCAGCGCACAG 764 |
| | TRBV7-4 | CCACTCTGAAGATCCAGCGCACAG 765 |
| | TRBV7-6 | CACTCTGACGATCCAGCGCACAG 766 |
| | TRBV7-7 | CCACTCTGACGATTCAGCGCACAG 767 |
| | TRBV7-8 | CCACTCTGAAGATCCAGCGCACAC 768 |
| | TRBV7-9 | CACCTTGGAGATCCAGCGCACAG 769 |
| | TRBV9 | GCACTCTGAACTAAACCTGAGCTCTCTG 770 |
| | TRBV10-1 | CCCCTCACTCTGGAGTCTGCTG 771 |
| | TRBV10-2 | CCCCCTCACTCTGGAGTCAGCTA 772 |
| | TRBV10-3 | CCTCCTCACTCTGGAGTCCGCTA 773 |
| | TRBV11-1, 11-3 | CCACTCTCAAGATCCAGCCTGCAG 774 |
| | TRBV11-2 | CTCCACTCTCAAGATCCAGCCTGCAA 775 |
| | TRBV12-3, 12-4, 12-5 | CCACTCTGAAGATCCAGCCCTCAG 776 |
| | TRBV13 | CATTCTGAACTGAACATGAGCTCCTTGG 777 |
| | TRBV14 | CTACTCTGAAGGTGCAGCCTGCAG 778 |
| | TRBV15 | GATAACTTCCAATCCAGGAGGCCGAACA 779 |
| | TRBV16 | CTGTAGCCTTGAGATCCAGGCTACGA 780 |
| | TRBV17 | CTTCCACGCTGAAGATCCATCCCG 781 |
| | TRBV18 | GCATCCTGAGGATCCAGCAGGTAG 782 |
| | TRBV19 | CCTCTCACTGTGACATCGGCCC 783 |
| | TRBV20-1 | CTTGTCCACTCTGACAGTGACCAGTG 784 |
| | TRBV23-1 | CAGCCTGGCAATCCTGTCCTCAG 785 |
| | TRBV24-1 | CTCCCTGTCCCTAGAGTCTGCCAT 786 |
| | TRBV25-1 | CCCTGACCCTGGAGTCTGCCA 787 |
| | TRBV27 | CCCTGATCCTGGAGTCGCCCA 788 |
| | TRBV28 | CTCCCTGATTCTGGAGTCCGCCA 789 |
| | TRBV29-1 | CTAACATTCTCAACTCTGACTGTGAGCAACA 790 |
| | TRBV30 | CGGCAGTTCATCCTGAGTTCTAAGAAGC 791 |
| BJ-R | TRBJ1-1 | TCACGAAGGTCCCCAGTATCCAACTTTACCTACAACT GTGAGTCTGGTGCCTTGTCCAAA 792 |
| | TRBJ1-2 | TCACGAAGGTCCCCAGTATCCAACTACCTACAACGGT TAACCTGGTCCCCGAACCGAA 793 |
| | TRBJ1-3 | TCACGAAGGTCCCCAGTATCCAACTACCTACAACAGT GAGCCAACTTCCCTCTCCAAA 794 |
| | TRBJ1-4 | TCACGAAGGTCCCCAGTATCCAACTCCAAGACAGAG AGCTGGGTTCCACTGCCAAA 795 |
| | TRBJ1-6 | TCACGAAGGTCCCCAGTATCCAACTCTGTCACAGTGA GCCTGGTCCCGTTCCCAAA 796 |
| | TRBJ2-1 | TCACGAAGGTCCCCAGTATCCAACTCGGTGAGCCGTG TCCCTGGCCCGAA 797 |
| | TRBJ2-2 | TCACGAAGGTCCCCAGTATCCAACTCCAGTACGGTCA GCCTAGAGCCTTCTCCAAA 798 |
| | TRBJ2-3 | TCACGAAGGTCCCCAGTATCCAACTACTGTCAGCCGG GTGCCTGGGCCAAA 799 |
| | TRBJ2-4 | TCACGAAGGTCCCCAGTATCCAACTAGAGCCGGGTCC CGGCGCCGAA 800 |
| | TRBJ2-5 | TCACGAAGGTCCCCAGTATCCAACTGGAGCCGCGTGC CTGGCCCGAA 801 |
| | TRBJ2-6 | TCACGAAGGTCCCCAGTATCCAACTGTCAGCCTGCTG CCGGCCCCGAA 802 |
| | TRBJ2-7 | TCACGAAGGTCCCCAGTATCCAACTGTGAGCCTGGTG CCCGGCCCGAA 803 |

TABLE 6

Amino acid sequences of V-J joint in TCR β CDR3 of dominant neoantigen-specific T cells in 135TILs

| TRBV REPERTOIRE | Paired V-D-J sequence V segment | Joint (-NDN-) | J segment | TRBJ repertoire |
|---|---|---|---|---|
| Amino acid sequences (CDR3 β) of potentially functional PCDHB16-reactive TCRs | | | | |
| TRBV6-2 | TSVYFCAS | SYDTGSGDYT | DTQYFGPGTR | TRBJ2-3 |
| | SAVYLCAS | SLGAW | GYTFGSGTR | TRBJ1-2 |
| TRBV7-2 | SAVYLCAS | IGVIGG | NEQFFGPGTR | TRBJ2-1 |
| | SAVYLCAS | SLGP | NEQFFGPGTR | TRBJ2-1 |
| TRBV7-6 | SAMYRCAS | SLHRAD | GANVLTFGPGTR | TRBJ2-6 |
| TRBV7-9 | SAMYLCAS | SQRGTE | NEKLFFWQWNP | TRBJ1-4 |
| TRBV10-2 | TSVYFCAS | SGTLGYN | SPLHFGNGTR | TRBJ1-6 |
| TRBV11-2 | SAVYLCAS | SPTSGP | DTQYFGPGTR | TRBJ2-3 |
| TRBV12-3 | SAVYFCAS | SFPLA | GELFFGEGSR | TRBJ2-2 |
| TRBV19 | TAFYLCAS | TTTSGTY | NEQFFGPGTR | TRBJ2-1 |
| | TAFYLCAS | SSWVY | GYTFGSGTR | TRBJ1-2 |
| TRBV25-1 | TSQYLCAS | PKARTGD | YEQYFGPGTR | TRBJ2-7 |
| | TSLYFCAS | TPVGQGIW | SPLHFGNGTR | TRBJ1-6 |
| TRBV27 | TSLYFCAS | SSISTGYWT | EAFFGQGTR | TRBJ1-1 |
| | TSLYFCAS | SFRTGGGGSY | GYTFGSGTR | TRBJ1-2 |
| Amino acid sequences (CDR3 β) of potentially functional MPG-reactive TCRs | | | | |
| TRBV5-4 | SALYLCAS | STRLAGYT | DTQYFGPGTR | TRBJ2-3 |
| TRBV5-8 | SALYLCAS | SPREDGT | DTQYFGPGTR | TRBJ2-3 |
| TRBV6-1 | TSVYFCAS | SDRGSG | NTIYFGEGSW | TRBJ1-3 |
| TRBV6-3 | TSVYFCAS | SYDTGSGDYT | DTQYFGPGTR | TRBJ2-3 |
| TRBV6-4 | TSVYFCAS | RNRDRDT | EAFFGQGTR | TRBJ1-1 |
| | TSVYFCAS | RNRDWDT | EAFFGQGTR | TRBJ1-1 |
| TRBV7-9 | SAMYLCAS | SPRQGDQM | NTQYFGPGTR | TRBJ2-3 |
| TRBV19 | TAFYLCAS | RDRQGDT | EAFFGQGTR | TRBJ1-1 |
| TRBV25-1 | TSQYLCAS | SENPNSG | NTIYFGEGSW | TRBJ1-3 |
| TRBV28 | TSMYLCAS | RSAPL | EAFFGQGTR | TRBJ1-1 |

V segment, Joint (-NDN-) and J segment are sections of a single contiguous sequence. Each sequence is depicted here to emphasize the different segments.

(16) TCRα/β Chain Variable Regions and Full-Length TCRα/β Chain Cloning

TCRα/β chain variable regions (CDR3) were amplified from a single T cell by three rounds of nested PCR. The first one-step RT-PCR was performed with the OneStep RT-PCR kit (Qiagen) in a 25 μl reaction and the following primers (Table 7): mixα1 (38 primers mixed, 10 μM each) and pCal (TCRα), mixβ1 (36 primers mixed, 10 μM each) and pCβ1 (TCRβ). 2 μl of PBS containing at least one T cell was added as the DNA template. The one-step RT-PCR was performed by reverse transcription (50° C., 30 min) followed by PCR for 25 cycles (94° C. for 30 s, 62° C. for 1 min, and 72° C. for 1 min), according to the manufacturer's instructions. The second and third PCR reactions were performed with KOD Hot Start DNA polymerase (Millipore Sigma) following the manufacturer's instructions. One μl of the first-round PCR product was added as a template for the second-round PCR in a 25 μl reaction. The second-round PCR was performed with the following primers (Table 7): mixα2 (36 primers mixed, 10 μM each) and pCα2 (TCRα), mixβ2 (36 primers mixed, 10 μM each) and pCβ2 (TCRβ) for 25 cycles (94° C. for 30 s, 64° C. for 1 min, and 70° C. for 1 min). One μl of the second-round PCR product was added as a template for the third-round PCR in a 25 μl reaction. The third-round PCR was performed with the following primers (Table 7): pF3 and pCα3 (TCRα), pF3 and pCβ3 (TCRβ), for 35 cycles (94° C. for 30 s, 64° C. for 1 min, and 70° C. for 1 min). The final PCR amplicons were gel-purified (Zymo Research) and sequenced (Genewiz). The genotypes of TCRs were determined by search with the online tools V-QUEST (IMGT) and Igblast (NCBI).

TABLE 7

Primers for TCRα/β chain variable regions (CDR3) amplification

| | Primer Name | Sequence (5'→3') |
|---|---|---|
| 1st round of mixα1 nested PCR | TRAV1 | CTG CAC GTA CCA GAC ATC TGG GTT 804 |
| | TRAV2 | GGC TCA AAG CCT TCT CAG CAG G 805 |
| | TRAV3 | GGA TAA CCT GGT TAA AGG CAG CTA 806 |
| | TRAV4 | GGA TAC AAG ACA AAA GTT ACA AAC GA 807 |
| | TRAV5 | GCT GAC GTA TAT TTT TTC AAA TAT GGA 808 |
| | TRAV6 | GGA AGA GGC CCT GTT TTC TTG CT 809 |
| | TRAV7 | GCT GGA TAT GAG AAG CAG AAA GGA 810 |
| | TRAV8 | AGG ACT CCA GCT TCT CCT GAA GTA 811 |
| | TRAV9 | GTA TGT CCA ATA TCC TGG AGA AGG T 812 |
| | TRAV10 | CAG TCA GAA CAC AAA GTC GAA CGG 813 |
| | TRAV12.1 | CCT AAG TTG CTG ATG TCC GTA TAC 814 |
| | TRAV12.2 | GGG AAA AGC CCT GAG TTG ATA ATG T 815 |
| | TRAV12.3 | GCT GAT GTA CAC ATA CTC CAG TGG 816 |
| | TRAV13.1 | CCC TTG GTA TAA GCA AGA ACT TGG 817 |
| | TRAV13.2 | CCT CAA TTC ATT ATA GAC ATT CGT TC 818 |
| | TRAV14 | GCA AAA TGC AAC AGA AGG TCG CTA 819 |
| | TRAV16 | TAG AGA GAG CAT CAA AGG CTT CAC 820 |
| | TRAV17 | CGT TCA AAT GAA AGA GAG AAA CAC AG 821 |
| | TRAV18 | CCT GAA AAG TTC AGA AAA CCA GGA G 822 |
| | TRAV19 | GGT CGG TAT TCT TGG AAC TTC CAG 823 |
| | TRAV20 | GCT GGG GAA GAA AAG GAG AAA GAA A 824 |
| | TRAV21 | GTC AGA GAG AGC AAA CAA GTG GAA 825 |
| | TRAV22 | GGA CAA AAC AGA ATG GAA GAT TAA GC 826 |
| | TRAV23 | CCA GAT GTG AGT GAA AAG AAA GAA G 827 |
| | TRAV24 | GAC TTT AAA TGG GGA TGA AAA GAA GA 828 |
| | TRAV25 | GGA GAA GTG AAG AAG CAG AAA AGA C 829 |
| | TRAV26.1 | CCA ATG AAA TGG CCT CTC TGA TCA 830 |
| | TRAV26.2 | GCA ATG TGA ACA ACA GAA TGG CCT 831 |
| | TRAV27 | GGT GGA GAA GTG AAG AAG CTC AAG 832 |
| | TRAV29 | GGA TAA AAA TGA AGA TGG AAG ATT CAC 833 |
| | TRAV30 | CCT GAT GAT ATT ACT GAA GGG TGG A 834 |
| | TRAV34 | GGT GGG GAA GAG AAA AGT CAT GAA 835 |
| | TRAV35 | GGT GAA TTG ACC TCA AAT GGA AGA C 836 |
| | TRAV36 | GCT AAC TTC AAG TGG AAT TGA AAA GA 837 |
| | TRAV38 | GAA GCT TAT AAG CAA CAG AAT GCA AC 838 |
| | TRAV39 | GGA GCA GTG AAG CAG GAG GGA C 839 |
| | TRAV40 | GAG AGA CAA TGG AAA ACA GCA AAA AC 840 |
| | TRAV41 | GCT GAG CTC AGG GAA GAA GAA GC 841 |

TABLE 7-continued

Primers for TCRα/β chain variable regions (CDR3) amplification

| | Primer Name | Sequence (5'→3') |
|---|---|---|
| mixβ1 | TRBV2 | CTG AAA TAT TCG ATG ATC AAT TCT CAG 842 |
| | TRBV3-1 | TCA TTA TAA ATG AAA CAG TTC CAA ATC G 843 |
| | TRBV4 | AGT GTG CCA AGT CGC TTC TCA C 844 |
| | TRBV5-4,8 | CAG AGG AAA CTT CCC TCC TAG ATT 845 |
| | TRBV5-1 | GAG ACA CAG AGA AAC AAA GGA AAC TTC 846 |
| | TRBV6-1 | GGT ACC ACT GAC AAA GGA GAA GTC C 847 |
| | TRBV6-2,3 | GAG GGT ACA ACT GCC AAA GGA 848 |
| | TRBV6-4 | GGC AAA GGA GAA GTC CCT GAT GGT T 849 |
| | TRBV6-5,6 | AAG GAG AAG TCC CCA ATG GCT ACA A 850 |
| | TRBV6-8 | CTG ACA AAG AAG TCC CCA ATG GCT AC 851 |
| | TRBV6-9 | CAC TGA CAA AGG AGA AGT CCC CGA T 852 |
| | TRBV7-2 | AGA CAA ATC AGG GCT GCC CAG TGA 853 |
| | TRBV7-3 | GAC TCA GGG CTG CCC AAC GAT 854 |
| | TRBV7-8 | CCA GAA TGA AGC TCA ACT AGA CAA 855 |
| | TRBV7-4,6 | GGT TCT CTG CAG AGA GGC CTG AG 856 |
| | TRBV7-7 | GGC TGC CCA GTG ATC GGT TCT C 857 |
| | TRBV7-9 | GAC TTA CTT CCA GAA TGA AGC TCA ACT 858 |
| | TRBV9 | GAG CAA AAG GAA ACA TTC TTG AAC GAT T 859 |
| | TRBV10-1,3 | GGC TGA TCC ATT ACT CAT ATG GTG TT 860 |
| | TRBV10-2 | GAT AAA GGA GAA GTC CCC GAT GGC T 861 |
| | TRBV11 | GAT TCA CAG TTG CCT AAG GAT CGA T 862 |
| | TRBV12-3,4 | GAT TCA GGG ATG CCC GAG GAT CG 863 |
| | TRBV12-5 | GAT TCG GGG ATG CCG AAG GAT CG 864 |
| | TRBV13 | GCA GAG CGA TAA AGG AAG CAT CCC T 865 |
| | TRBV14 | TCC GGT ATG CCC AAC AAT CGA TTC T 866 |
| | TRBV15 | GAT TTT AAC AAT GAA GCA GAC ACC CCT 867 |
| | TRBV16 | GAT GAA ACA GGT ATG CCC AAG GAA AG 868 |
| | TRBV18 | TAT CAT AGA TGA GTC AGG AAT GCC AAA G 869 |
| | TRBV19 | GAC TTT CAG AAA GGA GAT ATA GCT GAA 870 |
| | TRBV20-1 | CAA GGC CAC ATA CGA GCA AGG CGT C 871 |
| | TRBV24-1 | CAA AGA TAT AAA CAA AGG AGA GAT CTC T 872 |
| | TRBV25-1 | AGA GAA GGG AGA TCT TTC CTC TGA GT 873 |
| | TRBV27-1 | GAC TGA TAA GGG AGA TGT TCC TGA AG 874 |
| | TRBV28 | GGC TGA TCT ATT TCT CAT ATG ATG TTA A 875 |
| | TRBV29 | GCC ACA TAT GAG AGT GGA TTT GTC ATT 876 |
| | TRBV30 | GGT GCC CCA GAA TCT CTC AGC CT 877 |
| | pCα1 | CGG TGA ATA GGC AGA CAG ACT TGT 878 |

TABLE 7-continued

Primers for TCRα/β chain variable regions (CDR3) amplification

| | Primer Name | Sequence (5'→3') |
|---|---|---|
| | pCβ1 | ACC AGT GTG GCC TTT TGG GTG TG 879 |
| 2nd round of mixα2 nested PCR | 2TRAV1 | CCA GGG TTT TCC CAG TCA CGA CAG GTC GTT TTT CTT CAT TCC TTA GTC 880 |
| | 2TRAV2 | CCA GGG TTT TCC CAG TCA CGA CAC GAT ACA ACA TGA CCT ATG AAC GG 881 |
| | 2TRAV3.1 | CCA GGG TTT TCC CAG TCA CGA CCT TTG AAG CTG AAT TTA ACA AGA GCC 882 |
| | 2TRAV4.1 | CCA GGG TTT TCC CAG TCA CGA CCT CCC TGT TTA TCC CTG CCG AC 883 |
| | 2TRAV5.1 | CCA GGG TTT TCC CAG TCA CGA CAA ACA AGA CCA AAG ACT CAC TGT TC 884 |
| | 2TRAV6 | CCA GGG TTT TCC CAG TCA CGA CAA GAC TGA AGG TCA CCT TTG ATA CC 885 |
| | 2TRAV7 | CCA GGG TTT TCC CAG TCACGA CAC TAA ATG CTA CAT TAC TGA AGA ATG G 886 |
| | 2TRAV8 | CCA GGG TTT TCC CAG TCACGA CGC ATC AAC GGT TTT GAG GCT GAA TTT AA 887 |
| | 2TRAV9 | CCA GGG TTT TCC CAG TCA CGA CGA AAC CAC TTC TTT CCA CTT GGA GAA 888 |
| | 2TRAV10 | CCA GGG TTT TCC CAG TCA CGA CTA CAG CAA CTC TGG ATG CAG ACA C 889 |
| | 2TRAV12 | CCA GGG TTT TCC CAG TCA CGA CGA AGA TGG AAG GTT TAC AGC ACA 890 |
| | 2TRAV13.1 | CCA GGG TTT TCC CAG TCA CGA CGA CAT TCG TTC AAA TGT GGG CGA A 891 |
| | 2TRAV13.2 | CCA GGG TTT TCC CAG TCA CGA CGG CAA GGC CAA AGA GTC ACC GT 892 |
| | 2TRAV14 | CCA GGG TTT TCC CAG TCA CGA CTC CAG AAG GCA AGA AAA TCC GCC A 893 |
| | 2TRAV16 | CCA GGG TTT TCC CAG TCA CGA CGC TGA CCT TAA CAA AGG CGA GAC A 894 |
| | 2TRAV17 | CCA GGG TTT TCC CAG TCA CGA CTT AAG AGT CAC GCT TGA CAC TTC CA 895 |
| | 2TRAV18 | CCA GGG TTT TCC CAG TCA CGA CGC AGA GGT TTT CAG GCC AGT CCT 896 |
| | 2TRAV19 | CCA GGG TTT TCC CAG TCA CGA CTC CAC CAG TTC CTT CAA CTT CAC C 897 |
| | 2TRAV20 | CCA GGG TTT TCC CAG TCA CGA CGC CAC ATT AAC AAA GAA GGA AAG CT 898 |
| | 2TRAV21 | CCA GGG TTT TCC CAG TCA CGA CGC CTC GCT GGA TAA ATC ATC AGG A 899 |
| | 2TRAV22 | CCA GGG TTT TCC CAG TCA CGA CAC GAC TGT CGC TAC GGA ACG CTA 900 |
| | 2TRAV23 | CCA GGG TTT TCC CAG TCA CGA CCA CAA TCT CCT TCA ATA AAA GTG CCA 901 |
| | 2TRAV24 | CCA GGG TTT TCC CAG TCA CGA CAC GAA TAA GTG CCA CTC TTA ATA CCA 902 |
| | 2TRAV25 | CCA GGG TTT TCC CAG TCA CGA CGT TTG GAG AAG CAA AAA AGA ACA GCT 903 |
| | 2TRAV26.1 | CCA GGG TTT TCC CAG TCA CGA CCA GAA GAC AGA AAG TCC AGC ACC T 904 |

TABLE 7-continued

Primers for TCRα/β chain variable regions (CDR3) amplification

| | Primer Name | Sequence (5'→3') |
| --- | --- | --- |
| | 2TRAV26.2 | CCA GGG TTT TCC CAG TCA CGA CAT CGC TGA AGA CAG AAA GTC CAG T 905 |
| | 2TRAV27 | CCA GGG TTT TCC CAG TCA CGA CAC TAA CCT TTC AGT TTG GTG ATG CAA 906 |
| | 2TRAV29 | CCA GGG TTT TCC CAG TCA CGA CCT TAA ACA AAA GTG CCA AGC ACC TC 907 |
| | 2TRAV30 | CCA GGG TTT TCC CAG TCA CGA CAA TAT CTG CTT CAT TTA ATG AAA AAA AGC 908 |
| | 2TRAV34 | CCA GGG TTT TCC CAG TCA CGA CCC AAG TTG GAT GAG AAA AAG CAG CA 909 |
| | 2TRAV35 | CCA GGG TTT TCC CAG TCA CGA CCT CAG TTT GGT ATA ACC AGA AAG GA 910 |
| | 2TRAV36 | CCA GGG TTT TCC CAG TCA CGA CGG AAG ACT AAG TAG CAT ATT AGA TAA G 911 |
| | 2TRAV38 | CCA GGG TTT TCC CAG TCA CGA CCT GTG AAC TTC CAG AAA GCA GCC A 912 |
| | 2TRAV39 | CCA GGG TTT TCC CAG TCA CGA CCC TCA CTT GAT ACC AAA GCC CGT 913 |
| | 2TRAV40 | CCA GGG TTT TCC CAG TCA CGA CAG GCG GAA ATA TTA AAG ACA AAA ACT C 914 |
| | 2TRAV41 | CCA GGG TTT TCC CAG TCA CGA CGA TTA ATT GCC ACA ATA AAC ATA CAG G 915 |
| mixβ2 | 2TRBV2 | CCA GGG TTT TCC CAG TCA CGA CGC CTG ATG GAT CAA ATT TCA CTC TG 916 |
| | 2TRBV3-1 | CCA GGG TTT TCC CAG TCA CGA CTC TCA CCT AAA TCT CCA GAC AAA GCT 917 |
| | 2TRBV4 | CCA GGG TTT TCC CAG TCA CGA CCC TGA ATG CCC CAA CAG CTC TC 918 |
| | 2TRBV5-4,8 | CCA GGG TTT TCC CAG TCA CGA CCT CTG AGC TGA ATG TGA ACG CCT 919 |
| | 2TRBV5-1 | CCA GGG TTT TCC CAG TCA CGA CCG ATT CTC AGG GCG CCA GTT CTC T 920 |
| | 2TRBV6-1 | CCA GGG TTT TCC CAG TCA CGA CTG GCT ACA ATG TCT CCA GAT TAA ACA A 921 |
| | 2TRBV6-2,3 | CCA GGG TTT TCC CAG TCA CGA CCC CTG ATG GCT ACA ATG TCT CCA GA 922 |
| | 2TRBV6-4 | CCA GGG TTT TCC CAG TCA CGA CGT GTC TCC AGA GCA AAC ACA GAT GAT T 923 |
| | 2TRBV6-5,6 | CCA GGG TTT TCC CAG TCA CGA CGT CTC CAG ATC AAC CAC AGA GGA T 924 |
| | 2TRBV6-8 | CCA GGG TTT TCC CAG TCA CGA CGT CTC TAG ATT AAA CAC AGA GGA TTT C 925 |
| | 2TRBV6-9 | CCA GGG TTT TCC CAG TCA CGA CGG CTA CAA TGT ATC CAG ATC AAA CA 926 |
| | 2TRBV7-2 | CCA GGG TTT TCC CAG TCA CGA CTC GCT TCT CTG CAG AGA GGA CTG G 927 |
| | 2TRBV7-3 | CCA GGG TTT TCC CAG TCA CGA CCG GTT CTT TGC AGT CAG GCC TGA 928 |

TABLE 7-continued

Primers for TCRα/β chain variable regions (CDR3) amplification

| Primer Name | Sequence (5'→3') |
|---|---|
| 2TRBV7-8 | CCA GGG TTT TCC CAG TCA CGA CCC AGT GAT CGC TTC TTT GCA GAA A 929 |
| 2TRBV7-4,6 | CCA GGG TTT TCC CAG TCA CGA CTC TCC ACT CTG AAG ATC CAG CGC A 930 |
| 2TRBV7-7 | CCA GGG TTT TCC CAG TCA CGA CGC AGA GAG GCC TGA GGG ATC CAT 931 |
| 2TRBV7-9 | CCA GGG TTT TCC CAG TCA CGA CCT GCA GAG AGG CCT AAG GGA TCT 932 |
| 2TRBV9 | CCA GGG TTT TCC CAG TCA CGA CCT CCG CAC AAC AGT TCC CTG ACT T 933 |
| 2TRBV10-1.3 | CCA GGG TTT TCC CAG TCA CGA CCA GAT GGC TAT AGT GTC TCT AGA TCA AA 934 |
| 2TRBV10-2 | CCA GGG TTT TCC CAG TCA CGA CGT TGT CTC CAG ATC CAA GAC AGA GAA 935 |
| 2TRBV11 | CCA GGG TTT TCC CAG TCA CGA CGC AGA GAG GCT CAA AGG AGT AGA CT 936 |
| 2TRBV12-3.4 | CCA GGG TTT TCC CAG TCA CGA CGC TAA GAT GCC TAA TGC ATC ATT CTC 937 |
| 2TRBV12-5 | CCA GGG TTT TCC CAG TCA CGA CCT CAG CAG AGA TGC CTG ATG CAA CT 938 |
| 2TRBV13 | CCA GGG TTT TCC CAG TCA CGA CTC TCA GCT CAA CAG TTC AGT GAC TA 939 |
| 2TRBV14 | CCA GGG TTT TCC CAG TCA CGA CGC TGA AAG GAC TGG AGG GAC GTA T 940 |
| 2TRBV15 | CCA GGG TTT TCC CAG TCA CGA CGA TAA CTT CCA ATC CAG GAG GCC G 941 |
| 2TRBV16 | CCA GGG TTT TCC CAG TCA CGA CGC TAA GTG CCT CCC AAA TTC ACC C 942 |
| 2TRBV18 | CCA GGG TTT TCC CAG TCA CGA CGG AAC GAT TTT CTG CTG AAT TTC CCA 943 |
| 2TRBV19 | CCA GGG TTT TCC CAG TCA CGA CGG TAC AGC GTC TCT CGG GAG AAG A 944 |
| 2TRBV20-1 | CCA GGG TTT TCC CAG TCA CGA CGG ACA AGT TTC TCA TCA ACC ATG CAA 945 |
| 2TRBV24-1 | CCA GGG TTT TCC CAG TCA CGA CTG GAT ACA GTG TCT CTC GAC AGG C 946 |
| 2TRBV25-1 | CCA GGG TTT TCC CAG TCA CGA CCA ACA GTC TCC AGA ATA AGG ACG GA 947 |
| 2TRBV27-1 | CCA GGG TTT TCC CAG TCA CGA CTA CAA AGT CTC TCG AAA AGA GAA GAG GA 948 |
| 2TRBV28 | CCA GGG TTT TCC CAG TCA CGA CGG GGT ACA GTG TCT CTA GAG AGA 949 |
| 2TRBV29 | CCA GGG TTT TCC CAG TCA CGA CGT TTC CCA TCA GCC GCC CAA ACC TA 950 |
| 2TRBV30 | CCA GGG TTT TCC CAG TCA CGA CCA GAC CCC AGG ACC GGC AGT TCA T 951 |
| pCα2 | CAG ACA GAC TTG TCA CTG GAT TTA G 952 |
| pCβ2 | CTT TTG GGT GTG GGA GAT CTC TG 953 |

TABLE 7-continued

| Primers for TCRα/β chain variable regions (CDR3) amplification | | |
|---|---|---|
| | Primer Name | Sequence (5'→3') |
| 3rd round of nested PCR | pF3 | CCT ACA CGA CGC TCT TCC GAT CTN NGC AGA GAT AAG CCC AGG GTT TTC CCA GTC ACG AC (SEQ ID NO: 954) |
| | pCα3 | CTG CTG AAC CGC TCT TCC GAT CTN NGT TCA GTC ACT GGA TTT AGA GTC TCT CAG (SEQ ID NO: 955) |
| | pCβ3 | CTG CTG AAC CGC TCT TCC GAT CTN NGT TCA GAG ATC TCT GCT TCT GAT GGC TC (SEQ ID NO: 956) |

Once TCRα/β chain variable regions were determined, primers specific for leader sequence and constant region were used to amplify full-length TCRα/β chains. The PCR to amplify the intact TCRα- or β-chain and the following overlap PCR were performed with KOD Hot Start DNA polymerase (Millipore Sigma) according to the manufacturer's instructions. One μl of cDNA was added as a template in a 25 μl reaction together with the primers: pLα-P2A (based on TCR genotype), pRCα for amplifying full-length a chain or pLβ (based on TCR genotype), and pRCβ-P2A for amplifying full-length β chain. The PCR was performed for 20 cycles (94° C. for 30 s, 64° C. for 1 min, 70° C. for 1 min). 2 μl of TCRα and 2 μl of TCRβ chain PCR products were mixed in 25 μl of overlap PCR reaction. The primers pLβ and pRCα were also added. The overlap PCR was performed for 30 cycles (94° C. for 30 s, 60° C. for 1 min, and 70° C. for 90 s). The overlap PCR products (~1.5 kb) were gel-purified with DNA Recovery Kit (Zymo Research) and cloned into pMSGV vector with NEBuilder® HiFi DNA Assembly Master Mix (New England Biolabs).

(17) Retroviral Transduction of TCR in Naïve T Cells

The pMSGV DNA encoding full-length TCR was transfected into Phoenix-Ampho cells (ATCC) to produce retroviruses. Briefly, 6-well tissue culture plate was coated with Poly-L-lysine (50 μg/ml in PBS) for 10 min at 37° C. and rinsed with PBS once. Phoenix-Ampho cells were seeded onto the coated plate at $1.5\times10^6$ per well and cultured in DMEM with 10% (v/v) fetal bovine serum containing 1% penicillin-streptomycin at 37° C., 5% $CO_2$. Four h later, 4 μg of pMSGV plasmids was transfected into each well with 10 μl of Lipofectamine 2000. The culture medium was changed 6 h after the transfection and the retroviral supernatant was collected at 48 or 60 h after the transfection.

For preparation of activated naïve T cells, 24-well tissue culture plates were coated with 1 ml of PBS containing 0.5 μg/ml OKT3 per well and incubated at 4° C. overnight. After the plate was rinsed with PBS once, PBMCs from normal donors or bead-purified T cells were added in ($1.0\times10^6$/well) and cultured in TCM containing 300 IU/ml IL-2 at 37° C., 5% $CO_2$ for 48 h. The OKT3-stimulated T cells were ready for transduction after washed twice with TCM. 230. For retroviral transduction of activated T cells, 24-well non-tissue culture plates (Corning) were coated with 0.5 ml of human recombinant RetroNectin per well (Takara, 10m/ml in PBS) 1 day prior to the transduction and incubated at 4° C. overnight. After RetroNectin was removed, the plate was blocked with 2% (w/v) BSA in PBS at room temperature for 30 min. The plate was then washed twice with PBS containing 2.5% (v/v) HEPES. Retroviral supernatant of Phoenix-Ampho cells was added to the RetroNectin-coated plates (2.5 ml per well). The plate was centrifuged at 2000×g, 32° C. for 2 h. After the viral supernatant was discarded, OKT3-stimulated T cells were added to the plate ($5\times10^5$/well) and cultured in TCM containing 150 IU/ml IL-2 at 37° C., 5% $CO_2$ overnight. A second round of transduction was performed with fresh retroviral supernatant and RetroNectin-coated plates, as described above. The transduced T cells were ready to assay with tumor cells or 293APCs 72 h after transduction.

(18) Statistics

Comparisons between groups were calculated by Student's t-test using GraphPad Prism (GraphPad Software). $P<0.05$ was considered as statistically significant.

F. REFERENCES

Balachandran, V. P., Luksza, M., Zhao, J. N., Makarov, V., Moral, J. A., Remark, R., Herbst, B., Askan, G., Bhanot, U., Senbabaoglu, Y., et al. (2017). Identification of unique neoantigen qualities in long-term survivors of pancreatic cancer. Nature 551, 512-516.

Birnbaum, M. E., Mendoza, J. L., Sethi, D. K., Dong, S., Glanville, J., Dobbins, J., Ozkan, E., Davis, M. M., Wucherpfennig, K. W., and Garcia, K. C. (2014). Deconstructing the peptide-MHC specificity of T cell recognition. Cell 157, 1073-1087.

Bolotin, D. A., Poslaysky, S., Davydov, A. N., Frenkel, F. E., Fanchi, L., Zolotareva, O. I., Hemmers, S., Putintseva, E. V., Obraztsova, A. S., Shugay, M., et al. (2017). Antigen receptor repertoire profiling from RNA-seq data. Nature biotechnology 35, 908-911.

Braumuller, H. et al. T-helper-1-cell cytokines drive cancer into senescence. *Nature* 494, 361-365, doi:10.1038/nature11824 (2013).

Carpenter, A. C., Wohlfert, E., Chopp, L. B., Vacchio, M. S., Nie, J., Zhao, Y., Shetty, J., Xiao, Q., Deng, C., Tran, B., et al. (2017). Control of Regulatory T Cell Differentiation by the Transcription Factors Thpok and LRF. Journal of immunology 199, 1716-1728.

Carreno, B. M., Magrini, V., Becker-Hapak, M., Kaabinejadian, S., Hundal, J., Petti, A. A., Ly, A., Lie, W. R., Hildebrand, W. H., Mardis, E. R., et al. (2015). Cancer immunotherapy. A dendritic cell vaccine increases the breadth and diversity of melanoma neoantigen-specific T cells. Science 348, 803-808.

Chen, L., and Han, X. (2015). Anti-PD-1/PD-L1 therapy of human cancer: past, present, and future. The Journal of clinical investigation 125, 3384-3391.

Chen, Y. T., Scanlan, M. J., Sahin, U., Tureci, O., Gure, A. O., Tsang, S., Williamson, B., Stockert, E., Pfreundschuh, M., and Old, L. J. (1997). A testicular antigen aberrantly expressed in human cancers detected by autologous antibody screening. ProcNatlAcadSciUSA 94, 1914-1918.
Chowell, D., Morris, L. G. T., Grigg, C. M., Weber, J. K., Samstein, R. M., Makarov, V., Kuo, F., Kendall, S. M., Requena, D., Riaz, N., et al. (2018). Patient HLA class I genotype influences cancer response to checkpoint blockade immunotherapy. Science 359, 582-587.
Cibulskis, K., Lawrence, M. S., Carter, S. L., Sivachenko, A., Jaffe, D., Sougnez, C., Gabriel, S., Meyerson, M., Lander, E. S., and Getz, G. (2013). Sensitive detection of somatic point mutations in impure and heterogeneous cancer samples. Nature biotechnology 31, 213-219.
Cole, D. K. et al. Hotspot autoimmune T cell receptor binding underlies pathogen and insulin peptide cross-reactivity. *J. Clin. Invest.* 126, 2191-2204, doi:10.1172/JCI85679 (2016).
Cole, D. K., Bulek, A. M., Dolton, G., Schauenberg, A. J., Szomolay, B., Rittase, W., Trimby, A., Jothikumar, P., Fuller, A., Skowera, A., et al. (2016). Hotspot autoimmune T cell receptor binding underlies pathogen and insulin peptide cross-reactivity. The Journal of clinical investigation 126, 3626.
De la Herran-Arita, A. K. et al. CD4+ T cell autoimmunity to hypocretin/orexin and cross-reactivity to a 2009 $H_1N1$ influenza A epitope in narcolepsy. *Sci Transl Med* 5, 216ra176, doi:10.1126/scitranslmed.3007762 (2013).
Gubin, M. M., Zhang, X., Schuster, H., Caron, E., Ward, J. P., Noguchi, T., Ivanova, Y., Hundal, J., Arthur, C. D., Krebber, W. J., et al. (2014). Checkpoint blockade cancer immunotherapy targets tumour-specific mutant antigens. Nature 515, 577-581.
Han, A., Glanville, J., Hansmann, L., and Davis, M. M. (2014). Linking T-cell receptor sequence to functional phenotype at the single-cell level. Nature biotechnology 32, 684-692.
He, X., Park, K., and Kappes, D. J. (2010). The role of ThPOK in control of CD4/CD8 lineage commitment. Annual review of immunology 28, 295-320.
Hellmann, M. D., Callahan, M. K., Awad, M. M., Calvo, E., Ascierto, P. A., Atmaca, A., Rizvi, N. A., Hirsch, F. R., Selvaggi, G., Szustakowski, J. D., et al. (2018). Tumor Mutational Burden and Efficacy of Nivolumab Monotherapy and in Combination with Ipilimumab in Small-Cell Lung Cancer. Cancer cell 33, 853-861 e854.
Hung, K. et al. The Central Role of CD4(+) T Cells in the Antitumor Immune Response. *J. Exp. Med.* 188, 2357-2368 (1998).
Kang, T. W. et al. Senescence surveillance of pre-malignant hepatocytes limits liver cancer development. *Nature* 479, 547-551, doi:10.1038/nature10599 (2011).
Kastenmuller, W., Gasteiger, G., Gronau, J. H., Baier, R., Ljapoci, R., Busch, D. H., and Drexler, I. (2007). Cross-competition of CD8+ T cells shapes the immunodominance hierarchy during boost vaccination. The Journal of experimental medicine 204, 2187-2198.
Kreiter, S., Vormehr, M., van de Roemer, N., Diken, M., Lower, M., Diekmann, J., Boegel, S., Schrors, B., Vascotto, F., Castle, J. C., et al. (2015). Mutant MHC class II epitopes drive therapeutic immune responses to cancer. Nature 520, 692-696.
La Gruta, N. L., Gras, S., Daley, S. R., Thomas, P. G., and Rossjohn, J. (2018). Understanding the drivers of MHC restriction of T cell receptors. Nature reviews Immunology 18, 467-478.
Laumont, C. M., Vincent, K., Hesnard, L., Audemard, E., Bonneil, E., Laverdure, J. P., Gendron, P., Courcelles, M., Hardy, M. P., Cote, C., et al. (2018). Noncoding regions are the main source of targetable tumor-specific antigens. Science translational medicine 10.
Le, D. T., Durham, J. N., Smith, K. N., Wang, H., Bartlett, B. R., Aulakh, L. K., Lu, S., Kemberling, H., Wilt, C., Luber, B. S., et al. (2017). Mismatch repair deficiency predicts response of solid tumors to PD-1 blockade. Science 357, 409-413.
Li, H., and Durbin, R. (2009). Fast and accurate short read alignment with Burrows-Wheeler transform. Bioinformatics 25, 1754-1760.
Linnemann, C., van Buuren, M. M., Bies, L., Verdegaal, E. M., Schotte, R., Calis, J. J., Behjati, S., Velds, A., Hilkmann, H., Atmioui, D. E., et al. (2015). High-throughput epitope discovery reveals frequent recognition of neo-antigens by CD4+ T cells in human melanoma. Nat Med 21, 81-85.
Lu, Y. C., Yao, X., Crystal, J. S., Li, Y. F., El-Gamil, M., Gross, C., Davis, L., Dudley, M. E., Yang, J. C., Samuels, Y., et al. (2014). Efficient identification of mutated cancer antigens recognized by T cells associated with durable tumor regressions. Clinical cancer research: an official journal of the American Association for Cancer Research 20, 3401-3410.
Luckey, M. A. et al. The transcription factor ThPOK suppresses Runx3 and imposes CD4(+) lineage fate by inducing the SOCS suppressors of cytokine signaling. *Nature immunology* 15, 638-645, doi:10.1038/ni.2917 (2014).
Luksza, M., Riaz, N., Makarov, V., Balachandran, V. P., Hellmann, M. D., Solovyov, A., Rizvi, N. A., Merghoub, T., Levine, A. J., Chan, T. A., et al. (2017). A neoantigen fitness model predicts tumour response to checkpoint blockade immunotherapy. Nature 551, 517-520.
Malandro, N., Budhu, S., Kuhn, N. F., Liu, C., Murphy, J. T., Cortez, C., Zhong, H., Yang, X., Rizzuto, G., Altan-Bonnet, G., et al. (2016). Clonal Abundance of Tumor-Specific CD4(+) T Cells Potentiates Efficacy and Alters Susceptibility to Exhaustion. Immunity 44, 179-193.
Manguso, R. T., Pope, H. W., Zimmer, M. D., Brown, F. D., Yates, K. B., Miller, B. C., Collins, N. B., Bi, K., LaFleur, M. W., Juneja, V. R., et al. (2017). In vivo CRISPR screening identifies Ptpn2 as a cancer immunotherapy target. Nature 547, 413-418.
Marty Pyke, R., Thompson, W. K., Salem, R. M., Font-Burgada, J., Zanetti, M., and Carter, H. (2018). Evolutionary Pressure against MHC Class II Binding Cancer Mutations. Cell 175, 1991.
Marty, R., Kaabinejadian, S., Rossell, D., Slifker, M. J., van de Haar, J., Engin, H. B., de Prisco, N., Ideker, T., Hildebrand, W. H., Font-Burgada, J., et al. (2017). MHC-I Genotype Restricts the Oncogenic Mutational Landscape. Cell 171, 1272-1283 e1215.
McGranahan, N., Rosenthal, R., Hiley, C. T., Rowan, A. J., Watkins, T. B. K., Wilson, G. A., Birkbak, N. J., Veeriah, S., Van Loo, P., Herrero, J., et al. (2017). Allele-Specific HLA Loss and Immune Escape in Lung Cancer Evolution. Cell 171, 1259-1271 e1211.
McKenna, A., Hanna, M., Banks, E., Sivachenko, A., Cibulskis, K., Kernytsky, A., Garimella, K., Altshuler, D., Gabriel, S., Daly, M., et al. (2010). The Genome Analysis Toolkit: a MapReduce framework for analyzing next-generation DNA sequencing data. Genome research 20, 1297-1303.
Mucida, D. et al. Transcriptional reprogramming of mature CD4(+) helper T cells generates distinct MHC class II-restricted cytotoxic T lymphocytes. *Nature immunology* 14, 281-289, doi:10.1038/ni.2523 (2013).

Nelson, R. W., Beisang, D., Tubo, N. J., Dileepan, T., Wiesner, D. L., Nielsen, K., Wuthrich, M., Klein, B. S., Kotov, D. I., Spanier, J. A., et al. (2015). T cell receptor cross-reactivity between similar foreign and self peptides influences naïve cell population size and autoimmunity. Immunity 42, 95-107.

Pan, D., Kobayashi, A., Jiang, P., Ferrari de Andrade, L., Tay, R. E., Luoma, A. M., Tsoucas, D., Qiu, X., Lim, K., Rao, P., et al. (2018). A major chromatin regulator determines resistance of tumor cells to T cell-mediated killing. Science 359, 770-775.

Patel, S. J., Sanjana, N. E., Kishton, R. J., Eidizadeh, A., Vodnala, S. K., Cam, M., Gartner, J. J., Jia, L., Steinberg, S. M., Yamamoto, T. N., et al. (2017). Identification of essential genes for cancer immunotherapy. Nature 548, 537-542.

Porter, D. L., Levine, B. L., Kalos, M., Bagg, A., and June, C. H. (2011). Chimeric antigen receptor-modified T cells in chronic lymphoid leukemia. The New England journal of medicine 365, 725-733.

Rizvi, N. A., Hellmann, M. D., Snyder, A., Kvistborg, P., Makarov, V., Havel, J. J., Lee, W., Yuan, J., Wong, P., Ho, T. S., et al. (2015a). Cancer immunology. Mutational landscape determines sensitivity to PD-1 blockade in non-small cell lung cancer. Science 348, 124-128.

Rizvi, N. A., Hellmann, M. D., Snyder, A., Kvistborg, P., Makarov, V., Havel, J. J., Lee, W., Yuan, J., Wong, P., Ho, T. S., et al. (2015b). Mutational landscape determines sensitivity to PD-1 blockade in non-small cell lung cancer. Science 348, 124-128.

Robbins, P. F., Lu, Y. C., El-Gamil, M., Li, Y. F., Gross, C., Gartner, J., Lin, J. C., Teer, J. K., Cliften, P., Tycksen, E., et al. (2013). Mining exomic sequencing data to identify mutated antigens recognized by adoptively transferred tumor-reactive T cells. Nat Med 19, 747-752.

Robins, H. S., Campregher, P. V., Srivastava, S. K., Wacher, A., Turtle, C. J., Kahsai, O., Riddell, S. R., Warren, E. H., and Carlson, C. S. (2009). Comprehensive assessment of T-cell receptor beta-chain diversity in alphabeta T cells. Blood 114, 4099-4107.

Rosenberg, S. A., and Restifo, N. P. (2015). Adoptive cell transfer as personalized immunotherapy for human cancer. Science 348, 62-68.

Rosenberg, S. A., Tran, E., and Robbins, P. F. (2017). T-Cell Transfer Therapy Targeting Mutant KRAS. The New England journal of medicine 376, ell.

Schumacher, T. N., and Schreiber, R. D. (2015). Neoantigens in cancer immunotherapy. Science 348, 69-74.

Schumacher, T. N., Scheper, W., and Kvistborg, P. (2018). Cancer Neoantigens. Annu Rev Immunol.

Sercarz, E. E., Lehmann, P. V., Ametani, A., Benichou, G., Miller, A., and Moudgil, K. (1993). Dominance and crypticity of T cell antigenic determinants. Annual review of immunology 11, 729-766.

Sharma, P., and Allison, J. P. (2015). Immune checkpoint targeting in cancer therapy: toward combination strategies with curative potential. Cell 161, 205-214.

Shastri, N., Schwab, S., and Serwold, T. (2002). Producing nature's gene-chips: the generation of peptides for display by MHC class I molecules. Annu Rev Immunol 20, 463-493.

Shedlock, D. J. & Shen, H. Requirement for CD4 T cell help in generating functional CD8 T cell memory. *Science* 300, 337-339 (2003).

Starck, S. R. et al. Translation from the 5' untranslated region shapes the integrated stress response. *Science* 351, aad3867, doi:10.1126/science.aad3867 (2016).

Stronen, E., Toebes, M., Kelderman, S., van Buuren, M. M., Yang, W., van Rooij, N., Donia, M., Boschen, M. L., Lund-Johansen, F., Olweus, J., et al. (2016). Targeting of cancer neoantigens with donor-derived T cell receptor repertoires. Science 352, 1337-1341.

Sun, J. C. & Bevan, M. J. Defective CD8 T cell memory following acute infection without CD4 T cell help. *Science* 300, 339-342 (2003).

Topalian, S. L., Drake, C. G., and Pardoll, D. M. (2015). Immune checkpoint blockade: a common denominator approach to cancer therapy. Cancer cell 27, 450-461.

Tran, E., Ahmadzadeh, M., Lu, Y. C., Gros, A., Turcotte, S., Robbins, P. F., Gartner, J. J., Zheng, Z., Li, Y. F., Ray, S., et al. (2015). Immunogenicity of somatic mutations in human gastrointestinal cancers. Science 350, 1387-1390.

Tran, E., Turcotte, S., Gros, A., Robbins, P. F., Lu, Y. C., Dudley, M. E., Wunderlich, J. R., Somerville, R. P., Hogan, K., Hinrichs, C. S., et al. (2014). Cancer immunotherapy based on mutation-specific CD4+ T cells in a patient with epithelial cancer. Science 344, 641-645.

Vacchio, M. S. et al. A ThPOK-LRF transcriptional node maintains the integrity and effector potential of post-thymic CD4+ T cells. *Nature immunology* 15, 947-956, doi:10.1038/ni.2960 (2014).

Wang, H. Y., Lee, D. A., Peng, G., Guo, Z., Li, Y., Kiniwa, Y., Shevach, E. M., and Wang, R. F. (2004). Tumor-specific human CD4+ regulatory T cells and their ligands: implications for immunotherapy. Immunity 20, 107-118.

Wang, H. Y., Peng, G., Guo, Z., Shevach, E. M., and Wang, R.-F. (2005). Recognition of a new ARTC1 peptide ligand uniquely expressed in tumor cells by antigen-specific CD4+ gegulatory T cells. J Immunol 174, 2661-2670.

Wang, H. Y., Zhou, J., Zhu, K., Riker, A. I., Marincola, F. M., and Wang, R. F. (2002). Identification of a mutated fibronectin as a tumor antigen recognized by CD4+ T cells: its role in extracellular matrix formation and tumor metastasis. The Journal of experimental medicine 195, 1397-1406.

Wang, R.-F. The role of MHC class II-restricted tumor antigens and CD4+ T cells in antitumor immunity. *Trends in Immunology* 22, 269-276 (2001).

Wang, R. F., and Wang, H. Y. (2017). Immune targets and neoantigens for cancer immunotherapy and precision medicine. Cell research 27, 11-37.

Wang, R.-F., Johnston, S. L., Zeng, G., Schwartzentruber, D. J., and Rosenberg, S. A. (1998). A breast and melanoma-shared tumor antigen: T cell responses to antigenic peptides translated from different open reading frames. J Immunol 161, 3596-3606.

Wang, R. F., Parkhurst, M. R., Kawakami, Y., Robbins, P. F., and Rosenberg, S. A. (1996). Utilization of an alternative open reading frame of a normal gene in generating a novel human cancer antigen. J Exp Med 183, 1131-1140.

Wang, R. F., Wang, X., and Rosenberg, S. A. (1999b). Identification of a novel major histocompatibility complex class II-restricted tumor antigen resulting from a chromosomal rearrangement recognized by CD4(+) T cells. J Exp Med 189, 1659-1668.

Wang, R. F., Wang, X., Atwood, A. C., Topalian, S. L., and Rosenberg, S. A. (1999). Cloning genes encoding MHC class II-restricted antigens: mutated $CDCl_27$ as a tumor antigen. Science 284, 1351-1354.

Zacharakis, N., Chinnasamy, H., Black, M., Xu, H., Lu, Y. C., Zheng, Z., Pasetto, A., Langhan, M., Shelton, T., Prickett, T., et al. (2018). Immune recognition of somatic mutations leading to complete durable regression in metastatic breast cancer. Nature medicine 24, 724-730.

We claim:

1. A composition comprising a therapeutically effective amount of one or more T cell receptor (TCR) T cells engineered to express a T cell receptor that recognize a tumor antigen and a lysine-specific histone demethylase 1 (LSD1) inhibitor that enhances the anti-tumor activity of the T cells, wherein the LSD1 inhibitor is Tranylcypromine (2-PCPA).

2. The composition of claim 1, wherein the LSD1 inhibitor reprograms stem cell-like T cells to prolong survival of the T cells.

3. The composition of claim 1 or 2, wherein the TCR-T cells have been engineered to express a receptor for a cancer neoantigen.

4. The composition of claim 3, wherein the cancer neoantigen is the amino acid sequence selected from the group consisting of: SEQ ID NO: 2, SEQ ID NO: 3, SEQ ID NO: 4, SEQ ID NO: 5, SEQ ID NO: 6, SEQ ID NO: 7, SEQ ID NO: 9, SEQ ID NO: 12, SEQ ID NO: 14, SEQ ID NO: 17, SEQ ID NO: 19, SEQ ID NO: 21, SEQ ID NO: 22, SEQ ID NO: 23, SEQ ID NO: 24, SEQ ID NO: 26, SEQ ID NO: 28, SEQ ID NO: 29, SEQ ID NO: 30, SEQ ID NO: 32, SEQ ID NO: 33, SEQ ID NO: 34, SEQ ID NO: 35, SEQ ID NO: 36, SEQ ID NO: 37, SEQ ID NO: 39, SEQ ID NO: 41, SEQ ID NO: 42, SEQ ID NO: 43, SEQ ID NO: 44, SEQ ID NO: 46, SEQ ID NO: 49, SEQ ID NO: 50, SEQ ID NO: 51, SEQ ID NO: 52, SEQ ID NO: 53, SEQ ID NO: 54, SEQ ID NO: 57, SEQ ID NO: 60, SEQ ID NO: 61, SEQ ID NO: 62, SEQ ID NO: 63, SEQ ID NO: 64, SEQ ID NO: 67, SEQ ID NO: 68, SEQ ID NO: 69, SEQ ID NO: 70, SEQ ID NO: 73, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, and SEQ ID NO: 163.

* * * * *

SEQUENCE LISTING

<160> NUMBER OF SEQ ID NOS: 956

<210> SEQ ID NO 1
<211> LENGTH: 22
<212> TYPE: PRT
<213> ORGANISM: Artificial Sequence
<220> FEATURE:
<223> OTHER INFORMATION: Synthetic Construct

<400> SEQUENCE: 1

Ala Glu Pro Lys Arg Lys Ser Ser Leu Phe Trp His Thr Phe Asn Arg
1               5                   10                  15

Leu Thr Pro Phe Arg Lys
            20

<210> SEQ ID NO 2
<211> LENGTH: 22
<212> TYPE: PRT
<213> ORGANISM: Artificial Sequence
<220> FEATURE:
<223> OTHER INFORMATION: Synthetic Construct

<400> SEQUENCE: 2

Ala Glu Pro Lys Arg Lys Ser Ser Leu Phe Trp His Ala Phe Asn Arg
1               5                   10                  15

Leu Thr Pro Phe Arg Lys
            20

<210> SEQ ID NO 3
<211> LENGTH: 13
<212> TYPE: PRT
<213> ORGANISM: Artificial Sequence
<220> FEATURE:
<223> OTHER INFORMATION: Synthetic Construct

<400> SEQUENCE: 3

Arg Lys Ser Ser Leu Phe Trp His Ala Phe Asn Arg Leu
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Synthetic Construct

<400> SEQUENCE: 4

Ser Ser Leu Phe Trp His Ala Phe Asn Arg Leu Thr Pro
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthetic Construct

<400> SEQUENCE: 5

Leu Phe Trp His Ala Phe Asn Arg Leu Thr Pro Phe Arg
1               5                   10

<210> SEQ ID NO 6
<211> LENGTH: 17
<212> TYPE: PRT
<213> ORGANISM: Artificial Sequence
<220> FEATURE:

<223> OTHER INFORMATION: Synthetic Construct

<400> SEQUENCE: 6

Arg Lys Ser Ser Leu Phe Trp His Ala Phe Asn Arg Leu Thr Pro Phe
1 5 10 15

Arg

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct

<400> SEQUENCE: 7

Leu Phe Trp His Ala Phe Asn Arg Leu
1 5

<210> SEQ ID NO 8
<211> LENGTH: 25
<212> TYPE: PRT
<213> ORGANISM: Artificial Sequence
<220> FEATURE:
<223> OTHER INFORMATION: Synthetic Construct

<400> SEQUENCE: 8

Phe Gln Leu Leu Leu Glu Lys Pro Phe Gln Ile Phe Arg Ala Glu Leu
1 5 10 15

Trp Val Arg Asp Ile Asn Asp His Ala
20 25

<210> SEQ ID NO 9
<211> LENGTH: 25
<212> TYPE: PRT
<213> ORGANISM: Artificial Sequence
<220> FEATURE:
<223> OTHER INFORMATION: Synthetic Construct

<400> SEQUENCE: 9

Phe Gln Leu Leu Leu Glu Lys Pro Phe Gln Ile Phe Cys Ala Glu Leu
1 5 10 15

Trp Val Arg Asp Ile Asn Asp His Ala
20 25

<210> SEQ ID NO 10
<211> LENGTH: 13
<212> TYPE: PRT
<213> ORGANISM: Artificial Sequence
<220> FEATURE:
<223> OTHER INFORMATION: Synthetic Construct

<400> SEQUENCE: 10

Phe Gln Ile Phe Cys Ala Glu Leu Trp Val Arg Asp Ile
1 5 10

<210> SEQ ID NO 11
<211> LENGTH: 13
<212> TYPE: PRT
<213> ORGANISM: Artificial Sequence
<220> FEATURE:
<223> OTHER INFORMATION: Synthetic Construct

<400> SEQUENCE: 11

Lys Pro Phe Gln Ile Phe Cys Ala Glu Leu Trp Val Arg
1 5 10

<210> SEQ ID NO 12
<211> LENGTH: 13
<212> TYPE: PRT
<213> ORGANISM: Artificial Sequence
<220> FEATURE:
<223> OTHER INFORMATION: Synthetic Construct

<400> SEQUENCE: 12

```
Leu Glu Lys Pro Phe Gln Ile Phe Cys Ala Glu Leu Trp
1               5                   10
```

<210> SEQ ID NO 13
<211> LENGTH: 25
<212> TYPE: PRT
<213> ORGANISM: Artificial Sequence
<220> FEATURE:
<223> OTHER INFORMATION: Synthetic Construct

<400> SEQUENCE: 13

```
Glu Asn Ser Phe Leu Gly Thr Glu Phe Pro Leu Asn His Ala Leu Asp
1               5                   10                  15

Leu Asp Val Gly Ser Asn Asn Val Gln
            20                  25
```

<210> SEQ ID NO 14
<211> LENGTH: 25
<212> TYPE: PRT
<213> ORGANISM: Artificial Sequence
<220> FEATURE:
<223> OTHER INFORMATION: Synthetic Construct

<400> SEQUENCE: 14

```
Glu Asn Ser Pro Leu Gly Thr Glu Phe Pro Leu Asn Tyr Ala Leu Asp
1               5                   10                  15

Leu Asp Val Gly Ser Asn Asn Val Gln
            20                  25
```

<210> SEQ ID NO 15
<211> LENGTH: 13
<212> TYPE: PRT
<213> ORGANISM: Artificial Sequence
<220> FEATURE:
<223> OTHER INFORMATION: Synthetic Construct

<400> SEQUENCE: 15

```
Phe Pro Leu Asn Tyr Ala Leu Asp Leu Asp Val Gly Ser
1               5                   10
```

<210> SEQ ID NO 16
<211> LENGTH: 13
<212> TYPE: PRT
<213> ORGANISM: Artificial Sequence
<220> FEATURE:
<223> OTHER INFORMATION: Synthetic Construct

<400> SEQUENCE: 16

```
Thr Glu Phe Pro Leu Asn Tyr Ala Leu Asp Leu Asp Val
1               5                   10
```

<210> SEQ ID NO 17
<211> LENGTH: 13
<212> TYPE: PRT
<213> ORGANISM: Artificial Sequence
<220> FEATURE:
<223> OTHER INFORMATION: Synthetic Construct

<400> SEQUENCE: 17

Leu Gly Thr Glu Phe Pro Leu Asn Tyr Ala Leu Asp Leu
1               5                   10

<210> SEQ ID NO 18
<211> LENGTH: 21
<212> TYPE: PRT
<213> ORGANISM: Artificial Sequence
<220> FEATURE:
<223> OTHER INFORMATION: Synthetic Construct

<400> SEQUENCE: 18

Met Thr Asp Asp Lys Asp Val Leu Arg Asp Val Trp Phe Gly Arg Ile
1               5                   10                  15

Pro Thr Cys Phe Thr
            20

<210> SEQ ID NO 19
<211> LENGTH: 21
<212> TYPE: PRT
<213> ORGANISM: Artificial Sequence
<220> FEATURE:
<223> OTHER INFORMATION: Synthetic Construct

<400> SEQUENCE: 19

Met Thr Asp Asp Lys Asp Val Leu Arg Asn Val Trp Phe Gly Arg Ile
1               5                   10                  15

Pro Thr Cys Phe Thr
            20

<210> SEQ ID NO 20
<211> LENGTH: 13
<212> TYPE: PRT
<213> ORGANISM: Artificial Sequence
<220> FEATURE:
<223> OTHER INFORMATION: Synthetic Construct

<400> SEQUENCE: 20

Val Leu Arg Asn Val Trp Phe Gly Arg Ile Pro Thr Cys
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Synthetic Construct

<400> SEQUENCE: 21

Lys Asp Val Leu Arg Asn Val Trp Phe Gly Arg Ile Pro
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Synthetic Construct

<400> SEQUENCE: 22

Asp Asp Lys Asp Val Leu Arg Asn Val Trp Phe Gly Arg
1               5                   10

<210> SEQ ID NO 23

-continued

<211> LENGTH: 11
<212> TYPE: PRT
<213> ORGANISM: Artificial Sequence
<220> FEATURE:
<223> OTHER INFORMATION: Synthetic Construct

<400> SEQUENCE: 23

Lys Asp Val Leu Arg Asn Val Trp Phe Gly Arg
1 5 10

<210> SEQ ID NO 24
<211> LENGTH: 15
<212> TYPE: PRT
<213> ORGANISM: Artificial Sequence
<220> FEATURE:
<223> OTHER INFORMATION: Synthetic Construct

<400> SEQUENCE: 24

Asp Asp Lys Asp Val Leu Arg Asn Val Trp Phe Gly Arg Ile Pro
1 5 10 15

<210> SEQ ID NO 25
<211> LENGTH: 25
<212> TYPE: PRT
<213> ORGANISM: Artificial Sequence
<220> FEATURE:
<223> OTHER INFORMATION: Synthetic Construct

<400> SEQUENCE: 25

Arg Leu Lys Ala Ser Leu Asp Arg Pro Phe Thr Asn Leu Glu Ser Ala
1 5 10 15

Phe Tyr Ser Ile Val Gly Leu Ser Ser
20 25

<210> SEQ ID NO 26
<211> LENGTH: 25
<212> TYPE: PRT
<213> ORGANISM: Artificial Sequence
<220> FEATURE:
<223> OTHER INFORMATION: Synthetic Construct

<400> SEQUENCE: 26

Arg Leu Lys Ala Ser Leu Asp Arg Pro Phe Thr Asn Ser Glu Ser Ala
1 5 10 15

Phe Tyr Ser Ile Val Gly Leu Ser Ser
20 25

<210> SEQ ID NO 27
<211> LENGTH: 13
<212> TYPE: PRT
<213> ORGANISM: Artificial Sequence
<220> FEATURE:
<223> OTHER INFORMATION: Synthetic Construct

<400> SEQUENCE: 27

Ser Leu Asp Arg Pro Phe Thr Asn Ser Glu Ser Ala Phe
1 5 10

<210> SEQ ID NO 28
<211> LENGTH: 13
<212> TYPE: PRT
<213> ORGANISM: Artificial Sequence
<220> FEATURE:
<223> OTHER INFORMATION: Synthetic Construct

<400> SEQUENCE: 28

-continued

```
Asp Arg Pro Phe Thr Asn Ser Glu Ser Ala Phe Tyr Ser
1               5                   10


<210> SEQ ID NO 29
<211> LENGTH: 13
<212> TYPE: PRT
<213> ORGANISM: Artificial Sequence
<220> FEATURE:
<223> OTHER INFORMATION: Synthetic Construct

<400> SEQUENCE: 29

Pro Phe Thr Asn Ser Glu Ser Ala Phe Tyr Ser Ile Val
1               5                   10


<210> SEQ ID NO 30
<211> LENGTH: 10
<212> TYPE: PRT
<213> ORGANISM: Artificial Sequence
<220> FEATURE:
<223> OTHER INFORMATION: Synthetic Construct

<400> SEQUENCE: 30

Pro Phe Thr Asn Ser Glu Ser Ala Phe Tyr
1               5                   10


<210> SEQ ID NO 31
<211> LENGTH: 25
<212> TYPE: PRT
<213> ORGANISM: Artificial Sequence
<220> FEATURE:
<223> OTHER INFORMATION: Synthetic Construct

<400> SEQUENCE: 31

Gly Ser Gly Glu Lys Val Ala Gly Arg Val Ile Val Glu Val Cys Glu
1               5                   10                  15

Val Thr Arg Val Lys Ala Val Arg Ile
            20                  25


<210> SEQ ID NO 32
<211> LENGTH: 25
<212> TYPE: PRT
<213> ORGANISM: Artificial Sequence
<220> FEATURE:
<223> OTHER INFORMATION: Synthetic Construct

<400> SEQUENCE: 32

Gly Ser Gly Glu Lys Val Ala Gly Arg Val Ile Val Lys Val Cys Glu
1               5                   10                  15

Val Thr Arg Val Lys Ala Val Arg Ile
            20                  25


<210> SEQ ID NO 33
<211> LENGTH: 13
<212> TYPE: PRT
<213> ORGANISM: Artificial Sequence
<220> FEATURE:
<223> OTHER INFORMATION: Synthetic Construct

<400> SEQUENCE: 33

Lys Val Ala Gly Arg Val Ile Val Lys Val Cys Glu Val
1               5                   10


<210> SEQ ID NO 34
<211> LENGTH: 13
<212> TYPE: PRT
<213> ORGANISM: Artificial Sequence
```

-continued

```
<220> FEATURE:
<223> OTHER INFORMATION: Synthetic Construct

<400> SEQUENCE: 34

Ala Gly Arg Val Ile Val Lys Val Cys Glu Val Thr Arg
1               5                   10


<210> SEQ ID NO 35
<211> LENGTH: 13
<212> TYPE: PRT
<213> ORGANISM: Artificial Sequence
<220> FEATURE:
<223> OTHER INFORMATION: Synthetic Construct

<400> SEQUENCE: 35

Arg Val Ile Val Lys Val Cys Glu Val Thr Arg Val Lys
1               5                   10


<210> SEQ ID NO 36
<211> LENGTH: 9
<212> TYPE: PRT
<213> ORGANISM: Artificial Sequence
<220> FEATURE:
<223> OTHER INFORMATION: Synthetic Construct

<400> SEQUENCE: 36

Arg Val Ile Val Lys Val Cys Glu Val
1               5


<210> SEQ ID NO 37
<211> LENGTH: 17
<212> TYPE: PRT
<213> ORGANISM: Artificial Sequence
<220> FEATURE:
<223> OTHER INFORMATION: Synthetic Construct

<400> SEQUENCE: 37

Lys Val Ala Gly Arg Val Ile Val Lys Val Cys Glu Val Thr Arg Val
1               5                   10                  15

Lys


<210> SEQ ID NO 38
<211> LENGTH: 25
<212> TYPE: PRT
<213> ORGANISM: Artificial Sequence
<220> FEATURE:
<223> OTHER INFORMATION: Synthetic Construct

<400> SEQUENCE: 38

Tyr Gly Met Tyr Phe Cys Met Asn Ile Ser Ser Gln Gly Asp Gly Ala
1               5                   10                  15

Cys Val Leu Leu Arg Ala Leu Glu Pro
            20                  25


<210> SEQ ID NO 39
<211> LENGTH: 25
<212> TYPE: PRT
<213> ORGANISM: Artificial Sequence
<220> FEATURE:
<223> OTHER INFORMATION: Synthetic Construct

<400> SEQUENCE: 39

Tyr Gly Met Tyr Phe Cys Met Asn Ile Ser Ser Gln Glu Asp Gly Ala
1               5                   10                  15

Cys Val Leu Leu Arg Ala Leu Glu Pro
```

-continued 20 25

<210> SEQ ID NO 40
<211> LENGTH: 13
<212> TYPE: PRT
<213> ORGANISM: Artificial Sequence
<220> FEATURE:
<223> OTHER INFORMATION: Synthetic Construct

<400> SEQUENCE: 40

Phe Cys Met Asn Ile Ser Ser Gln Glu Asp Gly Ala Cys
1 5 10

<210> SEQ ID NO 41
<211> LENGTH: 13
<212> TYPE: PRT
<213> ORGANISM: Artificial Sequence
<220> FEATURE:
<223> OTHER INFORMATION: Synthetic Construct

<400> SEQUENCE: 41

Met Asn Ile Ser Ser Gln Glu Asp Gly Ala Cys Val Leu
1 5 10

<210> SEQ ID NO 42
<211> LENGTH: 13
<212> TYPE: PRT
<213> ORGANISM: Artificial Sequence
<220> FEATURE:
<223> OTHER INFORMATION: Synthetic Construct

<400> SEQUENCE: 42

Ile Ser Ser Gln Glu Asp Gly Ala Cys Val Leu Leu Arg
1 5 10

<210> SEQ ID NO 43
<211> LENGTH: 10
<212> TYPE: PRT
<213> ORGANISM: Artificial Sequence
<220> FEATURE:
<223> OTHER INFORMATION: Synthetic Construct

<400> SEQUENCE: 43

Ile Ser Ser Gln Glu Asp Gly Ala Cys Val
1 5 10

<210> SEQ ID NO 44
<211> LENGTH: 15
<212> TYPE: PRT
<213> ORGANISM: Artificial Sequence
<220> FEATURE:
<223> OTHER INFORMATION: Synthetic Construct

<400> SEQUENCE: 44

Met Asn Ile Ser Ser Gln Glu Asp Gly Ala Cys Val Leu Leu Arg
1 5 10 15

<210> SEQ ID NO 45
<211> LENGTH: 606
<212> TYPE: DNA
<213> ORGANISM: Artificial Sequence
<220> FEATURE:
<223> OTHER INFORMATION: Synthetic Construct

<400> SEQUENCE: 45
ccctgtacac aggcttttcc atcctggtga ctctgctcct cgctggccag gccaccaccg 60

-continued

```
cctacttcct gtaccagcag cagggccggc tggacaaact gacagtcacc tcccaaaacc    120

tgcagctgga aaacctgcgc atgaaggcta gcgaattgtg ccaaggggct ggaaaggcag    180

aggctccgga gccatgaaat taacatcact gatgtgtaat ccagtaaaat ctcccttttt    240

cgggtgtgta tctgggcatg tgcccatttc tatgtgtgtg tctacgtgca cctcactacc    300

aacagcctca tgtgcacttg acctgacagt gctcgctgag aactctcacc accttggcgc    360

ctgaatgcct tactctcagc agtcagaggc ttgcttgctc tgtgcagatt tttaattttc    420

tttttggcc ctaggctggt tgggacctct acagcttcat tctttcacca ttaaatagtg    480

gccttttca gtattttccc tcttcccctt tataaattat gctaaagcca caaagcacat    540

ttttggggat catagaaggt tggggttcca gaaaggcatc tgtgtgatgg ttccattgat    600

gtggga                                                              606
```

```
<210> SEQ ID NO 46
<211> LENGTH: 56
<212> TYPE: PRT
<213> ORGANISM: Artificial Sequence
<220> FEATURE:
<223> OTHER INFORMATION: Synthetic Construct

<400> SEQUENCE: 46

Met Lys Leu Thr Ser Leu Met Cys Asn Pro Val Lys Ser Pro Phe Phe
1               5                   10                  15

Gly Cys Val Cys Gly His Val Pro Ile Ser Met Cys Val Ser Thr Cys
            20                  25                  30

Ser Ser Leu Pro Thr Ala Ser Cys Ala Leu Asp Leu Thr Val Leu Ala
        35                  40                  45

Glu Asn Ser His Gln Val Gly Ala
    50                  55
```

```
<210> SEQ ID NO 47
<211> LENGTH: 520
<212> TYPE: DNA
<213> ORGANISM: Artificial Sequence
<220> FEATURE:
<223> OTHER INFORMATION: Synthetic Construct

<400> SEQUENCE: 47

ctgtacacag gcttttccat cctggtgact ctgctcctcg ctggccaggc caccaccgcc     60

tacttcctgt accagcagca gggccggctg gacaaactga cagtcacctc ccaaaacctg    120

gctccggagc catgcaggcc gaaggccggg gcacaggggg ttcgacgggc gatgctgatg    180

gcccaggagg ccctggcatt cctgatggcc caggggggcaa tgctggcggc ccaggagagg    240

cggtgccacg ggcggcagag gtccccgggg cgcaggggca gcaagggcct cgggccaaga    300

ggaggccccc cgcggggtcc gcatggcggt gccgcttctg cgcaggatgg aaggtgcccc    360

tgcggggcca ggaggccgga cagccgcctg cttgagttgc acatcacgat gcctttctcg    420

tcccccatgg aagcggagct ggtccgcagg atcctgtccc gggatgccgc accgctcccc    480

cgaccagggg cccttctcaa ggacttcacc gtgtccggca                          520
```

```
<210> SEQ ID NO 48
<211> LENGTH: 109
<212> TYPE: PRT
<213> ORGANISM: Artificial Sequence
<220> FEATURE:
<223> OTHER INFORMATION: Synthetic Construct

<400> SEQUENCE: 48
```

```
Met Leu Met Ala Gln Glu Ala Leu Ala Phe Leu Met Ala Gln Gly Ala
1               5                   10                  15

Met Leu Ala Ala Gln Glu Arg Arg Val Pro Arg Ala Ala Glu Val Pro
            20                  25                  30

Gly Ala Gln Gly Gln Gln Gly Pro Arg Gly Arg Glu Glu Ala Pro Arg
        35                  40                  45

Gly Val Arg Met Ala Val Pro Leu Leu Arg Arg Met Glu Gly Ala Pro
    50                  55                  60

Ala Gly Pro Gly Gly Arg Thr Ala Ala Cys Leu Ser Cys Thr Ser Arg
65                  70                  75                  80

Cys Leu Ser Arg Arg Pro Trp Lys Arg Ser Trp Ser Ala Gly Ser Cys
                85                  90                  95

Pro Gly Met Pro His Arg Ser Pro Asp Gln Gly Arg Phe
            100                 105
```

<210> SEQ ID NO 49
<211> LENGTH: 50
<212> TYPE: PRT
<213> ORGANISM: Artificial Sequence
<220> FEATURE:
<223> OTHER INFORMATION: Synthetic Construct

<400> SEQUENCE: 49

```
Met Cys Asn Pro Val Lys Ser Pro Phe Phe Gly Cys Val Cys Gly His
1               5                   10                  15

Val Pro Ile Ser Met Cys Val Ser Thr Cys Ser Ser Leu Pro Thr Ala
            20                  25                  30

Ser Cys Ala Leu Asp Leu Thr Val Leu Ala Glu Asn Ser His Gln Val
        35                  40                  45

Gly Ala
    50
```

<210> SEQ ID NO 50
<211> LENGTH: 45
<212> TYPE: PRT
<213> ORGANISM: Artificial Sequence
<220> FEATURE:
<223> OTHER INFORMATION: Synthetic Construct

<400> SEQUENCE: 50

```
Lys Ser Pro Phe Phe Gly Cys Val Cys Gly His Val Pro Ile Ser Met
1               5                   10                  15

Cys Val Ser Thr Cys Ser Ser Leu Pro Thr Ala Ser Cys Ala Leu Asp
            20                  25                  30

Leu Thr Val Leu Ala Glu Asn Ser His Gln Val Gly Ala
        35                  40                  45
```

<210> SEQ ID NO 51
<211> LENGTH: 40
<212> TYPE: PRT
<213> ORGANISM: Artificial Sequence
<220> FEATURE:
<223> OTHER INFORMATION: Synthetic Construct

<400> SEQUENCE: 51

```
Gly Cys Val Cys Gly His Val Pro Ile Ser Met Cys Val Ser Thr Cys
1               5                   10                  15

Ser Ser Leu Pro Thr Ala Ser Cys Ala Leu Asp Leu Thr Val Leu Ala
            20                  25                  30
```

-continued

```
Glu Asn Ser His Gln Val Gly Ala
        35                  40


<210> SEQ ID NO 52
<211> LENGTH: 36
<212> TYPE: PRT
<213> ORGANISM: Artificial Sequence
<220> FEATURE:
<223> OTHER INFORMATION: Synthetic Construct

<400> SEQUENCE: 52

Gly His Val Pro Ile Ser Met Cys Val Ser Thr Cys Ser Ser Leu Pro
1               5                   10                  15

Thr Ala Ser Cys Ala Leu Asp Leu Thr Val Leu Ala Glu Asn Ser His
            20                  25                  30

Gln Val Gly Ala
        35


<210> SEQ ID NO 53
<211> LENGTH: 31
<212> TYPE: PRT
<213> ORGANISM: Artificial Sequence
<220> FEATURE:
<223> OTHER INFORMATION: Synthetic Construct

<400> SEQUENCE: 53

Ser Met Cys Val Ser Thr Cys Ser Ser Leu Pro Thr Ala Ser Cys Ala
1               5                   10                  15

Leu Asp Leu Thr Val Leu Ala Glu Asn Ser His Gln Val Gly Ala
            20                  25                  30


<210> SEQ ID NO 54
<211> LENGTH: 28
<212> TYPE: PRT
<213> ORGANISM: Artificial Sequence
<220> FEATURE:
<223> OTHER INFORMATION: Synthetic Construct

<400> SEQUENCE: 54

Val Ser Thr Cys Ser Ser Leu Pro Thr Ala Ser Cys Ala Leu Asp Leu
1               5                   10                  15

Thr Val Leu Ala Glu Asn Ser His Gln Val Gly Ala
            20                  25


<210> SEQ ID NO 55
<211> LENGTH: 27
<212> TYPE: PRT
<213> ORGANISM: Artificial Sequence
<220> FEATURE:
<223> OTHER INFORMATION: Synthetic Construct

<400> SEQUENCE: 55

Ser Thr Cys Ser Ser Leu Pro Thr Ala Ser Cys Ala Leu Asp Leu Thr
1               5                   10                  15

Val Leu Ala Glu Asn Ser His Gln Val Gly Ala
            20                  25


<210> SEQ ID NO 56
<211> LENGTH: 23
<212> TYPE: PRT
<213> ORGANISM: Artificial Sequence
<220> FEATURE:
<223> OTHER INFORMATION: Synthetic Construct

<400> SEQUENCE: 56
```

Ser Leu Pro Thr Ala Ser Cys Ala Leu Asp Leu Thr Val Leu Ala Glu
1 5 10 15

Asn Ser His Gln Val Gly Ala
20

<210> SEQ ID NO 57
<211> LENGTH: 48
<212> TYPE: PRT
<213> ORGANISM: Artificial Sequence
<220> FEATURE:
<223> OTHER INFORMATION: Synthetic Construct

<400> SEQUENCE: 57

Met Cys Asn Pro Val Lys Ser Pro Phe Phe Gly Cys Val Cys Gly His
1 5 10 15

Val Pro Ile Ser Met Cys Val Ser Thr Cys Ser Ser Leu Pro Thr Ala
20 25 30

Ser Cys Ala Leu Asp Leu Thr Val Leu Ala Glu Asn Ser His Gln Val
35 40 45

<210> SEQ ID NO 58
<211> LENGTH: 47
<212> TYPE: PRT
<213> ORGANISM: Artificial Sequence
<220> FEATURE:
<223> OTHER INFORMATION: Synthetic Construct

<400> SEQUENCE: 58

Met Cys Asn Pro Val Lys Ser Pro Phe Phe Gly Cys Val Cys Gly His
1 5 10 15

Val Pro Ile Ser Met Cys Val Ser Thr Cys Ser Ser Leu Pro Thr Ala
20 25 30

Ser Cys Ala Leu Asp Leu Thr Val Leu Ala Glu Asn Ser His Gln
35 40 45

<210> SEQ ID NO 59
<211> LENGTH: 46
<212> TYPE: PRT
<213> ORGANISM: Artificial Sequence
<220> FEATURE:
<223> OTHER INFORMATION: Synthetic Construct

<400> SEQUENCE: 59

Met Cys Asn Pro Val Lys Ser Pro Phe Phe Gly Cys Val Cys Gly His
1 5 10 15

Val Pro Ile Ser Met Cys Val Ser Thr Cys Ser Ser Leu Pro Thr Ala
20 25 30

Ser Cys Ala Leu Asp Leu Thr Val Leu Ala Glu Asn Ser His
35 40 45

<210> SEQ ID NO 60
<211> LENGTH: 26
<212> TYPE: PRT
<213> ORGANISM: Artificial Sequence
<220> FEATURE:
<223> OTHER INFORMATION: Synthetic Construct

<400> SEQUENCE: 60

Val Ser Thr Cys Ser Ser Leu Pro Thr Ala Ser Cys Ala Leu Asp Leu
1 5 10 15

Thr Val Leu Ala Glu Asn Ser His Gln Val
20 25

<210> SEQ ID NO 61
<211> LENGTH: 99
<212> TYPE: PRT
<213> ORGANISM: Artificial Sequence
<220> FEATURE:
<223> OTHER INFORMATION: Synthetic Construct

<400> SEQUENCE: 61

Glu Ala Leu Ala Phe Leu Met Ala Gln Gly Ala Met Leu Ala Ala Gln
1 5 10 15

Glu Arg Arg Val Pro Arg Ala Ala Glu Val Pro Gly Ala Gln Gly Gln
20 25 30

Gln Gly Pro Arg Gly Arg Glu Glu Ala Pro Arg Gly Val Arg Met Ala
35 40 45

Val Pro Leu Leu Arg Arg Met Glu Gly Ala Pro Ala Gly Pro Gly Gly
50 55 60

Arg Thr Ala Ala Cys Leu Ser Cys Thr Ser Arg Cys Leu Ser Arg Arg
65 70 75 80

Pro Trp Lys Arg Ser Trp Ser Ala Gly Ser Cys Pro Gly Met Pro His
85 90 95

Arg Ser Pro

<210> SEQ ID NO 62
<211> LENGTH: 94
<212> TYPE: PRT
<213> ORGANISM: Artificial Sequence
<220> FEATURE:
<223> OTHER INFORMATION: Synthetic Construct

<400> SEQUENCE: 62

Glu Ala Leu Ala Phe Leu Met Ala Gln Gly Ala Met Leu Ala Ala Gln
1 5 10 15

Glu Arg Arg Val Pro Arg Ala Ala Glu Val Pro Gly Ala Gln Gly Gln
20 25 30

Gln Gly Pro Arg Gly Arg Glu Glu Ala Pro Arg Gly Val Arg Met Ala
35 40 45

Val Pro Leu Leu Arg Arg Met Glu Gly Ala Pro Ala Gly Pro Gly Gly
50 55 60

Arg Thr Ala Ala Cys Leu Ser Cys Thr Ser Arg Cys Leu Ser Arg Arg
65 70 75 80

Pro Trp Lys Arg Ser Trp Ser Ala Gly Ser Cys Pro Gly Met
85 90

<210> SEQ ID NO 63
<211> LENGTH: 89
<212> TYPE: PRT
<213> ORGANISM: Artificial Sequence
<220> FEATURE:
<223> OTHER INFORMATION: Synthetic Construct

<400> SEQUENCE: 63

Glu Ala Leu Ala Phe Leu Met Ala Gln Gly Ala Met Leu Ala Ala Gln
1 5 10 15

Glu Arg Arg Val Pro Arg Ala Ala Glu Val Pro Gly Ala Gln Gly Gln
20 25 30

Gln Gly Pro Arg Gly Arg Glu Glu Ala Pro Arg Gly Val Arg Met Ala
35 40 45

Val Pro Leu Leu Arg Arg Met Glu Gly Ala Pro Ala Gly Pro Gly Gly

```
    50                  55                  60

Arg Thr Ala Ala Cys Leu Ser Cys Thr Ser Arg Cys Leu Ser Arg Arg
65                  70                  75                  80

Pro Trp Lys Arg Ser Trp Ser Ala Gly
                85


<210> SEQ ID NO 64
<211> LENGTH: 84
<212> TYPE: PRT
<213> ORGANISM: Artificial Sequence
<220> FEATURE:
<223> OTHER INFORMATION: Synthetic Construct

<400> SEQUENCE: 64

Glu Ala Leu Ala Phe Leu Met Ala Gln Gly Ala Met Leu Ala Ala Gln
1               5                   10                  15

Glu Arg Arg Val Pro Arg Ala Ala Glu Val Pro Gly Ala Gln Gly Gln
            20                  25                  30

Gln Gly Pro Arg Gly Arg Glu Glu Ala Pro Arg Gly Val Arg Met Ala
        35                  40                  45

Val Pro Leu Leu Arg Arg Met Glu Gly Ala Pro Ala Gly Pro Gly Gly
    50                  55                  60

Arg Thr Ala Ala Cys Leu Ser Cys Thr Ser Arg Cys Leu Ser Arg Arg
65                  70                  75                  80

Pro Trp Lys Arg


<210> SEQ ID NO 65
<211> LENGTH: 79
<212> TYPE: PRT
<213> ORGANISM: Artificial Sequence
<220> FEATURE:
<223> OTHER INFORMATION: Synthetic Construct

<400> SEQUENCE: 65

Glu Ala Leu Ala Phe Leu Met Ala Gln Gly Ala Met Leu Ala Ala Gln
1               5                   10                  15

Glu Arg Arg Val Pro Arg Ala Ala Glu Val Pro Gly Ala Gln Gly Gln
            20                  25                  30

Gln Gly Pro Arg Gly Arg Glu Glu Ala Pro Arg Gly Val Arg Met Ala
        35                  40                  45

Val Pro Leu Leu Arg Arg Met Glu Gly Ala Pro Ala Gly Pro Gly Gly
    50                  55                  60

Arg Thr Ala Ala Cys Leu Ser Cys Thr Ser Arg Cys Leu Ser Arg
65                  70                  75


<210> SEQ ID NO 66
<211> LENGTH: 74
<212> TYPE: PRT
<213> ORGANISM: Artificial Sequence
<220> FEATURE:
<223> OTHER INFORMATION: Synthetic Construct

<400> SEQUENCE: 66

Glu Ala Leu Ala Phe Leu Met Ala Gln Gly Ala Met Leu Ala Ala Gln
1               5                   10                  15

Glu Arg Arg Val Pro Arg Ala Ala Glu Val Pro Gly Ala Gln Gly Gln
            20                  25                  30

Gln Gly Pro Arg Gly Arg Glu Glu Ala Pro Arg Gly Val Arg Met Ala
        35                  40                  45
```

```
Val Pro Leu Leu Arg Arg Met Glu Gly Ala Pro Ala Gly Pro Gly Gly
    50                  55                  60

Arg Thr Ala Ala Cys Leu Ser Cys Thr Ser
65                  70


<210> SEQ ID NO 67
<211> LENGTH: 104
<212> TYPE: PRT
<213> ORGANISM: Artificial Sequence
<220> FEATURE:
<223> OTHER INFORMATION: Synthetic Construct

<400> SEQUENCE: 67

Glu Ala Leu Ala Phe Leu Met Ala Gln Gly Ala Met Leu Ala Ala Gln
1               5                   10                  15

Glu Arg Arg Val Pro Arg Ala Ala Glu Val Pro Gly Ala Gln Gly Gln
            20                  25                  30

Gln Gly Pro Arg Gly Arg Glu Glu Ala Pro Arg Gly Val Arg Met Ala
        35                  40                  45

Val Pro Leu Leu Arg Arg Met Glu Gly Ala Pro Ala Gly Pro Gly Gly
    50                  55                  60

Arg Thr Ala Ala Cys Leu Ser Cys Thr Ser Arg Cys Leu Ser Arg Arg
65                  70                  75                  80

Pro Trp Lys Arg Ser Trp Ser Ala Gly Ser Cys Pro Gly Met Pro His
                85                  90                  95

Arg Ser Pro Asp Gln Gly Arg Phe
            100


<210> SEQ ID NO 68
<211> LENGTH: 99
<212> TYPE: PRT
<213> ORGANISM: Artificial Sequence
<220> FEATURE:
<223> OTHER INFORMATION: Synthetic Construct

<400> SEQUENCE: 68

Leu Met Ala Gln Gly Ala Met Leu Ala Ala Gln Glu Arg Arg Val Pro
1               5                   10                  15

Arg Ala Ala Glu Val Pro Gly Ala Gln Gly Gln Gln Gly Pro Arg Gly
            20                  25                  30

Arg Glu Glu Ala Pro Arg Gly Val Arg Met Ala Val Pro Leu Leu Arg
        35                  40                  45

Arg Met Glu Gly Ala Pro Ala Gly Pro Gly Gly Arg Thr Ala Ala Cys
    50                  55                  60

Leu Ser Cys Thr Ser Arg Cys Leu Ser Arg Arg Pro Trp Lys Arg Ser
65                  70                  75                  80

Trp Ser Ala Gly Ser Cys Pro Gly Met Pro His Arg Ser Pro Asp Gln
                85                  90                  95

Gly Arg Phe


<210> SEQ ID NO 69
<211> LENGTH: 94
<212> TYPE: PRT
<213> ORGANISM: Artificial Sequence
<220> FEATURE:
<223> OTHER INFORMATION: Synthetic Construct

<400> SEQUENCE: 69

Ala Met Leu Ala Ala Gln Glu Arg Arg Val Pro Arg Ala Ala Glu Val
1               5                   10                  15
```

```
Pro Gly Ala Gln Gly Gln Gln Gly Pro Arg Gly Arg Glu Glu Ala Pro
            20                  25                  30

Arg Gly Val Arg Met Ala Val Pro Leu Leu Arg Arg Met Glu Gly Ala
        35                  40                  45

Pro Ala Gly Pro Gly Gly Arg Thr Ala Ala Cys Leu Ser Cys Thr Ser
    50                  55                  60

Arg Cys Leu Ser Arg Arg Pro Trp Lys Arg Ser Trp Ser Ala Gly Ser
65                  70                  75                  80

Cys Pro Gly Met Pro His Arg Ser Pro Asp Gln Gly Arg Phe
                85                  90


<210> SEQ ID NO 70
<211> LENGTH: 89
<212> TYPE: PRT
<213> ORGANISM: Artificial Sequence
<220> FEATURE:
<223> OTHER INFORMATION: Synthetic Construct

<400> SEQUENCE: 70

Gln Glu Arg Arg Val Pro Arg Ala Ala Glu Val Pro Gly Ala Gln Gly
1               5                   10                  15

Gln Gln Gly Pro Arg Gly Arg Glu Glu Ala Pro Arg Gly Val Arg Met
            20                  25                  30

Ala Val Pro Leu Leu Arg Arg Met Glu Gly Ala Pro Ala Gly Pro Gly
        35                  40                  45

Gly Arg Thr Ala Ala Cys Leu Ser Cys Thr Ser Arg Cys Leu Ser Arg
    50                  55                  60

Arg Pro Trp Lys Arg Ser Trp Ser Ala Gly Ser Cys Pro Gly Met Pro
65                  70                  75                  80

His Arg Ser Pro Asp Gln Gly Arg Phe
                85


<210> SEQ ID NO 71
<211> LENGTH: 84
<212> TYPE: PRT
<213> ORGANISM: Artificial Sequence
<220> FEATURE:
<223> OTHER INFORMATION: Synthetic Construct

<400> SEQUENCE: 71

Pro Arg Ala Ala Glu Val Pro Gly Ala Gln Gly Gln Gln Gly Pro Arg
1               5                   10                  15

Gly Arg Glu Glu Ala Pro Arg Gly Val Arg Met Ala Val Pro Leu Leu
            20                  25                  30

Arg Arg Met Glu Gly Ala Pro Ala Gly Pro Gly Gly Arg Thr Ala Ala
        35                  40                  45

Cys Leu Ser Cys Thr Ser Arg Cys Leu Ser Arg Arg Pro Trp Lys Arg
    50                  55                  60

Ser Trp Ser Ala Gly Ser Cys Pro Gly Met Pro His Arg Ser Pro Asp
65                  70                  75                  80

Gln Gly Arg Phe


<210> SEQ ID NO 72
<211> LENGTH: 79
<212> TYPE: PRT
<213> ORGANISM: Artificial Sequence
<220> FEATURE:
<223> OTHER INFORMATION: Synthetic Construct
```

```
<400> SEQUENCE: 72

Val Pro Gly Ala Gln Gly Gln Gln Gly Pro Arg Gly Arg Glu Glu Ala
1               5                   10                  15

Pro Arg Gly Val Arg Met Ala Val Pro Leu Leu Arg Arg Met Glu Gly
            20                  25                  30

Ala Pro Ala Gly Pro Gly Gly Arg Thr Ala Ala Cys Leu Ser Cys Thr
        35                  40                  45

Ser Arg Cys Leu Ser Arg Arg Pro Trp Lys Arg Ser Trp Ser Ala Gly
    50                  55                  60

Ser Cys Pro Gly Met Pro His Arg Ser Pro Asp Gln Gly Arg Phe
65                  70                  75


<210> SEQ ID NO 73
<211> LENGTH: 61
<212> TYPE: PRT
<213> ORGANISM: Artificial Sequence
<220> FEATURE:
<223> OTHER INFORMATION: Synthetic Construct

<400> SEQUENCE: 73

Val Pro Arg Ala Ala Glu Val Pro Gly Ala Gln Gly Gln Gln Gly Pro
1               5                   10                  15

Arg Gly Arg Glu Glu Ala Pro Arg Gly Val Arg Met Ala Val Pro Leu
            20                  25                  30

Leu Arg Arg Met Glu Gly Ala Pro Ala Gly Pro Gly Gly Arg Thr Ala
        35                  40                  45

Ala Cys Leu Ser Cys Thr Ser Arg Cys Leu Ser Arg Arg
    50                  55                  60


<210> SEQ ID NO 74
<211> LENGTH: 69
<212> TYPE: PRT
<213> ORGANISM: Artificial Sequence
<220> FEATURE:
<223> OTHER INFORMATION: Synthetic Construct

<400> SEQUENCE: 74

Gln Glu Arg Arg Val Pro Arg Ala Ala Glu Val Pro Gly Ala Gln Gly
1               5                   10                  15

Gln Gln Gly Pro Arg Gly Arg Glu Glu Ala Pro Arg Gly Val Arg Met
            20                  25                  30

Ala Val Pro Leu Leu Arg Arg Met Glu Gly Ala Pro Ala Gly Pro Gly
        35                  40                  45

Gly Arg Thr Ala Ala Cys Leu Ser Cys Thr Ser Arg Cys Leu Ser Arg
    50                  55                  60

Arg Pro Trp Lys Arg
65


<210> SEQ ID NO 75
<211> LENGTH: 25
<212> TYPE: PRT
<213> ORGANISM: Artificial Sequence
<220> FEATURE:
<223> OTHER INFORMATION: Synthetic Construct

<400> SEQUENCE: 75

Lys Asp Ala Ala Arg Pro Ala Tyr Trp Val Pro Asp His Glu Ile Leu
1               5                   10                  15

His Cys His Asn Cys Arg Lys Glu Phe
            20                  25
```

<210> SEQ ID NO 76
<211> LENGTH: 25
<212> TYPE: PRT
<213> ORGANISM: Artificial Sequence
<220> FEATURE:
<223> OTHER INFORMATION: Synthetic Construct

<400> SEQUENCE: 76

Lys Asp Ala Ala Arg Pro Ala Tyr Trp Val Pro Asp Tyr Glu Ile Leu
1 5 10 15

His Cys His Asn Cys Arg Lys Glu Phe
20 25

<210> SEQ ID NO 77
<211> LENGTH: 25
<212> TYPE: PRT
<213> ORGANISM: Artificial Sequence
<220> FEATURE:
<223> OTHER INFORMATION: Synthetic Construct

<400> SEQUENCE: 77

Ser Met Pro Leu Trp Asp Phe Gln Gly Ser Thr Met Leu Thr Ser Gln
1 5 10 15

Tyr Val Arg Leu Thr Pro Asp Glu Arg
20 25

<210> SEQ ID NO 78
<211> LENGTH: 25
<212> TYPE: PRT
<213> ORGANISM: Artificial Sequence
<220> FEATURE:
<223> OTHER INFORMATION: Synthetic Construct

<400> SEQUENCE: 78

Ser Met Pro Leu Trp Asp Phe Gln Gly Ser Thr Met Arg Thr Ser Gln
1 5 10 15

Tyr Val Arg Leu Thr Pro Asp Glu Arg
20 25

<210> SEQ ID NO 79
<211> LENGTH: 25
<212> TYPE: PRT
<213> ORGANISM: Artificial Sequence
<220> FEATURE:
<223> OTHER INFORMATION: Synthetic Construct

<400> SEQUENCE: 79

Tyr Pro Gly Ile Lys Phe Glu Glu Leu Phe Pro Asp Trp Ile Phe Pro
1 5 10 15

Ser Glu Ser Glu Arg Asp Lys Ile Lys
20 25

<210> SEQ ID NO 80
<211> LENGTH: 25
<212> TYPE: PRT
<213> ORGANISM: Artificial Sequence
<220> FEATURE:
<223> OTHER INFORMATION: Synthetic Construct

<400> SEQUENCE: 80

Tyr Pro Gly Ile Lys Phe Glu Glu Leu Phe Pro Asp Cys Ile Phe Pro
1 5 10 15

Ser Glu Ser Glu Arg Asp Lys Ile Lys 20 25

<210> SEQ ID NO 81
<211> LENGTH: 25
<212> TYPE: PRT
<213> ORGANISM: Artificial Sequence
<220> FEATURE:
<223> OTHER INFORMATION: Synthetic Construct

<400> SEQUENCE: 81

Leu Leu Lys Thr Arg Arg Ile Leu Lys Cys Ser Tyr Pro Tyr Gly Phe
1 5 10 15

Phe Leu Glu Pro Lys Ser Thr Lys Lys
20 25

<210> SEQ ID NO 82
<211> LENGTH: 25
<212> TYPE: PRT
<213> ORGANISM: Artificial Sequence
<220> FEATURE:
<223> OTHER INFORMATION: Synthetic Construct

<400> SEQUENCE: 82

Leu Leu Lys Thr Arg Arg Ile Leu Lys Cys Ser Tyr Leu Tyr Gly Phe
1 5 10 15

Phe Leu Glu Pro Lys Ser Thr Lys Lys
20 25

<210> SEQ ID NO 83
<211> LENGTH: 25
<212> TYPE: PRT
<213> ORGANISM: Artificial Sequence
<220> FEATURE:
<223> OTHER INFORMATION: Synthetic Construct

<400> SEQUENCE: 83

Pro Phe Tyr Leu Gly His Thr Ile Lys Ser Gly Asp Leu Glu Tyr Val
1 5 10 15

Gly Met Glu Gly Gly Ile Val Leu Ser
20 25

<210> SEQ ID NO 84
<211> LENGTH: 25
<212> TYPE: PRT
<213> ORGANISM: Artificial Sequence
<220> FEATURE:
<223> OTHER INFORMATION: Synthetic Construct

<400> SEQUENCE: 84

Pro Phe Tyr Leu Gly His Thr Ile Lys Ser Gly Asp Phe Glu Tyr Val
1 5 10 15

Gly Met Glu Gly Gly Ile Val Leu Ser
20 25

<210> SEQ ID NO 85
<211> LENGTH: 25
<212> TYPE: PRT
<213> ORGANISM: Artificial Sequence
<220> FEATURE:
<223> OTHER INFORMATION: Synthetic Construct

<400> SEQUENCE: 85

Leu Leu Leu Ala Gly Tyr Leu Ala Gln Gln Tyr Leu Pro Leu Pro Thr
1 5 10 15

```
Pro Lys Val Ile Gly Ile Asp Leu Gly
            20                  25


<210> SEQ ID NO 86
<211> LENGTH: 25
<212> TYPE: PRT
<213> ORGANISM: Artificial Sequence
<220> FEATURE:
<223> OTHER INFORMATION: Synthetic Construct

<400> SEQUENCE: 86

Leu Leu Leu Ala Gly Tyr Leu Ala Gln Gln Tyr Leu Leu Leu Pro Thr
1               5                   10                  15

Pro Lys Val Ile Gly Ile Asp Leu Gly
            20                  25


<210> SEQ ID NO 87
<211> LENGTH: 22
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(2)
<223> OTHER INFORMATION: X = T or S
<220> FEATURE:
<221> NAME/KEY: VARIANT
<222> LOCATION: (2)..(3)
<223> OTHER INFORMATION: X = A or S
<220> FEATURE:
<221> NAME/KEY: VARIANT
<222> LOCATION: (3)..(4)
<223> OTHER INFORMATION: X = V, M, F, Q or L
<220> FEATURE:
<221> NAME/KEY: VARIANT
<222> LOCATION: (5)..(6)
<223> OTHER INFORMATION: X = F, L or R
<220> FEATURE:
<221> NAME/KEY: VARIANT
<222> LOCATION: (9)..(10)
<223> OTHER INFORMATION: X = S, I, T or P
<220> FEATURE:
<221> NAME/KEY: VARIANT
<222> LOCATION: (10)..(11)
<223> OTHER INFORMATION: X = Y, L, G, Q, P, F, T, S, or K
<220> FEATURE:
<221> NAME/KEY: VARIANT
<222> LOCATION: (11)..(12)
<223> OTHER INFORMATION: X = D, G, V, H, R, T, P, W, A or I
<220> FEATURE:
<221> NAME/KEY: VARIANT
<222> LOCATION: (12)..(13)
<223> OTHER INFORMATION: X = T, A, I, P, R, G, L, S or V
<220> FEATURE:
<221> NAME/KEY: VARIANT
<222> LOCATION: (13)..(14)
<223> OTHER INFORMATION: X = G, W, A, T, Y, Q or N
<220> FEATURE:
<221> NAME/KEY: VARIANT
<222> LOCATION: (14)..(15)
<223> OTHER INFORMATION: X = S, G, D, E, Y, P or T
<220> FEATURE:
<221> NAME/KEY: VARIANT
<222> LOCATION: (15)..(16)
<223> OTHER INFORMATION: X = G, N, Y, Q, D, E, I or W
<220> FEATURE:
<221> NAME/KEY: VARIANT
<222> LOCATION: (16)..(17)
<223> OTHER INFORMATION: X = D, T, E, F, A, S, L, Y, W or G
<220> FEATURE:
<221> NAME/KEY: VARIANT
<222> LOCATION: (17)..(18)
<223> OTHER INFORMATION: X = Y, F, Q, N, K, L, E or S
<220> FEATURE:
```

<221> NAME/KEY: VARIANT
<222> LOCATION: (18)..(19)
<223> OTHER INFORMATION: X = T, G, F, V, L, H, Y, Q, P or A
<220> FEATURE:
<221> NAME/KEY: VARIANT
<222> LOCATION: (19)..(20)
<223> OTHER INFORMATION: X = D, S, F, P, L, G or Y
<220> FEATURE:
<221> NAME/KEY: VARIANT
<222> LOCATION: (20)..(21)
<223> OTHER INFORMATION: X = T, G, F, E, H or Y
<220> FEATURE:
<221> NAME/KEY: VARIANT
<222> LOCATION: (21)..(22)
<223> OTHER INFORMATION: X = Q,T, P, F, W, N or G
<220> FEATURE:
<221> NAME/KEY: VARIANT
<222> LOCATION: (22)..(22)
<223> OTHER INFORMATION: X = Y, R, G, Q, S, P or F

<400> SEQUENCE: 87

```
Xaa Xaa Xaa Tyr Xaa Cys Ala Ser Xaa Xaa Xaa Xaa Xaa Xaa Xaa Xaa
1               5                   10                  15

Xaa Xaa Xaa Xaa Xaa Xaa
            20
```

<210> SEQ ID NO 88
<211> LENGTH: 10
<212> TYPE: PRT
<213> ORGANISM: Artificial Sequence
<220> FEATURE:
<223> OTHER INFORMATION: Synthetic Construct

<400> SEQUENCE: 88

```
Ser Leu Phe Trp His Ala Phe Asn Arg Leu
1               5                   10
```

<210> SEQ ID NO 89
<211> LENGTH: 11
<212> TYPE: PRT
<213> ORGANISM: Artificial Sequence
<220> FEATURE:
<223> OTHER INFORMATION: Synthetic Construct

<400> SEQUENCE: 89

```
Ser Ser Leu Phe Trp His Ala Phe Asn Arg Leu
1               5                   10
```

<210> SEQ ID NO 90
<211> LENGTH: 12
<212> TYPE: PRT
<213> ORGANISM: Artificial Sequence
<220> FEATURE:
<223> OTHER INFORMATION: Synthetic Construct

<400> SEQUENCE: 90

```
Ser Ser Leu Phe Trp His Ala Phe Asn Arg Leu Thr
1               5                   10
```

<210> SEQ ID NO 91
<211> LENGTH: 10
<212> TYPE: PRT
<213> ORGANISM: Artificial Sequence
<220> FEATURE:
<223> OTHER INFORMATION: Synthetic Construct

<400> SEQUENCE: 91

```
Leu Phe Trp His Ala Phe Asn Arg Leu Thr
1               5                   10
```

-continued

<210> SEQ ID NO 92
<211> LENGTH: 11
<212> TYPE: PRT
<213> ORGANISM: Artificial Sequence
<220> FEATURE:
<223> OTHER INFORMATION: Synthetic Construct

<400> SEQUENCE: 92

Leu Phe Trp His Ala Phe Asn Arg Leu Thr Pro
1               5                   10

<210> SEQ ID NO 93
<211> LENGTH: 11
<212> TYPE: PRT
<213> ORGANISM: Artificial Sequence
<220> FEATURE:
<223> OTHER INFORMATION: Synthetic Construct

<400> SEQUENCE: 93

Ser Leu Phe Trp His Ala Phe Asn Arg Leu Thr
1               5                   10

<210> SEQ ID NO 94
<211> LENGTH: 12
<212> TYPE: PRT
<213> ORGANISM: Artificial Sequence
<220> FEATURE:
<223> OTHER INFORMATION: Synthetic Construct

<400> SEQUENCE: 94

Leu Phe Trp His Ala Phe Asn Arg Leu Thr Pro Phe
1               5                   10

<210> SEQ ID NO 95
<211> LENGTH: 14
<212> TYPE: PRT
<213> ORGANISM: Artificial Sequence
<220> FEATURE:
<223> OTHER INFORMATION: Synthetic Construct

<400> SEQUENCE: 95

Leu Glu Lys Pro Phe Gln Ile Phe Cys Ala Glu Leu Trp Val
1               5                   10

<210> SEQ ID NO 96
<211> LENGTH: 15
<212> TYPE: PRT
<213> ORGANISM: Artificial Sequence
<220> FEATURE:
<223> OTHER INFORMATION: Synthetic Construct

<400> SEQUENCE: 96

Leu Glu Lys Pro Phe Gln Ile Phe Cys Ala Glu Leu Trp Val Arg
1               5                   10                  15

<210> SEQ ID NO 97
<211> LENGTH: 14
<212> TYPE: PRT
<213> ORGANISM: Artificial Sequence
<220> FEATURE:
<223> OTHER INFORMATION: Synthetic Construct

<400> SEQUENCE: 97

Leu Gly Thr Glu Phe Pro Leu Asn Tyr Ala Leu Asp Leu Asp
1               5                   10

<210> SEQ ID NO 98
<211> LENGTH: 15
<212> TYPE: PRT
<213> ORGANISM: Artificial Sequence
<220> FEATURE:
<223> OTHER INFORMATION: Synthetic Construct

<400> SEQUENCE: 98

Leu Gly Thr Glu Phe Pro Leu Asn Tyr Ala Leu Asp Leu Asp Val
1 5 10 15

<210> SEQ ID NO 99
<211> LENGTH: 16
<212> TYPE: PRT
<213> ORGANISM: Artificial Sequence
<220> FEATURE:
<223> OTHER INFORMATION: Synthetic Construct

<400> SEQUENCE: 99

Leu Gly Thr Glu Phe Pro Leu Asn Tyr Ala Leu Asp Leu Asp Val Gly
1 5 10 15

<210> SEQ ID NO 100
<211> LENGTH: 17
<212> TYPE: PRT
<213> ORGANISM: Artificial Sequence
<220> FEATURE:
<223> OTHER INFORMATION: Synthetic Construct

<400> SEQUENCE: 100

Leu Gly Thr Glu Phe Pro Leu Asn Tyr Ala Leu Asp Leu Asp Val Gly
1 5 10 15

Ser

<210> SEQ ID NO 101
<211> LENGTH: 18
<212> TYPE: PRT
<213> ORGANISM: Artificial Sequence
<220> FEATURE:
<223> OTHER INFORMATION: Synthetic Construct

<400> SEQUENCE: 101

Leu Gly Thr Glu Phe Pro Leu Asn Tyr Ala Leu Asp Leu Asp Val Gly
1 5 10 15

Ser Asn

<210> SEQ ID NO 102
<211> LENGTH: 19
<212> TYPE: PRT
<213> ORGANISM: Artificial Sequence
<220> FEATURE:
<223> OTHER INFORMATION: Synthetic Construct

<400> SEQUENCE: 102

Leu Gly Thr Glu Phe Pro Leu Asn Tyr Ala Leu Asp Leu Asp Val Gly
1 5 10 15

Ser Asn Asn

<210> SEQ ID NO 103
<211> LENGTH: 20
<212> TYPE: PRT
<213> ORGANISM: Artificial Sequence
<220> FEATURE:
<223> OTHER INFORMATION: Synthetic Construct

<400> SEQUENCE: 103

Leu Gly Thr Glu Phe Pro Leu Asn Tyr Ala Leu Asp Leu Asp Val Gly
1 5 10 15

Ser Asn Asn Val
20

<210> SEQ ID NO 104
<211> LENGTH: 21
<212> TYPE: PRT
<213> ORGANISM: Artificial Sequence
<220> FEATURE:
<223> OTHER INFORMATION: Synthetic Construct

<400> SEQUENCE: 104

Leu Gly Thr Glu Phe Pro Leu Asn Tyr Ala Leu Asp Leu Asp Val Gly
1 5 10 15

Ser Asn Asn Val Gln
20

<210> SEQ ID NO 105
<211> LENGTH: 17
<212> TYPE: PRT
<213> ORGANISM: Artificial Sequence
<220> FEATURE:
<223> OTHER INFORMATION: Synthetic Construct

<400> SEQUENCE: 105

Glu Asn Ser Pro Leu Gly Thr Glu Phe Pro Leu Asn Tyr Ala Leu Asp
1 5 10 15

Leu

<210> SEQ ID NO 106
<211> LENGTH: 16
<212> TYPE: PRT
<213> ORGANISM: Artificial Sequence
<220> FEATURE:
<223> OTHER INFORMATION: Synthetic Construct

<400> SEQUENCE: 106

Asn Ser Pro Leu Gly Thr Glu Phe Pro Leu Asn Tyr Ala Leu Asp Leu
1 5 10 15

<210> SEQ ID NO 107
<211> LENGTH: 15
<212> TYPE: PRT
<213> ORGANISM: Artificial Sequence
<220> FEATURE:
<223> OTHER INFORMATION: Synthetic Construct

<400> SEQUENCE: 107

Ser Pro Leu Gly Thr Glu Phe Pro Leu Asn Tyr Ala Leu Asp Leu
1 5 10 15

<210> SEQ ID NO 108
<211> LENGTH: 14
<212> TYPE: PRT
<213> ORGANISM: Artificial Sequence
<220> FEATURE:
<223> OTHER INFORMATION: Synthetic Construct

<400> SEQUENCE: 108

Pro Leu Gly Thr Glu Phe Pro Leu Asn Tyr Ala Leu Asp Leu
1 5 10

<210> SEQ ID NO 109
<211> LENGTH: 15
<212> TYPE: PRT
<213> ORGANISM: Artificial Sequence
<220> FEATURE:
<223> OTHER INFORMATION: Synthetic Construct

<400> SEQUENCE: 109

Pro Leu Gly Thr Glu Phe Pro Leu Asn Tyr Ala Leu Asp Leu Asp
1 5 10 15

<210> SEQ ID NO 110
<211> LENGTH: 16
<212> TYPE: PRT
<213> ORGANISM: Artificial Sequence
<220> FEATURE:
<223> OTHER INFORMATION: Synthetic Construct

<400> SEQUENCE: 110

Pro Leu Gly Thr Glu Phe Pro Leu Asn Tyr Ala Leu Asp Leu Asp Val
1 5 10 15

<210> SEQ ID NO 111
<211> LENGTH: 16
<212> TYPE: PRT
<213> ORGANISM: Artificial Sequence
<220> FEATURE:
<223> OTHER INFORMATION: Synthetic Construct

<400> SEQUENCE: 111

Ser Pro Leu Gly Thr Glu Phe Pro Leu Asn Tyr Ala Leu Asp Leu Asp
1 5 10 15

<210> SEQ ID NO 112
<211> LENGTH: 17
<212> TYPE: PRT
<213> ORGANISM: Artificial Sequence
<220> FEATURE:
<223> OTHER INFORMATION: Synthetic Construct

<400> SEQUENCE: 112

Ser Pro Leu Gly Thr Glu Phe Pro Leu Asn Tyr Ala Leu Asp Leu Asp
1 5 10 15

Val

<210> SEQ ID NO 113
<211> LENGTH: 18
<212> TYPE: PRT
<213> ORGANISM: Artificial Sequence
<220> FEATURE:
<223> OTHER INFORMATION: Synthetic Construct

<400> SEQUENCE: 113

Asn Ser Pro Leu Gly Thr Glu Phe Pro Leu Asn Tyr Ala Leu Asp Leu
1 5 10 15

Asp Val

<210> SEQ ID NO 114
<211> LENGTH: 19
<212> TYPE: PRT
<213> ORGANISM: Artificial Sequence
<220> FEATURE:
<223> OTHER INFORMATION: Synthetic Construct

<400> SEQUENCE: 114

Glu Asn Ser Pro Leu Gly Thr Glu Phe Pro Leu Asn Tyr Ala Leu Asp

-continued 1 5 10 15

Leu Asp Val

<210> SEQ ID NO 115
<211> LENGTH: 12
<212> TYPE: PRT
<213> ORGANISM: Artificial Sequence
<220> FEATURE:
<223> OTHER INFORMATION: Synthetic Construct

<400> SEQUENCE: 115

Asp Lys Asp Val Leu Arg Asn Val Trp Phe Gly Arg
1 5 10

<210> SEQ ID NO 116
<211> LENGTH: 12
<212> TYPE: PRT
<213> ORGANISM: Artificial Sequence
<220> FEATURE:
<223> OTHER INFORMATION: Synthetic Construct

<400> SEQUENCE: 116

Lys Asp Val Leu Arg Asn Val Trp Phe Gly Arg Ile
1 5 10

<210> SEQ ID NO 117
<211> LENGTH: 13
<212> TYPE: PRT
<213> ORGANISM: Artificial Sequence
<220> FEATURE:
<223> OTHER INFORMATION: Synthetic Construct

<400> SEQUENCE: 117

Asp Lys Asp Val Leu Arg Asn Val Trp Phe Gly Arg Ile
1 5 10

<210> SEQ ID NO 118
<211> LENGTH: 14
<212> TYPE: PRT
<213> ORGANISM: Artificial Sequence
<220> FEATURE:
<223> OTHER INFORMATION: Synthetic Construct

<400> SEQUENCE: 118

Asp Lys Asp Val Leu Arg Asn Val Trp Phe Gly Arg Ile Pro
1 5 10

<210> SEQ ID NO 119
<211> LENGTH: 14
<212> TYPE: PRT
<213> ORGANISM: Artificial Sequence
<220> FEATURE:
<223> OTHER INFORMATION: Synthetic Construct

<400> SEQUENCE: 119

Asp Asp Lys Asp Val Leu Arg Asn Val Trp Phe Gly Arg Ile
1 5 10

<210> SEQ ID NO 120
<211> LENGTH: 16
<212> TYPE: PRT
<213> ORGANISM: Artificial Sequence
<220> FEATURE:
<223> OTHER INFORMATION: Synthetic Construct

<400> SEQUENCE: 120

-continued

Asp Asp Lys Asp Val Leu Arg Asn Val Trp Phe Gly Arg Ile Pro Thr
1 5 10 15

<210> SEQ ID NO 121
<211> LENGTH: 17
<212> TYPE: PRT
<213> ORGANISM: Artificial Sequence
<220> FEATURE:
<223> OTHER INFORMATION: Synthetic Construct

<400> SEQUENCE: 121

Asp Asp Lys Asp Val Leu Arg Asn Val Trp Phe Gly Arg Ile Pro Thr
1 5 10 15

Cys

<210> SEQ ID NO 122
<211> LENGTH: 17
<212> TYPE: PRT
<213> ORGANISM: Artificial Sequence
<220> FEATURE:
<223> OTHER INFORMATION: Synthetic Construct

<400> SEQUENCE: 122

Thr Asp Asp Lys Asp Val Leu Arg Asn Val Trp Phe Gly Arg Ile Pro
1 5 10 15

Thr

<210> SEQ ID NO 123
<211> LENGTH: 11
<212> TYPE: PRT
<213> ORGANISM: Artificial Sequence
<220> FEATURE:
<223> OTHER INFORMATION: Synthetic Construct

<400> SEQUENCE: 123

Pro Phe Thr Asn Ser Glu Ser Ala Phe Tyr Ser
1 5 10

<210> SEQ ID NO 124
<211> LENGTH: 12
<212> TYPE: PRT
<213> ORGANISM: Artificial Sequence
<220> FEATURE:
<223> OTHER INFORMATION: Synthetic Construct

<400> SEQUENCE: 124

Pro Phe Thr Asn Ser Glu Ser Ala Phe Tyr Ser Ile
1 5 10

<210> SEQ ID NO 125
<211> LENGTH: 11
<212> TYPE: PRT
<213> ORGANISM: Artificial Sequence
<220> FEATURE:
<223> OTHER INFORMATION: Synthetic Construct

<400> SEQUENCE: 125

Arg Pro Phe Thr Asn Ser Glu Ser Ala Phe Tyr
1 5 10

<210> SEQ ID NO 126
<211> LENGTH: 12
<212> TYPE: PRT
<213> ORGANISM: Artificial Sequence
<220> FEATURE:
<223> OTHER INFORMATION: Synthetic Construct

<400> SEQUENCE: 126

Arg Pro Phe Thr Asn Ser Glu Ser Ala Phe Tyr Ser
1 5 10

<210> SEQ ID NO 127
<211> LENGTH: 13
<212> TYPE: PRT
<213> ORGANISM: Artificial Sequence
<220> FEATURE:
<223> OTHER INFORMATION: Synthetic Construct

<400> SEQUENCE: 127

Arg Pro Phe Thr Asn Ser Glu Ser Ala Phe Tyr Ser Ile
1 5 10

<210> SEQ ID NO 128
<211> LENGTH: 14
<212> TYPE: PRT
<213> ORGANISM: Artificial Sequence
<220> FEATURE:
<223> OTHER INFORMATION: Synthetic Construct

<400> SEQUENCE: 128

Arg Pro Phe Thr Asn Ser Glu Ser Ala Phe Tyr Ser Ile Val
1 5 10

<210> SEQ ID NO 129
<211> LENGTH: 12
<212> TYPE: PRT
<213> ORGANISM: Artificial Sequence
<220> FEATURE:
<223> OTHER INFORMATION: Synthetic Construct

<400> SEQUENCE: 129

Asp Arg Pro Phe Thr Asn Ser Glu Ser Ala Phe Tyr
1 5 10

<210> SEQ ID NO 130
<211> LENGTH: 14
<212> TYPE: PRT
<213> ORGANISM: Artificial Sequence
<220> FEATURE:
<223> OTHER INFORMATION: Synthetic Construct

<400> SEQUENCE: 130

Asp Arg Pro Phe Thr Asn Ser Glu Ser Ala Phe Tyr Ser Ile
1 5 10

<210> SEQ ID NO 131
<211> LENGTH: 15
<212> TYPE: PRT
<213> ORGANISM: Artificial Sequence
<220> FEATURE:
<223> OTHER INFORMATION: Synthetic Construct

<400> SEQUENCE: 131

Asp Arg Pro Phe Thr Asn Ser Glu Ser Ala Phe Tyr Ser Ile Val
1 5 10 15

<210> SEQ ID NO 132
<211> LENGTH: 11
<212> TYPE: PRT
<213> ORGANISM: Artificial Sequence
<220> FEATURE:
<223> OTHER INFORMATION: Synthetic Construct

<400> SEQUENCE: 132

Ile Ser Ser Gln Glu Asp Gly Ala Cys Val Leu
1 5 10

<210> SEQ ID NO 133
<211> LENGTH: 12
<212> TYPE: PRT
<213> ORGANISM: Artificial Sequence
<220> FEATURE:
<223> OTHER INFORMATION: Synthetic Construct

<400> SEQUENCE: 133

Ile Ser Ser Gln Glu Asp Gly Ala Cys Val Leu Leu
1 5 10

<210> SEQ ID NO 134
<211> LENGTH: 11
<212> TYPE: PRT
<213> ORGANISM: Artificial Sequence
<220> FEATURE:
<223> OTHER INFORMATION: Synthetic Construct

<400> SEQUENCE: 134

Asn Ile Ser Ser Gln Glu Asp Gly Ala Cys Val
1 5 10

<210> SEQ ID NO 135
<211> LENGTH: 12
<212> TYPE: PRT
<213> ORGANISM: Artificial Sequence
<220> FEATURE:
<223> OTHER INFORMATION: Synthetic Construct

<400> SEQUENCE: 135

Asn Ile Ser Ser Gln Glu Asp Gly Ala Cys Val Leu
1 5 10

<210> SEQ ID NO 136
<211> LENGTH: 13
<212> TYPE: PRT
<213> ORGANISM: Artificial Sequence
<220> FEATURE:
<223> OTHER INFORMATION: Synthetic Construct

<400> SEQUENCE: 136

Asn Ile Ser Ser Gln Glu Asp Gly Ala Cys Val Leu Leu
1 5 10

<210> SEQ ID NO 137
<211> LENGTH: 14
<212> TYPE: PRT
<213> ORGANISM: Artificial Sequence
<220> FEATURE:
<223> OTHER INFORMATION: Synthetic Construct

<400> SEQUENCE: 137

Asn Ile Ser Ser Gln Glu Asp Gly Ala Cys Val Leu Leu Arg
1 5 10

<210> SEQ ID NO 138
<211> LENGTH: 14
<212> TYPE: PRT
<213> ORGANISM: Artificial Sequence
<220> FEATURE:
<223> OTHER INFORMATION: Synthetic Construct

<400> SEQUENCE: 138

Met Asn Ile Ser Ser Gln Glu Asp Gly Ala Cys Val Leu Leu
1 5 10

<210> SEQ ID NO 139
<211> LENGTH: 27
<212> TYPE: PRT
<213> ORGANISM: Artificial Sequence
<220> FEATURE:
<223> OTHER INFORMATION: Synthetic Construct

<400> SEQUENCE: 139

Val Ser Thr Cys Ser Ser Leu Pro Thr Ala Ser Cys Ala Leu Asp Leu
1 5 10 15

Thr Val Leu Ala Glu Asn Ser His Gln Val Gly
20 25

<210> SEQ ID NO 140
<211> LENGTH: 27
<212> TYPE: PRT
<213> ORGANISM: Artificial Sequence
<220> FEATURE:
<223> OTHER INFORMATION: Synthetic Construct

<400> SEQUENCE: 140

Cys Val Ser Thr Cys Ser Ser Leu Pro Thr Ala Ser Cys Ala Leu Asp
1 5 10 15

Leu Thr Val Leu Ala Glu Asn Ser His Gln Val
20 25

<210> SEQ ID NO 141
<211> LENGTH: 28
<212> TYPE: PRT
<213> ORGANISM: Artificial Sequence
<220> FEATURE:
<223> OTHER INFORMATION: Synthetic Construct

<400> SEQUENCE: 141

Met Cys Val Ser Thr Cys Ser Ser Leu Pro Thr Ala Ser Cys Ala Leu
1 5 10 15

Asp Leu Thr Val Leu Ala Glu Asn Ser His Gln Val
20 25

<210> SEQ ID NO 142
<211> LENGTH: 29
<212> TYPE: PRT
<213> ORGANISM: Artificial Sequence
<220> FEATURE:
<223> OTHER INFORMATION: Synthetic Construct

<400> SEQUENCE: 142

Met Cys Val Ser Thr Cys Ser Ser Leu Pro Thr Ala Ser Cys Ala Leu
1 5 10 15

Asp Leu Thr Val Leu Ala Glu Asn Ser His Gln Val Gly
20 25

<210> SEQ ID NO 143
<211> LENGTH: 29
<212> TYPE: PRT
<213> ORGANISM: Artificial Sequence
<220> FEATURE:
<223> OTHER INFORMATION: Synthetic Construct

<400> SEQUENCE: 143

Ser Met Cys Val Ser Thr Cys Ser Ser Leu Pro Thr Ala Ser Cys Ala 1 5 10 15

Leu Asp Leu Thr Val Leu Ala Glu Asn Ser His Gln Val
20 25

<210> SEQ ID NO 144
<211> LENGTH: 30
<212> TYPE: PRT
<213> ORGANISM: Artificial Sequence
<220> FEATURE:
<223> OTHER INFORMATION: Synthetic Construct

<400> SEQUENCE: 144

Ser Met Cys Val Ser Thr Cys Ser Ser Leu Pro Thr Ala Ser Cys Ala
1 5 10 15

Leu Asp Leu Thr Val Leu Ala Glu Asn Ser His Gln Val Gly
20 25 30

<210> SEQ ID NO 145
<211> LENGTH: 62
<212> TYPE: PRT
<213> ORGANISM: Artificial Sequence
<220> FEATURE:
<223> OTHER INFORMATION: Synthetic Construct

<400> SEQUENCE: 145

Arg Val Pro Arg Ala Ala Glu Val Pro Gly Ala Gln Gly Gln Gln Gly
1 5 10 15

Pro Arg Gly Arg Glu Glu Ala Pro Arg Gly Val Arg Met Ala Val Pro
20 25 30

Leu Leu Arg Arg Met Glu Gly Ala Pro Ala Gly Pro Gly Gly Arg Thr
35 40 45

Ala Ala Cys Leu Ser Cys Thr Ser Arg Cys Leu Ser Arg Arg
50 55 60

<210> SEQ ID NO 146
<211> LENGTH: 63
<212> TYPE: PRT
<213> ORGANISM: Artificial Sequence
<220> FEATURE:
<223> OTHER INFORMATION: Synthetic Construct

<400> SEQUENCE: 146

Arg Arg Val Pro Arg Ala Ala Glu Val Pro Gly Ala Gln Gly Gln Gln
1 5 10 15

Gly Pro Arg Gly Arg Glu Glu Ala Pro Arg Gly Val Arg Met Ala Val
20 25 30

Pro Leu Leu Arg Arg Met Glu Gly Ala Pro Ala Gly Pro Gly Gly Arg
35 40 45

Thr Ala Ala Cys Leu Ser Cys Thr Ser Arg Cys Leu Ser Arg Arg
50 55 60

<210> SEQ ID NO 147
<211> LENGTH: 64
<212> TYPE: PRT
<213> ORGANISM: Artificial Sequence
<220> FEATURE:
<223> OTHER INFORMATION: Synthetic Construct

<400> SEQUENCE: 147

Glu Arg Arg Val Pro Arg Ala Ala Glu Val Pro Gly Ala Gln Gly Gln
1 5 10 15

Gln Gly Pro Arg Gly Arg Glu Glu Ala Pro Arg Gly Val Arg Met Ala

```
            20                  25                  30

Val Pro Leu Leu Arg Arg Met Glu Gly Ala Pro Ala Gly Pro Gly Gly
        35                  40                  45

Arg Thr Ala Ala Cys Leu Ser Cys Thr Ser Arg Cys Leu Ser Arg Arg
    50                  55                  60


<210> SEQ ID NO 148
<211> LENGTH: 65
<212> TYPE: PRT
<213> ORGANISM: Artificial Sequence
<220> FEATURE:
<223> OTHER INFORMATION: Synthetic Construct

<400> SEQUENCE: 148

Gln Glu Arg Arg Val Pro Arg Ala Ala Glu Val Pro Gly Ala Gln Gly
1               5                   10                  15

Gln Gln Gly Pro Arg Gly Arg Glu Glu Ala Pro Arg Gly Val Arg Met
            20                  25                  30

Ala Val Pro Leu Leu Arg Arg Met Glu Gly Ala Pro Ala Gly Pro Gly
        35                  40                  45

Gly Arg Thr Ala Ala Cys Leu Ser Cys Thr Ser Arg Cys Leu Ser Arg
    50                  55                  60

Arg
65


<210> SEQ ID NO 149
<211> LENGTH: 63
<212> TYPE: PRT
<213> ORGANISM: Artificial Sequence
<220> FEATURE:
<223> OTHER INFORMATION: Synthetic Construct

<400> SEQUENCE: 149

Arg Val Pro Arg Ala Ala Glu Val Pro Gly Ala Gln Gly Gln Gln Gly
1               5                   10                  15

Pro Arg Gly Arg Glu Glu Ala Pro Arg Gly Val Arg Met Ala Val Pro
            20                  25                  30

Leu Leu Arg Arg Met Glu Gly Ala Pro Ala Gly Pro Gly Gly Arg Thr
        35                  40                  45

Ala Ala Cys Leu Ser Cys Thr Ser Arg Cys Leu Ser Arg Arg Pro
    50                  55                  60


<210> SEQ ID NO 150
<211> LENGTH: 64
<212> TYPE: PRT
<213> ORGANISM: Artificial Sequence
<220> FEATURE:
<223> OTHER INFORMATION: Synthetic Construct

<400> SEQUENCE: 150

Arg Arg Val Pro Arg Ala Ala Glu Val Pro Gly Ala Gln Gly Gln Gln
1               5                   10                  15

Gly Pro Arg Gly Arg Glu Glu Ala Pro Arg Gly Val Arg Met Ala Val
            20                  25                  30

Pro Leu Leu Arg Arg Met Glu Gly Ala Pro Ala Gly Pro Gly Gly Arg
        35                  40                  45

Thr Ala Ala Cys Leu Ser Cys Thr Ser Arg Cys Leu Ser Arg Arg Pro
    50                  55                  60


<210> SEQ ID NO 151
```

<211> LENGTH: 65
<212> TYPE: PRT
<213> ORGANISM: Artificial Sequence
<220> FEATURE:
<223> OTHER INFORMATION: Synthetic Construct

<400> SEQUENCE: 151

Glu Arg Arg Val Pro Arg Ala Ala Glu Val Pro Gly Ala Gln Gly Gln
1 5 10 15

Gln Gly Pro Arg Gly Arg Glu Glu Ala Pro Arg Gly Val Arg Met Ala
20 25 30

Val Pro Leu Leu Arg Arg Met Glu Gly Ala Pro Ala Gly Pro Gly Gly
35 40 45

Arg Thr Ala Ala Cys Leu Ser Cys Thr Ser Arg Cys Leu Ser Arg Arg
50 55 60

Pro
65

<210> SEQ ID NO 152
<211> LENGTH: 66
<212> TYPE: PRT
<213> ORGANISM: Artificial Sequence
<220> FEATURE:
<223> OTHER INFORMATION: Synthetic Construct

<400> SEQUENCE: 152

Gln Glu Arg Arg Val Pro Arg Ala Ala Glu Val Pro Gly Ala Gln Gly
1 5 10 15

Gln Gln Gly Pro Arg Gly Arg Glu Glu Ala Pro Arg Gly Val Arg Met
20 25 30

Ala Val Pro Leu Leu Arg Arg Met Glu Gly Ala Pro Ala Gly Pro Gly
35 40 45

Gly Arg Thr Ala Ala Cys Leu Ser Cys Thr Ser Arg Cys Leu Ser Arg
50 55 60

Arg Pro
65

<210> SEQ ID NO 153
<211> LENGTH: 64
<212> TYPE: PRT
<213> ORGANISM: Artificial Sequence
<220> FEATURE:
<223> OTHER INFORMATION: Synthetic Construct

<400> SEQUENCE: 153

Arg Val Pro Arg Ala Ala Glu Val Pro Gly Ala Gln Gly Gln Gln Gly
1 5 10 15

Pro Arg Gly Arg Glu Glu Ala Pro Arg Gly Val Arg Met Ala Val Pro
20 25 30

Leu Leu Arg Arg Met Glu Gly Ala Pro Ala Gly Pro Gly Gly Arg Thr
35 40 45

Ala Ala Cys Leu Ser Cys Thr Ser Arg Cys Leu Ser Arg Arg Pro Trp
50 55 60

<210> SEQ ID NO 154
<211> LENGTH: 65
<212> TYPE: PRT
<213> ORGANISM: Artificial Sequence
<220> FEATURE:
<223> OTHER INFORMATION: Synthetic Construct

<400> SEQUENCE: 154

Arg Arg Val Pro Arg Ala Ala Glu Val Pro Gly Ala Gln Gly Gln Gln
1 5 10 15

Gly Pro Arg Gly Arg Glu Glu Ala Pro Arg Gly Val Arg Met Ala Val
20 25 30

Pro Leu Leu Arg Arg Met Glu Gly Ala Pro Ala Gly Pro Gly Gly Arg
35 40 45

Thr Ala Ala Cys Leu Ser Cys Thr Ser Arg Cys Leu Ser Arg Arg Pro
50 55 60

Trp
65

<210> SEQ ID NO 155
<211> LENGTH: 66
<212> TYPE: PRT
<213> ORGANISM: Artificial Sequence
<220> FEATURE:
<223> OTHER INFORMATION: Synthetic Construct

<400> SEQUENCE: 155

Glu Arg Arg Val Pro Arg Ala Ala Glu Val Pro Gly Ala Gln Gly Gln
1 5 10 15

Gln Gly Pro Arg Gly Arg Glu Glu Ala Pro Arg Gly Val Arg Met Ala
20 25 30

Val Pro Leu Leu Arg Arg Met Glu Gly Ala Pro Ala Gly Pro Gly Gly
35 40 45

Arg Thr Ala Ala Cys Leu Ser Cys Thr Ser Arg Cys Leu Ser Arg Arg
50 55 60

Pro Trp
65

<210> SEQ ID NO 156
<211> LENGTH: 67
<212> TYPE: PRT
<213> ORGANISM: Artificial Sequence
<220> FEATURE:
<223> OTHER INFORMATION: Synthetic Construct

<400> SEQUENCE: 156

Gln Glu Arg Arg Val Pro Arg Ala Ala Glu Val Pro Gly Ala Gln Gly
1 5 10 15

Gln Gln Gly Pro Arg Gly Arg Glu Glu Ala Pro Arg Gly Val Arg Met
20 25 30

Ala Val Pro Leu Leu Arg Arg Met Glu Gly Ala Pro Ala Gly Pro Gly
35 40 45

Gly Arg Thr Ala Ala Cys Leu Ser Cys Thr Ser Arg Cys Leu Ser Arg
50 55 60

Arg Pro Trp
65

<210> SEQ ID NO 157
<211> LENGTH: 65
<212> TYPE: PRT
<213> ORGANISM: Artificial Sequence
<220> FEATURE:
<223> OTHER INFORMATION: Synthetic Construct

<400> SEQUENCE: 157

Arg Val Pro Arg Ala Ala Glu Val Pro Gly Ala Gln Gly Gln Gln Gly
1 5 10 15

```
Pro Arg Gly Arg Glu Glu Ala Pro Arg Gly Val Arg Met Ala Val Pro
            20                  25                  30

Leu Leu Arg Arg Met Glu Gly Ala Pro Ala Gly Pro Gly Gly Arg Thr
        35                  40                  45

Ala Ala Cys Leu Ser Cys Thr Ser Arg Cys Leu Ser Arg Arg Pro Trp
    50                  55                  60

Lys
65


<210> SEQ ID NO 158
<211> LENGTH: 66
<212> TYPE: PRT
<213> ORGANISM: Artificial Sequence
<220> FEATURE:
<223> OTHER INFORMATION: Synthetic Construct

<400> SEQUENCE: 158

Arg Arg Val Pro Arg Ala Ala Glu Val Pro Gly Ala Gln Gly Gln Gln
1               5                   10                  15

Gly Pro Arg Gly Arg Glu Glu Ala Pro Arg Gly Val Arg Met Ala Val
            20                  25                  30

Pro Leu Leu Arg Arg Met Glu Gly Ala Pro Ala Gly Pro Gly Gly Arg
        35                  40                  45

Thr Ala Ala Cys Leu Ser Cys Thr Ser Arg Cys Leu Ser Arg Arg Pro
    50                  55                  60

Trp Lys
65


<210> SEQ ID NO 159
<211> LENGTH: 67
<212> TYPE: PRT
<213> ORGANISM: Artificial Sequence
<220> FEATURE:
<223> OTHER INFORMATION: Synthetic Construct

<400> SEQUENCE: 159

Glu Arg Arg Val Pro Arg Ala Ala Glu Val Pro Gly Ala Gln Gly Gln
1               5                   10                  15

Gln Gly Pro Arg Gly Arg Glu Glu Ala Pro Arg Gly Val Arg Met Ala
            20                  25                  30

Val Pro Leu Leu Arg Arg Met Glu Gly Ala Pro Ala Gly Pro Gly Gly
        35                  40                  45

Arg Thr Ala Ala Cys Leu Ser Cys Thr Ser Arg Cys Leu Ser Arg Arg
    50                  55                  60

Pro Trp Lys
65


<210> SEQ ID NO 160
<211> LENGTH: 68
<212> TYPE: PRT
<213> ORGANISM: Artificial Sequence
<220> FEATURE:
<223> OTHER INFORMATION: Synthetic Construct

<400> SEQUENCE: 160

Gln Glu Arg Arg Val Pro Arg Ala Ala Glu Val Pro Gly Ala Gln Gly
1               5                   10                  15

Gln Gln Gly Pro Arg Gly Arg Glu Glu Ala Pro Arg Gly Val Arg Met
            20                  25                  30

Ala Val Pro Leu Leu Arg Arg Met Glu Gly Ala Pro Ala Gly Pro Gly
```

35 40 45

Gly Arg Thr Ala Ala Cys Leu Ser Cys Thr Ser Arg Cys Leu Ser Arg
50 55 60

Arg Pro Trp Lys
65

<210> SEQ ID NO 161
<211> LENGTH: 66
<212> TYPE: PRT
<213> ORGANISM: Artificial Sequence
<220> FEATURE:
<223> OTHER INFORMATION: Synthetic Construct

<400> SEQUENCE: 161

Arg Val Pro Arg Ala Ala Glu Val Pro Gly Ala Gln Gly Gln Gln Gly
1 5 10 15

Pro Arg Gly Arg Glu Glu Ala Pro Arg Gly Val Arg Met Ala Val Pro
20 25 30

Leu Leu Arg Arg Met Glu Gly Ala Pro Ala Gly Pro Gly Gly Arg Thr
35 40 45

Ala Ala Cys Leu Ser Cys Thr Ser Arg Cys Leu Ser Arg Arg Pro Trp
50 55 60

Lys Arg
65

<210> SEQ ID NO 162
<211> LENGTH: 67
<212> TYPE: PRT
<213> ORGANISM: Artificial Sequence
<220> FEATURE:
<223> OTHER INFORMATION: Synthetic Construct

<400> SEQUENCE: 162

Arg Arg Val Pro Arg Ala Ala Glu Val Pro Gly Ala Gln Gly Gln Gln
1 5 10 15

Gly Pro Arg Gly Arg Glu Glu Ala Pro Arg Gly Val Arg Met Ala Val
20 25 30

Pro Leu Leu Arg Arg Met Glu Gly Ala Pro Ala Gly Pro Gly Gly Arg
35 40 45

Thr Ala Ala Cys Leu Ser Cys Thr Ser Arg Cys Leu Ser Arg Arg Pro
50 55 60

Trp Lys Arg
65

<210> SEQ ID NO 163
<211> LENGTH: 68
<212> TYPE: PRT
<213> ORGANISM: Artificial Sequence
<220> FEATURE:
<223> OTHER INFORMATION: Synthetic Construct

<400> SEQUENCE: 163

Glu Arg Arg Val Pro Arg Ala Ala Glu Val Pro Gly Ala Gln Gly Gln
1 5 10 15

Gln Gly Pro Arg Gly Arg Glu Glu Ala Pro Arg Gly Val Arg Met Ala
20 25 30

Val Pro Leu Leu Arg Arg Met Glu Gly Ala Pro Ala Gly Pro Gly Gly
35 40 45

Arg Thr Ala Ala Cys Leu Ser Cys Thr Ser Arg Cys Leu Ser Arg Arg
50 55 60

Pro Trp Lys Arg
65

<210> SEQ ID NO 164
<211> LENGTH: 22
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(2)
<223> OTHER INFORMATION: X = S or T
<220> FEATURE:
<221> NAME/KEY: VARIANT
<222> LOCATION: (2)..(3)
<223> OTHER INFORMATION: X = A or S
<220> FEATURE:
<221> NAME/KEY: VARIANT
<222> LOCATION: (3)..(4)
<223> OTHER INFORMATION: X = L, F, M, F or Q
<220> FEATURE:
<221> NAME/KEY: VARIANT
<222> LOCATION: (5)..(6)
<223> OTHER INFORMATION: X = L or F
<220> FEATURE:
<221> NAME/KEY: VARIANT
<222> LOCATION: (9)..(10)
<223> OTHER INFORMATION: X = S or R
<220> FEATURE:
<221> NAME/KEY: VARIANT
<222> LOCATION: (10)..(11)
<223> OTHER INFORMATION: X = T, P, D, Y, N, E or S
<220> FEATURE:
<221> NAME/KEY: VARIANT
<222> LOCATION: (11)..(12)
<223> OTHER INFORMATION: X = R, D, N or A
<220> FEATURE:
<221> NAME/KEY: VARIANT
<222> LOCATION: (12)..(13)
<223> OTHER INFORMATION: X = L, E, G, T, D, Q or P
<220> FEATURE:
<221> NAME/KEY: VARIANT
<222> LOCATION: (13)..(14)
<223> OTHER INFORMATION: X = A, D,S, G, R, W, N or L
<220> FEATURE:
<221> NAME/KEY: VARIANT
<222> LOCATION: (14)..(15)
<223> OTHER INFORMATION: X = G, S, D or E
<220> FEATURE:
<221> NAME/KEY: VARIANT
<222> LOCATION: (15)..(16)
<223> OTHER INFORMATION: X = Y, T, N, G, Q or A
<220> FEATURE:
<221> NAME/KEY: VARIANT
<222> LOCATION: (16)..(17)
<223> OTHER INFORMATION: X = T, D, E, M, N  or F
<220> FEATURE:
<221> NAME/KEY: VARIANT
<222> LOCATION: (17)..(18)
<223> OTHER INFORMATION: X = D, T, I, Y, A, N or F
<220> FEATURE:
<221> NAME/KEY: VARIANT
<222> LOCATION: (18)..(19)
<223> OTHER INFORMATION: X = T, Q, Y, F, I or G
<220> FEATURE:
<221> NAME/KEY: VARIANT
<222> LOCATION: (19)..(20)
<223> OTHER INFORMATION: X = Q, Y, F or D
<220> FEATURE:
<221> NAME/KEY: VARIANT
<222> LOCATION: (20)..(21)
<223> OTHER INFORMATION: X = Y, F, G or T
<220> FEATURE:
<221> NAME/KEY: VARIANT
<222> LOCATION: (21)..(22)
<223> OTHER INFORMATION: X = F, G, E or Q

```
<220> FEATURE:
<221> NAME/KEY: VARIANT
<222> LOCATION: (22)..(22)
<223> OTHER INFORMATION: X = G, P, E or R

<400> SEQUENCE: 164

Xaa Xaa Xaa Tyr Xaa Cys Ala Ser Xaa Xaa Xaa Xaa Xaa Xaa Xaa Xaa
1               5                   10                  15

Xaa Xaa Xaa Xaa Xaa Xaa
            20


<210> SEQ ID NO 165
<211> LENGTH: 25
<212> TYPE: PRT
<213> ORGANISM: Artificial Sequence
<220> FEATURE:
<223> OTHER INFORMATION: Synthetic Construct

<400> SEQUENCE: 165

Thr Ser Met Leu Ile Leu Ser Asn Leu Val Phe Leu Gly Gly Asn Glu
1               5                   10                  15

Val Gly Lys Thr Tyr Trp Asn Arg Ile
            20                  25


<210> SEQ ID NO 166
<211> LENGTH: 25
<212> TYPE: PRT
<213> ORGANISM: Artificial Sequence
<220> FEATURE:
<223> OTHER INFORMATION: Synthetic Construct

<400> SEQUENCE: 166

Thr Ser Met Leu Ile Leu Ser Asn Leu Val Phe Leu Glu Gly Asn Glu
1               5                   10                  15

Val Gly Lys Thr Tyr Trp Asn Arg Ile
            20                  25


<210> SEQ ID NO 167
<211> LENGTH: 25
<212> TYPE: PRT
<213> ORGANISM: Artificial Sequence
<220> FEATURE:
<223> OTHER INFORMATION: Synthetic Construct

<400> SEQUENCE: 167

Val Asp Thr Leu Ala Phe Asp Gly Arg Thr Phe Val Gly Tyr Leu Asn
1               5                   10                  15

Ala Val Thr Glu Ser Glu Lys Ala Leu
            20                  25


<210> SEQ ID NO 168
<211> LENGTH: 25
<212> TYPE: PRT
<213> ORGANISM: Artificial Sequence
<220> FEATURE:
<223> OTHER INFORMATION: Synthetic Construct

<400> SEQUENCE: 168

Lys Lys Ala Gly Gly Arg Ser Arg Gly Gly Leu His Ser Arg Gly Thr
1               5                   10                  15

Pro Pro Thr Ala Gln Glu Pro Pro Gly
            20                  25


<210> SEQ ID NO 169
```

<211> LENGTH: 25
<212> TYPE: PRT
<213> ORGANISM: Artificial Sequence
<220> FEATURE:
<223> OTHER INFORMATION: Synthetic Construct

<400> SEQUENCE: 169

```
Gly Ile Tyr Asp Ile His Val Gly Leu Arg Gly Val Leu Leu Leu Glu
1               5                   10                  15

Trp Glu Thr Glu Val Glu Met Asp Lys
            20                  25
```

<210> SEQ ID NO 170
<211> LENGTH: 25
<212> TYPE: PRT
<213> ORGANISM: Artificial Sequence
<220> FEATURE:
<223> OTHER INFORMATION: Synthetic Construct

<400> SEQUENCE: 170

```
Pro Leu Val Pro Glu Pro Arg Arg Leu Pro Val Gly Leu Leu Leu Arg
1               5                   10                  15

Ala Leu Ala Thr Cys His Ala Leu Ser
            20                  25
```

<210> SEQ ID NO 171
<211> LENGTH: 25
<212> TYPE: PRT
<213> ORGANISM: Artificial Sequence
<220> FEATURE:
<223> OTHER INFORMATION: Synthetic Construct

<400> SEQUENCE: 171

```
Glu Lys Met Gln Arg Lys Leu Arg Ala Ala Glu Val Lys Ile Lys Asp
1               5                   10                  15

Leu Gln Ser Glu Phe Gln Leu Glu Lys
            20                  25
```

<210> SEQ ID NO 172
<211> LENGTH: 25
<212> TYPE: PRT
<213> ORGANISM: Artificial Sequence
<220> FEATURE:
<223> OTHER INFORMATION: Synthetic Construct

<400> SEQUENCE: 172

```
Trp Asn Arg Ser Cys Val Ala Cys Gly Asn Asp Ile Val Leu Ile Lys
1               5                   10                  15

Leu Ser Arg Ser Ala Gln Leu Gly Asp
            20                  25
```

<210> SEQ ID NO 173
<211> LENGTH: 25
<212> TYPE: PRT
<213> ORGANISM: Artificial Sequence
<220> FEATURE:
<223> OTHER INFORMATION: Synthetic Construct

<400> SEQUENCE: 173

```
Gln Ser Phe Asn Pro Ser Ile Glu Val Gln Thr Leu Glu Glu Ala Ala
1               5                   10                  15

Ser Gly Ser Arg Asp Gln Ser Pro Ala
            20                  25
```

-continued

<210> SEQ ID NO 174
<211> LENGTH: 25
<212> TYPE: PRT
<213> ORGANISM: Artificial Sequence
<220> FEATURE:
<223> OTHER INFORMATION: Synthetic Construct

<400> SEQUENCE: 174

Cys Ala Pro Gly His Phe Gly Ala Asp Cys Arg Leu Arg Cys Gln Cys
1 5 10 15

Gln Asn Gly Gly Thr Cys Asp Arg Phe
20 25

<210> SEQ ID NO 175
<211> LENGTH: 25
<212> TYPE: PRT
<213> ORGANISM: Artificial Sequence
<220> FEATURE:
<223> OTHER INFORMATION: Synthetic Construct

<400> SEQUENCE: 175

Lys His Pro Leu Leu Arg Gly Pro Ala Ser Asn Tyr Leu Asn Ser Lys
1 5 10 15

Gly Asp Lys Lys Ser Ser Val Asn His
20 25

<210> SEQ ID NO 176
<211> LENGTH: 25
<212> TYPE: PRT
<213> ORGANISM: Artificial Sequence
<220> FEATURE:
<223> OTHER INFORMATION: Synthetic Construct

<400> SEQUENCE: 176

Gly Ser Gly Glu Lys Val Ala Gly Arg Val Ile Val Lys Val Cys Glu
1 5 10 15

Val Thr Arg Val Lys Ala Val Arg Ile
20 25

<210> SEQ ID NO 177
<211> LENGTH: 25
<212> TYPE: PRT
<213> ORGANISM: Artificial Sequence
<220> FEATURE:
<223> OTHER INFORMATION: Synthetic Construct

<400> SEQUENCE: 177

Pro Arg Thr Val Pro Val Ser Ser Asn Asp Thr Pro Leu Ser Ala Leu
1 5 10 15

Gln Glu Ala Ala Pro Leu Thr Ser Ser
20 25

<210> SEQ ID NO 178
<211> LENGTH: 25
<212> TYPE: PRT
<213> ORGANISM: Artificial Sequence
<220> FEATURE:
<223> OTHER INFORMATION: Synthetic Construct

<400> SEQUENCE: 178

Lys Ile Cys Gly Asp Lys Ser Ser Gly Ile His Tyr Arg Val Ile Thr
1 5 10 15

Cys Glu Gly Cys Lys Gly Phe Phe Arg
20 25

<210> SEQ ID NO 179
<211> LENGTH: 25
<212> TYPE: PRT
<213> ORGANISM: Artificial Sequence
<220> FEATURE:
<223> OTHER INFORMATION: Synthetic Construct

<400> SEQUENCE: 179

Val His Glu Arg His Glu Thr Thr Tyr Gly Gln Thr Glu Glu Ala Thr
1 5 10 15

Gly His Gly His Ser Gly His Gly Gln
20 25

<210> SEQ ID NO 180
<211> LENGTH: 25
<212> TYPE: PRT
<213> ORGANISM: Artificial Sequence
<220> FEATURE:
<223> OTHER INFORMATION: Synthetic Construct

<400> SEQUENCE: 180

Glu Gln Gln Val Gly Gln Pro Lys Asn Leu Glu Gln Lys Glu Lys Gln
1 5 10 15

Leu Glu Leu Pro Glu Gln Gln Glu Gly
20 25

<210> SEQ ID NO 181
<211> LENGTH: 25
<212> TYPE: PRT
<213> ORGANISM: Artificial Sequence
<220> FEATURE:
<223> OTHER INFORMATION: Synthetic Construct

<400> SEQUENCE: 181

Thr Pro Gly Gln Leu Gln Pro Ile Tyr Glu Asn Glu Leu Arg Glu Gln
1 5 10 15

Ser Val Ala Val His Gly Arg Gln Gln
20 25

<210> SEQ ID NO 182
<211> LENGTH: 25
<212> TYPE: PRT
<213> ORGANISM: Artificial Sequence
<220> FEATURE:
<223> OTHER INFORMATION: Synthetic Construct

<400> SEQUENCE: 182

Ser Glu Ser Asn Gly Gly Ser Ile Leu Thr Val Ser Gln Thr Pro Cys
1 5 10 15

Asp Pro Asp Leu Pro Tyr Ile Cys Thr
20 25

<210> SEQ ID NO 183
<211> LENGTH: 25
<212> TYPE: PRT
<213> ORGANISM: Artificial Sequence
<220> FEATURE:
<223> OTHER INFORMATION: Synthetic Construct

<400> SEQUENCE: 183

Trp Thr Ser Leu Ser Ser Thr Pro His Ala Ser Ile Met Ser Val Pro
1 5 10 15

His Thr Asn Gly Pro Ile Asn Pro Gly
20 25

<210> SEQ ID NO 184
<211> LENGTH: 25
<212> TYPE: PRT
<213> ORGANISM: Artificial Sequence
<220> FEATURE:
<223> OTHER INFORMATION: Synthetic Construct

<400> SEQUENCE: 184

Leu Gly Ile Phe Leu His Lys Ser Glu Leu Gly Cys Asn Thr Gly Ser
1 5 10 15

Thr Gly Lys Phe Glu Trp Gly Ser Lys
20 25

<210> SEQ ID NO 185
<211> LENGTH: 25
<212> TYPE: PRT
<213> ORGANISM: Artificial Sequence
<220> FEATURE:
<223> OTHER INFORMATION: Synthetic Construct

<400> SEQUENCE: 185

Leu Glu Glu Ala Tyr Thr Leu Val Gln His Gln Val Pro Glu Gly Leu
1 5 10 15

Ser Ala Leu Lys Glu Glu Cys Arg Ala
20 25

<210> SEQ ID NO 186
<211> LENGTH: 25
<212> TYPE: PRT
<213> ORGANISM: Artificial Sequence
<220> FEATURE:
<223> OTHER INFORMATION: Synthetic Construct

<400> SEQUENCE: 186

Gln Leu Phe Leu Lys Ala Gln Lys Ile Val His Lys Phe Phe Ser Leu
1 5 10 15

Ser Lys Arg Cys His Lys Gln Pro Leu
20 25

<210> SEQ ID NO 187
<211> LENGTH: 25
<212> TYPE: PRT
<213> ORGANISM: Artificial Sequence
<220> FEATURE:
<223> OTHER INFORMATION: Synthetic Construct

<400> SEQUENCE: 187

Gln Pro Val Leu Gln Gly Phe Glu Cys Ile Ala Asn Val Val Phe Asn
1 5 10 15

Gly Gln Ser Gly Gln Ile Leu Phe Arg
20 25

<210> SEQ ID NO 188
<211> LENGTH: 18
<212> TYPE: PRT
<213> ORGANISM: Artificial Sequence
<220> FEATURE:
<223> OTHER INFORMATION: Synthetic Construct

<400> SEQUENCE: 188

Asn Leu Asp Phe Lys Pro Glu Asp Gln Pro His Phe Tyr Ile Lys Asp
1 5 10 15

Glu Phe

<210> SEQ ID NO 189
<211> LENGTH: 25
<212> TYPE: PRT
<213> ORGANISM: Artificial Sequence
<220> FEATURE:
<223> OTHER INFORMATION: Synthetic Construct

<400> SEQUENCE: 189

```
Leu Pro Pro Arg Leu Ser Ser Ala Thr Pro Thr Ser Ile Gln Val Val
1               5                   10                  15

Trp Ser Thr Pro Ala Arg Asn Asn Ala
            20                  25
```

<210> SEQ ID NO 190
<211> LENGTH: 25
<212> TYPE: PRT
<213> ORGANISM: Artificial Sequence
<220> FEATURE:
<223> OTHER INFORMATION: Synthetic Construct

<400> SEQUENCE: 190

```
His Ala Val Glu Gly Gln Lys Lys Val Gln Asp Thr Ser Leu Ser Ser
1               5                   10                  15

Leu Ile Asn Tyr Gln Ala Arg Lys Val
            20                  25
```

<210> SEQ ID NO 191
<211> LENGTH: 25
<212> TYPE: PRT
<213> ORGANISM: Artificial Sequence
<220> FEATURE:
<223> OTHER INFORMATION: Synthetic Construct

<400> SEQUENCE: 191

```
Leu Met Asp Gly Arg Thr Val Leu Val Ile Ala His Cys Leu Ser Thr
1               5                   10                  15

Ile Lys Asn Ala Asn Met Val Ala Val
            20                  25
```

<210> SEQ ID NO 192
<211> LENGTH: 25
<212> TYPE: PRT
<213> ORGANISM: Artificial Sequence
<220> FEATURE:
<223> OTHER INFORMATION: Synthetic Construct

<400> SEQUENCE: 192

```
Ala Leu Gly Asn His Arg Val Ala His Ala Leu Cys Asn His Val Asp
1               5                   10                  15

Glu Pro Gln Leu Leu Tyr Ala Ile Glu
            20                  25
```

<210> SEQ ID NO 193
<211> LENGTH: 25
<212> TYPE: PRT
<213> ORGANISM: Artificial Sequence
<220> FEATURE:
<223> OTHER INFORMATION: Synthetic Construct

<400> SEQUENCE: 193

```
Tyr Ala Pro Phe Val Tyr Thr Tyr Leu Arg Pro Arg Phe Leu Arg Ser
1               5                   10                  15

Pro Thr Glu Asp Lys Val Leu Ala Val
```

20 25

<210> SEQ ID NO 194
<211> LENGTH: 25
<212> TYPE: PRT
<213> ORGANISM: Artificial Sequence
<220> FEATURE:
<223> OTHER INFORMATION: Synthetic Construct

<400> SEQUENCE: 194

Asn Asn Thr Phe Ala Ser Pro Asp Ser Asp Ser Asn Arg Met Tyr Asp
1 5 10 15

Lys Asn Leu Asn Cys Val Trp Ile Ile
20 25

<210> SEQ ID NO 195
<211> LENGTH: 25
<212> TYPE: PRT
<213> ORGANISM: Artificial Sequence
<220> FEATURE:
<223> OTHER INFORMATION: Synthetic Construct

<400> SEQUENCE: 195

Gln Arg Ala Arg Asp Glu Tyr Arg His His Ser Leu Cys Ala Ile Gln
1 5 10 15

Lys Gly Thr Val Ala Gly Leu Ser Ser
20 25

<210> SEQ ID NO 196
<211> LENGTH: 25
<212> TYPE: PRT
<213> ORGANISM: Artificial Sequence
<220> FEATURE:
<223> OTHER INFORMATION: Synthetic Construct

<400> SEQUENCE: 196

Ala Asn Ile Cys His Leu His Thr Gly Lys Cys Phe Arg Thr Thr Lys
1 5 10 15

Gly Ile Lys Gly Asp Gln Cys Gln Leu
20 25

<210> SEQ ID NO 197
<211> LENGTH: 25
<212> TYPE: PRT
<213> ORGANISM: Artificial Sequence
<220> FEATURE:
<223> OTHER INFORMATION: Synthetic Construct

<400> SEQUENCE: 197

Val Gln Leu Arg Arg Gly Pro Asp Gly Ser Ile Ser Trp Ile Ile Val
1 5 10 15

Glu Leu Gly Ala Ser Val Val Thr Val
20 25

<210> SEQ ID NO 198
<211> LENGTH: 25
<212> TYPE: PRT
<213> ORGANISM: Artificial Sequence
<220> FEATURE:
<223> OTHER INFORMATION: Synthetic Construct

<400> SEQUENCE: 198

Leu Cys Leu Met Val Asp Phe Ile Leu Ile Ala Val Phe Tyr Thr Leu
1 5 10 15

-continued

Ile Leu Lys Thr Val Leu Gly Ile Ala
20 25

<210> SEQ ID NO 199
<211> LENGTH: 25
<212> TYPE: PRT
<213> ORGANISM: Artificial Sequence
<220> FEATURE:
<223> OTHER INFORMATION: Synthetic Construct

<400> SEQUENCE: 199

Val Gly Gly Glu Ala Leu Gly Arg Leu Leu Val Val Phe Pro Trp Thr
1 5 10 15

Gln Arg Phe Phe Glu Ser Phe Gly Asp
20 25

<210> SEQ ID NO 200
<211> LENGTH: 25
<212> TYPE: PRT
<213> ORGANISM: Artificial Sequence
<220> FEATURE:
<223> OTHER INFORMATION: Synthetic Construct

<400> SEQUENCE: 200

Ile His Ile Leu Leu Ala Asn Leu Tyr Val Val Val Leu Pro Ala Leu
1 5 10 15

Asn Pro Val Ile Tyr Gly Val Arg Thr
20 25

<210> SEQ ID NO 201
<211> LENGTH: 25
<212> TYPE: PRT
<213> ORGANISM: Artificial Sequence
<220> FEATURE:
<223> OTHER INFORMATION: Synthetic Construct

<400> SEQUENCE: 201

Ile Gly Val Gly Leu Val Leu Leu Ile Val Leu Ile Ser Trp Lys Lys
1 5 10 15

Ile Cys Asn Lys Ser Ser Ser Ala Tyr
20 25

<210> SEQ ID NO 202
<211> LENGTH: 25
<212> TYPE: PRT
<213> ORGANISM: Artificial Sequence
<220> FEATURE:
<223> OTHER INFORMATION: Synthetic Construct

<400> SEQUENCE: 202

Pro Val Thr Ser Ser Glu Leu Thr Ala Val Asn Phe Ser Ser Phe His
1 5 10 15

Val Thr Pro Leu Lys Leu Met Val Ser
20 25

<210> SEQ ID NO 203
<211> LENGTH: 25
<212> TYPE: PRT
<213> ORGANISM: Artificial Sequence
<220> FEATURE:
<223> OTHER INFORMATION: Synthetic Construct

<400> SEQUENCE: 203

His Gly Thr Ile Leu Phe Leu Tyr Cys Val Pro Asn Phe Lys Asn Ser
1 5 10 15

```
Arg His Thr Val Lys Val Ala Ser Val
            20                  25


<210> SEQ ID NO 204
<211> LENGTH: 25
<212> TYPE: PRT
<213> ORGANISM: Artificial Sequence
<220> FEATURE:
<223> OTHER INFORMATION: Synthetic Construct

<400> SEQUENCE: 204

Val Thr Ile Asp Cys Gly His Ser Phe Cys Arg Pro Ser Phe Tyr Leu
1               5                   10                  15

Asn Trp Gln Asp Ile Pro Phe Leu Val
            20                  25


<210> SEQ ID NO 205
<211> LENGTH: 25
<212> TYPE: PRT
<213> ORGANISM: Artificial Sequence
<220> FEATURE:
<223> OTHER INFORMATION: Synthetic Construct

<400> SEQUENCE: 205

Leu Arg Cys Ser Glu Cys Gly Ala Arg Pro Leu Ala Phe Arg Ile Val
1               5                   10                  15

Gly Gly Gln Ser Val Ala Pro Gly Arg
            20                  25


<210> SEQ ID NO 206
<211> LENGTH: 25
<212> TYPE: PRT
<213> ORGANISM: Artificial Sequence
<220> FEATURE:
<223> OTHER INFORMATION: Synthetic Construct

<400> SEQUENCE: 206

Glu Glu Ile Leu Arg Leu His Gln Gln Lys Glu Gln Phe Leu Ser Ser
1               5                   10                  15

Leu Arg Glu Arg Leu Gln Lys Ala Ile
            20                  25


<210> SEQ ID NO 207
<211> LENGTH: 25
<212> TYPE: PRT
<213> ORGANISM: Artificial Sequence
<220> FEATURE:
<223> OTHER INFORMATION: Synthetic Construct

<400> SEQUENCE: 207

Pro Leu Leu Leu His Ala Val Leu Lys Arg Ser Pro Lys Ala Arg Ala
1               5                   10                  15

Gln Glu Ala Leu Asn Ala Met Ile Glu
            20                  25


<210> SEQ ID NO 208
<211> LENGTH: 25
<212> TYPE: PRT
<213> ORGANISM: Artificial Sequence
<220> FEATURE:
<223> OTHER INFORMATION: Synthetic Construct

<400> SEQUENCE: 208

Val Tyr Ala Glu Pro Thr Met Tyr Gly Glu Ile Leu Phe Pro Asn Tyr
```

```
1               5                   10                  15

Pro Gln Ala Tyr Pro Ser Glu Val Glu
            20                  25


<210> SEQ ID NO 209
<211> LENGTH: 25
<212> TYPE: PRT
<213> ORGANISM: Artificial Sequence
<220> FEATURE:
<223> OTHER INFORMATION: Synthetic Construct

<400> SEQUENCE: 209

Lys Leu Leu Tyr Phe Asn Leu Ser Ala Ile Lys Glu Gly Glu Gln Leu
1               5                   10                  15

Thr Leu Ala Gln Leu Gly Leu Asp Leu
            20                  25


<210> SEQ ID NO 210
<211> LENGTH: 25
<212> TYPE: PRT
<213> ORGANISM: Artificial Sequence
<220> FEATURE:
<223> OTHER INFORMATION: Synthetic Construct

<400> SEQUENCE: 210

Ala Ala Val Ala Gln Ser Glu Gln Gln Gly Glu Ala Thr Leu Ser Asp
1               5                   10                  15

Ala Arg Cys Lys Leu Ala Glu Leu Glu
            20                  25


<210> SEQ ID NO 211
<211> LENGTH: 25
<212> TYPE: PRT
<213> ORGANISM: Artificial Sequence
<220> FEATURE:
<223> OTHER INFORMATION: Synthetic Construct

<400> SEQUENCE: 211

Ser Arg Gln Trp Glu Cys Asp Gly Glu Asn Asp Cys Leu Asp Gln Ser
1               5                   10                  15

Asp Glu Ala Pro Lys Asn Pro His Cys
            20                  25


<210> SEQ ID NO 212
<211> LENGTH: 25
<212> TYPE: PRT
<213> ORGANISM: Artificial Sequence
<220> FEATURE:
<223> OTHER INFORMATION: Synthetic Construct

<400> SEQUENCE: 212

Arg Leu Gln Glu Val Ser Gly His Gln Arg Lys Arg Ile Ala Glu Val
1               5                   10                  15

Leu Asn Gly Leu Met Lys Asp Leu Ser
            20                  25


<210> SEQ ID NO 213
<211> LENGTH: 25
<212> TYPE: PRT
<213> ORGANISM: Artificial Sequence
<220> FEATURE:
<223> OTHER INFORMATION: Synthetic Construct

<400> SEQUENCE: 213
```

Ser Arg Ala Phe Asp Thr Leu Ala Lys Ala Leu Asn Ala Gly Glu Ser
1               5                   10                  15

Thr Ala Cys Gln Ser Ser Val Ala Gly
            20                  25

<210> SEQ ID NO 214
<211> LENGTH: 25
<212> TYPE: PRT
<213> ORGANISM: Artificial Sequence
<220> FEATURE:
<223> OTHER INFORMATION: Synthetic Construct

<400> SEQUENCE: 214

Glu Val Ala Pro Arg Gly Arg Ser Val Pro Pro Ser Leu Pro Glu Arg
1               5                   10                  15

Pro Ser Leu Ala Thr Ala Ser Gln Asn
            20                  25

<210> SEQ ID NO 215
<211> LENGTH: 25
<212> TYPE: PRT
<213> ORGANISM: Artificial Sequence
<220> FEATURE:
<223> OTHER INFORMATION: Synthetic Construct

<400> SEQUENCE: 215

Leu Lys Tyr Asp Val Gly Gly Gly Glu Arg Phe Asp Ala Leu Thr Asp
1               5                   10                  15

Leu Val Glu His Tyr Lys Lys Asn Pro
            20                  25

<210> SEQ ID NO 216
<211> LENGTH: 25
<212> TYPE: PRT
<213> ORGANISM: Artificial Sequence
<220> FEATURE:
<223> OTHER INFORMATION: Synthetic Construct

<400> SEQUENCE: 216

Phe Pro Ser Asp His Ala Thr Trp Gln Gly Asn Tyr Gly Phe Gly Thr
1               5                   10                  15

Gln Thr Ile Leu Asn Ser Met His Lys
            20                  25

<210> SEQ ID NO 217
<211> LENGTH: 25
<212> TYPE: PRT
<213> ORGANISM: Artificial Sequence
<220> FEATURE:
<223> OTHER INFORMATION: Synthetic Construct

<400> SEQUENCE: 217

Pro Pro Pro Pro Gly Leu Pro Ala Gly Ser Gly Pro Phe Ala Gly Pro
1               5                   10                  15

His His Ala Trp Asp Glu Glu Pro Lys
            20                  25

<210> SEQ ID NO 218
<211> LENGTH: 22
<212> TYPE: PRT
<213> ORGANISM: Artificial Sequence
<220> FEATURE:
<223> OTHER INFORMATION: Synthetic Construct

<400> SEQUENCE: 218

Ala Glu Pro Lys Arg Lys Ser Ser Leu Phe Trp His Ala Phe Asn Arg
1 5 10 15

Leu Thr Pro Phe Arg Lys
20

<210> SEQ ID NO 219
<211> LENGTH: 25
<212> TYPE: PRT
<213> ORGANISM: Artificial Sequence
<220> FEATURE:
<223> OTHER INFORMATION: Synthetic Construct

<400> SEQUENCE: 219

Pro Ser Gln Pro Lys Leu Pro Ile Ser Ser Gly Ala Glu Lys Ser Arg
1 5 10 15

Leu Ala Asn Ser Asn Glu Gly Ile Ser
20 25

<210> SEQ ID NO 220
<211> LENGTH: 25
<212> TYPE: PRT
<213> ORGANISM: Artificial Sequence
<220> FEATURE:
<223> OTHER INFORMATION: Synthetic Construct

<400> SEQUENCE: 220

Thr Pro Gly Pro Thr Gly Pro Ala Gly Gln Lys Gly Lys Pro Gly Ser
1 5 10 15

Asp Gly Ile Pro Gly Ser Ala Gly Glu
20 25

<210> SEQ ID NO 221
<211> LENGTH: 25
<212> TYPE: PRT
<213> ORGANISM: Artificial Sequence
<220> FEATURE:
<223> OTHER INFORMATION: Synthetic Construct

<400> SEQUENCE: 221

Arg His Gln Arg Glu Ile Val Glu Lys Ala Lys Glu Lys Phe Gln Glu
1 5 10 15

Met Leu Phe Glu His Ser Glu Leu Phe
20 25

<210> SEQ ID NO 222
<211> LENGTH: 25
<212> TYPE: PRT
<213> ORGANISM: Artificial Sequence
<220> FEATURE:
<223> OTHER INFORMATION: Synthetic Construct

<400> SEQUENCE: 222

Ala Ala Leu Ser Lys Cys Lys Arg Leu Glu Gln Glu Phe His His Val
1 5 10 15

Lys Glu Gln Asn Gln Thr Ser Ala Asn
20 25

<210> SEQ ID NO 223
<211> LENGTH: 25
<212> TYPE: PRT
<213> ORGANISM: Artificial Sequence
<220> FEATURE:
<223> OTHER INFORMATION: Synthetic Construct

<400> SEQUENCE: 223

Glu Glu Ala Glu Tyr Arg Arg Glu Leu Ala Leu Arg His Glu Leu Ile
1 5 10 15

Arg Gln Glu Lys Leu Glu Gln Leu Ala
20 25

<210> SEQ ID NO 224
<211> LENGTH: 25
<212> TYPE: PRT
<213> ORGANISM: Artificial Sequence
<220> FEATURE:
<223> OTHER INFORMATION: Synthetic Construct

<400> SEQUENCE: 224

Gly Gln Ala Ala Trp Asp Pro Thr Gly His Ser Met Thr Ala Ala Pro
1 5 10 15

Gln Gly Ala Ser Asn Ile Pro Val Phe
20 25

<210> SEQ ID NO 225
<211> LENGTH: 25
<212> TYPE: PRT
<213> ORGANISM: Artificial Sequence
<220> FEATURE:
<223> OTHER INFORMATION: Synthetic Construct

<400> SEQUENCE: 225

Tyr His Ile Leu Cys Ser Leu Tyr Ser Leu Gly Thr Arg Lys Asn Ile
1 5 10 15

Tyr Val Glu Arg Gln Arg Pro Ala Leu
20 25

<210> SEQ ID NO 226
<211> LENGTH: 25
<212> TYPE: PRT
<213> ORGANISM: Artificial Sequence
<220> FEATURE:
<223> OTHER INFORMATION: Synthetic Construct

<400> SEQUENCE: 226

Leu Leu Phe Asp His Leu Glu Pro Glu Glu Leu Ser Lys His Leu Thr
1 5 10 15

Tyr Leu Glu Phe Lys Ser Phe Arg Arg
20 25

<210> SEQ ID NO 227
<211> LENGTH: 19
<212> TYPE: PRT
<213> ORGANISM: Artificial Sequence
<220> FEATURE:
<223> OTHER INFORMATION: Synthetic Construct

<400> SEQUENCE: 227

Met Gly Thr Leu Gly Lys Glu Arg Glu Ala Pro Arg Lys Pro Ser His
1 5 10 15

Gly Cys Arg

<210> SEQ ID NO 228
<211> LENGTH: 25
<212> TYPE: PRT
<213> ORGANISM: Artificial Sequence
<220> FEATURE:
<223> OTHER INFORMATION: Synthetic Construct

<400> SEQUENCE: 228

Lys Lys Leu Pro Leu Leu Lys Gly His Pro Gln Cys Gln Glu His Gly
1 5 10 15

Glu Asn Leu Lys Leu Phe Ser Lys Pro
20 25

<210> SEQ ID NO 229
<211> LENGTH: 25
<212> TYPE: PRT
<213> ORGANISM: Artificial Sequence
<220> FEATURE:
<223> OTHER INFORMATION: Synthetic Construct

<400> SEQUENCE: 229

Phe Gly Glu Arg Gln Gly Met Leu Glu Glu Val Val Ser Pro Glu Ala
1 5 10 15

Gln Arg Phe Ile Asp Ala Ile Tyr Gln
20 25

<210> SEQ ID NO 230
<211> LENGTH: 25
<212> TYPE: PRT
<213> ORGANISM: Artificial Sequence
<220> FEATURE:
<223> OTHER INFORMATION: Synthetic Construct

<400> SEQUENCE: 230

Arg Arg Met Val Pro His Ile Gly Lys Cys Leu Arg Lys Met Tyr Thr
1 5 10 15

Thr His Glu Asp Val Glu Val Gly Arg
20 25

<210> SEQ ID NO 231
<211> LENGTH: 25
<212> TYPE: PRT
<213> ORGANISM: Artificial Sequence
<220> FEATURE:
<223> OTHER INFORMATION: Synthetic Construct

<400> SEQUENCE: 231

Tyr Gly Met Tyr Phe Cys Met Asn Ile Ser Ser Gln Glu Asp Gly Ala
1 5 10 15

Cys Val Leu Leu Arg Ala Leu Glu Pro
20 25

<210> SEQ ID NO 232
<211> LENGTH: 25
<212> TYPE: PRT
<213> ORGANISM: Artificial Sequence
<220> FEATURE:
<223> OTHER INFORMATION: Synthetic Construct

<400> SEQUENCE: 232

Val Ala Arg Ser Ala Ala Val Glu Thr Ala Ser Leu Phe Pro Ser Leu
1 5 10 15

Val Pro Ala Arg Gln Pro Thr Ile Ser
20 25

<210> SEQ ID NO 233
<211> LENGTH: 25
<212> TYPE: PRT
<213> ORGANISM: Artificial Sequence
<220> FEATURE:
<223> OTHER INFORMATION: Synthetic Construct

<400> SEQUENCE: 233

Val Ile Ile Pro Ala Lys Pro Pro Val Ser Phe Phe Phe Leu Arg Ser
1 5 10 15

Pro Val Leu Asp Leu Phe Gln Gly Gln
20 25

<210> SEQ ID NO 234
<211> LENGTH: 25
<212> TYPE: PRT
<213> ORGANISM: Artificial Sequence
<220> FEATURE:
<223> OTHER INFORMATION: Synthetic Construct

<400> SEQUENCE: 234

Pro Gln Ile Leu Lys Leu Leu Ile Lys Phe Val Asn Asn Thr Lys Ala
1 5 10 15

Pro Asp Trp Gln Gly Tyr Phe Tyr Thr
20 25

<210> SEQ ID NO 235
<211> LENGTH: 25
<212> TYPE: PRT
<213> ORGANISM: Artificial Sequence
<220> FEATURE:
<223> OTHER INFORMATION: Synthetic Construct

<400> SEQUENCE: 235

Pro Ala Pro Ser Leu Ser Leu Gly Val Pro Leu His Leu Leu Val Ser
1 5 10 15

Ser Val Phe Glu Leu Gln Gln Leu Val
20 25

<210> SEQ ID NO 236
<211> LENGTH: 25
<212> TYPE: PRT
<213> ORGANISM: Artificial Sequence
<220> FEATURE:
<223> OTHER INFORMATION: Synthetic Construct

<400> SEQUENCE: 236

Tyr Val Glu Cys Leu Leu Arg Arg Trp Leu Arg Ala Phe Ala Leu Leu
1 5 10 15

Thr Trp Ala Cys Leu Val Ala Leu Gly
20 25

<210> SEQ ID NO 237
<211> LENGTH: 25
<212> TYPE: PRT
<213> ORGANISM: Artificial Sequence
<220> FEATURE:
<223> OTHER INFORMATION: Synthetic Construct

<400> SEQUENCE: 237

Val Glu Cys Leu Leu Arg Arg Trp Leu Arg Ala Leu Thr Leu Leu Thr
1 5 10 15

Trp Ala Cys Leu Val Ala Leu Gly Tyr
20 25

<210> SEQ ID NO 238
<211> LENGTH: 25
<212> TYPE: PRT
<213> ORGANISM: Artificial Sequence
<220> FEATURE:

<223> OTHER INFORMATION: Synthetic Construct

<400> SEQUENCE: 238

Lys Leu Gln Gly Ala Glu His Gly Lys Lys Gly Arg Asp Leu Glu Tyr
1 5 10 15

Leu Tyr Leu Ser Val His Asp Glu Asp
20 25

<210> SEQ ID NO 239
<211> LENGTH: 25
<212> TYPE: PRT
<213> ORGANISM: Artificial Sequence
<220> FEATURE:
<223> OTHER INFORMATION: Synthetic Construct

<400> SEQUENCE: 239

Arg Ala Pro Gly Leu Arg Gly Leu Arg Leu Glu Cys Cys Gly Glu Lys
1 5 10 15

Pro Leu Phe Asp Ala Gly Arg Asp Val
20 25

<210> SEQ ID NO 240
<211> LENGTH: 25
<212> TYPE: PRT
<213> ORGANISM: Artificial Sequence
<220> FEATURE:
<223> OTHER INFORMATION: Synthetic Construct

<400> SEQUENCE: 240

Ile Arg Pro Lys Val Ser Ser Leu Leu Gly Lys Leu Ile Ser Tyr Thr
1 5 10 15

Asn Leu Thr Gln Gly Ala Lys Glu His
20 25

<210> SEQ ID NO 241
<211> LENGTH: 25
<212> TYPE: PRT
<213> ORGANISM: Artificial Sequence
<220> FEATURE:
<223> OTHER INFORMATION: Synthetic Construct

<400> SEQUENCE: 241

Asp His Ser Lys Val Arg Ile Tyr Thr Ser Pro Cys Ile Ile Gln Glu
1 5 10 15

His Gln Glu Thr Gln Lys Arg Leu Ser
20 25

<210> SEQ ID NO 242
<211> LENGTH: 25
<212> TYPE: PRT
<213> ORGANISM: Artificial Sequence
<220> FEATURE:
<223> OTHER INFORMATION: Synthetic Construct

<400> SEQUENCE: 242

Asp Asp Leu Glu Leu Thr Leu Ala Lys Val Glu Lys Lys Lys His Ala
1 5 10 15

Thr Glu Asn Lys Val Lys Asn Leu Thr
20 25

<210> SEQ ID NO 243
<211> LENGTH: 25
<212> TYPE: PRT
<213> ORGANISM: Artificial Sequence
<220> FEATURE:
<223> OTHER INFORMATION: Synthetic Construct

<400> SEQUENCE: 243

Ser Pro Glu Gly His Ile Ile Pro Gln Gly Ile Leu Gln Asn Ser Ile
1               5                   10                  15

Lys Ile Thr Asn Glu Pro Pro Thr Gly
            20                  25

<210> SEQ ID NO 244
<211> LENGTH: 25
<212> TYPE: PRT
<213> ORGANISM: Artificial Sequence
<220> FEATURE:
<223> OTHER INFORMATION: Synthetic Construct

<400> SEQUENCE: 244

Glu Asp Thr Gln Lys Leu Leu Ser Ile Leu Gly Ala Phe Glu Glu Asp
1               5                   10                  15

Asn Val Lys Leu Leu Lys Phe Trp Met
            20                  25

<210> SEQ ID NO 245
<211> LENGTH: 25
<212> TYPE: PRT
<213> ORGANISM: Artificial Sequence
<220> FEATURE:
<223> OTHER INFORMATION: Synthetic Construct

<400> SEQUENCE: 245

Leu Lys Leu Asn Arg Thr Gly Leu Cys Tyr Leu Pro Lys Glu Leu Ala
1               5                   10                  15

Ala Leu Gln Lys Leu Glu His Leu Ser
            20                  25

<210> SEQ ID NO 246
<211> LENGTH: 25
<212> TYPE: PRT
<213> ORGANISM: Artificial Sequence
<220> FEATURE:
<223> OTHER INFORMATION: Synthetic Construct

<400> SEQUENCE: 246

Thr Pro Ala Leu Thr Ser Arg Gly Leu Leu Glu Lys Asn Phe Gln Lys
1               5                   10                  15

Val Ala His Phe Ile His Arg Gly Ile
            20                  25

<210> SEQ ID NO 247
<211> LENGTH: 25
<212> TYPE: PRT
<213> ORGANISM: Artificial Sequence
<220> FEATURE:
<223> OTHER INFORMATION: Synthetic Construct

<400> SEQUENCE: 247

Arg Ile Tyr Thr Ala Leu Asp Pro Phe Arg Val Asn Ala Glu Phe Val
1               5                   10                  15

Leu Leu Thr Val Lys Glu Glu Lys Glu
            20                  25

<210> SEQ ID NO 248
<211> LENGTH: 25
<212> TYPE: PRT

<213> ORGANISM: Artificial Sequence
<220> FEATURE:
<223> OTHER INFORMATION: Synthetic Construct

<400> SEQUENCE: 248

Leu Arg Glu Lys Gly Phe Arg Ala Gln Arg Gly Arg Leu Arg Val Lys
1 5 10 15

Lys Leu His Pro Gln Gln Val Leu Asn
20 25

<210> SEQ ID NO 249
<211> LENGTH: 25
<212> TYPE: PRT
<213> ORGANISM: Artificial Sequence
<220> FEATURE:
<223> OTHER INFORMATION: Synthetic Construct

<400> SEQUENCE: 249

Gly Leu Phe Ser Gly Gly Glu Lys Gln Thr Met Gln Ser Leu Asn Asp
1 5 10 15

Arg Leu Ala Asn Tyr Leu Asp Lys Val
20 25

<210> SEQ ID NO 250
<211> LENGTH: 25
<212> TYPE: PRT
<213> ORGANISM: Artificial Sequence
<220> FEATURE:
<223> OTHER INFORMATION: Synthetic Construct

<400> SEQUENCE: 250

Leu Gln Ala Gln His Asn Leu Arg Asp Ser Leu Glu Lys Thr Leu Thr
1 5 10 15

Glu Ser Glu Ala Arg Tyr Ser Ser Gln
20 25

<210> SEQ ID NO 251
<211> LENGTH: 25
<212> TYPE: PRT
<213> ORGANISM: Artificial Sequence
<220> FEATURE:
<223> OTHER INFORMATION: Synthetic Construct

<400> SEQUENCE: 251

Pro Asp Thr Val Pro Leu Gly Thr Gly Thr Ser Ile Phe Ser Lys Gln
1 5 10 15

Val Gln Asn Lys Pro Lys Thr Gly Arg
20 25

<210> SEQ ID NO 252
<211> LENGTH: 25
<212> TYPE: PRT
<213> ORGANISM: Artificial Sequence
<220> FEATURE:
<223> OTHER INFORMATION: Synthetic Construct

<400> SEQUENCE: 252

Ser Ser Val Ser Tyr Ile Asp Ser Ala Val Ile Ser Ser Asp Thr Val
1 5 10 15

Pro Leu Gly Thr Gly Thr Ser Ile Leu
20 25

<210> SEQ ID NO 253
<211> LENGTH: 25

<212> TYPE: PRT
<213> ORGANISM: Artificial Sequence
<220> FEATURE:
<223> OTHER INFORMATION: Synthetic Construct

<400> SEQUENCE: 253

```
Gly Ser Gly Pro Lys Asp Leu Asp Leu Pro Pro Gly Phe Pro Gly Arg
1               5                   10                  15

Cys Thr Pro Lys Ser Ser Glu Pro Ala
            20                  25
```

<210> SEQ ID NO 254
<211> LENGTH: 25
<212> TYPE: PRT
<213> ORGANISM: Artificial Sequence
<220> FEATURE:
<223> OTHER INFORMATION: Synthetic Construct

<400> SEQUENCE: 254

```
Val Ala Ile Met Val Ser Gly Arg Leu Arg Cys Ile Cys Ser Ile Gln
1               5                   10                  15

His Leu Lys Ser Lys Phe Gly Lys Asp
            20                  25
```

<210> SEQ ID NO 255
<211> LENGTH: 25
<212> TYPE: PRT
<213> ORGANISM: Artificial Sequence
<220> FEATURE:
<223> OTHER INFORMATION: Synthetic Construct

<400> SEQUENCE: 255

```
Thr Leu Phe Arg Ala Gly His Asp Gln Val Val Val Gln Leu His Asp
1               5                   10                  15

Val Arg Asp Val Ser Val Glu Glu Glu
            20                  25
```

<210> SEQ ID NO 256
<211> LENGTH: 25
<212> TYPE: PRT
<213> ORGANISM: Artificial Sequence
<220> FEATURE:
<223> OTHER INFORMATION: Synthetic Construct

<400> SEQUENCE: 256

```
Ala Gln Ser Ala Pro Gly Ser Pro Leu Ser Ser Gln Ser Val Leu Ile
1               5                   10                  15

Thr Val Gln Arg Gln Leu Pro Gln Ala
            20                  25
```

<210> SEQ ID NO 257
<211> LENGTH: 25
<212> TYPE: PRT
<213> ORGANISM: Artificial Sequence
<220> FEATURE:
<223> OTHER INFORMATION: Synthetic Construct

<400> SEQUENCE: 257

```
Asn Gly Phe Gln Ile Gly Met Arg Leu Glu Gly Ile His Pro Arg His
1               5                   10                  15

Pro Ser Val Phe Cys Val Leu Ser Val
            20                  25
```

<210> SEQ ID NO 258

```
<211> LENGTH: 25
<212> TYPE: PRT
<213> ORGANISM: Artificial Sequence
<220> FEATURE:
<223> OTHER INFORMATION: Synthetic Construct

<400> SEQUENCE: 258

Met Cys Thr Thr Thr Val Thr Val Lys Ile Ile Asp Asn Asp Glu Gly
1               5                   10                  15

Pro Glu Cys His Pro Pro Val Lys Val
            20                  25


<210> SEQ ID NO 259
<211> LENGTH: 25
<212> TYPE: PRT
<213> ORGANISM: Artificial Sequence
<220> FEATURE:
<223> OTHER INFORMATION: Synthetic Construct

<400> SEQUENCE: 259

Gly Thr Leu Phe His Leu Thr Lys His Lys Thr Asp Lys Met Glu Asp
1               5                   10                  15

Lys Ile Ala Glu Val Arg Arg Lys Phe
            20                  25


<210> SEQ ID NO 260
<211> LENGTH: 25
<212> TYPE: PRT
<213> ORGANISM: Artificial Sequence
<220> FEATURE:
<223> OTHER INFORMATION: Synthetic Construct

<400> SEQUENCE: 260

Val Ser His Ser Lys Gly His Lys Ser Ser Arg Gln Lys Lys Arg Pro
1               5                   10                  15

Leu Cys Ala Gln Gly Asp Trp His Ser
            20                  25


<210> SEQ ID NO 261
<211> LENGTH: 25
<212> TYPE: PRT
<213> ORGANISM: Artificial Sequence
<220> FEATURE:
<223> OTHER INFORMATION: Synthetic Construct

<400> SEQUENCE: 261

Glu Met Asp Glu Asn Gln Ile Gln Met Ala Gly Asp Asn Val Asp Leu
1               5                   10                  15

Pro Glu Asp Leu Arg Lys Met Val Asp
            20                  25


<210> SEQ ID NO 262
<211> LENGTH: 25
<212> TYPE: PRT
<213> ORGANISM: Artificial Sequence
<220> FEATURE:
<223> OTHER INFORMATION: Synthetic Construct

<400> SEQUENCE: 262

Val Asp Thr Arg Ser Gly Val Pro Thr Thr Thr Ile Leu Pro Ser Ile
1               5                   10                  15

Pro Gly Val Val Thr Ser Gln Val Thr
            20                  25
```

<210> SEQ ID NO 263
<211> LENGTH: 25
<212> TYPE: PRT
<213> ORGANISM: Artificial Sequence
<220> FEATURE:
<223> OTHER INFORMATION: Synthetic Construct

<400> SEQUENCE: 263

```
Leu Arg Thr His Ala Gly Glu Lys Pro Tyr Glu Cys Ile Lys Cys Gly
1               5                   10                  15

Lys Ala Phe Thr Glu Arg Ser Tyr Leu
            20                  25
```

<210> SEQ ID NO 264
<211> LENGTH: 25
<212> TYPE: PRT
<213> ORGANISM: Artificial Sequence
<220> FEATURE:
<223> OTHER INFORMATION: Synthetic Construct

<400> SEQUENCE: 264

```
Cys Gln Pro Thr Val Asp Val Ser Gln Ala Asp Phe Leu Leu Glu Ser
1               5                   10                  15

Phe His Cys Thr Ser Pro Arg Lys Met
            20                  25
```

<210> SEQ ID NO 265
<211> LENGTH: 25
<212> TYPE: PRT
<213> ORGANISM: Artificial Sequence
<220> FEATURE:
<223> OTHER INFORMATION: Synthetic Construct

<400> SEQUENCE: 265

```
Lys Arg Ile His Thr Gly Glu Lys Pro Tyr Lys Cys Glu Glu Cys Gly
1               5                   10                  15

Lys Ala Phe Ser Asn Ser Ser Thr Leu
            20                  25
```

<210> SEQ ID NO 266
<211> LENGTH: 25
<212> TYPE: PRT
<213> ORGANISM: Artificial Sequence
<220> FEATURE:
<223> OTHER INFORMATION: Synthetic Construct

<400> SEQUENCE: 266

```
Leu Val Pro Pro Glu Ala Pro Gln Val Leu Gly Gly Leu Ser Val Ser
1               5                   10                  15

Leu Val Ala Gly Val Pro Ala Asn Leu
            20                  25
```

<210> SEQ ID NO 267
<211> LENGTH: 25
<212> TYPE: PRT
<213> ORGANISM: Artificial Sequence
<220> FEATURE:
<223> OTHER INFORMATION: Synthetic Construct

<400> SEQUENCE: 267

```
Thr Ala Pro His Thr Phe Glu Ser Val Glu Lys Pro Phe Lys Cys Glu
1               5                   10                  15

Glu Cys Gly Lys Ala Phe Ser Val His
            20                  25
```

<210> SEQ ID NO 268
<211> LENGTH: 25
<212> TYPE: PRT
<213> ORGANISM: Artificial Sequence
<220> FEATURE:
<223> OTHER INFORMATION: Synthetic Construct

<400> SEQUENCE: 268

Ala Thr Phe Asp Trp Leu Phe Lys Gly Tyr Gly Val Val Phe Ser Asn
1 5 10 15

Gly Glu Arg Ala Lys Gln Leu Arg Arg
20 25

<210> SEQ ID NO 269
<211> LENGTH: 25
<212> TYPE: PRT
<213> ORGANISM: Artificial Sequence
<220> FEATURE:
<223> OTHER INFORMATION: Synthetic Construct

<400> SEQUENCE: 269

Arg Tyr Ile Thr His Glu Ser Asp Asp Ala Arg Trp Glu Gln Phe Ala
1 5 10 15

Ala Glu His Pro Leu Pro Gly Ser Gly
20 25

<210> SEQ ID NO 270
<211> LENGTH: 25
<212> TYPE: PRT
<213> ORGANISM: Artificial Sequence
<220> FEATURE:
<223> OTHER INFORMATION: Synthetic Construct

<400> SEQUENCE: 270

Arg Trp Glu Gln Phe Ala Ala Glu His Pro Leu Pro Glu Ser Gly Leu
1 5 10 15

Pro Thr Asp Arg Asp Leu Gly Gly Ala
20 25

<210> SEQ ID NO 271
<211> LENGTH: 25
<212> TYPE: PRT
<213> ORGANISM: Artificial Sequence
<220> FEATURE:
<223> OTHER INFORMATION: Synthetic Construct

<400> SEQUENCE: 271

Lys Cys Arg Thr Gly Thr Ser Met Thr Ser Val Asn Leu Leu Thr Pro
1 5 10 15

Asn Gly Thr Leu Met Thr His Gly Ser
20 25

<210> SEQ ID NO 272
<211> LENGTH: 25
<212> TYPE: PRT
<213> ORGANISM: Artificial Sequence
<220> FEATURE:
<223> OTHER INFORMATION: Synthetic Construct

<400> SEQUENCE: 272

Ser Thr Gln Ala Pro Glu Ser Gln Glu Ser Gln Glu Lys Leu His Tyr
1 5 10 15

Ala Thr Leu Asn Phe Pro Gly Val Arg
20 25

```
<210> SEQ ID NO 273
<211> LENGTH: 25
<212> TYPE: PRT
<213> ORGANISM: Artificial Sequence
<220> FEATURE:
<223> OTHER INFORMATION: Synthetic Construct

<400> SEQUENCE: 273

Phe Pro Leu Gly Pro Ala Thr His Gly Gly Thr Tyr Lys Cys Phe Gly
1               5                   10                  15

Ser Phe His Asp Ser Pro Tyr Glu Trp
            20                  25


<210> SEQ ID NO 274
<211> LENGTH: 25
<212> TYPE: PRT
<213> ORGANISM: Artificial Sequence
<220> FEATURE:
<223> OTHER INFORMATION: Synthetic Construct

<400> SEQUENCE: 274

Cys Gly Asp Trp Glu Lys Lys Lys Pro Val Pro Val Ile Leu Gly Ser
1               5                   10                  15

Leu Leu Asn Arg Val Met Leu Pro Lys
            20                  25


<210> SEQ ID NO 275
<211> LENGTH: 25
<212> TYPE: PRT
<213> ORGANISM: Artificial Sequence
<220> FEATURE:
<223> OTHER INFORMATION: Synthetic Construct

<400> SEQUENCE: 275

Asn Asn Lys Lys Leu Thr Tyr Leu Asn Val Ser Cys Lys Gln Leu Asp
1               5                   10                  15

Thr Gly Val Pro Leu Leu Cys Glu Ala
            20                  25


<210> SEQ ID NO 276
<211> LENGTH: 25
<212> TYPE: PRT
<213> ORGANISM: Artificial Sequence
<220> FEATURE:
<223> OTHER INFORMATION: Synthetic Construct

<400> SEQUENCE: 276

Phe Phe Thr Gly Glu Lys Ser Ser Asp Ile Phe Val Lys Gly Trp Leu
1               5                   10                  15

Lys Gly Gln Gln Glu Asp Lys Gln Asp
            20                  25


<210> SEQ ID NO 277
<211> LENGTH: 25
<212> TYPE: PRT
<213> ORGANISM: Artificial Sequence
<220> FEATURE:
<223> OTHER INFORMATION: Synthetic Construct

<400> SEQUENCE: 277

Val Phe Ser Ser Ser Pro Leu His Leu Gln Pro Pro Ser Leu Gly Lys
1               5                   10                  15

Lys Ser Asp His Gly Asn Ala Phe Phe
```

20 25

<210> SEQ ID NO 278
<211> LENGTH: 25
<212> TYPE: PRT
<213> ORGANISM: Artificial Sequence
<220> FEATURE:
<223> OTHER INFORMATION: Synthetic Construct

<400> SEQUENCE: 278

Ala Pro Gly Asp Leu Gly Glu Gly Ala Glu Gly Leu Ser Gly Leu Leu
1 5 10 15

Thr Pro Pro Ser Gly Glu Gly Gly Ser
20 25

<210> SEQ ID NO 279
<211> LENGTH: 25
<212> TYPE: PRT
<213> ORGANISM: Artificial Sequence
<220> FEATURE:
<223> OTHER INFORMATION: Synthetic Construct

<400> SEQUENCE: 279

Met Tyr Phe Val Ile Ala Ser Leu Ser Glu Ile Asp Leu Met Tyr Gln
1 5 10 15

Tyr Ser Leu Lys Tyr Phe Lys Gln Leu
20 25

<210> SEQ ID NO 280
<211> LENGTH: 25
<212> TYPE: PRT
<213> ORGANISM: Artificial Sequence
<220> FEATURE:
<223> OTHER INFORMATION: Synthetic Construct

<400> SEQUENCE: 280

Lys Ser Pro Leu Met His Pro Asp Ala Leu Val Thr Val Phe Gln Gln
1 5 10 15

Ser Gly Ser Gln Ser Pro Asp Ser Arg
20 25

<210> SEQ ID NO 281
<211> LENGTH: 25
<212> TYPE: PRT
<213> ORGANISM: Artificial Sequence
<220> FEATURE:
<223> OTHER INFORMATION: Synthetic Construct

<400> SEQUENCE: 281

Gly Asp Val Gln Glu Met Pro Ala Pro Glu Ser Pro Leu Gly Arg Asp
1 5 10 15

Pro Ala Ala Asn Leu Ser Leu Ala Leu
20 25

<210> SEQ ID NO 282
<211> LENGTH: 25
<212> TYPE: PRT
<213> ORGANISM: Artificial Sequence
<220> FEATURE:
<223> OTHER INFORMATION: Synthetic Construct

<400> SEQUENCE: 282

Gly Gly Leu Lys Ser Ser Asp Lys Thr Glu Pro Ser Leu Gly Glu Ala
1 5 10 15

-continued

Ile Leu Pro Gln Lys Pro Ser Pro Asn
            20                  25

<210> SEQ ID NO 283
<211> LENGTH: 25
<212> TYPE: PRT
<213> ORGANISM: Artificial Sequence
<220> FEATURE:
<223> OTHER INFORMATION: Synthetic Construct

<400> SEQUENCE: 283

Arg Phe Val Cys Glu Ala Ile Leu Lys Val Tyr Glu Asp Gly Phe Val
1               5                   10                  15

Lys Pro Leu Thr Thr Ser Thr Asn Lys
            20                  25

<210> SEQ ID NO 284
<211> LENGTH: 18
<212> TYPE: PRT
<213> ORGANISM: Artificial Sequence
<220> FEATURE:
<223> OTHER INFORMATION: Synthetic Construct

<400> SEQUENCE: 284

Leu Lys Val Tyr Glu Glu Gly Phe Val Lys Pro Leu Lys Thr Ser Thr
1               5                   10                  15

Asn Lys

<210> SEQ ID NO 285
<211> LENGTH: 25
<212> TYPE: PRT
<213> ORGANISM: Artificial Sequence
<220> FEATURE:
<223> OTHER INFORMATION: Synthetic Construct

<400> SEQUENCE: 285

Phe Tyr Val Asn Thr Phe Gln Ser Ile Ala Gly Leu Gln Glu Asn Phe
1               5                   10                  15

His Lys Glu Met Ser Lys Leu Asn Gln
            20                  25

<210> SEQ ID NO 286
<211> LENGTH: 25
<212> TYPE: PRT
<213> ORGANISM: Artificial Sequence
<220> FEATURE:
<223> OTHER INFORMATION: Synthetic Construct

<400> SEQUENCE: 286

Gln Ala Ala Lys Gln Ala Ser Glu Val Glu Tyr Arg Val Lys His Arg
1               5                   10                  15

Lys Glu Gly Ser His Gly Leu Ser Met
            20                  25

<210> SEQ ID NO 287
<211> LENGTH: 25
<212> TYPE: PRT
<213> ORGANISM: Artificial Sequence
<220> FEATURE:
<223> OTHER INFORMATION: Synthetic Construct

<400> SEQUENCE: 287

Thr Val Ala Asp Arg Pro Asp Ile Lys Lys Ala Thr Leu Ala Ala Lys
1               5                   10                  15

-continued

Gln Ala Ser Glu Val Glu Tyr Arg Ala
20 25

<210> SEQ ID NO 288
<211> LENGTH: 25
<212> TYPE: PRT
<213> ORGANISM: Artificial Sequence
<220> FEATURE:
<223> OTHER INFORMATION: Synthetic Construct

<400> SEQUENCE: 288

Gln His Pro Asp Thr Val Lys Phe Thr Ser Val Pro Asn Ser Met Gly
1 5 10 15

Met Val Leu Ala Gln His Asn Thr Lys
20 25

<210> SEQ ID NO 289
<211> LENGTH: 25
<212> TYPE: PRT
<213> ORGANISM: Artificial Sequence
<220> FEATURE:
<223> OTHER INFORMATION: Synthetic Construct

<400> SEQUENCE: 289

Thr Val Arg Leu Leu Ser Ser Ser Gln Ile Ile Thr Leu Val Val Ser
1 5 10 15

Val Val Lys Glu Leu Ile Glu Asn Ser
20 25

<210> SEQ ID NO 290
<211> LENGTH: 25
<212> TYPE: PRT
<213> ORGANISM: Artificial Sequence
<220> FEATURE:
<223> OTHER INFORMATION: Synthetic Construct

<400> SEQUENCE: 290

Gly Thr Tyr Thr Phe Asn Gly Ser Gln Val Leu Ala Gln Ile Leu Gly
1 5 10 15

Leu Glu Lys Leu Leu Lys Gln Asn Ser
20 25

<210> SEQ ID NO 291
<211> LENGTH: 25
<212> TYPE: PRT
<213> ORGANISM: Artificial Sequence
<220> FEATURE:
<223> OTHER INFORMATION: Synthetic Construct

<400> SEQUENCE: 291

Leu Leu Ile Pro Pro Pro Leu Ser Asn Arg Gly Ile Met Gly Pro Val
1 5 10 15

Gln Ser Pro Cys Pro Ser Arg Asp Pro
20 25

<210> SEQ ID NO 292
<211> LENGTH: 25
<212> TYPE: PRT
<213> ORGANISM: Artificial Sequence
<220> FEATURE:
<223> OTHER INFORMATION: Synthetic Construct

<400> SEQUENCE: 292

Pro Leu Pro Glu Asp Pro Gly Asp Glu Glu Gly Gly Phe Ser Glu Pro
1 5 10 15

Glu Glu Met Ala Asp Leu Leu Pro Gly
20 25

<210> SEQ ID NO 293
<211> LENGTH: 25
<212> TYPE: PRT
<213> ORGANISM: Artificial Sequence
<220> FEATURE:
<223> OTHER INFORMATION: Synthetic Construct

<400> SEQUENCE: 293

Leu Gly Leu Phe Tyr Phe Ile Ala Gly Ile Val Phe Trp Leu His Ser
1 5 10 15

Ser Asn Lys Ser Ser Leu Tyr Ser Gly
20 25

<210> SEQ ID NO 294
<211> LENGTH: 25
<212> TYPE: PRT
<213> ORGANISM: Artificial Sequence
<220> FEATURE:
<223> OTHER INFORMATION: Synthetic Construct

<400> SEQUENCE: 294

Val Ser Val Val Ala Asn Thr Pro Ser Gly Pro Val Lys Ala Phe Asp
1 5 10 15

Phe Asp Glu Tyr Gln Pro Glu Met Leu
20 25

<210> SEQ ID NO 295
<211> LENGTH: 25
<212> TYPE: PRT
<213> ORGANISM: Artificial Sequence
<220> FEATURE:
<223> OTHER INFORMATION: Synthetic Construct

<400> SEQUENCE: 295

Pro Asp Glu Gly Tyr Tyr Gln Gly Gly Lys Phe Gln Leu Glu Thr Glu
1 5 10 15

Val Pro Asp Ala Tyr Asn Met Val Pro
20 25

<210> SEQ ID NO 296
<211> LENGTH: 25
<212> TYPE: PRT
<213> ORGANISM: Artificial Sequence
<220> FEATURE:
<223> OTHER INFORMATION: Synthetic Construct

<400> SEQUENCE: 296

Leu Thr His Glu Ile Met Cys Ser Arg Cys Cys Asp Gln Lys Ser Cys
1 5 10 15

Gly Asn Arg Asn Glu Thr Pro Ser Asp
20 25

<210> SEQ ID NO 297
<211> LENGTH: 25
<212> TYPE: PRT
<213> ORGANISM: Artificial Sequence
<220> FEATURE:
<223> OTHER INFORMATION: Synthetic Construct

<400> SEQUENCE: 297

Ile Ser Glu Asp Ser Asn His Gly Ser Ala Pro Leu Phe Leu Ser Ser 1 5 10 15

Asp Pro Gly Lys Val Asn His Lys Thr
20 25

<210> SEQ ID NO 298
<211> LENGTH: 25
<212> TYPE: PRT
<213> ORGANISM: Artificial Sequence
<220> FEATURE:
<223> OTHER INFORMATION: Synthetic Construct

<400> SEQUENCE: 298

Leu Ser Lys Pro Ser Glu Tyr Ser Asp Leu Lys Trp Lys Tyr Gln Arg
1 5 10 15

Ala Ser Ser Ser Ser Pro Leu Asp Tyr
20 25

<210> SEQ ID NO 299
<211> LENGTH: 25
<212> TYPE: PRT
<213> ORGANISM: Artificial Sequence
<220> FEATURE:
<223> OTHER INFORMATION: Synthetic Construct

<400> SEQUENCE: 299

Ile Ser Lys Glu Glu Phe Val Ile His Thr Ile Phe Ser Pro Asn Gly
1 5 10 15

Met Asn Leu Tyr Lys Asn Asn His Ser
20 25

<210> SEQ ID NO 300
<211> LENGTH: 25
<212> TYPE: PRT
<213> ORGANISM: Artificial Sequence
<220> FEATURE:
<223> OTHER INFORMATION: Synthetic Construct

<400> SEQUENCE: 300

Arg Leu Lys Ala Ser Leu Asp Arg Pro Phe Thr Asn Ser Glu Ser Ala
1 5 10 15

Phe Tyr Ser Ile Val Gly Leu Ser Ser
20 25

<210> SEQ ID NO 301
<211> LENGTH: 25
<212> TYPE: PRT
<213> ORGANISM: Artificial Sequence
<220> FEATURE:
<223> OTHER INFORMATION: Synthetic Construct

<400> SEQUENCE: 301

Asp Asn Phe Gln Gln Trp Arg Thr Pro His Gln Lys Leu Thr Glu Gln
1 5 10 15

Pro Gln Gln Ala Lys Lys Leu Gly Tyr
20 25

<210> SEQ ID NO 302
<211> LENGTH: 25
<212> TYPE: PRT
<213> ORGANISM: Artificial Sequence
<220> FEATURE:
<223> OTHER INFORMATION: Synthetic Construct

<400> SEQUENCE: 302

His Gly Cys Arg Lys Asn Phe Phe Leu Ser Lys Ile Trp Ser His Val
1 5 10 15

Ala Thr Cys Ser Lys Tyr Gln Asn Tyr
20 25

<210> SEQ ID NO 303
<211> LENGTH: 25
<212> TYPE: PRT
<213> ORGANISM: Artificial Sequence
<220> FEATURE:
<223> OTHER INFORMATION: Synthetic Construct

<400> SEQUENCE: 303

Leu Val Met Val Ala Leu Gln His Phe Ala Gly Arg Ser Tyr Leu Gln
1 5 10 15

Ile Ile Arg Phe Leu Leu Leu Phe Ser
20 25

<210> SEQ ID NO 304
<211> LENGTH: 25
<212> TYPE: PRT
<213> ORGANISM: Artificial Sequence
<220> FEATURE:
<223> OTHER INFORMATION: Synthetic Construct

<400> SEQUENCE: 304

Pro Phe Lys Cys Ser Met Cys Lys Tyr Ala Ser Val Lys Val Lys Pro
1 5 10 15

Phe Leu Asp Leu Lys Leu His Gly Ile
20 25

<210> SEQ ID NO 305
<211> LENGTH: 25
<212> TYPE: PRT
<213> ORGANISM: Artificial Sequence
<220> FEATURE:
<223> OTHER INFORMATION: Synthetic Construct

<400> SEQUENCE: 305

Pro Phe Lys Cys Ser Met Cys Lys Tyr Ala Ser Val Lys Glu Arg His
1 5 10 15

Met Thr Ala His Ile Arg Thr His Thr
20 25

<210> SEQ ID NO 306
<211> LENGTH: 25
<212> TYPE: PRT
<213> ORGANISM: Artificial Sequence
<220> FEATURE:
<223> OTHER INFORMATION: Synthetic Construct

<400> SEQUENCE: 306

Lys Ala Gly Tyr Asp Gly Glu Ser Ile Gly Asn Cys Ser Phe Ser Gln
1 5 10 15

Arg Leu Phe Met Ile Leu Trp Leu Lys
20 25

<210> SEQ ID NO 307
<211> LENGTH: 15
<212> TYPE: PRT
<213> ORGANISM: Artificial Sequence
<220> FEATURE:
<223> OTHER INFORMATION: Synthetic Construct

<400> SEQUENCE: 307

-continued

Trp Lys Lys Arg Trp Asp Lys Phe Ile Ala Asp Val Asp Thr Lys
1 5 10 15

<210> SEQ ID NO 308
<211> LENGTH: 25
<212> TYPE: PRT
<213> ORGANISM: Artificial Sequence
<220> FEATURE:
<223> OTHER INFORMATION: Synthetic Construct

<400> SEQUENCE: 308

Gln Val Ala Gln Met Arg Ile Glu Tyr Leu Glu Gln Phe Thr Val Asp
1 5 10 15

Arg Ala Ile Val Ser Arg Gln Glu Ala
20 25

<210> SEQ ID NO 309
<211> LENGTH: 25
<212> TYPE: PRT
<213> ORGANISM: Artificial Sequence
<220> FEATURE:
<223> OTHER INFORMATION: Synthetic Construct

<400> SEQUENCE: 309

Leu Ala Ala Val Arg Gln Thr Leu Gln Thr Asp Leu Lys Thr Ser Ile
1 5 10 15

Arg Arg Ile Ala Asp Leu Gln Ala Ala
20 25

<210> SEQ ID NO 310
<211> LENGTH: 25
<212> TYPE: PRT
<213> ORGANISM: Artificial Sequence
<220> FEATURE:
<223> OTHER INFORMATION: Synthetic Construct

<400> SEQUENCE: 310

Gly Val Val Leu Ser Pro Asn Trp Pro Glu Pro Tyr Leu Glu Gly Glu
1 5 10 15

Asp Cys Ile Trp Lys Ile His Val Gly
20 25

<210> SEQ ID NO 311
<211> LENGTH: 25
<212> TYPE: PRT
<213> ORGANISM: Artificial Sequence
<220> FEATURE:
<223> OTHER INFORMATION: Synthetic Construct

<400> SEQUENCE: 311

Val Thr Lys Asn Tyr Asp Arg Leu Gln Cys Glu Ser Ser Arg Glu Phe
1 5 10 15

Ala Gly Tyr Pro Leu Leu Val Pro Arg
20 25

<210> SEQ ID NO 312
<211> LENGTH: 25
<212> TYPE: PRT
<213> ORGANISM: Artificial Sequence
<220> FEATURE:
<223> OTHER INFORMATION: Synthetic Construct

<400> SEQUENCE: 312

Ile Lys Leu Asn Asp Thr Leu Leu Leu Gly Pro Asp Ser Leu Gly Asn 1 5 10 15

Phe Leu Ser Ile Ala Val Lys Ser Ile
20 25

<210> SEQ ID NO 313
<211> LENGTH: 25
<212> TYPE: PRT
<213> ORGANISM: Artificial Sequence
<220> FEATURE:
<223> OTHER INFORMATION: Synthetic Construct

<400> SEQUENCE: 313

Gly Pro Pro Thr Val Ser Pro Val Leu Val Pro Lys Asn Gln Leu Leu
1 5 10 15

Ser Glu His Leu Gln Lys Asp Glu Gln
20 25

<210> SEQ ID NO 314
<211> LENGTH: 25
<212> TYPE: PRT
<213> ORGANISM: Artificial Sequence
<220> FEATURE:
<223> OTHER INFORMATION: Synthetic Construct

<400> SEQUENCE: 314

Val Ser Asp Gly Glu Asn Val Leu Val Ser Asp Phe Trp Ser Lys Asp
1 5 10 15

Glu Val Val Asp Ala Leu Val Cys Ser
20 25

<210> SEQ ID NO 315
<211> LENGTH: 25
<212> TYPE: PRT
<213> ORGANISM: Artificial Sequence
<220> FEATURE:
<223> OTHER INFORMATION: Synthetic Construct

<400> SEQUENCE: 315

Asp Arg Leu Asn Glu Ile Lys Gly His Leu Glu Ile Gly Leu Leu Glu
1 5 10 15

Lys His Phe Leu Gln Glu Glu Leu Arg
20 25

<210> SEQ ID NO 316
<211> LENGTH: 25
<212> TYPE: PRT
<213> ORGANISM: Artificial Sequence
<220> FEATURE:
<223> OTHER INFORMATION: Synthetic Construct

<400> SEQUENCE: 316

Thr Leu Val Ala Leu Asp Glu Ala Leu Asp Asn Tyr Ile Ile Thr Phe
1 5 10 15

Leu Ile Arg Gly Val Ala Ile Gly Gln
20 25

<210> SEQ ID NO 317
<211> LENGTH: 25
<212> TYPE: PRT
<213> ORGANISM: Artificial Sequence
<220> FEATURE:
<223> OTHER INFORMATION: Synthetic Construct

<400> SEQUENCE: 317

-continued

```
Ile Val Ala Ser Gln Leu Asp Asn Leu Phe Pro Pro Lys Pro Lys Pro
1               5                   10                  15

Glu Glu Pro Pro Ala Arg Gly Gly Leu
            20                  25


<210> SEQ ID NO 318
<211> LENGTH: 25
<212> TYPE: PRT
<213> ORGANISM: Artificial Sequence
<220> FEATURE:
<223> OTHER INFORMATION: Synthetic Construct

<400> SEQUENCE: 318

Glu Ile Tyr Asn Trp Phe Thr Arg Met Phe Ala Tyr Leu Arg Arg Asn
1               5                   10                  15

Ala Ala Thr Trp Lys Gly Ala Ile Arg
            20                  25


<210> SEQ ID NO 319
<211> LENGTH: 25
<212> TYPE: PRT
<213> ORGANISM: Artificial Sequence
<220> FEATURE:
<223> OTHER INFORMATION: Synthetic Construct

<400> SEQUENCE: 319

Lys Pro Tyr Pro Glu Val Ser Gln Ser Glu Pro Ala Ser Leu Glu Thr
1               5                   10                  15

Arg Gly Ile Pro Phe Ile Pro Met Ile
            20                  25


<210> SEQ ID NO 320
<211> LENGTH: 25
<212> TYPE: PRT
<213> ORGANISM: Artificial Sequence
<220> FEATURE:
<223> OTHER INFORMATION: Synthetic Construct

<400> SEQUENCE: 320

Thr Lys Val Ala Leu Phe Asn Arg Leu Arg Ser Gln Arg Val Ser Thr
1               5                   10                  15

Arg Tyr Leu His Val Glu Gly Gly Asn
            20                  25


<210> SEQ ID NO 321
<211> LENGTH: 25
<212> TYPE: PRT
<213> ORGANISM: Artificial Sequence
<220> FEATURE:
<223> OTHER INFORMATION: Synthetic Construct

<400> SEQUENCE: 321

Ser Ser Leu Ser Glu Asp Leu Glu Ser Thr Arg Gln Lys Ile Gln Lys
1               5                   10                  15

Val Asn Glu Ser Val Val Ser Ile Ala
            20                  25


<210> SEQ ID NO 322
<211> LENGTH: 25
<212> TYPE: PRT
<213> ORGANISM: Artificial Sequence
<220> FEATURE:
<223> OTHER INFORMATION: Synthetic Construct

<400> SEQUENCE: 322
```

```
Arg Arg Gln Ser Asp Asp Asp Lys Phe Cys Gly Leu Ser Lys Lys Gln
1               5                   10                  15

Asp Arg Ala Arg Ile Glu Ser Pro Ala
            20                  25


<210> SEQ ID NO 323
<211> LENGTH: 25
<212> TYPE: PRT
<213> ORGANISM: Artificial Sequence
<220> FEATURE:
<223> OTHER INFORMATION: Synthetic Construct

<400> SEQUENCE: 323

His Trp Val Phe Gly Glu Ala Met Cys Lys Leu Asn Leu Phe Val Gln
1               5                   10                  15

Cys Val Ser Ile Thr Val Ser Ile Phe
            20                  25


<210> SEQ ID NO 324
<211> LENGTH: 25
<212> TYPE: PRT
<213> ORGANISM: Artificial Sequence
<220> FEATURE:
<223> OTHER INFORMATION: Synthetic Construct

<400> SEQUENCE: 324

Ile Gly Phe Gly Leu Glu Gln Asn Asn Thr Val Lys Arg Lys Val Pro
1               5                   10                  15

Leu Gln Phe Ser Gly Gln Asn Glu Lys
            20                  25


<210> SEQ ID NO 325
<211> LENGTH: 25
<212> TYPE: PRT
<213> ORGANISM: Artificial Sequence
<220> FEATURE:
<223> OTHER INFORMATION: Synthetic Construct

<400> SEQUENCE: 325

Gly Lys Asn Cys Asp Lys Phe Gly Ile Val Val His Lys Leu Gly His
1               5                   10                  15

Val Ile Gly Phe Trp His Glu His Thr
            20                  25


<210> SEQ ID NO 326
<211> LENGTH: 25
<212> TYPE: PRT
<213> ORGANISM: Artificial Sequence
<220> FEATURE:
<223> OTHER INFORMATION: Synthetic Construct

<400> SEQUENCE: 326

Ile Arg Cys Asn Glu Ala Gly Asp Ile Glu Ala Lys Asn Lys Thr Ala
1               5                   10                  15

Gly Glu Glu Glu Met Ile Lys Ile Arg
            20                  25


<210> SEQ ID NO 327
<211> LENGTH: 25
<212> TYPE: PRT
<213> ORGANISM: Artificial Sequence
<220> FEATURE:
<223> OTHER INFORMATION: Synthetic Construct
```

<400> SEQUENCE: 327

Asp Met Ile Ser Lys Leu Tyr Thr Lys Gln Lys Tyr Asn Pro Pro Leu
1 5 10 15

Ala Arg Asn Gln Pro Pro Ile Ala Gly
20 25

<210> SEQ ID NO 328
<211> LENGTH: 25
<212> TYPE: PRT
<213> ORGANISM: Artificial Sequence
<220> FEATURE:
<223> OTHER INFORMATION: Synthetic Construct

<400> SEQUENCE: 328

Asp His Tyr Phe Lys Gly Phe Trp Ser Glu Trp Ser Ser Ser Tyr Tyr
1 5 10 15

Phe Arg Thr Pro Glu Ile Asn Asn Ser
20 25

<210> SEQ ID NO 329
<211> LENGTH: 25
<212> TYPE: PRT
<213> ORGANISM: Artificial Sequence
<220> FEATURE:
<223> OTHER INFORMATION: Synthetic Construct

<400> SEQUENCE: 329

His Cys Gln Gly Arg Asn Tyr Thr Leu Thr Gly Arg Asn Ser Cys Thr
1 5 10 15

Leu Pro Ala Ser Ala Glu Lys Ala Cys
20 25

<210> SEQ ID NO 330
<211> LENGTH: 25
<212> TYPE: PRT
<213> ORGANISM: Artificial Sequence
<220> FEATURE:
<223> OTHER INFORMATION: Synthetic Construct

<400> SEQUENCE: 330

Asn Val Cys Ser His Gly Leu Cys Val Asp Leu Gln Arg Ser Tyr Gln
1 5 10 15

Cys Ile Cys His Asn Gly Phe Lys Ala
20 25

<210> SEQ ID NO 331
<211> LENGTH: 25
<212> TYPE: PRT
<213> ORGANISM: Artificial Sequence
<220> FEATURE:
<223> OTHER INFORMATION: Synthetic Construct

<400> SEQUENCE: 331

Ile Ile Phe Phe Leu Glu Arg Tyr Tyr Arg Leu Leu Ser Gly Ala Val
1 5 10 15

Gln Ile Val Leu Phe Ile Phe Leu Glu
20 25

<210> SEQ ID NO 332
<211> LENGTH: 25
<212> TYPE: PRT
<213> ORGANISM: Artificial Sequence
<220> FEATURE:
<223> OTHER INFORMATION: Synthetic Construct

<400> SEQUENCE: 332

Phe Gln Leu Leu Leu Glu Lys Pro Phe Gln Ile Phe Cys Ala Glu Leu
1               5                   10                  15

Trp Val Arg Asp Ile Asn Asp His Ala
            20                  25

<210> SEQ ID NO 333
<211> LENGTH: 25
<212> TYPE: PRT
<213> ORGANISM: Artificial Sequence
<220> FEATURE:
<223> OTHER INFORMATION: Synthetic Construct

<400> SEQUENCE: 333

Glu Asn Ser Pro Leu Gly Thr Glu Phe Pro Leu Asn Tyr Ala Leu Asp
1               5                   10                  15

Leu Asp Val Gly Ser Asn Asn Val Gln
            20                  25

<210> SEQ ID NO 334
<211> LENGTH: 25
<212> TYPE: PRT
<213> ORGANISM: Artificial Sequence
<220> FEATURE:
<223> OTHER INFORMATION: Synthetic Construct

<400> SEQUENCE: 334

Glu Gly Arg Asp Gln Thr Thr Ser Asp Gln Ser Asn Lys Phe Gly Ile
1               5                   10                  15

Phe Asn Ser Leu Trp Phe Ser Leu Gly
            20                  25

<210> SEQ ID NO 335
<211> LENGTH: 25
<212> TYPE: PRT
<213> ORGANISM: Artificial Sequence
<220> FEATURE:
<223> OTHER INFORMATION: Synthetic Construct

<400> SEQUENCE: 335

Arg Lys Asp Asn Gly Leu Leu Val Arg Gln Glu Ala Cys Ile Ser Trp
1               5                   10                  15

Phe Gly Ser Pro Thr Thr Ser Phe Leu
            20                  25

<210> SEQ ID NO 336
<211> LENGTH: 25
<212> TYPE: PRT
<213> ORGANISM: Artificial Sequence
<220> FEATURE:
<223> OTHER INFORMATION: Synthetic Construct

<400> SEQUENCE: 336

Arg Asn Val Leu Tyr Phe Ile Leu Glu Thr Tyr Val Leu Ser Thr Phe
1               5                   10                  15

Leu Val Val Leu Ser Trp Val Ser Phe
            20                  25

<210> SEQ ID NO 337
<211> LENGTH: 25
<212> TYPE: PRT
<213> ORGANISM: Artificial Sequence
<220> FEATURE:

<223> OTHER INFORMATION: Synthetic Construct

<400> SEQUENCE: 337

Leu Pro Thr Val Glu Leu Gln Gly Val Val Pro Arg Asp Val Asn Leu
1 5 10 15

Gln Glu Phe Leu Asn Val Thr Ser Val
20 25

<210> SEQ ID NO 338
<211> LENGTH: 25
<212> TYPE: PRT
<213> ORGANISM: Artificial Sequence
<220> FEATURE:
<223> OTHER INFORMATION: Synthetic Construct

<400> SEQUENCE: 338

Asn Glu His Arg Arg Ser His Thr Gly Glu Lys Pro His Gln Cys Lys
1 5 10 15

Glu Cys Gly Lys Ala Phe Ser Ala Ser
20 25

<210> SEQ ID NO 339
<211> LENGTH: 25
<212> TYPE: PRT
<213> ORGANISM: Artificial Sequence
<220> FEATURE:
<223> OTHER INFORMATION: Synthetic Construct

<400> SEQUENCE: 339

Ser Gln Ile Ile Leu Lys Gly Ser Gly Gln Gln Ala Ser Ser Asn Val
1 5 10 15

Ser Gly Gly Leu Leu Val His Arg Gln
20 25

<210> SEQ ID NO 340
<211> LENGTH: 25
<212> TYPE: PRT
<213> ORGANISM: Artificial Sequence
<220> FEATURE:
<223> OTHER INFORMATION: Synthetic Construct

<400> SEQUENCE: 340

Cys Ile Phe Arg Tyr Lys Asn Ser Tyr Ser Ile Ala Ala Lys Asp Val
1 5 10 15

Ile Val His Pro Leu Pro Leu Lys Leu
20 25

<210> SEQ ID NO 341
<211> LENGTH: 25
<212> TYPE: PRT
<213> ORGANISM: Artificial Sequence
<220> FEATURE:
<223> OTHER INFORMATION: Synthetic Construct

<400> SEQUENCE: 341

Thr Leu Ser Arg Asn Ile Ser Asn Ile Ala Gly Gly Lys Thr Leu Val
1 5 10 15

Ile Gly Val Ala Arg Leu Met Asn Tyr
20 25

<210> SEQ ID NO 342
<211> LENGTH: 25
<212> TYPE: PRT
<213> ORGANISM: Artificial Sequence
<220> FEATURE:
<223> OTHER INFORMATION: Synthetic Construct

<400> SEQUENCE: 342

Lys His Ala Asn Lys Ile Thr Leu Thr Gly Phe His Phe Pro Phe Asn
1               5                   10                  15

Gly Glu Val Ile Tyr Ala Ala Met Cys
            20                  25

<210> SEQ ID NO 343
<211> LENGTH: 25
<212> TYPE: PRT
<213> ORGANISM: Artificial Sequence
<220> FEATURE:
<223> OTHER INFORMATION: Synthetic Construct

<400> SEQUENCE: 343

Cys Ser Cys Leu Ser Glu Glu Asp Ser Gln Glu Tyr Trp Tyr Leu Cys
1               5                   10                  15

Phe Leu Arg Trp Ala Gly Asn Met Tyr
            20                  25

<210> SEQ ID NO 344
<211> LENGTH: 25
<212> TYPE: PRT
<213> ORGANISM: Artificial Sequence
<220> FEATURE:
<223> OTHER INFORMATION: Synthetic Construct

<400> SEQUENCE: 344

Val Pro Ala Thr His Pro His Leu Leu Ser Gly Ser Phe Cys Ser Ser
1               5                   10                  15

Pro Ala Phe His Leu Gly Pro Asn Thr
            20                  25

<210> SEQ ID NO 345
<211> LENGTH: 25
<212> TYPE: PRT
<213> ORGANISM: Artificial Sequence
<220> FEATURE:
<223> OTHER INFORMATION: Synthetic Construct

<400> SEQUENCE: 345

Ser Ser Ser Ser Ser Ala Gly Glu Met Ile Glu Ala Leu Ser Gln Val
1               5                   10                  15

Leu Asn Phe Glu Glu Ile Asp Tyr Lys
            20                  25

<210> SEQ ID NO 346
<211> LENGTH: 21
<212> TYPE: PRT
<213> ORGANISM: Artificial Sequence
<220> FEATURE:
<223> OTHER INFORMATION: Synthetic Construct

<400> SEQUENCE: 346

Met Thr Asp Asp Lys Asp Val Leu Arg Asn Val Trp Phe Gly Arg Ile
1               5                   10                  15

Pro Thr Cys Phe Thr
            20

<210> SEQ ID NO 347
<211> LENGTH: 25
<212> TYPE: PRT

```
<213> ORGANISM: Artificial Sequence
<220> FEATURE:
<223> OTHER INFORMATION: Synthetic Construct

<400> SEQUENCE: 347

Ala Ala Asp Glu Lys Ala Leu Phe His Glu Ile Ala Ser Ile Ile Lys
1               5                   10                  15

Arg Tyr Asp Pro Asp Ile Leu Leu Gly
            20                  25


<210> SEQ ID NO 348
<211> LENGTH: 25
<212> TYPE: PRT
<213> ORGANISM: Artificial Sequence
<220> FEATURE:
<223> OTHER INFORMATION: Synthetic Construct

<400> SEQUENCE: 348

Ala Pro Ala Asn Arg Glu Asn Gly Ser Gln Ala Met Ser Tyr Asn Cys
1               5                   10                  15

Arg Asn Asn Leu Ala Phe Pro Ala His
            20                  25


<210> SEQ ID NO 349
<211> LENGTH: 25
<212> TYPE: PRT
<213> ORGANISM: Artificial Sequence
<220> FEATURE:
<223> OTHER INFORMATION: Synthetic Construct

<400> SEQUENCE: 349

Leu Glu Glu Trp Ile Gln Gly Gly Met Thr Thr Ile Ser Leu Leu Val
1               5                   10                  15

Leu Leu Gly Leu Glu Asn Asn Val Lys
            20                  25


<210> SEQ ID NO 350
<211> LENGTH: 25
<212> TYPE: PRT
<213> ORGANISM: Artificial Sequence
<220> FEATURE:
<223> OTHER INFORMATION: Synthetic Construct

<400> SEQUENCE: 350

Pro Glu Asn Asn Asn Lys Lys Pro Lys Thr Ser Gly Phe Gln Asp Ser
1               5                   10                  15

Gln Pro Ser Pro Leu Ala Leu Leu Ala
            20                  25


<210> SEQ ID NO 351
<211> LENGTH: 25
<212> TYPE: PRT
<213> ORGANISM: Artificial Sequence
<220> FEATURE:
<223> OTHER INFORMATION: Synthetic Construct

<400> SEQUENCE: 351

Ile Val Leu Ser Val Gly Val Asn Phe Gly Leu Phe Phe Asn Ile Ile
1               5                   10                  15

Arg Ile Leu Val Arg Lys Leu Glu Pro
            20                  25


<210> SEQ ID NO 352
<211> LENGTH: 25
```

<212> TYPE: PRT
<213> ORGANISM: Artificial Sequence
<220> FEATURE:
<223> OTHER INFORMATION: Synthetic Construct

<400> SEQUENCE: 352

Leu Phe Glu Tyr His Asp Ser Arg Val His Val Cys Phe Tyr Phe Ile
1 5 10 15

Ser Pro Thr Gly His Ser Leu Lys Ser
20 25

<210> SEQ ID NO 353
<211> LENGTH: 25
<212> TYPE: PRT
<213> ORGANISM: Artificial Sequence
<220> FEATURE:
<223> OTHER INFORMATION: Synthetic Construct

<400> SEQUENCE: 353

Lys Glu Gln Gly Lys Pro Glu Gly Ile Ile Lys Pro Leu Leu Gln Gln
1 5 10 15

Gln Pro Pro Lys Pro Ile Pro Lys Gln
20 25

<210> SEQ ID NO 354
<211> LENGTH: 25
<212> TYPE: PRT
<213> ORGANISM: Artificial Sequence
<220> FEATURE:
<223> OTHER INFORMATION: Synthetic Construct

<400> SEQUENCE: 354

Ile Lys Tyr Val Lys Tyr Leu Tyr Leu Asp Lys Asn Lys Ile Lys Thr
1 5 10 15

Phe Gln Gly Ala Asp Ser Gly Asp Leu
20 25

<210> SEQ ID NO 355
<211> LENGTH: 25
<212> TYPE: PRT
<213> ORGANISM: Artificial Sequence
<220> FEATURE:
<223> OTHER INFORMATION: Synthetic Construct

<400> SEQUENCE: 355

Ser Val Glu Leu Leu Lys Pro Ser Leu Ser Arg Ile Leu Glu His Thr
1 5 10 15

Ser Met Ala Asn Ser Phe Asn Thr His
20 25

<210> SEQ ID NO 356
<211> LENGTH: 25
<212> TYPE: PRT
<213> ORGANISM: Artificial Sequence
<220> FEATURE:
<223> OTHER INFORMATION: Synthetic Construct

<400> SEQUENCE: 356

Arg Asn Arg Asn Phe Trp Ile Leu Arg Leu Pro Pro Asp Ser Lys Gly
1 5 10 15

Glu Ala Pro Lys Val Pro Val Thr Phe
20 25

<210> SEQ ID NO 357

<211> LENGTH: 25
<212> TYPE: PRT
<213> ORGANISM: Artificial Sequence
<220> FEATURE:
<223> OTHER INFORMATION: Synthetic Construct

<400> SEQUENCE: 357

Val Ala Val Leu Ala Gly Ala Ala Ala Phe Ile Tyr Lys Lys Arg Gly
1 5 10 15

Gly Thr Tyr Trp Ala Leu Leu Arg Thr
20 25

<210> SEQ ID NO 358
<211> LENGTH: 25
<212> TYPE: PRT
<213> ORGANISM: Artificial Sequence
<220> FEATURE:
<223> OTHER INFORMATION: Synthetic Construct

<400> SEQUENCE: 358

Thr Gln Val Gly Phe Ala Gly Gly Tyr Thr Ser Asn Ser Thr Tyr Lys
1 5 10 15

Glu Val Cys Ser Glu Lys Thr Gly His
20 25

<210> SEQ ID NO 359
<211> LENGTH: 25
<212> TYPE: PRT
<213> ORGANISM: Artificial Sequence
<220> FEATURE:
<223> OTHER INFORMATION: Synthetic Construct

<400> SEQUENCE: 359

Gln Val Asn Glu Cys Glu Ala Ile Met Glu His Cys Phe Asp Cys Phe
1 5 10 15

Asp Phe Ser Leu Ser Val Pro Phe Thr
20 25

<210> SEQ ID NO 360
<211> LENGTH: 25
<212> TYPE: PRT
<213> ORGANISM: Artificial Sequence
<220> FEATURE:
<223> OTHER INFORMATION: Synthetic Construct

<400> SEQUENCE: 360

Thr Arg Ile Thr Gly Glu Glu Val Glu Val Gln Asp Phe Val Pro Ala
1 5 10 15

Asp Ser Gly Leu Tyr Ala Cys Val Thr
20 25

<210> SEQ ID NO 361
<211> LENGTH: 25
<212> TYPE: PRT
<213> ORGANISM: Artificial Sequence
<220> FEATURE:
<223> OTHER INFORMATION: Synthetic Construct

<400> SEQUENCE: 361

Pro Gln Asn Leu Leu Arg Glu Lys Ile Met Lys Leu Ser Leu Pro Glu
1 5 10 15

Ser Leu Lys Ala Tyr Leu Thr Tyr Phe
20 25

<210> SEQ ID NO 362
<211> LENGTH: 25
<212> TYPE: PRT
<213> ORGANISM: Artificial Sequence
<220> FEATURE:
<223> OTHER INFORMATION: Synthetic Construct

<400> SEQUENCE: 362

```
Met His Pro Ser Leu Pro Arg Asn Ile Ala Pro Lys Leu Asn Asn Gln
1               5                   10                  15

Met Pro Val Thr Val Ser Ile Ala Asn
            20                  25
```

<210> SEQ ID NO 363
<211> LENGTH: 25
<212> TYPE: PRT
<213> ORGANISM: Artificial Sequence
<220> FEATURE:
<223> OTHER INFORMATION: Synthetic Construct

<400> SEQUENCE: 363

```
Ala Gln Leu Gly Arg Gly Ser Phe Met Leu Gly Leu Gln Thr His Asp
1               5                   10                  15

Arg Lys Ser Glu Asp Lys Leu Ala Lys
            20                  25
```

<210> SEQ ID NO 364
<211> LENGTH: 25
<212> TYPE: PRT
<213> ORGANISM: Artificial Sequence
<220> FEATURE:
<223> OTHER INFORMATION: Synthetic Construct

<400> SEQUENCE: 364

```
Phe Tyr Gln Val Leu Thr Ser Glu Ala Ser Gln Asp Arg Leu Gly Cys
1               5                   10                  15

Val Lys Cys Pro Glu Gly Ser Tyr Ser
            20                  25
```

<210> SEQ ID NO 365
<211> LENGTH: 25
<212> TYPE: PRT
<213> ORGANISM: Artificial Sequence
<220> FEATURE:
<223> OTHER INFORMATION: Synthetic Construct

<400> SEQUENCE: 365

```
Ala Pro Gly Gln Ala Lys Ile Ala Gly Gly Ala Ala Glu Ser Asp Ser
1               5                   10                  15

Ser Ser Thr Ser Met Asn Val Tyr Ser
            20                  25
```

<210> SEQ ID NO 366
<211> LENGTH: 25
<212> TYPE: PRT
<213> ORGANISM: Artificial Sequence
<220> FEATURE:
<223> OTHER INFORMATION: Synthetic Construct

<400> SEQUENCE: 366

```
Gly Ala Val Ala Arg Pro Thr Gly Gly Ile Ile Asp Ile Ala Ser Ser
1               5                   10                  15

Thr Phe Gln Gly Ile Lys Arg Ala Thr
            20                  25
```

<210> SEQ ID NO 367
<211> LENGTH: 25
<212> TYPE: PRT
<213> ORGANISM: Artificial Sequence
<220> FEATURE:
<223> OTHER INFORMATION: Synthetic Construct

<400> SEQUENCE: 367

Met Leu Val Gly Asn Lys Cys Asp Glu Ser Pro Ser Cys Glu Val Gln
1               5                   10                  15

Ser Ser Glu Ala Glu Ala Leu Ala Arg
            20                  25

<210> SEQ ID NO 368
<211> LENGTH: 25
<212> TYPE: PRT
<213> ORGANISM: Artificial Sequence
<220> FEATURE:
<223> OTHER INFORMATION: Synthetic Construct

<400> SEQUENCE: 368

Glu Glu Arg Ile Gln Ala Leu Glu Glu Asp Leu Arg Lys Lys Glu Arg
1               5                   10                  15

Glu Ile Ala Thr Glu Lys Lys Asn Ser
            20                  25

<210> SEQ ID NO 369
<211> LENGTH: 25
<212> TYPE: PRT
<213> ORGANISM: Artificial Sequence
<220> FEATURE:
<223> OTHER INFORMATION: Synthetic Construct

<400> SEQUENCE: 369

Arg His Leu Ser Asn Asn Leu Glu Thr Leu Leu Lys Trp Asp Phe Leu
1               5                   10                  15

Lys Leu Leu Pro Leu Glu Leu Ser Phe
            20                  25

<210> SEQ ID NO 370
<211> LENGTH: 25
<212> TYPE: PRT
<213> ORGANISM: Artificial Sequence
<220> FEATURE:
<223> OTHER INFORMATION: Synthetic Construct

<400> SEQUENCE: 370

Leu Trp Asp Leu Arg Arg Val Arg Gly Glu Ala Ala Phe Ala Gln Pro
1               5                   10                  15

Leu Gly Gln Gly Pro Ser Ser Gly Gln
            20                  25

<210> SEQ ID NO 371
<211> LENGTH: 25
<212> TYPE: PRT
<213> ORGANISM: Artificial Sequence
<220> FEATURE:
<223> OTHER INFORMATION: Synthetic Construct

<400> SEQUENCE: 371

Ser Val Asn Lys Ile Ser Pro Ser Gly Asp Ser Ser Lys Val Gly Phe
1               5                   10                  15

Cys Ser Asn Ala Arg Thr Ser Val Glu
            20                  25

<210> SEQ ID NO 372
<211> LENGTH: 25
<212> TYPE: PRT
<213> ORGANISM: Artificial Sequence
<220> FEATURE:
<223> OTHER INFORMATION: Synthetic Construct

<400> SEQUENCE: 372

```
Ile Trp Lys Phe Met Asn Val Leu Gly Ala Tyr Asp Glu Glu Glu His
1               5                   10                  15

Leu Ile Tyr Gly Glu Pro Arg Lys Phe
            20                  25
```

<210> SEQ ID NO 373
<211> LENGTH: 25
<212> TYPE: PRT
<213> ORGANISM: Artificial Sequence
<220> FEATURE:
<223> OTHER INFORMATION: Synthetic Construct

<400> SEQUENCE: 373

```
Pro Pro Glu Ala Gly Val Ser His Leu Cys Pro Glu Leu Pro Lys Thr
1               5                   10                  15

Arg Val Pro Pro Leu Arg Pro Glu Thr
            20                  25
```

<210> SEQ ID NO 374
<211> LENGTH: 25
<212> TYPE: PRT
<213> ORGANISM: Artificial Sequence
<220> FEATURE:
<223> OTHER INFORMATION: Synthetic Construct

<400> SEQUENCE: 374

```
Phe Thr Ile Cys Phe Val Pro Tyr His Ala Phe Arg Leu Ile Tyr Ile
1               5                   10                  15

Ser Ser Gln Leu Asn Val Ser Ser Cys
            20                  25
```

<210> SEQ ID NO 375
<211> LENGTH: 25
<212> TYPE: PRT
<213> ORGANISM: Artificial Sequence
<220> FEATURE:
<223> OTHER INFORMATION: Synthetic Construct

<400> SEQUENCE: 375

```
Cys Gly Lys Ala Phe Thr Gln Lys Ser Thr Leu Arg Thr His Gln Arg
1               5                   10                  15

Ile His Thr Gly Glu Arg Ser Tyr Ile
            20                  25
```

<210> SEQ ID NO 376
<211> LENGTH: 25
<212> TYPE: PRT
<213> ORGANISM: Artificial Sequence
<220> FEATURE:
<223> OTHER INFORMATION: Synthetic Construct

<400> SEQUENCE: 376

```
Leu Glu Phe Gln Pro Gln Leu Val Leu Val Ala Ala Arg Phe Asp Ala
1               5                   10                  15

Leu Gln Gly Asp Pro Lys Gly Glu Met
```

20 25

<210> SEQ ID NO 377
<211> LENGTH: 17
<212> TYPE: PRT
<213> ORGANISM: Artificial Sequence
<220> FEATURE:
<223> OTHER INFORMATION: Synthetic Construct

<400> SEQUENCE: 377

Met Ile Trp Arg Gly Arg Ser Thr Cys Arg Pro Arg Pro Arg Arg Ser
1 5 10 15

Val

<210> SEQ ID NO 378
<211> LENGTH: 25
<212> TYPE: PRT
<213> ORGANISM: Artificial Sequence
<220> FEATURE:
<223> OTHER INFORMATION: Synthetic Construct

<400> SEQUENCE: 378

Ser Trp Val Glu Asn Leu Trp Pro Glu Glu Cys Val Val Glu Arg Pro
1 5 10 15

Asn Val Gln Lys Tyr Cys Leu Met Ser
20 25

<210> SEQ ID NO 379
<211> LENGTH: 25
<212> TYPE: PRT
<213> ORGANISM: Artificial Sequence
<220> FEATURE:
<223> OTHER INFORMATION: Synthetic Construct

<400> SEQUENCE: 379

Ser Leu Glu Ser Arg Ala Asn Glu Ala Gln Trp Phe Gln Lys Thr Ala
1 5 10 15

Trp Asn Leu Ala Val Gln Cys Asp Lys
20 25

<210> SEQ ID NO 380
<211> LENGTH: 25
<212> TYPE: PRT
<213> ORGANISM: Artificial Sequence
<220> FEATURE:
<223> OTHER INFORMATION: Synthetic Construct

<400> SEQUENCE: 380

Ser Asp Asp Ser Glu Ala Pro Asp Asp Ser Ser Asp Asn Ser Glu Ala
1 5 10 15

Ser Asp Asp Ser Ser Asp Asp Ser Glu
20 25

<210> SEQ ID NO 381
<211> LENGTH: 25
<212> TYPE: PRT
<213> ORGANISM: Artificial Sequence
<220> FEATURE:
<223> OTHER INFORMATION: Synthetic Construct

<400> SEQUENCE: 381

Pro Leu His Leu Lys Ser Ser Leu Pro Thr Lys Pro Phe Val Ser Tyr
1 5 10 15

Thr Ile Ala Leu Ala Pro Pro Ala Arg 20 25

<210> SEQ ID NO 382
<211> LENGTH: 25
<212> TYPE: PRT
<213> ORGANISM: Artificial Sequence
<220> FEATURE:
<223> OTHER INFORMATION: Synthetic Construct

<400> SEQUENCE: 382

Val Gly Lys Ile Ser Pro Pro Val Tyr Leu Thr Asn Lys Trp Val Gly
1 5 10 15

Tyr Asn Ala Leu Ser Glu Ile Phe Arg
20 25

<210> SEQ ID NO 383
<211> LENGTH: 25
<212> TYPE: PRT
<213> ORGANISM: Artificial Sequence
<220> FEATURE:
<223> OTHER INFORMATION: Synthetic Construct

<400> SEQUENCE: 383

Thr Gly Pro Gln Gly Phe Thr Gly Ser Thr Gly Leu Leu Gly Leu Lys
1 5 10 15

Gly Glu Arg Gly Phe Pro Gly Leu Leu
20 25

<210> SEQ ID NO 384
<211> LENGTH: 25
<212> TYPE: PRT
<213> ORGANISM: Artificial Sequence
<220> FEATURE:
<223> OTHER INFORMATION: Synthetic Construct

<400> SEQUENCE: 384

Lys Leu Thr Cys Ser Asp Thr Ser Leu Asn Glu Phe Ile Ile Leu Ile
1 5 10 15

Thr Ser Ile Phe Thr Leu Leu Leu Pro
20 25

<210> SEQ ID NO 385
<211> LENGTH: 25
<212> TYPE: PRT
<213> ORGANISM: Artificial Sequence
<220> FEATURE:
<223> OTHER INFORMATION: Synthetic Construct

<400> SEQUENCE: 385

Glu Asp Ser Leu Ser Pro Leu His Phe Pro Gln Phe Ser Pro Gln Gly
1 5 10 15

Glu Asp Phe Gln Ser Ser Leu Gln Ser
20 25

<210> SEQ ID NO 386
<211> LENGTH: 25
<212> TYPE: PRT
<213> ORGANISM: Artificial Sequence
<220> FEATURE:
<223> OTHER INFORMATION: Synthetic Construct

<400> SEQUENCE: 386

Lys Ser Met Leu Pro His Phe Ala Met Val Gly Asn Cys Gln Glu Pro
1 5 10 15

Arg Lys Leu Gln Glu Ser Gly Thr Val
20 25

<210> SEQ ID NO 387
<211> LENGTH: 25
<212> TYPE: PRT
<213> ORGANISM: Artificial Sequence
<220> FEATURE:
<223> OTHER INFORMATION: Synthetic Construct

<400> SEQUENCE: 387

Gly Thr Gln Thr Asp Ile Thr Phe Glu His Ile Met Val Leu Gly Lys
1 5 10 15

Leu Arg Pro Pro Thr Pro Pro Met Val
20 25

<210> SEQ ID NO 388
<211> LENGTH: 25
<212> TYPE: PRT
<213> ORGANISM: Artificial Sequence
<220> FEATURE:
<223> OTHER INFORMATION: Synthetic Construct

<400> SEQUENCE: 388

Val Gly Lys Ser Ala Asp Phe Val Val Glu Ala Ile Glu Asp Asp Val
1 5 10 15

Gly Thr Leu Gly Phe Ser Val Glu Gly
20 25

<210> SEQ ID NO 389
<211> LENGTH: 25
<212> TYPE: PRT
<213> ORGANISM: Artificial Sequence
<220> FEATURE:
<223> OTHER INFORMATION: Synthetic Construct

<400> SEQUENCE: 389

Ile Lys Trp Asn Glu Ala Asn Arg Pro Gly Lys Val Leu Phe Leu Arg
1 5 10 15

Val Ala Thr Glu Ser Ser Ala Lys Thr
20 25

<210> SEQ ID NO 390
<211> LENGTH: 25
<212> TYPE: PRT
<213> ORGANISM: Artificial Sequence
<220> FEATURE:
<223> OTHER INFORMATION: Synthetic Construct

<400> SEQUENCE: 390

Pro Leu Val Pro Glu Pro Arg Arg Leu Pro Val Gly Ser Leu Leu Arg
1 5 10 15

Ala Leu Ala Thr Cys His Ala Leu Ser
20 25

<210> SEQ ID NO 391
<211> LENGTH: 25
<212> TYPE: PRT
<213> ORGANISM: Artificial Sequence
<220> FEATURE:
<223> OTHER INFORMATION: Synthetic Construct

<400> SEQUENCE: 391

Lys Asp Glu Gly Tyr Tyr Gln Gly Gly Lys Phe Gln Leu Glu Thr Glu
1 5 10 15

Val Pro Asp Ala Tyr Asn Met Val Pro
20 25

<210> SEQ ID NO 392
<211> LENGTH: 25
<212> TYPE: PRT
<213> ORGANISM: Artificial Sequence
<220> FEATURE:
<223> OTHER INFORMATION: Synthetic Construct

<400> SEQUENCE: 392

Asp Asn Phe Gln Gln Trp Arg Thr Pro His Gln Lys Ser Thr Glu Gln
1 5 10 15

Pro Gln Gln Ala Lys Lys Leu Gly Tyr
20 25

<210> SEQ ID NO 393
<211> LENGTH: 25
<212> TYPE: PRT
<213> ORGANISM: Artificial Sequence
<220> FEATURE:
<223> OTHER INFORMATION: Synthetic Construct

<400> SEQUENCE: 393

Pro Phe Lys Cys Ser Met Cys Lys Tyr Ala Ser Val Lys Ala Ser Lys
1 5 10 15

Leu Lys Arg His Val Arg Ser His Thr
20 25

<210> SEQ ID NO 394
<211> LENGTH: 25
<212> TYPE: PRT
<213> ORGANISM: Artificial Sequence
<220> FEATURE:
<223> OTHER INFORMATION: Synthetic Construct

<400> SEQUENCE: 394

Glu Ile Tyr Asn Trp Phe Thr Arg Met Phe Ala Tyr Leu Arg Arg Asn
1 5 10 15

Ala Ala Thr Trp Lys Asn Ala Val Arg
20 25

<210> SEQ ID NO 395
<211> LENGTH: 25
<212> TYPE: PRT
<213> ORGANISM: Artificial Sequence
<220> FEATURE:
<223> OTHER INFORMATION: Synthetic Construct

<400> SEQUENCE: 395

Leu Pro Thr Val Glu Leu Gln Gly Val Val Pro Arg Ser Val Asn Leu
1 5 10 15

Gln Glu Phe Leu Asn Val Thr Ser Val
20 25

<210> SEQ ID NO 396
<211> LENGTH: 25
<212> TYPE: PRT
<213> ORGANISM: Artificial Sequence
<220> FEATURE:
<223> OTHER INFORMATION: Synthetic Construct

<400> SEQUENCE: 396

Phe Tyr Gln Val Leu Thr Ser Glu Ala Ser Gln Asp Glu Leu Gly Cys 1 5 10 15

Val Lys Cys Pro Glu Gly Ser Tyr Ser
20 25

<210> SEQ ID NO 397
<211> LENGTH: 25
<212> TYPE: PRT
<213> ORGANISM: Artificial Sequence
<220> FEATURE:
<223> OTHER INFORMATION: Synthetic Construct

<400> SEQUENCE: 397

Leu Glu Phe Gln Pro Gln Leu Val Leu Val Ala Ala Glu Phe Asp Ala
1 5 10 15

Leu Gln Gly Asp Pro Lys Gly Glu Met
20 25

<210> SEQ ID NO 398
<211> LENGTH: 25
<212> TYPE: PRT
<213> ORGANISM: Artificial Sequence
<220> FEATURE:
<223> OTHER INFORMATION: Synthetic Construct

<400> SEQUENCE: 398

Lys Ser Met Leu Pro His Phe Ala Met Val Gly Asn Cys Gln Glu Pro
1 5 10 15

Arg Lys Leu Gln Glu Ser Gly Lys Lys
20 25

<210> SEQ ID NO 399
<211> LENGTH: 25
<212> TYPE: PRT
<213> ORGANISM: Artificial Sequence
<220> FEATURE:
<223> OTHER INFORMATION: Synthetic Construct

<400> SEQUENCE: 399

Ala Pro Val Ser Gln His Pro Gly Val Leu Thr Asn Tyr Leu Gly Thr
1 5 10 15

Ser Ala Ser Ser Pro Thr Ser Glu Ser
20 25

<210> SEQ ID NO 400
<211> LENGTH: 25
<212> TYPE: PRT
<213> ORGANISM: Artificial Sequence
<220> FEATURE:
<223> OTHER INFORMATION: Synthetic Construct

<400> SEQUENCE: 400

Leu Ile Arg Phe Asn Ala Val Leu Thr Asn Pro Gln Glu Asp Tyr Asp
1 5 10 15

Thr Ser Thr Gly Lys Phe Thr Cys Lys
20 25

<210> SEQ ID NO 401
<211> LENGTH: 25
<212> TYPE: PRT
<213> ORGANISM: Artificial Sequence
<220> FEATURE:
<223> OTHER INFORMATION: Synthetic Construct

<400> SEQUENCE: 401

Gln Arg Ser Lys Asn Asn Lys Thr Leu Glu Lys Pro Asn Leu Gly Phe
1 5 10 15

Leu Ser Pro Gln Val Phe Val Tyr Val
20 25

<210> SEQ ID NO 402
<211> LENGTH: 25
<212> TYPE: PRT
<213> ORGANISM: Artificial Sequence
<220> FEATURE:
<223> OTHER INFORMATION: Synthetic Construct

<400> SEQUENCE: 402

Gly Ala Ala Thr Tyr Ala Val Val Ser Ser Pro Ala Ala Ile Leu Ser
1 5 10 15

Leu Thr Leu Leu Glu Arg Ala Gly Tyr
20 25

<210> SEQ ID NO 403
<211> LENGTH: 25
<212> TYPE: PRT
<213> ORGANISM: Artificial Sequence
<220> FEATURE:
<223> OTHER INFORMATION: Synthetic Construct

<400> SEQUENCE: 403

Phe Leu Gly Pro Gln Gln Ile Lys Asp Leu Leu Leu Gly Ala Leu Glu
1 5 10 15

Gly Leu Lys Gly Ser Ser Glu Ala Pro
20 25

<210> SEQ ID NO 404
<211> LENGTH: 25
<212> TYPE: PRT
<213> ORGANISM: Artificial Sequence
<220> FEATURE:
<223> OTHER INFORMATION: Synthetic Construct

<400> SEQUENCE: 404

Asn Ala Val Leu Arg Glu Lys Lys Gln His Phe Phe Ser Ala Tyr Pro
1 5 10 15

Gln Pro Ile Tyr Thr Thr His Pro Lys
20 25

<210> SEQ ID NO 405
<211> LENGTH: 25
<212> TYPE: PRT
<213> ORGANISM: Artificial Sequence
<220> FEATURE:
<223> OTHER INFORMATION: Synthetic Construct

<400> SEQUENCE: 405

Trp Cys Gln Met Glu Pro Cys Leu Pro Gly Glu Glu Tyr Lys Val Leu
1 5 10 15

Pro Asp Leu Ser Gly Trp Ser Cys Ser
20 25

<210> SEQ ID NO 406
<211> LENGTH: 25
<212> TYPE: PRT
<213> ORGANISM: Artificial Sequence
<220> FEATURE:
<223> OTHER INFORMATION: Synthetic Construct

<400> SEQUENCE: 406

Gly Pro Phe Ala Thr Gly Val Ala Gly Gly Leu Leu Thr Ile Ala Gly
1 5 10 15

Leu Ala Ala Gly Ala Leu Leu Leu Tyr
20 25

<210> SEQ ID NO 407
<211> LENGTH: 24
<212> TYPE: PRT
<213> ORGANISM: Artificial Sequence
<220> FEATURE:
<223> OTHER INFORMATION: Synthetic Construct

<400> SEQUENCE: 407

Met Leu Pro Arg Leu Leu Leu Leu Ile Cys Ala Leu Leu Cys Glu Pro
1 5 10 15

Ala Glu Leu Phe Leu Ile Ala Ser
20

<210> SEQ ID NO 408
<211> LENGTH: 25
<212> TYPE: PRT
<213> ORGANISM: Artificial Sequence
<220> FEATURE:
<223> OTHER INFORMATION: Synthetic Construct

<400> SEQUENCE: 408

Asp His Tyr Leu Ala Ile Cys Ser Pro Leu His Tyr Ser Ser Ile Met
1 5 10 15

Thr Pro Lys Leu Cys Thr Gln Leu Thr
20 25

<210> SEQ ID NO 409
<211> LENGTH: 25
<212> TYPE: PRT
<213> ORGANISM: Artificial Sequence
<220> FEATURE:
<223> OTHER INFORMATION: Synthetic Construct

<400> SEQUENCE: 409

Ser Ile Asn Leu Met Asn Leu Gln Val Ser Asp Thr Val Thr Tyr Glu
1 5 10 15

Cys Arg Val Lys Lys Thr Thr Met Ala
20 25

<210> SEQ ID NO 410
<211> LENGTH: 25
<212> TYPE: PRT
<213> ORGANISM: Artificial Sequence
<220> FEATURE:
<223> OTHER INFORMATION: Synthetic Construct

<400> SEQUENCE: 410

Gln Asn Gly Ser Arg Ser Arg Gln Gln Ser Ser Ser Phe Arg Glu Ser
1 5 10 15

Pro Val Pro Lys Val Arg Ala Ile Gln
20 25

<210> SEQ ID NO 411
<211> LENGTH: 25
<212> TYPE: PRT
<213> ORGANISM: Artificial Sequence
<220> FEATURE:
<223> OTHER INFORMATION: Synthetic Construct

<400> SEQUENCE: 411

Thr Ser Met Leu Ile Leu Ser Asn Leu Val Phe Leu Glu Gly Asn Glu
1               5                   10                  15

Val Gly Lys Thr Tyr Trp Asn Arg Ile
            20                  25

<210> SEQ ID NO 412
<211> LENGTH: 25
<212> TYPE: PRT
<213> ORGANISM: Artificial Sequence
<220> FEATURE:
<223> OTHER INFORMATION: Synthetic Construct

<400> SEQUENCE: 412

Tyr Val Pro Gly Glu Gly Tyr Asn Gln Lys Phe Arg Lys Leu Tyr Lys
1               5                   10                  15

Ile Gly Ile Thr Cys Tyr Leu Leu Leu
            20                  25

<210> SEQ ID NO 413
<211> LENGTH: 25
<212> TYPE: PRT
<213> ORGANISM: Artificial Sequence
<220> FEATURE:
<223> OTHER INFORMATION: Synthetic Construct

<400> SEQUENCE: 413

Thr Glu Cys Ile Leu Leu Ala Asp Met Ala Leu Asp Trp Tyr Ile Ala
1               5                   10                  15

Val Cys Lys Pro Leu His Tyr Val Val
            20                  25

<210> SEQ ID NO 414
<211> LENGTH: 25
<212> TYPE: PRT
<213> ORGANISM: Artificial Sequence
<220> FEATURE:
<223> OTHER INFORMATION: Synthetic Construct

<400> SEQUENCE: 414

Thr Asp Ser Arg Thr Phe Tyr Ile Ala Glu Gln Val Phe His His Pro
1               5                   10                  15

Pro Val Ser Ala Phe His Val Ser Asn
            20                  25

<210> SEQ ID NO 415
<211> LENGTH: 25
<212> TYPE: PRT
<213> ORGANISM: Artificial Sequence
<220> FEATURE:
<223> OTHER INFORMATION: Synthetic Construct

<400> SEQUENCE: 415

Thr Ile Ser Lys Ile Leu Tyr Pro Val Met Met Phe Phe Tyr Phe Ala
1               5                   10                  15

Gly Leu Ser Phe Leu Ser Ala Val Ser
            20                  25

<210> SEQ ID NO 416
<211> LENGTH: 25
<212> TYPE: PRT
<213> ORGANISM: Artificial Sequence
<220> FEATURE:
<223> OTHER INFORMATION: Synthetic Construct -continued

<400> SEQUENCE: 416

Phe Arg Val Gln Asn Thr Arg Lys Asp Ala Thr Tyr Cys Phe Thr Ile
1 5 10 15

Val Asn Leu Leu Lys Pro Lys Ser Leu
20 25

<210> SEQ ID NO 417
<211> LENGTH: 25
<212> TYPE: PRT
<213> ORGANISM: Artificial Sequence
<220> FEATURE:
<223> OTHER INFORMATION: Synthetic Construct

<400> SEQUENCE: 417

Asp Ala Ile Tyr Ser Thr Ala Met Ser Pro Lys Leu Ile Ile Asp Leu
1 5 10 15

Leu Cys Asp Lys Ile Ala Ile Ser Leu
20 25

<210> SEQ ID NO 418
<211> LENGTH: 25
<212> TYPE: PRT
<213> ORGANISM: Artificial Sequence
<220> FEATURE:
<223> OTHER INFORMATION: Synthetic Construct

<400> SEQUENCE: 418

Arg Leu Tyr Met Ile Pro Val Gly Ala Phe Ile Phe Phe Leu Gly Asn
1 5 10 15

Met Gln Asn Gln Ser Phe Val Thr Glu
20 25

<210> SEQ ID NO 419
<211> LENGTH: 25
<212> TYPE: PRT
<213> ORGANISM: Artificial Sequence
<220> FEATURE:
<223> OTHER INFORMATION: Synthetic Construct

<400> SEQUENCE: 419

Phe Leu Gly Phe Leu Ser Phe Leu Asp Ala Cys Phe Ala Ser Val Ile
1 5 10 15

Thr Pro Lys Met Ile Val Asp Ser Leu
20 25

<210> SEQ ID NO 420
<211> LENGTH: 25
<212> TYPE: PRT
<213> ORGANISM: Artificial Sequence
<220> FEATURE:
<223> OTHER INFORMATION: Synthetic Construct

<400> SEQUENCE: 420

Met Leu Asn Pro Leu Ile Tyr Ser Leu Arg Ser Lys Lys Val Lys Lys
1 5 10 15

Ala Leu Ala Asn Val Ile Ser Arg Lys
20 25

<210> SEQ ID NO 421
<211> LENGTH: 25
<212> TYPE: PRT
<213> ORGANISM: Artificial Sequence
<220> FEATURE:

<223> OTHER INFORMATION: Synthetic Construct

<400> SEQUENCE: 421

Met Ile Tyr Val Ile Ser Val Met Gly Asn Leu Gly Ile Ile Val Leu
1 5 10 15

Thr Lys Leu Asp Ser Arg Leu Gln Thr
20 25

<210> SEQ ID NO 422
<211> LENGTH: 25
<212> TYPE: PRT
<213> ORGANISM: Artificial Sequence
<220> FEATURE:
<223> OTHER INFORMATION: Synthetic Construct

<400> SEQUENCE: 422

Phe Phe Val Phe Phe Leu Leu Ser Arg Trp Leu Val Lys Ser Ala Arg
1 5 10 15

Trp Leu Ile Ile Thr Asn Lys Leu Asp
20 25

<210> SEQ ID NO 423
<211> LENGTH: 25
<212> TYPE: PRT
<213> ORGANISM: Artificial Sequence
<220> FEATURE:
<223> OTHER INFORMATION: Synthetic Construct

<400> SEQUENCE: 423

Pro Pro Pro Ile Met Leu Ile Gly His Ser Met Gly Ala Ala Ile Ala
1 5 10 15

Val His Thr Ala Ser Ser Asn Leu Val
20 25

<210> SEQ ID NO 424
<211> LENGTH: 25
<212> TYPE: PRT
<213> ORGANISM: Artificial Sequence
<220> FEATURE:
<223> OTHER INFORMATION: Synthetic Construct

<400> SEQUENCE: 424

Val Gln Ala Gly Tyr Pro Arg Gly Ile His Thr Leu Ser Phe Pro Pro
1 5 10 15

Thr Ile Arg Lys Ile Asp Ala Ala Val
20 25

<210> SEQ ID NO 425
<211> LENGTH: 25
<212> TYPE: PRT
<213> ORGANISM: Artificial Sequence
<220> FEATURE:
<223> OTHER INFORMATION: Synthetic Construct

<400> SEQUENCE: 425

Val Val Ala Glu Phe Val Asp Glu Arg Pro Glu Glu Leu Lys Gln Met
1 5 10 15

Glu Ala Phe Arg Ser Ser Ala Lys Trp
20 25

<210> SEQ ID NO 426
<211> LENGTH: 25
<212> TYPE: PRT
<213> ORGANISM: Artificial Sequence
<220> FEATURE:
<223> OTHER INFORMATION: Synthetic Construct

<400> SEQUENCE: 426

Thr Val Glu Val Leu Ser Val Gly Lys Met Thr Pro Leu Arg Val Arg
1 5 10 15

Tyr Ser Phe Tyr Leu Pro Lys Glu Pro
20 25

<210> SEQ ID NO 427
<211> LENGTH: 25
<212> TYPE: PRT
<213> ORGANISM: Artificial Sequence
<220> FEATURE:
<223> OTHER INFORMATION: Synthetic Construct

<400> SEQUENCE: 427

Gln Gly Val Pro Ile Ser Glu Val Ala Glu Ser Gly Leu Gly Leu Ala
1 5 10 15

Phe Ile Ala Phe Pro Lys Ala Val Thr
20 25

<210> SEQ ID NO 428
<211> LENGTH: 25
<212> TYPE: PRT
<213> ORGANISM: Artificial Sequence
<220> FEATURE:
<223> OTHER INFORMATION: Synthetic Construct

<400> SEQUENCE: 428

Ala Gly Val Ile Cys Ser Asp Lys Ala Asp Leu Asp Ile Arg Leu Val
1 5 10 15

Gly Ala His Ser Pro Cys Tyr Gly Arg
20 25

<210> SEQ ID NO 429
<211> LENGTH: 25
<212> TYPE: PRT
<213> ORGANISM: Artificial Sequence
<220> FEATURE:
<223> OTHER INFORMATION: Synthetic Construct

<400> SEQUENCE: 429

Val Thr Glu Phe Tyr Leu Leu Ala Ala Met Ser Tyr Asn Arg Cys Met
1 5 10 15

Ala Ile Cys Lys Pro Leu His Tyr Thr
20 25

<210> SEQ ID NO 430
<211> LENGTH: 25
<212> TYPE: PRT
<213> ORGANISM: Artificial Sequence
<220> FEATURE:
<223> OTHER INFORMATION: Synthetic Construct

<400> SEQUENCE: 430

Leu Ser Trp Ile Ser Gln Gly Met Ser Val Val Tyr Glu Ala Leu Cys
1 5 10 15

Ile Gly Met Ala Ala Leu Ala Ser Leu
20 25

<210> SEQ ID NO 431
<211> LENGTH: 25
<212> TYPE: PRT

<213> ORGANISM: Artificial Sequence
<220> FEATURE:
<223> OTHER INFORMATION: Synthetic Construct

<400> SEQUENCE: 431

Met Phe Ser Gln Ser Glu Leu Arg Thr Ile Glu Gln Phe Leu Leu Ala
1 5 10 15

Thr Arg Val Gly Ser Ile Ala Glu Leu
20 25

<210> SEQ ID NO 432
<211> LENGTH: 25
<212> TYPE: PRT
<213> ORGANISM: Artificial Sequence
<220> FEATURE:
<223> OTHER INFORMATION: Synthetic Construct

<400> SEQUENCE: 432

Lys Lys Arg Tyr Val Trp Leu Ser Gly Glu Thr Leu Phe Phe Ser Lys
1 5 10 15

Ser Pro Glu Trp Gln Met Cys His Ser
20 25

<210> SEQ ID NO 433
<211> LENGTH: 25
<212> TYPE: PRT
<213> ORGANISM: Artificial Sequence
<220> FEATURE:
<223> OTHER INFORMATION: Synthetic Construct

<400> SEQUENCE: 433

Met Ser Arg Arg Thr Cys Thr Val Leu Val Met Ile Phe Trp Ala Val
1 5 10 15

Ser Leu Val His Thr Leu Ser Gln Leu
20 25

<210> SEQ ID NO 434
<211> LENGTH: 22
<212> TYPE: PRT
<213> ORGANISM: Artificial Sequence
<220> FEATURE:
<223> OTHER INFORMATION: Synthetic Construct

<400> SEQUENCE: 434

Pro Phe Val His Pro Thr Thr Leu Pro Leu Leu Phe Phe Leu Ala Met
1 5 10 15

Leu Thr Met Phe Ala Trp
20

<210> SEQ ID NO 435
<211> LENGTH: 25
<212> TYPE: PRT
<213> ORGANISM: Artificial Sequence
<220> FEATURE:
<223> OTHER INFORMATION: Synthetic Construct

<400> SEQUENCE: 435

Gln Ser Leu His Lys Val Leu Glu Pro Phe Leu Leu Gln Arg Val Lys
1 5 10 15

Lys Asp Val Glu Lys Ser Leu Pro Ala
20 25

<210> SEQ ID NO 436
<211> LENGTH: 25

<212> TYPE: PRT
<213> ORGANISM: Artificial Sequence
<220> FEATURE:
<223> OTHER INFORMATION: Synthetic Construct

<400> SEQUENCE: 436

Thr Ile Lys His Tyr Pro Phe Gln Arg Leu Asp Gly Phe Ile Lys Gly
1 5 10 15

Glu Ile Arg Lys Gln Ala Leu Asp His
20 25

<210> SEQ ID NO 437
<211> LENGTH: 25
<212> TYPE: PRT
<213> ORGANISM: Artificial Sequence
<220> FEATURE:
<223> OTHER INFORMATION: Synthetic Construct

<400> SEQUENCE: 437

Pro Leu Ser Pro Phe Ser Ser Asp Ile Asn Asn Met Leu Leu Gln Glu
1 5 10 15

Leu Ser Asn Ala Leu Met Ala Ala Glu
20 25

<210> SEQ ID NO 438
<211> LENGTH: 25
<212> TYPE: PRT
<213> ORGANISM: Artificial Sequence
<220> FEATURE:
<223> OTHER INFORMATION: Synthetic Construct

<400> SEQUENCE: 438

Val Ile Leu Ser Ala Gly Ile Phe Phe Val Ser Ala Arg Leu Ser Asn
1 5 10 15

Ile Ile Gly Ile Ile Val Tyr Ile Ser
20 25

<210> SEQ ID NO 439
<211> LENGTH: 25
<212> TYPE: PRT
<213> ORGANISM: Artificial Sequence
<220> FEATURE:
<223> OTHER INFORMATION: Synthetic Construct

<400> SEQUENCE: 439

Arg Gln Ala Ser Phe Phe Pro Pro Pro Val Pro Asn Ser Phe Val Gln
1 5 10 15

Gln Thr Gln Ile Gly Ser Ala Arg Arg
20 25

<210> SEQ ID NO 440
<211> LENGTH: 25
<212> TYPE: PRT
<213> ORGANISM: Artificial Sequence
<220> FEATURE:
<223> OTHER INFORMATION: Synthetic Construct

<400> SEQUENCE: 440

Arg Gln Ala Ser Phe Phe Pro Pro Pro Val Pro Asn Leu Phe Val Gln
1 5 10 15

Gln Thr Gln Ile Gly Ser Ala Arg Arg
20 25

<210> SEQ ID NO 441

-continued

<211> LENGTH: 25
<212> TYPE: PRT
<213> ORGANISM: Artificial Sequence
<220> FEATURE:
<223> OTHER INFORMATION: Synthetic Construct

<400> SEQUENCE: 441

Ser Phe Leu Phe Met Tyr Leu Val Thr Val Ala Gly Ser Leu Leu Ile
1               5                   10                  15

Ile Leu Val Ile Ile Thr Asp Thr Gln
            20                  25

<210> SEQ ID NO 442
<211> LENGTH: 25
<212> TYPE: PRT
<213> ORGANISM: Artificial Sequence
<220> FEATURE:
<223> OTHER INFORMATION: Synthetic Construct

<400> SEQUENCE: 442

Thr Leu Arg Lys Gly Tyr Gln Ile Gln Asp Phe Lys Ile Asp Leu Ala
1               5                   10                  15

Ser Leu Cys Leu Lys Ala Gly Val Lys
            20                  25

<210> SEQ ID NO 443
<211> LENGTH: 25
<212> TYPE: PRT
<213> ORGANISM: Artificial Sequence
<220> FEATURE:
<223> OTHER INFORMATION: Synthetic Construct

<400> SEQUENCE: 443

Asp Ile Leu Met Glu Phe Gly His Leu Phe Pro Pro Ser Thr Pro Ile
1               5                   10                  15

Phe Ala Gly Gly Ala Asn Asp Arg Trp
            20                  25

<210> SEQ ID NO 444
<211> LENGTH: 25
<212> TYPE: PRT
<213> ORGANISM: Artificial Sequence
<220> FEATURE:
<223> OTHER INFORMATION: Synthetic Construct

<400> SEQUENCE: 444

Ala Gln Val His His Ile Pro Gln Pro His Leu Thr Leu Ile Ser Leu
1               5                   10                  15

Ser His Leu Thr His Ser Ile Ile Pro
            20                  25

<210> SEQ ID NO 445
<211> LENGTH: 25
<212> TYPE: PRT
<213> ORGANISM: Artificial Sequence
<220> FEATURE:
<223> OTHER INFORMATION: Synthetic Construct

<400> SEQUENCE: 445

Val Val Glu Thr Leu Leu Lys His Gly Ala Asn Ile Tyr Asp Gln Leu
1               5                   10                  15

Tyr Asp Gly Ala Thr Ala Leu Phe Leu
            20                  25

<210> SEQ ID NO 446
<211> LENGTH: 25
<212> TYPE: PRT
<213> ORGANISM: Artificial Sequence
<220> FEATURE:
<223> OTHER INFORMATION: Synthetic Construct

<400> SEQUENCE: 446

```
Gly Leu Arg Gln Leu Asp Met Leu Asp Leu Ser Asn Tyr Ser Leu Ala
1               5                   10                  15

Ser Val Pro Glu Gly Leu Trp Ala Ser
            20                  25
```

<210> SEQ ID NO 447
<211> LENGTH: 25
<212> TYPE: PRT
<213> ORGANISM: Artificial Sequence
<220> FEATURE:
<223> OTHER INFORMATION: Synthetic Construct

<400> SEQUENCE: 447

```
Pro Tyr Glu Cys Ser Asp Cys Gly Lys Ala Phe Ile Ser Gln Ser Ser
1               5                   10                  15

Leu Lys Lys His Met Arg Ser His Thr
            20                  25
```

<210> SEQ ID NO 448
<211> LENGTH: 25
<212> TYPE: PRT
<213> ORGANISM: Artificial Sequence
<220> FEATURE:
<223> OTHER INFORMATION: Synthetic Construct

<400> SEQUENCE: 448

```
Cys Phe Gln His Val Val Ala Val Glu Ala Tyr Thr Leu Glu Ala Cys
1               5                   10                  15

Ile Val Glu Ala Leu Gly Ile Gln Thr
            20                  25
```

<210> SEQ ID NO 449
<211> LENGTH: 25
<212> TYPE: PRT
<213> ORGANISM: Artificial Sequence
<220> FEATURE:
<223> OTHER INFORMATION: Synthetic Construct

<400> SEQUENCE: 449

```
Glu Cys Thr Asp Cys Gly Lys Ala Phe Thr Gln Lys Phe Thr Leu Lys
1               5                   10                  15

Ile His Gln Lys Ile His Thr Gly Glu
            20                  25
```

<210> SEQ ID NO 450
<211> LENGTH: 25
<212> TYPE: PRT
<213> ORGANISM: Artificial Sequence
<220> FEATURE:
<223> OTHER INFORMATION: Synthetic Construct

<400> SEQUENCE: 450

```
Cys Gln Glu Pro Leu Thr Met Met Ala Leu His Ile Ser Glu Glu Asn
1               5                   10                  15

Arg Cys Met Asp Ile Leu Glu Leu Ser
            20                  25
```

<210> SEQ ID NO 451
<211> LENGTH: 25
<212> TYPE: PRT
<213> ORGANISM: Artificial Sequence
<220> FEATURE:
<223> OTHER INFORMATION: Synthetic Construct

<400> SEQUENCE: 451

```
Cys Gln Glu Pro Leu Thr Met Met Ala Leu His Ile Leu Glu Glu Asn
1               5                   10                  15

Arg Cys Met Asp Ile Leu Glu Leu Ser
            20                  25
```

<210> SEQ ID NO 452
<211> LENGTH: 25
<212> TYPE: PRT
<213> ORGANISM: Artificial Sequence
<220> FEATURE:
<223> OTHER INFORMATION: Synthetic Construct

<400> SEQUENCE: 452

```
Cys Met Gly Gly Gly Asp Arg Asp Ile Leu Cys Lys Asp Leu Ala Ser
1               5                   10                  15

Tyr Val Ala Ala Cys Gln Ala Ala Gly
            20                  25
```

<210> SEQ ID NO 453
<211> LENGTH: 25
<212> TYPE: PRT
<213> ORGANISM: Artificial Sequence
<220> FEATURE:
<223> OTHER INFORMATION: Synthetic Construct

<400> SEQUENCE: 453

```
Val Pro Cys Ser Pro Ser Pro Leu Ala Gly Glu Ile Cys Arg Gly Thr
1               5                   10                  15

Ser Ala Ala Ser Arg Met Ile Thr Asn
            20                  25
```

<210> SEQ ID NO 454
<211> LENGTH: 25
<212> TYPE: PRT
<213> ORGANISM: Artificial Sequence
<220> FEATURE:
<223> OTHER INFORMATION: Synthetic Construct

<400> SEQUENCE: 454

```
Arg Ser Pro Asp Lys Pro Gly Lys Gly Ser Tyr Trp Val Leu His Pro
1               5                   10                  15

Ser Ser Gly Asn Met Phe Glu Asn Gly
            20                  25
```

<210> SEQ ID NO 455
<211> LENGTH: 25
<212> TYPE: PRT
<213> ORGANISM: Artificial Sequence
<220> FEATURE:
<223> OTHER INFORMATION: Synthetic Construct

<400> SEQUENCE: 455

```
Thr Arg Asp Lys His Gly Val Asp Lys Gly Leu Phe Leu Leu Tyr Tyr
1               5                   10                  15

Leu Tyr Leu Glu Thr Ser Asp Ser Leu
            20                  25
```

<210> SEQ ID NO 456
<211> LENGTH: 25
<212> TYPE: PRT
<213> ORGANISM: Artificial Sequence
<220> FEATURE:
<223> OTHER INFORMATION: Synthetic Construct

<400> SEQUENCE: 456

Tyr Lys Ile Ile Asp Ile Leu Val Asn Pro Thr Ser Phe Leu Ala Phe
1               5                   10                  15

Phe Asn Ser Cys Leu Asn Pro Met Leu
            20                  25

<210> SEQ ID NO 457
<211> LENGTH: 25
<212> TYPE: PRT
<213> ORGANISM: Artificial Sequence
<220> FEATURE:
<223> OTHER INFORMATION: Synthetic Construct

<400> SEQUENCE: 457

Ser Gln Gln Leu Gln Gln Gly Phe Pro Asn Leu Gly Ser Thr Cys Tyr
1               5                   10                  15

Met Asn Ala Val Leu Gln Ser Leu Phe
            20                  25

<210> SEQ ID NO 458
<211> LENGTH: 25
<212> TYPE: PRT
<213> ORGANISM: Artificial Sequence
<220> FEATURE:
<223> OTHER INFORMATION: Synthetic Construct

<400> SEQUENCE: 458

Gly Glu Arg Pro Tyr Glu Cys Ser Glu Cys Gly Lys Leu Phe His Arg
1               5                   10                  15

Ser Ser Ser Leu Leu Arg His Gln Arg
            20                  25

<210> SEQ ID NO 459
<211> LENGTH: 25
<212> TYPE: PRT
<213> ORGANISM: Artificial Sequence
<220> FEATURE:
<223> OTHER INFORMATION: Synthetic Construct

<400> SEQUENCE: 459

Asn Lys Leu Val Thr Glu Leu Arg Gly Leu Ser Asp Lys Ala Val Thr
1               5                   10                  15

Ser Leu Leu Pro Gln Leu Ile Glu Val
            20                  25

<210> SEQ ID NO 460
<211> LENGTH: 25
<212> TYPE: PRT
<213> ORGANISM: Artificial Sequence
<220> FEATURE:
<223> OTHER INFORMATION: Synthetic Construct

<400> SEQUENCE: 460

Ile Glu Leu Ala Glu Leu Gln Pro Pro Met Phe Asp Phe His Pro Met
1               5                   10                  15

Arg Ala Leu Phe Leu Met Thr Lys Ser 20 25

<210> SEQ ID NO 461
<211> LENGTH: 25
<212> TYPE: PRT
<213> ORGANISM: Artificial Sequence
<220> FEATURE:
<223> OTHER INFORMATION: Synthetic Construct

<400> SEQUENCE: 461

Arg Met Ser Phe Ile Val Phe Ser Thr Arg Gly Thr Ala Leu Met Lys
1 5 10 15

Leu Thr Glu Asp Arg Glu Gln Ile Arg
20 25

<210> SEQ ID NO 462
<211> LENGTH: 25
<212> TYPE: PRT
<213> ORGANISM: Artificial Sequence
<220> FEATURE:
<223> OTHER INFORMATION: Synthetic Construct

<400> SEQUENCE: 462

Glu Glu Val Trp Arg Met Glu Ile Tyr Leu Ser Leu Glu Val Leu Ala
1 5 10 15

Leu Gly Thr Leu Ser Leu Leu Ala Val
20 25

<210> SEQ ID NO 463
<211> LENGTH: 25
<212> TYPE: PRT
<213> ORGANISM: Artificial Sequence
<220> FEATURE:
<223> OTHER INFORMATION: Synthetic Construct

<400> SEQUENCE: 463

Asp Glu Leu Pro Asn Thr Ser Val Val Ile Val Phe Tyr Asn Glu Ala
1 5 10 15

Trp Ser Thr Leu Leu Arg Thr Val Tyr
20 25

<210> SEQ ID NO 464
<211> LENGTH: 25
<212> TYPE: PRT
<213> ORGANISM: Artificial Sequence
<220> FEATURE:
<223> OTHER INFORMATION: Synthetic Construct

<400> SEQUENCE: 464

Phe Leu Leu Asn Met Leu Pro Asp Gln Glu Tyr Lys Ala Ala Phe Thr
1 5 10 15

Lys Thr Phe Val Gln His Tyr Ala Phe
20 25

<210> SEQ ID NO 465
<211> LENGTH: 25
<212> TYPE: PRT
<213> ORGANISM: Artificial Sequence
<220> FEATURE:
<223> OTHER INFORMATION: Synthetic Construct

<400> SEQUENCE: 465

Phe Glu Val Thr Gly Leu Val Glu Asp His Arg Tyr Lys Phe Arg Val
1 5 10 15

-continued

```
Ile Ala Arg Asn Ala Ala Gly Val Phe
            20                  25


<210> SEQ ID NO 466
<211> LENGTH: 25
<212> TYPE: PRT
<213> ORGANISM: Artificial Sequence
<220> FEATURE:
<223> OTHER INFORMATION: Synthetic Construct

<400> SEQUENCE: 466

Phe Tyr Ile Thr Thr Lys Leu Arg Asn Pro His Tyr Phe Pro Glu Thr
1               5                   10                  15

Ser Val Lys Val Thr Leu Leu Asn Phe
            20                  25


<210> SEQ ID NO 467
<211> LENGTH: 25
<212> TYPE: PRT
<213> ORGANISM: Artificial Sequence
<220> FEATURE:
<223> OTHER INFORMATION: Synthetic Construct

<400> SEQUENCE: 467

Tyr His Gly Ile Ser Gly Ala Leu Arg Ala Thr Thr Leu Cys Ile Thr
1               5                   10                  15

Val Lys Asn Pro Ala Val Met Met Gly
            20                  25


<210> SEQ ID NO 468
<211> LENGTH: 25
<212> TYPE: PRT
<213> ORGANISM: Artificial Sequence
<220> FEATURE:
<223> OTHER INFORMATION: Synthetic Construct

<400> SEQUENCE: 468

Phe Ser Ser Ile Tyr Phe Leu Ala Val Met Ser Val Glu Arg Tyr Leu
1               5                   10                  15

Val Val Leu Ala Thr Val Arg Ser Arg
            20                  25


<210> SEQ ID NO 469
<211> LENGTH: 25
<212> TYPE: PRT
<213> ORGANISM: Artificial Sequence
<220> FEATURE:
<223> OTHER INFORMATION: Synthetic Construct

<400> SEQUENCE: 469

Leu Leu Leu Ala Gly Tyr Leu Ala Gln Gln Tyr Leu Leu Leu Pro Thr
1               5                   10                  15

Pro Lys Val Ile Gly Ile Asp Leu Gly
            20                  25


<210> SEQ ID NO 470
<211> LENGTH: 25
<212> TYPE: PRT
<213> ORGANISM: Artificial Sequence
<220> FEATURE:
<223> OTHER INFORMATION: Synthetic Construct

<400> SEQUENCE: 470

Lys Leu Leu Pro Met Phe Ile Ile Val Val Pro Gly Arg Ile Ser Arg
1               5                   10                  15
```

Ile Leu Phe Thr Asp Asp Ile Ala Cys
20 25

<210> SEQ ID NO 471
<211> LENGTH: 25
<212> TYPE: PRT
<213> ORGANISM: Artificial Sequence
<220> FEATURE:
<223> OTHER INFORMATION: Synthetic Construct

<400> SEQUENCE: 471

Asp Ser Trp Asp Ser Ala Gln Arg Thr Lys Asp Val Phe Pro Gln Leu
1 5 10 15

Asn Ser Ala Thr Ile Ile Asp Ile His
20 25

<210> SEQ ID NO 472
<211> LENGTH: 25
<212> TYPE: PRT
<213> ORGANISM: Artificial Sequence
<220> FEATURE:
<223> OTHER INFORMATION: Synthetic Construct

<400> SEQUENCE: 472

Arg Ala Ile Arg Gln Ala Arg Ala Arg Ala Arg Leu Ser Val Thr Thr
1 5 10 15

Trp Arg Ile Ser Ala Gly Ser Gly Gly
20 25

<210> SEQ ID NO 473
<211> LENGTH: 25
<212> TYPE: PRT
<213> ORGANISM: Artificial Sequence
<220> FEATURE:
<223> OTHER INFORMATION: Synthetic Construct

<400> SEQUENCE: 473

Cys Val Ile Leu Phe Phe Thr Thr Phe Phe Leu Ser Leu Phe Leu Lys
1 5 10 15

Gln Phe Lys Thr Lys Arg Tyr Phe Pro
20 25

<210> SEQ ID NO 474
<211> LENGTH: 25
<212> TYPE: PRT
<213> ORGANISM: Artificial Sequence
<220> FEATURE:
<223> OTHER INFORMATION: Synthetic Construct

<400> SEQUENCE: 474

Leu Arg Glu Met Glu Glu Gly Pro Glu Phe Trp Ala Glu Leu Asn Leu
1 5 10 15

Val Ala Pro Ala Ile Lys Glu Arg Met
20 25

<210> SEQ ID NO 475
<211> LENGTH: 25
<212> TYPE: PRT
<213> ORGANISM: Artificial Sequence
<220> FEATURE:
<223> OTHER INFORMATION: Synthetic Construct

<400> SEQUENCE: 475

Thr Lys Val Lys Val Asn Phe Asp Asn Val Gly Ala Glu Tyr Leu Ala 1 5 10 15

Leu Leu Gln Val Tyr Glu Glu Gln Pro
20 25

<210> SEQ ID NO 476
<211> LENGTH: 25
<212> TYPE: PRT
<213> ORGANISM: Artificial Sequence
<220> FEATURE:
<223> OTHER INFORMATION: Synthetic Construct

<400> SEQUENCE: 476

Phe Ser Ile Leu Arg Thr Leu Leu Pro Leu Val Ser Gln Arg Val Cys
1 5 10 15

Thr Thr Ala Gly Gly Val Pro Val Thr
20 25

<210> SEQ ID NO 477
<211> LENGTH: 25
<212> TYPE: PRT
<213> ORGANISM: Artificial Sequence
<220> FEATURE:
<223> OTHER INFORMATION: Synthetic Construct

<400> SEQUENCE: 477

Ser Ser Ser Ser Phe Arg Glu Gly Glu Ala Trp Thr Leu Val Cys Leu
1 5 10 15

Pro Lys Phe Asn Ala Ala Gly Phe Phe
20 25

<210> SEQ ID NO 478
<211> LENGTH: 25
<212> TYPE: PRT
<213> ORGANISM: Artificial Sequence
<220> FEATURE:
<223> OTHER INFORMATION: Synthetic Construct

<400> SEQUENCE: 478

Gln Thr Phe Leu Asn Leu Glu Glu Lys Thr Ser Asp Arg Tyr Met Asn
1 5 10 15

Gly Asn Tyr Leu Val Ile Leu Val Ser
20 25

<210> SEQ ID NO 479
<211> LENGTH: 25
<212> TYPE: PRT
<213> ORGANISM: Artificial Sequence
<220> FEATURE:
<223> OTHER INFORMATION: Synthetic Construct

<400> SEQUENCE: 479

Cys Pro Ile Arg Gly Gly Phe Phe Ile Leu Gln Leu Tyr Asp Glu Leu
1 5 10 15

Leu Tyr Glu Val Ala Glu Glu Asp Val
20 25

<210> SEQ ID NO 480
<211> LENGTH: 25
<212> TYPE: PRT
<213> ORGANISM: Artificial Sequence
<220> FEATURE:
<223> OTHER INFORMATION: Synthetic Construct

<400> SEQUENCE: 480

Leu His Phe His Arg Ser Thr Leu Arg Asn Leu Gln Arg Asn Pro Met
1 5 10 15

Leu Ala Ala Thr Ala Pro His Phe Glu
20 25

<210> SEQ ID NO 481
<211> LENGTH: 25
<212> TYPE: PRT
<213> ORGANISM: Artificial Sequence
<220> FEATURE:
<223> OTHER INFORMATION: Synthetic Construct

<400> SEQUENCE: 481

Ile Asp Glu Met Gly Val Arg Tyr Glu Phe Val Glu Phe Phe Met Ser
1 5 10 15

Thr Gly Ser Gln Pro Thr Cys Gln Ala
20 25

<210> SEQ ID NO 482
<211> LENGTH: 25
<212> TYPE: PRT
<213> ORGANISM: Artificial Sequence
<220> FEATURE:
<223> OTHER INFORMATION: Synthetic Construct

<400> SEQUENCE: 482

Ala Phe Leu Tyr Val Lys Gln Gln Pro Trp Tyr Cys Lys Val Tyr Gln
1 5 10 15

Tyr Ser Glu Cys Phe Leu Ala Asn Gln
20 25

<210> SEQ ID NO 483
<211> LENGTH: 25
<212> TYPE: PRT
<213> ORGANISM: Artificial Sequence
<220> FEATURE:
<223> OTHER INFORMATION: Synthetic Construct

<400> SEQUENCE: 483

Gly Ser Pro Glu Glu Met Leu Phe His Phe Gly Met Ile Trp Gln Ile
1 5 10 15

Asn Gly Thr Gly Leu Leu Gly Lys Arg
20 25

<210> SEQ ID NO 484
<211> LENGTH: 25
<212> TYPE: PRT
<213> ORGANISM: Artificial Sequence
<220> FEATURE:
<223> OTHER INFORMATION: Synthetic Construct

<400> SEQUENCE: 484

Ser Leu Pro Val Thr Asp Ala Ser Ser Val Phe Thr Ser His Ala Thr
1 5 10 15

Ser Leu Pro Val Thr Ile Pro Ser Ser
20 25

<210> SEQ ID NO 485
<211> LENGTH: 25
<212> TYPE: PRT
<213> ORGANISM: Artificial Sequence
<220> FEATURE:
<223> OTHER INFORMATION: Synthetic Construct

<400> SEQUENCE: 485

Ile Gln Thr Tyr Ile Pro Cys Ile Met Thr Val Ile Pro Ser Gln Val
1 5 10 15

Ser Phe Trp Ile Asn Lys Glu Ser Val
20 25

<210> SEQ ID NO 486
<211> LENGTH: 25
<212> TYPE: PRT
<213> ORGANISM: Artificial Sequence
<220> FEATURE:
<223> OTHER INFORMATION: Synthetic Construct

<400> SEQUENCE: 486

Leu Arg Pro Lys Thr Gly Val Arg Gly Leu His Lys Leu Leu Thr Asp
1 5 10 15

Val Ala Leu Glu His His Glu Glu Cys
20 25

<210> SEQ ID NO 487
<211> LENGTH: 25
<212> TYPE: PRT
<213> ORGANISM: Artificial Sequence
<220> FEATURE:
<223> OTHER INFORMATION: Synthetic Construct

<400> SEQUENCE: 487

Leu Asp Val Gly Val Leu Pro Arg Trp Val Pro Lys Lys Ala Leu Thr
1 5 10 15

Gly Leu Val Cys Leu Val Cys Phe Leu
20 25

<210> SEQ ID NO 488
<211> LENGTH: 25
<212> TYPE: PRT
<213> ORGANISM: Artificial Sequence
<220> FEATURE:
<223> OTHER INFORMATION: Synthetic Construct

<400> SEQUENCE: 488

Val Asn Lys Pro Glu Trp Pro Ala Ala Glu Leu Leu Phe Ser Leu Leu
1 5 10 15

Gly Arg Leu Leu Val His Gln Phe Ser
20 25

<210> SEQ ID NO 489
<211> LENGTH: 25
<212> TYPE: PRT
<213> ORGANISM: Artificial Sequence
<220> FEATURE:
<223> OTHER INFORMATION: Synthetic Construct

<400> SEQUENCE: 489

Thr Ala Glu Asp Asp Leu Lys Thr Asp Phe Tyr Lys Asn Leu Thr Ser
1 5 10 15

Leu Gly His Asn Glu Asn Gln Gln Gly
20 25

<210> SEQ ID NO 490
<211> LENGTH: 25
<212> TYPE: PRT
<213> ORGANISM: Artificial Sequence
<220> FEATURE:
<223> OTHER INFORMATION: Synthetic Construct

<400> SEQUENCE: 490

Cys His Val Phe His Leu Thr Met Ala Gln Leu Thr Ser Asn Met Glu
1 5 10 15

Ser Glu Ser Thr Gln Asp Glu Gln Glu
20 25

<210> SEQ ID NO 491
<211> LENGTH: 25
<212> TYPE: PRT
<213> ORGANISM: Artificial Sequence
<220> FEATURE:
<223> OTHER INFORMATION: Synthetic Construct

<400> SEQUENCE: 491

Asn Ser Pro Phe Val Leu Tyr Pro Leu Gln Asn Gly Phe Ala Pro Cys
1 5 10 15

Thr Glu Leu Val Pro Arg Ala Ala Glu
20 25

<210> SEQ ID NO 492
<211> LENGTH: 25
<212> TYPE: PRT
<213> ORGANISM: Artificial Sequence
<220> FEATURE:
<223> OTHER INFORMATION: Synthetic Construct

<400> SEQUENCE: 492

Arg Arg Gly Phe Ile His Asn Gly Ile Met Val Leu Ser Arg Gln Thr
1 5 10 15

Cys Gly Leu Phe Thr His Thr Ile Phe
20 25

<210> SEQ ID NO 493
<211> LENGTH: 25
<212> TYPE: PRT
<213> ORGANISM: Artificial Sequence
<220> FEATURE:
<223> OTHER INFORMATION: Synthetic Construct

<400> SEQUENCE: 493

Pro Gly Trp Ala Gly Val Gly Ala Ala Val Arg Ala Pro Leu Ala Leu
1 5 10 15

Ala Leu Ala Leu Ala Ser Val Leu Ser
20 25

<210> SEQ ID NO 494
<211> LENGTH: 25
<212> TYPE: PRT
<213> ORGANISM: Artificial Sequence
<220> FEATURE:
<223> OTHER INFORMATION: Synthetic Construct

<400> SEQUENCE: 494

Arg Leu Arg Asn His Glu Arg Arg Glu Ile Gln Arg Lys Ile Leu Ser
1 5 10 15

Ile Leu Gly Leu Pro His Arg Pro Arg
20 25

<210> SEQ ID NO 495
<211> LENGTH: 25
<212> TYPE: PRT
<213> ORGANISM: Artificial Sequence
<220> FEATURE:
<223> OTHER INFORMATION: Synthetic Construct

<400> SEQUENCE: 495

Val Arg Asn Ile Arg Cys Leu Thr Pro Thr Arg Ser Leu Tyr Pro Ala
1 5 10 15

Pro Gly Pro Trp Pro Lys Ser Phe Ser
20 25

<210> SEQ ID NO 496
<211> LENGTH: 25
<212> TYPE: PRT
<213> ORGANISM: Artificial Sequence
<220> FEATURE:
<223> OTHER INFORMATION: Synthetic Construct

<400> SEQUENCE: 496

Lys His Thr Met Ile Leu Met Tyr Asn Trp Phe Thr Asn Ser Val Leu
1 5 10 15

Tyr Gln Gly Leu Ile Met His Met Gly
20 25

<210> SEQ ID NO 497
<211> LENGTH: 25
<212> TYPE: PRT
<213> ORGANISM: Artificial Sequence
<220> FEATURE:
<223> OTHER INFORMATION: Synthetic Construct

<400> SEQUENCE: 497

Asp Cys Leu Ile Phe Lys Ala Thr Ser Pro Ser Gly Phe Lys Met Gln
1 5 10 15

Leu Leu Glu Thr Glu Phe Ser His Thr
20 25

<210> SEQ ID NO 498
<211> LENGTH: 25
<212> TYPE: PRT
<213> ORGANISM: Artificial Sequence
<220> FEATURE:
<223> OTHER INFORMATION: Synthetic Construct

<400> SEQUENCE: 498

Glu Asp Phe Gln Thr Phe His Ala Ser Leu Gln His Trp Lys Pro Arg
1 5 10 15

Leu Ala Arg Lys His Ile Tyr Leu Gln
20 25

<210> SEQ ID NO 499
<211> LENGTH: 25
<212> TYPE: PRT
<213> ORGANISM: Artificial Sequence
<220> FEATURE:
<223> OTHER INFORMATION: Synthetic Construct

<400> SEQUENCE: 499

His Lys Gly Glu Arg Gly Tyr Pro Gly Asn Ile Gly Leu Val Gly Ala
1 5 10 15

Ala Gly Ala Pro Gly Pro His Gly Pro
20 25

<210> SEQ ID NO 500
<211> LENGTH: 25
<212> TYPE: PRT
<213> ORGANISM: Artificial Sequence
<220> FEATURE:

<223> OTHER INFORMATION: Synthetic Construct

<400> SEQUENCE: 500

Ile Pro Ser Asp Thr Phe Thr Ile Ile Pro Asp Phe Asn Ile Tyr Tyr
1 5 10 15

Val Tyr Gly Phe Ser Ser Gly Asn Phe
20 25

<210> SEQ ID NO 501
<211> LENGTH: 25
<212> TYPE: PRT
<213> ORGANISM: Artificial Sequence
<220> FEATURE:
<223> OTHER INFORMATION: Synthetic Construct

<400> SEQUENCE: 501

Gln Tyr Leu Leu Arg Ala Pro Ser Arg Met Pro Arg Ser Leu Leu Ala
1 5 10 15

Pro Ala Ala Pro Gln Lys Trp Pro Ser
20 25

<210> SEQ ID NO 502
<211> LENGTH: 25
<212> TYPE: PRT
<213> ORGANISM: Artificial Sequence
<220> FEATURE:
<223> OTHER INFORMATION: Synthetic Construct

<400> SEQUENCE: 502

Trp Asn Gly Asp Leu Ala Lys Met Thr His Leu Gln Val Gly Leu Ser
1 5 10 15

Pro Glu Thr Ile Glu Lys Ala Arg Leu
20 25

<210> SEQ ID NO 503
<211> LENGTH: 25
<212> TYPE: PRT
<213> ORGANISM: Artificial Sequence
<220> FEATURE:
<223> OTHER INFORMATION: Synthetic Construct

<400> SEQUENCE: 503

Thr Asp Ile Ser Lys Arg Ser Ile Tyr Asp Lys Tyr Arg Ser Leu Gly
1 5 10 15

Leu Tyr Val Ala Glu Gln Phe Gly Asp
20 25

<210> SEQ ID NO 504
<211> LENGTH: 25
<212> TYPE: PRT
<213> ORGANISM: Artificial Sequence
<220> FEATURE:
<223> OTHER INFORMATION: Synthetic Construct

<400> SEQUENCE: 504

Leu Glu Asn Tyr Ile Val Glu Asn Met Lys Ser Glu Ile Ala Gln Ile
1 5 10 15

Gln Gln Asn Ala Val Gln Asn His Thr
20 25

<210> SEQ ID NO 505
<211> LENGTH: 19
<212> TYPE: PRT
<213> ORGANISM: Artificial Sequence -continued
<220> FEATURE:
<223> OTHER INFORMATION: Synthetic Construct

<400> SEQUENCE: 505

Met Ala Pro Lys Pro Gly Thr Glu Trp Ser Thr Ala Leu Ser His Leu
1 5 10 15

Val Leu Gly

<210> SEQ ID NO 506
<211> LENGTH: 25
<212> TYPE: PRT
<213> ORGANISM: Artificial Sequence
<220> FEATURE:
<223> OTHER INFORMATION: Synthetic Construct

<400> SEQUENCE: 506

Ala Pro Ser Gly His Pro Arg Ser Ala Val Ser Phe Val Tyr Ala Ala
1 5 10 15

Gly Ala Gly Gln Leu Arg Ser Ala Val
20 25

<210> SEQ ID NO 507
<211> LENGTH: 25
<212> TYPE: PRT
<213> ORGANISM: Artificial Sequence
<220> FEATURE:
<223> OTHER INFORMATION: Synthetic Construct

<400> SEQUENCE: 507

Ser Ser Ser Glu Gly Gly Pro Asp Ala Val Ile Ile Arg Met Thr Lys
1 5 10 15

Ile Pro Val Ile Glu Asn Pro Gln Tyr
20 25

<210> SEQ ID NO 508
<211> LENGTH: 25
<212> TYPE: PRT
<213> ORGANISM: Artificial Sequence
<220> FEATURE:
<223> OTHER INFORMATION: Synthetic Construct

<400> SEQUENCE: 508

Ile Leu Ala Val Leu Lys Leu Ala Cys Ala Asp Ile Phe Leu Asn Ile
1 5 10 15

Ile Thr Met Val Ile Ser Asn Met Ala
20 25

<210> SEQ ID NO 509
<211> LENGTH: 25
<212> TYPE: PRT
<213> ORGANISM: Artificial Sequence
<220> FEATURE:
<223> OTHER INFORMATION: Synthetic Construct

<400> SEQUENCE: 509

Pro Lys Leu Gln Thr Val Phe Phe Val Leu Ile Leu Leu Met Tyr Leu
1 5 10 15

Met Ile Leu Leu Gly Asn Gly Val Leu
20 25

<210> SEQ ID NO 510
<211> LENGTH: 25
<212> TYPE: PRT
<213> ORGANISM: Artificial Sequence

```
<220> FEATURE:
<223> OTHER INFORMATION: Synthetic Construct

<400> SEQUENCE: 510

Val Leu Ile Leu Trp Met Tyr Leu Met Ile Leu Leu Glu Asn Gly Val
1               5                   10                  15

Leu Ile Ser Val Ile Ile Phe Asp Ser
            20                  25


<210> SEQ ID NO 511
<211> LENGTH: 25
<212> TYPE: PRT
<213> ORGANISM: Artificial Sequence
<220> FEATURE:
<223> OTHER INFORMATION: Synthetic Construct

<400> SEQUENCE: 511

Ile Gln Asp Asn Val Arg Arg Gln Ser Ser Arg Val Leu Trp Ala Glu
1               5                   10                  15

Ala Arg Ala Pro His Val Cys Arg Pro
            20                  25


<210> SEQ ID NO 512
<211> LENGTH: 25
<212> TYPE: PRT
<213> ORGANISM: Artificial Sequence
<220> FEATURE:
<223> OTHER INFORMATION: Synthetic Construct

<400> SEQUENCE: 512

Asp Pro His Ser Asn Phe Tyr His Phe Thr Arg Pro Phe Ile Lys Pro
1               5                   10                  15

Gln Cys Ala Ala Tyr Gly Lys Ala Leu
            20                  25


<210> SEQ ID NO 513
<211> LENGTH: 25
<212> TYPE: PRT
<213> ORGANISM: Artificial Sequence
<220> FEATURE:
<223> OTHER INFORMATION: Synthetic Construct

<400> SEQUENCE: 513

Tyr Gln Asn Ile Lys Ile Leu His Ser Lys Gln Phe Glu Asn Ile Leu
1               5                   10                  15

Ile Leu Ser Gly Asp Val Asn Leu Ala
            20                  25


<210> SEQ ID NO 514
<211> LENGTH: 25
<212> TYPE: PRT
<213> ORGANISM: Artificial Sequence
<220> FEATURE:
<223> OTHER INFORMATION: Synthetic Construct

<400> SEQUENCE: 514

Asn Gln Thr Val Glu Gln Leu Gln Lys Met Leu Arg Lys Met Arg Gly
1               5                   10                  15

Ser Ile Thr Phe Lys Ile Val Pro Ser
            20                  25


<210> SEQ ID NO 515
<211> LENGTH: 25
<212> TYPE: PRT
```

-continued

```
<213> ORGANISM: Artificial Sequence
<220> FEATURE:
<223> OTHER INFORMATION: Synthetic Construct

<400> SEQUENCE: 515

Ser Gly Ser Leu Phe Gln Glu Ala Leu Val Leu Gln Lys Lys Thr Asp
1               5                   10                  15

Ala Glu Glu Asp Ser Leu Lys Asn Leu
            20                  25


<210> SEQ ID NO 516
<211> LENGTH: 25
<212> TYPE: PRT
<213> ORGANISM: Artificial Sequence
<220> FEATURE:
<223> OTHER INFORMATION: Synthetic Construct

<400> SEQUENCE: 516

Ala Ala Phe His Trp Ser Leu Leu Gly Pro Glu His Ser Leu Ala Ser
1               5                   10                  15

Leu Lys Val Arg Ala His Gln Leu Val
            20                  25


<210> SEQ ID NO 517
<211> LENGTH: 25
<212> TYPE: PRT
<213> ORGANISM: Artificial Sequence
<220> FEATURE:
<223> OTHER INFORMATION: Synthetic Construct

<400> SEQUENCE: 517

Cys His Ala Leu Pro Phe Ile Thr Ser Gly Thr Tyr Ile Cys Thr Asn
1               5                   10                  15

Gly Val Leu Leu Asp Ser Arg Cys Asp
            20                  25


<210> SEQ ID NO 518
<211> LENGTH: 25
<212> TYPE: PRT
<213> ORGANISM: Artificial Sequence
<220> FEATURE:
<223> OTHER INFORMATION: Synthetic Construct

<400> SEQUENCE: 518

Tyr Gln Leu Tyr Val Ser Leu Ile Ser Ala Glu Val Leu Leu Gly Arg
1               5                   10                  15

Val Val Leu Met Val Phe Ser Leu Val
            20                  25


<210> SEQ ID NO 519
<211> LENGTH: 25
<212> TYPE: PRT
<213> ORGANISM: Artificial Sequence
<220> FEATURE:
<223> OTHER INFORMATION: Synthetic Construct

<400> SEQUENCE: 519

Pro Phe Tyr Leu Gly His Thr Ile Lys Ser Gly Asp Phe Glu Tyr Val
1               5                   10                  15

Gly Met Glu Gly Gly Ile Val Leu Ser
            20                  25


<210> SEQ ID NO 520
<211> LENGTH: 25
```

<212> TYPE: PRT
<213> ORGANISM: Artificial Sequence
<220> FEATURE:
<223> OTHER INFORMATION: Synthetic Construct

<400> SEQUENCE: 520

Asn Val Val Leu Lys Ser Tyr Arg Gly Asn Gln Asn Tyr Leu His Leu
1               5                   10                  15

Thr Leu Gln Asn Asn Asn Gly Leu Phe
            20                  25

<210> SEQ ID NO 521
<211> LENGTH: 25
<212> TYPE: PRT
<213> ORGANISM: Artificial Sequence
<220> FEATURE:
<223> OTHER INFORMATION: Synthetic Construct

<400> SEQUENCE: 521

Leu Glu Tyr Arg Glu Val Pro Asn Ser Ser Pro Pro Cys Tyr Glu Phe
1               5                   10                  15

Leu Trp Gly Pro Arg Ala His Ser Glu
            20                  25

<210> SEQ ID NO 522
<211> LENGTH: 13
<212> TYPE: PRT
<213> ORGANISM: Artificial Sequence
<220> FEATURE:
<223> OTHER INFORMATION: Synthetic Construct

<400> SEQUENCE: 522

Ile Lys Asp Leu Glu Glu Lys Ser Asn Arg Lys His Glu
1               5                   10

<210> SEQ ID NO 523
<211> LENGTH: 14
<212> TYPE: PRT
<213> ORGANISM: Artificial Sequence
<220> FEATURE:
<223> OTHER INFORMATION: Synthetic Construct

<400> SEQUENCE: 523

Pro Thr Pro Ser Met Gln Leu Pro Pro Ala Leu Pro Leu Gln
1               5                   10

<210> SEQ ID NO 524
<211> LENGTH: 14
<212> TYPE: PRT
<213> ORGANISM: Artificial Sequence
<220> FEATURE:
<223> OTHER INFORMATION: Synthetic Construct

<400> SEQUENCE: 524

Met Asn Leu Phe Asp Phe Phe Arg Asp Trp Asp Leu Glu Gln
1               5                   10

<210> SEQ ID NO 525
<211> LENGTH: 25
<212> TYPE: PRT
<213> ORGANISM: Artificial Sequence
<220> FEATURE:
<223> OTHER INFORMATION: Synthetic Construct

<400> SEQUENCE: 525

Gly Val Asp Ser Gly Arg Pro Arg Ala Pro Leu Val Ser Ser Glu Gly 1 5 10 15

Ser Ser Ala Trp Asp Ser Ser Asp Arg
20 25

<210> SEQ ID NO 526
<211> LENGTH: 25
<212> TYPE: PRT
<213> ORGANISM: Artificial Sequence
<220> FEATURE:
<223> OTHER INFORMATION: Synthetic Construct

<400> SEQUENCE: 526

Ala Leu Ala Lys Leu Asp Lys Ala Arg Tyr Gln Glu Lys Met Met Asn
1 5 10 15

Tyr Val Gly Lys Arg Lys Lys Arg Arg
20 25

<210> SEQ ID NO 527
<211> LENGTH: 25
<212> TYPE: PRT
<213> ORGANISM: Artificial Sequence
<220> FEATURE:
<223> OTHER INFORMATION: Synthetic Construct

<400> SEQUENCE: 527

Ser Ile Ser Gly Glu Ile Cys Gly Ser Gln Gln Ala Glu Gly Gly Ala
1 5 10 15

Gly Thr Thr Thr Ala Lys Lys Arg Arg
20 25

<210> SEQ ID NO 528
<211> LENGTH: 25
<212> TYPE: PRT
<213> ORGANISM: Artificial Sequence
<220> FEATURE:
<223> OTHER INFORMATION: Synthetic Construct

<400> SEQUENCE: 528

Asp Gln Ser Ser Gln Gly Asp Glu Glu Lys Asp Pro Leu Lys Ser His
1 5 10 15

Pro Tyr Ser Val Glu Thr Pro Tyr Gly
20 25

<210> SEQ ID NO 529
<211> LENGTH: 25
<212> TYPE: PRT
<213> ORGANISM: Artificial Sequence
<220> FEATURE:
<223> OTHER INFORMATION: Synthetic Construct

<400> SEQUENCE: 529

Ser Glu Glu Glu Asp Phe Gly Asp Pro Arg Thr Tyr Asn Pro Asp Phe
1 5 10 15

Lys Gly Pro Val Ala Asn Arg Ser Cys
20 25

<210> SEQ ID NO 530
<211> LENGTH: 25
<212> TYPE: PRT
<213> ORGANISM: Artificial Sequence
<220> FEATURE:
<223> OTHER INFORMATION: Synthetic Construct

<400> SEQUENCE: 530

Pro Val Trp Phe His Val Leu Phe Tyr Leu Ala Val Glu Ile Met Phe
1 5 10 15

Leu Val Asn Thr Val Leu Trp Val Thr
20 25

<210> SEQ ID NO 531
<211> LENGTH: 25
<212> TYPE: PRT
<213> ORGANISM: Artificial Sequence
<220> FEATURE:
<223> OTHER INFORMATION: Synthetic Construct

<400> SEQUENCE: 531

Asp Asp Glu Ile Tyr Glu Gly Glu Tyr Gln Gly Ile Leu Arg Ala Glu
1 5 10 15

Ser Gly Gly Lys Gly Glu Arg Met Ala
20 25

<210> SEQ ID NO 532
<211> LENGTH: 25
<212> TYPE: PRT
<213> ORGANISM: Artificial Sequence
<220> FEATURE:
<223> OTHER INFORMATION: Synthetic Construct

<400> SEQUENCE: 532

Phe Gly Glu Gln Glu Gly Asn Leu Ala Thr Gln Ser Leu Pro Pro Lys
1 5 10 15

Glu Ala Thr Gln Arg Pro Cys Glu Asp
20 25

<210> SEQ ID NO 533
<211> LENGTH: 25
<212> TYPE: PRT
<213> ORGANISM: Artificial Sequence
<220> FEATURE:
<223> OTHER INFORMATION: Synthetic Construct

<400> SEQUENCE: 533

Ser Ser Ser Ser Tyr Gly Gln His Gly Ser Gly Ser His Gln Ser Leu
1 5 10 15

Gly His Gly Gln His Gly Ser Gly Ser
20 25

<210> SEQ ID NO 534
<211> LENGTH: 25
<212> TYPE: PRT
<213> ORGANISM: Artificial Sequence
<220> FEATURE:
<223> OTHER INFORMATION: Synthetic Construct

<400> SEQUENCE: 534

Gln Ala Arg Asp Ser Ser Arg His Ser Ala Ser Gln Lys Gly Gln Asp
1 5 10 15

Thr Ile Arg Gly His Pro Gly Ser Ser
20 25

<210> SEQ ID NO 535
<211> LENGTH: 25
<212> TYPE: PRT
<213> ORGANISM: Artificial Sequence
<220> FEATURE:
<223> OTHER INFORMATION: Synthetic Construct

<400> SEQUENCE: 535

Gly Ser Gly Arg Arg Gly Gly Arg Phe Ser Ala Gln Glu Met Gly Thr
1 5 10 15

Phe Asn Pro Ala Asp Tyr Ala Glu Pro
20 25

<210> SEQ ID NO 536
<211> LENGTH: 25
<212> TYPE: PRT
<213> ORGANISM: Artificial Sequence
<220> FEATURE:
<223> OTHER INFORMATION: Synthetic Construct

<400> SEQUENCE: 536

Gly Ile Arg Ala Gln Asn Ile Cys Lys Val Leu Asn Cys Tyr Leu Asp
1 5 10 15

Ile Lys Glu Ile Leu Gln Ser Leu Leu
20 25

<210> SEQ ID NO 537
<211> LENGTH: 25
<212> TYPE: PRT
<213> ORGANISM: Artificial Sequence
<220> FEATURE:
<223> OTHER INFORMATION: Synthetic Construct

<400> SEQUENCE: 537

Ile Ile Val Thr Ile Ile Cys Ile Asp His His Leu Tyr Thr Pro Met
1 5 10 15

Tyr Phe Phe Leu Ser Met Leu Ala Ser
20 25

<210> SEQ ID NO 538
<211> LENGTH: 25
<212> TYPE: PRT
<213> ORGANISM: Artificial Sequence
<220> FEATURE:
<223> OTHER INFORMATION: Synthetic Construct

<400> SEQUENCE: 538

Ile Phe Thr Cys Ile Cys Gly Ile Gln His Leu Glu Gln Ile Gly Lys
1 5 10 15

Lys Leu Asn Leu Phe Asp Ser Leu Tyr
20 25

<210> SEQ ID NO 539
<211> LENGTH: 25
<212> TYPE: PRT
<213> ORGANISM: Artificial Sequence
<220> FEATURE:
<223> OTHER INFORMATION: Synthetic Construct

<400> SEQUENCE: 539

Gly Asp Ile Val Glu Phe Val Cys Lys Ser Gly Tyr Gln Pro Thr Lys
1 5 10 15

Ser His Ser Phe Arg Ala Met Cys Gln
20 25

<210> SEQ ID NO 540
<211> LENGTH: 25
<212> TYPE: PRT
<213> ORGANISM: Artificial Sequence
<220> FEATURE:
<223> OTHER INFORMATION: Synthetic Construct

<400> SEQUENCE: 540

Pro Leu Thr Leu Gln Cys Asn Pro Pro Pro Gly Leu Ser Ser Pro Val
1 5 10 15

Ile Phe Trp Met Ser Ser Ser Met Glu
20 25

<210> SEQ ID NO 541
<211> LENGTH: 25
<212> TYPE: PRT
<213> ORGANISM: Artificial Sequence
<220> FEATURE:
<223> OTHER INFORMATION: Synthetic Construct

<400> SEQUENCE: 541

Gly Met Asp Glu Met Glu Phe Thr Glu Ala Glu Ser Ser Met Asn Asp
1 5 10 15

Leu Val Ser Glu Tyr Gln Gln Tyr Gln
20 25

<210> SEQ ID NO 542
<211> LENGTH: 25
<212> TYPE: PRT
<213> ORGANISM: Artificial Sequence
<220> FEATURE:
<223> OTHER INFORMATION: Synthetic Construct

<400> SEQUENCE: 542

Gly Ala Glu Val Leu Thr Ala Gln Phe Val Gln Lys Ile Lys Leu Asp
1 5 10 15

Arg Lys Asn Gln Glu Ala Pro Ile Ser
20 25

<210> SEQ ID NO 543
<211> LENGTH: 25
<212> TYPE: PRT
<213> ORGANISM: Artificial Sequence
<220> FEATURE:
<223> OTHER INFORMATION: Synthetic Construct

<400> SEQUENCE: 543

Glu Ile Gln Glu Gly Lys Asp Lys Leu Leu Glu Lys Lys Ala Leu Pro
1 5 10 15

His Ser His Met Pro Ser Phe Leu Ala
20 25

<210> SEQ ID NO 544
<211> LENGTH: 25
<212> TYPE: PRT
<213> ORGANISM: Artificial Sequence
<220> FEATURE:
<223> OTHER INFORMATION: Synthetic Construct

<400> SEQUENCE: 544

Gly Arg Asp Gly Val Lys Gly Asp Pro Gly Pro Pro Ser Pro Met Gly
1 5 10 15

Pro Pro Gly Glu Thr Pro Cys Pro Pro
20 25

<210> SEQ ID NO 545
<211> LENGTH: 25
<212> TYPE: PRT
<213> ORGANISM: Artificial Sequence
<220> FEATURE:
<223> OTHER INFORMATION: Synthetic Construct

<400> SEQUENCE: 545

Gly Arg Asp Gly Leu Lys Gly Asp Pro Gly Pro Pro Ser Pro Met Gly
1 5 10 15

Pro Pro Gly Glu Met Pro Cys Pro Pro
20 25

<210> SEQ ID NO 546
<211> LENGTH: 25
<212> TYPE: PRT
<213> ORGANISM: Artificial Sequence
<220> FEATURE:
<223> OTHER INFORMATION: Synthetic Construct

<400> SEQUENCE: 546

Ile Glu Glu Leu Leu Gln Thr Glu Arg Asp Tyr Ile Trp Asp Leu Glu
1 5 10 15

Met Cys Ile Glu Arg Ile Met Val Pro
20 25

<210> SEQ ID NO 547
<211> LENGTH: 25
<212> TYPE: PRT
<213> ORGANISM: Artificial Sequence
<220> FEATURE:
<223> OTHER INFORMATION: Synthetic Construct

<400> SEQUENCE: 547

Leu Gln Trp Gln Leu Ile Asn Lys Gly Cys Pro Thr Asn Glu Thr Val
1 5 10 15

Leu Val His Glu Asn Gly Arg Asp His
20 25

<210> SEQ ID NO 548
<211> LENGTH: 25
<212> TYPE: PRT
<213> ORGANISM: Artificial Sequence
<220> FEATURE:
<223> OTHER INFORMATION: Synthetic Construct

<400> SEQUENCE: 548

Thr Pro Gly His Thr Thr Ala Thr Ser Arg Thr Thr Thr Thr Ala Thr
1 5 10 15

Pro Ser Lys Thr Arg Thr Ser Thr Leu
20 25

<210> SEQ ID NO 549
<211> LENGTH: 25
<212> TYPE: PRT
<213> ORGANISM: Artificial Sequence
<220> FEATURE:
<223> OTHER INFORMATION: Synthetic Construct

<400> SEQUENCE: 549

Glu Ala Lys Tyr Glu Arg Leu Ala Leu Asp Leu Phe Phe Glu Cys Tyr
1 5 10 15

Ser Asn Ser Glu Ala Arg Ala Phe Ala
20 25

<210> SEQ ID NO 550
<211> LENGTH: 25
<212> TYPE: PRT
<213> ORGANISM: Artificial Sequence
<220> FEATURE:

<223> OTHER INFORMATION: Synthetic Construct

<400> SEQUENCE: 550

Gln Gly Leu Glu Gly Leu His Gly Trp Ile Ser Ile Ser Phe Cys Phe
1 5 10 15

Ile Tyr Leu Thr Val Ile Leu Gly Asn
20 25

<210> SEQ ID NO 551
<211> LENGTH: 25
<212> TYPE: PRT
<213> ORGANISM: Artificial Sequence
<220> FEATURE:
<223> OTHER INFORMATION: Synthetic Construct

<400> SEQUENCE: 551

Ser Asn Arg Val Pro Ile Pro Trp Val Ser Gly Thr Leu Ala Ser Thr
1 5 10 15

Pro Val Phe Gly Gly Ile Leu Ser Leu
20 25

<210> SEQ ID NO 552
<211> LENGTH: 25
<212> TYPE: PRT
<213> ORGANISM: Artificial Sequence
<220> FEATURE:
<223> OTHER INFORMATION: Synthetic Construct

<400> SEQUENCE: 552

His Ile Ser Cys Ala Gln Leu Ala Ala Ala Ser Trp Cys Ser Gly Phe
1 5 10 15

Ser Val Ala Thr Val Gln Thr Thr Trp
20 25

<210> SEQ ID NO 553
<211> LENGTH: 25
<212> TYPE: PRT
<213> ORGANISM: Artificial Sequence
<220> FEATURE:
<223> OTHER INFORMATION: Synthetic Construct

<400> SEQUENCE: 553

Val Asp Asp Glu Ser Lys His Ser Asp His Met Phe Phe Asp Lys Ser
1 5 10 15

Pro Asn Pro Asp Val Trp Thr Ser Glu
20 25

<210> SEQ ID NO 554
<211> LENGTH: 25
<212> TYPE: PRT
<213> ORGANISM: Artificial Sequence
<220> FEATURE:
<223> OTHER INFORMATION: Synthetic Construct

<400> SEQUENCE: 554

Gln Asp Glu Gly Arg Pro Cys Ser Met Lys His Lys Lys Ser Pro Pro
1 5 10 15

Ser Asn Ala Thr Ala Glu Thr Glu Pro
20 25

<210> SEQ ID NO 555
<211> LENGTH: 25
<212> TYPE: PRT
<213> ORGANISM: Artificial Sequence
<220> FEATURE:
<223> OTHER INFORMATION: Synthetic Construct

<400> SEQUENCE: 555

Asp Lys Ile Asp Ala Asn Asn Val Ala Tyr Thr Thr Trp Lys Leu Ser
1 5 10 15

Phe His Thr Asp Tyr Pro Ala Leu His
20 25

<210> SEQ ID NO 556
<211> LENGTH: 25
<212> TYPE: PRT
<213> ORGANISM: Artificial Sequence
<220> FEATURE:
<223> OTHER INFORMATION: Synthetic Construct

<400> SEQUENCE: 556

Phe Phe Ile Val Glu Thr Val Cys Ile Val Trp Phe Phe Phe Glu Phe
1 5 10 15

Val Val Arg Cys Phe Ala Cys Pro Ser
20 25

<210> SEQ ID NO 557
<211> LENGTH: 25
<212> TYPE: PRT
<213> ORGANISM: Artificial Sequence
<220> FEATURE:
<223> OTHER INFORMATION: Synthetic Construct

<400> SEQUENCE: 557

Cys Leu Ala Gly Tyr Thr Gly Gln Arg Cys Glu Asn Phe Leu Glu Glu
1 5 10 15

Arg Asn Cys Ser Asp Pro Gly Gly Pro
20 25

<210> SEQ ID NO 558
<211> LENGTH: 25
<212> TYPE: PRT
<213> ORGANISM: Artificial Sequence
<220> FEATURE:
<223> OTHER INFORMATION: Synthetic Construct

<400> SEQUENCE: 558

Arg Ile Lys Ile Gln Gly Trp Ile Arg Ser Val Arg Phe Gln Lys Glu
1 5 10 15

Val Leu Phe Leu His Val Asn Asp Gly
20 25

<210> SEQ ID NO 559
<211> LENGTH: 25
<212> TYPE: PRT
<213> ORGANISM: Artificial Sequence
<220> FEATURE:
<223> OTHER INFORMATION: Synthetic Construct

<400> SEQUENCE: 559

Val Asp Asn Ser Gln Val Ala Leu Gln Leu Trp Asp Met Ala Gly Gln
1 5 10 15

Glu Arg Tyr Arg Cys Ile Thr Gln Gln
20 25

<210> SEQ ID NO 560
<211> LENGTH: 25
<212> TYPE: PRT

<213> ORGANISM: Artificial Sequence
<220> FEATURE:
<223> OTHER INFORMATION: Synthetic Construct

<400> SEQUENCE: 560

Asn Ser Leu Gln Gln Tyr Arg Gln Asp Gln Arg Asp Glu Ser Lys Ser
1 5 10 15

Glu Asp Glu Leu Asp Gln Ala Ser Thr
20 25

<210> SEQ ID NO 561
<211> LENGTH: 25
<212> TYPE: PRT
<213> ORGANISM: Artificial Sequence
<220> FEATURE:
<223> OTHER INFORMATION: Synthetic Construct

<400> SEQUENCE: 561

Ser Arg Val Gly Leu Leu Trp Val Leu Val Leu Asn Cys Tyr Ala Thr
1 5 10 15

Glu Leu Asn Pro Ala Phe Asn Ser Ile
20 25

<210> SEQ ID NO 562
<211> LENGTH: 20
<212> TYPE: PRT
<213> ORGANISM: Artificial Sequence
<220> FEATURE:
<223> OTHER INFORMATION: Synthetic Construct

<400> SEQUENCE: 562

Gly Ser Met Ala Leu Ile Ile Ile Asp Trp Ile Tyr Asn Pro Pro Asn
1 5 10 15

Ser Lys His His
20

<210> SEQ ID NO 563
<211> LENGTH: 25
<212> TYPE: PRT
<213> ORGANISM: Artificial Sequence
<220> FEATURE:
<223> OTHER INFORMATION: Synthetic Construct

<400> SEQUENCE: 563

His Leu Ser Pro Glu Leu Glu Lys Pro Pro Leu Ser Ser Arg Pro Glu
1 5 10 15

Lys Pro Pro Glu Glu Pro Gly Gln Cys
20 25

<210> SEQ ID NO 564
<211> LENGTH: 25
<212> TYPE: PRT
<213> ORGANISM: Artificial Sequence
<220> FEATURE:
<223> OTHER INFORMATION: Synthetic Construct

<400> SEQUENCE: 564

Leu Ser His Asn Glu Leu Ala Asp Ser Gly Ile Pro Glu Asn Ser Phe
1 5 10 15

Asn Val Ser Ser Leu Val Glu Leu Asp
20 25

<210> SEQ ID NO 565
<211> LENGTH: 25

<212> TYPE: PRT
<213> ORGANISM: Artificial Sequence
<220> FEATURE:
<223> OTHER INFORMATION: Synthetic Construct

<400> SEQUENCE: 565

```
Val Ser Glu Ala Val Leu Ala Ile Asn Leu Leu Ile Glu Lys Lys Asn
1               5                   10                  15

Thr Arg Met His Lys Val Asn Gln Val
            20                  25
```

<210> SEQ ID NO 566
<211> LENGTH: 25
<212> TYPE: PRT
<213> ORGANISM: Artificial Sequence
<220> FEATURE:
<223> OTHER INFORMATION: Synthetic Construct

<400> SEQUENCE: 566

```
Thr Pro Ala Lys Pro Ile Arg Val Ser Asp Ile Tyr Phe Ser Lys Glu
1               5                   10                  15

Gln Ile Asn Ser Gln Thr Pro Gly Asn
            20                  25
```

<210> SEQ ID NO 567
<211> LENGTH: 25
<212> TYPE: PRT
<213> ORGANISM: Artificial Sequence
<220> FEATURE:
<223> OTHER INFORMATION: Synthetic Construct

<400> SEQUENCE: 567

```
Phe Ser Asp Ser Leu Ser Thr Ser Ile Lys Tyr Ser Gln Pro Gly Glu
1               5                   10                  15

Thr Asp Gly Thr Arg Leu Leu Leu Ile
            20                  25
```

<210> SEQ ID NO 568
<211> LENGTH: 25
<212> TYPE: PRT
<213> ORGANISM: Artificial Sequence
<220> FEATURE:
<223> OTHER INFORMATION: Synthetic Construct

<400> SEQUENCE: 568

```
Asp Thr Pro Ile Leu Asn Ala Ala Asp Ala Asp Val Ser Leu Asp Asp
1               5                   10                  15

Leu Thr Phe Thr Ile Thr Gln Phe Pro
            20                  25
```

<210> SEQ ID NO 569
<211> LENGTH: 25
<212> TYPE: PRT
<213> ORGANISM: Artificial Sequence
<220> FEATURE:
<223> OTHER INFORMATION: Synthetic Construct

<400> SEQUENCE: 569

```
Pro Val Met Ile Lys Thr Glu Pro Thr Ser Pro Thr Ser Ser Ala Phe
1               5                   10                  15

Lys Gly Pro Ser His Ser Gly Asn Pro
            20                  25
```

<210> SEQ ID NO 570

<211> LENGTH: 25
<212> TYPE: PRT
<213> ORGANISM: Artificial Sequence
<220> FEATURE:
<223> OTHER INFORMATION: Synthetic Construct

<400> SEQUENCE: 570

Pro Ala Thr Thr Thr Asn Thr Ala Asp Thr Ile Leu Gln Ser Leu Thr
1 5 10 15

Asp Ala Val Pro Leu Ser Val Leu Ile
20 25

<210> SEQ ID NO 571
<211> LENGTH: 25
<212> TYPE: PRT
<213> ORGANISM: Artificial Sequence
<220> FEATURE:
<223> OTHER INFORMATION: Synthetic Construct

<400> SEQUENCE: 571

Tyr Ala Ser Tyr Thr Gln Glu His Tyr Arg Phe Ala Glu Lys Glu Ile
1 5 10 15

Val Ile Gln Glu Ser Ile Glu Ser Tyr
20 25

<210> SEQ ID NO 572
<211> LENGTH: 25
<212> TYPE: PRT
<213> ORGANISM: Artificial Sequence
<220> FEATURE:
<223> OTHER INFORMATION: Synthetic Construct

<400> SEQUENCE: 572

Pro Leu Ser Pro Lys Arg Lys Asp Gln Lys Gly Arg Ile Thr Ile Arg
1 5 10 15

Asp Leu Lys Arg Glu Leu Ser Thr Lys
20 25

<210> SEQ ID NO 573
<211> LENGTH: 25
<212> TYPE: PRT
<213> ORGANISM: Artificial Sequence
<220> FEATURE:
<223> OTHER INFORMATION: Synthetic Construct

<400> SEQUENCE: 573

Asp Asp Lys Ala Trp Ala Met Tyr Val Asp Asn Asn Gln Ser Trp Phe
1 5 10 15

Met His Asn Asn Ser His Thr Asn Arg
20 25

<210> SEQ ID NO 574
<211> LENGTH: 25
<212> TYPE: PRT
<213> ORGANISM: Artificial Sequence
<220> FEATURE:
<223> OTHER INFORMATION: Synthetic Construct

<400> SEQUENCE: 574

Glu Ala Gln Gln Asn Pro Arg Glu Gly Ile Val Ile Ser Glu Cys Ala
1 5 10 15

Pro Gly Gly Leu Tyr Lys Pro Val Gln
20 25

<210> SEQ ID NO 575
<211> LENGTH: 25
<212> TYPE: PRT
<213> ORGANISM: Artificial Sequence
<220> FEATURE:
<223> OTHER INFORMATION: Synthetic Construct

<400> SEQUENCE: 575

```
Lys Asp Ala Ala Arg Pro Ala Tyr Trp Val Pro Asp Tyr Glu Ile Leu
1               5                   10                  15

His Cys His Asn Cys Arg Lys Glu Phe
            20                  25
```

<210> SEQ ID NO 576
<211> LENGTH: 25
<212> TYPE: PRT
<213> ORGANISM: Artificial Sequence
<220> FEATURE:
<223> OTHER INFORMATION: Synthetic Construct

<400> SEQUENCE: 576

```
Val Ala Ile Cys Val Gly Ala Cys Val Val Arg Asp Thr Thr Gly Asn
1               5                   10                  15

Met Asn Asp Thr Ile Ile Ser Gly Met
            20                  25
```

<210> SEQ ID NO 577
<211> LENGTH: 25
<212> TYPE: PRT
<213> ORGANISM: Artificial Sequence
<220> FEATURE:
<223> OTHER INFORMATION: Synthetic Construct

<400> SEQUENCE: 577

```
Ser Thr His Asn Leu Ser Thr Glu Glu Asp Glu Ala Gly Lys Glu Phe
1               5                   10                  15

Ser Leu Ser Pro Thr Phe Ser Tyr Arg
            20                  25
```

<210> SEQ ID NO 578
<211> LENGTH: 25
<212> TYPE: PRT
<213> ORGANISM: Artificial Sequence
<220> FEATURE:
<223> OTHER INFORMATION: Synthetic Construct

<400> SEQUENCE: 578

```
Pro Val Leu Asp Gly Ala Arg Ser Arg Arg Ser Ser Leu Ser Ser Thr
1               5                   10                  15

Thr Pro Thr Ser Ala Asn Ser Leu Tyr
            20                  25
```

<210> SEQ ID NO 579
<211> LENGTH: 25
<212> TYPE: PRT
<213> ORGANISM: Artificial Sequence
<220> FEATURE:
<223> OTHER INFORMATION: Synthetic Construct

<400> SEQUENCE: 579

```
Leu Asn Gln Asp Ser Tyr Asn Asp Val Val Val Gly Thr Pro Leu Glu
1               5                   10                  15

Asp Asn His Ala Gly Ala Ile Tyr Ile
            20                  25
```

<210> SEQ ID NO 580
<211> LENGTH: 25
<212> TYPE: PRT
<213> ORGANISM: Artificial Sequence
<220> FEATURE:
<223> OTHER INFORMATION: Synthetic Construct

<400> SEQUENCE: 580

```
Ala Gln Asn Pro Ala Asp Glu Pro Thr Pro Gly Ala Ser Ala Pro Gln
1               5                   10                  15

Glu Leu Gly Ala Ala Gly Glu Gln Asp
            20                  25
```

<210> SEQ ID NO 581
<211> LENGTH: 25
<212> TYPE: PRT
<213> ORGANISM: Artificial Sequence
<220> FEATURE:
<223> OTHER INFORMATION: Synthetic Construct

<400> SEQUENCE: 581

```
Leu Glu Glu Pro Glu Leu Arg Leu Glu His Cys Ile Lys Phe Val Val
1               5                   10                  15

Arg Gly Asn Pro Pro Pro Thr Leu His
            20                  25
```

<210> SEQ ID NO 582
<211> LENGTH: 25
<212> TYPE: PRT
<213> ORGANISM: Artificial Sequence
<220> FEATURE:
<223> OTHER INFORMATION: Synthetic Construct

<400> SEQUENCE: 582

```
Leu Ala Glu Ala Gly Ile Pro Leu Glu Met Lys Arg His Val Phe Pro
1               5                   10                  15

Phe Thr Trp Arg Pro Arg His Ser Ser
            20                  25
```

<210> SEQ ID NO 583
<211> LENGTH: 21
<212> TYPE: PRT
<213> ORGANISM: Artificial Sequence
<220> FEATURE:
<223> OTHER INFORMATION: Synthetic Construct

<400> SEQUENCE: 583

```
Pro Arg Arg Glu Ser Pro Arg Lys Glu Arg Pro Lys Glu Val Asp Asn
1               5                   10                  15

Leu Ala Leu Glu Pro
            20
```

<210> SEQ ID NO 584
<211> LENGTH: 25
<212> TYPE: PRT
<213> ORGANISM: Artificial Sequence
<220> FEATURE:
<223> OTHER INFORMATION: Synthetic Construct

<400> SEQUENCE: 584

```
Leu Ser Asn Tyr Ser Glu Asp Glu Ala Trp Pro Ser Phe Phe Asp Thr
1               5                   10                  15

Phe Val Glu Trp Glu Met Glu Arg Arg
            20                  25
```

<210> SEQ ID NO 585
<211> LENGTH: 25
<212> TYPE: PRT
<213> ORGANISM: Artificial Sequence
<220> FEATURE:
<223> OTHER INFORMATION: Synthetic Construct

<400> SEQUENCE: 585

Gln Gly Leu Val Leu Phe Asp Val Thr Gly Gln Val Trp Leu Arg His
1 5 10 15

Ala Asp Leu Glu Ile Arg Leu Ala Gln
20 25

<210> SEQ ID NO 586
<211> LENGTH: 25
<212> TYPE: PRT
<213> ORGANISM: Artificial Sequence
<220> FEATURE:
<223> OTHER INFORMATION: Synthetic Construct

<400> SEQUENCE: 586

Ala Lys Leu Thr Glu Asp Leu Phe Asn Gln Val Pro Glu Ile His Cys
1 5 10 15

Asn Pro Leu Gln Gly Ala Met Tyr Ala
20 25

<210> SEQ ID NO 587
<211> LENGTH: 25
<212> TYPE: PRT
<213> ORGANISM: Artificial Sequence
<220> FEATURE:
<223> OTHER INFORMATION: Synthetic Construct

<400> SEQUENCE: 587

Asp Asn Ile Leu Glu Gly Arg Ile Gln Val Pro Phe Ser Thr Gln Arg
1 5 10 15

Ser Asp Ser Ile Arg Pro Ala Leu Asn
20 25

<210> SEQ ID NO 588
<211> LENGTH: 25
<212> TYPE: PRT
<213> ORGANISM: Artificial Sequence
<220> FEATURE:
<223> OTHER INFORMATION: Synthetic Construct

<400> SEQUENCE: 588

Gly Ser Ala Thr Thr Ala Ser Pro Ala Ala Ser His Ser Leu Ala Ser
1 5 10 15

Ser Pro Leu Ser Gly Pro Pro Ser Pro
20 25

<210> SEQ ID NO 589
<211> LENGTH: 25
<212> TYPE: PRT
<213> ORGANISM: Artificial Sequence
<220> FEATURE:
<223> OTHER INFORMATION: Synthetic Construct

<400> SEQUENCE: 589

Gln Leu Pro Ala Ser Pro Ser Cys Arg Asp Pro Pro Cys Pro Gln Gln
1 5 10 15

Leu Leu Ala Cys Ser Pro Ala Trp Ala 20 25

<210> SEQ ID NO 590
<211> LENGTH: 25
<212> TYPE: PRT
<213> ORGANISM: Artificial Sequence
<220> FEATURE:
<223> OTHER INFORMATION: Synthetic Construct

<400> SEQUENCE: 590

Arg Ala Glu Ala Thr Asp Ala Asp Asp Pro Glu Thr Asn Asn Ala Ala
1 5 10 15

Leu Arg Phe Ser Ile Leu Gln Gln Gly
20 25

<210> SEQ ID NO 591
<211> LENGTH: 25
<212> TYPE: PRT
<213> ORGANISM: Artificial Sequence
<220> FEATURE:
<223> OTHER INFORMATION: Synthetic Construct

<400> SEQUENCE: 591

Gly Glu Thr Gly Thr Gly Ser Ala Asp Pro Pro Gly Arg Pro Arg Pro
1 5 10 15

Gly Leu Thr Arg Arg Ala Pro Val Lys
20 25

<210> SEQ ID NO 592
<211> LENGTH: 25
<212> TYPE: PRT
<213> ORGANISM: Artificial Sequence
<220> FEATURE:
<223> OTHER INFORMATION: Synthetic Construct

<400> SEQUENCE: 592

Ser Ser Asn Leu Ile Ile His Gln Arg Ile His Thr Arg Asn Lys Pro
1 5 10 15

Tyr Val Cys Asn Glu Cys Gly Lys Asp
20 25

<210> SEQ ID NO 593
<211> LENGTH: 25
<212> TYPE: PRT
<213> ORGANISM: Artificial Sequence
<220> FEATURE:
<223> OTHER INFORMATION: Synthetic Construct

<400> SEQUENCE: 593

Gly Gly Pro Gly Pro Gly Pro Gly Gly Gly Gly Gly Leu Ser Gly Ser
1 5 10 15

Gly Ser Gly Pro Gly Ser Asn Gly Gly
20 25

<210> SEQ ID NO 594
<211> LENGTH: 25
<212> TYPE: PRT
<213> ORGANISM: Artificial Sequence
<220> FEATURE:
<223> OTHER INFORMATION: Synthetic Construct

<400> SEQUENCE: 594

Gly Gly Pro Gly Pro Gly Pro Gly Gly Gly Gly Gly Ser Ser Gly Ser
1 5 10 15

```
Gly Ser Gly Pro Gly Ser Asn Gly Gly
            20                  25


<210> SEQ ID NO 595
<211> LENGTH: 25
<212> TYPE: PRT
<213> ORGANISM: Artificial Sequence
<220> FEATURE:
<223> OTHER INFORMATION: Synthetic Construct

<400> SEQUENCE: 595

Thr Asp Ser Ala Ile Asp Ile Leu Gly Phe Thr Asn Lys Glu Lys Val
1               5                   10                  15

Ser Ile Tyr Lys Leu Thr Gly Ala Val
            20                  25


<210> SEQ ID NO 596
<211> LENGTH: 25
<212> TYPE: PRT
<213> ORGANISM: Artificial Sequence
<220> FEATURE:
<223> OTHER INFORMATION: Synthetic Construct

<400> SEQUENCE: 596

Val Glu Glu Leu Arg Met Gln Leu Gln Lys Gln Lys Lys Asn Asn Cys
1               5                   10                  15

Ser Glu Lys Lys Pro Leu Pro Phe Leu
            20                  25


<210> SEQ ID NO 597
<211> LENGTH: 25
<212> TYPE: PRT
<213> ORGANISM: Artificial Sequence
<220> FEATURE:
<223> OTHER INFORMATION: Synthetic Construct

<400> SEQUENCE: 597

Ser Leu Asn Trp Thr Thr Gln Ala Ile Gln Asn Asn Lys Glu Asn Val
1               5                   10                  15

Leu Ile Thr Glu Asp Asp Glu Tyr Val
            20                  25


<210> SEQ ID NO 598
<211> LENGTH: 25
<212> TYPE: PRT
<213> ORGANISM: Artificial Sequence
<220> FEATURE:
<223> OTHER INFORMATION: Synthetic Construct

<400> SEQUENCE: 598

Lys Lys Lys Pro Asn Ala Thr Ala Glu Pro Thr Pro Ser Asp Arg Trp
1               5                   10                  15

Ala Asn Val Lys Val Glu Cys Glu Pro
            20                  25


<210> SEQ ID NO 599
<211> LENGTH: 25
<212> TYPE: PRT
<213> ORGANISM: Artificial Sequence
<220> FEATURE:
<223> OTHER INFORMATION: Synthetic Construct

<400> SEQUENCE: 599

Leu Leu Trp Ala Trp Glu Gly Trp Arg Asp Lys Ala Arg Arg Ala Ile
1               5                   10                  15
```

```
Leu Gln Phe Tyr Pro Lys Tyr Val Glu
            20                  25


<210> SEQ ID NO 600
<211> LENGTH: 25
<212> TYPE: PRT
<213> ORGANISM: Artificial Sequence
<220> FEATURE:
<223> OTHER INFORMATION: Synthetic Construct

<400> SEQUENCE: 600

Val Gln Val Thr Ile Asp Pro Ala Pro Val Thr Gln Ala Glu Thr Ser
1               5                   10                  15

Ser Ser Pro Thr Leu Thr Gly His His
            20                  25


<210> SEQ ID NO 601
<211> LENGTH: 25
<212> TYPE: PRT
<213> ORGANISM: Artificial Sequence
<220> FEATURE:
<223> OTHER INFORMATION: Synthetic Construct

<400> SEQUENCE: 601

His Pro Leu Leu Glu Asp Gly Cys Ile Glu Asp Asp Leu Ala Pro His
1               5                   10                  15

Lys Lys Val Gly Phe Val Gly Ile Ser
            20                  25


<210> SEQ ID NO 602
<211> LENGTH: 25
<212> TYPE: PRT
<213> ORGANISM: Artificial Sequence
<220> FEATURE:
<223> OTHER INFORMATION: Synthetic Construct

<400> SEQUENCE: 602

Pro Tyr Gly Val Phe Thr Ile Asn Pro Arg Thr Gly Lys Ile Asn Ile
1               5                   10                  15

Thr Ser Val Val Asp Arg Glu Ile Thr
            20                  25


<210> SEQ ID NO 603
<211> LENGTH: 25
<212> TYPE: PRT
<213> ORGANISM: Artificial Sequence
<220> FEATURE:
<223> OTHER INFORMATION: Synthetic Construct

<400> SEQUENCE: 603

Arg Leu Gln Ala Ile Asp Leu Asp Glu Glu Gly Thr Asn Asn Trp Leu
1               5                   10                  15

Ala Gln Tyr Leu Ile Leu Ser Gly Asn
            20                  25


<210> SEQ ID NO 604
<211> LENGTH: 25
<212> TYPE: PRT
<213> ORGANISM: Artificial Sequence
<220> FEATURE:
<223> OTHER INFORMATION: Synthetic Construct

<400> SEQUENCE: 604

Pro Leu Pro Thr Leu Gln Phe Gln Asp Val Thr Gly Ser Ser Phe Leu
```

```
1               5                   10                  15

Pro Gln Ala Leu His Gln Gln Tyr Leu
            20                  25


<210> SEQ ID NO 605
<211> LENGTH: 25
<212> TYPE: PRT
<213> ORGANISM: Artificial Sequence
<220> FEATURE:
<223> OTHER INFORMATION: Synthetic Construct

<400> SEQUENCE: 605

Ala Ser Val Val Asp Val Ala Lys Gly Val Val Gln Arg Gly Leu Asp
1               5                   10                  15

Thr Thr Arg Ser Ala Leu Thr Gly Thr
            20                  25


<210> SEQ ID NO 606
<211> LENGTH: 25
<212> TYPE: PRT
<213> ORGANISM: Artificial Sequence
<220> FEATURE:
<223> OTHER INFORMATION: Synthetic Construct

<400> SEQUENCE: 606

Thr Arg Gly Asn Ser Lys Tyr His Tyr Tyr Gly Ile Cys Leu Lys Pro
1               5                   10                  15

Asp Ser Pro Leu Asn Arg Leu Gln Glu
            20                  25


<210> SEQ ID NO 607
<211> LENGTH: 25
<212> TYPE: PRT
<213> ORGANISM: Artificial Sequence
<220> FEATURE:
<223> OTHER INFORMATION: Synthetic Construct

<400> SEQUENCE: 607

Leu Ser Met Gly Ala Lys Ser Ala Gly Ser Leu Arg Ser Ser Gln Ser
1               5                   10                  15

Leu Asp Cys Cys His Arg Gly Asp Leu
            20                  25


<210> SEQ ID NO 608
<211> LENGTH: 25
<212> TYPE: PRT
<213> ORGANISM: Artificial Sequence
<220> FEATURE:
<223> OTHER INFORMATION: Synthetic Construct

<400> SEQUENCE: 608

Glu Ala Ser Ser Ala Val Leu Thr Val Ser Pro Glu Glu Pro Gly Met
1               5                   10                  15

Val Thr Ser Leu Val Thr Ser Ser Arg
            20                  25


<210> SEQ ID NO 609
<211> LENGTH: 17
<212> TYPE: PRT
<213> ORGANISM: Artificial Sequence
<220> FEATURE:
<223> OTHER INFORMATION: Synthetic Construct

<400> SEQUENCE: 609
```

```
Tyr Lys Ala His Gln Cys Gly Asp Asp Asp Lys Thr Trp Pro Leu Val
1               5                   10                  15

Lys


<210> SEQ ID NO 610
<211> LENGTH: 25
<212> TYPE: PRT
<213> ORGANISM: Artificial Sequence
<220> FEATURE:
<223> OTHER INFORMATION: Synthetic Construct

<400> SEQUENCE: 610

Pro Pro Ala Pro Ser Pro Pro Pro Ala Pro Ala Thr Phe Ser Arg Arg
1               5                   10                  15

Pro Leu Leu Leu Arg Ala Pro Gln Phe
            20                  25


<210> SEQ ID NO 611
<211> LENGTH: 25
<212> TYPE: PRT
<213> ORGANISM: Artificial Sequence
<220> FEATURE:
<223> OTHER INFORMATION: Synthetic Construct

<400> SEQUENCE: 611

Thr Gln Lys Ser Thr Leu Lys Met His Gln Lys Ile Tyr Thr Gly Glu
1               5                   10                  15

Arg Ser Tyr Ile Cys Ile Glu Cys Gly
            20                  25


<210> SEQ ID NO 612
<211> LENGTH: 25
<212> TYPE: PRT
<213> ORGANISM: Artificial Sequence
<220> FEATURE:
<223> OTHER INFORMATION: Synthetic Construct

<400> SEQUENCE: 612

Gly Glu Cys Glu Arg Asn Val Ser Phe Ser Arg Ala Phe Val Gly Ser
1               5                   10                  15

Pro Ser Ser Gly Glu Gly His Leu Ala
            20                  25


<210> SEQ ID NO 613
<211> LENGTH: 25
<212> TYPE: PRT
<213> ORGANISM: Artificial Sequence
<220> FEATURE:
<223> OTHER INFORMATION: Synthetic Construct

<400> SEQUENCE: 613

Gly Tyr His Ser His Tyr His Asp Glu Gly Tyr Gly Leu Pro Pro Pro
1               5                   10                  15

His Tyr Glu Gly Arg Arg Met Gly Pro
            20                  25


<210> SEQ ID NO 614
<211> LENGTH: 25
<212> TYPE: PRT
<213> ORGANISM: Artificial Sequence
<220> FEATURE:
<223> OTHER INFORMATION: Synthetic Construct

<400> SEQUENCE: 614
```

Glu His Arg Tyr Val Cys Ser Glu Cys Asn Gln Leu Cys Gly Ser Leu
1 5 10 15

Glu Glu Val Leu Met His Gln Asn Ser
20 25

<210> SEQ ID NO 615
<211> LENGTH: 25
<212> TYPE: PRT
<213> ORGANISM: Artificial Sequence
<220> FEATURE:
<223> OTHER INFORMATION: Synthetic Construct

<400> SEQUENCE: 615

Glu Phe Pro Met Ser Pro Val Thr Ser Ala His Ala Glu Thr Tyr Arg
1 5 10 15

Cys Tyr Gly Ser Arg Ser Ser Asn Pro
20 25

<210> SEQ ID NO 616
<211> LENGTH: 25
<212> TYPE: PRT
<213> ORGANISM: Artificial Sequence
<220> FEATURE:
<223> OTHER INFORMATION: Synthetic Construct

<400> SEQUENCE: 616

Cys Asp Ala Leu Leu His Pro Asn Cys Thr Leu Ile Leu Leu Val Leu
1 5 10 15

Val Phe Cys Cys Leu Thr Glu Asn Cys
20 25

<210> SEQ ID NO 617
<211> LENGTH: 25
<212> TYPE: PRT
<213> ORGANISM: Artificial Sequence
<220> FEATURE:
<223> OTHER INFORMATION: Synthetic Construct

<400> SEQUENCE: 617

Phe Arg Pro Arg Thr Val Val Leu His Gly Lys Ser Glu Ile Gly Lys
1 5 10 15

Ser Ala Leu Ala Arg Arg Ile Val Leu
20 25

<210> SEQ ID NO 618
<211> LENGTH: 25
<212> TYPE: PRT
<213> ORGANISM: Artificial Sequence
<220> FEATURE:
<223> OTHER INFORMATION: Synthetic Construct

<400> SEQUENCE: 618

Asp Leu Ile Val His Glu Arg Val His Thr Gly Glu Ser Pro Tyr Glu
1 5 10 15

Cys Ser Glu Cys Gly Lys Ser Phe Thr
20 25

<210> SEQ ID NO 619
<211> LENGTH: 25
<212> TYPE: PRT
<213> ORGANISM: Artificial Sequence
<220> FEATURE:
<223> OTHER INFORMATION: Synthetic Construct

<400> SEQUENCE: 619

Ile Ile Ala Ile Met Asp Gly Val Glu Cys Ile His Ile Phe Gly Ala
1 5 10 15

Asp Phe Arg Asp Val Arg Gly Phe Leu
20 25

<210> SEQ ID NO 620
<211> LENGTH: 25
<212> TYPE: PRT
<213> ORGANISM: Artificial Sequence
<220> FEATURE:
<223> OTHER INFORMATION: Synthetic Construct

<400> SEQUENCE: 620

Ala Thr Thr Ser Leu Arg Gln Ala Asn Gln Glu Lys Ile Leu Gly Glu
1 5 10 15

Tyr Ser Lys Lys Ala Ala Met Lys Pro
20 25

<210> SEQ ID NO 621
<211> LENGTH: 25
<212> TYPE: PRT
<213> ORGANISM: Artificial Sequence
<220> FEATURE:
<223> OTHER INFORMATION: Synthetic Construct

<400> SEQUENCE: 621

Asp Ala Gly His Leu Ser Phe Val Glu Glu Val Phe Lys Asn Gln Thr
1 5 10 15

Arg Leu Pro Gly Gly Gln Trp Ile Tyr
20 25

<210> SEQ ID NO 622
<211> LENGTH: 25
<212> TYPE: PRT
<213> ORGANISM: Artificial Sequence
<220> FEATURE:
<223> OTHER INFORMATION: Synthetic Construct

<400> SEQUENCE: 622

Ala Asp Ile Ser Glu Ile Arg Val Phe Thr Lys Pro Ser Asp Leu Val
1 5 10 15

Met Thr Val Met Glu Ala Ile Ser Ile
20 25

<210> SEQ ID NO 623
<211> LENGTH: 25
<212> TYPE: PRT
<213> ORGANISM: Artificial Sequence
<220> FEATURE:
<223> OTHER INFORMATION: Synthetic Construct

<400> SEQUENCE: 623

Gly Ala Pro Gly Pro Pro Gly Pro Pro Ala Glu Lys Glu Ala Lys Gly
1 5 10 15

Ala Met Gly Arg Asp Gly Ala Thr Gly
20 25

<210> SEQ ID NO 624
<211> LENGTH: 25
<212> TYPE: PRT
<213> ORGANISM: Artificial Sequence
<220> FEATURE:
<223> OTHER INFORMATION: Synthetic Construct

<400> SEQUENCE: 624

Leu Thr Ser Asn Val Ala Ser Ser Lys Ser Glu Ser Ser Val Pro Gln
1 5 10 15

Asn Glu Lys Ala Thr Ser Ala Gln Pro
20 25

<210> SEQ ID NO 625
<211> LENGTH: 25
<212> TYPE: PRT
<213> ORGANISM: Artificial Sequence
<220> FEATURE:
<223> OTHER INFORMATION: Synthetic Construct

<400> SEQUENCE: 625

Glu Ser Asp Phe Glu Asn Leu Asn Thr Glu Glu Phe Asn Ser Glu Ser
1 5 10 15

Asp Met Glu Glu Ser Lys Glu Lys Leu
20 25

<210> SEQ ID NO 626
<211> LENGTH: 25
<212> TYPE: PRT
<213> ORGANISM: Artificial Sequence
<220> FEATURE:
<223> OTHER INFORMATION: Synthetic Construct

<400> SEQUENCE: 626

Lys Leu Gly Ser Lys Lys Pro Gln Lys Pro Ile Pro Gln Pro Gly Asn
1 5 10 15

Lys Phe Gln Gly Met Val Phe Asp Phe
20 25

<210> SEQ ID NO 627
<211> LENGTH: 25
<212> TYPE: PRT
<213> ORGANISM: Artificial Sequence
<220> FEATURE:
<223> OTHER INFORMATION: Synthetic Construct

<400> SEQUENCE: 627

Glu Leu Lys Ser Arg Lys Lys Asp Glu Ser Tyr Glu Lys Leu Leu Arg
1 5 10 15

Lys Thr Lys Asp Glu Leu Leu His Trp
20 25

<210> SEQ ID NO 628
<211> LENGTH: 25
<212> TYPE: PRT
<213> ORGANISM: Artificial Sequence
<220> FEATURE:
<223> OTHER INFORMATION: Synthetic Construct

<400> SEQUENCE: 628

Phe Ser Ala Met Phe Gly Phe Gly Gly Arg Thr Leu Val Leu Ala Glu
1 5 10 15

Lys Tyr Arg Trp Met Ser Pro Asn Gln
20 25

<210> SEQ ID NO 629
<211> LENGTH: 25
<212> TYPE: PRT
<213> ORGANISM: Artificial Sequence
<220> FEATURE:
<223> OTHER INFORMATION: Synthetic Construct

<400> SEQUENCE: 629

Gln Ser His Ala Glu Tyr Met Glu Arg Phe Gly Lys Glu Gly Lys Leu
1 5 10 15

Pro His Gln Val Asp Asp Ser Tyr Val
20 25

<210> SEQ ID NO 630
<211> LENGTH: 25
<212> TYPE: PRT
<213> ORGANISM: Artificial Sequence
<220> FEATURE:
<223> OTHER INFORMATION: Synthetic Construct

<400> SEQUENCE: 630

Lys His His Thr Leu Leu Lys Glu Lys Met Leu Thr Phe Leu Glu Arg
1 5 10 15

Asp Lys Val Val Gly Gln Ile Ser Gly
20 25

<210> SEQ ID NO 631
<211> LENGTH: 25
<212> TYPE: PRT
<213> ORGANISM: Artificial Sequence
<220> FEATURE:
<223> OTHER INFORMATION: Synthetic Construct

<400> SEQUENCE: 631

Pro Leu Ala Gln Ala Asp Pro Ala Gly Val Gly Thr Leu Pro Thr Gly
1 5 10 15

Trp Asp Cys Leu Pro Ser Asp Cys Thr
20 25

<210> SEQ ID NO 632
<211> LENGTH: 25
<212> TYPE: PRT
<213> ORGANISM: Artificial Sequence
<220> FEATURE:
<223> OTHER INFORMATION: Synthetic Construct

<400> SEQUENCE: 632

Asp Val Glu Ile Ala Thr Tyr Arg Lys Leu Leu Glu Glu Glu Glu Ser
1 5 10 15

Arg Ile Asn Leu Pro Ile Gln Thr Tyr
20 25

<210> SEQ ID NO 633
<211> LENGTH: 25
<212> TYPE: PRT
<213> ORGANISM: Artificial Sequence
<220> FEATURE:
<223> OTHER INFORMATION: Synthetic Construct

<400> SEQUENCE: 633

Ile Pro Gly Ser Leu Gly Lys Cys Gly Asp Pro Gly Phe Pro Gly Pro
1 5 10 15

Asp Gly Glu Pro Gly Ile Pro Gly Ile
20 25

<210> SEQ ID NO 634
<211> LENGTH: 25
<212> TYPE: PRT
<213> ORGANISM: Artificial Sequence
<220> FEATURE:

<223> OTHER INFORMATION: Synthetic Construct

<400> SEQUENCE: 634

Ser His Arg Val Pro Asp Ser Ser Thr Ala Thr Thr Phe Ser Lys Glu
1 5 10 15

Ile Tyr Leu Lys Gly Ile Ala Gly Glu
20 25

<210> SEQ ID NO 635
<211> LENGTH: 25
<212> TYPE: PRT
<213> ORGANISM: Artificial Sequence
<220> FEATURE:
<223> OTHER INFORMATION: Synthetic Construct

<400> SEQUENCE: 635

Ser Leu Tyr Lys Asp Cys Val Phe Asn Thr Leu Asn Lys Leu Glu Val
1 5 10 15

Glu Leu Leu Lys Phe Val Ser Glu Val
20 25

<210> SEQ ID NO 636
<211> LENGTH: 25
<212> TYPE: PRT
<213> ORGANISM: Artificial Sequence
<220> FEATURE:
<223> OTHER INFORMATION: Synthetic Construct

<400> SEQUENCE: 636

Gln Leu Ser Gly Lys Leu Leu Gln Thr His Val Thr Gln Glu Gly Glu
1 5 10 15

Arg Ile Leu Leu Asn Gln Ala Thr Val
20 25

<210> SEQ ID NO 637
<211> LENGTH: 25
<212> TYPE: PRT
<213> ORGANISM: Artificial Sequence
<220> FEATURE:
<223> OTHER INFORMATION: Synthetic Construct

<400> SEQUENCE: 637

Val Asn Pro Ser Gln Gly Ser Pro Ser Gln Gly Ser Phe Arg Gln Glu
1 5 10 15

Ser Thr Ser Gln Ala Ser Pro Ser Gln
20 25

<210> SEQ ID NO 638
<211> LENGTH: 25
<212> TYPE: PRT
<213> ORGANISM: Artificial Sequence
<220> FEATURE:
<223> OTHER INFORMATION: Synthetic Construct

<400> SEQUENCE: 638

Tyr Phe Arg Thr Phe Gln Asp Asp Gly Leu Gly Thr Val Gln Leu His
1 5 10 15

Tyr Gln Ala Phe Met Leu Ser Cys Asn
20 25

<210> SEQ ID NO 639
<211> LENGTH: 21
<212> TYPE: PRT
<213> ORGANISM: Artificial Sequence
<220> FEATURE:
<223> OTHER INFORMATION: Synthetic Construct

<400> SEQUENCE: 639

Gly Glu Ala Ile Pro Glu Asp Ser Leu Trp Val Pro Thr Gly Ser Thr
1 5 10 15

Ala Ile Thr Phe Cys
20

<210> SEQ ID NO 640
<211> LENGTH: 25
<212> TYPE: PRT
<213> ORGANISM: Artificial Sequence
<220> FEATURE:
<223> OTHER INFORMATION: Synthetic Construct

<400> SEQUENCE: 640

Ser Pro Glu Asp Tyr Tyr Thr Asp Thr Val Pro Phe Tyr Ser Ala Pro
1 5 10 15

Lys Gly Ile Ser Leu Pro Gly Cys Ser
20 25

<210> SEQ ID NO 641
<211> LENGTH: 25
<212> TYPE: PRT
<213> ORGANISM: Artificial Sequence
<220> FEATURE:
<223> OTHER INFORMATION: Synthetic Construct

<400> SEQUENCE: 641

Asp Pro Lys Leu Asp Thr Ala Ser Ala Leu Ile Asn Lys Glu Leu Tyr
1 5 10 15

Ala Gly Val Tyr Ile Asp Phe Met Gly
20 25

<210> SEQ ID NO 642
<211> LENGTH: 25
<212> TYPE: PRT
<213> ORGANISM: Artificial Sequence
<220> FEATURE:
<223> OTHER INFORMATION: Synthetic Construct

<400> SEQUENCE: 642

Ala Ser Phe Phe Ser Leu Arg Leu Leu Glu Tyr Lys Lys Leu Lys Gly
1 5 10 15

Asp Gly Pro Phe Thr Ile Phe Val Pro
20 25

<210> SEQ ID NO 643
<211> LENGTH: 19
<212> TYPE: PRT
<213> ORGANISM: Artificial Sequence
<220> FEATURE:
<223> OTHER INFORMATION: Synthetic Construct

<400> SEQUENCE: 643

Gln Thr Asn Asp Pro Gly Lys Val Glu Glu Lys Glu Gln Phe Asp Ser
1 5 10 15

Ser Pro Ala

<210> SEQ ID NO 644
<211> LENGTH: 22
<212> TYPE: PRT
<213> ORGANISM: Artificial Sequence
<220> FEATURE:
<223> OTHER INFORMATION: Synthetic Construct

<400> SEQUENCE: 644

Pro Leu Ala Gln Thr Asn Asp Pro Gly Lys Val Glu Lys Lys Glu Arg
1 5 10 15

Phe Asp Ser Ser Pro Ala
20

<210> SEQ ID NO 645
<211> LENGTH: 25
<212> TYPE: PRT
<213> ORGANISM: Artificial Sequence
<220> FEATURE:
<223> OTHER INFORMATION: Synthetic Construct

<400> SEQUENCE: 645

Leu Ala Glu Ile Pro Ser His Leu Pro Pro Gln Thr Gln Thr Leu His
1 5 10 15

Leu Gln Asp Asn Gln Ile His His Leu
20 25

<210> SEQ ID NO 646
<211> LENGTH: 25
<212> TYPE: PRT
<213> ORGANISM: Artificial Sequence
<220> FEATURE:
<223> OTHER INFORMATION: Synthetic Construct

<400> SEQUENCE: 646

Ser Pro Arg Leu Pro Arg Ser Pro Arg Leu Gly His Gln Arg Thr Ser
1 5 10 15

Ser Gly Gly Gly Gly Gly Thr Gly Lys
20 25

<210> SEQ ID NO 647
<211> LENGTH: 25
<212> TYPE: PRT
<213> ORGANISM: Artificial Sequence
<220> FEATURE:
<223> OTHER INFORMATION: Synthetic Construct

<400> SEQUENCE: 647

Pro Gly Leu Pro Gly His Gly Ile Pro Gly Ile Lys Glu Lys Pro Gly
1 5 10 15

Pro Gln Gly Tyr Pro Gly Val Gly Lys
20 25

<210> SEQ ID NO 648
<211> LENGTH: 25
<212> TYPE: PRT
<213> ORGANISM: Artificial Sequence
<220> FEATURE:
<223> OTHER INFORMATION: Synthetic Construct

<400> SEQUENCE: 648

Asn Ser Gln Gly Ser Ile Glu Ala Thr Met Glu Arg Ser Leu Glu Lys
1 5 10 15

Pro Ser Cys Ser Leu Gly Ile Lys Thr
20 25

<210> SEQ ID NO 649
<211> LENGTH: 25
<212> TYPE: PRT

```
<213> ORGANISM: Artificial Sequence
<220> FEATURE:
<223> OTHER INFORMATION: Synthetic Construct

<400> SEQUENCE: 649

Lys Gln Gln Tyr Ile Glu Gln Ser Gln Ala Glu Ile Phe His Asn Arg
1               5                   10                  15

Phe Asp Ala Val Gln Ser Ala His Arg
            20                  25


<210> SEQ ID NO 650
<211> LENGTH: 25
<212> TYPE: PRT
<213> ORGANISM: Artificial Sequence
<220> FEATURE:
<223> OTHER INFORMATION: Synthetic Construct

<400> SEQUENCE: 650

Asp Trp Ser Ile Ser Ser Phe Ser Thr Phe Thr Ser His Asp Glu Gln
1               5                   10                  15

Asp Phe Arg Asn Gly Leu Ala Ala Leu
            20                  25


<210> SEQ ID NO 651
<211> LENGTH: 25
<212> TYPE: PRT
<213> ORGANISM: Artificial Sequence
<220> FEATURE:
<223> OTHER INFORMATION: Synthetic Construct

<400> SEQUENCE: 651

Tyr Leu Thr Ala Gly Met Leu Asp Gln Pro Gly Phe Ser Asp Cys Ser
1               5                   10                  15

Ile Glu Ala Ala Met Val Lys Val Phe
            20                  25


<210> SEQ ID NO 652
<211> LENGTH: 25
<212> TYPE: PRT
<213> ORGANISM: Artificial Sequence
<220> FEATURE:
<223> OTHER INFORMATION: Synthetic Construct

<400> SEQUENCE: 652

Tyr Ile Ser Gln Val Ile Glu Asp Ser Thr Gly Val Cys Arg Val Val
1               5                   10                  15

Val Thr Pro Gln Ser Pro Glu Cys Tyr
            20                  25


<210> SEQ ID NO 653
<211> LENGTH: 25
<212> TYPE: PRT
<213> ORGANISM: Artificial Sequence
<220> FEATURE:
<223> OTHER INFORMATION: Synthetic Construct

<400> SEQUENCE: 653

Ile Met Ala Tyr Arg Gly Arg Glu Val Val Glu Asn His Leu Pro Leu
1               5                   10                  15

Arg Ser Ala Pro Gly Cys Glu Ser Arg
            20                  25


<210> SEQ ID NO 654
<211> LENGTH: 25
```

<212> TYPE: PRT
<213> ORGANISM: Artificial Sequence
<220> FEATURE:
<223> OTHER INFORMATION: Synthetic Construct

<400> SEQUENCE: 654

Leu Glu Ile Lys Ile Pro Glu Thr Tyr Pro Phe Asn Ser Pro Lys Tyr
1 5 10 15

Lys Gln Asn Pro Glu Met Phe Lys Gln
20 25

<210> SEQ ID NO 655
<211> LENGTH: 25
<212> TYPE: PRT
<213> ORGANISM: Artificial Sequence
<220> FEATURE:
<223> OTHER INFORMATION: Synthetic Construct

<400> SEQUENCE: 655

Gly His Pro Ser Ser Ser Thr Leu Pro Glu Glu Glu Lys Glu Glu Asp
1 5 10 15

Glu Glu Gly Tyr Cys Pro Arg Cys Gln
20 25

<210> SEQ ID NO 656
<211> LENGTH: 25
<212> TYPE: PRT
<213> ORGANISM: Artificial Sequence
<220> FEATURE:
<223> OTHER INFORMATION: Synthetic Construct

<400> SEQUENCE: 656

Gly Asn Ile Leu Leu Ser Thr Leu Glu Ile Arg Asn Lys Thr Ser Gly
1 5 10 15

Ser Glu Val Leu Thr Ser Val Ser Asp
20 25

<210> SEQ ID NO 657
<211> LENGTH: 25
<212> TYPE: PRT
<213> ORGANISM: Artificial Sequence
<220> FEATURE:
<223> OTHER INFORMATION: Synthetic Construct

<400> SEQUENCE: 657

Met Gly Gly Lys Glu Arg Met Ala Gly Phe Pro Pro Phe Val Ala Glu
1 5 10 15

Asp Ile Met Leu Lys Glu Gly Leu Gly
20 25

<210> SEQ ID NO 658
<211> LENGTH: 25
<212> TYPE: PRT
<213> ORGANISM: Artificial Sequence
<220> FEATURE:
<223> OTHER INFORMATION: Synthetic Construct

<400> SEQUENCE: 658

Arg Thr Thr Thr Leu Ser Pro Gly Arg Ser Thr Thr Ser Ser Val Ser
1 5 10 15

Gly Arg Arg Asn Arg Ser Thr Ser Thr
20 25

<210> SEQ ID NO 659

<211> LENGTH: 25
<212> TYPE: PRT
<213> ORGANISM: Artificial Sequence
<220> FEATURE:
<223> OTHER INFORMATION: Synthetic Construct

<400> SEQUENCE: 659

Lys Lys Val Ser Val Pro Ser Thr Val Ile Ser Arg Gly Ile Gly Arg
1 5 10 15

Gly Gly Cys Asn Ile Asn Ala Ile Arg
20 25

<210> SEQ ID NO 660
<211> LENGTH: 25
<212> TYPE: PRT
<213> ORGANISM: Artificial Sequence
<220> FEATURE:
<223> OTHER INFORMATION: Synthetic Construct

<400> SEQUENCE: 660

His Val Glu Glu Val Thr Lys Glu Gly Val Lys Lys Phe Pro Ser Pro
1 5 10 15

Gly Tyr Pro Leu Val Cys Val Thr Pro
20 25

<210> SEQ ID NO 661
<211> LENGTH: 25
<212> TYPE: PRT
<213> ORGANISM: Artificial Sequence
<220> FEATURE:
<223> OTHER INFORMATION: Synthetic Construct

<400> SEQUENCE: 661

Glu Ala Cys Gly Thr Ser Val Ile Val Gly Val Pro Leu Asp Ser Gln
1 5 10 15

Asn Leu Ser Met Asn Pro Met Leu Leu
20 25

<210> SEQ ID NO 662
<211> LENGTH: 25
<212> TYPE: PRT
<213> ORGANISM: Artificial Sequence
<220> FEATURE:
<223> OTHER INFORMATION: Synthetic Construct

<400> SEQUENCE: 662

Ala Asp Gly Ala Glu Ala Asn Glu Met Glu Gly Glu Glu Lys Gln Asn
1 5 10 15

Gly Ser Gly Met Glu Thr Lys His Ser
20 25

<210> SEQ ID NO 663
<211> LENGTH: 25
<212> TYPE: PRT
<213> ORGANISM: Artificial Sequence
<220> FEATURE:
<223> OTHER INFORMATION: Synthetic Construct

<400> SEQUENCE: 663

Asn Asp Ala Gly Asp His Val Thr Lys Leu Leu Arg Phe Ser Val Leu
1 5 10 15

Gly Phe Ala Cys Lys Met Gly Asp Arg
20 25

-continued

```
<210> SEQ ID NO 664
<211> LENGTH: 25
<212> TYPE: PRT
<213> ORGANISM: Artificial Sequence
<220> FEATURE:
<223> OTHER INFORMATION: Synthetic Construct

<400> SEQUENCE: 664

Ser Gly Leu Gly Ser Pro Leu Gly Arg Ser Arg His Thr Ser Ser Gln
1               5                   10                  15

Ser Asp Leu Thr Ser Ser Ser Ser Ser
            20                  25


<210> SEQ ID NO 665
<211> LENGTH: 25
<212> TYPE: PRT
<213> ORGANISM: Artificial Sequence
<220> FEATURE:
<223> OTHER INFORMATION: Synthetic Construct

<400> SEQUENCE: 665

Cys Arg Arg Thr Leu Phe Gly Asp Tyr Ser Leu Lys Ala Arg Lys Pro
1               5                   10                  15

Ser Pro Ser Cys Ser Ser Gly Gly Ser
            20                  25


<210> SEQ ID NO 666
<211> LENGTH: 25
<212> TYPE: PRT
<213> ORGANISM: Artificial Sequence
<220> FEATURE:
<223> OTHER INFORMATION: Synthetic Construct

<400> SEQUENCE: 666

Met Ser Arg Gly Leu Ser Thr Ser Leu Pro Asp Leu Gly Ser Glu Pro
1               5                   10                  15

Trp Ile Glu Val Lys Lys Arg His Gln
            20                  25


<210> SEQ ID NO 667
<211> LENGTH: 25
<212> TYPE: PRT
<213> ORGANISM: Artificial Sequence
<220> FEATURE:
<223> OTHER INFORMATION: Synthetic Construct

<400> SEQUENCE: 667

Ser Gln Leu Ser Ser Ser Ser Lys Phe Ile Pro Gly Asp Pro Thr Cys
1               5                   10                  15

Phe Glu Ile Lys Pro Glu Glu Asn Ser
            20                  25


<210> SEQ ID NO 668
<211> LENGTH: 25
<212> TYPE: PRT
<213> ORGANISM: Artificial Sequence
<220> FEATURE:
<223> OTHER INFORMATION: Synthetic Construct

<400> SEQUENCE: 668

Leu Pro Gln Phe Leu Leu Lys Glu Glu Lys Asp Leu Gln Tyr Cys Thr
1               5                   10                  15

Lys His Tyr Asn Thr Gly Lys Phe Thr
            20                  25
```

<210> SEQ ID NO 669
<211> LENGTH: 25
<212> TYPE: PRT
<213> ORGANISM: Artificial Sequence
<220> FEATURE:
<223> OTHER INFORMATION: Synthetic Construct

<400> SEQUENCE: 669

```
Ile His Asp Val Lys Asp Tyr Ile Thr Asp Val Asn Asn Trp Leu Val
1               5                   10                  15

Thr Phe Gly Phe His Leu His Asn Ala
            20                  25
```

<210> SEQ ID NO 670
<211> LENGTH: 25
<212> TYPE: PRT
<213> ORGANISM: Artificial Sequence
<220> FEATURE:
<223> OTHER INFORMATION: Synthetic Construct

<400> SEQUENCE: 670

```
His His Ser Gly Arg Ser Lys Lys Ser Arg Thr His Gln Lys Ser His
1               5                   10                  15

Gly Lys Ser Arg Ser His Ser Lys Thr
            20                  25
```

<210> SEQ ID NO 671
<211> LENGTH: 25
<212> TYPE: PRT
<213> ORGANISM: Artificial Sequence
<220> FEATURE:
<223> OTHER INFORMATION: Synthetic Construct

<400> SEQUENCE: 671

```
Gln Ser Gly Val Val Thr Leu Pro Gly Thr Arg Asp Gly His Gly Arg
1               5                   10                  15

Ala Val Val Gln Val Arg Thr Arg Ser
            20                  25
```

<210> SEQ ID NO 672
<211> LENGTH: 25
<212> TYPE: PRT
<213> ORGANISM: Artificial Sequence
<220> FEATURE:
<223> OTHER INFORMATION: Synthetic Construct

<400> SEQUENCE: 672

```
Phe Gly Ala Leu Gly Trp Asn Ile Pro Tyr Glu Phe Ser Gln Ala Asp
1               5                   10                  15

Phe Asn Ala Thr Val Gln Phe Ile Gln
            20                  25
```

<210> SEQ ID NO 673
<211> LENGTH: 25
<212> TYPE: PRT
<213> ORGANISM: Artificial Sequence
<220> FEATURE:
<223> OTHER INFORMATION: Synthetic Construct

<400> SEQUENCE: 673

```
Asp Met Ile Ser Lys Leu Tyr Thr Lys Gln Lys Tyr Asn Pro Pro Leu
1               5                   10                  15

Ala Arg Asn Gln Pro Pro Ile Ala Gly
            20                  25
```

<210> SEQ ID NO 674
<211> LENGTH: 25
<212> TYPE: PRT
<213> ORGANISM: Artificial Sequence
<220> FEATURE:
<223> OTHER INFORMATION: Synthetic Construct

<400> SEQUENCE: 674

Lys Pro Lys Val Phe Val Thr Glu Gly Asn Asp Val Ser Leu Thr Gly
1 5 10 15

Val Cys Val Phe Phe Ile Arg Thr Asp
20 25

<210> SEQ ID NO 675
<211> LENGTH: 25
<212> TYPE: PRT
<213> ORGANISM: Artificial Sequence
<220> FEATURE:
<223> OTHER INFORMATION: Synthetic Construct

<400> SEQUENCE: 675

Pro Ser Gln His Asn Pro Arg Ser Ser Tyr His Asn Phe Thr Asp Val
1 5 10 15

Cys Glu Leu Ala Val Gly Pro Ala Gly
20 25

<210> SEQ ID NO 676
<211> LENGTH: 25
<212> TYPE: PRT
<213> ORGANISM: Artificial Sequence
<220> FEATURE:
<223> OTHER INFORMATION: Synthetic Construct

<400> SEQUENCE: 676

Ala Ala Ile Gly Arg Gly Arg Ser Leu Lys Asn Leu Gln Val Arg Gly
1 5 10 15

Arg Asn Asp Ser Gly Glu Glu Asn Val
20 25

<210> SEQ ID NO 677
<211> LENGTH: 25
<212> TYPE: PRT
<213> ORGANISM: Artificial Sequence
<220> FEATURE:
<223> OTHER INFORMATION: Synthetic Construct

<400> SEQUENCE: 677

Phe Ile Pro Asn Glu Glu Ile Leu Met Phe Leu Glu Lys Met Leu Asp
1 5 10 15

Gly Leu Glu Ser Leu Asn Pro Thr Cys
20 25

<210> SEQ ID NO 678
<211> LENGTH: 25
<212> TYPE: PRT
<213> ORGANISM: Artificial Sequence
<220> FEATURE:
<223> OTHER INFORMATION: Synthetic Construct

<400> SEQUENCE: 678

Ser Glu Gly Asp Ser Val Asn Ser Glu Ala Ser Phe Ser Ser Arg Asn
1 5 10 15

Ser Asp Thr Asp Asp Gly Thr Gly Ile 20 25

<210> SEQ ID NO 679
<211> LENGTH: 25
<212> TYPE: PRT
<213> ORGANISM: Artificial Sequence
<220> FEATURE:
<223> OTHER INFORMATION: Synthetic Construct

<400> SEQUENCE: 679

Pro Phe Pro Ser Gln His Arg Thr Glu Ile Glu Leu Leu Pro Tyr Ser
1 5 10 15

Gly Asp Lys Ile Leu Val Glu Gly Ile
20 25

<210> SEQ ID NO 680
<211> LENGTH: 25
<212> TYPE: PRT
<213> ORGANISM: Artificial Sequence
<220> FEATURE:
<223> OTHER INFORMATION: Synthetic Construct

<400> SEQUENCE: 680

Leu Ser Thr Pro Gln Pro Pro Ala Ser Thr Lys Phe Tyr Pro Asp Ile
1 5 10 15

Asn Val Tyr Ile Ile Glu Val Arg Glu
20 25

<210> SEQ ID NO 681
<211> LENGTH: 25
<212> TYPE: PRT
<213> ORGANISM: Artificial Sequence
<220> FEATURE:
<223> OTHER INFORMATION: Synthetic Construct

<400> SEQUENCE: 681

Ser Pro His Val Glu Thr Thr Phe Ser Thr Glu Pro Ile Gly Leu Val
1 5 10 15

Leu Ser Thr Val Met Asp Arg Val Val
20 25

<210> SEQ ID NO 682
<211> LENGTH: 25
<212> TYPE: PRT
<213> ORGANISM: Artificial Sequence
<220> FEATURE:
<223> OTHER INFORMATION: Synthetic Construct

<400> SEQUENCE: 682

Phe Thr Gly Leu Glu Gly Ala Phe Gly Thr Val Asn Ser Lys Tyr His
1 5 10 15

Pro Ser Arg Asn Asn Thr Ile Ala Asn
20 25

<210> SEQ ID NO 683
<211> LENGTH: 25
<212> TYPE: PRT
<213> ORGANISM: Artificial Sequence
<220> FEATURE:
<223> OTHER INFORMATION: Synthetic Construct

<400> SEQUENCE: 683

Leu Lys Val Gly Met Arg Arg Glu Ala Val Gln Arg Glu Arg Met Pro
1 5 10 15

Pro Thr Gln Pro Asn Pro Gly Gln Tyr
20 25

<210> SEQ ID NO 684
<211> LENGTH: 25
<212> TYPE: PRT
<213> ORGANISM: Artificial Sequence
<220> FEATURE:
<223> OTHER INFORMATION: Synthetic Construct

<400> SEQUENCE: 684

Ala Ser Thr Ser Gly Thr Leu Asp Asp Ala Asp Asp Ser Ser Thr Ser
1 5 10 15

Val Gly Ala Tyr His Tyr Met Leu Glu
20 25

<210> SEQ ID NO 685
<211> LENGTH: 25
<212> TYPE: PRT
<213> ORGANISM: Artificial Sequence
<220> FEATURE:
<223> OTHER INFORMATION: Synthetic Construct

<400> SEQUENCE: 685

Thr Ala Ala Gln Leu Gly Ala Tyr Ala Ile Gln Ser Lys Leu Gly Asp
1 5 10 15

Tyr Asp Pro Tyr Lys His Thr Ala Gly
20 25

<210> SEQ ID NO 686
<211> LENGTH: 25
<212> TYPE: PRT
<213> ORGANISM: Artificial Sequence
<220> FEATURE:
<223> OTHER INFORMATION: Synthetic Construct

<400> SEQUENCE: 686

Asp Ile Arg Ser Glu Glu Pro Leu Lys Thr Asp Ser Trp Ala Ser Asn
1 5 10 15

Ser Asn Ser Glu Leu Lys Ala Ile Arg
20 25

<210> SEQ ID NO 687
<211> LENGTH: 25
<212> TYPE: PRT
<213> ORGANISM: Artificial Sequence
<220> FEATURE:
<223> OTHER INFORMATION: Synthetic Construct

<400> SEQUENCE: 687

Pro Glu Lys Lys Leu Asn Gln Lys Ser Asp Gly Lys Leu Arg Lys Val
1 5 10 15

Arg Phe Lys Ile Ser Ser Ser Tyr Ser
20 25

<210> SEQ ID NO 688
<211> LENGTH: 25
<212> TYPE: PRT
<213> ORGANISM: Artificial Sequence
<220> FEATURE:
<223> OTHER INFORMATION: Synthetic Construct

<400> SEQUENCE: 688

Asn Leu Glu Lys Met Gly Pro Arg Ile Leu Asp Leu His Leu Glu Phe
1 5 10 15

Asp Glu Lys Ala Val Leu Met Glu Asn
            20                  25

<210> SEQ ID NO 689
<211> LENGTH: 25
<212> TYPE: PRT
<213> ORGANISM: Artificial Sequence
<220> FEATURE:
<223> OTHER INFORMATION: Synthetic Construct

<400> SEQUENCE: 689

Asp Val Ala Val Ala Pro Leu Thr Ile Thr Leu Val Leu Glu Glu Val
1               5                   10                  15

Ile Asp Phe Ser Lys Pro Phe Met Ser
            20                  25

<210> SEQ ID NO 690
<211> LENGTH: 17
<212> TYPE: PRT
<213> ORGANISM: Artificial Sequence
<220> FEATURE:
<223> OTHER INFORMATION: Synthetic Construct

<400> SEQUENCE: 690

Gly Phe Thr Pro Leu Ser Glu Ser Ile Pro Asp Ser Ser Lys Arg Met
1               5                   10                  15

Glu

<210> SEQ ID NO 691
<211> LENGTH: 25
<212> TYPE: PRT
<213> ORGANISM: Artificial Sequence
<220> FEATURE:
<223> OTHER INFORMATION: Synthetic Construct

<400> SEQUENCE: 691

Ser Ser Trp Ser His Asn Ser Asn Ser Met Cys Trp Glu Lys Asp Gln
1               5                   10                  15

Cys Pro Tyr Ser Gly Cys Lys Glu Ala
            20                  25

<210> SEQ ID NO 692
<211> LENGTH: 25
<212> TYPE: PRT
<213> ORGANISM: Artificial Sequence
<220> FEATURE:
<223> OTHER INFORMATION: Synthetic Construct

<400> SEQUENCE: 692

Ser Arg Pro Pro Ala Pro Glu Leu Gly Ser Pro Gly Thr Val Arg Pro
1               5                   10                  15

Arg Val Gly Ser Cys Ala Pro Gly Pro
            20                  25

<210> SEQ ID NO 693
<211> LENGTH: 25
<212> TYPE: PRT
<213> ORGANISM: Artificial Sequence
<220> FEATURE:
<223> OTHER INFORMATION: Synthetic Construct

<400> SEQUENCE: 693

Trp Lys Arg Ser Ser Val Glu Val Gly Asp Thr Arg Phe Trp Arg Leu
1               5                   10                  15

```
Tyr Gln Phe Ser Phe Val Gly Leu Arg
            20                  25


<210> SEQ ID NO 694
<211> LENGTH: 24
<212> TYPE: PRT
<213> ORGANISM: Artificial Sequence
<220> FEATURE:
<223> OTHER INFORMATION: Synthetic Construct

<400> SEQUENCE: 694

Leu Gly Ala Gln Gly Pro Ser Gly Ser Ser Glu Trp Lys Asp Glu Gln
1               5                   10                  15

Ser Glu Tyr Ser Asp Ile Arg Arg
            20


<210> SEQ ID NO 695
<211> LENGTH: 25
<212> TYPE: PRT
<213> ORGANISM: Artificial Sequence
<220> FEATURE:
<223> OTHER INFORMATION: Synthetic Construct

<400> SEQUENCE: 695

Leu Arg Ala Arg Arg Pro Pro Gly Pro Asp Leu Ser Ser Asp Gly Pro
1               5                   10                  15

Arg Ser Ser Glu Gly Pro Leu Ser Phe
            20                  25


<210> SEQ ID NO 696
<211> LENGTH: 25
<212> TYPE: PRT
<213> ORGANISM: Artificial Sequence
<220> FEATURE:
<223> OTHER INFORMATION: Synthetic Construct

<400> SEQUENCE: 696

Ser Met Pro Leu Trp Asp Phe Gln Gly Ser Thr Met Arg Thr Ser Gln
1               5                   10                  15

Tyr Val Arg Leu Thr Pro Asp Glu Arg
            20                  25


<210> SEQ ID NO 697
<211> LENGTH: 25
<212> TYPE: PRT
<213> ORGANISM: Artificial Sequence
<220> FEATURE:
<223> OTHER INFORMATION: Synthetic Construct

<400> SEQUENCE: 697

Tyr Pro Gly Ile Lys Phe Glu Glu Leu Phe Pro Asp Cys Ile Phe Pro
1               5                   10                  15

Ser Glu Ser Glu Arg Asp Lys Ile Lys
            20                  25


<210> SEQ ID NO 698
<211> LENGTH: 25
<212> TYPE: PRT
<213> ORGANISM: Artificial Sequence
<220> FEATURE:
<223> OTHER INFORMATION: Synthetic Construct

<400> SEQUENCE: 698

Arg Glu Glu Ser Glu Glu Glu Glu Asp Glu Asp Asp Asp Glu Glu Glu
```

```
1               5                   10                  15

Glu Glu Glu Lys Gly Lys Gly Gln Lys
            20                  25


<210> SEQ ID NO 699
<211> LENGTH: 25
<212> TYPE: PRT
<213> ORGANISM: Artificial Sequence
<220> FEATURE:
<223> OTHER INFORMATION: Synthetic Construct

<400> SEQUENCE: 699

Leu Ile Lys Ser Arg Ser Lys Ser Glu Arg Pro Pro Lys Ile Leu Met
1               5                   10                  15

Thr Glu Glu Pro Ser Ser Pro Lys Gly
            20                  25


<210> SEQ ID NO 700
<211> LENGTH: 25
<212> TYPE: PRT
<213> ORGANISM: Artificial Sequence
<220> FEATURE:
<223> OTHER INFORMATION: Synthetic Construct

<400> SEQUENCE: 700

Leu Glu Pro Ser Lys Thr Thr Gly Ala Pro Ile Tyr Ser Gly Phe Pro
1               5                   10                  15

Lys Val Thr Glu Val His His Glu Gln
            20                  25


<210> SEQ ID NO 701
<211> LENGTH: 25
<212> TYPE: PRT
<213> ORGANISM: Artificial Sequence
<220> FEATURE:
<223> OTHER INFORMATION: Synthetic Construct

<400> SEQUENCE: 701

Leu Glu Pro Ser Lys Thr Thr Gly Ala Pro Ile Tyr Leu Gly Phe Pro
1               5                   10                  15

Lys Val Thr Glu Val His His Glu Gln
            20                  25


<210> SEQ ID NO 702
<211> LENGTH: 16
<212> TYPE: PRT
<213> ORGANISM: Artificial Sequence
<220> FEATURE:
<223> OTHER INFORMATION: Synthetic Construct

<400> SEQUENCE: 702

Ser Asp Pro Ser Gly Leu Pro Arg Pro Gln Lys Ile Ser Ile Ser Ala
1               5                   10                  15


<210> SEQ ID NO 703
<211> LENGTH: 25
<212> TYPE: PRT
<213> ORGANISM: Artificial Sequence
<220> FEATURE:
<223> OTHER INFORMATION: Synthetic Construct

<400> SEQUENCE: 703

Met Leu Arg Trp Thr Val His Leu Glu Gly Gly Pro Cys Arg Val Asn
1               5                   10                  15
```

His Ala Ala Val Ala Val Gly His Arg
20 25

<210> SEQ ID NO 704
<211> LENGTH: 25
<212> TYPE: PRT
<213> ORGANISM: Artificial Sequence
<220> FEATURE:
<223> OTHER INFORMATION: Synthetic Construct

<400> SEQUENCE: 704

Leu Cys Lys Leu Met Lys Glu Ile Leu Asp Lys Lys Ala Glu Lys Val
1 5 10 15

Thr Ile Ser Asn Arg Leu Val Ser Ser
20 25

<210> SEQ ID NO 705
<211> LENGTH: 25
<212> TYPE: PRT
<213> ORGANISM: Artificial Sequence
<220> FEATURE:
<223> OTHER INFORMATION: Synthetic Construct

<400> SEQUENCE: 705

Ala Gly Ala Ala Glu Ser Gln Arg Gly Lys Gln Thr Leu Ala His Ser
1 5 10 15

Leu Glu Gln Leu Arg Arg Leu Pro Leu
20 25

<210> SEQ ID NO 706
<211> LENGTH: 25
<212> TYPE: PRT
<213> ORGANISM: Artificial Sequence
<220> FEATURE:
<223> OTHER INFORMATION: Synthetic Construct

<400> SEQUENCE: 706

Cys Gln Gln Glu Thr Phe Cys Leu Phe Asp Ile Gly Asn Asn Phe Ser
1 5 10 15

Asn Ser Gln Glu His Leu Asp Leu Leu
20 25

<210> SEQ ID NO 707
<211> LENGTH: 25
<212> TYPE: PRT
<213> ORGANISM: Artificial Sequence
<220> FEATURE:
<223> OTHER INFORMATION: Synthetic Construct

<400> SEQUENCE: 707

His Glu Gly Thr Gln Ile Glu Lys Ala Val Pro Lys Lys Thr Ser Asn
1 5 10 15

Thr Val Tyr Leu Asp Tyr Arg Pro His
20 25

<210> SEQ ID NO 708
<211> LENGTH: 25
<212> TYPE: PRT
<213> ORGANISM: Artificial Sequence
<220> FEATURE:
<223> OTHER INFORMATION: Synthetic Construct

<400> SEQUENCE: 708

Thr Val Val Leu Pro Glu Phe Pro Glu Asp Ser Tyr Ser Asp Val Pro
1 5 10 15

Glu Met Glu Pro Phe Lys Glu Lys Ile
20 25

<210> SEQ ID NO 709
<211> LENGTH: 25
<212> TYPE: PRT
<213> ORGANISM: Artificial Sequence
<220> FEATURE:
<223> OTHER INFORMATION: Synthetic Construct

<400> SEQUENCE: 709

Glu Ala Ser Lys Glu Lys Gly Ser Glu Lys Gly Arg Thr Glu Gly Glu
1 5 10 15

Trp Glu Asp Gln Glu Ala Leu Asp Tyr
20 25

<210> SEQ ID NO 710
<211> LENGTH: 25
<212> TYPE: PRT
<213> ORGANISM: Artificial Sequence
<220> FEATURE:
<223> OTHER INFORMATION: Synthetic Construct

<400> SEQUENCE: 710

Phe Gly Asp Ser Asn Ser Leu Asp Leu Ser Asp Met Arg Val Val Ser
1 5 10 15

Arg Asn Cys Thr Glu Asp Gly Trp Ser
20 25

<210> SEQ ID NO 711
<211> LENGTH: 25
<212> TYPE: PRT
<213> ORGANISM: Artificial Sequence
<220> FEATURE:
<223> OTHER INFORMATION: Synthetic Construct

<400> SEQUENCE: 711

Glu Lys Ala Arg Leu Ala Ala Glu Glu Gln Gln Lys Lys Met Glu Ala
1 5 10 15

Lys Ser Gln Ala Glu Glu Gly Ala Ser
20 25

<210> SEQ ID NO 712
<211> LENGTH: 25
<212> TYPE: PRT
<213> ORGANISM: Artificial Sequence
<220> FEATURE:
<223> OTHER INFORMATION: Synthetic Construct

<400> SEQUENCE: 712

Leu Leu Lys Thr Arg Arg Ile Leu Lys Cys Ser Tyr Leu Tyr Gly Phe
1 5 10 15

Phe Leu Glu Pro Lys Ser Thr Lys Lys
20 25

<210> SEQ ID NO 713
<211> LENGTH: 25
<212> TYPE: PRT
<213> ORGANISM: Artificial Sequence
<220> FEATURE:
<223> OTHER INFORMATION: Synthetic Construct

<400> SEQUENCE: 713

Leu Thr Val Lys Ile Gly Asp Phe Gly Leu Ala Thr Glu Lys Ser Arg 1 5 10 15

Trp Ser Gly Ser His Gln Phe Glu Gln
20 25

<210> SEQ ID NO 714
<211> LENGTH: 25
<212> TYPE: PRT
<213> ORGANISM: Artificial Sequence
<220> FEATURE:
<223> OTHER INFORMATION: Synthetic Construct

<400> SEQUENCE: 714

Thr Tyr His Leu Arg Val His Asn Ser Thr Glu Arg Leu Phe Pro Cys
1 5 10 15

Pro Asp Cys Pro Lys Arg Phe Ala Asp
20 25

<210> SEQ ID NO 715
<211> LENGTH: 25
<212> TYPE: PRT
<213> ORGANISM: Artificial Sequence
<220> FEATURE:
<223> OTHER INFORMATION: Synthetic Construct

<400> SEQUENCE: 715

Lys Gly Gly Leu Tyr Ala Glu Leu Ile Arg Arg Gln Thr Leu Asp Ala
1 5 10 15

Pro Arg Thr Ala Ala Pro Pro Pro Lys
20 25

<210> SEQ ID NO 716
<211> LENGTH: 25
<212> TYPE: PRT
<213> ORGANISM: Artificial Sequence
<220> FEATURE:
<223> OTHER INFORMATION: Synthetic Construct

<400> SEQUENCE: 716

Arg Glu Val Asn Glu Thr Val Thr Lys Thr Pro Val Ser Ser Asp Val
1 5 10 15

Phe Phe Val Asn Ser Leu Trp Lys Gly
20 25

<210> SEQ ID NO 717
<211> LENGTH: 23
<212> TYPE: PRT
<213> ORGANISM: Artificial Sequence
<220> FEATURE:
<223> OTHER INFORMATION: Synthetic Construct

<400> SEQUENCE: 717

His Phe Leu Pro Arg Pro Val Asp Pro Glu Arg Val Ser Glu Leu Tyr
1 5 10 15

Lys Asp Leu Leu Met Tyr Thr
20

<210> SEQ ID NO 718
<211> LENGTH: 25
<212> TYPE: PRT
<213> ORGANISM: Artificial Sequence
<220> FEATURE:
<223> OTHER INFORMATION: Synthetic Construct

<400> SEQUENCE: 718

-continued

```
Thr Leu Asn Ile Cys Ser Arg Cys Ala Arg Leu Gln Glu Asp Asn Leu
1               5                   10                  15

Glu Glu Arg Thr Glu Glu Ser Leu Pro
            20                  25


<210> SEQ ID NO 719
<211> LENGTH: 25
<212> TYPE: PRT
<213> ORGANISM: Artificial Sequence
<220> FEATURE:
<223> OTHER INFORMATION: Synthetic Construct

<400> SEQUENCE: 719

Met Asp Ala Thr Asp Gln Val Val Tyr Lys His Cys Ala Val Ser Gly
1               5                   10                  15

Gln Thr Asp Ala Ala Lys Asn Ala Ala
            20                  25


<210> SEQ ID NO 720
<211> LENGTH: 25
<212> TYPE: PRT
<213> ORGANISM: Artificial Sequence
<220> FEATURE:
<223> OTHER INFORMATION: Synthetic Construct

<400> SEQUENCE: 720

Gly Ala Asn Val Lys Pro Arg Asn Ser Thr Pro Pro Arg Leu Ala Arg
1               5                   10                  15

Asn Pro Ala Pro Gly Val Leu Thr Asn
            20                  25


<210> SEQ ID NO 721
<211> LENGTH: 25
<212> TYPE: PRT
<213> ORGANISM: Artificial Sequence
<220> FEATURE:
<223> OTHER INFORMATION: Synthetic Construct

<400> SEQUENCE: 721

Ala Asn His Thr Asn Pro Leu Thr Val Ser Lys Ile Tyr Thr Glu Met
1               5                   10                  15

Arg Lys Arg Leu Cys Gly Glu Phe Glu
            20                  25


<210> SEQ ID NO 722
<211> LENGTH: 25
<212> TYPE: PRT
<213> ORGANISM: Artificial Sequence
<220> FEATURE:
<223> OTHER INFORMATION: Synthetic Construct

<400> SEQUENCE: 722

Phe Asn Asn Gln Ile Leu Lys Val Glu Pro Gly Tyr Ser Arg Ser Ile
1               5                   10                  15

Leu Lys Asp Phe Met Gly Cys Asp Gly
            20                  25


<210> SEQ ID NO 723
<211> LENGTH: 25
<212> TYPE: PRT
<213> ORGANISM: Artificial Sequence
<220> FEATURE:
<223> OTHER INFORMATION: Synthetic Construct

<400> SEQUENCE: 723
```

```
Val Gln Val Ile Thr Leu Glu Asn Trp Glu Thr Thr Asp Ala Ile Asn
1               5                   10                  15

Glu Val Gln Lys Ile Lys Val Thr Ser
            20                  25


<210> SEQ ID NO 724
<211> LENGTH: 25
<212> TYPE: PRT
<213> ORGANISM: Artificial Sequence
<220> FEATURE:
<223> OTHER INFORMATION: Synthetic Construct

<400> SEQUENCE: 724

Pro Tyr His Ile Arg Arg Cys Met Thr Ile Ser Ile Cys Ile Asn Ser
1               5                   10                  15

Arg Glu Leu Leu Val Tyr Lys Asn Cys
            20                  25


<210> SEQ ID NO 725
<211> LENGTH: 25
<212> TYPE: PRT
<213> ORGANISM: Artificial Sequence
<220> FEATURE:
<223> OTHER INFORMATION: Synthetic Construct

<400> SEQUENCE: 725

Val Thr Val Thr Val Glu Ser Pro Ser Ser Ser Glu Ala Glu Glu Val
1               5                   10                  15

Asp Asp Ser Ser Glu Ser Val His Glu
            20                  25


<210> SEQ ID NO 726
<211> LENGTH: 25
<212> TYPE: PRT
<213> ORGANISM: Artificial Sequence
<220> FEATURE:
<223> OTHER INFORMATION: Synthetic Construct

<400> SEQUENCE: 726

Ala Thr Leu Gln Asp Glu Ala Glu Lys Val Asp Ala Val Leu His Thr
1               5                   10                  15

Met Leu Leu Lys Gln Glu Pro Gln Arg
            20                  25


<210> SEQ ID NO 727
<211> LENGTH: 25
<212> TYPE: PRT
<213> ORGANISM: Artificial Sequence
<220> FEATURE:
<223> OTHER INFORMATION: Synthetic Construct

<400> SEQUENCE: 727

Leu Gly Ser Thr Leu His Gly Arg Gly Pro Pro Gly Phe Arg Lys Pro
1               5                   10                  15

Gly Glu Gly Ala Arg Ala Glu Ala Leu
            20                  25


<210> SEQ ID NO 728
<211> LENGTH: 25
<212> TYPE: PRT
<213> ORGANISM: Artificial Sequence
<220> FEATURE:
<223> OTHER INFORMATION: Synthetic Construct
```

<400> SEQUENCE: 728

Asp Trp Lys Arg Ser Pro Pro Asn Val Gln Pro Asn Arg Ile Trp Pro
1               5                   10                  15

Ile Ser Glu Trp Asp Glu Val Ile Gln
            20                  25

<210> SEQ ID NO 729
<211> LENGTH: 25
<212> TYPE: PRT
<213> ORGANISM: Artificial Sequence
<220> FEATURE:
<223> OTHER INFORMATION: Synthetic Construct

<400> SEQUENCE: 729

Ile Phe Phe Thr Asp Leu Asp Asn Phe Leu Leu Thr Thr Met Ala Tyr
1               5                   10                  15

Asp Arg Tyr Val Ala Ile Cys His Pro
            20                  25

<210> SEQ ID NO 730
<211> LENGTH: 25
<212> TYPE: PRT
<213> ORGANISM: Artificial Sequence
<220> FEATURE:
<223> OTHER INFORMATION: Synthetic Construct

<400> SEQUENCE: 730

Tyr Pro Gly Gln Glu Glu Glu Glu Asp Asp Glu Glu Asn Ala Gly Gly
1               5                   10                  15

Leu Gly Ala Glu Pro Pro Gly Gly Ala
            20                  25

<210> SEQ ID NO 731
<211> LENGTH: 25
<212> TYPE: PRT
<213> ORGANISM: Artificial Sequence
<220> FEATURE:
<223> OTHER INFORMATION: Synthetic Construct

<400> SEQUENCE: 731

Ser Gln Glu Ser Gln Val Glu Glu Pro Leu Ser Gln Lys Ser Glu Met
1               5                   10                  15

Glu Glu Pro Leu Ser Gln Glu Ser Glu
            20                  25

<210> SEQ ID NO 732
<211> LENGTH: 25
<212> TYPE: PRT
<213> ORGANISM: Artificial Sequence
<220> FEATURE:
<223> OTHER INFORMATION: Synthetic Construct

<400> SEQUENCE: 732

Asn Lys Arg Gln Asn Lys Glu Leu Ser Ser Ser Asn Leu Ser Leu Ser
1               5                   10                  15

Ser Thr Ser Glu Thr Pro Asn Glu Ser
            20                  25

<210> SEQ ID NO 733
<211> LENGTH: 25
<212> TYPE: PRT
<213> ORGANISM: Artificial Sequence
<220> FEATURE:
<223> OTHER INFORMATION: Synthetic Construct

<400> SEQUENCE: 733

Lys Leu Ser Ser His Arg Thr Lys Ser Ser Gly Trp Leu Pro Pro Ser
1 5 10 15

Gly Thr Trp Gly Leu Ser Gln Val Pro
20 25

<210> SEQ ID NO 734
<211> LENGTH: 25
<212> TYPE: PRT
<213> ORGANISM: Artificial Sequence
<220> FEATURE:
<223> OTHER INFORMATION: Synthetic Construct

<400> SEQUENCE: 734

Ser Gln Leu Leu Glu Met Cys Tyr Asp Val Cys Glu Ser Met Ala Phe
1 5 10 15

Leu Glu Ser His Gln Phe Ile His Arg
20 25

<210> SEQ ID NO 735
<211> LENGTH: 25
<212> TYPE: PRT
<213> ORGANISM: Artificial Sequence
<220> FEATURE:
<223> OTHER INFORMATION: Synthetic Construct

<400> SEQUENCE: 735

Glu Leu Leu Glu Lys Ser Ile Ser Arg Arg Arg Asp Ile Glu Ala Ile
1 5 10 15

Gln Lys Ala Lys Ile Leu Tyr Ser Ser
20 25

<210> SEQ ID NO 736
<211> LENGTH: 25
<212> TYPE: PRT
<213> ORGANISM: Artificial Sequence
<220> FEATURE:
<223> OTHER INFORMATION: Synthetic Construct

<400> SEQUENCE: 736

Glu Asp Lys Ser Phe Gly Ser Ser Leu Met Glu Ser Lys Val Asn Leu
1 5 10 15

Asp Arg Tyr Gln Thr Ala Leu Glu Glu
20 25

<210> SEQ ID NO 737
<211> LENGTH: 25
<212> TYPE: PRT
<213> ORGANISM: Artificial Sequence
<220> FEATURE:
<223> OTHER INFORMATION: Synthetic Construct

<400> SEQUENCE: 737

Cys Pro Glu Pro Pro Glu Thr Arg Val Ser Pro Leu Cys Gln Leu Pro
1 5 10 15

Pro Glu Ala Gly Val Ser His Leu Cys
20 25

<210> SEQ ID NO 738
<211> LENGTH: 25
<212> TYPE: PRT
<213> ORGANISM: Artificial Sequence
<220> FEATURE:

<223> OTHER INFORMATION: Synthetic Construct

<400> SEQUENCE: 738

Pro Lys Glu Cys Ser Arg Met Gly Gly Arg Arg Ser Arg Gly Thr Arg
1 5 10 15

Gly Arg Ser Ile Gln Asn Arg Arg Lys
20 25

<210> SEQ ID NO 739
<211> LENGTH: 25
<212> TYPE: PRT
<213> ORGANISM: Artificial Sequence
<220> FEATURE:
<223> OTHER INFORMATION: Synthetic Construct

<400> SEQUENCE: 739

Leu Asp Asp Ala Leu Arg Lys Phe Gln Ser His Ile Gln Val Gln Gly
1 5 10 15

Glu Ala Gln Lys Val Glu Arg Leu Ile
20 25

<210> SEQ ID NO 740
<211> LENGTH: 25
<212> TYPE: PRT
<213> ORGANISM: Artificial Sequence
<220> FEATURE:
<223> OTHER INFORMATION: Synthetic Construct

<400> SEQUENCE: 740

Thr Gly Glu Ile Phe Thr Thr Gly Ala Arg Ile Asp Cys Glu Lys Leu
1 5 10 15

Cys Ala Gly Ile Pro Arg Asp Glu His
20 25

<210> SEQ ID NO 741
<211> LENGTH: 25
<212> TYPE: PRT
<213> ORGANISM: Artificial Sequence
<220> FEATURE:
<223> OTHER INFORMATION: Synthetic Construct

<400> SEQUENCE: 741

Thr Ser Val Thr Ser Met Gly Ser Gln Met Pro Asp Tyr Asp Gln Asn
1 5 10 15

Glu Gly Phe His Cys Arg Glu Glu Cys
20 25

<210> SEQ ID NO 742
<211> LENGTH: 25
<212> TYPE: PRT
<213> ORGANISM: Artificial Sequence
<220> FEATURE:
<223> OTHER INFORMATION: Synthetic Construct

<400> SEQUENCE: 742

Cys Arg His Gly Trp Lys Gly Pro Glu Cys Asp Val Ser Glu Glu Gln
1 5 10 15

Cys Ile Asp Pro Thr Cys Phe Gly His
20 25

<210> SEQ ID NO 743
<211> LENGTH: 25
<212> TYPE: PRT
<213> ORGANISM: Artificial Sequence
<220> FEATURE:
<223> OTHER INFORMATION: Synthetic Construct

<400> SEQUENCE: 743

Met Lys Ile Ala Gln Lys Thr Met Gly Arg Glu Asn Ser Gly Asp Thr
1 5 10 15

His Ser Val Gln Lys Trp His Arg Ala
20 25

<210> SEQ ID NO 744
<211> LENGTH: 25
<212> TYPE: PRT
<213> ORGANISM: Artificial Sequence
<220> FEATURE:
<223> OTHER INFORMATION: Synthetic Construct

<400> SEQUENCE: 744

Pro Leu Glu Ile Ser Gln Ser Pro Pro Glu Gly Glu Asn Val Gln Ser
1 5 10 15

Pro Leu Gln Asn Pro Ala Ser Ser Phe
20 25

<210> SEQ ID NO 745
<211> LENGTH: 25
<212> TYPE: PRT
<213> ORGANISM: Artificial Sequence
<220> FEATURE:
<223> OTHER INFORMATION: Synthetic Construct

<400> SEQUENCE: 745

Val Ala Tyr Asn Pro Trp Met Asp Ile Arg Gln Arg Lys Asp Val Gln
1 5 10 15

Ala Leu Asn Ile Ser Val Pro Tyr Gly
20 25

<210> SEQ ID NO 746
<211> LENGTH: 20
<212> TYPE: PRT
<213> ORGANISM: Artificial Sequence
<220> FEATURE:
<223> OTHER INFORMATION: Synthetic Construct

<400> SEQUENCE: 746

Met Pro Val Leu Ser Arg Pro Gly Pro Trp Arg Gly Asn Thr Leu Lys
1 5 10 15

Arg Thr Ala Val
20

<210> SEQ ID NO 747
<211> LENGTH: 31
<212> TYPE: DNA
<213> ORGANISM: Artificial Sequence
<220> FEATURE:
<223> OTHER INFORMATION: Synthetic Construct

<400> SEQUENCE: 747
tcaaatttca ctctgaagat ccggtccaca a 31

<210> SEQ ID NO 748
<211> LENGTH: 31
<212> TYPE: DNA
<213> ORGANISM: Artificial Sequence
<220> FEATURE:
<223> OTHER INFORMATION: Synthetic Construct

<400> SEQUENCE: 748
gctcacttaa atcttcacat caattccctg g 31

<210> SEQ ID NO 749
<211> LENGTH: 26
<212> TYPE: DNA
<213> ORGANISM: Artificial Sequence
<220> FEATURE:
<223> OTHER INFORMATION: Synthetic Construct

<400> SEQUENCE: 749
cttaaacctt cacctacacg ccctgc 26

<210> SEQ ID NO 750
<211> LENGTH: 26
<212> TYPE: DNA
<213> ORGANISM: Artificial Sequence
<220> FEATURE:
<223> OTHER INFORMATION: Synthetic Construct

<400> SEQUENCE: 750
cttattcctt cacctacaca ccctgc 26

<210> SEQ ID NO 751
<211> LENGTH: 26
<212> TYPE: DNA
<213> ORGANISM: Artificial Sequence
<220> FEATURE:
<223> OTHER INFORMATION: Synthetic Construct

<400> SEQUENCE: 751
gctctgagat gaatgtgagc accttg 26

<210> SEQ ID NO 752
<211> LENGTH: 26
<212> TYPE: DNA
<213> ORGANISM: Artificial Sequence
<220> FEATURE:
<223> OTHER INFORMATION: Synthetic Construct

<400> SEQUENCE: 752
gctctgagat gaatgtgagt gccttg 26

<210> SEQ ID NO 753
<211> LENGTH: 26
<212> TYPE: DNA
<213> ORGANISM: Artificial Sequence
<220> FEATURE:
<223> OTHER INFORMATION: Synthetic Construct

<400> SEQUENCE: 753
gctctgagct gaatgtgaac gccttg 26

<210> SEQ ID NO 754
<211> LENGTH: 22
<212> TYPE: DNA
<213> ORGANISM: Artificial Sequence
<220> FEATURE:
<223> OTHER INFORMATION: Synthetic Construct

<400> SEQUENCE: 754
tcgctcaggc tggagtcggc tg 22

<210> SEQ ID NO 755
<211> LENGTH: 20

<212> TYPE: DNA
<213> ORGANISM: Artificial Sequence
<220> FEATURE:
<223> OTHER INFORMATION: Synthetic Construct

<400> SEQUENCE: 755
gctggggttg gagtcggctg 20

<210> SEQ ID NO 756
<211> LENGTH: 21
<212> TYPE: DNA
<213> ORGANISM: Artificial Sequence
<220> FEATURE:
<223> OTHER INFORMATION: Synthetic Construct

<400> SEQUENCE: 756
ccctcacgtt ggcgtctgct g 21

<210> SEQ ID NO 757
<211> LENGTH: 20
<212> TYPE: DNA
<213> ORGANISM: Artificial Sequence
<220> FEATURE:
<223> OTHER INFORMATION: Synthetic Construct

<400> SEQUENCE: 757
gctcaggctg ctgtcggctg 20

<210> SEQ ID NO 758
<211> LENGTH: 21
<212> TYPE: DNA
<213> ORGANISM: Artificial Sequence
<220> FEATURE:
<223> OTHER INFORMATION: Synthetic Construct

<400> SEQUENCE: 758
cgctcaggct ggagttggct g 21

<210> SEQ ID NO 759
<211> LENGTH: 22
<212> TYPE: DNA
<213> ORGANISM: Artificial Sequence
<220> FEATURE:
<223> OTHER INFORMATION: Synthetic Construct

<400> SEQUENCE: 759
cccctcaagc tggagtcagc tg 22

<210> SEQ ID NO 760
<211> LENGTH: 21
<212> TYPE: DNA
<213> ORGANISM: Artificial Sequence
<220> FEATURE:
<223> OTHER INFORMATION: Synthetic Construct

<400> SEQUENCE: 760
cactcaggct ggtgtcggct g 21

<210> SEQ ID NO 761
<211> LENGTH: 21
<212> TYPE: DNA
<213> ORGANISM: Artificial Sequence
<220> FEATURE:
<223> OTHER INFORMATION: Synthetic Construct

<400> SEQUENCE: 761

-continued cgctcaggct ggagtcagct g 21

<210> SEQ ID NO 762
<211> LENGTH: 24
<212> TYPE: DNA
<213> ORGANISM: Artificial Sequence
<220> FEATURE:
<223> OTHER INFORMATION: Synthetic Construct

<400> SEQUENCE: 762
ccactctgaa gttccagcgc acac 24

<210> SEQ ID NO 763
<211> LENGTH: 23
<212> TYPE: DNA
<213> ORGANISM: Artificial Sequence
<220> FEATURE:
<223> OTHER INFORMATION: Synthetic Construct

<400> SEQUENCE: 763
cactctgacg atccagcgca cac 23

<210> SEQ ID NO 764
<211> LENGTH: 26
<212> TYPE: DNA
<213> ORGANISM: Artificial Sequence
<220> FEATURE:
<223> OTHER INFORMATION: Synthetic Construct

<400> SEQUENCE: 764
ctctactctg aagatccagc gcacag 26

<210> SEQ ID NO 765
<211> LENGTH: 24
<212> TYPE: DNA
<213> ORGANISM: Artificial Sequence
<220> FEATURE:
<223> OTHER INFORMATION: Synthetic Construct

<400> SEQUENCE: 765
ccactctgaa gatccagcgc acag 24

<210> SEQ ID NO 766
<211> LENGTH: 23
<212> TYPE: DNA
<213> ORGANISM: Artificial Sequence
<220> FEATURE:
<223> OTHER INFORMATION: Synthetic Construct

<400> SEQUENCE: 766
cactctgacg atccagcgca cag 23

<210> SEQ ID NO 767
<211> LENGTH: 24
<212> TYPE: DNA
<213> ORGANISM: Artificial Sequence
<220> FEATURE:
<223> OTHER INFORMATION: Synthetic Construct

<400> SEQUENCE: 767
ccactctgac gattcagcgc acag 24

<210> SEQ ID NO 768
<211> LENGTH: 24
<212> TYPE: DNA
<213> ORGANISM: Artificial Sequence
<220> FEATURE:
<223> OTHER INFORMATION: Synthetic Construct

<400> SEQUENCE: 768
ccactctgaa gatccagcgc acac 24

<210> SEQ ID NO 769
<211> LENGTH: 23
<212> TYPE: DNA
<213> ORGANISM: Artificial Sequence
<220> FEATURE:
<223> OTHER INFORMATION: Synthetic Construct

<400> SEQUENCE: 769
caccttggag atccagcgca cag 23

<210> SEQ ID NO 770
<211> LENGTH: 28
<212> TYPE: DNA
<213> ORGANISM: Artificial Sequence
<220> FEATURE:
<223> OTHER INFORMATION: Synthetic Construct

<400> SEQUENCE: 770
gcactctgaa ctaaacctga gctctctg 28

<210> SEQ ID NO 771
<211> LENGTH: 22
<212> TYPE: DNA
<213> ORGANISM: Artificial Sequence
<220> FEATURE:
<223> OTHER INFORMATION: Synthetic Construct

<400> SEQUENCE: 771
cccctcactc tggagtctgc tg 22

<210> SEQ ID NO 772
<211> LENGTH: 23
<212> TYPE: DNA
<213> ORGANISM: Artificial Sequence
<220> FEATURE:
<223> OTHER INFORMATION: Synthetic Construct

<400> SEQUENCE: 772
ccccctcact ctggagtcag cta 23

<210> SEQ ID NO 773
<211> LENGTH: 23
<212> TYPE: DNA
<213> ORGANISM: Artificial Sequence
<220> FEATURE:
<223> OTHER INFORMATION: Synthetic Construct

<400> SEQUENCE: 773
cctcctcact ctggagtccg cta 23

<210> SEQ ID NO 774
<211> LENGTH: 24
<212> TYPE: DNA
<213> ORGANISM: Artificial Sequence
<220> FEATURE:
<223> OTHER INFORMATION: Synthetic Construct

<400> SEQUENCE: 774
ccactctcaa gatccagcct gcag 24

<210> SEQ ID NO 775
<211> LENGTH: 26
<212> TYPE: DNA
<213> ORGANISM: Artificial Sequence
<220> FEATURE:
<223> OTHER INFORMATION: Synthetic Construct

<400> SEQUENCE: 775
ctccactctc aagatccagc ctgcaa 26

<210> SEQ ID NO 776
<211> LENGTH: 24
<212> TYPE: DNA
<213> ORGANISM: Artificial Sequence
<220> FEATURE:
<223> OTHER INFORMATION: Synthetic Construct

<400> SEQUENCE: 776
ccactctgaa gatccagccc tcag 24

<210> SEQ ID NO 777
<211> LENGTH: 28
<212> TYPE: DNA
<213> ORGANISM: Artificial Sequence
<220> FEATURE:
<223> OTHER INFORMATION: Synthetic Construct

<400> SEQUENCE: 777
cattctgaac tgaacatgag ctccttgg 28

<210> SEQ ID NO 778
<211> LENGTH: 24
<212> TYPE: DNA
<213> ORGANISM: Artificial Sequence
<220> FEATURE:
<223> OTHER INFORMATION: Synthetic Construct

<400> SEQUENCE: 778
ctactctgaa ggtgcagcct gcag 24

<210> SEQ ID NO 779
<211> LENGTH: 28
<212> TYPE: DNA
<213> ORGANISM: Artificial Sequence
<220> FEATURE:
<223> OTHER INFORMATION: Synthetic Construct

<400> SEQUENCE: 779
gataacttcc aatccaggag gccgaaca 28

<210> SEQ ID NO 780
<211> LENGTH: 26
<212> TYPE: DNA
<213> ORGANISM: Artificial Sequence
<220> FEATURE:
<223> OTHER INFORMATION: Synthetic Construct

<400> SEQUENCE: 780
ctgtagcctt gagatccagg ctacga 26

<210> SEQ ID NO 781
<211> LENGTH: 24
<212> TYPE: DNA
<213> ORGANISM: Artificial Sequence
<220> FEATURE:
<223> OTHER INFORMATION: Synthetic Construct

<400> SEQUENCE: 781
cttccacgct gaagatccat cccg 24

<210> SEQ ID NO 782
<211> LENGTH: 24
<212> TYPE: DNA
<213> ORGANISM: Artificial Sequence
<220> FEATURE:
<223> OTHER INFORMATION: Synthetic Construct

<400> SEQUENCE: 782
gcatcctgag gatccagcag gtag 24

<210> SEQ ID NO 783
<211> LENGTH: 22
<212> TYPE: DNA
<213> ORGANISM: Artificial Sequence
<220> FEATURE:
<223> OTHER INFORMATION: Synthetic Construct

<400> SEQUENCE: 783
cctctcactg tgacatcggc cc 22

<210> SEQ ID NO 784
<211> LENGTH: 26
<212> TYPE: DNA
<213> ORGANISM: Artificial Sequence
<220> FEATURE:
<223> OTHER INFORMATION: Synthetic Construct

<400> SEQUENCE: 784
cttgtccact ctgacagtga ccagtg 26

<210> SEQ ID NO 785
<211> LENGTH: 23
<212> TYPE: DNA
<213> ORGANISM: Artificial Sequence
<220> FEATURE:
<223> OTHER INFORMATION: Synthetic Construct

<400> SEQUENCE: 785
cagcctggca atcctgtcct cag 23

<210> SEQ ID NO 786
<211> LENGTH: 24
<212> TYPE: DNA
<213> ORGANISM: Artificial Sequence
<220> FEATURE:
<223> OTHER INFORMATION: Synthetic Construct

<400> SEQUENCE: 786
ctccctgtcc ctagagtctg ccat 24

<210> SEQ ID NO 787
<211> LENGTH: 21
<212> TYPE: DNA
<213> ORGANISM: Artificial Sequence
<220> FEATURE:
<223> OTHER INFORMATION: Synthetic Construct

<400> SEQUENCE: 787
ccctgaccct ggagtctgcc a 21

<210> SEQ ID NO 788

<211> LENGTH: 21
<212> TYPE: DNA
<213> ORGANISM: Artificial Sequence
<220> FEATURE:
<223> OTHER INFORMATION: Synthetic Construct

<400> SEQUENCE: 788
ccctgatcct ggagtcgccc a 21

<210> SEQ ID NO 789
<211> LENGTH: 23
<212> TYPE: DNA
<213> ORGANISM: Artificial Sequence
<220> FEATURE:
<223> OTHER INFORMATION: Synthetic Construct

<400> SEQUENCE: 789
ctccctgatt ctggagtccg cca 23

<210> SEQ ID NO 790
<211> LENGTH: 31
<212> TYPE: DNA
<213> ORGANISM: Artificial Sequence
<220> FEATURE:
<223> OTHER INFORMATION: Synthetic Construct

<400> SEQUENCE: 790
ctaacattct caactctgac tgtgagcaac a 31

<210> SEQ ID NO 791
<211> LENGTH: 28
<212> TYPE: DNA
<213> ORGANISM: Artificial Sequence
<220> FEATURE:
<223> OTHER INFORMATION: Synthetic Construct

<400> SEQUENCE: 791
cggcagttca tcctgagttc taagaagc 28

<210> SEQ ID NO 792
<211> LENGTH: 60
<212> TYPE: DNA
<213> ORGANISM: Artificial Sequence
<220> FEATURE:
<223> OTHER INFORMATION: Synthetic Construct

<400> SEQUENCE: 792
tcacgaaggt ccccagtatc caactttacc tacaactgtg agtctggtgc cttgtccaaa 60

<210> SEQ ID NO 793
<211> LENGTH: 58
<212> TYPE: DNA
<213> ORGANISM: Artificial Sequence
<220> FEATURE:
<223> OTHER INFORMATION: Synthetic Construct

<400> SEQUENCE: 793
tcacgaaggt ccccagtatc caactaccta caacggttaa cctggtcccc gaaccgaa 58

<210> SEQ ID NO 794
<211> LENGTH: 58
<212> TYPE: DNA
<213> ORGANISM: Artificial Sequence
<220> FEATURE:
<223> OTHER INFORMATION: Synthetic Construct

<400> SEQUENCE: 794
tcacgaaggt ccccagtatc caactaccta caacagtgag ccaacttccc tctccaaa 58

<210> SEQ ID NO 795
<211> LENGTH: 56
<212> TYPE: DNA
<213> ORGANISM: Artificial Sequence
<220> FEATURE:
<223> OTHER INFORMATION: Synthetic Construct

<400> SEQUENCE: 795
tcacgaaggt ccccagtatc caactccaag acagagagct gggttccact gccaaa 56

<210> SEQ ID NO 796
<211> LENGTH: 56
<212> TYPE: DNA
<213> ORGANISM: Artificial Sequence
<220> FEATURE:
<223> OTHER INFORMATION: Synthetic Construct

<400> SEQUENCE: 796
tcacgaaggt ccccagtatc caactctgtc acagtgagcc tggtcccgtt cccaaa 56

<210> SEQ ID NO 797
<211> LENGTH: 50
<212> TYPE: DNA
<213> ORGANISM: Artificial Sequence
<220> FEATURE:
<223> OTHER INFORMATION: Synthetic Construct

<400> SEQUENCE: 797
tcacgaaggt ccccagtatc caactcggtg agccgtgtcc ctggcccgaa 50

<210> SEQ ID NO 798
<211> LENGTH: 50
<212> TYPE: DNA
<213> ORGANISM: Artificial Sequence
<220> FEATURE:
<223> OTHER INFORMATION: Synthetic Construct

<400> SEQUENCE: 798
tcacgaaggt ccccagtatc caactcggtg agccgtgtcc ctggcccgaa 50

<210> SEQ ID NO 799
<211> LENGTH: 51
<212> TYPE: DNA
<213> ORGANISM: Artificial Sequence
<220> FEATURE:
<223> OTHER INFORMATION: Synthetic Construct

<400> SEQUENCE: 799
tcacgaaggt ccccagtatc caactactgt cagccgggtg cctgggccaa a 51

<210> SEQ ID NO 800
<211> LENGTH: 47
<212> TYPE: DNA
<213> ORGANISM: Artificial Sequence
<220> FEATURE:
<223> OTHER INFORMATION: Synthetic Construct

<400> SEQUENCE: 800
tcacgaaggt ccccagtatc caactagagc cgggtcccgg cgccgaa 47

<210> SEQ ID NO 801
<211> LENGTH: 47
<212> TYPE: DNA

<213> ORGANISM: Artificial Sequence
<220> FEATURE:
<223> OTHER INFORMATION: Synthetic Construct

<400> SEQUENCE: 801
tcacgaaggt ccccagtatc caactggagc cgcgtgcctg gcccgaa 47

<210> SEQ ID NO 802
<211> LENGTH: 48
<212> TYPE: DNA
<213> ORGANISM: Artificial Sequence
<220> FEATURE:
<223> OTHER INFORMATION: Synthetic Construct

<400> SEQUENCE: 802
tcacgaaggt ccccagtatc caactgtcag cctgctgccg gccccgaa 48

<210> SEQ ID NO 803
<211> LENGTH: 48
<212> TYPE: DNA
<213> ORGANISM: Artificial Sequence
<220> FEATURE:
<223> OTHER INFORMATION: Synthetic Construct

<400> SEQUENCE: 803
tcacgaaggt ccccagtatc caactgtgag cctggtgccc ggcccgaa 48

<210> SEQ ID NO 804
<211> LENGTH: 24
<212> TYPE: DNA
<213> ORGANISM: Artificial Sequence
<220> FEATURE:
<223> OTHER INFORMATION: Synthetic Construct

<400> SEQUENCE: 804
ctgcacgtac cagacatctg ggtt 24

<210> SEQ ID NO 805
<211> LENGTH: 22
<212> TYPE: DNA
<213> ORGANISM: Artificial Sequence
<220> FEATURE:
<223> OTHER INFORMATION: Synthetic Construct

<400> SEQUENCE: 805
ggctcaaagc cttctcagca gg 22

<210> SEQ ID NO 806
<211> LENGTH: 24
<212> TYPE: DNA
<213> ORGANISM: Artificial Sequence
<220> FEATURE:
<223> OTHER INFORMATION: Synthetic Construct

<400> SEQUENCE: 806
ggataacctg gttaaaggca gcta 24

<210> SEQ ID NO 807
<211> LENGTH: 26
<212> TYPE: DNA
<213> ORGANISM: Artificial Sequence
<220> FEATURE:
<223> OTHER INFORMATION: Synthetic Construct

<400> SEQUENCE: 807
ggatacaaga caaaagttac aaacga 26

<210> SEQ ID NO 808
<211> LENGTH: 27
<212> TYPE: DNA
<213> ORGANISM: Artificial Sequence
<220> FEATURE:
<223> OTHER INFORMATION: Synthetic Construct

<400> SEQUENCE: 808
gctgacgtat attttttcaa atatgga 27

<210> SEQ ID NO 809
<211> LENGTH: 23
<212> TYPE: DNA
<213> ORGANISM: Artificial Sequence
<220> FEATURE:
<223> OTHER INFORMATION: Synthetic Construct

<400> SEQUENCE: 809
ggaagaggcc ctgttttctt gct 23

<210> SEQ ID NO 810
<211> LENGTH: 24
<212> TYPE: DNA
<213> ORGANISM: Artificial Sequence
<220> FEATURE:
<223> OTHER INFORMATION: Synthetic Construct

<400> SEQUENCE: 810
gctggatatg agaagcagaa agga 24

<210> SEQ ID NO 811
<211> LENGTH: 24
<212> TYPE: DNA
<213> ORGANISM: Artificial Sequence
<220> FEATURE:
<223> OTHER INFORMATION: Synthetic Construct

<400> SEQUENCE: 811
aggactccag cttctcctga agta 24

<210> SEQ ID NO 812
<211> LENGTH: 25
<212> TYPE: DNA
<213> ORGANISM: Artificial Sequence
<220> FEATURE:
<223> OTHER INFORMATION: Synthetic Construct

<400> SEQUENCE: 812
gtatgtccaa tatcctggag aaggt 25

<210> SEQ ID NO 813
<211> LENGTH: 24
<212> TYPE: DNA
<213> ORGANISM: Artificial Sequence
<220> FEATURE:
<223> OTHER INFORMATION: Synthetic Construct

<400> SEQUENCE: 813
cagtcagaac acaaagtcga acgg 24

<210> SEQ ID NO 814
<211> LENGTH: 24
<212> TYPE: DNA
<213> ORGANISM: Artificial Sequence
<220> FEATURE:

<223> OTHER INFORMATION: Synthetic Construct

<400> SEQUENCE: 814
cctaagttgc tgatgtccgt atac 24

<210> SEQ ID NO 815
<211> LENGTH: 25
<212> TYPE: DNA
<213> ORGANISM: Artificial Sequence
<220> FEATURE:
<223> OTHER INFORMATION: Synthetic Construct

<400> SEQUENCE: 815
gggaaaagcc ctgagttgat aatgt 25

<210> SEQ ID NO 816
<211> LENGTH: 24
<212> TYPE: DNA
<213> ORGANISM: Artificial Sequence
<220> FEATURE:
<223> OTHER INFORMATION: Synthetic Construct

<400> SEQUENCE: 816
gctgatgtac acatactcca gtgg 24

<210> SEQ ID NO 817
<211> LENGTH: 24
<212> TYPE: DNA
<213> ORGANISM: Artificial Sequence
<220> FEATURE:
<223> OTHER INFORMATION: Synthetic Construct

<400> SEQUENCE: 817
cccttggtat aagcaagaac ttgg 24

<210> SEQ ID NO 818
<211> LENGTH: 26
<212> TYPE: DNA
<213> ORGANISM: Artificial Sequence
<220> FEATURE:
<223> OTHER INFORMATION: Synthetic Construct

<400> SEQUENCE: 818
cctcaattca ttatagacat tcgttc 26

<210> SEQ ID NO 819
<211> LENGTH: 24
<212> TYPE: DNA
<213> ORGANISM: Artificial Sequence
<220> FEATURE:
<223> OTHER INFORMATION: Synthetic Construct

<400> SEQUENCE: 819
gcaaaatgca acagaaggtc gcta 24

<210> SEQ ID NO 820
<211> LENGTH: 24
<212> TYPE: DNA
<213> ORGANISM: Artificial Sequence
<220> FEATURE:
<223> OTHER INFORMATION: Synthetic Construct

<400> SEQUENCE: 820
tagagagagc atcaaaggct tcac 24

<210> SEQ ID NO 821
<211> LENGTH: 26
<212> TYPE: DNA
<213> ORGANISM: Artificial Sequence
<220> FEATURE:
<223> OTHER INFORMATION: Synthetic Construct

<400> SEQUENCE: 821
cgttcaaatg aaagagagaa acacag 26

<210> SEQ ID NO 822
<211> LENGTH: 25
<212> TYPE: DNA
<213> ORGANISM: Artificial Sequence
<220> FEATURE:
<223> OTHER INFORMATION: Synthetic Construct

<400> SEQUENCE: 822
cctgaaaagt tcagaaaacc aggag 25

<210> SEQ ID NO 823
<211> LENGTH: 24
<212> TYPE: DNA
<213> ORGANISM: Artificial Sequence
<220> FEATURE:
<223> OTHER INFORMATION: Synthetic Construct

<400> SEQUENCE: 823
ggtcggtatt cttggaactt ccag 24

<210> SEQ ID NO 824
<211> LENGTH: 25
<212> TYPE: DNA
<213> ORGANISM: Artificial Sequence
<220> FEATURE:
<223> OTHER INFORMATION: Synthetic Construct

<400> SEQUENCE: 824
gctggggaag aaaaggagaa agaaa 25

<210> SEQ ID NO 825
<211> LENGTH: 24
<212> TYPE: DNA
<213> ORGANISM: Artificial Sequence
<220> FEATURE:
<223> OTHER INFORMATION: Synthetic Construct

<400> SEQUENCE: 825
gtcagagaga gcaaacaagt ggaa 24

<210> SEQ ID NO 826
<211> LENGTH: 26
<212> TYPE: DNA
<213> ORGANISM: Artificial Sequence
<220> FEATURE:
<223> OTHER INFORMATION: Synthetic Construct

<400> SEQUENCE: 826
ggacaaaaca gaatggaaga ttaagc 26

<210> SEQ ID NO 827
<211> LENGTH: 25
<212> TYPE: DNA
<213> ORGANISM: Artificial Sequence
<220> FEATURE:
<223> OTHER INFORMATION: Synthetic Construct

<400> SEQUENCE: 827
ccagatgtga gtgaaaagaa agaag 25

<210> SEQ ID NO 828
<211> LENGTH: 26
<212> TYPE: DNA
<213> ORGANISM: Artificial Sequence
<220> FEATURE:
<223> OTHER INFORMATION: Synthetic Construct

<400> SEQUENCE: 828
gactttaaat ggggatgaaa agaaga 26

<210> SEQ ID NO 829
<211> LENGTH: 25
<212> TYPE: DNA
<213> ORGANISM: Artificial Sequence
<220> FEATURE:
<223> OTHER INFORMATION: Synthetic Construct

<400> SEQUENCE: 829
ggagaagtga agaagcagaa aagac 25

<210> SEQ ID NO 830
<211> LENGTH: 24
<212> TYPE: DNA
<213> ORGANISM: Artificial Sequence
<220> FEATURE:
<223> OTHER INFORMATION: Synthetic Construct

<400> SEQUENCE: 830
ccaatgaaat ggcctctctg atca 24

<210> SEQ ID NO 831
<211> LENGTH: 24
<212> TYPE: DNA
<213> ORGANISM: Artificial Sequence
<220> FEATURE:
<223> OTHER INFORMATION: Synthetic Construct

<400> SEQUENCE: 831
gcaatgtgaa caacagaatg gcct 24

<210> SEQ ID NO 832
<211> LENGTH: 24
<212> TYPE: DNA
<213> ORGANISM: Artificial Sequence
<220> FEATURE:
<223> OTHER INFORMATION: Synthetic Construct

<400> SEQUENCE: 832
ggtggagaag tgaagaagct caag 24

<210> SEQ ID NO 833
<211> LENGTH: 27
<212> TYPE: DNA
<213> ORGANISM: Artificial Sequence
<220> FEATURE:
<223> OTHER INFORMATION: Synthetic Construct

<400> SEQUENCE: 833
ggataaaaat gaagatggaa gattcac 27

<210> SEQ ID NO 834
<211> LENGTH: 25

<212> TYPE: DNA
<213> ORGANISM: Artificial Sequence
<220> FEATURE:
<223> OTHER INFORMATION: Synthetic Construct

<400> SEQUENCE: 834
cctgatgata ttactgaagg gtgga 25

<210> SEQ ID NO 835
<211> LENGTH: 24
<212> TYPE: DNA
<213> ORGANISM: Artificial Sequence
<220> FEATURE:
<223> OTHER INFORMATION: Synthetic Construct

<400> SEQUENCE: 835
ggtggggaag agaaaagtca tgaa 24

<210> SEQ ID NO 836
<211> LENGTH: 25
<212> TYPE: DNA
<213> ORGANISM: Artificial Sequence
<220> FEATURE:
<223> OTHER INFORMATION: Synthetic Construct

<400> SEQUENCE: 836
ggtgaattga cctcaaatgg aagac 25

<210> SEQ ID NO 837
<211> LENGTH: 26
<212> TYPE: DNA
<213> ORGANISM: Artificial Sequence
<220> FEATURE:
<223> OTHER INFORMATION: Synthetic Construct

<400> SEQUENCE: 837
gctaacttca agtggaattg aaaaga 26

<210> SEQ ID NO 838
<211> LENGTH: 26
<212> TYPE: DNA
<213> ORGANISM: Artificial Sequence
<220> FEATURE:
<223> OTHER INFORMATION: Synthetic Construct

<400> SEQUENCE: 838
gaagcttata agcaacagaa tgcaac 26

<210> SEQ ID NO 839
<211> LENGTH: 22
<212> TYPE: DNA
<213> ORGANISM: Artificial Sequence
<220> FEATURE:
<223> OTHER INFORMATION: Synthetic Construct

<400> SEQUENCE: 839
ggagcagtga agcaggaggg ac 22

<210> SEQ ID NO 840
<211> LENGTH: 26
<212> TYPE: DNA
<213> ORGANISM: Artificial Sequence
<220> FEATURE:
<223> OTHER INFORMATION: Synthetic Construct

<400> SEQUENCE: 840
gagagacaat ggaaaacagc aaaaac 26

<210> SEQ ID NO 841
<211> LENGTH: 23
<212> TYPE: DNA
<213> ORGANISM: Artificial Sequence
<220> FEATURE:
<223> OTHER INFORMATION: Synthetic Construct

<400> SEQUENCE: 841
gctgagctca gggaagaaga agc 23

<210> SEQ ID NO 842
<211> LENGTH: 27
<212> TYPE: DNA
<213> ORGANISM: Artificial Sequence
<220> FEATURE:
<223> OTHER INFORMATION: Synthetic Construct

<400> SEQUENCE: 842
ctgaaatatt cgatgatcaa ttctcag 27

<210> SEQ ID NO 843
<211> LENGTH: 28
<212> TYPE: DNA
<213> ORGANISM: Artificial Sequence
<220> FEATURE:
<223> OTHER INFORMATION: Synthetic Construct

<400> SEQUENCE: 843
tcattataaa tgaaacagtt ccaaatcg 28

<210> SEQ ID NO 844
<211> LENGTH: 22
<212> TYPE: DNA
<213> ORGANISM: Artificial Sequence
<220> FEATURE:
<223> OTHER INFORMATION: Synthetic Construct

<400> SEQUENCE: 844
agtgtgccaa gtcgcttctc ac 22

<210> SEQ ID NO 845
<211> LENGTH: 24
<212> TYPE: DNA
<213> ORGANISM: Artificial Sequence
<220> FEATURE:
<223> OTHER INFORMATION: Synthetic Construct

<400> SEQUENCE: 845
cagaggaaac ttccctccta gatt 24

<210> SEQ ID NO 846
<211> LENGTH: 27
<212> TYPE: DNA
<213> ORGANISM: Artificial Sequence
<220> FEATURE:
<223> OTHER INFORMATION: Synthetic Construct

<400> SEQUENCE: 846
gagacacaga gaaacaaagg aaacttc 27

<210> SEQ ID NO 847
<211> LENGTH: 25
<212> TYPE: DNA
<213> ORGANISM: Artificial Sequence
<220> FEATURE:
<223> OTHER INFORMATION: Synthetic Construct

<400> SEQUENCE: 847
ggtaccactg acaaaggaga agtcc 25

<210> SEQ ID NO 848
<211> LENGTH: 21
<212> TYPE: DNA
<213> ORGANISM: Artificial Sequence
<220> FEATURE:
<223> OTHER INFORMATION: Synthetic Construct

<400> SEQUENCE: 848
gagggtacaa ctgccaaagg a 21

<210> SEQ ID NO 849
<211> LENGTH: 25
<212> TYPE: DNA
<213> ORGANISM: Artificial Sequence
<220> FEATURE:
<223> OTHER INFORMATION: Synthetic Construct

<400> SEQUENCE: 849
ggcaaaggag aagtccctga tggtt 25

<210> SEQ ID NO 850
<211> LENGTH: 25
<212> TYPE: DNA
<213> ORGANISM: Artificial Sequence
<220> FEATURE:
<223> OTHER INFORMATION: Synthetic Construct

<400> SEQUENCE: 850
aaggagaagt ccccaatggc tacaa 25

<210> SEQ ID NO 851
<211> LENGTH: 26
<212> TYPE: DNA
<213> ORGANISM: Artificial Sequence
<220> FEATURE:
<223> OTHER INFORMATION: Synthetic Construct

<400> SEQUENCE: 851
ctgacaaaga agtccccaat ggctac 26

<210> SEQ ID NO 852
<211> LENGTH: 25
<212> TYPE: DNA
<213> ORGANISM: Artificial Sequence
<220> FEATURE:
<223> OTHER INFORMATION: Synthetic Construct

<400> SEQUENCE: 852
cactgacaaa ggagaagtcc ccgat 25

<210> SEQ ID NO 853
<211> LENGTH: 24
<212> TYPE: DNA
<213> ORGANISM: Artificial Sequence
<220> FEATURE:
<223> OTHER INFORMATION: Synthetic Construct

<400> SEQUENCE: 853
agacaaatca gggctgccca gtga 24

<210> SEQ ID NO 854
<211> LENGTH: 21
<212> TYPE: DNA
<213> ORGANISM: Artificial Sequence
<220> FEATURE:
<223> OTHER INFORMATION: Synthetic Construct

<400> SEQUENCE: 854
gactcagggc tgcccaacga t 21

<210> SEQ ID NO 855
<211> LENGTH: 24
<212> TYPE: DNA
<213> ORGANISM: Artificial Sequence
<220> FEATURE:
<223> OTHER INFORMATION: Synthetic Construct

<400> SEQUENCE: 855
ccagaatgaa gctcaactag acaa 24

<210> SEQ ID NO 856
<211> LENGTH: 23
<212> TYPE: DNA
<213> ORGANISM: Artificial Sequence
<220> FEATURE:
<223> OTHER INFORMATION: Synthetic Construct

<400> SEQUENCE: 856
ggttctctgc agagaggcct gag 23

<210> SEQ ID NO 857
<211> LENGTH: 22
<212> TYPE: DNA
<213> ORGANISM: Artificial Sequence
<220> FEATURE:
<223> OTHER INFORMATION: Synthetic Construct

<400> SEQUENCE: 857
ggctgcccag tgatcggttc tc 22

<210> SEQ ID NO 858
<211> LENGTH: 27
<212> TYPE: DNA
<213> ORGANISM: Artificial Sequence
<220> FEATURE:
<223> OTHER INFORMATION: Synthetic Construct

<400> SEQUENCE: 858
gacttacttc cagaatgaag ctcaact 27

<210> SEQ ID NO 859
<211> LENGTH: 28
<212> TYPE: DNA
<213> ORGANISM: Artificial Sequence
<220> FEATURE:
<223> OTHER INFORMATION: Synthetic Construct

<400> SEQUENCE: 859
gagcaaaagg aaacattctt gaacgatt 28

<210> SEQ ID NO 860
<211> LENGTH: 26
<212> TYPE: DNA
<213> ORGANISM: Artificial Sequence
<220> FEATURE:
<223> OTHER INFORMATION: Synthetic Construct

<400> SEQUENCE: 860
ggctgatcca ttactcatat ggtgtt 26

<210> SEQ ID NO 861
<211> LENGTH: 25
<212> TYPE: DNA
<213> ORGANISM: Artificial Sequence
<220> FEATURE:
<223> OTHER INFORMATION: Synthetic Construct

<400> SEQUENCE: 861
gataaaggag aagtccccga tggct 25

<210> SEQ ID NO 862
<211> LENGTH: 25
<212> TYPE: DNA
<213> ORGANISM: Artificial Sequence
<220> FEATURE:
<223> OTHER INFORMATION: Synthetic Construct

<400> SEQUENCE: 862
gattcacagt tgcctaagga tcgat 25

<210> SEQ ID NO 863
<211> LENGTH: 23
<212> TYPE: DNA
<213> ORGANISM: Artificial Sequence
<220> FEATURE:
<223> OTHER INFORMATION: Synthetic Construct

<400> SEQUENCE: 863
gattcaggga tgcccgagga tcg 23

<210> SEQ ID NO 864
<211> LENGTH: 23
<212> TYPE: DNA
<213> ORGANISM: Artificial Sequence
<220> FEATURE:
<223> OTHER INFORMATION: Synthetic Construct

<400> SEQUENCE: 864
gattcgggga tgccgaagga tcg 23

<210> SEQ ID NO 865
<211> LENGTH: 25
<212> TYPE: DNA
<213> ORGANISM: Artificial Sequence
<220> FEATURE:
<223> OTHER INFORMATION: Synthetic Construct

<400> SEQUENCE: 865
gcagagcgat aaaggaagca tccct 25

<210> SEQ ID NO 866
<211> LENGTH: 25
<212> TYPE: DNA
<213> ORGANISM: Artificial Sequence
<220> FEATURE:
<223> OTHER INFORMATION: Synthetic Construct

<400> SEQUENCE: 866
tccggtatgc ccaacaatcg attct 25

<210> SEQ ID NO 867

<211> LENGTH: 27
<212> TYPE: DNA
<213> ORGANISM: Artificial Sequence
<220> FEATURE:
<223> OTHER INFORMATION: Synthetic Construct

<400> SEQUENCE: 867
gattttaaca atgaagcaga cacccct 27

<210> SEQ ID NO 868
<211> LENGTH: 26
<212> TYPE: DNA
<213> ORGANISM: Artificial Sequence
<220> FEATURE:
<223> OTHER INFORMATION: Synthetic Construct

<400> SEQUENCE: 868
gatgaaacag gtatgcccaa ggaaag 26

<210> SEQ ID NO 869
<211> LENGTH: 28
<212> TYPE: DNA
<213> ORGANISM: Artificial Sequence
<220> FEATURE:
<223> OTHER INFORMATION: Synthetic Construct

<400> SEQUENCE: 869
tatcatagat gagtcaggaa tgccaaag 28

<210> SEQ ID NO 870
<211> LENGTH: 27
<212> TYPE: DNA
<213> ORGANISM: Artificial Sequence
<220> FEATURE:
<223> OTHER INFORMATION: Synthetic Construct

<400> SEQUENCE: 870
gactttcaga aaggagatat agctgaa 27

<210> SEQ ID NO 871
<211> LENGTH: 25
<212> TYPE: DNA
<213> ORGANISM: Artificial Sequence
<220> FEATURE:
<223> OTHER INFORMATION: Synthetic Construct

<400> SEQUENCE: 871
caaggccaca tacgagcaag gcgtc 25

<210> SEQ ID NO 872
<211> LENGTH: 28
<212> TYPE: DNA
<213> ORGANISM: Artificial Sequence
<220> FEATURE:
<223> OTHER INFORMATION: Synthetic Construct

<400> SEQUENCE: 872
caaagatata aacaaaggag agatctct 28

<210> SEQ ID NO 873
<211> LENGTH: 26
<212> TYPE: DNA
<213> ORGANISM: Artificial Sequence
<220> FEATURE:
<223> OTHER INFORMATION: Synthetic Construct

<400> SEQUENCE: 873
agagaaggga gatctttcct ctgagt 26

<210> SEQ ID NO 874
<211> LENGTH: 26
<212> TYPE: DNA
<213> ORGANISM: Artificial Sequence
<220> FEATURE:
<223> OTHER INFORMATION: Synthetic Construct

<400> SEQUENCE: 874
gactgataag ggagatgttc ctgaag 26

<210> SEQ ID NO 875
<211> LENGTH: 28
<212> TYPE: DNA
<213> ORGANISM: Artificial Sequence
<220> FEATURE:
<223> OTHER INFORMATION: Synthetic Construct

<400> SEQUENCE: 875
ggctgatcta tttctcatat gatgttaa 28

<210> SEQ ID NO 876
<211> LENGTH: 27
<212> TYPE: DNA
<213> ORGANISM: Artificial Sequence
<220> FEATURE:
<223> OTHER INFORMATION: Synthetic Construct

<400> SEQUENCE: 876
gccacatatg agagtggatt tgtcatt 27

<210> SEQ ID NO 877
<211> LENGTH: 23
<212> TYPE: DNA
<213> ORGANISM: Artificial Sequence
<220> FEATURE:
<223> OTHER INFORMATION: Synthetic Construct

<400> SEQUENCE: 877
ggtgccccag aatctctcag cct 23

<210> SEQ ID NO 878
<211> LENGTH: 24
<212> TYPE: DNA
<213> ORGANISM: Artificial Sequence
<220> FEATURE:
<223> OTHER INFORMATION: Synthetic Construct

<400> SEQUENCE: 878
cggtgaatag gcagacagac ttgt 24

<210> SEQ ID NO 879
<211> LENGTH: 23
<212> TYPE: DNA
<213> ORGANISM: Artificial Sequence
<220> FEATURE:
<223> OTHER INFORMATION: Synthetic Construct

<400> SEQUENCE: 879
accagtgtgg ccttttgggt gtg 23

<210> SEQ ID NO 880
<211> LENGTH: 48
<212> TYPE: DNA

<213> ORGANISM: Artificial Sequence
<220> FEATURE:
<223> OTHER INFORMATION: Synthetic Construct

<400> SEQUENCE: 880
ccagggtttt cccagtcacg acaggtcgtt tttcttcatt ccttagtc 48

<210> SEQ ID NO 881
<211> LENGTH: 47
<212> TYPE: DNA
<213> ORGANISM: Artificial Sequence
<220> FEATURE:
<223> OTHER INFORMATION: Synthetic Construct

<400> SEQUENCE: 881
ccagggtttt cccagtcacg acacgataca acatgaccta tgaacgg 47

<210> SEQ ID NO 882
<211> LENGTH: 48
<212> TYPE: DNA
<213> ORGANISM: Artificial Sequence
<220> FEATURE:
<223> OTHER INFORMATION: Synthetic Construct

<400> SEQUENCE: 882
ccagggtttt cccagtcacg acctttgaag ctgaatttaa caagagcc 48

<210> SEQ ID NO 883
<211> LENGTH: 44
<212> TYPE: DNA
<213> ORGANISM: Artificial Sequence
<220> FEATURE:
<223> OTHER INFORMATION: Synthetic Construct

<400> SEQUENCE: 883
ccagggtttt cccagtcacg acctccctgt ttatccctgc cgac 44

<210> SEQ ID NO 884
<211> LENGTH: 47
<212> TYPE: DNA
<213> ORGANISM: Artificial Sequence
<220> FEATURE:
<223> OTHER INFORMATION: Synthetic Construct

<400> SEQUENCE: 884
ccagggtttt cccagtcacg acaaacaaga ccaaagactc actgttc 47

<210> SEQ ID NO 885
<211> LENGTH: 47
<212> TYPE: DNA
<213> ORGANISM: Artificial Sequence
<220> FEATURE:
<223> OTHER INFORMATION: Synthetic Construct

<400> SEQUENCE: 885
ccagggtttt cccagtcacg acaagactga aggtcacctt tgatacc 47

<210> SEQ ID NO 886
<211> LENGTH: 49
<212> TYPE: DNA
<213> ORGANISM: Artificial Sequence
<220> FEATURE:
<223> OTHER INFORMATION: Synthetic Construct

<400> SEQUENCE: 886
ccagggtttt cccagtcacg acactaaatg ctacattact gaagaatgg 49

<210> SEQ ID NO 887
<211> LENGTH: 50
<212> TYPE: DNA
<213> ORGANISM: Artificial Sequence
<220> FEATURE:
<223> OTHER INFORMATION: Synthetic Construct

<400> SEQUENCE: 887
ccagggtttt cccagtcacg acgcatcaac ggttttgagg ctgaatttaa 50

<210> SEQ ID NO 888
<211> LENGTH: 48
<212> TYPE: DNA
<213> ORGANISM: Artificial Sequence
<220> FEATURE:
<223> OTHER INFORMATION: Synthetic Construct

<400> SEQUENCE: 888
ccagggtttt cccagtcacg acgaaaccac ttctttccac ttggagaa 48

<210> SEQ ID NO 889
<211> LENGTH: 46
<212> TYPE: DNA
<213> ORGANISM: Artificial Sequence
<220> FEATURE:
<223> OTHER INFORMATION: Synthetic Construct

<400> SEQUENCE: 889
ccagggtttt cccagtcacg actacagcaa ctctggatgc agacac 46

<210> SEQ ID NO 890
<211> LENGTH: 45
<212> TYPE: DNA
<213> ORGANISM: Artificial Sequence
<220> FEATURE:
<223> OTHER INFORMATION: Synthetic Construct

<400> SEQUENCE: 890
ccagggtttt cccagtcacg acgaagatgg aaggtttaca gcaca 45

<210> SEQ ID NO 891
<211> LENGTH: 46
<212> TYPE: DNA
<213> ORGANISM: Artificial Sequence
<220> FEATURE:
<223> OTHER INFORMATION: Synthetic Construct

<400> SEQUENCE: 891
ccagggtttt cccagtcacg acgacattcg ttcaaatgtg ggcgaa 46

<210> SEQ ID NO 892
<211> LENGTH: 44
<212> TYPE: DNA
<213> ORGANISM: Artificial Sequence
<220> FEATURE:
<223> OTHER INFORMATION: Synthetic Construct

<400> SEQUENCE: 892
ccagggtttt cccagtcacg acggcaaggc caaagagtca ccgt 44

<210> SEQ ID NO 893
<211> LENGTH: 46
<212> TYPE: DNA
<213> ORGANISM: Artificial Sequence
<220> FEATURE:

<223> OTHER INFORMATION: Synthetic Construct

<400> SEQUENCE: 893
ccagggtttt cccagtcacg actccagaag gcaagaaaat ccgcca 46

<210> SEQ ID NO 894
<211> LENGTH: 46
<212> TYPE: DNA
<213> ORGANISM: Artificial Sequence
<220> FEATURE:
<223> OTHER INFORMATION: Synthetic Construct

<400> SEQUENCE: 894
ccagggtttt cccagtcacg acgctgacct taacaaaggc gagaca 46

<210> SEQ ID NO 895
<211> LENGTH: 47
<212> TYPE: DNA
<213> ORGANISM: Artificial Sequence
<220> FEATURE:
<223> OTHER INFORMATION: Synthetic Construct

<400> SEQUENCE: 895
ccagggtttt cccagtcacg acttaagagt cacgcttgac acttcca 47

<210> SEQ ID NO 896
<211> LENGTH: 45
<212> TYPE: DNA
<213> ORGANISM: Artificial Sequence
<220> FEATURE:
<223> OTHER INFORMATION: Synthetic Construct

<400> SEQUENCE: 896
ccagggtttt cccagtcacg acgcagaggt tttcaggcca gtcct 45

<210> SEQ ID NO 897
<211> LENGTH: 46
<212> TYPE: DNA
<213> ORGANISM: Artificial Sequence
<220> FEATURE:
<223> OTHER INFORMATION: Synthetic Construct

<400> SEQUENCE: 897
ccagggtttt cccagtcacg actccaccag ttccttcaac ttcacc 46

<210> SEQ ID NO 898
<211> LENGTH: 47
<212> TYPE: DNA
<213> ORGANISM: Artificial Sequence
<220> FEATURE:
<223> OTHER INFORMATION: Synthetic Construct

<400> SEQUENCE: 898
ccagggtttt cccagtcacg acgccacatt aacaaagaag gaaagct 47

<210> SEQ ID NO 899
<211> LENGTH: 46
<212> TYPE: DNA
<213> ORGANISM: Artificial Sequence
<220> FEATURE:
<223> OTHER INFORMATION: Synthetic Construct

<400> SEQUENCE: 899
ccagggtttt cccagtcacg acgcctcgct ggataaatca tcagga 46

<210> SEQ ID NO 900
<211> LENGTH: 45
<212> TYPE: DNA
<213> ORGANISM: Artificial Sequence
<220> FEATURE:
<223> OTHER INFORMATION: Synthetic Construct

<400> SEQUENCE: 900
ccagggtttt cccagtcacg acacgactgt cgctacggaa cgcta 45

<210> SEQ ID NO 901
<211> LENGTH: 48
<212> TYPE: DNA
<213> ORGANISM: Artificial Sequence
<220> FEATURE:
<223> OTHER INFORMATION: Synthetic Construct

<400> SEQUENCE: 901
ccagggtttt cccagtcacg accacaatct ccttcaataa aagtgcca 48

<210> SEQ ID NO 902
<211> LENGTH: 48
<212> TYPE: DNA
<213> ORGANISM: Artificial Sequence
<220> FEATURE:
<223> OTHER INFORMATION: Synthetic Construct

<400> SEQUENCE: 902
ccagggtttt cccagtcacg acacgaataa gtgccactct taatacca 48

<210> SEQ ID NO 903
<211> LENGTH: 48
<212> TYPE: DNA
<213> ORGANISM: Artificial Sequence
<220> FEATURE:
<223> OTHER INFORMATION: Synthetic Construct

<400> SEQUENCE: 903
ccagggtttt cccagtcacg acgtttggag aagcaaaaaa gaacagct 48

<210> SEQ ID NO 904
<211> LENGTH: 46
<212> TYPE: DNA
<213> ORGANISM: Artificial Sequence
<220> FEATURE:
<223> OTHER INFORMATION: Synthetic Construct

<400> SEQUENCE: 904
ccagggtttt cccagtcacg accagaagac agaaagtcca gcacct 46

<210> SEQ ID NO 905
<211> LENGTH: 46
<212> TYPE: DNA
<213> ORGANISM: Artificial Sequence
<220> FEATURE:
<223> OTHER INFORMATION: Synthetic Construct

<400> SEQUENCE: 905
ccagggtttt cccagtcacg acatcgctga agacagaaag tccagt 46

<210> SEQ ID NO 906
<211> LENGTH: 48
<212> TYPE: DNA
<213> ORGANISM: Artificial Sequence
<220> FEATURE:
<223> OTHER INFORMATION: Synthetic Construct

<400> SEQUENCE: 906
ccagggtttt cccagtcacg acactaacct ttcagtttgg tgatgcaa 48

<210> SEQ ID NO 907
<211> LENGTH: 47
<212> TYPE: DNA
<213> ORGANISM: Artificial Sequence
<220> FEATURE:
<223> OTHER INFORMATION: Synthetic Construct

<400> SEQUENCE: 907
ccagggtttt cccagtcacg accttaaaca aaagtgccaa gcacctc 47

<210> SEQ ID NO 908
<211> LENGTH: 51
<212> TYPE: DNA
<213> ORGANISM: Artificial Sequence
<220> FEATURE:
<223> OTHER INFORMATION: Synthetic Construct

<400> SEQUENCE: 908
ccagggtttt cccagtcacg acaatatctg cttcatttaa tgaaaaaaag c 51

<210> SEQ ID NO 909
<211> LENGTH: 47
<212> TYPE: DNA
<213> ORGANISM: Artificial Sequence
<220> FEATURE:
<223> OTHER INFORMATION: Synthetic Construct

<400> SEQUENCE: 909
ccagggtttt cccagtcacg acccaagttg gatgagaaaa agcagca 47

<210> SEQ ID NO 910
<211> LENGTH: 47
<212> TYPE: DNA
<213> ORGANISM: Artificial Sequence
<220> FEATURE:
<223> OTHER INFORMATION: Synthetic Construct

<400> SEQUENCE: 910
ccagggtttt cccagtcacg acctcagttt ggtataacca gaaagga 47

<210> SEQ ID NO 911
<211> LENGTH: 49
<212> TYPE: DNA
<213> ORGANISM: Artificial Sequence
<220> FEATURE:
<223> OTHER INFORMATION: Synthetic Construct

<400> SEQUENCE: 911
ccagggtttt cccagtcacg acggaagact aagtagcata ttagataag 49

<210> SEQ ID NO 912
<211> LENGTH: 46
<212> TYPE: DNA
<213> ORGANISM: Artificial Sequence
<220> FEATURE:
<223> OTHER INFORMATION: Synthetic Construct

<400> SEQUENCE: 912
ccagggtttt cccagtcacg acctgtgaac ttccagaaag cagcca 46

<210> SEQ ID NO 913
<211> LENGTH: 45

<212> TYPE: DNA
<213> ORGANISM: Artificial Sequence
<220> FEATURE:
<223> OTHER INFORMATION: Synthetic Construct

<400> SEQUENCE: 913
ccagggtttt cccagtcacg accctcactt gataccaaag cccgt 45

<210> SEQ ID NO 914
<211> LENGTH: 49
<212> TYPE: DNA
<213> ORGANISM: Artificial Sequence
<220> FEATURE:
<223> OTHER INFORMATION: Synthetic Construct

<400> SEQUENCE: 914
ccagggtttt cccagtcacg acaggcggaa atattaaaga caaaaactc 49

<210> SEQ ID NO 915
<211> LENGTH: 49
<212> TYPE: DNA
<213> ORGANISM: Artificial Sequence
<220> FEATURE:
<223> OTHER INFORMATION: Synthetic Construct

<400> SEQUENCE: 915
ccagggtttt cccagtcacg acgattaatt gccacaataa acatacagg 49

<210> SEQ ID NO 916
<211> LENGTH: 47
<212> TYPE: DNA
<213> ORGANISM: Artificial Sequence
<220> FEATURE:
<223> OTHER INFORMATION: Synthetic Construct

<400> SEQUENCE: 916
ccagggtttt cccagtcacg acgcctgatg gatcaaattt cactctg 47

<210> SEQ ID NO 917
<211> LENGTH: 48
<212> TYPE: DNA
<213> ORGANISM: Artificial Sequence
<220> FEATURE:
<223> OTHER INFORMATION: Synthetic Construct

<400> SEQUENCE: 917
ccagggtttt cccagtcacg actctcacct aaatctccag acaaagct 48

<210> SEQ ID NO 918
<211> LENGTH: 44
<212> TYPE: DNA
<213> ORGANISM: Artificial Sequence
<220> FEATURE:
<223> OTHER INFORMATION: Synthetic Construct

<400> SEQUENCE: 918
ccagggtttt cccagtcacg accctgaatg ccccaacagc tctc 44

<210> SEQ ID NO 919
<211> LENGTH: 45
<212> TYPE: DNA
<213> ORGANISM: Artificial Sequence
<220> FEATURE:
<223> OTHER INFORMATION: Synthetic Construct

<400> SEQUENCE: 919
ccagggtttt cccagtcacg acctctgagc tgaatgtgaa cgcct 45

<210> SEQ ID NO 920
<211> LENGTH: 46
<212> TYPE: DNA
<213> ORGANISM: Artificial Sequence
<220> FEATURE:
<223> OTHER INFORMATION: Synthetic Construct

<400> SEQUENCE: 920
ccagggtttt cccagtcacg accgattctc agggcgccag ttctct 46

<210> SEQ ID NO 921
<211> LENGTH: 49
<212> TYPE: DNA
<213> ORGANISM: Artificial Sequence
<220> FEATURE:
<223> OTHER INFORMATION: Synthetic Construct

<400> SEQUENCE: 921
ccagggtttt cccagtcacg actggctaca atgtctccag attaaacaa 49

<210> SEQ ID NO 922
<211> LENGTH: 47
<212> TYPE: DNA
<213> ORGANISM: Artificial Sequence
<220> FEATURE:
<223> OTHER INFORMATION: Synthetic Construct

<400> SEQUENCE: 922
ccagggtttt cccagtcacg acccctgatg gctacaatgt ctccaga 47

<210> SEQ ID NO 923
<211> LENGTH: 49
<212> TYPE: DNA
<213> ORGANISM: Artificial Sequence
<220> FEATURE:
<223> OTHER INFORMATION: Synthetic Construct

<400> SEQUENCE: 923
ccagggtttt cccagtcacg acgtgtctcc agagcaaaca cagatgatt 49

<210> SEQ ID NO 924
<211> LENGTH: 46
<212> TYPE: DNA
<213> ORGANISM: Artificial Sequence
<220> FEATURE:
<223> OTHER INFORMATION: Synthetic Construct

<400> SEQUENCE: 924
ccagggtttt cccagtcacg acgtctccag atcaaccaca gaggat 46

<210> SEQ ID NO 925
<211> LENGTH: 49
<212> TYPE: DNA
<213> ORGANISM: Artificial Sequence
<220> FEATURE:
<223> OTHER INFORMATION: Synthetic Construct

<400> SEQUENCE: 925
ccagggtttt cccagtcacg acgtctctag attaaacaca gaggatttc 49

<210> SEQ ID NO 926
<211> LENGTH: 47
<212> TYPE: DNA
<213> ORGANISM: Artificial Sequence
<220> FEATURE:
<223> OTHER INFORMATION: Synthetic Construct

<400> SEQUENCE: 926
ccagggtttt cccagtcacg acggctacaa tgtatccaga tcaaaca 47

<210> SEQ ID NO 927
<211> LENGTH: 46
<212> TYPE: DNA
<213> ORGANISM: Artificial Sequence
<220> FEATURE:
<223> OTHER INFORMATION: Synthetic Construct

<400> SEQUENCE: 927
ccagggtttt cccagtcacg actcgcttct ctgcagagag gactgg 46

<210> SEQ ID NO 928
<211> LENGTH: 45
<212> TYPE: DNA
<213> ORGANISM: Artificial Sequence
<220> FEATURE:
<223> OTHER INFORMATION: Synthetic Construct

<400> SEQUENCE: 928
ccagggtttt cccagtcacg accggttctt tgcagtcagg cctga 45

<210> SEQ ID NO 929
<211> LENGTH: 46
<212> TYPE: DNA
<213> ORGANISM: Artificial Sequence
<220> FEATURE:
<223> OTHER INFORMATION: Synthetic Construct

<400> SEQUENCE: 929
ccagggtttt cccagtcacg acccagtgat cgcttctttg cagaaa 46

<210> SEQ ID NO 930
<211> LENGTH: 46
<212> TYPE: DNA
<213> ORGANISM: Artificial Sequence
<220> FEATURE:
<223> OTHER INFORMATION: Synthetic Construct

<400> SEQUENCE: 930
ccagggtttt cccagtcacg actctccact ctgaagatcc agcgca 46

<210> SEQ ID NO 931
<211> LENGTH: 45
<212> TYPE: DNA
<213> ORGANISM: Artificial Sequence
<220> FEATURE:
<223> OTHER INFORMATION: Synthetic Construct

<400> SEQUENCE: 931
ccagggtttt cccagtcacg acgcagagag gcctgaggga tccat 45

<210> SEQ ID NO 932
<211> LENGTH: 45
<212> TYPE: DNA
<213> ORGANISM: Artificial Sequence
<220> FEATURE:
<223> OTHER INFORMATION: Synthetic Construct

<400> SEQUENCE: 932
ccagggtttt cccagtcacg acctgcagag aggcctaagg gatct 45

<210> SEQ ID NO 933
<211> LENGTH: 46
<212> TYPE: DNA
<213> ORGANISM: Artificial Sequence
<220> FEATURE:
<223> OTHER INFORMATION: Synthetic Construct

<400> SEQUENCE: 933
ccagggtttt cccagtcacg acctccgcac aacagttccc tgactt 46

<210> SEQ ID NO 934
<211> LENGTH: 50
<212> TYPE: DNA
<213> ORGANISM: Artificial Sequence
<220> FEATURE:
<223> OTHER INFORMATION: Synthetic Construct

<400> SEQUENCE: 934
ccagggtttt cccagtcacg accagatggc tatagtgtct ctagatcaaa 50

<210> SEQ ID NO 935
<211> LENGTH: 48
<212> TYPE: DNA
<213> ORGANISM: Artificial Sequence
<220> FEATURE:
<223> OTHER INFORMATION: Synthetic Construct

<400> SEQUENCE: 935
ccagggtttt cccagtcacg acgttgtctc cagatccaag acagagaa 48

<210> SEQ ID NO 936
<211> LENGTH: 47
<212> TYPE: DNA
<213> ORGANISM: Artificial Sequence
<220> FEATURE:
<223> OTHER INFORMATION: Synthetic Construct

<400> SEQUENCE: 936
ccagggtttt cccagtcacg acgcagagag gctcaaagga gtagact 47

<210> SEQ ID NO 937
<211> LENGTH: 48
<212> TYPE: DNA
<213> ORGANISM: Artificial Sequence
<220> FEATURE:
<223> OTHER INFORMATION: Synthetic Construct

<400> SEQUENCE: 937
ccagggtttt cccagtcacg acgctaagat gcctaatgca tcattctc 48

<210> SEQ ID NO 938
<211> LENGTH: 47
<212> TYPE: DNA
<213> ORGANISM: Artificial Sequence
<220> FEATURE:
<223> OTHER INFORMATION: Synthetic Construct

<400> SEQUENCE: 938
ccagggtttt cccagtcacg acctcagcag agatgcctga tgcaact 47

<210> SEQ ID NO 939
<211> LENGTH: 47
<212> TYPE: DNA
<213> ORGANISM: Artificial Sequence
<220> FEATURE:
<223> OTHER INFORMATION: Synthetic Construct

<400> SEQUENCE: 939
ccagggtttt cccagtcacg actctcagct caacagttca gtgacta 47

<210> SEQ ID NO 940
<211> LENGTH: 46
<212> TYPE: DNA
<213> ORGANISM: Artificial Sequence
<220> FEATURE:
<223> OTHER INFORMATION: Synthetic Construct

<400> SEQUENCE: 940
ccagggtttt cccagtcacg acgctgaaag gactggaggg acgtat 46

<210> SEQ ID NO 941
<211> LENGTH: 46
<212> TYPE: DNA
<213> ORGANISM: Artificial Sequence
<220> FEATURE:
<223> OTHER INFORMATION: Synthetic Construct

<400> SEQUENCE: 941
ccagggtttt cccagtcacg acgataactt ccaatccagg aggccg 46

<210> SEQ ID NO 942
<211> LENGTH: 46
<212> TYPE: DNA
<213> ORGANISM: Artificial Sequence
<220> FEATURE:
<223> OTHER INFORMATION: Synthetic Construct

<400> SEQUENCE: 942
ccagggtttt cccagtcacg acgctaagtg cctcccaaat tcaccc 46

<210> SEQ ID NO 943
<211> LENGTH: 48
<212> TYPE: DNA
<213> ORGANISM: Artificial Sequence
<220> FEATURE:
<223> OTHER INFORMATION: Synthetic Construct

<400> SEQUENCE: 943
ccagggtttt cccagtcacg acggaacgat tttctgctga atttccca 48

<210> SEQ ID NO 944
<211> LENGTH: 46
<212> TYPE: DNA
<213> ORGANISM: Artificial Sequence
<220> FEATURE:
<223> OTHER INFORMATION: Synthetic Construct

<400> SEQUENCE: 944
ccagggtttt cccagtcacg acggtacagc gtctctcggg agaaga 46

<210> SEQ ID NO 945
<211> LENGTH: 48
<212> TYPE: DNA
<213> ORGANISM: Artificial Sequence
<220> FEATURE:
<223> OTHER INFORMATION: Synthetic Construct

<400> SEQUENCE: 945
ccagggtttt cccagtcacg acggacaagt ttctcatcaa ccatgcaa 48

<210> SEQ ID NO 946

<211> LENGTH: 46
<212> TYPE: DNA
<213> ORGANISM: Artificial Sequence
<220> FEATURE:
<223> OTHER INFORMATION: Synthetic Construct

<400> SEQUENCE: 946
ccagggtttt cccagtcacg actggataca gtgtctctcg acaggc 46

<210> SEQ ID NO 947
<211> LENGTH: 47
<212> TYPE: DNA
<213> ORGANISM: Artificial Sequence
<220> FEATURE:
<223> OTHER INFORMATION: Synthetic Construct

<400> SEQUENCE: 947
ccagggtttt cccagtcacg accaacagtc tccagaataa ggacgga 47

<210> SEQ ID NO 948
<211> LENGTH: 50
<212> TYPE: DNA
<213> ORGANISM: Artificial Sequence
<220> FEATURE:
<223> OTHER INFORMATION: Synthetic Construct

<400> SEQUENCE: 948
ccagggtttt cccagtcacg actacaaagt ctctcgaaaa gagaagagga 50

<210> SEQ ID NO 949
<211> LENGTH: 45
<212> TYPE: DNA
<213> ORGANISM: Artificial Sequence
<220> FEATURE:
<223> OTHER INFORMATION: Synthetic Construct

<400> SEQUENCE: 949
ccagggtttt cccagtcacg acggggtaca gtgtctctag agaga 45

<210> SEQ ID NO 950
<211> LENGTH: 47
<212> TYPE: DNA
<213> ORGANISM: Artificial Sequence
<220> FEATURE:
<223> OTHER INFORMATION: Synthetic Construct

<400> SEQUENCE: 950
ccagggtttt cccagtcacg acgtttccca tcagccgccc aaaccta 47

<210> SEQ ID NO 951
<211> LENGTH: 46
<212> TYPE: DNA
<213> ORGANISM: Artificial Sequence
<220> FEATURE:
<223> OTHER INFORMATION: Synthetic Construct

<400> SEQUENCE: 951
ccagggtttt cccagtcacg accagacccc aggaccggca gttcat 46

<210> SEQ ID NO 952
<211> LENGTH: 25
<212> TYPE: DNA
<213> ORGANISM: Artificial Sequence
<220> FEATURE:
<223> OTHER INFORMATION: Synthetic Construct

<400> SEQUENCE: 952
cagacagact tgtcactgga tttag 25

<210> SEQ ID NO 953
<211> LENGTH: 23
<212> TYPE: DNA
<213> ORGANISM: Artificial Sequence
<220> FEATURE:
<223> OTHER INFORMATION: Synthetic Construct

<400> SEQUENCE: 953
cttttgggtg tgggagatct ctg 23

<210> SEQ ID NO 954
<211> LENGTH: 59
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (26)..(27)
<223> OTHER INFORMATION: N = Adenosine, Cytosine, Thymine, or Guanine
<220> FEATURE:
<221> NAME/KEY: misc_feature
<222> LOCATION: (27)..(28)
<223> OTHER INFORMATION: N = Adenosine, Cytosine, Thymine, or Guanine

<400> SEQUENCE: 954
cctacacgac gctcttccga tctnngcaga gataagccca gggttttccc agtcacgac 59

<210> SEQ ID NO 955
<211> LENGTH: 54
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (26)..(27)
<223> OTHER INFORMATION: N = Adenosine, Cytosine, Thymine, or Guanine
<220> FEATURE:
<221> NAME/KEY: misc_feature
<222> LOCATION: (27)..(28)
<223> OTHER INFORMATION: N = Adenosine, Cytosine, Thymine, or Guanine

<400> SEQUENCE: 955
ctgctgaacc gctcttccga tctnngttca gtcactggat ttagagtctc tcag 54

<210> SEQ ID NO 956
<211> LENGTH: 53
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (26)..(27)
<223> OTHER INFORMATION: N = Adenosine, Cytosine, Thymine, or Guanine
<220> FEATURE:

-continued

<221> NAME/KEY: misc_feature
<222> LOCATION: (27)..(28)
<223> OTHER INFORMATION: N = Adenosine, Cytosine, Thymine, or Guanine

<400> SEQUENCE: 956
ctgctgaacc gctcttccga tctnngttca gagatctctg cttctgatgg ctc 53